(12) United States Patent
Breitenbucher et al.

(10) Patent No.: US 12,098,145 B2
(45) Date of Patent: Sep. 24, 2024

(54) OXAZOLE TRPML1 AGONISTS AND USES THEREOF

(71) Applicant: Libra Therapeutics, Inc., San Diego, CA (US)

(72) Inventors: James Guy Breitenbucher, Escondido, CA (US); Maria Pia Catalani, Verona (IT); Ali Munaim Yousif, Pomezia (IT)

(73) Assignee: Libra Therapeutics, Inc., San Diego, CA (US)

( * ) Notice: Subject to any disclaimer, the term of this patent is extended or adjusted under 35 U.S.C. 154(b) by 0 days.

(21) Appl. No.: 18/543,599

(22) Filed: Dec. 18, 2023

(65) Prior Publication Data

US 2024/0158381 A1    May 16, 2024

Related U.S. Application Data

(63) Continuation of application No. PCT/US2023/069679, filed on Jul. 6, 2023.

(60) Provisional application No. 63/359,080, filed on Jul. 7, 2022.

(51) Int. Cl.
| | |
|---|---|
| C07D 263/48 | (2006.01) |
| A61K 31/422 | (2006.01) |
| C07D 413/04 | (2006.01) |
| C07D 413/12 | (2006.01) |
| C07D 413/14 | (2006.01) |
| C07D 491/048 | (2006.01) |
| C07D 491/056 | (2006.01) |
| C07D 491/08 | (2006.01) |
| C07D 491/107 | (2006.01) |
| C07D 495/10 | (2006.01) |
| C07D 498/04 | (2006.01) |

(52) U.S. Cl.
CPC ......... *C07D 413/04* (2013.01); *C07D 263/48* (2013.01); *C07D 413/12* (2013.01); *C07D 413/14* (2013.01); *C07D 491/048* (2013.01); *C07D 491/056* (2013.01); *C07D 491/08* (2013.01); *C07D 491/107* (2013.01); *C07D 495/10* (2013.01); *C07D 498/04* (2013.01)

(58) Field of Classification Search
CPC ........................... C07D 263/48; A61K 31/422
USPC .......................................... 548/233; 514/377
See application file for complete search history.

(56) References Cited

U.S. PATENT DOCUMENTS 8,304,547 B2    11/2012    Sugasawa et al.

FOREIGN PATENT DOCUMENTS

| WO | WO-2018005713 A1 | 1/2018 |
|---|---|---|
| WO | WO-2021094974 A1 | 5/2021 |
| WO | WO-2021127328 A1 | 6/2021 |
| WO | WO-2021127337 A1 | 6/2021 |
| WO | WO-2022032073 A2 | 2/2022 |
| WO | WO-2022076383 A1 | 4/2022 |
| WO | WO-2024011155 A1 | 1/2024 |

OTHER PUBLICATIONS

PCT/US2023/069679 International Search Report and Written Opinion dated Aug. 16, 2023.

*Primary Examiner* — Charanjit Aulakh
(74) *Attorney, Agent, or Firm* — WILSON SONSINI GOODRICH & ROSATI

(57) ABSTRACT

Described herein are oxazole TRPML1 agonists and pharmaceutical compositions comprising said agonists. The subject compounds and compositions are useful for the treatment of TRPML1-mediated disorders or diseases.

26 Claims, No Drawings

OXAZOLE TRPML1 AGONISTS AND USES THEREOF

CROSS-REFERENCE

This patent application is a continuation of International Application No. PCT/US2023/069679, filed Jul. 6, 2023, which claims the benefit of U.S. Provisional Application Ser. No. 63/359,080 filed Jul. 7, 2022, each of which is herein incorporated by reference in their entirety.

BACKGROUND OF THE INVENTION

TRPML1, also named Mucolipin-1, is a ligand-gated cation channel expressed mostly in intracellular organelles like the late endosome and lysosome of many mammalian cells. This channel is member of the large family of Transient receptor potential (TRP) channels and has, with TRPML2 and TRPML3, two close analogues. Loss-of-function mutations in the gene encoding for TRPML1, the 12,000 base pair gene MCOLN-1 located in human chromosome 19p13, are the direct cause of Type IV mucolipidosis (MLIV), an autosomal recessive lysosomal storage disease.

At the molecular level, TRPML1 is a $Ca^{2+}$-permeable, non-selective cation channel formed of four six-transmembrane spanning proteins each of 580 amino acids. The channel opens upon binding of its endogenous ligand phosphatidylinositol-3,5-bisphosphate (PtdIns(3,5)P2)) to its pore region. Channel activity is modulated by pH and PtdIns(4,5) P2 levels. TRPML1 is an inwardly rectifying channel permeable to different mono- and divalent cations, including $Na^+$, $K^+$, $Ca^{2+}$, and $Fe^{2+}$. Its N-terminal AP1 sequence targets the channel to the lysosome while a C-terminal AP2 sequence is responsible for intracellular trafficking and internalization. In addition, TRPML1 has four putative N-linked glycosylation sites in its luminal loop between TM1 and 2. It is reported that TRPML channels can be formed as homo-tetramers (e.g. TRPML1, TRPML2, TRPML3) but also in some cases as hetero-tetramers where one channel is composed of different members of the TRPML family.

TRPML1 is found in all mammalian tissues with highest expression levels in brain, spleen, liver, kidney, and heart. Expression is found in many cell types, including neurons, myeloid cells, macrophages, microglia, podocytes, and muscle cells. TRPML1 is involved in function of late endosome/lysosomes (LELs), more specifically in protein trafficking, lysis, and autophagy.

Lysosomes are organelles filled with hydrolytic enzymes, characterized by a low luminal pH of about 5, a high luminal $Ca^{2+}$ concentration of about 0.5 mM, and a membrane polarization of about +60 mV.

TRPML1 in LELs is reported to be responsible for the formation of transport vesicles, and it is required for the reformation of lysosomes from LEL hybrid organelles and autolysosomes, mostly due to its $Ca^{2+}$ permeability. TRPML1 is likely also important for iron release from the lysosome after degradation of iron-binding proteins like cytochrome C. In addition, TRPML1 is reported to regulate autophagy, probably in an mTOR-independent manner, by promoting TFEB translocation to the nucleus via calcineurin activation.

SUMMARY OF THE INVENTION

In MLIV, the lack of functional TRPML1 leads to severe intellectual disability, motor deficits, retinal degeneration, and systemic symptoms leading to a strongly reduced life expectancy. Cells from MLIV patients show increased autophagosomes, accumulation of lysofuscin, and lipid accumulation in the lysosomes.

Failure of TRPML1-dependent autophagosome-lysosome fusion is also thought to impair clearance of apoptotic neurons by macrophages and microglia cells. Experimental results suggest involvement of TRPML1 in neurodegenerative diseases like Alzheimer's and amyotrophic lateral sclerosis (ALS). For example, Alzheimer's disease related loss-of-function mutations in presenilin 1 lead to dysregulation of lysosomal $Ca^{2+}$ homeostasis via TRPML1 modulation. On the other side, over-expression of TRPML1 in rodent Alzheimer's models reduced neuronal apoptosis and rescued memory impairments. Pharmacological activation of TRPML1 showed similar effects, clearing accumulated sphingolipids and Aβ peptides from lysosomes. In another study TRPML1 activation was sufficient to upregulate lysosomal exocytosis, rescue defective α-syn secretion and prevent α-syn accumulation in iPSC-derived dopaminergic neurons from patients expressing mutant PARK9. Similarly, TRPML1 activation rescued motor neurons from death and ER stress induced by the cycad neurotoxin beta-methyl-amino-L-alanine, L-BMAA as a model for ALS.

Therefore, it is desired to develop TRPML1 modulators to rescue impaired lysosomal function and cellular autophagy in neurodegenerative diseases.

Despite widespread interest for several years across the pharmaceutical industry, currently described small molecule TRPML1 agonists are not optimized for functional activity and drug like properties. Consequently, there is still an unmet need for compounds which can efficiently stimulate TRPML1 and that can be delivered to the different target organs which are sites of any TRPML1-mediated pathology.

Disclosed herein is a compound of Formula (I), or a pharmaceutically acceptable salt, solvate, or stereoisomer thereof:

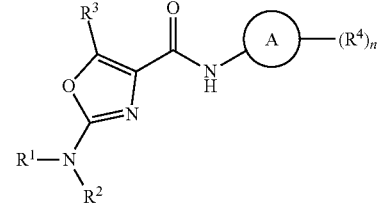

Formula (I)

as defined herein.

Disclosed herein is a compound of Formula (Ia), or a pharmaceutically acceptable salt, solvate, or stereoisomer thereof:

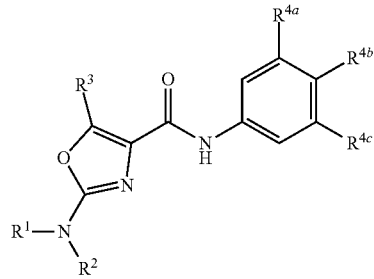

Formula (Ia)

as defined herein.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating a TRPML1-mediated disorder or disease in a subject in need thereof, the method comprising administering a compound disclosed herein, or a pharmaceutically acceptable salt, solvate, or stereoisomer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.
"Amine" refers to —NH$_2$;
"hydroxy" refers to —OH;
"Carboxyl" refers to —COOH.

"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl. In some embodiments, the alkyl is a $C_1$-$C_6$alkyl. In some embodiments, the alkyl is a $C_1$-$C_5$ alkyl. In some embodiments, the alkyl is a $C_1$-$C_4$ alkyl. In some embodiments, the alkyl is a $C_1$-$C_3$ alkyl. Unless stated otherwise specifically in the specification, an alkyl group may be optionally substituted, for example, with one or more oxo, halogen, amino, nitrile, nitro, hydroxyl, haloalkyl, alkoxy, carboxyl, carboxylate, aryl, cycloalkyl, heterocycloalkyl, or heteroaryl, and the like. In some embodiments, the alkyl is optionally substituted with one or more oxo, halogen, —CN, —COOH, —COOMe, —OH, —OMe, —NH$_2$, or —NO$_2$. In some embodiments, the alkyl is optionally substituted with one or more halogen, —CN, —OH, or —OMe. In some embodiments, the alkyl is optionally substituted with halogen.

"Alkenyl" refers to a straight-chain or branched-chain hydrocarbon monoradical having one or more carbon-carbon double-bonds and having from two to about ten carbon atoms, more preferably two to about six carbon atoms. The group may be in either the cis or trans or Z or E conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkenyl is optionally substituted with one or more oxo, halogen, —CN, —COOH, —COOMe, —OH, —OMe, —NH$_2$, or —NO$_2$. In some embodiments, the alkenyl is optionally substituted with one or more halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkynyl is optionally substituted with one or more oxo, halogen, —CN, —COOH, —COOMe, —OH, —OMe, —NH$_2$, or —NO$_2$. In some embodiments, the alkynyl is optionally substituted with one or more halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkylene is optionally substituted with one or more oxo, halogen, —CN, —COOH, —COOMe, —OH, —OMe, —NH$_2$, or —NO$_2$. In some embodiments, the alkylene is optionally substituted with one or more halogen, —CN, —OH, or —OMe. In some embodiments, the alkylene is optionally substituted with halogen.

"Alkoxy" refers to a radical of the formula —Oalkyl where alkyl is defined as above. Unless stated otherwise specifically in the specification, an alkoxy group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkoxy is optionally substituted with one or more halogen, —CN, —COOH, —COOMe, —OH, —OMe, —NH$_2$, or —NO$_2$. In some embodiments, the alkoxy is optionally substituted with one or more halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to anthracenyl, naphthyl, phenanthrenyl, azulenyl, phenyl, chrysenyl, fluoranthenyl, fluorenyl, as-indacenyl, s-indacenyl, indanyl, indenyl, phenalenyl, phenanthrenyl, pleiadenyl, pyrenyl, and triphenylenyl. Unless stated otherwise specifically in the specification, an aryl may be optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the aryl is optionally substituted with one or more halogen, methyl, ethyl, —CN, —COOH, —COOMe, —CF$_3$, —OH, —OMe, —NH$_2$, or —NO$_2$. In some embodiments, the aryl is optionally substituted with one or more halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, and/or bridged ring systems. In some embodiments, the cycloalkyl is fully saturated. Representative cycloalkyls include, but are not limited to, cycloalkyls having from three to fifteen carbon atoms (e.g., C$_3$-C$_{15}$ fully saturated cycloalkyl or C$_3$-C$_{15}$ cycloalkenyl), from three to ten carbon atoms (e.g., C$_3$-C$_{10}$ fully saturated cycloalkyl or C$_3$-C$_{10}$ cycloalkenyl), from three to eight carbon atoms (e.g., C$_3$-C$_8$ fully saturated cycloalkyl or C$_3$-C$_8$ cycloalkenyl), from three to six carbon atoms (e.g., C$_3$-C$_6$ fully saturated cycloalkyl or C$_3$-C$_6$ cycloalkenyl), from three to five carbon atoms (e.g., C$_3$-C$_5$ fully saturated cycloalkyl or C$_3$-C$_5$ cycloalkenyl), or three to four carbon atoms (e.g., C$_3$-C$_4$ fully saturated cycloalkyl or C$_3$-C$_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octyl, bicyclo[4.3.0]nonyl, cis-decalinyl, trans-decalinyl, bicyclo[2.1.1]hexyl, bicyclo[2.2.1]heptyl, bicyclo[2.2.2]octyl, bicyclo[3.2.1]octyl, bicyclo[3.2.2]nonyl, and bicyclo[3.3.2]decyl, bicyclo[1.1.1]pentyl, bicyclo[3.1.0]hexyl, bicyclo[3.1.1]heptyl, 7,7-dimethyl-bicyclo[2.2.1]heptanyl, Spiro[4.2]heptyl, sprio[4.3]octyl, spiro[5.2]octyl, spiro[3.3]heptyl, and spiro[5.3]nonyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, a cycloalkyl is optionally substituted with one or more oxo, halogen, methyl, ethyl, —CN, —COOH, —COOMe, —CF$_3$, —OH, —OMe, —NH$_2$, or —NO$_2$. In some embodiments, a cycloalkyl is optionally substituted with one or more oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 2-fluoroethyl, 3-bromo-2-fluoropropyl, 1,2-dibromoethyl, and the like.

"Haloalkoxy" refers to —O-haloalkyl, with haloalkyl as defined above.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl includes, for example, hydroxymethyl, hydroxyethyl, hydroxypropyl, hydroxybuhyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl includes, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen, sulfur, phosphorus, or combinations thereof. A heteroalkyl is attached to the rest of the molecule at a carbon atom of the heteroalkyl. In one aspect, a heteroalkyl is a $C_1$-$C_6$heteroalkyl wherein the heteroalkyl is comprised of 1 to 6 carbon atoms and one or more atoms other than carbon, e.g., oxygen, nitrogen, sulfur, phosphorus, or combinations thereof wherein the heteroalkyl is attached to the rest of the molecule at a carbon atom of the heteroalkyl. In one aspect, a heteroalkyl is a $C_1$-$C_6$heteroalkyl wherein the heteroalkyl is comprised of 1 to 6 carbon atoms and one or two atoms selected from the group consisting of oxygen, nitrogen, and sulfur wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —$CH_2CH_2NHCH_3$, or —$CH_2CH_2N(CH_3)_2$. Unless stated otherwise specifically in the specification, a heteroalkyl is optionally substituted for example, with one or more oxo, halogen, amino, nitrile, nitro, hydroxyl, alkyl, alkenyl, alkynyl, haloalkyl, alkoxy, aryl, cycloalkyl, heterocycloalkyl, or heteroaryl, and the like. In some embodiments, a heteroalkyl is optionally substituted with one or more oxo, halogen, methyl, ethyl, —CN, —$CF_3$, —OH, —OMe, —$NH_2$, or —$NO_2$. In some embodiments, a heteroalkyl is optionally substituted with one or more oxo, halogen, methyl, ethyl, —CN, —$CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl is C-linked. In some embodiments, the heterocycloalkyl is N-linked. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_7$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with one or more oxo, halogen, methyl, ethyl, —CN, —COOH, —COOMe, —$CF_3$, —OH, —OMe, —$NH_2$, or —$NO_2$. In some embodiments, the heterocycloalkyl is optionally substituted with one or more halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. In some embodiments, the heteroaryl is C-linked. In some embodiments, the heteroaryl is N-linked. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. In some embodiments, the heteroaryl is a 5- to 6-membered ring comprising 1, 2, or 3 heteroatoms selected from the group consisting of oxygen, nitrogen, or sulfur. Examples include, but are not limited to, azepinyl, acridinyl, benzimidazolyl, benzothiazolyl, benzindolyl, benzodioxolyl, benzofuranyl, benzoxazolyl, benzothiadiazolyl, benzo[b][1,4]dioxepinyl, 1,4-benzodioxanyl, benzonaphthofuranyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the heteroaryl is optionally substituted with one or more halogen, methyl, ethyl, —CN, —COOH, —COOMe, —CF$_3$, —OH, —OMe, —NH$_2$, or —NO$_2$. In some embodiments, the heteroaryl is optionally substituted with one or more halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, or four, or more substituents. In some embodiments, the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with TRPML1" or, alternatively, "a TRPML1-mediated disease or disorder" means any disease or other deleterious condition in which TRPML1, or a mutant thereof, is known or suspected to play a role.

Compounds

Described herein are compounds, or a pharmaceutically acceptable salt, solvate, or stereoisomer thereof useful in the treatment of a TRPML1-mediated disease or disorder.

Disclosed herein is a compound of Formula (I), or a pharmaceutically acceptable salt, solvate, or stereoisomer thereof:

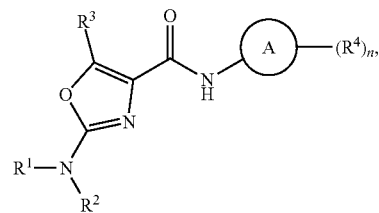

Formula (I)

wherein:

R$^1$ is C$_1$-C$_6$alkyl optionally substituted with one or more R;

R$^2$ is C$_1$-C$_6$alkyl optionally substituted with one or more R;

or R$^1$ and R$^2$ are taken together to form a heterocycloalkyl or heteroaryl; each optionally substituted with one or more R$^{1a}$;

each $R^{1a}$ is independently deuterium, halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)R$^a$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently and optionally substituted with one or more R;

or two $R^{1a}$ on the same atom are taken together to form an oxo;

$R^3$ is $C_1$-$C_6$alkyl, $C_1$-$C_6$haloalkyl, $C_1$-$C_6$deuteroalkyl, $C_2$-$C_6$alkenyl, $C_2$-$C_6$alkynyl, $C_1$-$C_6$hydroxyalkyl, $C_1$-$C_6$aminoalkyl, $C_1$-$C_6$heteroalkyl, cycloalkyl, or heterocycloalkyl, wherein each alkyl, alkenyl, alkynyl, cycloalkyl, and heterocycloalkyl is independently and optionally substituted with one or more R;

Ring A is aryl or heteroaryl;

each $R^4$ is independently deuterium, halogen, —CN, —NO₂, —OH, —OR$^a$, —OC(=O)R$^a$, —OC(=O)OR$^b$, —OC(=O)NR$^c$R$^d$, —O-cycloalkyl, —O-heterocycloalkyl, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)R$^a$, —NR$^b$S(=O)₂R$^a$, —NR$^b$— cycloalkyl, —NR$^b$-heterocycloalkyl, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(ayl), or $C_1$-$C_6$alkylene(heteroaryl); wherein each alkyl, alkylene, alkenyl, alkynyl, cycloalkyl, heterocycloalkyl, aryl, and heteroaryl is independently and optionally substituted with one or more R;

n is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently and optionally substituted with one or more R;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently and optionally substituted with one or more R;

each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently and optionally substituted with one or more R;

or $R^c$ and $R^d$ are taken together with the atom to which they are attached to form a heterocycloalkyl optionally substituted with one or more R; and each R is independently deuterium, halogen, —CN, —OH, —S(=O)$C_1$-$C_3$alkyl, —S(=O)₂$C_1$-$C_3$alkyl, —S(=O)₂NH₂, —S(=O)₂NH$C_1$-$C_3$alkyl, —S(=O)₂N($C_1$-$C_3$alkyl)₂, —NH₂, —NH$C_1$-$C_3$alkyl, —N($C_1$-$C_3$alkyl)₂, —C(=O)$C_1$-$C_3$alkyl, —C(=O)OH, —C(=O)O$C_1$-$C_3$alkyl, —C(=O)NH₂, —C(=O)NH$C_1$-$C_3$alkyl, —C(=O)N($C_1$-$C_3$alkyl)₂, $C_1$-$C_3$alkyl, $C_1$-$C_3$alkoxy, $C_1$-$C_3$haloalkyl, $C_1$-$C_3$deuteroalkyl, $C_1$-$C_3$haloalkoxy, $C_1$-$C_3$hydroxyalkyl, $C_1$-$C_3$aminoalkyl, $C_1$-$C_3$heteroalkyl, $C_3$-$C_6$cycloalkyl, or 3- to 6-membered heterocycloalkyl; wherein each cycloalkyl and heterocycloalkyl is independently optionally substituted with one or more halogen;

or two R on the same atom form an oxo.

In some embodiments of a compound of Formula (I), n is 1-4. In some embodiments of a compound of Formula (I), n is 1-3. In some embodiments of a compound of Formula (I), n is 2-4. In some embodiments of a compound of Formula (I), n is 2 or 3. In some embodiments of a compound of Formula (I), n is 2. In some embodiments of a compound of Formula (I), n is 3.

In some embodiments of a compound of Formula (I), Ring A is aryl or heteroaryl. In some embodiments of a compound of Formula (I), Ring A is phenyl. In some embodiments of a compound of Formula (I), Ring A is a 5- or 6-membered heteroaryl. In some embodiments of a compound of Formula (I), Ring A is a 6-membered heteroaryl.

In some embodiments of a compound of Formula (I), Ring A is a bicyclic ring. In some embodiments of a compound of Formula (I), Ring A is a bicyclic aryl. In some embodiments of a compound of Formula (I), Ring A is a bicyclic heteroaryl. In some embodiments of a compound of Formula (I), Ring A is indolinyl.

In some embodiments of a compound of Formula (I), each $R^4$ is independently deuterium, halogen, —CN, —NO₂, —OH, —OR$^a$, —OC(=O)R$^a$, —OC(=O)OR$^b$, —OC(=O)NR$^c$R$^d$, —O-cycloalkyl, —O— heterocycloalkyl, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)R$^a$, —NR$^b$S(=O)₂R$^a$, —NR$^b$-cycloalkyl, —NR$^b$-heterocycloalkyl, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently and optionally substituted with one or more R.

In some embodiments of a compound of Formula (I), each $R^4$ is independently deuterium, halogen, —CN, —OH, —OR$^a$, —O-cycloalkyl, —O-heterocycloalkyl, —NR$^c$R$^d$, —NR$^b$-cycloalkyl, —NR$^b$— heterocycloalkyl, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), or $C_1$-$C_6$alkylene(heterocycloalkyl); wherein each alkyl, alkylene, cycloalkyl, and heterocycloalkyl is independently and optionally substituted with one or more R.

In some embodiments of a compound of Formula (I), each $R^4$ is independently deuterium, halogen, —CN, —OH, —$OR^a$, —O-cycloalkyl, —O-heterocycloalkyl, —$NR^cR^d$, —$NR^b$-cycloalkyl, —$NR^b$— heterocycloalkyl, $C_1$-$C_6$alkyl, $C_1$-$C_6$haloalkyl, cycloalkyl, heterocycloalkyl, $C_1$-$C_6$alkylene(cycloalkyl), or $C_1$-$C_6$alkylene(heterocycloalkyl); wherein each alkyl, alkylene, cycloalkyl, and heterocycloalkyl is independently and optionally substituted with one or more R.

In some embodiments of a compound of Formula (I), each $R^4$ is independently deuterium, halogen, —CN, —OH, —$OR^a$, —O-cycloalkyl, —O-heterocycloalkyl, —$NR^cR^d$, —$NR^b$-cycloalkyl, $C_1$-$C_6$alkyl, $C_1$-$C_6$haloalkyl, heterocycloalkyl, or $C_1$-$C_6$alkylene(heterocycloalkyl); wherein each alkyl, alkylene, and heterocycloalkyl is independently and optionally substituted with one or more R.

In some embodiments of a compound of Formula (I), each $R^4$ is independently deuterium, halogen, —CN, —OH, —$OR^a$, —O-cycloalkyl, —O-heterocycloalkyl, —$NR^cR^d$, —$NR^b$-cycloalkyl, —$NR^b$— heterocycloalkyl, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently and optionally substituted with one or more R. In some embodiments of a compound of Formula (I), each $R^4$ is independently deuterium, halogen, —CN, —OH, —$OR^a$, —O-cycloalkyl, —O-heterocycloalkyl, —$NR^cR^d$, —$NR^b$-cycloalkyl, —$NR^b$-heterocycloalkyl, $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently and optionally substituted with one or more R.

In some embodiments of a compound of Formula (I), each $R^4$ is independently halogen, —CN, —OH, —$OR^a$, —O-cycloalkyl, —O-heterocycloalkyl, —$NR^cR^d$, —$NR^b$-cycloalkyl, —$NR^b$-heterocycloalkyl, $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently and optionally substituted with one or more R. In some embodiments of a compound of Formula (I), each $R^4$ is independently halogen, —CN, —OH, —$OR^a$, —O— cycloalkyl, —O-heterocycloalkyl, —$NR^cR^d$, —$NR^b$-cycloalkyl, $C_1$-$C_6$alkyl, $C_1$-$C_6$haloalkyl, or heterocycloalkyl. In some embodiments of a compound of Formula (I), each $R^4$ is independently halogen, —CN, —OH, —$OR^a$, —O-cycloalkyl, —O-heterocycloalkyl, —$NR^cR^d$, —$NR^b$-cycloalkyl, $C_1$-$C_6$alkyl, $C_1$-$C_6$haloalkyl, or heterocycloalkyl. In some embodiments of a compound of Formula (I), each $R^4$ is independently halogen, —OH, —O-cycloalkyl, —O— heterocycloalkyl, —$NR^cR^d$, —$NR^b$-cycloalkyl, $C_1$-$C_6$alkyl, or heterocycloalkyl.

In some embodiments of a compound of Formula (I), each $R^4$ is independently halogen, —OH, —O— cycloalkyl, —O-heterocycloalkyl, —$NR^cR^d$, —$NR^b$-cycloalkyl, or heterocycloalkyl. In some embodiments of a compound of Formula (I), each $R^4$ is independently halogen, —O-cycloalkyl, —O-heterocycloalkyl, —$NR^b$— cycloalkyl, $C_1$-$C_6$alkyl, or heterocycloalkyl. In some embodiments of a compound of Formula (I), each $R^4$ is independently halogen, —O-cycloalkyl, —O-heterocycloalkyl, —$NR^b$-cycloalkyl, or heterocycloalkyl. In some embodiments of a compound of Formula (I), each $R^4$ is independently halogen, —O— heterocycloalkyl, $C_1$-$C_6$alkyl, or heterocycloalkyl. In some embodiments of a compound of Formula (I), each $R^4$ is independently halogen, —O-cycloalkyl, —O-heterocycloalkyl, or heterocycloalkyl. In some embodiments of a compound of Formula (I), each $R^4$ is independently halogen, $C_1$-$C_6$alkyl, or heterocycloalkyl. In some embodiments of a compound of Formula (I), each $R^4$ is independently halogen or heterocycloalkyl. In some embodiments of a compound of Formula (I), each $R^4$ is independently halogen, —O-cycloalkyl, or $C_1$-$C_6$alkyl. In some embodiments of a compound of Formula (I), each $R^4$ is independently halogen or —O-cycloalkyl. In some embodiments of a compound of Formula (I), each $R^4$ is independently halogen, —O-heterocycloalkyl, or $C_1$-$C_6$alkyl. In some embodiments of a compound of Formula (I), each $R^4$ is independently halogen or —O— heterocycloalkyl.

In some embodiments of a compound of Formula (I), the compound is of Formula (Ia):

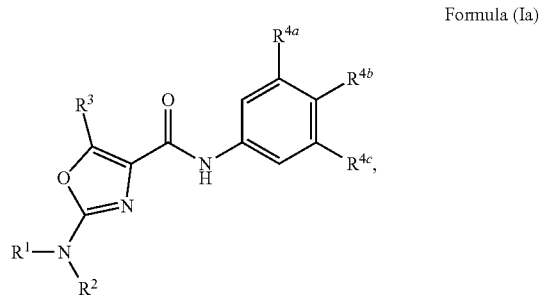

Formula (Ia)

wherein:
$R^{4a}$ is hydrogen, deuterium, halogen, —CN, —$NO_2$, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^{4b}$ is deuterium, halogen, —CN, —$NO_2$, —OH, —$OR^a$, —O-cycloalkyl, —O-heterocycloalkyl, —$NR^cR^d$, —$NR^b$-cycloalkyl, —$NR^b$-heterocycloalkyl, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R; and $R^{4c}$ is deuterium, halogen, —CN, —$NO_2$, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

In some embodiments of a compound of Formula (Ia), $R^{4a}$ is hydrogen, deuterium, halogen, —CN, —OH, —$OR^a$, —$NR^cR^d$, $C_1$-$C_6$alkyl, or $C_1$-$C_6$haloalkyl. In some embodiments of a compound of Formula (Ia), $R^{4a}$ is hydrogen, halogen, $C_1$-$C_6$alkyl, or $C_1$-$C_6$haloalkyl. In some embodiments of a compound of Formula (Ia), $R^{4a}$ is hydrogen, halogen, or $C_1$-$C_6$alkyl. In some embodiments of a compound of Formula (Ia), $R^{4a}$ is hydrogen or halogen. In some embodiments of a compound of Formula (Ia), $R^{4a}$ is hydrogen. In some embodiments of a compound of Formula (Ia), $R^{4a}$ is halogen. In some embodiments of a compound of Formula (Ia), $R^{4a}$ is $C_1$-$C_6$alkyl.

In some embodiments of a compound of Formula (Ia), $R^{4b}$ is deuterium, halogen, —CN, —OH, —OR$^a$, —O-cycloalkyl, —O-heterocycloalkyl, —NR$^c$R$^d$, —NR$^b$-cycloalkyl, —NR$^b$-heterocycloalkyl, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (Ia), $R^{4b}$ is deuterium, halogen, —CN, —OH, —OR$^a$, —O-cycloalkyl, —O-heterocycloalkyl, —NR$^c$R$^d$, —NR$^b$-cycloalkyl, —NR$^b$-heterocycloalkyl, $C_1$-$C_6$alkyl, $C_1$-$C_6$haloalkyl, or heterocycloalkyl. In some embodiments of a compound of Formula (Ia), $R^{4b}$ is —OR$^a$, —O-cycloalkyl, —O-heterocycloalkyl, —NR$^c$R$^d$, —NR$^b$-cycloalkyl, or heterocycloalkyl. In some embodiments of a compound of Formula (Ia), $R^{4b}$ is —O-cycloalkyl, —O-heterocycloalkyl, —NR$^b$-cycloalkyl, or heterocycloalkyl. In some embodiments of a compound of Formula (Ia), $R^{4b}$ is —O-cycloalkyl, —O— heterocycloalkyl, or heterocycloalkyl. In some embodiments of a compound of Formula (Ia), $R^{4b}$ is —O— cycloalkyl or —O-heterocycloalkyl. In some embodiments of a compound of Formula (Ia), $R^{4b}$ is —O— cycloalkyl. In some embodiments of a compound of Formula (Ia), $R^{4b}$ is —O-cycloalkyl wherein the cycloalkyl is monocyclic cycloalkyl. In some embodiments of a compound of Formula (Ia), $R^{4b}$ is —O— cycloalkyl wherein the cycloalkyl is bicyclic cycloalkyl. In some embodiments of a compound of Formula (Ia), $R^{4b}$ is heterocycloalkyl. In some embodiments of a compound of Formula (Ia), $R^{4b}$ is 3- to 10-membered heterocycloalkyl. In some embodiments of a compound of Formula (Ia), $R^{4b}$ is 5- to 10-membered heterocycloalkyl. In some embodiments of a compound of Formula (Ia), $R^{4b}$ is 5- to 8-membered heterocycloalkyl.

In some embodiments of a compound of Formula (Ia), $R^{4b}$ is

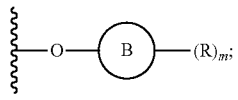

wherein Ring B is cycloalkyl or heterocycloalkyl and m is 0-4. In some embodiments of a compound of Formula (Ia), $R^{4b}$ is

wherein Ring B is cycloalkyl and m is 0-4. In some embodiments of a compound of Formula (Ia), $R^{4b}$ is

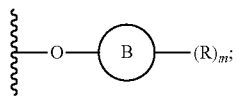

wherein Ring B is monocyclic cycloalkyl and m is 0-4. In some embodiments of a compound of Formula (Ia), $R^{4b}$ is

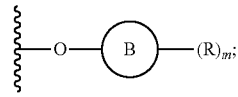

wherein Ring B is bicyclic cycloalkyl and m is 0-4.

In some embodiments of a compound of Formula (Ia), $R^{4b}$ is

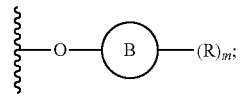

wherein Ring B is

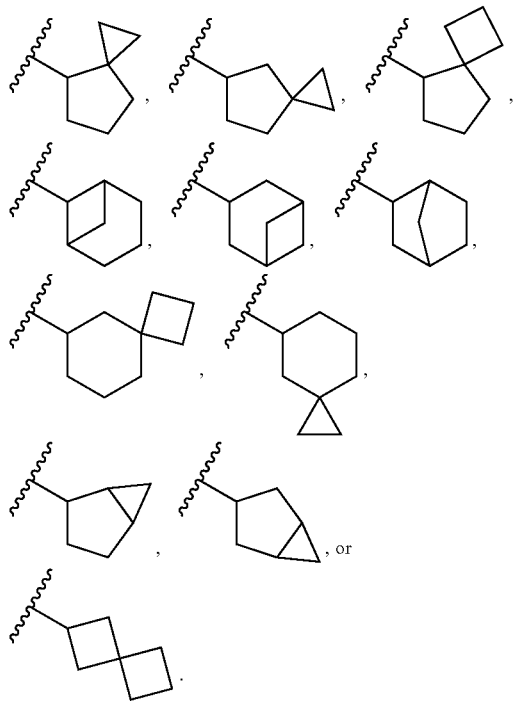

In some embodiments of a compound of Formula (Ia), $R^{4b}$ is

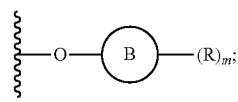

wherein Ring B is or

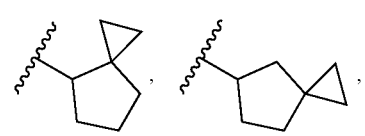

-continued

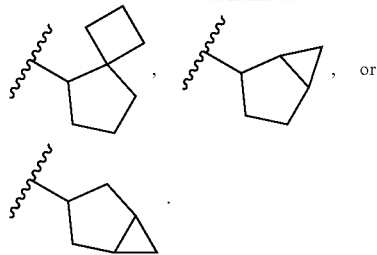

In some embodiments of a compound of Formula (Ia), $R^{4b}$ is

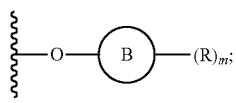

wherein Ring B is

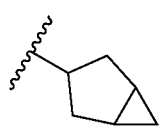

In some embodiments of a compound of Formula (Ia), $R^{4b}$ is

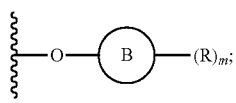

wherein Ring B is

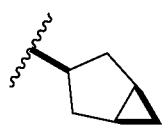

In some embodiments of a compound of Formula (Ia), $R^{4b}$ is

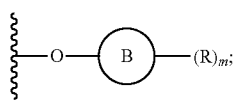

wherein Ring B is

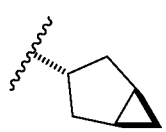

In some embodiments of a compound of Formula (Ia), $R^{4b}$ is

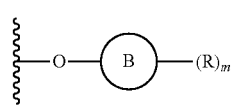

and m is 0-4. In some embodiments of a compound of Formula (Ia), $R^{4b}$ is

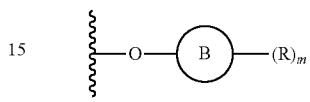

and m is 0 or 1. In some embodiments of a compound of Formula (Ia), $R^{4b}$ is

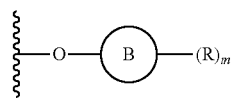

and m is 0-2. In some embodiments of a compound of Formula (Ia), $R^{4b}$ is

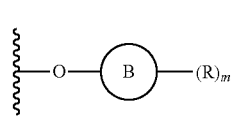

and m is 0. In some embodiments of a compound of Formula (Ia), $R^{4b}$ is

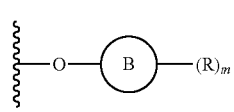

and m is 1.

In some embodiments of a compound of Formula (Ia), $R^{4b}$ is

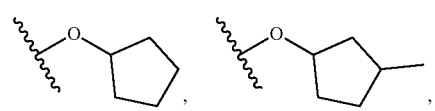
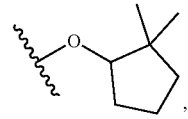
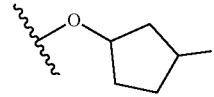

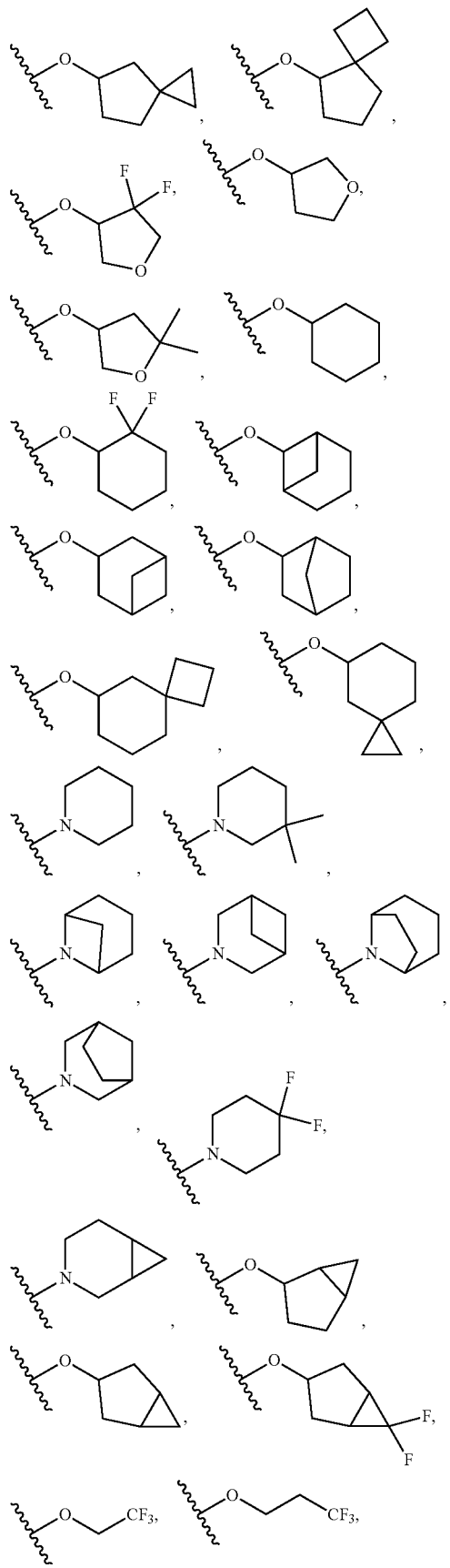
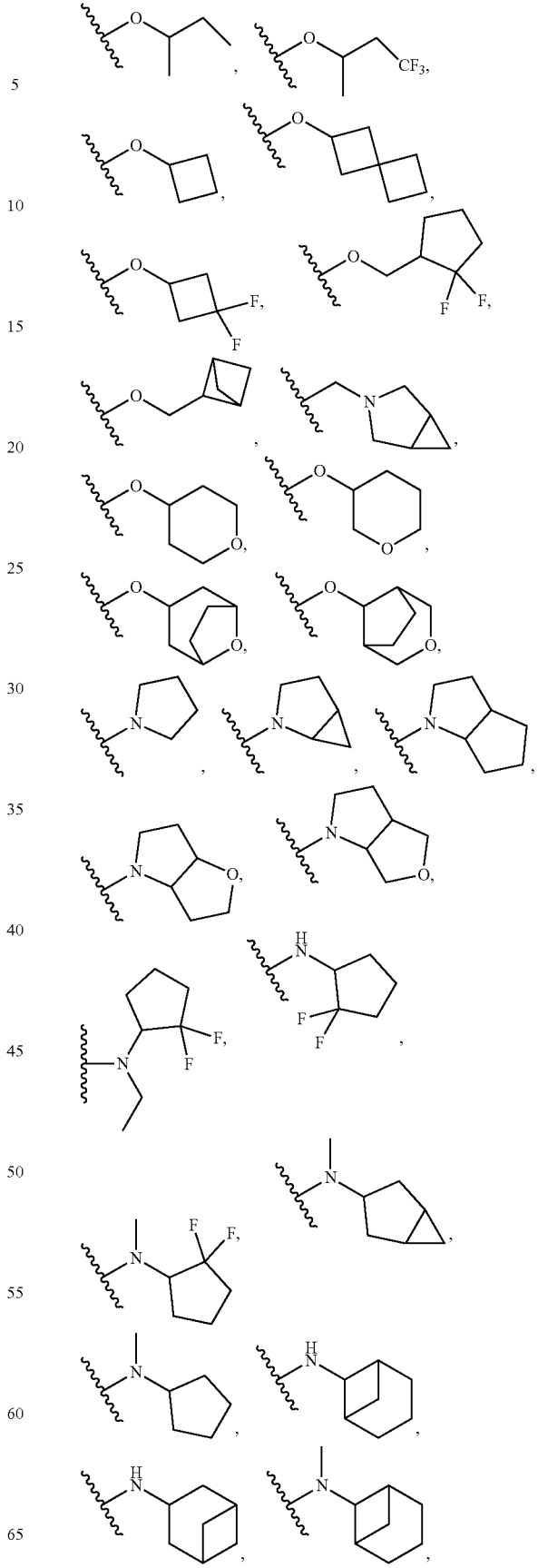

-continued
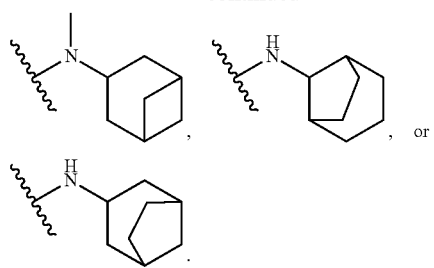
In some embodiments of a compound of Formula (Ia), $R^{4b}$ is
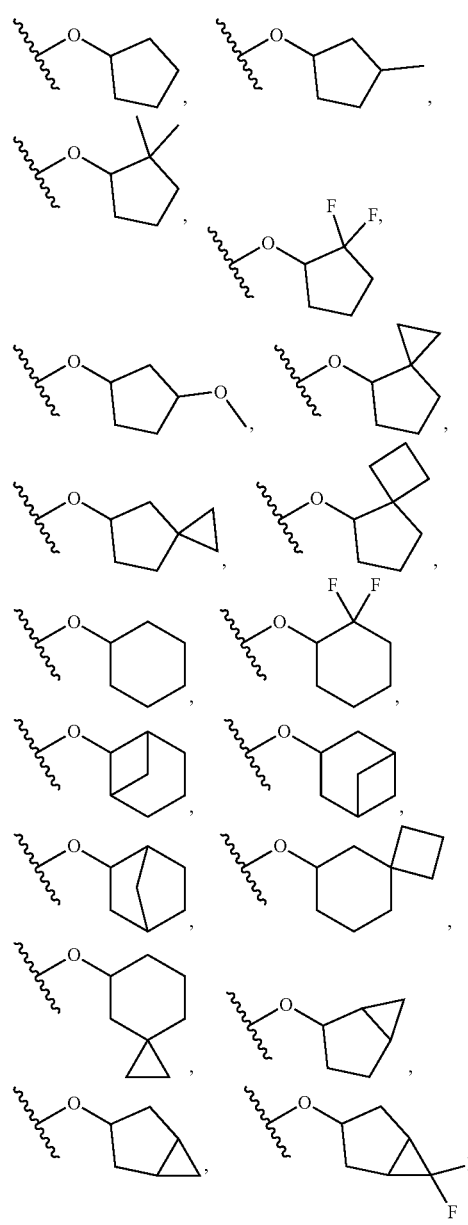
In some embodiments of a compound of Formula (Ia), $R^{4b}$ is
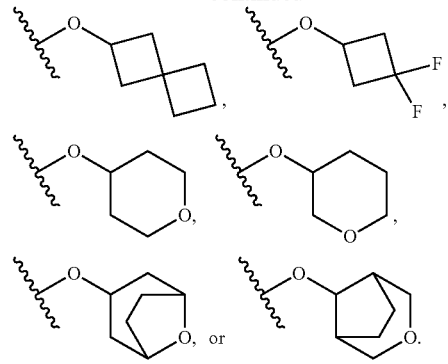

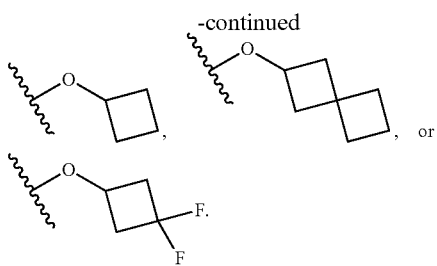

In some embodiments of a compound of Formula (Ia), $R^{4b}$ is

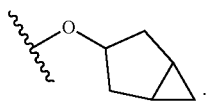 [SMILES: *OC1CC2CC2C1]

In some embodiments of a compound of Formula (Ia), $R^{4b}$ is

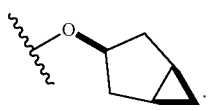

In some embodiments of a compound of Formula (Ia), $R^{4b}$ is

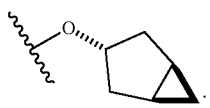

In some embodiments of a compound of Formula (Ia), $R^{4b}$ is

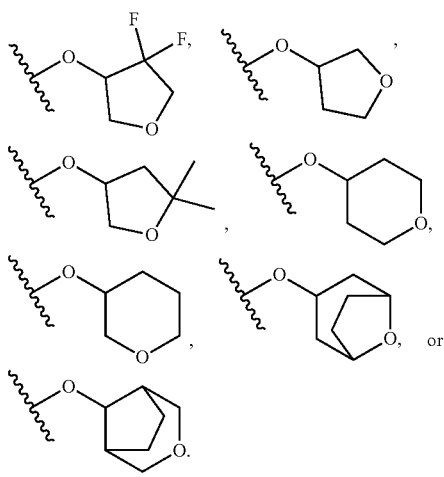

In some embodiments of a compound of Formula (Ia), $R^{4c}$ is deuterium, halogen, —CN, —OH, —$OR^a$, —$NR^cR^d$, $C_1$-$C_6$alkyl, or $C_1$-$C_6$haloalkyl. In some embodiments of a compound of Formula (Ia), $R^{4c}$ is halogen, —OH, or $C_1$-$C_6$haloalkyl. In some embodiments of a compound of Formula (Ia), $R^{4c}$ is halogen.

In some embodiments of a compound of Formula (I) or (Ia), $R^1$ is $C_1$-$C_6$alkyl.

In some embodiments of a compound of Formula (I) or (Ia), $R^2$ is $C_1$-$C_6$alkyl.

In some embodiments of a compound of Formula (I) or (Ia), $R^1$ and $R^2$ are taken together to form a heterocycloalkyl optionally substituted with one or more $R^{1a}$. In some embodiments of a compound of Formula (I) or (Ia), $R^1$ and $R^2$ are taken together to form a monocyclic heterocycloalkyl or a bicyclic heterocycloalkyl; each optionally substituted with one or more $R^{1a}$. In some embodiments of a compound of Formula (I) or (Ia), $R^1$ and $R^2$ are taken together to form a monocyclic heterocycloalkyl optionally substituted with one or more $R^{1a}$. In some embodiments of a compound of Formula (I) or (Ia), $R^1$ and $R^2$ are taken together to form a monocyclic 4- to 8-membered heterocycloalkyl optionally substituted with one or more $R^{1a}$. In some embodiments of a compound of Formula (I) or (Ia), $R^1$ and $R^2$ are taken together to form a monocyclic 4- to 7-membered heterocycloalkyl optionally substituted with one or more $R^{1a}$. In some embodiments of a compound of Formula (I) or (Ia), $R^1$ and $R^2$ are taken together to form a monocyclic 4- to 6-membered heterocycloalkyl optionally substituted with one or more $R^{1a}$. In some embodiments of a compound of Formula (I) or (Ia), $R^1$ and $R^2$ are taken together to form an azetidinyl, pyrrolidinyl, piperidinyl, morpholinyl, or piperazinyl; each optionally substituted with one or more $R^{1a}$. In some embodiments of a compound of Formula (I) or (Ia), $R^1$ and $R^2$ are taken together to form an azetidinyl optionally substituted with one or more $R^{1a}$. In some embodiments of a compound of Formula (I) or (Ia), $R^1$ and $R^2$ are taken together to form a pyrrolidinyl or piperidinyl; each optionally substituted with one or more $R^{1a}$. In some embodiments of a compound of Formula (I) or (Ia), $R^1$ and $R^2$ are taken together to form a pyrrolidinyl optionally substituted with one or more $R^{1a}$. In some embodiments of a compound of Formula (I) or (Ia), $R^1$ and $R^2$ are taken together to form a bicyclic heterocycloalkyl optionally substituted with one or more $R^{1a}$.

In some embodiments of a compound of Formula (I) or (Ia), $R^1$ and $R^2$ are taken together to form a heteroaryl optionally substituted with one or more $R^{1a}$. In some embodiments of a compound of Formula (I) or (Ia), $R^1$ and $R^2$ are taken together to form a 5- or 6-membered heteroaryl optionally substituted with one or more $R^{1a}$. In some embodiments of a compound of Formula (I) or (Ia), $R^1$ and $R^2$ are taken together to form a 5-membered heteroaryl optionally substituted with one or more $R^{1a}$.

In some embodiments of a compound of Formula (I) or (Ia), $R^1$ and $R^2$ are taken together to form

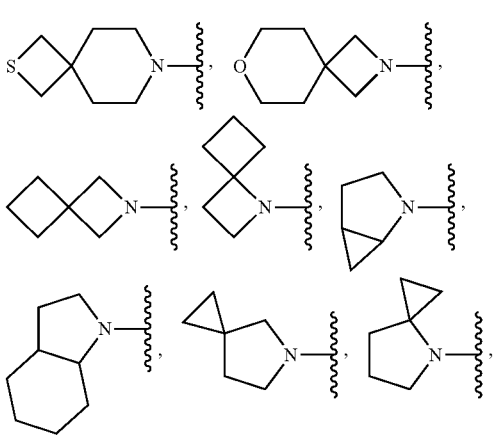

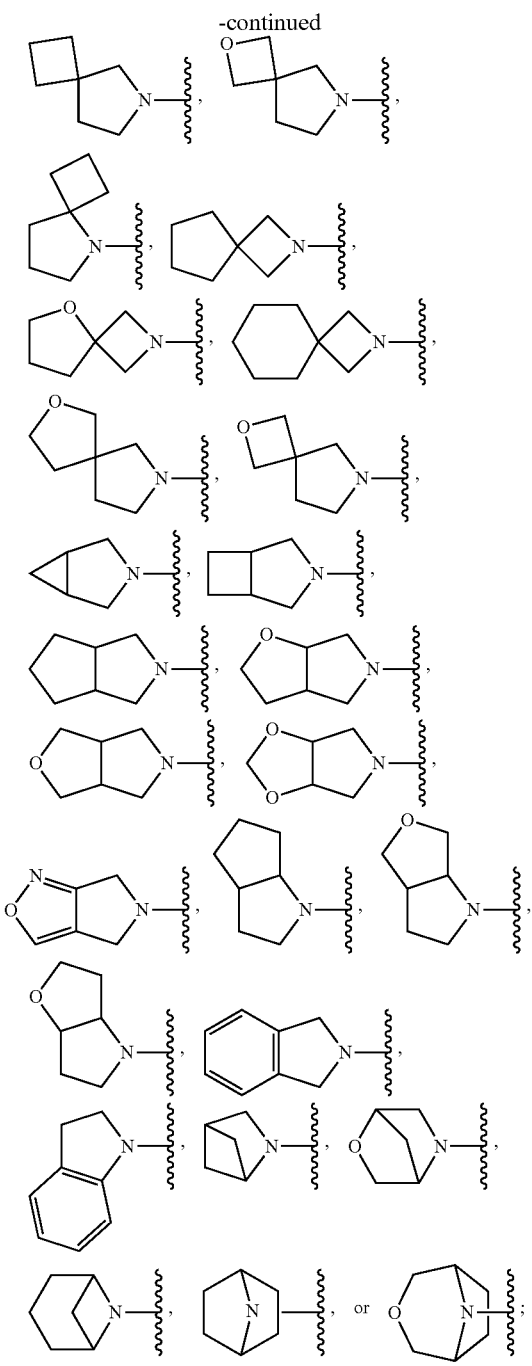

each optionally substituted with one or more $R^{1a}$.

In some embodiments of a compound of Formula (I) or (Ia), each $R^{1a}$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently and optionally substituted with one or more R. In some embodiments of a compound of Formula (I) or (Ia), $R^{1a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), or $C_1$-$C_6$alkylene(heterocycloalkyl); wherein each alkyl, alkylene, cycloalkyl, and heterocycloalkyl is independently and optionally substituted with one or more R. In some embodiments of a compound of Formula (I) or (Ia), $R^{1a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently and optionally substituted with one or more R. In some embodiments of a compound of Formula (I) or (Ia), each $R^{1a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia), each $R^{1a}$ is independently halogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia), each $R^{1a}$ is independently halogen, $C_1$-$C_6$alkyl, or $C_1$-$C_6$haloalkyl.

In some embodiments of a compound of Formula (I) or (Ia), each $R^{1a}$ is independently —OH, —OR$^a$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl.

In some embodiments of a compound of Formula (I) or (Ia), each $R^{1a}$ is independently —OH, —OR$^a$, $C_1$-$C_6$alkyl, $C_1$-$C_6$hydroxyalkyl, or $C_1$-$C_6$heteroalkyl.

In some embodiments of a compound of Formula (I) or (Ia), each $R^{1a}$ is independently —OR$^a$, $C_1$-$C_6$alkyl, $C_1$-$C_6$hydroxyalkyl, or $C_1$-$C_6$heteroalkyl.

In some embodiments of a compound of Formula (I) or (Ia), each $R^{1a}$ is independently $C_1$-$C_6$alkyl or $C_1$-$C_6$hydroxyalkyl.

In some embodiments of a compound of Formula (I) or (Ia), each $R^{1a}$ is independently —OR$^a$ or $C_1$-$C_6$alkyl. In some embodiments of a compound of Formula (I) or (Ia), each $R^{1a}$ is independently $C_1$-$C_6$alkyl. In some embodiments of a compound of Formula (I) or (Ia), each $R^{1a}$ is independently —Omethyl, or methyl.

In some embodiments of a compound of Formula (I) or (Ia), two $R^{1a}$ on the same atom are taken together to form an oxo.

In some embodiments of a compound of Formula (I) or (Ia), $R^3$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (I) or (Ia), $R^3$ is $C_1$-$C_6$alkyl, $C_1$-$C_6$haloalkyl, or $C_1$-$C_6$heteroalkyl. In some embodiments of a compound of Formula (I) or (Ia), $R^3$ is $C_1$-$C_6$haloalkyl. In some embodiments of a compound of Formula (I) or (Ia), $R^3$ is $C_1$-$C_6$heteroalkyl. In some embodiments of a compound of Formula (I) or (Ia), $R^3$ is —$CH_3$, —$CH_2CH_3$, —$CH_2CH_2CH_3$, —$CH_2CH(CH_3)_2$, —$CH_2CH_2F$, —$CH_2CF_3$, —$CH_2OCH_3$, —$CH_2OCH_2CH_3$, —$CH_2OCH(CH_3)_2$,

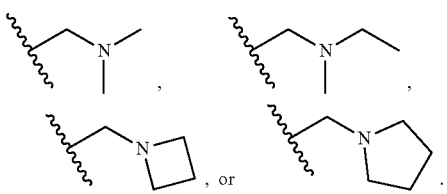

In some embodiments of a compound of Formula (I) or (Ia), $R^3$ is —CH$_3$, —CH$_2$CH$_3$, —CH$_2$CH$_2$CH$_3$, —CH$_2$CH(CH$_3$)$_2$, —CH$_2$CH$_2$F, —CH$_2$CF$_3$, —CH$_2$OCH$_3$, —CH$_2$OCH$_2$CH$_3$, or —CH$_2$OCH(CH$_3$)$_2$. In some embodiments of a compound of Formula (I) or (Ia), $R^3$ is —CH$_2$CH$_3$, —CH$_2$CH$_2$F, or —CH$_2$CF$_3$. In some embodiments of a compound of Formula (I) or (Ia), $R^3$ is —CH$_2$CH$_3$. In some embodiments of a compound of Formula (I) or (Ia), $R^3$ is —CH$_2$CH$_2$F. In some embodiments of a compound of Formula (I) or (Ia), $R^3$ is —CH$_2$CF$_3$.

In some embodiments of a compound disclosed herein, each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^a$ is independently C$_1$-C$_6$alkyl, C$_1$-C$_6$haloalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^a$ is independently C$_1$-C$_6$alkyl, C$_1$-C$_6$haloalkyl, cycloalkyl, or heterocycloalkyl; wherein each alkyl, cycloalkyl, and heterocycloalkyl is independently and optionally substituted with one or more R. In some embodiments of a compound disclosed herein, each $R^a$ is independently C$_1$-C$_6$alkyl, C$_1$-C$_6$haloalkyl, cycloalkyl, or heterocycloalkyl. In some embodiments of a compound disclosed herein, each $R^a$ is independently C$_1$-C$_6$alkyl or C$_1$-C$_6$haloalkyl; wherein each alkyl is independently and optionally substituted with one or more R. In some embodiments of a compound disclosed herein, each $R^a$ is independently cycloalkyl or heterocycloalkyl; wherein each cycloalkyl and heterocycloalkyl is independently and optionally substituted with one or more R. In some embodiments of a compound disclosed herein, each $R^a$ is independently C$_1$-C$_6$alkyl or C$_1$-C$_6$haloalkyl. In some embodiments of a compound disclosed herein, each $R^a$ is independently C$_1$-C$_6$alkyl.

In some embodiments of a compound disclosed herein, each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^b$ is independently hydrogen, C$_1$-C$_6$alkyl, C$_1$-C$_6$haloalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^b$ is independently hydrogen, C$_1$-C$_6$alkyl, C$_1$-C$_6$haloalkyl, cycloalkyl, or heterocycloalkyl; wherein each alkyl, cycloalkyl, and heterocycloalkyl is independently and optionally substituted with one or more R. In some embodiments of a compound disclosed herein, each $R^b$ is independently hydrogen, C$_1$-C$_6$alkyl, C$_1$-C$_6$haloalkyl, cycloalkyl, or heterocycloalkyl.

In some embodiments of a compound disclosed herein, each $R^b$ is independently hydrogen, C$_1$-C$_6$alkyl, or C$_1$-C$_6$haloalkyl; wherein each alkyl is independently and optionally substituted with one or more R. In some embodiments of a compound disclosed herein, each $R^b$ is independently hydrogen, cycloalkyl, or heterocycloalkyl; wherein each cycloalkyl and heterocycloalkyl is independently and optionally substituted with one or more R. In some embodiments of a compound disclosed herein, each $R^b$ is independently hydrogen, C$_1$-C$_6$alkyl, or C$_1$-C$_6$haloalkyl. In some embodiments of a compound disclosed herein, each $R^b$ is independently hydrogen or C$_1$-C$_6$alkyl. In some embodiments of a compound disclosed herein, each $R^b$ is hydrogen. In some embodiments of a compound disclosed herein, each $R^b$ is independently C$_1$-C$_6$alkyl.

In some embodiments of a compound disclosed herein, each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^c$ and $R^d$ are independently hydrogen, C$_1$-C$_6$alkyl, C$_1$-C$_6$haloalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R. In some embodiments of a compound disclosed herein, each $R^c$ and $R^d$ are independently hydrogen, C$_1$-C$_6$alkyl, C$_1$-C$_6$haloalkyl, cycloalkyl, or heterocycloalkyl; wherein each alkyl, cycloalkyl, and heterocycloalkyl is independently and optionally substituted with one or more R. In some embodiments of a compound disclosed herein, each $R^c$ and $R^d$ are independently hydrogen, C$_1$-C$_6$alkyl, C$_1$-C$_6$haloalkyl, cycloalkyl, or heterocycloalkyl. In some embodiments of a compound disclosed herein, each $R^c$ and $R^d$ are independently hydrogen, C$_1$-C$_6$alkyl, or C$_1$-C$_6$haloalkyl; wherein each alkyl is independently and optionally substituted with one or more R. In some embodiments of a compound disclosed herein, each $R^c$ and $R^d$ are independently hydrogen, cycloalkyl, or heterocycloalkyl; wherein each cycloalkyl and heterocycloalkyl is independently and optionally substituted with one or more R. In some embodiments of a compound disclosed herein, each $R^c$ and $R^d$ are independently hydrogen, C$_1$-C$_6$alkyl, or C$_1$-C$_6$haloalkyl. In some embodiments of a compound disclosed herein, each $R^c$ and $R^d$ are independently hydrogen or C$_1$-C$_6$alkyl. In some embodiments of a compound disclosed herein, each $R^c$ and $R^d$ are hydrogen. In some embodiments of a compound disclosed herein, each $R^c$ and $R^d$ are independently C$_1$-C$_6$alkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently deuterium, halogen, —CN, —OH, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —NH$_2$, —NHC$_1$-C$_3$alkyl, —N(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, C$_1$-C$_3$alkyl, C$_1$-C$_3$alkoxy, C$_1$-C$_3$haloalkyl, C$_1$-C$_3$deuteroalkyl, C$_1$-C$_3$haloalkoxy, C$_1$-C$_3$hydroxyalkyl, C$_1$-C$_3$aminoalkyl, C$_1$-C$_3$heteroalkyl, C$_3$-C$_6$cycloalkyl.

In some embodiments of a compound disclosed herein, each R is independently deuterium, halogen, —CN, —OH, —NH$_2$, —NHC$_1$-C$_3$alkyl, —N(C$_1$-C$_3$alkyl)$_2$, —C(=O)C$_1$-C$_3$alkyl, —C(=O)OH, —C(=O)OC$_1$-C$_3$alkyl, —C(=O)

NH$_2$, —C(=O)NHC$_1$-C$_3$alkyl, —C(=O)N(C$_1$-C$_3$alkyl)$_2$, C$_1$-C$_3$alkyl, C$_1$-C$_3$alkoxy, C$_1$-C$_3$haloalkyl, C$_1$-C$_3$deuteroalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl; or two R on the same atom form an oxo. In some embodiments of a compound disclosed herein, each R is independently deuterium, halogen, —CN, —OH, —NH$_2$, —NHC$_1$-C$_3$alkyl, —N(C$_1$-C$_3$alkyl)$_2$, C$_1$-C$_3$alkyl, C$_1$-C$_3$alkoxy, C$_1$-C$_3$haloalkyl, C$_1$-C$_3$deuteroalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl; or two R on the same atom form an oxo. In some embodiments of a compound disclosed herein, each R is independently deuterium, halogen, —CN, —OH, —NH$_2$, C$_1$-C$_3$alkyl, C$_1$-C$_3$alkoxy, C$_1$-C$_3$haloalkyl, C$_1$-C$_3$deuteroalkyl, or C$_1$-C$_3$haloalkoxy; or two R on the same atom form an oxo. In some embodiments of a compound disclosed herein, each R is independently deuterium, halogen, —CN, —OH, —NH$_2$, C$_1$-C$_3$alkyl, or C$_1$-C$_3$alkoxy; or two R on the same atom form an oxo. In some embodiments of a compound disclosed herein, each R is independently halogen, C$_1$-C$_3$alkyl, or C$_1$-C$_3$alkoxy; or two R on the same atom form an oxo.

Any combination of the groups described above for the various variables is contemplated herein. Throughout the specification, groups and substituents thereof are chosen by one skilled in the field to provide stable moieties and compounds.

In some embodiments, the compound is selected from a compound found in table 1:

| Ex. | Structures | Name |
|---|---|---|
| 1 | 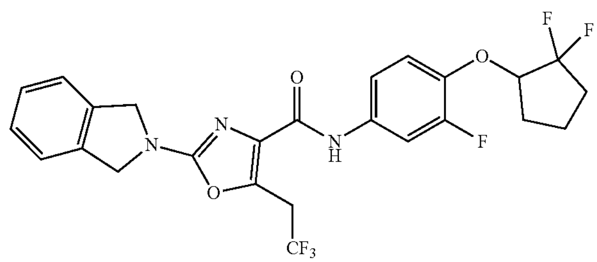 [SMILES: O=C(Nc1ccc(OC2CCCC2(F)F)c(F)c1)c1nc(N2Cc3ccccc3C2)oc1CC(F)(F)F] | N-(4-((2,2-difluorocyclopentyl)oxy)-3-fluorophenyl)-2-(isoindolin-2-yl)-5-(2,2,2-trifluoroethyl)oxazole-4-carboxamide |
| 2 | 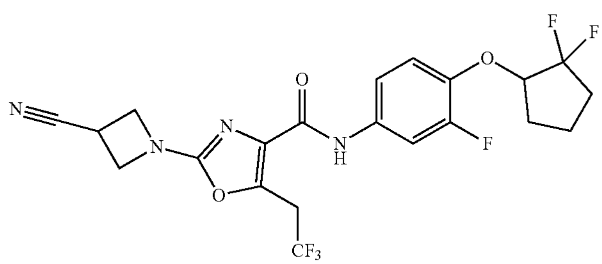 [SMILES: N#CC1CN(c2nc(C(=O)Nc3ccc(OC4CCCC4(F)F)c(F)c3)c(CC(F)(F)F)o2)C1] | 2-(3-cyanoazetidin-1-yl)-N-(4-((2,2-difluorocyclopentyl)oxy)-3-fluorophenyl)-5-(2,2,2-trifluoroethyl)oxazole-4-carboxamide |
| 3 | 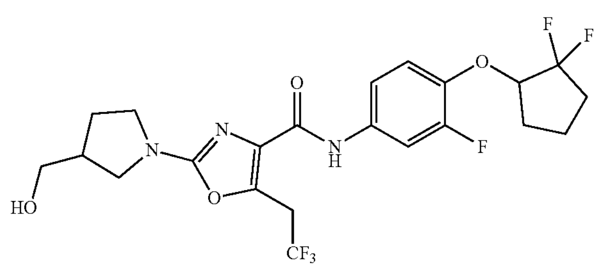 [SMILES: O=C(Nc1ccc(OC2CCCC2(F)F)c(F)c1)c1nc(N2CCC(CO)C2)oc1CC(F)(F)F] | N-(4-((2,2-difluorocyclopentyl)oxy)-3-fluorophenyl)-2-(3-(hydroxymethyl)pyrrolidin-1-yl)-5-(2,2,2-trifluoroethyl)oxazole-4-carboxamide |
| 4 | 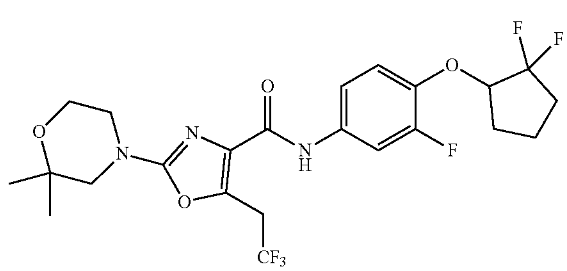 [SMILES: CC1(C)CN(c2nc(C(=O)Nc3ccc(OC4CCCC4(F)F)c(F)c3)c(CC(F)(F)F)o2)CCO1] | N-{4-[(2,2-difluorocyclopentyl)oxy]-3-fluorophenyl}-2-(2,2-dimethylmorpholin-4-yl)-5-(2,2,2-trifluoroethyl)-1,3-oxazole-4-carboxamide |

| Ex. | Structures | Name |
|---|---|---|
| 5 | 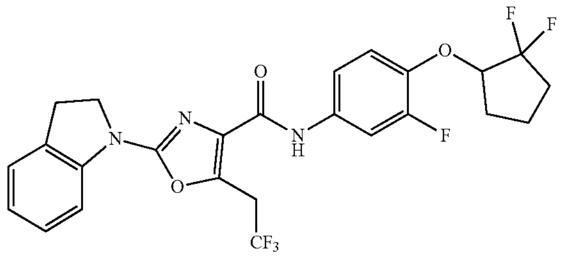 [SMILES: O=C(Nc1ccc(OC2CCCC2(F)F)c(F)c1)c1nc(N2CCc3ccccc32)oc1CC(F)(F)F] | N-(4-((2,2-difluorocyclopentyl)oxy)-3-fluorophenyl)-2-(indolin-1-yl)-5-(2,2,2-trifluoroethyl)oxazole-4-carboxamide |
| 6 | 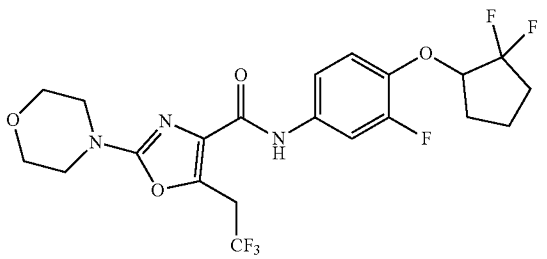 [SMILES: O=C(Nc1ccc(OC2CCCC2(F)F)c(F)c1)c1nc(N2CCOCC2)oc1CC(F)(F)F] | N-(4-((2,2-difluorocyclopentyl)oxy)-3-fluorophenyl)-2-morpholino-5-(2,2,2-trifluoroethyl)oxazole-4-carboxamide |
| 7 | 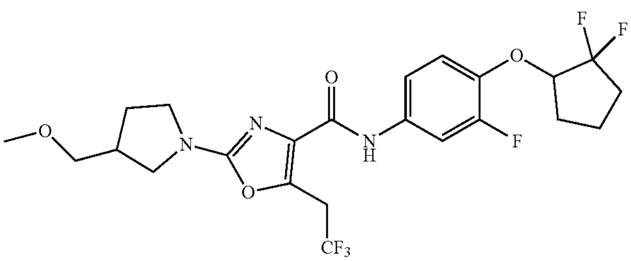 [SMILES: COCC1CCN(c2nc(C(=O)Nc3ccc(OC4CCCC4(F)F)c(F)c3)c(CC(F)(F)F)o2)C1] | N-(4-((2,2-difluorocyclopentyl)oxy)-3-fluorophenyl)-2-(3-(methoxymethyl)pyrrolidin-1-yl)-5-(2,2,2-trifluoroethyl)oxazole-4-carboxamide |
| 8 | 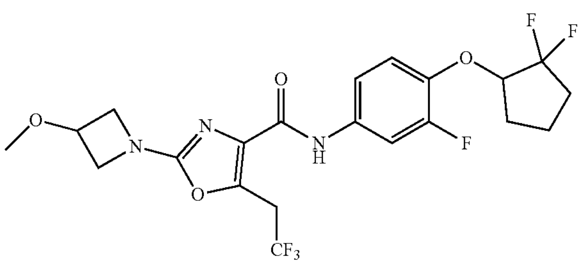 [SMILES: COC1CN(c2nc(C(=O)Nc3ccc(OC4CCCC4(F)F)c(F)c3)c(CC(F)(F)F)o2)C1] | -(4-((2,2-difluorocyclopentyl)oxy)-3-fluorophenyl)-2-(3-methoxyazetidin-1-yl)-5-(2,2,2-trifluoroethyl)oxazole-4-carboxamide |
| 9 | 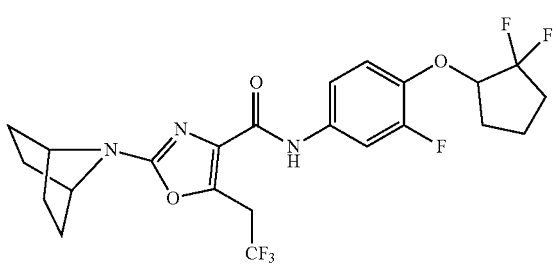 [SMILES: O=C(Nc1ccc(OC2CCCC2(F)F)c(F)c1)c1nc(N2C3CCC2CC3)oc1CC(F)(F)F] | 2-{7-azabicyclo[2.2.1]heptan-7-yl}-N-{4-[(2,2-difluorocyclopentyl)oxy]-3-fluorophenyl}-5-(2,2,2-trifluoroethyl)oxazole-4-carboxamide |
| 10 | 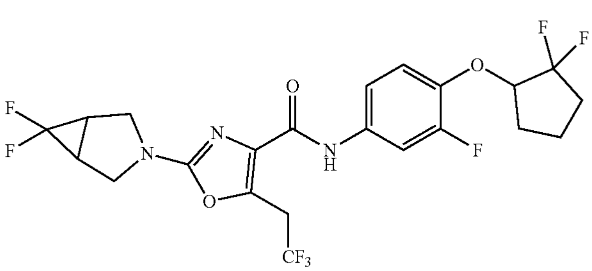 [SMILES: O=C(Nc1ccc(OC2CCCC2(F)F)c(F)c1)c1nc(N2CC3C(C2)C3(F)F)oc1CC(F)(F)F] | 2-{6,6-difluoro-3-azabicyclo[3.1.0]hexan-3-yl}-N-{4-[(2,2-difluorocyclopentyl)oxy]-3-fluorophenyl}-5-(2,2,2-trifluoroethyl)oxazole-4-carboxamide |

| Ex. | Structures | Name |
|---|---|---|
| 11 | 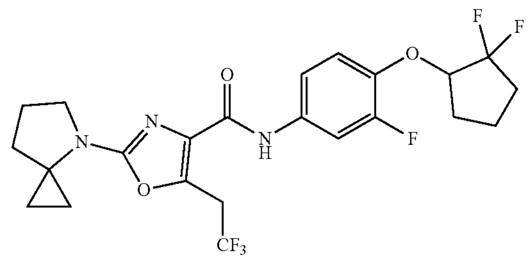 [SMILES: O=C(Nc1ccc(OC2CCCC2(F)F)c(F)c1)c1nc(N2CCCC23CC3)oc1CC(F)(F)F] | N-(4-((2,2-difluorocyclopentyl)oxy)-3-fluorophenyl)-2-(4-azaspiro[2.4]heptan-4-yl)-5-(2,2,2-trifluoroethyl)oxazole-4-carboxamide |
| 12 | 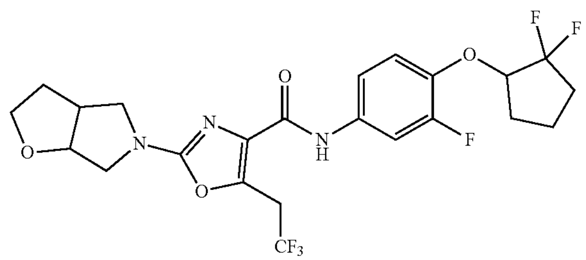 [SMILES: O=C(Nc1ccc(OC2CCCC2(F)F)c(F)c1)c1nc(N2CC3CCOC3C2)oc1CC(F)(F)F] | N-(4-((2,2-difluorocyclopentyl)oxy)-3-fluorophenyl)-2-(hexahydro-5H-furo[2,3-c]pyrrol-5-yl)-5-(2,2,2-trifluoroethyl)oxazole-4-carboxamide |
| 13 | 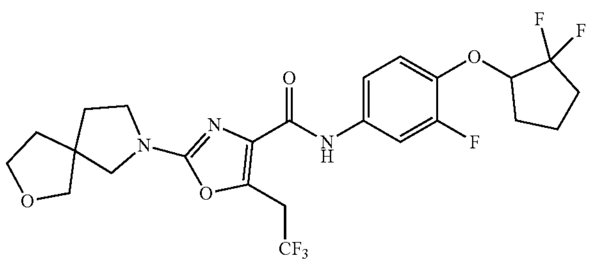 [SMILES: O=C(Nc1ccc(OC2CCCC2(F)F)c(F)c1)c1nc(N2CCC3(CCOC3)C2)oc1CC(F)(F)F] | N-(4-((2,2-difluorocyclopentyl)oxy)-3-fluorophenyl)-2-(2-oxa-7-azaspiro[4.4]nonan-7-yl)-5-(2,2,2-trifluoroethyl)oxazole-4-carboxamide |
| 14 | 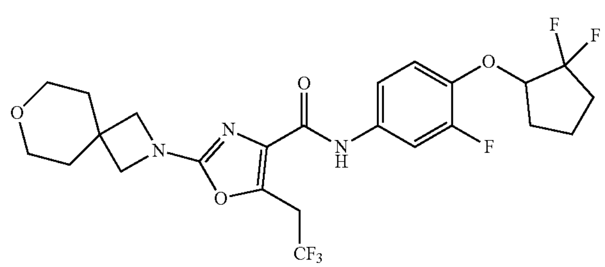 [SMILES: O=C(Nc1ccc(OC2CCCC2(F)F)c(F)c1)c1nc(N2CC3(CCOCC3)C2)oc1CC(F)(F)F] | N-(4-((2,2-difluorocyclopentyl)oxy)-3-fluorophenyl)-2-(7-oxa-2-azaspiro[3.5]nonan-2-yl)-5-(2,2,2-trifluoroethyl)oxazole-4-carboxamide |
| 15 | 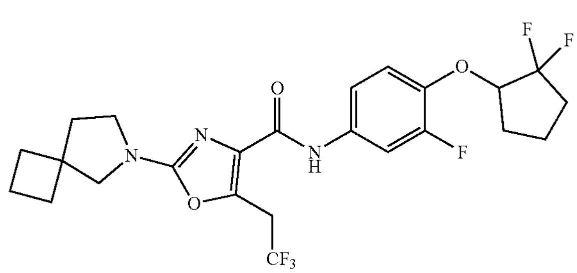 [SMILES: O=C(Nc1ccc(OC2CCCC2(F)F)c(F)c1)c1nc(N2CCC3(CCC3)C2)oc1CC(F)(F)F] | N-(4-((2,2-difluorocyclopentyl)oxy)-3-fluorophenyl)-2-(6-azaspiro[3.4]octan-6-yl)-5-(2,2,2-trifluoroethyl)oxazole-4-carboxamide |
| 16 | 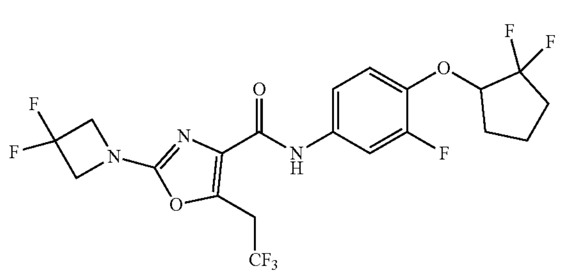 [SMILES: O=C(Nc1ccc(OC2CCCC2(F)F)c(F)c1)c1nc(N2CC(F)(F)C2)oc1CC(F)(F)F] | 2-(3,3-difluoroazetidin-1-yl)-N-{4-[(2,2-difluorocyclopentyl)oxy]-3-fluorophenyl}-5-(2,2,2-trifluoroethyl)oxazole-4-carboxamide |

| Ex. | Structures | Name |
|---|---|---|
| 17 | 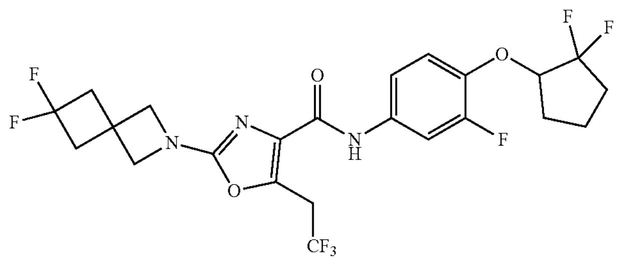 [SMILES: O=C(Nc1ccc(OC2CCCC2(F)F)c(F)c1)c1nc(N2CC3(C2)CC(F)(F)C3)oc1CC(F)(F)F] | 2-(6,6-difluoro-2-azaspiro[3.3]heptan-2-yl)-N-(4-((2,2-difluorocyclopentyl)oxy)-3-fluorophenyl)-5-(2,2,2-trifluoroethyl)oxazole-4-carboxamide |
| 18 | 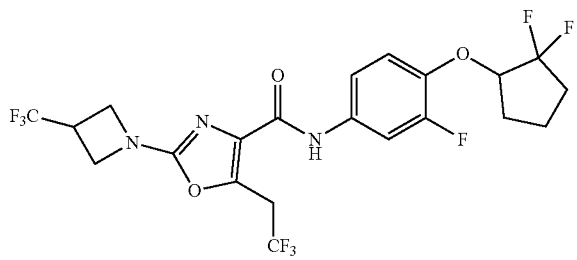 [SMILES: O=C(Nc1ccc(OC2CCCC2(F)F)c(F)c1)c1nc(N2CC(C(F)(F)F)C2)oc1CC(F)(F)F] | N-(4-((2,2-difluorocyclopentyl)oxy)-3-fluorophenyl)-5-(2,2,2-trifluoroethyl)-2-(3-(trifluoromethyl)azetidin-1-yl)oxazole-4-carboxamide |
| 19 | 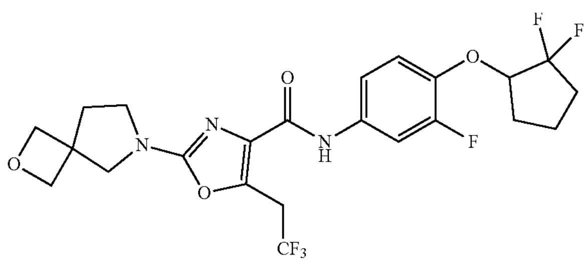 [SMILES: O=C(Nc1ccc(OC2CCCC2(F)F)c(F)c1)c1nc(N2CCC3(COC3)C2)oc1CC(F)(F)F] | N-{4-[(2,2-difluorocyclopentyl)oxy]-3-fluorophenyl}-2-{2-oxa-6-azaspiro[3.4]octan-6-yl}-5-(2,2,2-trifluoroethyl)oxazole-4-carboxamide |
| 20 | 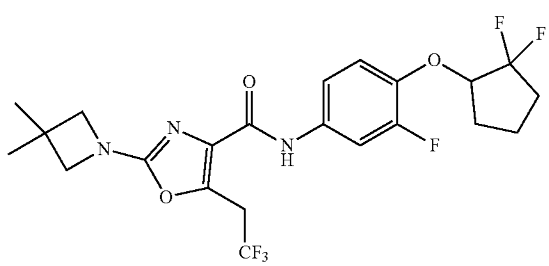 [SMILES: CC1(C)CN(c2nc(C(=O)Nc3ccc(OC4CCCC4(F)F)c(F)c3)c(CC(F)(F)F)o2)C1] | N-(4-((2,2-difluorocyclopentyl)oxy)-3-fluorophenyl)-2-(3,3-dimethylazetidin-1-yl)-5-(2,2,2-trifluoroethyl)oxazole-4-carboxamide |
| 21 | 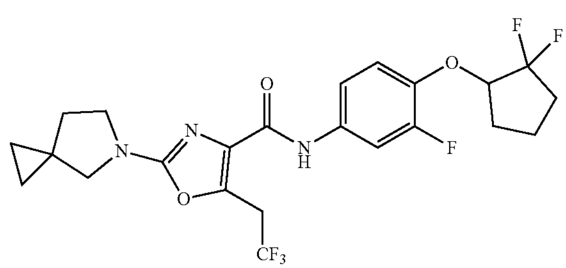 [SMILES: O=C(Nc1ccc(OC2CCCC2(F)F)c(F)c1)c1nc(N2CCC3(CC3)C2)oc1CC(F)(F)F] | N-(4-((2,2-difluorocyclopentyl)oxy)-3-fluorophenyl)-2-(5-azaspiro[2.4]heptan-5-yl)-5-(2,2,2-trifluoroethyl)oxazole-4-carboxamide |
| 22 | 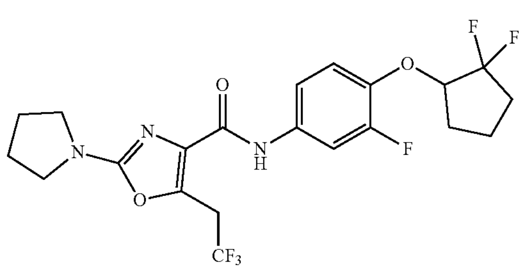 [SMILES: O=C(Nc1ccc(OC2CCCC2(F)F)c(F)c1)c1nc(N2CCCC2)oc1CC(F)(F)F] | N-{4-[(2,2-difluorocyclopentyl)oxy]-3-fluorophenyl}-2-(pyrrolidin-1-yl)-5-(2,2,2-trifluoroethyl)oxazole-4-carboxamide |

| Ex. | Structures | Name |
| --- | --- | --- |
| 23 | 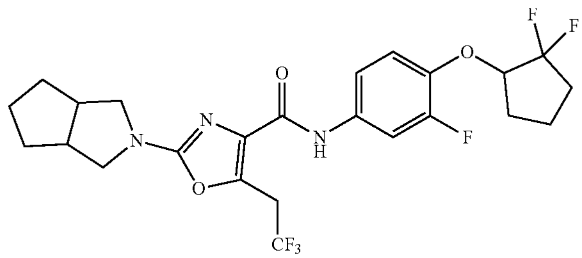 [SMILES: O=C(Nc1ccc(OC2CCCC2(F)F)c(F)c1)c1nc(N2CC3CCCC3C2)oc1CC(F)(F)F] | N-(4-((2,2-difluorocyclopentyl)oxy)-3-fluorophenyl)-2-(hexahydrocyclopenta[c]pyrrol-2(1H)-yl)-5-(2,2,2-trifluoroethyl)oxazole-4-carboxamide |
| 24 | 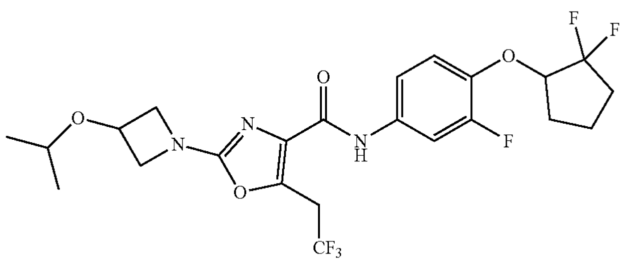 [SMILES: CC(C)OC1CN(c2nc(C(=O)Nc3ccc(OC4CCCC4(F)F)c(F)c3)c(CC(F)(F)F)o2)C1] | N-{4-[(2,2-difluorocyclopentyl)oxy]-3-fluorophenyl}-2-[3-(propan-2-yloxy)azetidin-1-yl]-5-(2,2,2-trifluoroethyl)oxazole-4-carboxamide |
| 25 | 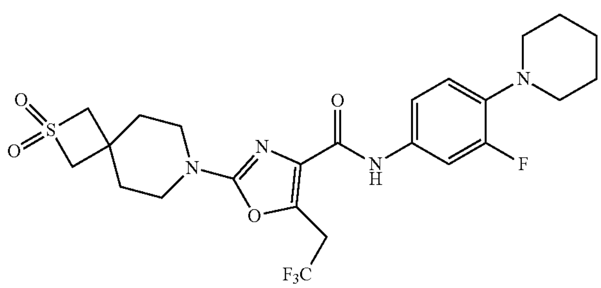 [SMILES: O=C(Nc1ccc(N2CCCCC2)c(F)c1)c1nc(N2CCC3(CC2)CS(=O)(=O)C3)oc1CC(F)(F)F] | 2-(2,2-dioxo-2-thia-7-azaspiro[3.5]nonan-7-yl)-N-[3-fluoro-4-(piperidin-1-yl)phenyl]-5-(2,2,2-trifluoroethyl) oxazole-4-carboxamide |
| 26 | 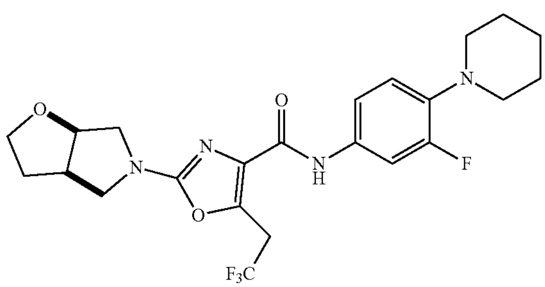 [SMILES: O=C(Nc1ccc(N2CCCCC2)c(F)c1)c1nc(N2C[C@H]3CCO[C@H]3C2)oc1CC(F)(F)F] | 2-[(3aR,6aR)-hexahydro-5H-furo[2,3-c]pyrrol-5-yl]-N-[3-fluoro-4-(piperidin-1-yl)phenyl]-5-(2,2,2-trifluoroethyl)oxazole-4-carboxamide |
| 27 | 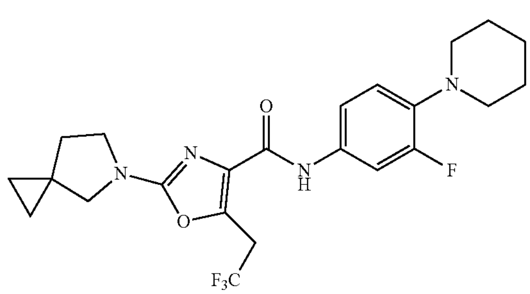 [SMILES: O=C(Nc1ccc(N2CCCCC2)c(F)c1)c1nc(N2CCC3(CC3)C2)oc1CC(F)(F)F] | 2-{5-azaspiro[2.4]heptan-5-yl}-N-[3-fluoro-4-(piperidin-1-yl)phenyl]-5-(2,2,2-trifluoroethyl)-1,3-oxazole-4-carboxamide |

| Ex. | Structures | Name |
|---|---|---|
| 28 | 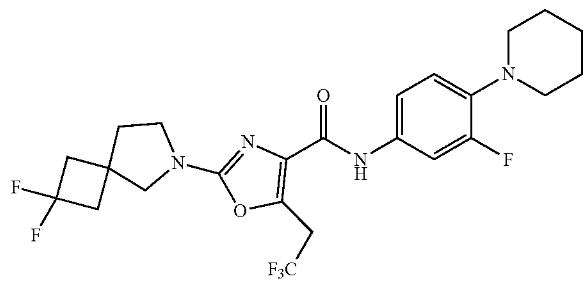 [SMILES: O=C(Nc1ccc(N2CCCCC2)c(F)c1)c1nc(N2CCC3(C2)CC(F)(F)C3)oc1CC(F)(F)F] | 2-(2,2-difluoro-6-azaspiro[3.4]octan-6-yl)-N-(3-fluoro-4-(piperidin-1-yl)phenyl)-5-(2,2,2-trifluoroethyl)oxazole-4-carboxamide |
| 29 | 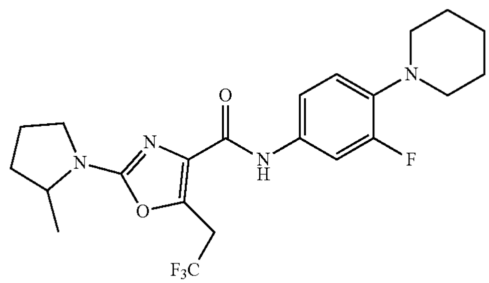 [SMILES: CC1CCCN1c1nc(C(=O)Nc2ccc(N3CCCCC3)c(F)c2)c(CC(F)(F)F)o1] | N-(3-fluoro-4-(piperidin-1-yl)phenyl)-2-(2-methylpyrrolidin-1-yl)-5-(2,2,2-trifluoroethyl)oxazole-4-carboxamide |
| 30 | 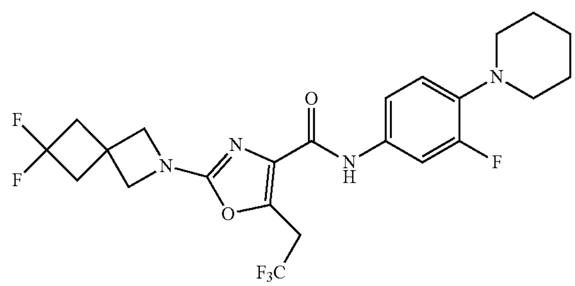 [SMILES: O=C(Nc1ccc(N2CCCCC2)c(F)c1)c1nc(N2CC3(C2)CC(F)(F)C3)oc1CC(F)(F)F] | 2-{6,6-difluoro-2-azaspiro[3.3]heptan-2-yl}-N-[3-fluoro-4-(piperidin-1-yl)phenyl]-5-(2,2,2-trifluoroethyl)oxazole-4-carboxamide |
| 31 | 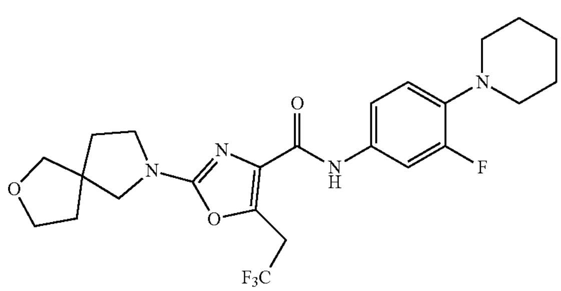 [SMILES: O=C(Nc1ccc(N2CCCCC2)c(F)c1)c1nc(N2CCC3(CCOC3)C2)oc1CC(F)(F)F] | N-(3-fluoro-4-(piperidin-1-yl)phenyl)-2-(2-oxa-7-azaspiro[4.4]nonan-7-yl)-5-(2,2,2-trifluoroethyl)oxazole-4-carboxamide |
| 32 | 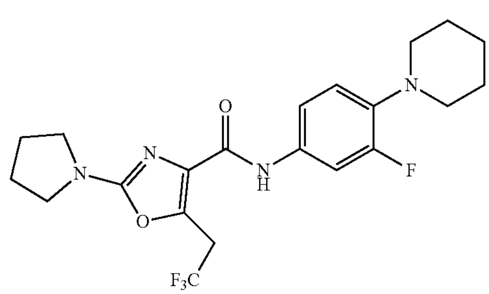 [SMILES: O=C(Nc1ccc(N2CCCCC2)c(F)c1)c1nc(N2CCCC2)oc1CC(F)(F)F] | N-(3-fluoro-4-(piperidin-1-yl)phenyl)-2-(pyrrolidin-1-yl)-5-(2,2,2-trifluoroethyl)oxazole-4-carboxamide |

-continued

| Ex. | Structures | Name |
|---|---|---|
| 33 | 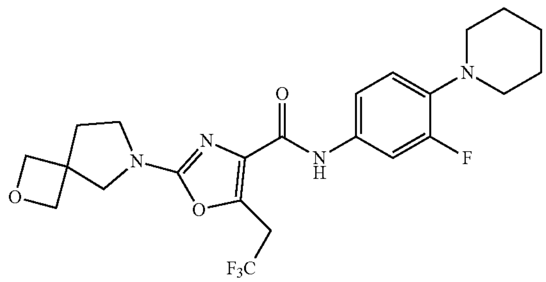 [SMILES: O=C(Nc1ccc(N2CCCCC2)c(F)c1)c1nc(N2CCC3(COC3)C2)oc1CC(F)(F)F] | N-(3-fluoro-4-(piperidin-1-yl)phenyl)-2-(2-oxa-6-azaspiro[3.4]octan-6-yl)-5-(2,2,2-trifluoroethyl)oxazole-4-carboxamide |
| 34 | 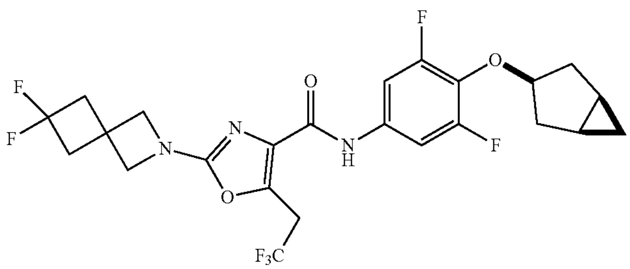 | N-(4-(cis-bicyclo[3.1.0]hexan-3-yloxy)-3,5-difluorophenyl)-2-(6,6-difluoro-2-azaspiro[3.3]heptan-2-yl)-5-(2,2,2-trifluoroethyl)oxazole-4-carboxamide |
| 35 | 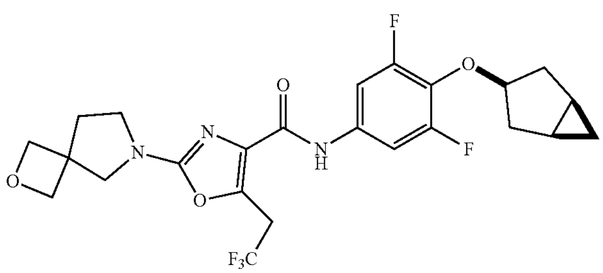 | N-(4-{cis-bicyclo[3.1.0]hexan-3-yloxy}-3,5-difluorophenyl)-2-{2-oxa-6-azaspiro[3.4]octan-6-yl}-5-(2,2,2-trifluoroethyl)oxazole-4-carboxamide |
| 36 | 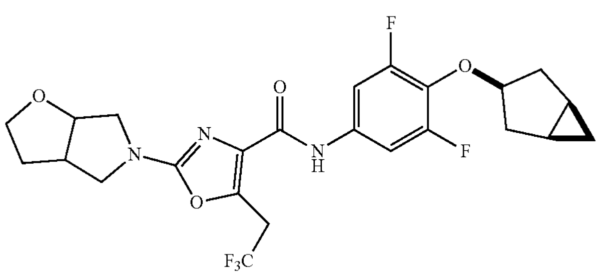 | N-(4-{cis-bicyclo[3.1.0]hexan-3-yloxy}-3,5-difluorophenyl)-2-{hexahydro-5H-furo[2,3-c]pyrrol-5-yl}-5-(2,2,2-trifluoroethyl)oxazole-4-carboxamide |
| 37 | 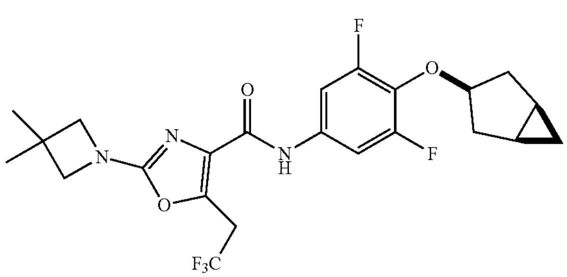 | N-(4-{cis-bicyclo[3.1.0]hexan-3-yloxy}-3,5-difluorophenyl)-2-(3,3-dimethylazetidin-1-yl)-5-(2,2,2-trifluoroethyl)oxazole-4-carboxamide |

| Ex. | Structures | Name |
|---|---|---|
| 38 | 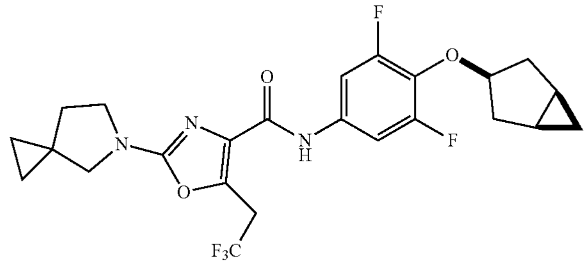 | N-(4-{cis-bicyclo[3.1.0]hexan-3-yloxy}-3,5-difluorophenyl)-2-{hexahydro-2H-furo[2,3-c]pyrrol-5-yl}-5-(2,2,2-trifluoroethyl)-1,3-oxazole-4-carboxamide |
| 39 | 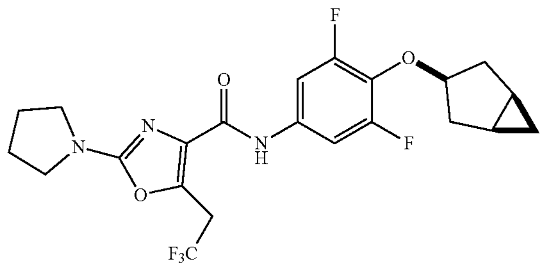 | N-(4-{cis-bicyclo[3.1.0]hexan-3-yloxy}-3,5-difluorophenyl)-2-(pyrrolidin-1-yl)-5-(2,2,2-trifluoroethyl)oxazole-4-carboxamide |
| 40 | 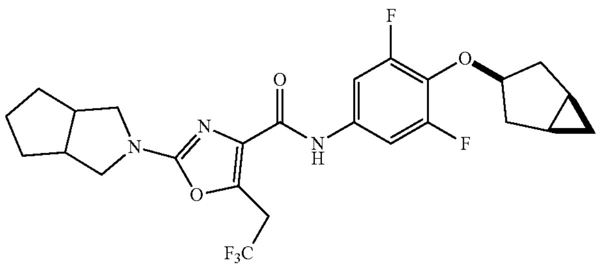 | N-(4-{cis-bicyclo[3.1.0]hexan-3-yloxy}-3,5-difluorophenyl)-2-{octahydrocyclopenta[c]pyrrol-2-yl}-5-(2,2,2-trifluoroethyl)oxazole-4-carboxamide |
| 41 | 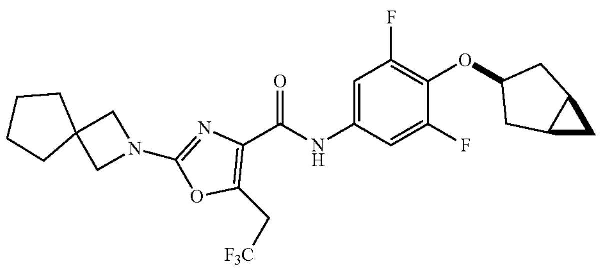 | N-(4-(cis-bicyclo[3.1.0]hexan-3-yloxy)-3,5-difluorophenyl)-2-(2-azaspiro[3.4]octan-2-yl)-5-(2,2,2-trifluoroethyl)oxazole-4-carboxamide |
| 42 | 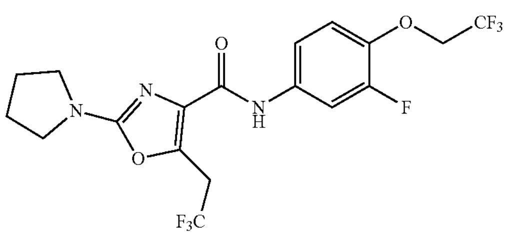 [SMILES: O=C(Nc1ccc(OCC(F)(F)F)c(F)c1)c1nc(N2CCCC2)oc1CC(F)(F)F] | N-(3-fluoro-4-(2,2,2-trifluoroethoxy)phenyl)-2-(pyrrolidin-1-yl)-5-(2,2,2-trifluoroethyl)oxazole-4-carboxamide |
| 43 | 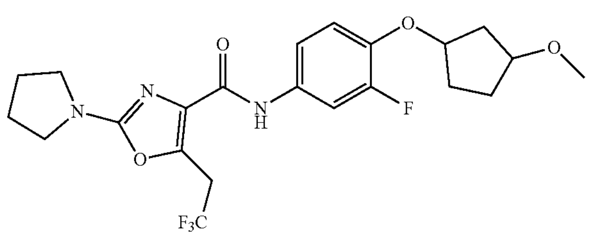 [SMILES: COC1CCC(Oc2ccc(NC(=O)c3nc(N4CCCC4)oc3CC(F)(F)F)cc2F)C1] | N-{3-fluoro-4-[(3-methoxycyclopentyl)oxy]phenyl}-2-(pyrrolidin-1-yl)-5-(2,2,2-trifluoroethyl)oxazole-4-carboxamide |

| Ex. | Structures | Name |
|---|---|---|
| 44 | 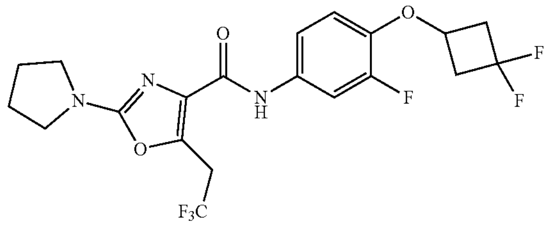 [SMILES: O=C(Nc1ccc(OC2CC(F)(F)C2)c(F)c1)c1nc(N2CCCC2)oc1CC(F)(F)F] | N-[4-(3,3-difluorocyclobutoxy)-3-fluorophenyl]-2-(pyrrolidin-1-yl)-5-(2,2,2-trifluoroethyl)oxazole-4-carboxamide |
| 45 | 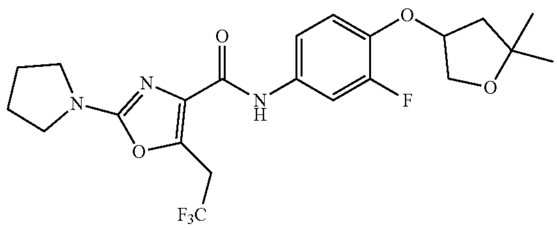 [SMILES: CC1(C)CC(Oc2ccc(NC(=O)c3nc(N4CCCC4)oc3CC(F)(F)F)cc2F)CO1] | N-{4-[(5,5-dimethyloxolan-3-yl)oxy]-3-fluorophenyl}-2-(pyrrolidin-1-yl)-5-(2,2,2-trifluoroethyl)oxazole-4-carboxamide |
| 46 | 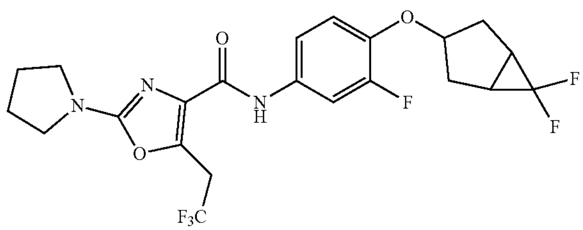 [SMILES: O=C(Nc1ccc(OC2CC3C(C2)C3(F)F)c(F)c1)c1nc(N2CCCC2)oc1CC(F)(F)F] | N-[4-({6,6-difluorobicyclo[3.1.0]hexan-3-yl}oxy)-3-fluorophenyl]-2-(pyrrolidin-1-yl)-5-(2,2,2-trifluoroethyl)oxazole-4-carboxamide |
| 47 | 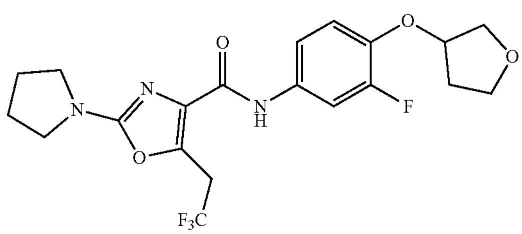 [SMILES: O=C(Nc1ccc(OC2CCOC2)c(F)c1)c1nc(N2CCCC2)oc1CC(F)(F)F] | N-[3-fluoro-4-(oxolan-3-yloxy)phenyl]-2-(pyrrolidin-1-yl)-5-(2,2,2-trifluoroethyl)oxazol-4-carboxamide |
| 48 | 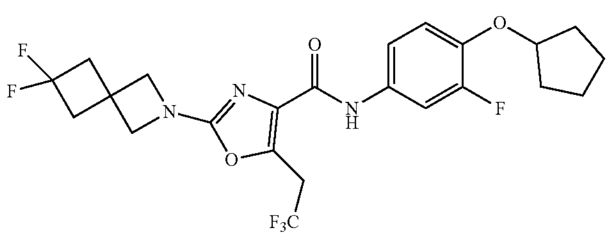 [SMILES: O=C(Nc1ccc(OC2CCCC2)c(F)c1)c1nc(N2CC3(C2)CC(F)(F)C3)oc1CC(F)(F)F] | N-[4-(cyclopentyloxy)-3-fluorophenyl]-2-{6,6-difluoro-2-azaspiro[3.3]heptan-2-yl}-5-(2,2,2-trifluoroethyl)oxazole-4-carboxamide |
| 49 | 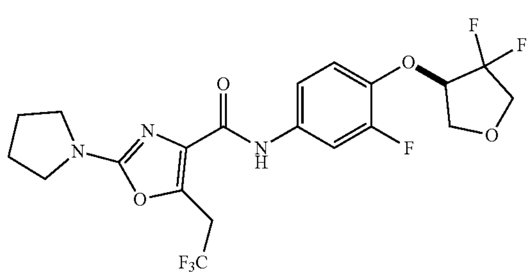 | (R)-N-(4-((4,4-difluorotetrahydrofuran-3-yl)oxy)-3-fluorophenyl)-2-(pyrrolidin-1-yl)-5-(2,2,2-trifluoroethyl)oxazole-4-carboxamide |

| Ex. | Structures | Name |
|---|---|---|
| 50 | 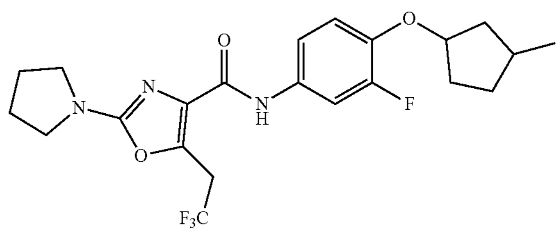 [SMILES: CC1CCC(Oc2ccc(NC(=O)c3nc(N4CCCC4)oc3CC(F)(F)F)cc2F)C1] | N-(3-fluoro-4-((3-methylcyclopentyl)oxy)phenyl)-2-(pyrrolidin-1-yl)-5-(2,2,2-trifluoroethyl)oxazole-4-carboxamide |
| 51 | 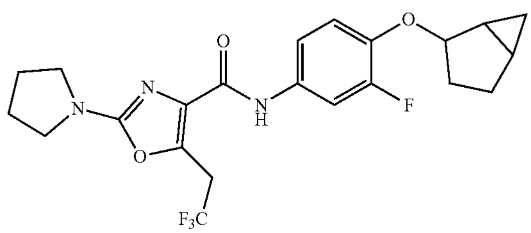 [SMILES: O=C(Nc1ccc(OC2CCC3CC32)c(F)c1)c1nc(N2CCCC2)oc1CC(F)(F)F] | N-(4-{bicyclo[3.1.0]hexan-2-yloxy}-3-fluorophenyl)-2-(pyrrolidin-1-yl)-5-(2,2,2-trifluoroethyl)oxazole-4-carboxamide |
| 52 | 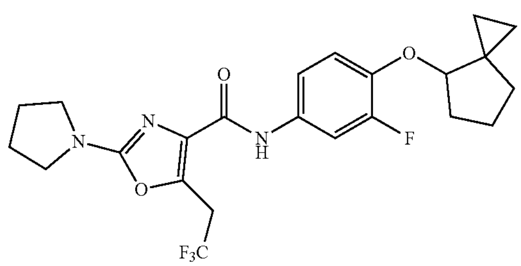 [SMILES: O=C(Nc1ccc(OC2CCCC23CC3)c(F)c1)c1nc(N2CCCC2)oc1CC(F)(F)F] | N-(3-fluoro-4-(spiro[2.4]heptan-4-yloxy)phenyl)-2-(pyrrolidin-1-yl)-5-(2,2,2-trifluoroethyl)oxazole-4-carboxamide |
| 53 | 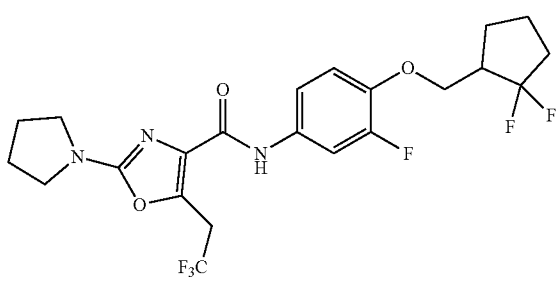 [SMILES: O=C(Nc1ccc(OCC2CCCC2(F)F)c(F)c1)c1nc(N2CCCC2)oc1CC(F)(F)F] | N-{4-[(2,2-difluorocyclopentyl)methoxy]-3-fluorophenyl}-2-(pyrrolidin-1-yl)-5-(2,2,2-trifluoroethyl)oxazole-4-carboxamide |
| 54 | 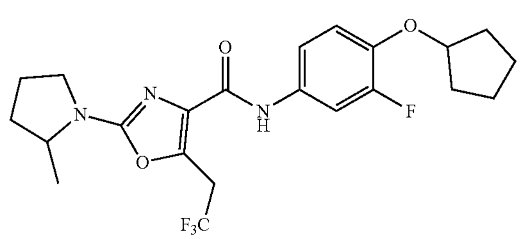 [SMILES: CC1CCCN1c1nc(C(=O)Nc2ccc(OC3CCCC3)c(F)c2)c(CC(F)(F)F)o1] | N-(4-(cyclopentyloxy)-3-fluorophenyl)-2-(2-methylpyrrolidin-1-yl)-5-(2,2,2-trifluoroethyl)oxazole-4-carboxamide |
| 55 | 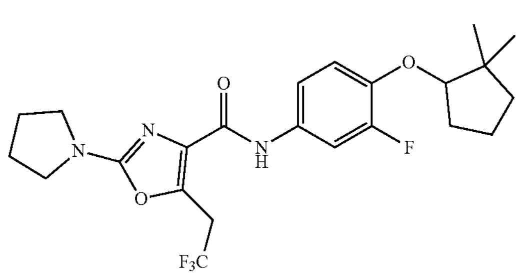 [SMILES: CC1(C)CCCC1Oc1ccc(NC(=O)c2nc(N3CCCC3)oc2CC(F)(F)F)cc1F] | N-(4-((2,2-dimethylcyclopentyl)oxy)-3-fluorophenyl)-2-(pyrrolidin-1-yl)-5-(2,2,2-trifluoroethyl)oxazole-4-carboxamide |

| Ex. | Structures | Name |
| --- | --- | --- |
| 56 | 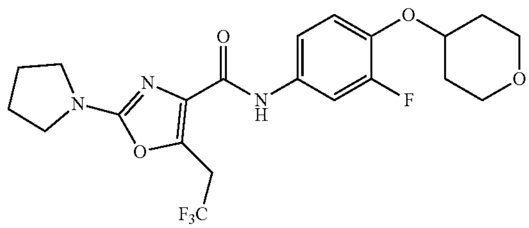 [SMILES: O=C(Nc1ccc(OC2CCOCC2)c(F)c1)c1nc(N2CCCC2)oc1CC(F)(F)F] | N-[3-fluoro-4-(oxan-4-yloxy)phenyl]-2-(pyrrolidin-1-yl)-5-(2,2,2-trifluoroethyl)oxazole-4-carboxamide |
| 57 | 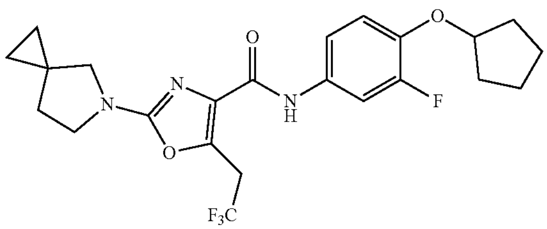 [SMILES: O=C(Nc1ccc(OC2CCCC2)c(F)c1)c1nc(N2CCC3(CC3)C2)oc1CC(F)(F)F] | N-(4-(cyclopentyloxy)-3-fluorophenyl)-2-(5-azaspiro[2.4]heptan-5-yl)-5-(2,2,2-trifluoroethyl)oxazole-4-carboxamide |
| 58 | 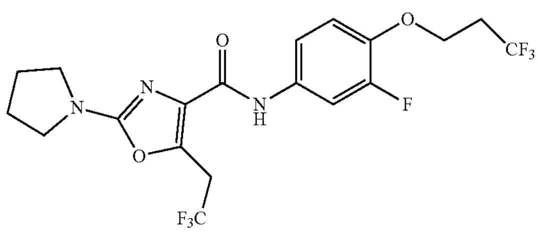 [SMILES: O=C(Nc1ccc(OCCC(F)(F)F)c(F)c1)c1nc(N2CCCC2)oc1CC(F)(F)F] | N-(3-fluoro-4-(3,3,3-trifluoropropoxy)phenyl)-2-(pyrrolidin-1-yl)-5-(2,2,2-trifluoroethyl)oxazole-4-carboxamide |
| 59 | 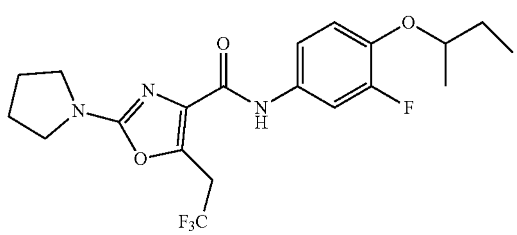 [SMILES: CCC(C)Oc1ccc(NC(=O)c2nc(N3CCCC3)oc2CC(F)(F)F)cc1F] | N-(4-(sec-butoxy)-3-fluorophenyl)-2-(pyrrolidin-1-yl)-5-(2,2,2-trifluoroethyl)oxazole-4-carboxamide |
| 60 | 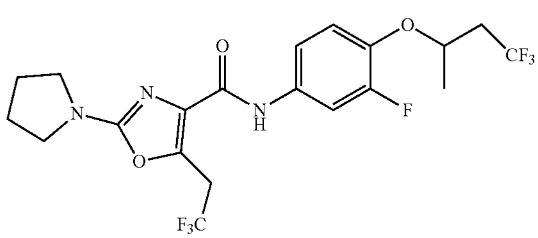 [SMILES: CC(CC(F)(F)F)Oc1ccc(NC(=O)c2nc(N3CCCC3)oc2CC(F)(F)F)cc1F] | N-(3-fluoro-4-((4,4,4-trifluorobutan-2-yl)oxy)phenyl)-2-(pyrrolidin-1-yl)-5-(2,2,2-trifluoroethyl)oxazole-4-carboxamide |
| 61 | 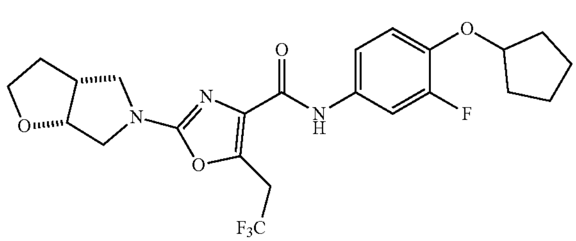 | N-(4-(cyclopentyloxy)-3-fluorophenyl)-2-((3aR,6aR)-hexahydro-5H-furo[2,3-c]pyrrol-5-yl)-5-(2,2,2-trifluoroethyl)oxazole-4-carboxamide |

| Ex. | Structures | Name |
|---|---|---|
| 62 | 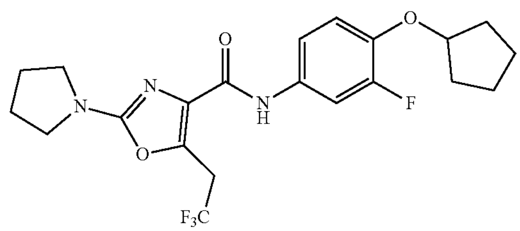 [SMILES: O=C(Nc1ccc(OC2CCCC2)c(F)c1)c1nc(N2CCCC2)oc1CC(F)(F)F] | N-[4-(cyclopentyloxy)-3-fluorophenyl]-2-(pyrrolidin-1-yl)-5-(2,2,2-trifluoroethyl)oxazole-4-carboxamide |
| 63 | 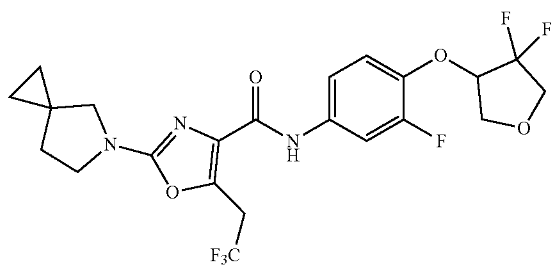 [SMILES: O=C(Nc1ccc(OC2COCC2(F)F)c(F)c1)c1nc(N2CCC3(CC3)C2)oc1CC(F)(F)F] | N-(4-((4,4-difluorotetrahydrofuran-3-yl)oxy)-3-fluorophenyl)-2-(5-azaspiro[2.4]heptan-5-yl)-5-(2,2,2-trifluoroethyl)oxazole-4-carboxamide |
| 64 | 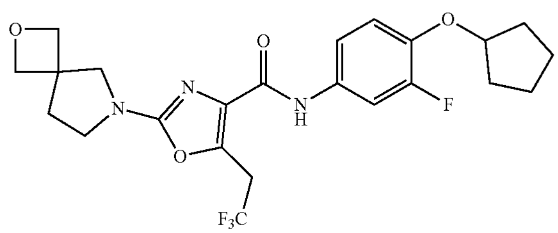 [SMILES: O=C(Nc1ccc(OC2CCCC2)c(F)c1)c1nc(N2CCC3(COC3)C2)oc1CC(F)(F)F] | N-(4-(cyclopentyloxy)-3-fluorophenyl)-2-(2-oxa-6-azaspiro[3.4]octan-6-yl)-5-(2,2,2-trifluoroethyl)oxazole-4-carboxamide |
| 65 | 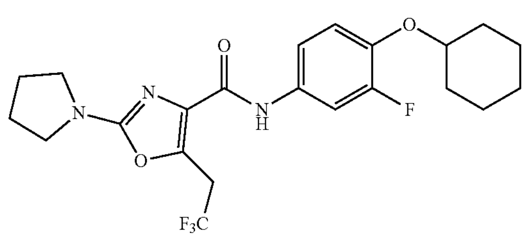 [SMILES: O=C(Nc1ccc(OC2CCCCC2)c(F)c1)c1nc(N2CCCC2)oc1CC(F)(F)F] | N-(4-(cyclohexyloxy)-3-fluorophenyl)-2-(pyrrolidin-1-yl)-5-(2,2,2-trifluoroethyl)oxazole-4-carboxamide |
| 66 | 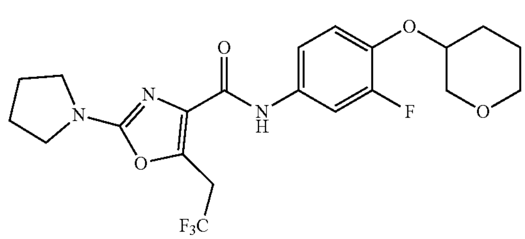 [SMILES: O=C(Nc1ccc(OC2CCCOC2)c(F)c1)c1nc(N2CCCC2)oc1CC(F)(F)F] | N-(4-(cyclohexyloxy)-3-fluorophenyl)-2-(pyrrolidin-1-yl)-5-(2,2,2-trifluoroethyl)oxazole-4-carboxamide |
| 67 | 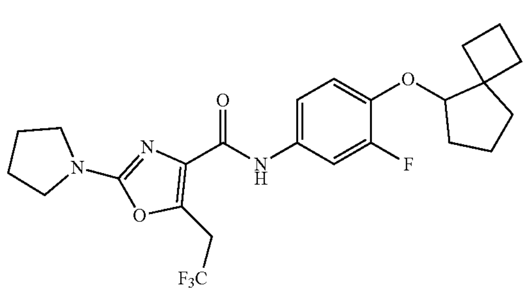 [SMILES: O=C(Nc1ccc(OC2CCCC23CCC3)c(F)c1)c1nc(N2CCCC2)oc1CC(F)(F)F] | N-(3-fluoro-4-{spiro[3.4]octan-5-yloxy}phenyl)-2-(pyrrolidin-1-yl)-5-(2,2,2-trifluoroethyl)oxazole-4-carboxamide |

-continued

| Ex. | Structures | Name |
|---|---|---|
| 68 | 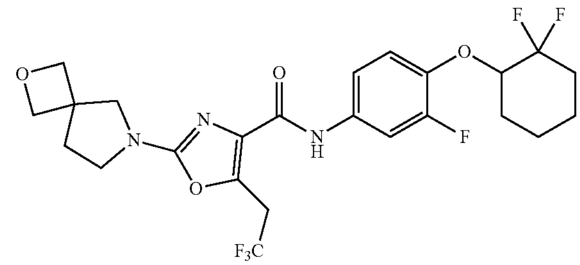 [SMILES: O=C(Nc1ccc(OC2CCCCC2(F)F)c(F)c1)c1nc(N2CCC3(COC3)C2)oc1CC(F)(F)F] | N-(4-((2,2-difluorocyclohexyl)oxy)-3-fluorophenyl)-2-(2-oxa-6-azaspiro[3.4]octan-6-yl)-5-(2,2,2-trifluoroethyl)oxazole-4-carboxamide |
| 69 | 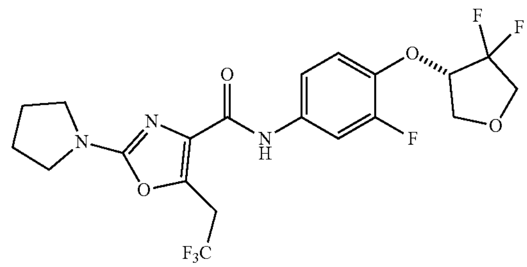 | (S)-N-(4-((4,4-difluorotetrahydrofuran-3-yl)oxy)-3-fluorophenyl)-2-(pyrrolidin-1-yl)-5-(2,2,2-trifluoroethyl)oxazole-4-carboxamide |
| 70 | 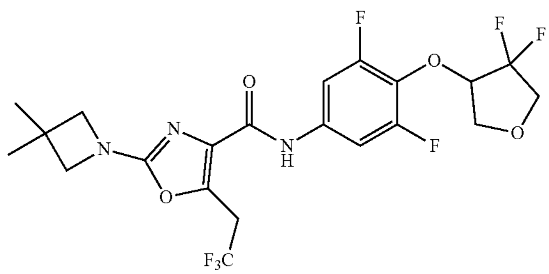 [SMILES: CC1(C)CN(c2nc(C(=O)Nc3cc(F)c(OC4COCC4(F)F)c(F)c3)c(CC(F)(F)F)o2)C1] | N-{4-[(4,4-difluorotetrahydrofuran-3-yl)oxy]-3,5-difluorophenyl}-2-(3,3-dimethylazetidin-1-yl)-5-(2,2,2-trifluoroethyl)oxazole-4-carboxamide |
| 71 | 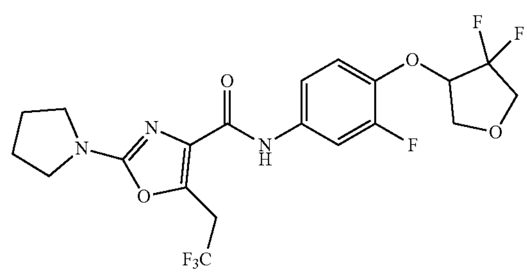 [SMILES: O=C(Nc1ccc(OC2COCC2(F)F)c(F)c1)c1nc(N2CCCC2)oc1CC(F)(F)F] | N-(4-((4,4-difluorotetrahydrofuran-3-yl)oxy)-3-fluorophenyl)-2-(pyrrolidin-1-yl)-5-(2,2,2-trifluoroethyl)oxazole-4-carboxamide |
| 72 | 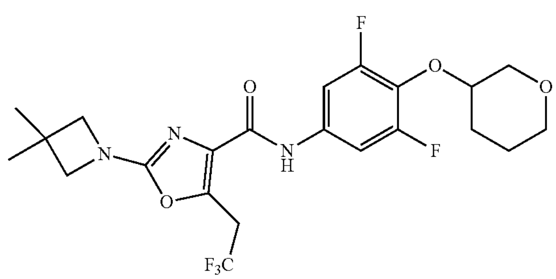 [SMILES: CC1(C)CN(c2nc(C(=O)Nc3cc(F)c(OC4CCCOC4)c(F)c3)c(CC(F)(F)F)o2)C1] | N-(3,5-difluoro-4-((tetrahydro-2H-pyran-3-yl)oxy)phenyl)-2-(3,3-dimethylazetidin-1-yl)-5-(2,2,2-trifluoroethyl)oxazole-4-carboxamide |
| 73 | 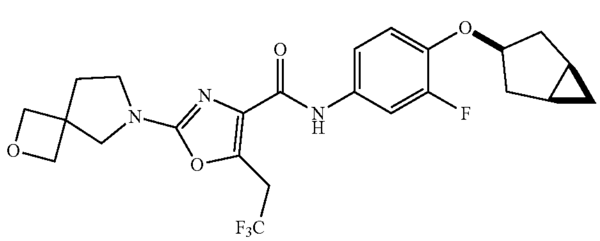 | N-(4-{cis-bicyclo[3.1.0]hexan-3-yloxy}-3-fluorophenyl)-2-{2-oxa-6-azaspiro[3.4]octan-6-yl}-5-(2,2,2-trifluoroethyl)oxazole-4-carboxamide |

-continued

| Ex. | Structures | Name |
| --- | --- | --- |
| 74 | 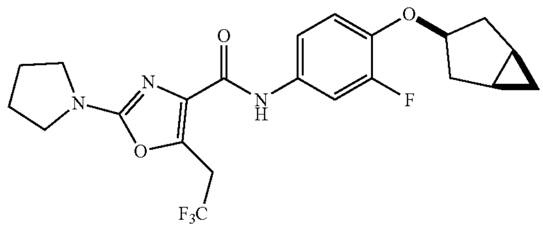 | N-(4-{cis-bicyclo[3.1.0]hexan-3-yloxy}-3-fluorophenyl)-2-(pyrrolidin-1-yl)-5-(2,2,2-trifluoroethyl)oxazole-4-carboxamide |
| 75 | 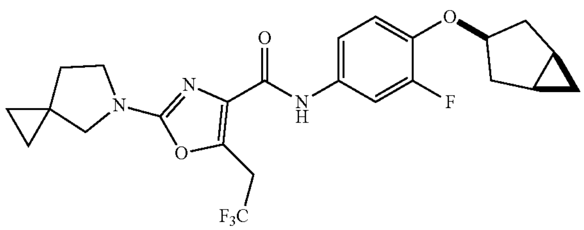 | 2-{5-azaspiro[2.4]heptan-5-yl}-N-(4-{cis-bicyclo[3.1.0]hexan-3-yloxy}-3-fluorophenyl)-5-(2,2,2-trifluoroethyl)oxazole-4-carboxamide |
| 76 | 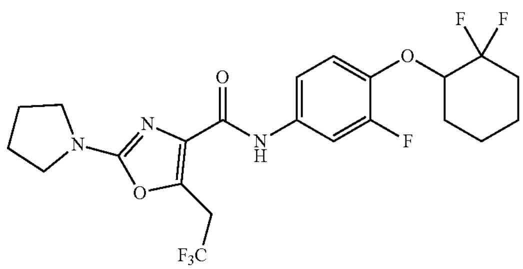 [SMILES: O=C(Nc1ccc(OC2CCCCC2(F)F)c(F)c1)c1nc(N2CCCC2)oc1CC(F)(F)F] | N-{4-[(2,2-difluorocyclohexyl)oxy]-3-fluorophenyl}-2-(pyrrolidin-1-yl)-5-(2,2,2-trifluoroethyl)oxazole-4-carboxamide |
| 77 | 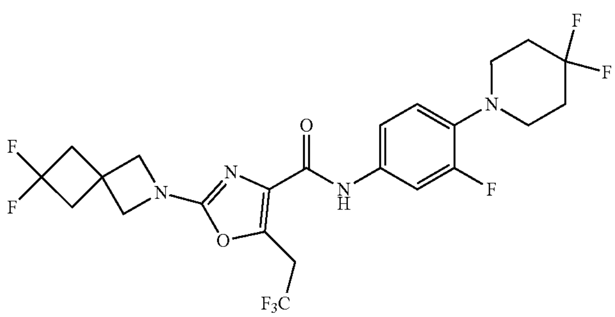 [SMILES: O=C(Nc1ccc(N2CCC(F)(F)CC2)c(F)c1)c1nc(N2CC3(C2)CC(F)(F)C3)oc1CC(F)(F)F] | 2-{6,6-difluoro-2-azaspiro[3.3]heptan-2-yl}-N-[4-(4,4-difluoropiperidin-1-yl)-3-fluorophenyl]-5-(2,2,2-trifluoroethyl)oxazole-4-carboxamide |
| 78 | 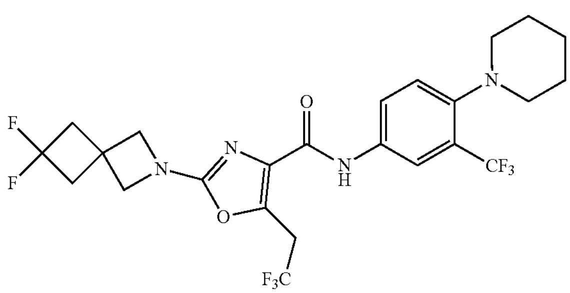 [SMILES: O=C(Nc1ccc(N2CCCCC2)c(C(F)(F)F)c1)c1nc(N2CC3(C2)CC(F)(F)C3)oc1CC(F)(F)F] | 2-{6,6-difluoro-2-azaspiro[3.3]heptan-2-yl}-N-[4-(piperidin-1-yl)-3-(trifluoromethyl)phenyl]-5-(2,2,2-trifluoroethyl)oxazole-4-carboxamide |

| Ex. | Structures | Name |
|---|---|---|
| 79 | 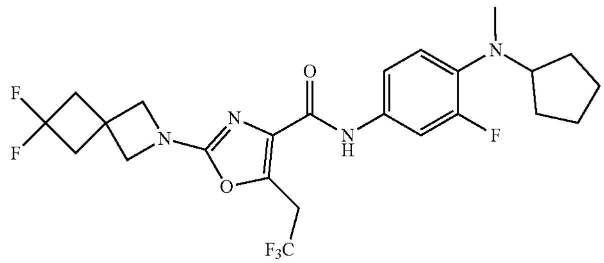 [SMILES: CN(c1ccc(NC(=O)c2nc(N3CC4(C3)CC(F)(F)C4)oc2CC(F)(F)F)cc1F)C1CCCC1] | N-{4-[cyclopentyl(methyl)amino]-3-fluorophenyl}-2-{6,6-difluoro-2-azaspiro[3.3]heptan-2-yl}-5-(2,2,2-trifluoroethyl)oxazole-4-carboxamide |
| 80 | 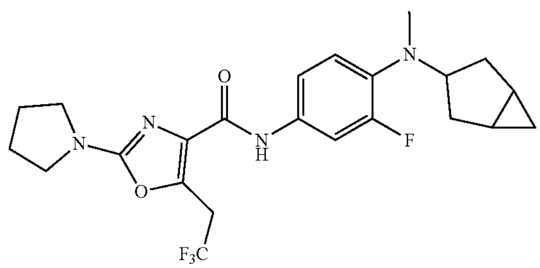 [SMILES: CN(c1ccc(NC(=O)c2nc(N3CCCC3)oc2CC(F)(F)F)cc1F)C1CC2CC2C1] | N-(4-{bicyclo[3.1.0]hexan-3-yl(methyl)amino}-3-fluorophenyl)-2-(pyrrolidin-1-yl)-5-(2,2,2-trifluoroethyl)oxazole-4-carboxamide |
| 81 | 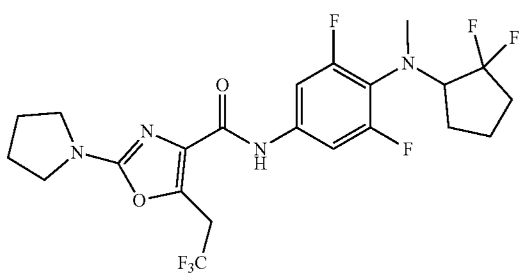 [SMILES: CN(c1c(F)cc(NC(=O)c2nc(N3CCCC3)oc2CC(F)(F)F)cc1F)C1CCCC1(F)F] | N-{4-[(2,2-difluorocyclopentyl)(methyl)amino]-3,5-difluorophenyl}-2-(pyrrolidin-1-yl)-5-(2,2,2-trifluoroethyl)oxazole-4-carboxamide |
| 82 | 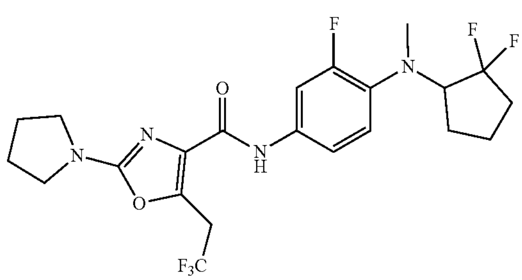 [SMILES: CN(c1ccc(NC(=O)c2nc(N3CCCC3)oc2CC(F)(F)F)cc1F)C1CCCC1(F)F] | N-{4-[(2,2-difluorocyclopentyl)(methyl)amino]-3-fluorophenyl}-2-(pyrrolidin-1-yl)-5-(2,2,2-trifluoroethyl)oxazole-4-carboxamide |
| 83 | 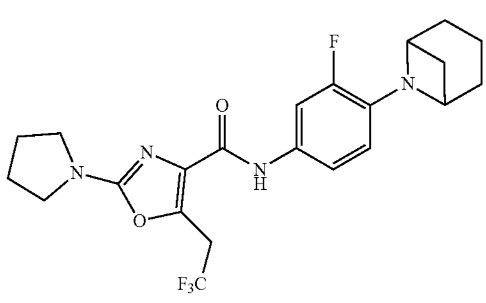 [SMILES: O=C(Nc1ccc(N2C3CCCC2C3)c(F)c1)c1nc(N2CCCC2)oc1CC(F)(F)F] | N-(4-{6-azabicyclo[3.1.1]heptan-6-yl}-3-fluorophenyl)-2-(pyrrolidin-1-yl)-5-(2,2,2-trifluoroethyl)oxazole-4-carboxamide |

| Ex. | Structures | Name |
|---|---|---|
| 84 | 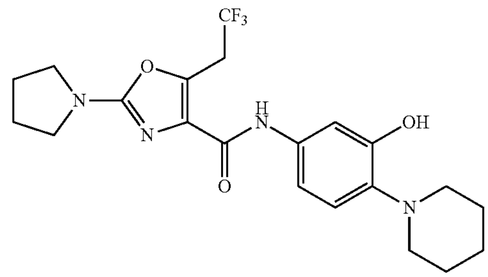 [SMILES: O=C(Nc1ccc(N2CCCCC2)c(O)c1)c1nc(N2CCCC2)oc1CC(F)(F)F] | N-(3-hydroxy-4-(piperidin-1-yl)phenyl)-2-(pyrrolidin-1-yl)-5-(2,2,2-trifluoroethyl)oxazole-4-carboxamide |
| 85 | 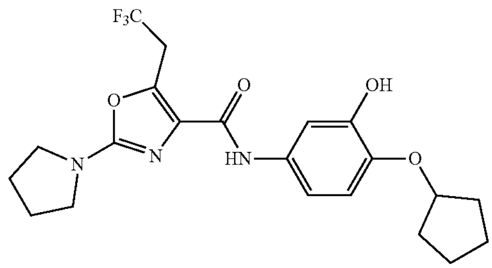 [SMILES: O=C(Nc1ccc(OC2CCCC2)c(O)c1)c1nc(N2CCCC2)oc1CC(F)(F)F] | N-(4-(cyclopentyloxy)-3-hydroxyphenyl)-2-(pyrrolidin-1-yl)-5-(2,2,2-trifluoroethyl)oxazole-4-carboxamide |
| 86 | 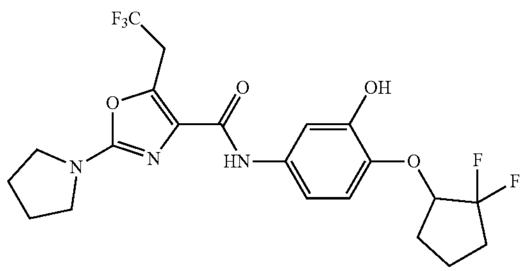 [SMILES: O=C(Nc1ccc(OC2CCCC2(F)F)c(O)c1)c1nc(N2CCCC2)oc1CC(F)(F)F] | N-(4-((2,2-difluorocyclopentyl)oxy)-3-hydroxyphenyl)-2-(pyrrolidin-1-yl)-5-(2,2,2-trifluoroethyl)oxazole-4-carboxamide |
| 87 | 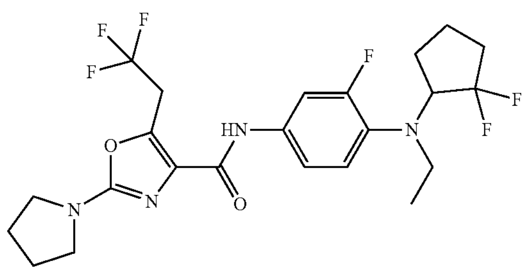 [SMILES: CCN(c1ccc(NC(=O)c2nc(N3CCCC3)oc2CC(F)(F)F)cc1F)C1CCCC1(F)F] | N-(4-((2,2-difluorocyclopentyl)(ethyl)amino)-3-fluorophenyl)-2-(pyrrolidin-1-yl)-5-(2,2,2-trifluoroethyl)oxazole-4-carboxamide |
| 88 | 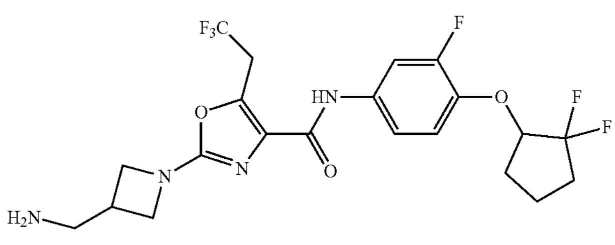 [SMILES: NCC1CN(c2nc(C(=O)Nc3ccc(OC4CCCC4(F)F)c(F)c3)c(CC(F)(F)F)o2)C1] | 2-(3-(aminomethyl)azetidin-1-yl)-N-(4-((2,2-difluorocyclopentyl)oxy)-3-fluorophenyl)-5-(2,2,2-trifluoroethyl)oxazole-4-carboxamide |
| 89 | 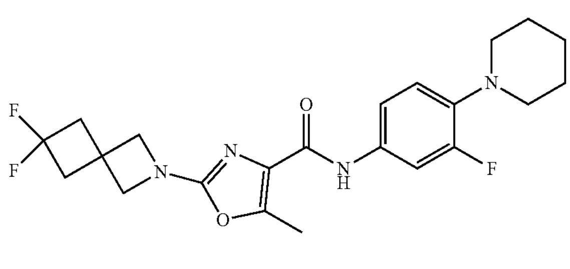 [SMILES: Cc1oc(N2CC3(C2)CC(F)(F)C3)nc1C(=O)Nc1ccc(N2CCCCC2)c(F)c1] | 2-(6,6-difluoro-2-azaspiro[3.3]heptan-2-yl)-N-(3-fluoro-4-(piperidin-1-yl)phenyl)-5-methyloxazole-4-carboxamide |

| Ex. | Structures | Name |
|---|---|---|
| 90 | 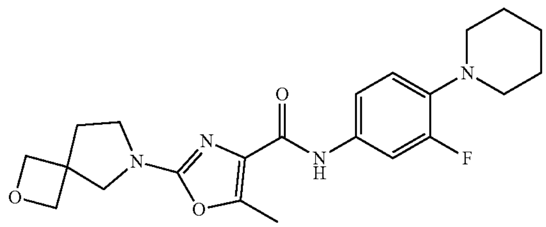 [SMILES: Cc1oc(N2CCC3(COC3)C2)nc1C(=O)Nc1ccc(N2CCCCC2)c(F)c1] | N-(3-fluoro-4-(piperidin-1-yl)phenyl)-5-methyl-2-(2-oxa-6-azaspiro[3.4]octan-6-yl)oxazole-4-carboxamide |
| 91 | 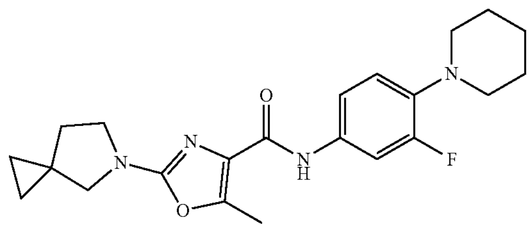 [SMILES: Cc1oc(N2CCC3(CC3)C2)nc1C(=O)Nc1ccc(N2CCCCC2)c(F)c1] | N-(3-fluoro-4-(piperidin-1-yl)phenyl)-5-methyl-2-(5-azaspiro[2.4]heptan-5-yl)oxazole-4-carboxamide |
| 92 | 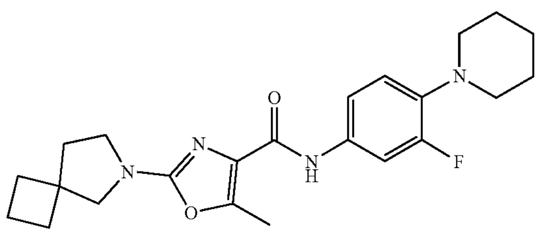 [SMILES: Cc1oc(N2CCC3(CCC3)C2)nc1C(=O)Nc1ccc(N2CCCCC2)c(F)c1] | N-(3-fluoro-4-(piperidin-1-yl)phenyl)-5-methyl-2-(6-azaspiro[3.4]octan-6-yl)oxazole-4-carboxamide |
| 93 | 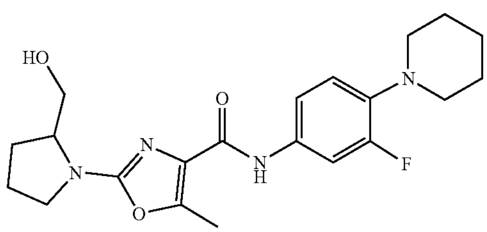 [SMILES: Cc1oc(N2CCCC2CO)nc1C(=O)Nc1ccc(N2CCCCC2)c(F)c1] | N-(3-fluoro-4-(piperidin-1-yl)phenyl)-2-(2-(hydroxymethyl)pyrrolidin-1-yl)-5-methyloxazole-4-carboxamide |
| 94 | 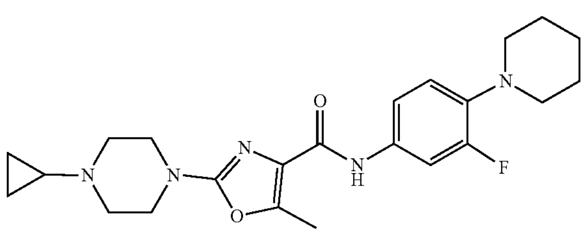 [SMILES: Cc1oc(N2CCN(C3CC3)CC2)nc1C(=O)Nc1ccc(N2CCCCC2)c(F)c1] | 2-(4-cyclopropylpiperazin-1-yl)-N-(3-fluoro-4-(piperidin-1-yl)phenyl)-5-methyloxazole-4-carboxamide |
| 95 | 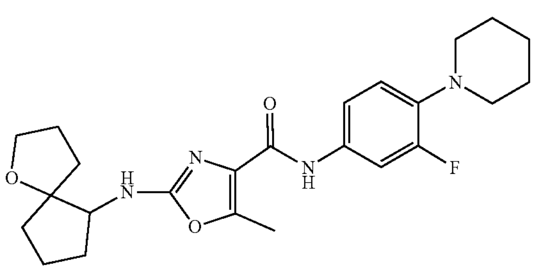 [SMILES: Cc1oc(NC2CCCC23CCCO3)nc1C(=O)Nc1ccc(N2CCCCC2)c(F)c1] | 2-(4-cyclopropylpiperazin-1-yl)-N-(3-fluoro-4-(piperidin-1-yl)phenyl)-5-methyloxazole-4-carboxamide |

| Ex. | Structures | Name |
|---|---|---|
| 96 | 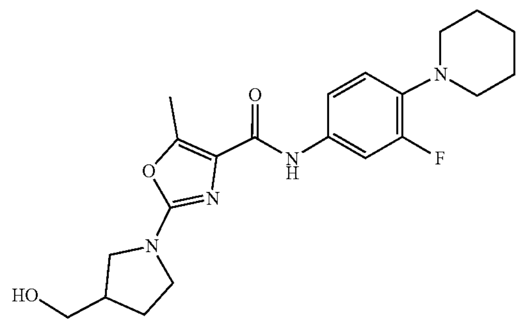 [SMILES: Cc1oc(N2CCC(CO)C2)nc1C(=O)Nc1ccc(N2CCCCC2)c(F)c1] | N-(3-fluoro-4-(piperidin-1-yl)phenyl)-2-(3-(hydroxymethyl)pyrrolidin-1-yl)-5-(2,2,2-trifluoroethyl)oxazole-4-carboxamide |
| 97 | 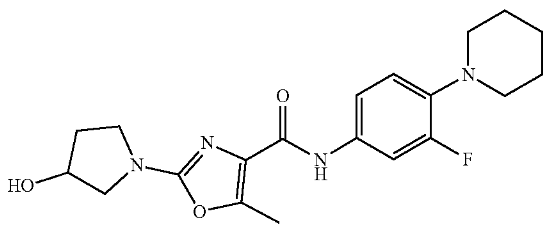 [SMILES: Cc1oc(N2CCC(O)C2)nc1C(=O)Nc1ccc(N2CCCCC2)c(F)c1] | N-(3-fluoro-4-(piperidin-1-yl)phenyl)-2-(3-hydroxypyrrolidin-1-yl)-5-methyloxazole-4-carboxamide |
| 98 | 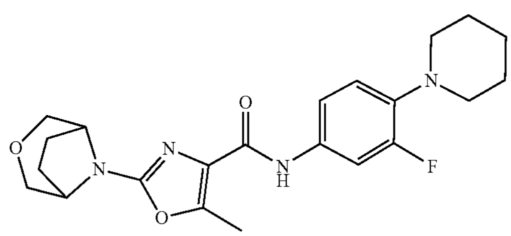 [SMILES: Cc1oc(N2C3CCC2COC3)nc1C(=O)Nc1ccc(N2CCCCC2)c(F)c1] | 2-(3-oxa-8-azabicyclo[3.2.1]octan-8-yl)-N-(3-fluoro-4-(piperidin-1-yl)phenyl)-5-methyloxazole-4-carboxamide |
| 99 | 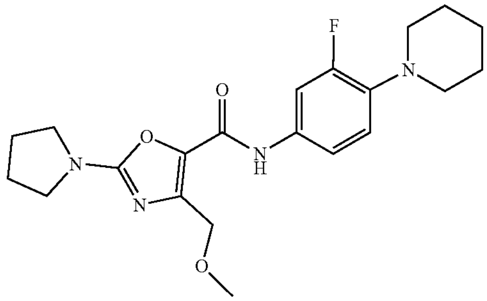 [SMILES: COCc1nc(N2CCCC2)oc1C(=O)Nc1ccc(N2CCCCC2)c(F)c1] | N-[3-fluoro-4-(piperidin-1-yl)phenyl]-5-(methoxymethyl)-2-(pyrrolidin-1-yl)oxazole-4-carboxamide |
| 100 | 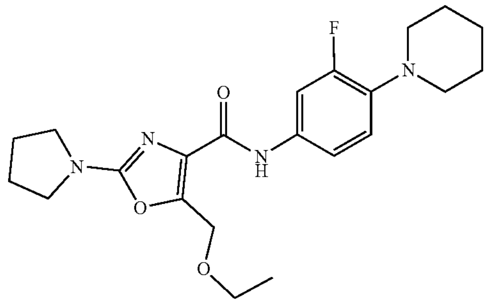 [SMILES: CCOCc1oc(N2CCCC2)nc1C(=O)Nc1ccc(N2CCCCC2)c(F)c1] | 5-(ethoxymethyl)-N-[3-fluoro-4-(piperidin-1-yl)phenyl]-2-(pyrrolidin-1-yl)oxazole-4-carboxamide |

| Ex. | Structures | Name |
|---|---|---|
| 101 | 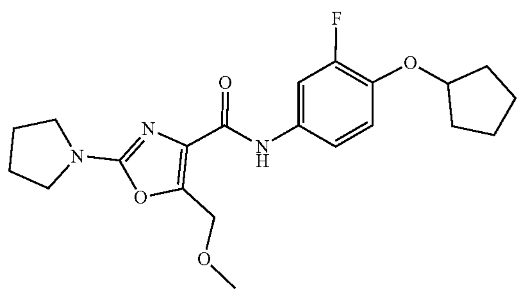 [SMILES: COCc1oc(N2CCCC2)nc1C(=O)Nc1ccc(OC2CCCC2)c(F)c1] | N-[4-(cyclopentyloxy)-3-fluorophenyl]-5-(methoxymethyl)-2-(pyrrolidin-1-yl)oxazole-4-carboxamide |
| 102 | 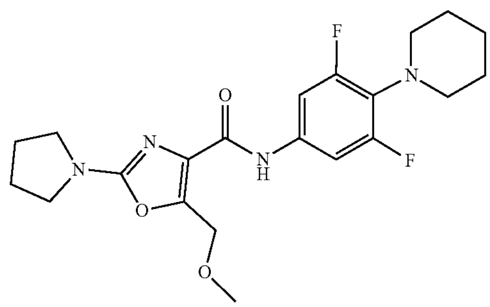 [SMILES: COCc1oc(N2CCCC2)nc1C(=O)Nc1cc(F)c(N2CCCCC2)c(F)c1] | N-[3,5-difluoro-4-(piperidin-1-yl)phenyl]-5-(methoxymethyl)-2-(pyrrolidin-1-yl)oxazole-4-carboxamide |
| 103 | 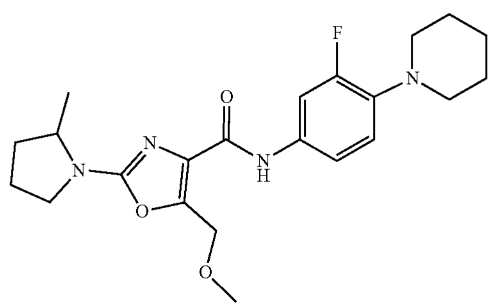 [SMILES: COCc1oc(N2CCCC2C)nc1C(=O)Nc1ccc(N2CCCCC2)c(F)c1] | N-(3-fluoro-4-(piperidin-1-yl)phenyl)-5-(methoxymethyl)-2-(2-methylpyrrolidin-1-yl)oxazole-4-carboxamide |
| 104 | 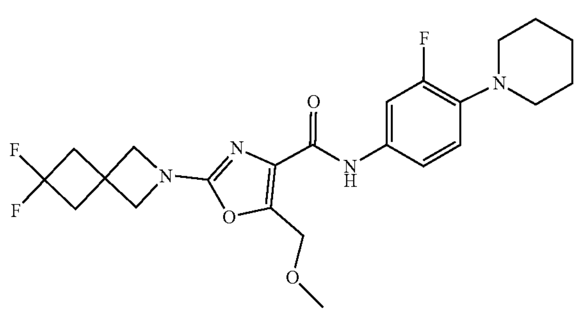 [SMILES: COCc1oc(N2CC3(C2)CC(F)(F)C3)nc1C(=O)Nc1ccc(N2CCCCC2)c(F)c1] | 2-{6,6-difluoro-2-azaspiro[3.3]heptan-2-yl}-N-[3-fluoro-4-(piperidin-1-yl)phenyl]-5-(methoxymethyl)oxazole-4-carboxamide |
| 105 | 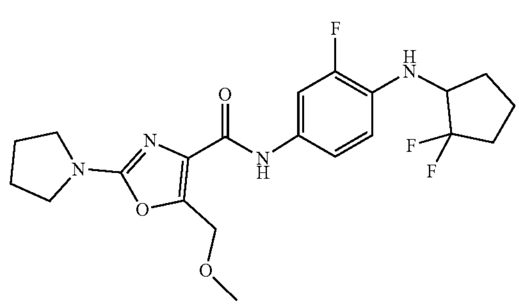 [SMILES: COCc1oc(N2CCCC2)nc1C(=O)Nc1ccc(NC2CCCC2(F)F)c(F)c1] | N-(4-((2,2-difluorocyclopentyl)oxy)-3-fluorophenyl)-5-(methoxymethyl)-2-(pyrrolidin-1-yl)oxazole-4-carboxamide |

| Ex. | Structures | Name |
|---|---|---|
| 106 | 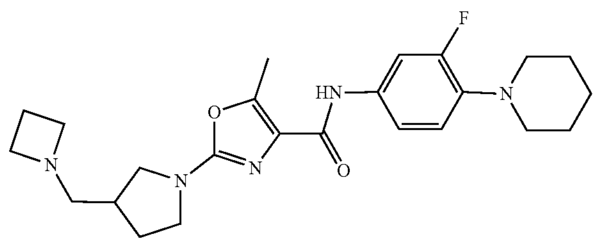 [SMILES: Cc1oc(N2CCC(CN3CCC3)C2)nc1C(=O)Nc1ccc(N2CCCCC2)c(F)c1] | 2-(3-(azetidin-1-ylmethyl)pyrrolidin-1-yl)-N-(3-fluoro-4-(piperidin-1-yl)phenyl)-5-methyloxazole-4-carboxamide |
| 107 | 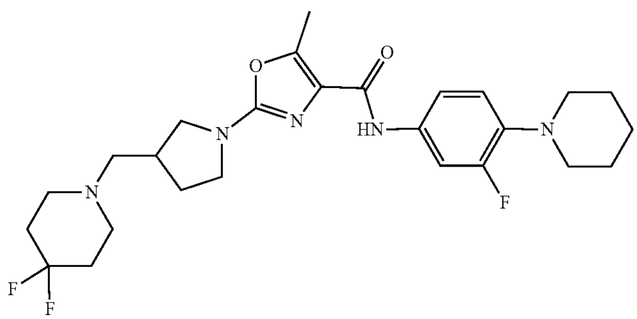 [SMILES: Cc1oc(N2CCC(CN3CCC(F)(F)CC3)C2)nc1C(=O)Nc1ccc(N2CCCCC2)c(F)c1] | 2-(3-((4,4-difluoropiperidin-1-yl)methyl)pyrrolidin-1-yl)-N-(3-fluoro-4-(piperidin-1-yl)phenyl)-5-methyloxazole-4-carboxamide |
| 108 | 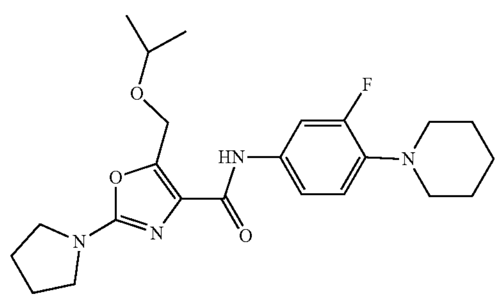 [SMILES: CC(C)OCc1oc(N2CCCC2)nc1C(=O)Nc1ccc(N2CCCCC2)c(F)c1] | N-(3-fluoro-4-(piperidin-1-yl)phenyl)-5-(isopropoxymethyl)-2-(pyrrolidin-1-yl)oxazole-4-carboxamide |
| 109 | 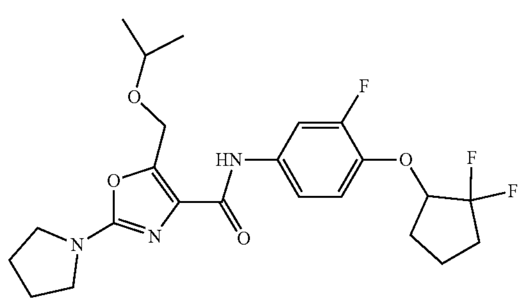 [SMILES: CC(C)OCc1oc(N2CCCC2)nc1C(=O)Nc1ccc(OC2CCCC2(F)F)c(F)c1] | N-(4-((2,2-difluorocyclopentyl)oxy)-3-fluorophenyl)-5-(isopropoxymethyl)-2-(pyrrolidin-1-yl)oxazole-4-carboxamide |
| 110 | 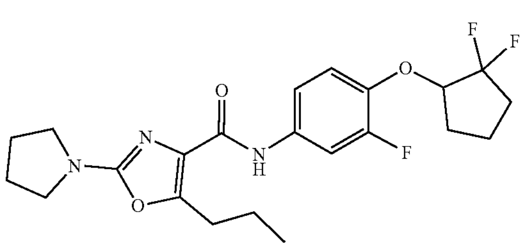 [SMILES: CCCc1oc(N2CCCC2)nc1C(=O)Nc1ccc(OC2CCCC2(F)F)c(F)c1] | N-(4-((2,2-difluorocyclopentyl)oxy)-3-fluorophenyl)-5-propyl-2-(pyrrolidin-1-yl)oxazole-4-carboxamide |

-continued

| Ex. | Structures | Name |
|---|---|---|
| 111 | 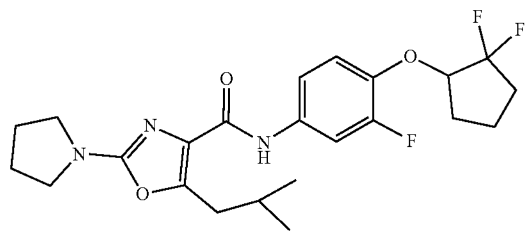 [SMILES: CC(C)Cc1oc(N2CCCC2)nc1C(=O)Nc1ccc(OC2CCCC2(F)F)c(F)c1] | N-(4-((2,2-difluorocyclopentyl)oxy)-3-fluorophenyl)-5-isobutyl-2-(pyrrolidin-1-yl)oxazole-4-carboxamide |
| 112 | 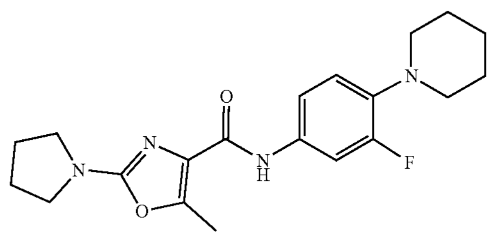 [SMILES: Cc1oc(N2CCCC2)nc1C(=O)Nc1ccc(N2CCCCC2)c(F)c1] | N-(3-fluoro-4-(piperidin-1-yl)phenyl)-5-methyl-2-(pyrrolidin-1-yl)oxazole-4-carboxamide |
| 113 | 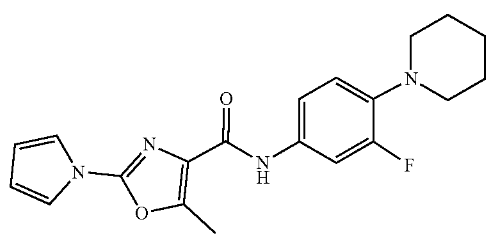 [SMILES: Cc1oc(-n2cccc2)nc1C(=O)Nc1ccc(N2CCCCC2)c(F)c1] | N-(3-fluoro-4-(piperidin-1-yl)phenyl)-5-methyl-2-(1H-pyrrol-1-yl)oxazole-4-carboxamide |
| 114 | 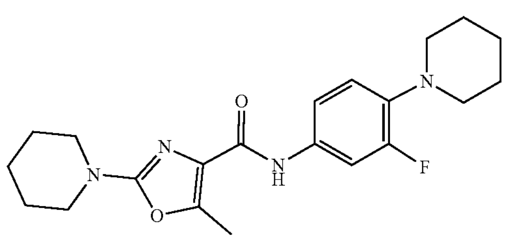 [SMILES: Cc1oc(N2CCCCC2)nc1C(=O)Nc1ccc(N2CCCCC2)c(F)c1] | N-(3-fluoro-4-(piperidin-1-yl)phenyl)-5-methyl-2-(piperidin-1-yl)oxazole-4-carboxamide |
| 115 | 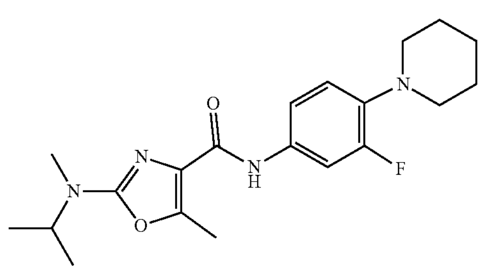 [SMILES: Cc1oc(N(C)C(C)C)nc1C(=O)Nc1ccc(N2CCCCC2)c(F)c1] | N-(3-fluoro-4-(piperidin-1-yl)phenyl)-2-(isopropyl(methyl)amino)-5-methyloxazole-4-carboxamide |
| 116 | 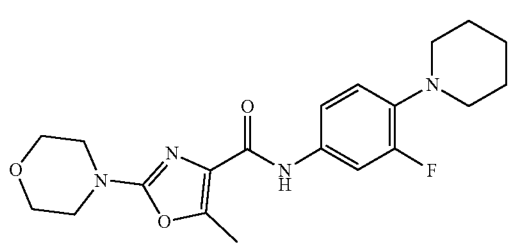 [SMILES: Cc1oc(N2CCOCC2)nc1C(=O)Nc1ccc(N2CCCCC2)c(F)c1] | N-(3-fluoro-4-(piperidin-1-yl)phenyl)-5-methyl-2-morpholinooxazole-4-carboxamide |

-continued

| Ex. | Structures | Name |
|---|---|---|
| 117 | 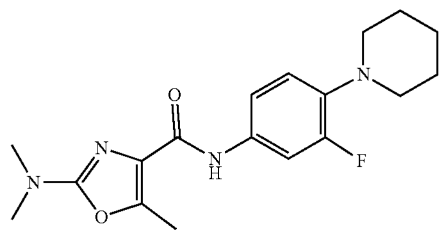 [SMILES: Cc1oc(N(C)C)nc1C(=O)Nc1ccc(N2CCCCC2)c(F)c1] | 2-(dimethylamino)-N-(3-fluoro-4-(piperidin-1-yl)phenyl)-5-methyloxazole-4-carboxamide |
| 118 | 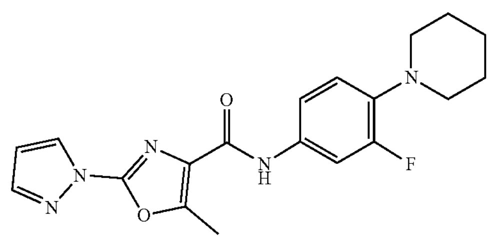 [SMILES: Cc1oc(-n2cccn2)nc1C(=O)Nc1ccc(N2CCCCC2)c(F)c1] | N-(3-fluoro-4-(piperidin-1-yl)phenyl)-5-methyl-2-(1H-pyrazol-1-yl)oxazole-4-carboxamide |
| 119 | 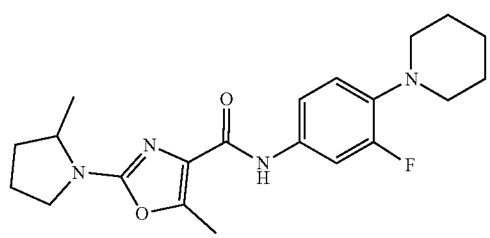 [SMILES: Cc1oc(N2CCCC2C)nc1C(=O)Nc1ccc(N2CCCCC2)c(F)c1] | N-(3-fluoro-4-(piperidin-1-yl)phenyl)-5-methyl-2-(2-methylpyrrolidin-1-yl)oxazole-4-carboxamide |
| 120 | 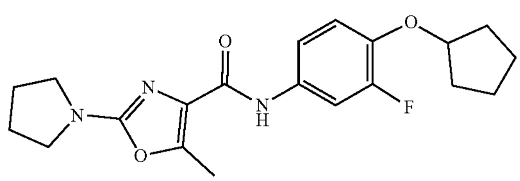 [SMILES: Cc1oc(N2CCCC2)nc1C(=O)Nc1ccc(OC2CCCC2)c(F)c1] | N-(4-(cyclopentyloxy)-3-fluorophenyl)-5-methyl-2-(pyrrolidin-1-yl)oxazole-4-carboxamide |
| 121 | 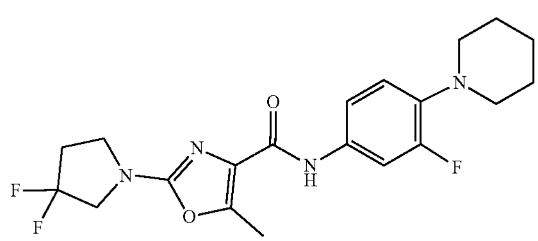 [SMILES: Cc1oc(N2CCC(F)(F)C2)nc1C(=O)Nc1ccc(N2CCCCC2)c(F)c1] | 2-(3,3-difluoropyrrolidin-1-yl)-N-(3-fluoro-4-(piperidin-1-yl)phenyl)-5-methyloxazole-4-carboxamide |
| 122 | 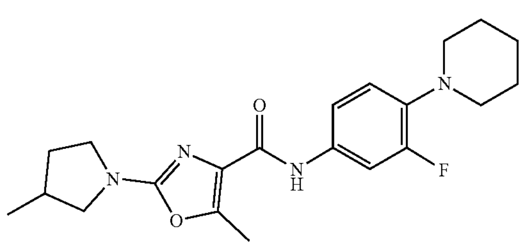 [SMILES: Cc1oc(N2CCC(C)C2)nc1C(=O)Nc1ccc(N2CCCCC2)c(F)c1] | N-(3-fluoro-4-(piperidin-1-yl)phenyl)-5-methyl-2-(3-methylpyrrolidin-1-yl)oxazole-4-carboxamide |

| Ex. | Structures | Name |
|---|---|---|
| 123 | 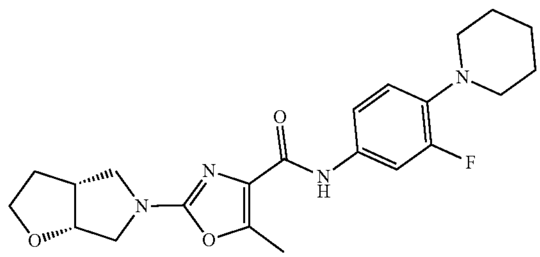 [SMILES: Cc1oc(N2C[C@H]3CCO[C@H]3C2)nc1C(=O)Nc1ccc(N2CCCCC2)c(F)c1] | N-(3-fluoro-4-(piperidin-1-yl)phenyl)-2-((3aR,6aR)-hexahydro-5H-furo[2,3-c]pyrrol-5-yl)-5-methyloxazole-4-carboxamide |
| 124 | 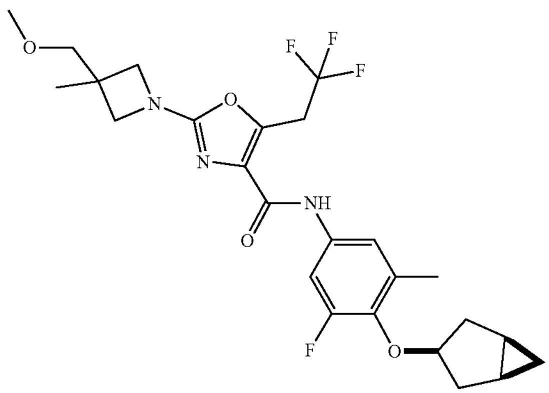 | N-(4-(cis-bicyclo[3.1.0]hexan-3-yloxy)-3-fluoro-5-methylphenyl)-2-(3-(methoxymethyl)-3-methylazetidin-1-yl)-5-(2,2,2-trifluoroethyl)oxazole-4-carboxamide |
| 125 | 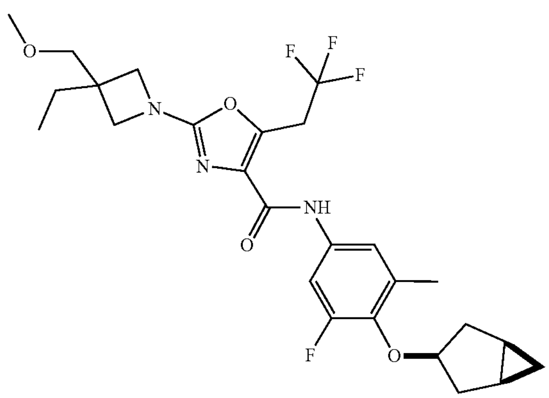 | N-(4-(cis-bicyclo[3.1.0]hexan-3-yloxy)-3-fluoro-5-methylphenyl)-2-(3-(methoxymethyl)-3-ethylazetidin-1-yl)-5-(2,2,2-trifluoroethyl)oxazole-4-carboxamide |
| 126 | 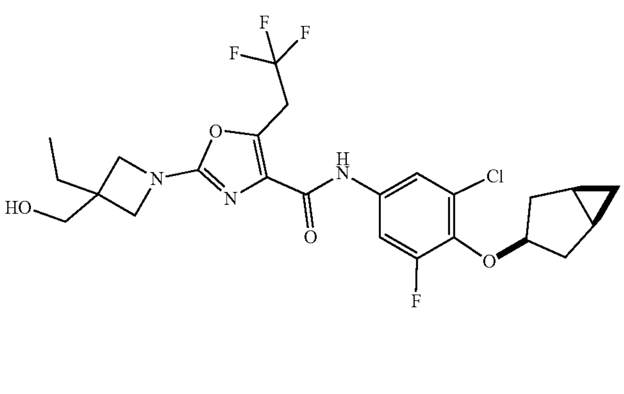 | N-(4-(cis-bicyclo[3.1.0]hexan-3-yloxy)-3-chloro-5-fluorophenyl)-2-(3-ethyl-3-(hydroxymethyl)azetidin-1-yl)-5-(2,2,2-trifluoroethyl)oxazole-4-carboxamide |

-continued

| Ex. | Structures | Name |
|---|---|---|
| 127 | 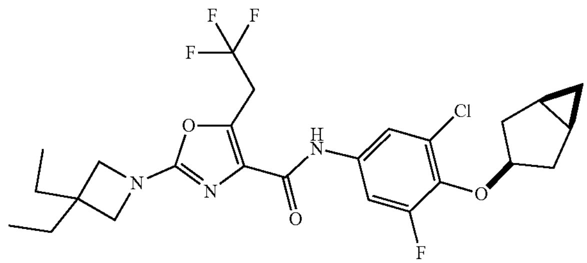 [SMILES: CCC1(CC)CN(c2nc(C(=O)Nc3cc(F)c(O[C@@H]4C[C@@H]5C[C@@H]5C4)c(Cl)c3)c(CC(F)(F)F)o2)C1] | N-(4-(cis-bicyclo[3.1.0]hexan-3-yloxy)-3-chloro-5-fluorophenyl)-2-(3,3-diethylazetidin-1-yl)-5-(2,2,2-trifluoroethyl)oxazole-4-carboxamide |
| 128 | 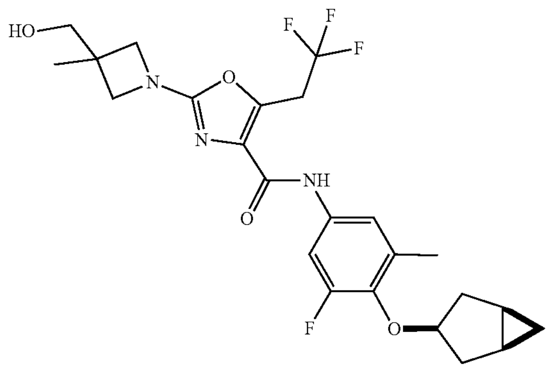 | N-(4-(cis-bicyclo[3.1.0]hexan-3-yloxy)-3-fluoro-5-methylphenyl)-2-(3-(methoxymethyl)-3-methylazetidin-1-yl)-5-(2,2,2-trifluoroethyl)oxazole-4-carboxamide |
| 129 | 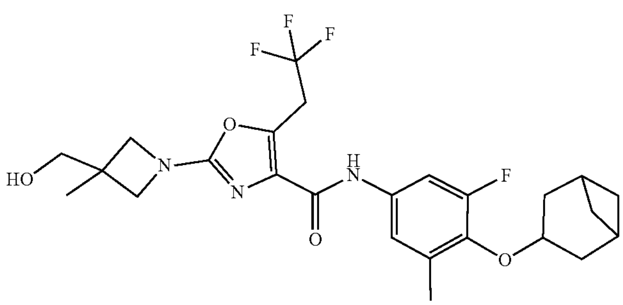 [SMILES: Cc1cc(NC(=O)c2nc(N3CC(C)(CO)C3)oc2CC(F)(F)F)cc(F)c1OC1CC2CC(C2)C1] | N-(4-(bicyclo[3.1.1]heptan-3-yloxy)-3-fluoro-5-methylphenyl)-2-(3-(hydroxymethyl)-3-methylazetidin-1-yl)-5-(2,2,2-trifluoroethyl)oxazole-4-carboxamide |
| 130 | 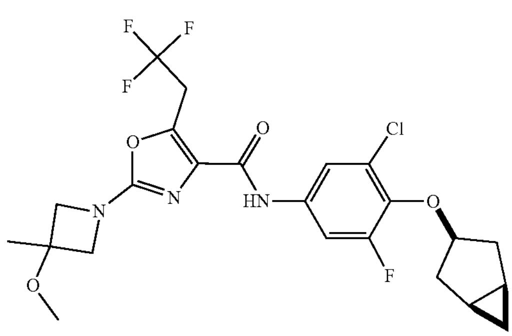 | N-(4-(cis-bicyclo[3.1.0]hexan-3-yloxy)-3-chloro-5-fluorophenyl)-2-(3-methoxy-3-methylazetidin-1-yl)-5-(2,2,2-trifluoroethyl)oxazole-4-carboxamide |

| Ex. | Structures | Name |
|---|---|---|
| 131 | 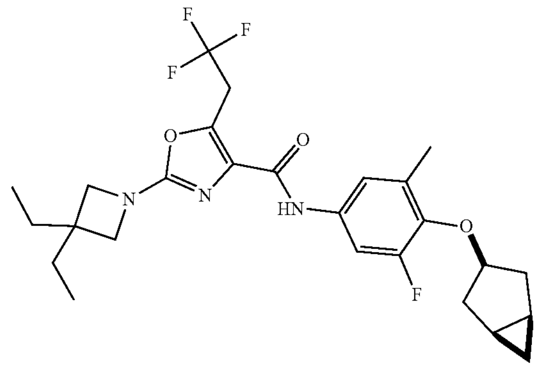 [SMILES: CCC1(CC)CN(c2nc(C(=O)Nc3cc(C)c(O[C@@H]4C[C@@H]5C[C@@H]5C4)c(F)c3)c(CC(F)(F)F)o2)C1] | N-(4-(cis-bicyclo[3.1.0]hexan-3-yloxy)-3-fluoro-5-methylphenyl)-2-(3,3-diethylazetidin-1-yl)-5-(2,2,2-trifluoroethyl)oxazole-4-carboxamide |
| 132 | 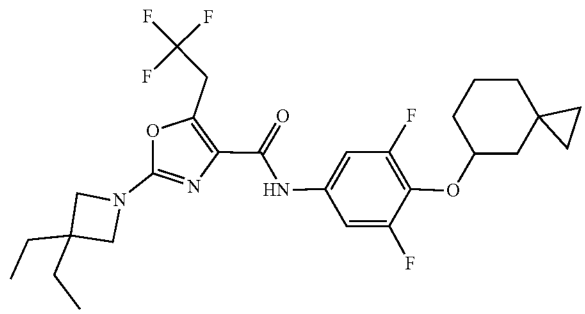 [SMILES: CCC1(CC)CN(c2nc(C(=O)Nc3cc(F)c(OC4CCCC5(CC5)C4)c(F)c3)c(CC(F)(F)F)o2)C1] | 2-(3,3-diethylazetidin-1-yl)-N-(3,5-difluoro-4-(spiro[2.5]octan-5-yloxy)phenyl)-5-(2,2,2-trifluoroethyl)oxazole-4-carboxamide |
| 133 | 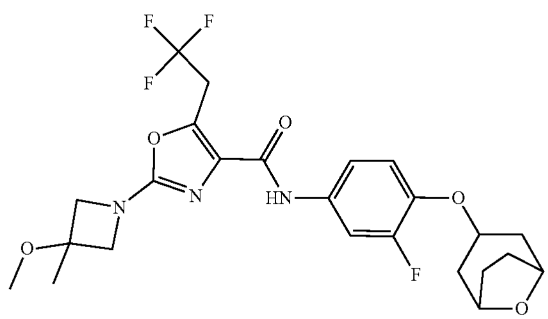 [SMILES: COC1(C)CN(c2nc(C(=O)Nc3ccc(OC4CC5CCC(C4)O5)c(F)c3)c(CC(F)(F)F)o2)C1] | N-(4-((8-oxabicyclo[3.2.1]octan-3-yl)oxy)-3-fluorophenyl)-2-(3-methoxy-3-methylazetidin-1-yl)-5-(2,2,2-trifluoroethyl)oxazole-4-carboxamide |
| 134 | 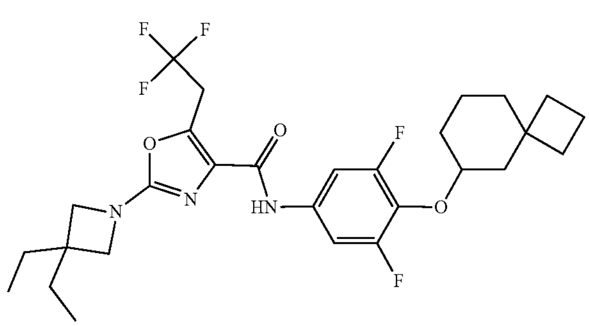 [SMILES: CCC1(CC)CN(c2nc(C(=O)Nc3cc(F)c(OC4CCCC5(CCC5)C4)c(F)c3)c(CC(F)(F)F)o2)C1] | 2-(3,3-diethylazetidin-1-yl)-N-(3,5-difluoro-4-(spiro[3.5]nonan-6-yloxy)phenyl)-5-(2,2,2-trifluoroethyl)oxazole-4-carboxamide |

-continued

| Ex. | Structures | Name |
|---|---|---|
| 135 | 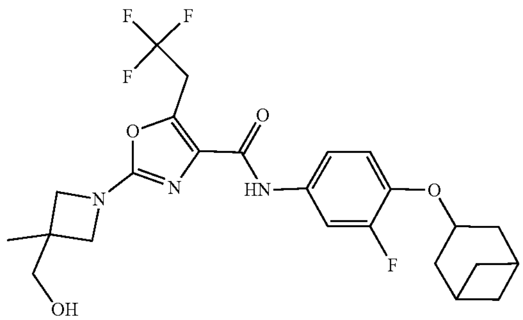 [SMILES: CC1(CO)CN(c2nc(C(=O)Nc3ccc(OC4CC5CC(C5)C4)c(F)c3)c(CC(F)(F)F)o2)C1] | N-(4-(bicyclo[3.1.1]heptan-3-yloxy)-3-fluorophenyl)-2-(3-(hydroxymethyl)-3-methylazetidin-1-yl)-5-(2,2,2-trifluoroethyl)oxazole-4-carboxamide |
| 136 | 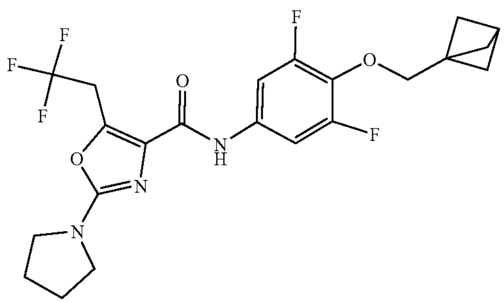 [SMILES: O=C(Nc1cc(F)c(OCC23CC(C2)C3)c(F)c1)c1nc(N2CCCC2)oc1CC(F)(F)F] | N-(4-(bicyclo[1.1.1]pentan-1-ylmethoxy)-3,5-difluorophenyl)-2-(pyrrolidin-1-yl)-5-(2,2,2-trifluoroethyl)oxazole-4-carboxamide |
| 137 | 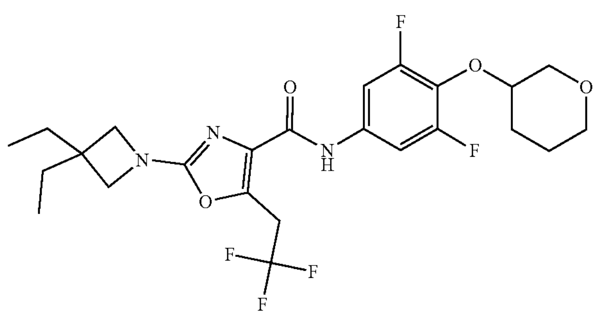 [SMILES: CCC1(CC)CN(c2nc(C(=O)Nc3cc(F)c(OC4CCCOC4)c(F)c3)c(CC(F)(F)F)o2)C1] | 2-(3,3-diethylazetidin-1-yl)-N-(3,5-difluoro-4-((tetrahydro-2H-pyran-3-yl)oxy)phenyl)-5-(2,2,2-trifluoroethyl)oxazole-4-carboxamide |
| 138 | 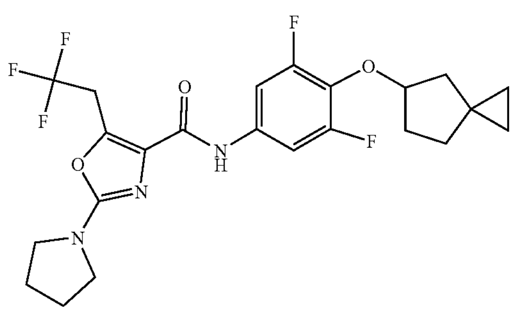 [SMILES: O=C(Nc1cc(F)c(OC2CCC3(CC3)C2)c(F)c1)c1nc(N2CCCC2)oc1CC(F)(F)F] | N-(3,5-difluoro-4-(spiro[2.4]heptan-5-yloxy)phenyl)-2-(pyrrolidin-1-yl)-5-(2,2,2-trifluoroethyl)oxazole-4-carboxamide |
| 139 | 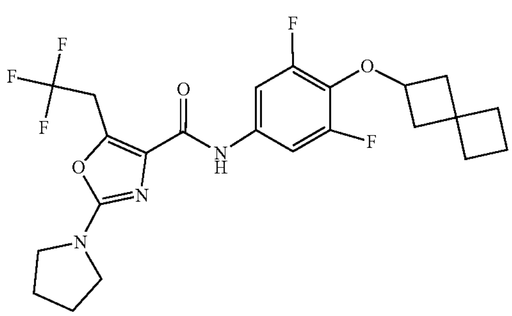 [SMILES: O=C(Nc1cc(F)c(OC2CC3(CCC3)C2)c(F)c1)c1nc(N2CCCC2)oc1CC(F)(F)F] | N-(3,5-difluoro-4-(spiro[3.3]heptan-2-yloxy)phenyl)-2-(pyrrolidin-1-yl)-5-(2,2,2-trifluoroethyl)oxazole-4-carboxamide |

| Ex. | Structures | Name |
|---|---|---|
| 140 | 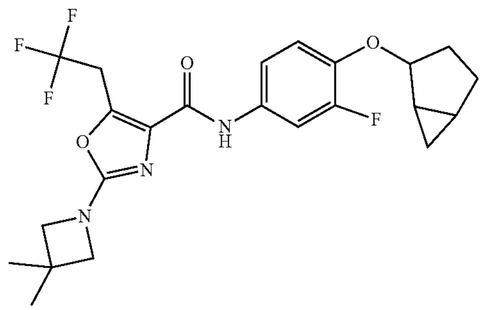 [SMILES: CC1(C)CN(c2nc(C(=O)Nc3ccc(OC4CCC5CC54)c(F)c3)c(CC(F)(F)F)o2)C1] | N-(4-(bicyclo[3.1.0]hexan-2-yloxy)-3-fluorophenyl)-2-(3,3-dimethylazetidin-1-yl)-5-(2,2,2-trifluoroethyl)oxazole-4-carboxamide |
| 141 | 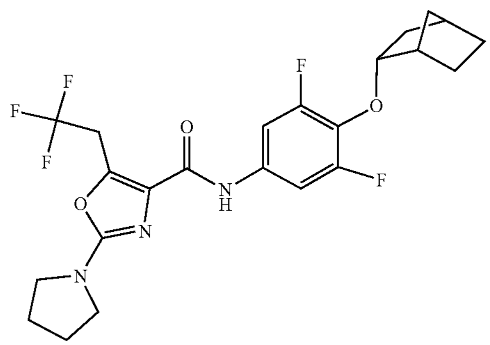 [SMILES: O=C(Nc1cc(F)c(OC2CC3CCC2C3)c(F)c1)c1nc(N2CCCC2)oc1CC(F)(F)F] | N-(4-(bicyclo[2.2.1]heptan-2-yloxy)-3,5-difluorophenyl)-2-(pyrrolidin-1-yl)-5-(2,2,2-trifluoroethyl)oxazole-4-carboxamide |
| 142 | 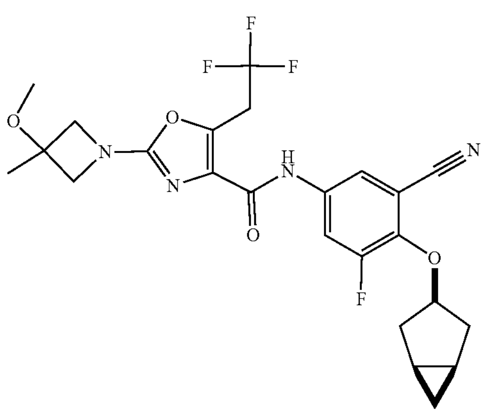 | N-(4-(cis-bicyclo[3.1.0]hexan-3-yloxy)-3-cyano-5-fluorophenyl)-2-(3-methoxy-3-methylazetidin-1-yl)-5-(2,2,2-trifluoroethyl)oxazole-4-carboxamide |
| 143 | 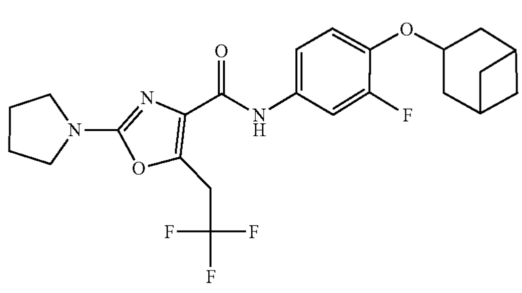 [SMILES: O=C(Nc1ccc(OC2CC3CC(C3)C2)c(F)c1)c1nc(N2CCCC2)oc1CC(F)(F)F] | N-(4-(bicyclo[3.1.1]heptan-3-yloxy)-3-fluorophenyl)-2-(pyrrolidin-1-yl)-5-(2,2,2-trifluoroethyl)oxazole-4-carboxamide |

-continued

| Ex. | Structures | Name |
| --- | --- | --- |
| 144 | 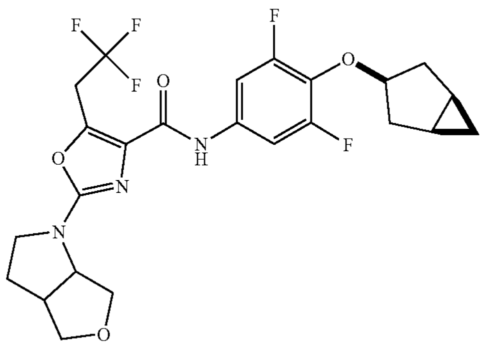 [SMILES: O=C(Nc1cc(F)c(O[C@@H]2C[C@@H]3C[C@@H]3C2)c(F)c1)c1nc(N2CCC3COCC32)oc1CC(F)(F)F] | N-(4-(cis-bicyclo[3.1.0]hexan-3-yloxy)-3,5-difluorophenyl)-2-(hexahydro-1H-furo[3,4-b]pyrrol-1-yl)-5-(2,2,2-trifluoroethyl)oxazole-4-carboxamide |
| 145 | 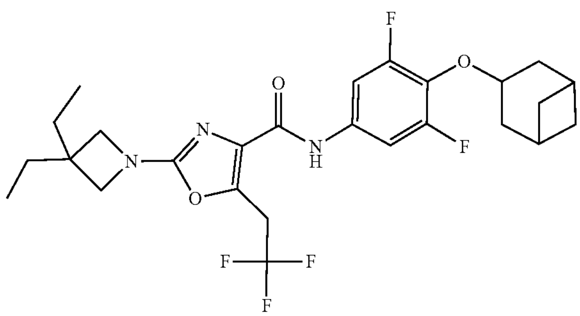 [SMILES: CCC1(CC)CN(c2nc(C(=O)Nc3cc(F)c(OC4CC5CC(C5)C4)c(F)c3)c(CC(F)(F)F)o2)C1] | N-(4-(bicyclo[3.1.1]heptan-3-yloxy)-3,5-difluorophenyl)-2-(3,3-diethylazetidin-1-yl)-5-(2,2,2-trifluoroethyl)oxazole-4-carboxamide |
| 146 | 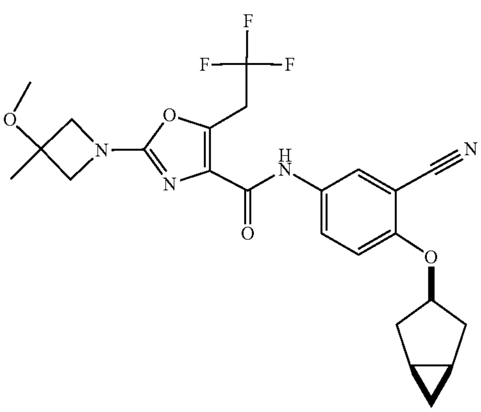 | N-(4-(cis-bicyclo[3.1.0]hexan-3-yloxy)-3-cyanophenyl)-2-(3-methoxy-3-methylazetidin-1-yl)-5-(2,2,2-trifluoroethyl)oxazole-4-carboxamide |
| 147 | 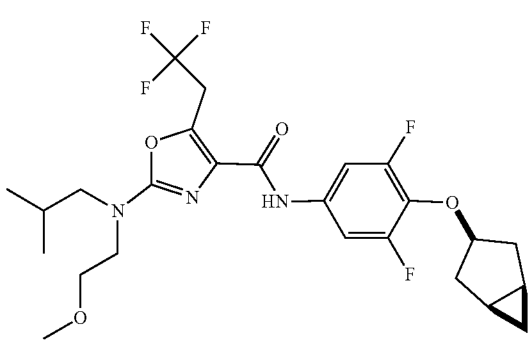 [SMILES: COCCN(CC(C)C)c1nc(C(=O)Nc2cc(F)c(O[C@@H]3C[C@@H]4C[C@@H]4C3)c(F)c2)c(CC(F)(F)F)o1] | N-(4-(cis-bicyclo[3.1.0]hexan-3-yloxy)-3,5-difluorophenyl)-2-(isobutyl(2-methoxyethyl)amino)-5-(2,2,2-trifluoroethyl)oxazole-4-carboxamide |

| Ex. | Structures | Name |
|---|---|---|
| 148 | 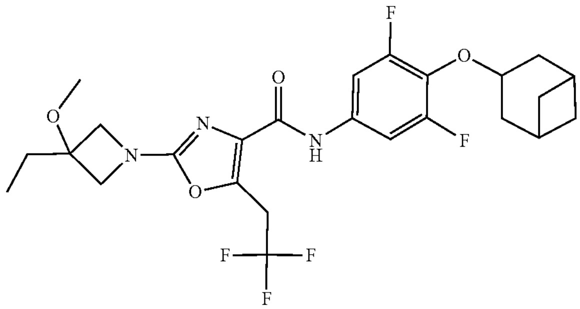 [SMILES: CCC1(OC)CN(c2nc(C(=O)Nc3cc(F)c(OC4CC5CC(C5)C4)c(F)c3)c(CC(F)(F)F)o2)C1] | N-(4-(bicyclo[3.1.1]heptan-3-yloxy)-3,5-difluorophenyl)-2-(3-ethyl-3-methoxyazetidin-1-yl)-5-(2,2,2-trifluoroethyl)oxazole-4-carboxamide |
| 149 | 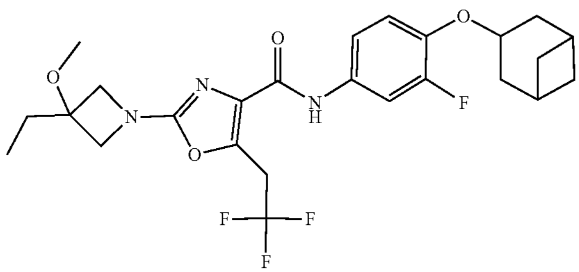 [SMILES: CCC1(OC)CN(c2nc(C(=O)Nc3ccc(OC4CC5CC(C5)C4)c(F)c3)c(CC(F)(F)F)o2)C1] | N-(4-(bicyclo[3.1.1]heptan-3-yloxy)-3-fluorophenyl)-2-(3-ethyl-3-methoxyazetidin-1-yl)-5-(2,2,2-trifluoroethyl)oxazole-4-carboxamide |
| 150 | 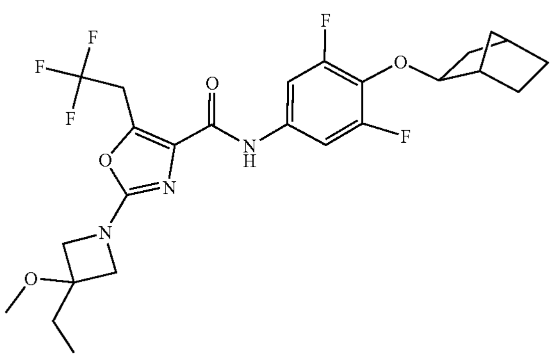 [SMILES: CCC1(OC)CN(c2nc(C(=O)Nc3cc(F)c(OC4CC5CCC4C5)c(F)c3)c(CC(F)(F)F)o2)C1] | N-(4-(bicyclo[2.2.1]heptan-2-yloxy)-3,5-difluorophenyl)-2-(3-ethyl-3-methoxyazetidin-1-yl)-5-(2,2,2-trifluoroethyl)oxazole-4-carboxamide |
| 151 | 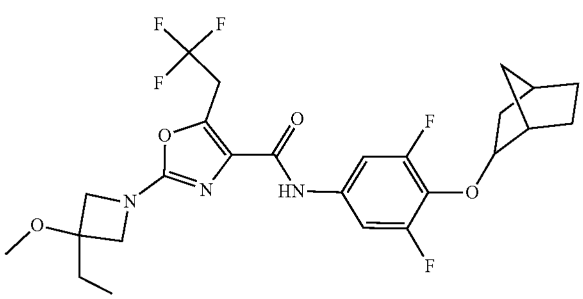 [SMILES: CCC1(OC)CN(c2nc(C(=O)Nc3cc(F)c(OC4CC5CCC4C5)c(F)c3)c(CC(F)(F)F)o2)C1] | N-(4-(((1S,4R)-bicyclo[2.2.1]heptan-2-yl)oxy)-3,5-difluorophenyl)-2-(3-ethyl-3-methoxyazetidin-1-yl)-5-(2,2,2-trifluoroethyl)oxazole-4-carboxamide |
| 152 | 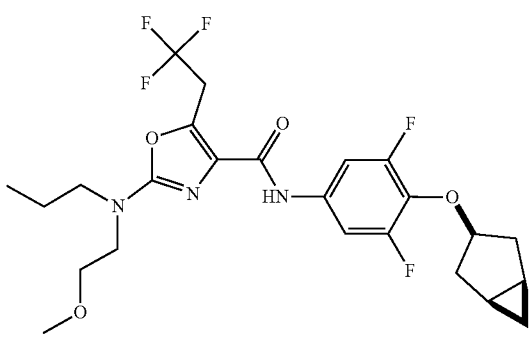 [SMILES: CCCN(CCOC)c1nc(C(=O)Nc2cc(F)c(O[C@@H]3C[C@@H]4C[C@@H]4C3)c(F)c2)c(CC(F)(F)F)o1] | N-(4-(cis-bicyclo[3.1.0]hexan-3-yloxy)-3,5-difluorophenyl)-2-((2-methoxyethyl)(propyl)amino)-5-(2,2,2-trifluoroethyl)oxazole-4-carboxamide |

| Ex. | Structures | Name |
|---|---|---|
| 153 | 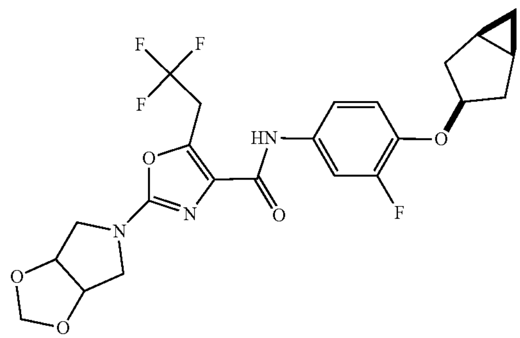 | N-(4-(cis-bicyclo[3.1.0]hexan-3-yloxy)-3-fluorophenyl)-2-(tetrahydro-5H-[1,3]dioxolo[4,5-c]pyrrol-5-yl)-5-(2,2,2-trifluoroethyl)oxazole-4-carboxamide |
| 154 | 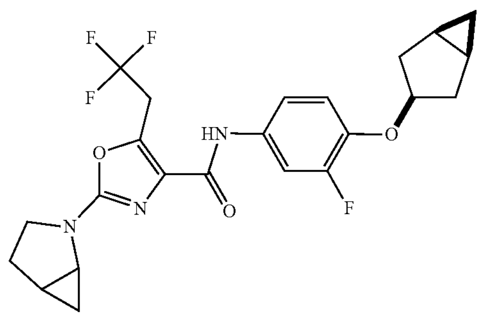 | 2-(2-azabicyclo[3.1.0]hexan-2-yl)-N-(4-(cis-bicyclo[3.1.0]hexan-3-yloxy)-3-fluorophenyl)-5-(2,2,2-trifluoroethyl)oxazole-4-carboxamide |
| 155 | 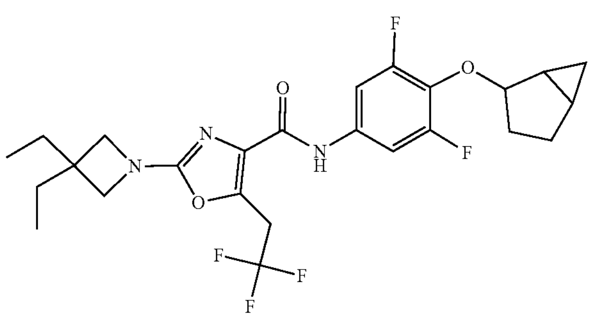 [SMILES: CCC1(CC)CN(c2nc(C(=O)Nc3cc(F)c(OC4CCC5CC54)c(F)c3)c(CC(F)(F)F)o2)C1] | N-(4-(bicyclo[3.1.0]hexan-2-yloxy)-3,5-difluorophenyl)-2-(3,3-diethylazetidin-1-yl)-5-(2,2,2-trifluoroethyl)oxazole-4-carboxamide |
| 156 | 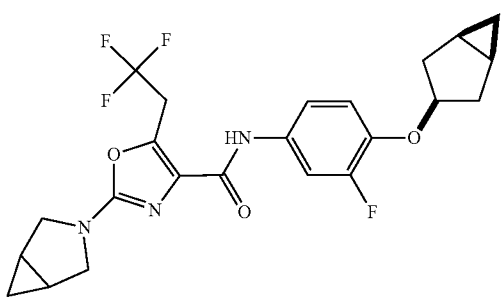 [SMILES: O=C(Nc1ccc(O[C@@H]2C[C@@H]3C[C@@H]3C2)c(F)c1)c1nc(N2CC3CC3C2)oc1CC(F)(F)F] | 2-(3-azabicyclo[3.1.0]hexan-3-yl)-N-(4-(cis-bicyclo[3.1.0]hexan-3-yloxy)-3-fluorophenyl)-5-(2,2,2-trifluoroethyl)oxazole-4-carboxamide |

| Ex. | Structures | Name |
|---|---|---|
| 157 | 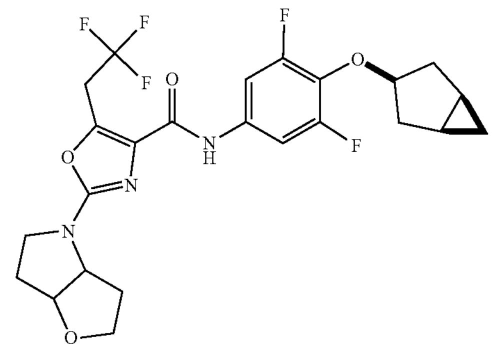 [SMILES: O=C(Nc1cc(F)c(O[C@@H]2C[C@@H]3C[C@@H]3C2)c(F)c1)c1nc(N2CCC3OCCC32)oc1CC(F)(F)F] | N-(4-(cis-bicyclo[3.1.0]hexan-3-yloxy)-3,5-difluorophenyl)-2-(hexahydro-4H-furo[3,2-b]pyrrol-4-yl)-5-(2,2,2-trifluoroethyl)oxazole-4-carboxamide |
| 158 | 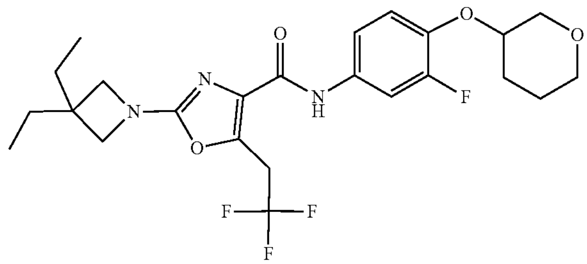 [SMILES: CCC1(CC)CN(c2nc(C(=O)Nc3ccc(OC4CCCOC4)c(F)c3)c(CC(F)(F)F)o2)C1] | 2-(3,3-diethylazetidin-1-yl)-N-(3-fluoro-4-((tetrahydro-2H-pyran-3-yl)oxy)phenyl)-5-(2,2,2-trifluoroethyl)oxazole-4-carboxamide |
| 159 | 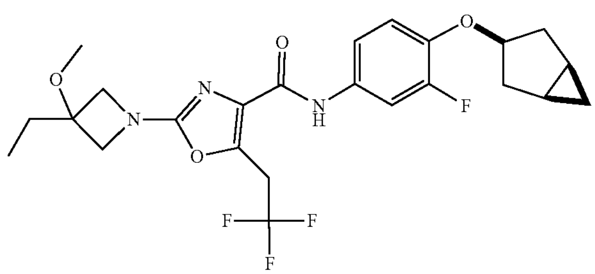 [SMILES: CCC1(OC)CN(c2nc(C(=O)Nc3ccc(O[C@@H]4C[C@@H]5C[C@@H]5C4)c(F)c3)c(CC(F)(F)F)o2)C1] | N-(4-(cis-bicyclo[3.1.0]hexan-3-yloxy)-3-fluorophenyl)-2-(3-ethyl-3-methoxyazetidin-1-yl)-5-(2,2,2-trifluoroethyl)oxazole-4-carboxamide |
| 160 | 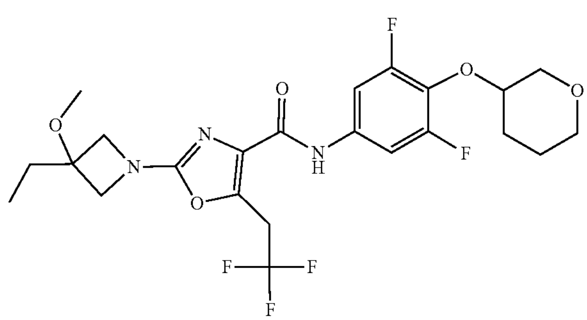 [SMILES: CCC1(OC)CN(c2nc(C(=O)Nc3cc(F)c(OC4CCCOC4)c(F)c3)c(CC(F)(F)F)o2)C1] | N-(3,5-difluoro-4-((tetrahydro-2H-pyran-3-yl)oxy)phenyl)-2-(3-ethyl-3-methoxyazetidin-1-yl)-5-(2,2,2-trifluoroethyl)oxazole-4-carboxamide |
| 161 | 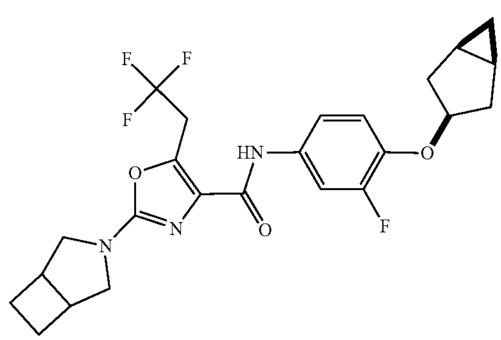 [SMILES: O=C(Nc1ccc(O[C@@H]2C[C@@H]3C[C@@H]3C2)c(F)c1)c1nc(N2CC3CCC3C2)oc1CC(F)(F)F] | N-(4-(cis-bicyclo[3.1.0]hexan-3-yloxy)-3-fluorophenyl)-2-(3-azabicyclo[3.2.0]heptan-3-yl)-5-(2,2,2-trifluoroethyl)oxazole-4-carboxamide |

| Ex. | Structures | Name |
|---|---|---|
| 162 | 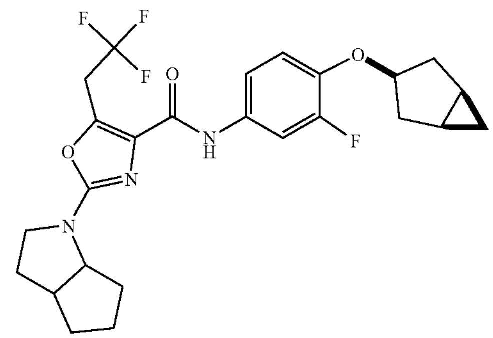 [SMILES: O=C(Nc1ccc(O[C@@H]2C[C@@H]3C[C@@H]3C2)c(F)c1)c1nc(N2CCC3CCCC32)oc1CC(F)(F)F] | N-(4-(cis-bicyclo[3.1.0]hexan-3-yloxy)-3-fluorophenyl)-2-(hexahydrocyclopenta[b]pyrrol-1(2H)-yl)-5-(2,2,2-trifluoroethyl)oxazole-4-carboxamide |
| 163 | 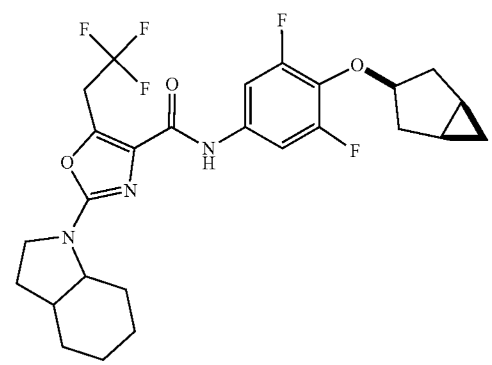 [SMILES: O=C(Nc1cc(F)c(O[C@@H]2C[C@@H]3C[C@@H]3C2)c(F)c1)c1nc(N2CCC3CCCCC32)oc1CC(F)(F)F] | N-(4-(cis-bicyclo[3.1.0]hexan-3-yloxy)-3,5-difluorophenyl)-2-(octahydro-1H-indol-1-yl)-5-(2,2,2-trifluoroethyl)oxazole-4-carboxamide |
| 164 | 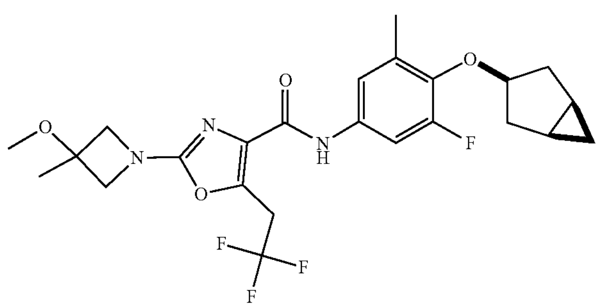 [SMILES: COC1(C)CN(c2nc(C(=O)Nc3cc(C)c(O[C@@H]4C[C@@H]5C[C@@H]5C4)c(F)c3)c(CC(F)(F)F)o2)C1] | N-(4-(cis-bicyclo[3.1.0]hexan-3-yloxy)-3-fluoro-5-methylphenyl)-2-(3-methoxy-3-methylazetidin-1-yl)-5-(2,2,2-trifluoroethyl)oxazole-4-carboxamide |
| 165 | 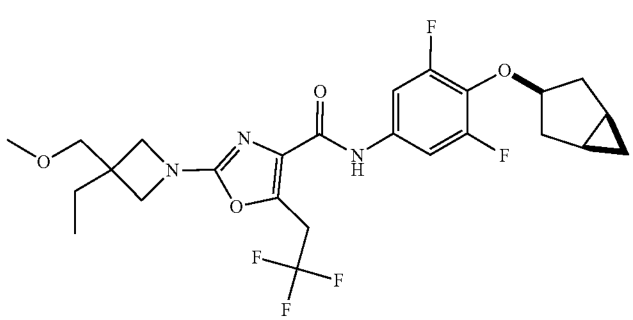 [SMILES: CCC1(COC)CN(c2nc(C(=O)Nc3cc(F)c(O[C@@H]4C[C@@H]5C[C@@H]5C4)c(F)c3)c(CC(F)(F)F)o2)C1] | N-(4-(cis-bicyclo[3.1.0]hexan-3-yloxy)-3,5-difluorophenyl)-2-(3-ethyl-3-(methoxymethyl)azetidin-1-yl)-5-(2,2,2-trifluoroethyl)oxazole-4-carboxamide |

| Ex. | Structures | Name |
|---|---|---|
| 166 | 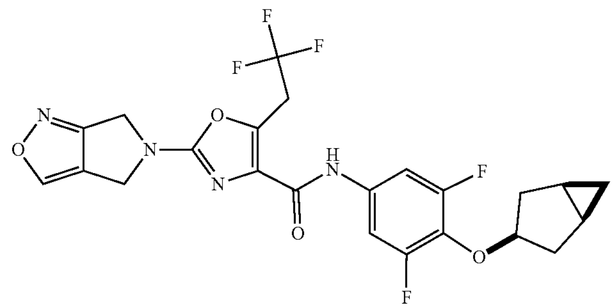 [SMILES: O=C(Nc1cc(F)c(O[C@@H]2C[C@@H]3C[C@@H]3C2)c(F)c1)c1nc(N2Cc3conc3C2)oc1CC(F)(F)F] | N-(4-(cis-bicyclo[3.1.0]hexan-3-yloxy)-3,5-difluorophenyl)-2-(4H-pyrrolo[3,4-c]isoxazol-5(6H)-yl)-5-(2,2,2-trifluoroethyl)oxazole-4-carboxamide |
| 167 | 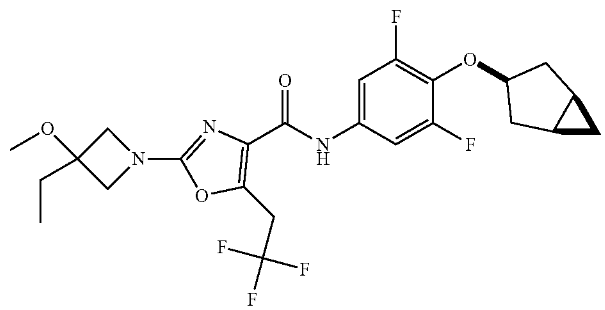 | N-(4-(cis-bicyclo[3.1.0]hexan-3-yloxy)-3,5-difluorophenyl)-2-(3-ethyl-3-methoxyazetidin-1-yl)-5-(2,2,2-trifluoroethyl)oxazole-4-carboxamide |
| 168 | 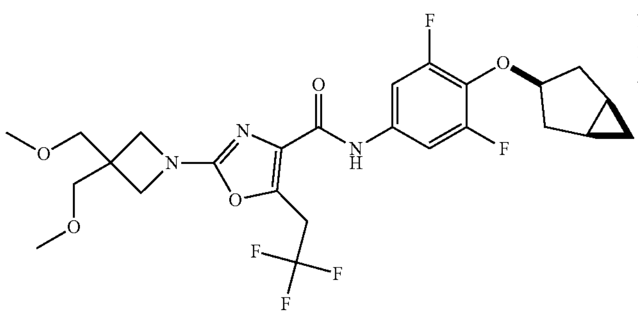 | N-(4-(cis-bicyclo[3.1.0]hexan-3-yloxy)-3,5-difluorophenyl)-2-(3,3-bis(methoxymethyl)azetidin-1-yl)-5-(2,2,2-trifluoroethyl)oxazole-4-carboxamide |
| 169 | 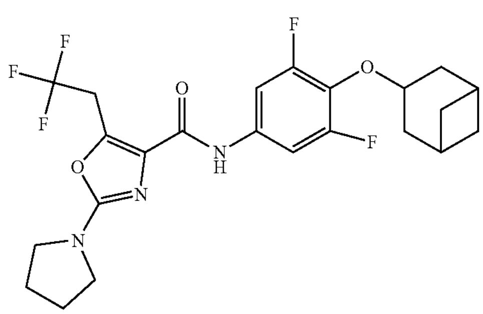 [SMILES: O=C(Nc1cc(F)c(OC2CC3CC(C3)C2)c(F)c1)c1nc(N2CCCC2)oc1CC(F)(F)F] | N-(4-(bicyclo[3.1.1]heptan-3-yloxy)-3,5-difluorophenyl)-2-(pyrrolidin-1-yl)-5-(2,2,2-trifluoroethyl)oxazole-4-carboxamide |
| 170 | 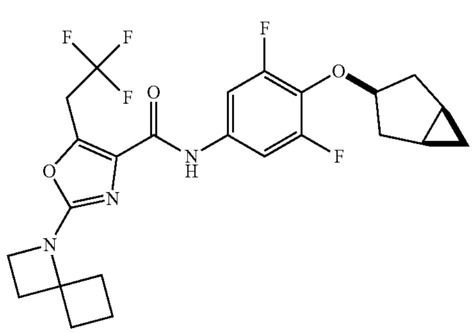 | N-(4-(cis-bicyclo[3.1.0]hexan-3-yloxy)-3,5-difluorophenyl)-2-(1-azaspiro[3.3]heptan-1-yl)-5-(2,2,2-trifluoroethyl)oxazole-4-carboxamide |

| Ex. | Structures | Name |
|---|---|---|
| 171 | 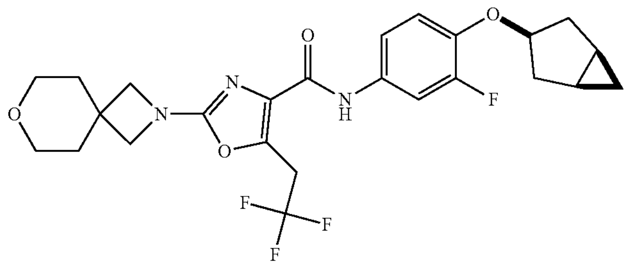 | N-(4-(cis-bicyclo[3.1.0]hexan-3-yloxy)-3-fluorophenyl)-2-(7-oxa-2-azaspiro[3.5]nonan-2-yl)-5-(2,2,2-trifluoroethyl)oxazole-4-carboxamide |
| 172 | 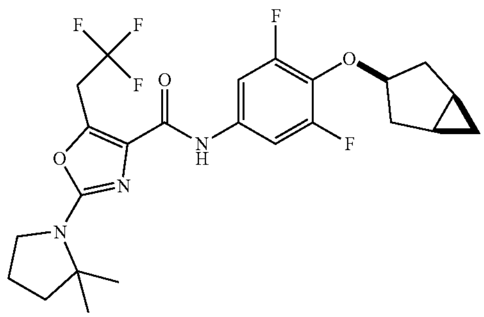 | N-(4-(cis-bicyclo[3.1.0]hexan-3-yloxy)-3,5-difluorophenyl)-2-(2,2-dimethylpyrrolidin-1-yl)-5-(2,2,2-trifluoroethyl)oxazole-4-carboxamide |
| 173 | 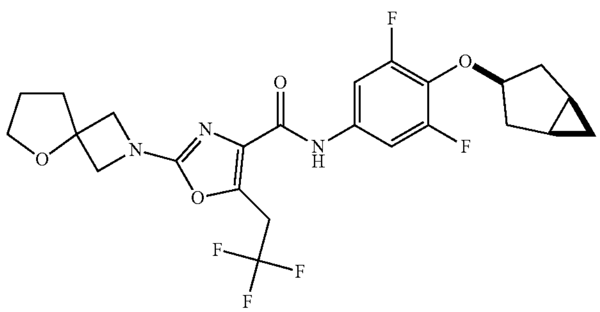 | N-(4-(cis-bicyclo[3.1.0]hexan-3-yloxy)-3,5-difluorophenyl)-2-(5-oxa-2-azaspiro[3.4]octan-2-yl)-5-(2,2,2-trifluoroethyl)oxazole-4-carboxamide |
| 174 | 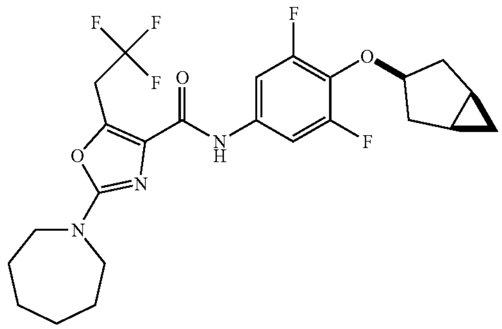 | 2-(azepan-1-yl)-N-(4-(cis-bicyclo[3.1.0]hexan-3-yloxy)-3,5-difluorophenyl)-5-(2,2,2-trifluoroethyl)oxazole-4-carboxamide |
| 175 | 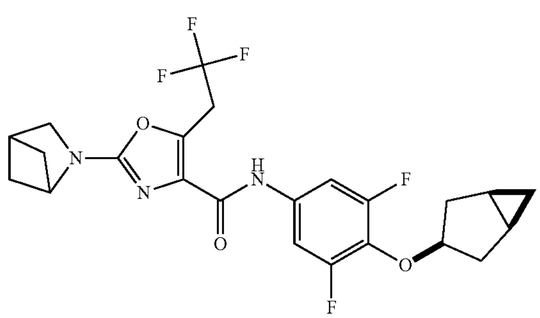 | 2-(2-azabicyclo[2.1.1]hexan-2-yl)-N-(4-(cis-bicyclo[3.1.0]hexan-3-yloxy)-3,5-difluorophenyl)-5-(2,2,2-trifluoroethyl)oxazole-4-carboxamide |

| Ex. | Structures | Name |
|---|---|---|
| 176 | 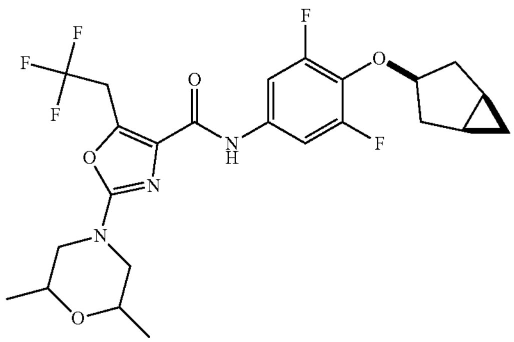 | N-(4-(cis-bicyclo[3.1.0]hexan-3-yloxy)-3,5-difluorophenyl)-2-(2,6-dimethylmorpholino)-5-(2,2,2-trifluoroethyl)oxazole-4-carboxamide |
| 177 | 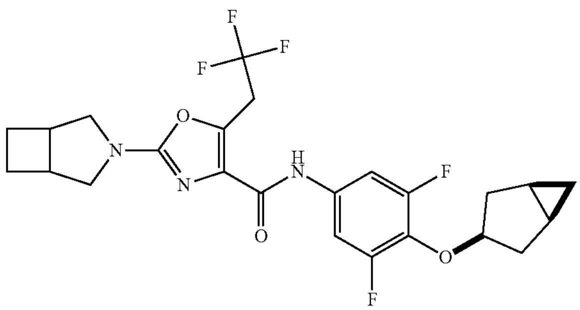 | N-(4-(cis-bicyclo[3.1.0]hexan-3-yloxy)-3,5-difluorophenyl)-2-(3-azabicyclo[3.2.0]heptan-3-yl)-5-(2,2,2-trifluoroethyl)oxazole-4-carboxamide |
| 178 | 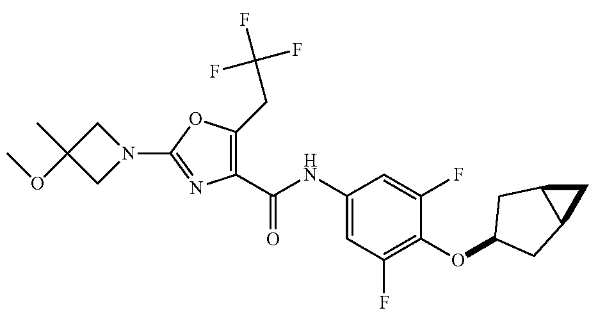 | N-(4-(cis-bicyclo[3.1.0]hexan-3-yloxy)-3,5-difluorophenyl)-2-(3-methoxy-3-methylazetidin-1-yl)-5-(2,2,2-trifluoroethyl)oxazole-4-carboxamide |
| 179 | 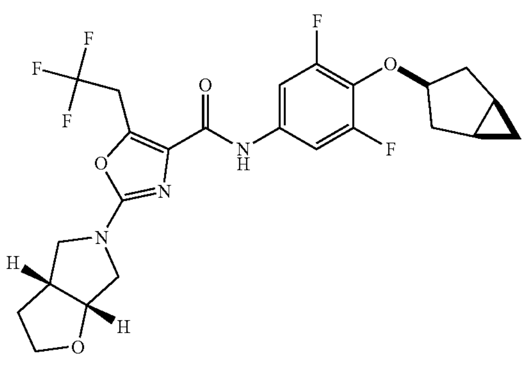 | N-(4-(cis-bicyclo[3.1.0]hexan-3-yloxy)-3,5-difluorophenyl)-2-((3aR,6aR)-hexahydro-5H-furo[2,3-c]pyrrol-5-yl)-5-(2,2,2-trifluoroethyl)oxazole-4-carboxamide |

| Ex. | Structures | Name |
|---|---|---|
| 180 | 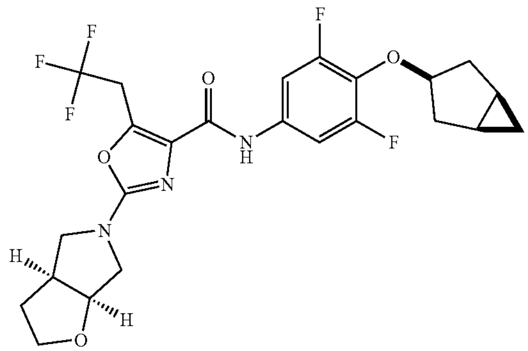 | N-(4-(cis-bicyclo[3.1.0]hexan-3-yloxy)-3,5-difluorophenyl)-2-((3aS,6aS)-hexahydro-5H-furo[2,3-c]pyrrol-5-yl)-5-(2,2,2-trifluoroethyl)oxazole-4-carboxamide |
| 181 | 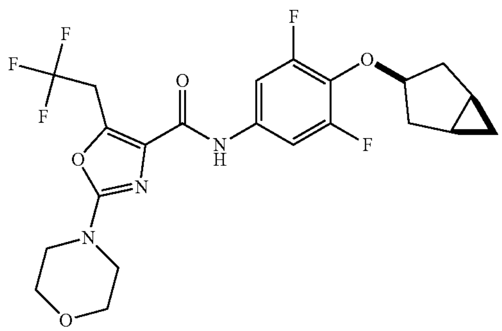 | N-(4-(cis-bicyclo[3.1.0]hexan-3-yloxy)-3,5-difluorophenyl)-2-morpholino-5-(2,2,2-trifluoroethyl)oxazole-4-carboxamide |
| 182 | 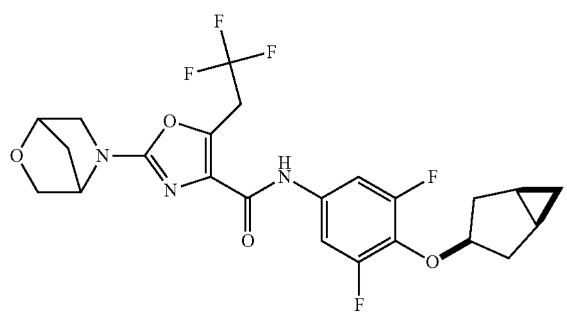 | 2-(2-oxa-5-azabicyclo[2.2.1]heptan-5-yl)-N-(4-(cis-bicyclo[3.1.0]hexan-3-yloxy)-3,5-difluorophenyl)-5-(2,2,2-trifluoroethyl)oxazole-4-carboxamide |
| 183 | 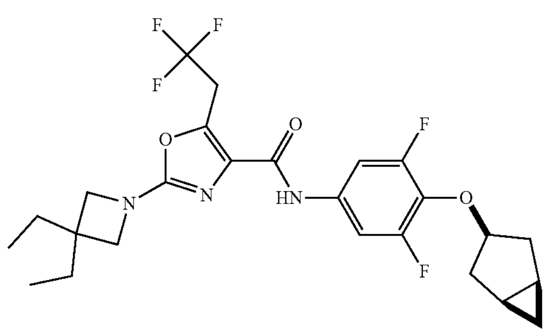 | N-(4-(cis-bicyclo[3.1.0]hexan-3-yloxy)-3,5-difluorophenyl)-2-(3,3-diethylazetidin-1-yl)-5-(2,2,2-trifluoroethyl)oxazole-4-carboxamide |

| Ex. | Structures | Name |
|---|---|---|
| 184 | 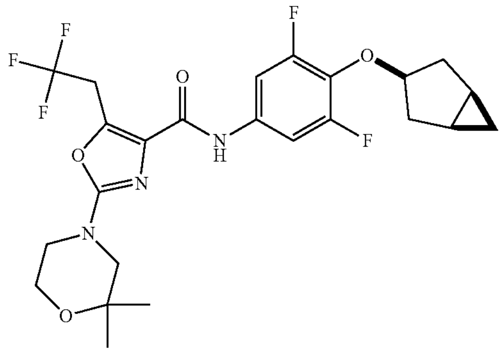 | N-(4-(cis-bicyclo[3.1.0]hexan-3-yloxy)-3,5-difluorophenyl)-2-(2,2-dimethylmorpholino)-5-(2,2,2-trifluoroethyl)oxazole-4-carboxamide |
| 185 | 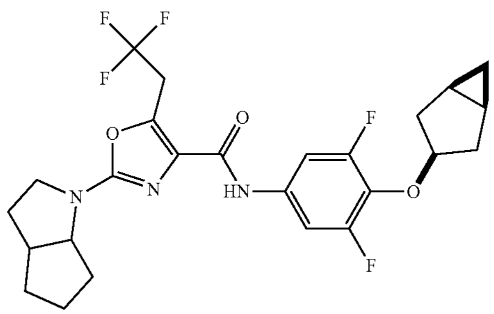 | N-(4-(cis-bicyclo[3.1.0]hexan-3-yloxy)-3,5-difluorophenyl)-2-(hexahydrocyclopenta[b]pyrrol-1(2H)-yl)-5-(2,2,2-trifluoroethyl)oxazole-4-carboxamide |
| 186 | 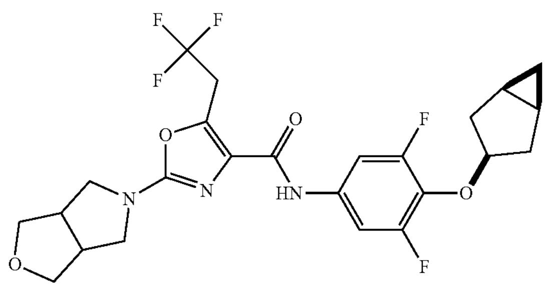 | N-(4-(cis-bicyclo[3.1.0]hexan-3-yloxy)-3,5-difluorophenyl)-2-(tetrahydro-1H-furo[3,4-c]pyrrol-5(3H)-yl)-5-(2,2,2-trifluoroethyl)oxazole-4-carboxamide |
| 187 | 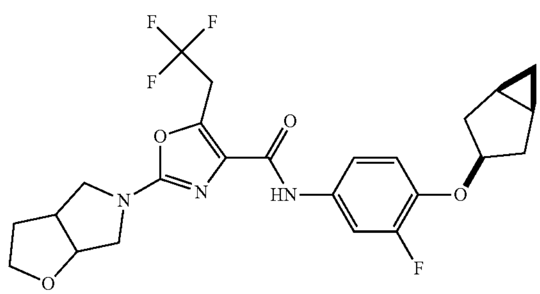 | N-(4-(cis-bicyclo[3.1.0]hexan-3-yloxy)-3-fluorophenyl)-2-(hexahydro-5H-furo[2,3-c]pyrrol-5-yl)-5-(2,2,2-trifluoroethyl)oxazole-4-carboxamide |
| 188 | 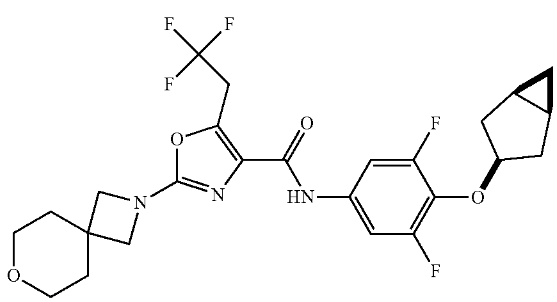 | N-(4-(cis-bicyclo[3.1.0]hexan-3-yloxy)-3,5-difluorophenyl)-2-(7-oxa-2-azaspiro[3.5]nonan-2-yl)-5-(2,2,2-trifluoroethyl)oxazole-4-carboxamide |

| Ex. | Structures | Name |
|---|---|---|
| 189 | 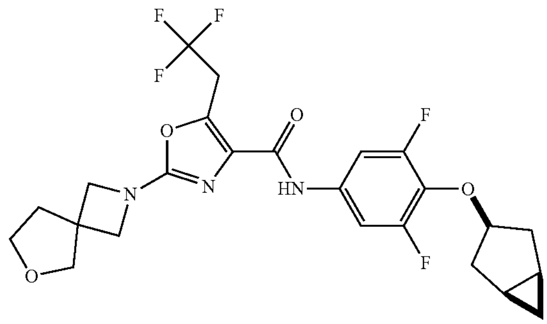 | N-(4-(cis-bicyclo[3.1.0]hexan-3-yloxy)-3,5-difluorophenyl)-2-(6-oxa-2-azaspiro[3.4]octan-2-yl)-5-(2,2,2-trifluoroethyl)oxazole-4-carboxamide |
| 190 | 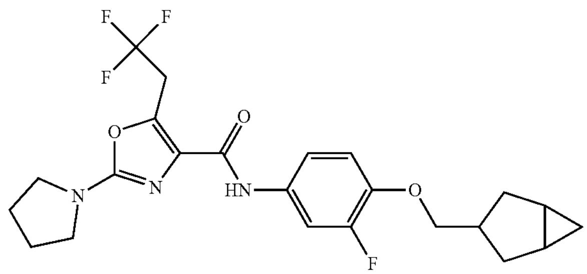 [SMILES: O=C(Nc1ccc(OCC2CC3CC3C2)c(F)c1)c1nc(N2CCCC2)oc1CC(F)(F)F] | N-(4-(bicyclo[3.1.0]hexan-3-ylmethoxy)-3-fluorophenyl)-2-(pyrrolidin-1-yl)-5-(2,2,2-trifluoroethyl)oxazole-4-carboxamide |
| 191 | 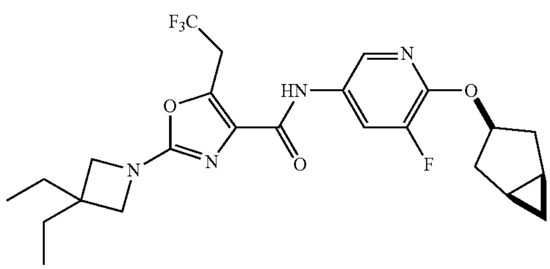 | N-(6-(cis-bicyclo[3.1.0]hexan-3-yloxy)-5-fluoropyridin-3-yl)-2-(3,3-diethylazetidin-1-yl)-5-(2,2,2-trifluoroethyl)oxazole-4-carboxamide |
| 192 | 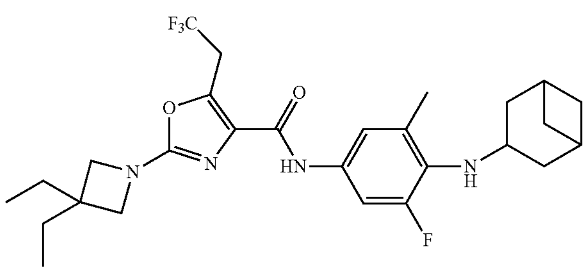 [SMILES: CCC1(CC)CN(c2nc(C(=O)Nc3cc(C)c(NC4CC5CC(C5)C4)c(F)c3)c(CC(F)(F)F)o2)C1] | N-(4-(bicyclo[3.1.1]heptan-3-ylamino)-3-fluoro-5-methylphenyl)-2-(3,3-diethylazetidin-1-yl)-5-(2,2,2-trifluoroethyl)oxazole-4-carboxamide |
| 193 | 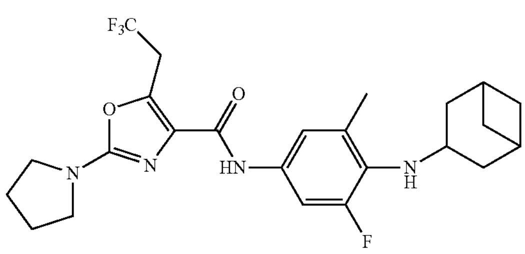 [SMILES: Cc1cc(NC(=O)c2nc(N3CCCC3)oc2CC(F)(F)F)cc(F)c1NC1CC2CC(C2)C1] | N-(4-(bicyclo[3.1.1]heptan-3-ylamino)-3-fluoro-5-methylphenyl)-2-(pyrrolidin-1-yl)-5-(2,2,2-trifluoroethyl)oxazole-4-carboxamide |

-continued

| Ex. | Structures | Name |
|---|---|---|
| 194 | 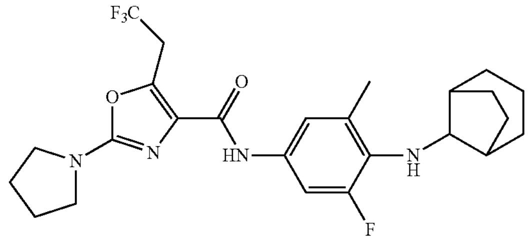 [SMILES: Cc1cc(NC(=O)c2nc(N3CCCC3)oc2CC(F)(F)F)cc(F)c1NC1C2CCCC1CC2] | N-(4-(bicyclo[3.2.1]octan-8-ylamino)-3-fluoro-5-methylphenyl)-2-(pyrrolidin-1-yl)-5-(2,2,2-trifluoroethyl)oxazole-4-carboxamide |
| 195 | 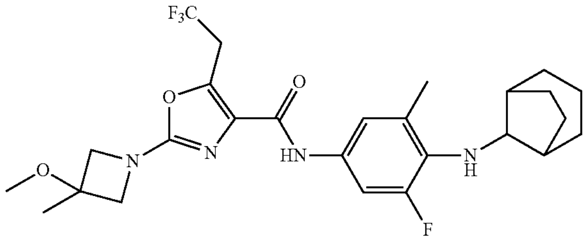 [SMILES: COC1(C)CN(c2nc(C(=O)Nc3cc(C)c(NC4C5CCCC4CC5)c(F)c3)c(CC(F)(F)F)o2)C1] | N-(4-(bicyclo[3.2.1]octan-8-ylamino)-3-fluoro-5-methylphenyl)-2-(3-methoxy-3-methylazetidin-1-yl)-5-(2,2,2-trifluoroethyl)oxazole-4-carboxamide |
| 196 | 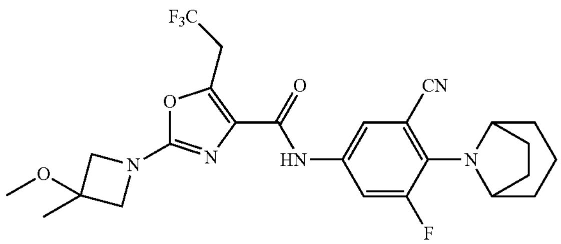 [SMILES: COC1(C)CN(c2nc(C(=O)Nc3cc(F)c(N4C5CCCC4CC5)c(C#N)c3)c(CC(F)(F)F)o2)C1] | N-(4-(8-azabicyclo[3.2.1]octan-8-yl)-3-cyano-5-fluorophenyl)-2-(3-methoxy-3-methylazetidin-1-yl)-5-(2,2,2-trifluoroethyl)oxazole-4-carboxamide |
| 197 | 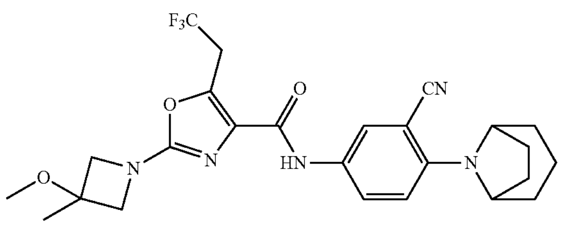 [SMILES: COC1(C)CN(c2nc(C(=O)Nc3ccc(N4C5CCCC4CC5)c(C#N)c3)c(CC(F)(F)F)o2)C1] | N-(4-(8-azabicyclo[3.2.1]octan-8-yl)-3-cyanophenyl)-2-(3-methoxy-3-methylazetidin-1-yl)-5-(2,2,2-trifluoroethyl)oxazole-4-carboxamide |
| 198 | 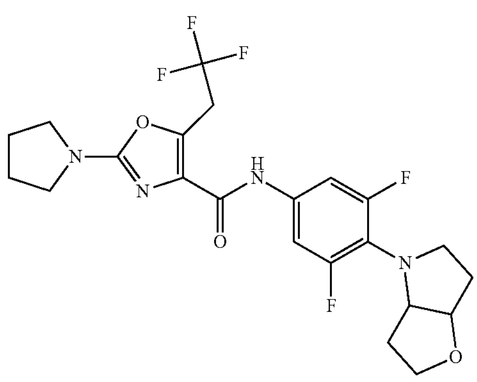 [SMILES: O=C(Nc1cc(F)c(N2CCC3OCCC32)c(F)c1)c1nc(N2CCCC2)oc1CC(F)(F)F] | N-(3,5-difluoro-4-(hexahydro-4H-furo[3,2-b]pyrrol-4-yl)phenyl)-2-(pyrrolidin-1-yl)-5-(2,2,2-trifluoroethyl)oxazole-4-carboxamide |
| 199 | 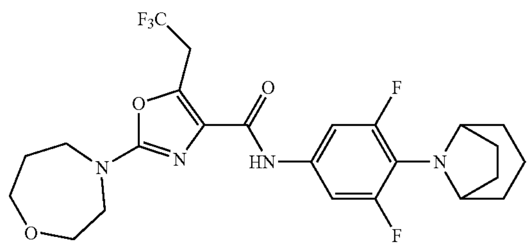 [SMILES: O=C(Nc1cc(F)c(N2C3CCCC2CC3)c(F)c1)c1nc(N2CCCOCC2)oc1CC(F)(F)F] | N-(4-(8-azabicyclo[3.2.1]octan-8-yl)-3,5-difluorophenyl)-2-(1,4-oxazepan-4-yl)-5-(2,2,2-trifluoroethyl)oxazole-4-carboxamide |

| Ex. | Structures | Name |
|---|---|---|
| 200 | 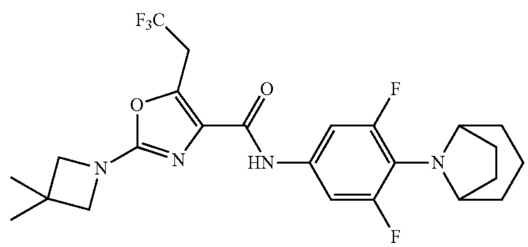 [SMILES: CC1(C)CN(c2nc(C(=O)Nc3cc(F)c(N4C5CCCC4CC5)c(F)c3)c(CC(F)(F)F)o2)C1] | N-(4-(8-azabicyclo[3.2.1]octan-8-yl)-3,5-difluorophenyl)-2-(3,3-dimethylazetidin-1-yl)-5-(2,2,2-trifluoroethyl)oxazole-4-carboxamide |
| 201 | 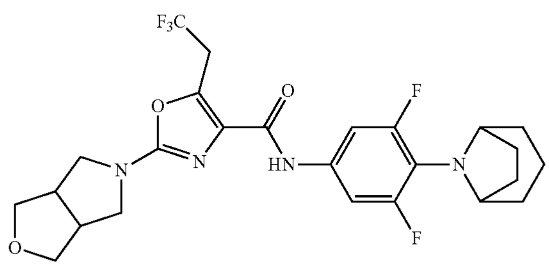 [SMILES: O=C(Nc1cc(F)c(N2C3CCCC2CC3)c(F)c1)c1nc(N2CC3COCC3C2)oc1CC(F)(F)F] | N-(4-(8-azabicyclo[3.2.1]octan-8-yl)-3,5-difluorophenyl)-2-(tetrahydro-1H-furo[3,4-c]pyrrol-5(3H)-yl)-5-(2,2,2-trifluoroethyl)oxazole-4-carboxamide |
| 202 | 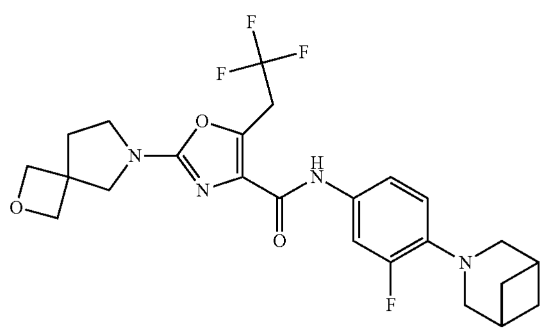 [SMILES: O=C(Nc1ccc(N2CC3CC(C3)C2)c(F)c1)c1nc(N2CCC3(COC3)C2)oc1CC(F)(F)F] | N-(4-(3-azabicyclo[3.1.1]heptan-3-yl)-3-fluorophenyl)-2-(2-oxa-6-azaspiro[3.4]octan-6-yl)-5-(2,2,2-trifluoroethyl)oxazole-4-carboxamide |
| 203 | 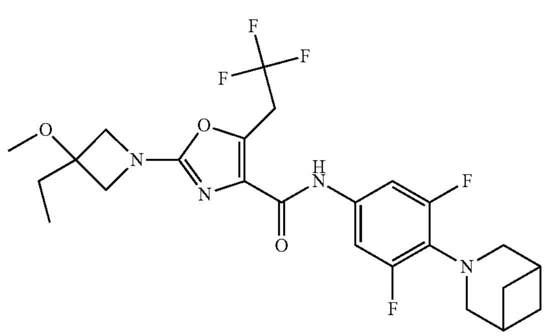 [SMILES: CCC1(OC)CN(c2nc(C(=O)Nc3cc(F)c(N4CC5CC(C5)C4)c(F)c3)c(CC(F)(F)F)o2)C1] | N-(4-(3-azabicyclo[3.1.1]heptan-3-yl)-3,5-difluorophenyl)-2-(3-ethyl-3-methoxyazetidin-1-yl)-5-(2,2,2-trifluoroethyl)oxazole-4-carboxamide |
| 204 | 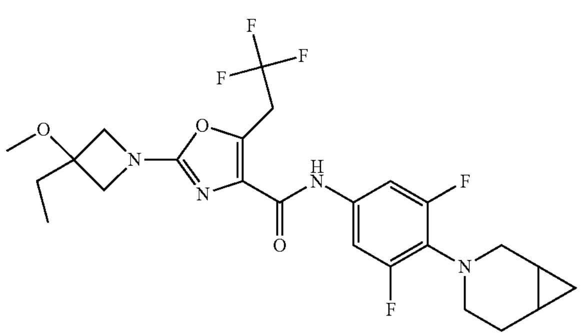 [SMILES: CCC1(OC)CN(c2nc(C(=O)Nc3cc(F)c(N4CCC5CC5C4)c(F)c3)c(CC(F)(F)F)o2)C1] | N-(4-(3-azabicyclo[4.1.0]heptan-3-yl)-3,5-difluorophenyl)-2-(3-ethyl-3-methoxyazetidin-1-yl)-5-(2,2,2-trifluoroethyl)oxazole-4-carboxamide |

-continued

| Ex. | Structures | Name |
|---|---|---|
| 205 | 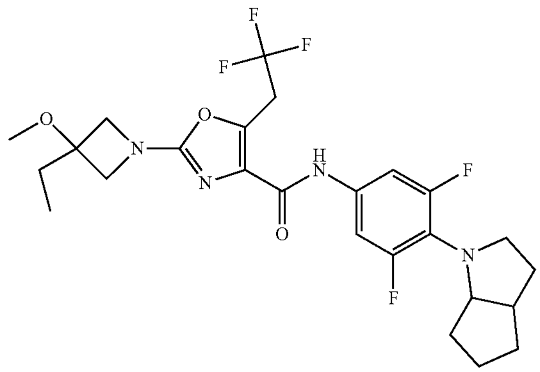 [SMILES: CCC1(OC)CN(c2nc(C(=O)Nc3cc(F)c(N4CCC5CCCC54)c(F)c3)c(CC(F)(F)F)o2)C1] | N-(3,5-difluoro-4-(hexahydrocyclopenta[b]pyrrol-1(2H)-yl)phenyl)-2-(3-ethyl-3-methoxyazetidin-1-yl)-5-(2,2,2-trifluoroethyl)oxazole-4-carboxamide |
| 206 | 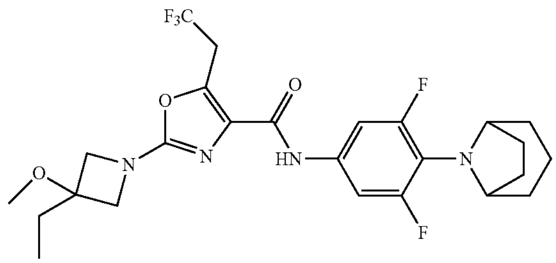 [SMILES: CCC1(OC)CN(c2nc(C(=O)Nc3cc(F)c(N4C5CCCC4CC5)c(F)c3)c(CC(F)(F)F)o2)C1] | N-(4-(8-azabicyclo[3.2.1]octan-8-yl)-3,5-difluorophenyl)-2-(3-ethyl-3-methoxyazetidin-1-yl)-5-(2,2,2-trifluoroethyl)oxazole-4-carboxamide |
| 207 | 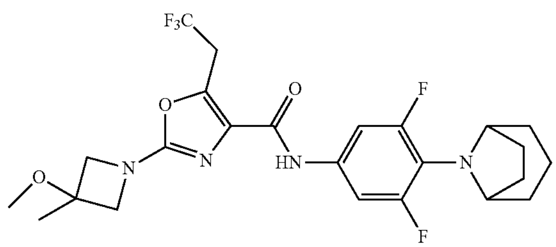 [SMILES: COC1(C)CN(c2nc(C(=O)Nc3cc(F)c(N4C5CCCC4CC5)c(F)c3)c(CC(F)(F)F)o2)C1] | N-(4-(8-azabicyclo[3.2.1]octan-8-yl)-3,5-difluorophenyl)-2-(3-methoxy-3-methylazetidin-1-yl)-5-(2,2,2-trifluoroethyl)oxazole-4-carboxamide |
| 208 | 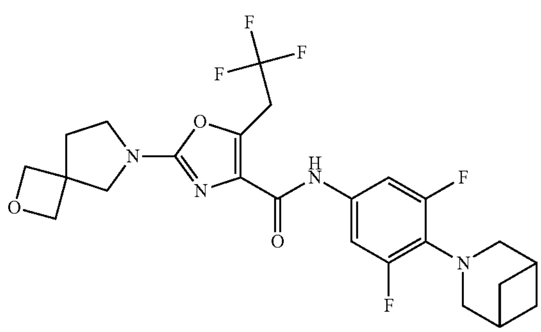 [SMILES: O=C(Nc1cc(F)c(N2CC3CC(C3)C2)c(F)c1)c1nc(N2CCC3(COC3)C2)oc1CC(F)(F)F] | N-(4-(3-azabicyclo[3.1.1]heptan-3-yl)-3,5-difluorophenyl)-2-(2-oxa-6-azaspiro[3.4]octan-6-yl)-5-(2,2,2-trifluoroethyl)oxazole-4-carboxamide |
| 209 | 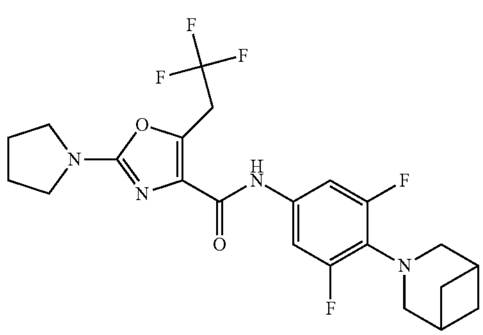 [SMILES: O=C(Nc1cc(F)c(N2CC3CC(C3)C2)c(F)c1)c1nc(N2CCCC2)oc1CC(F)(F)F] | N-(4-(3-azabicyclo[3.1.1]heptan-3-yl)-3,5-difluorophenyl)-2-(pyrrolidin-1-yl)-5-(2,2,2-trifluoroethyl)oxazole-4-carboxamide |

| Ex. | Structures | Name |
|---|---|---|
| 210 | 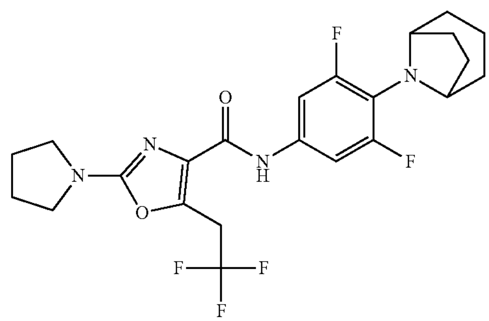 [SMILES: O=C(Nc1cc(F)c(N2C3CCCC2CC3)c(F)c1)c1nc(N2CCCC2)oc1CC(F)(F)F] | N-(4-(8-azabicyclo[3.2.1]octan-8-yl)-3,5-difluorophenyl)-2-(pyrrolidin-1-yl)-5-(2,2,2-trifluoroethyl)oxazole-4-carboxamide |
| 211 | 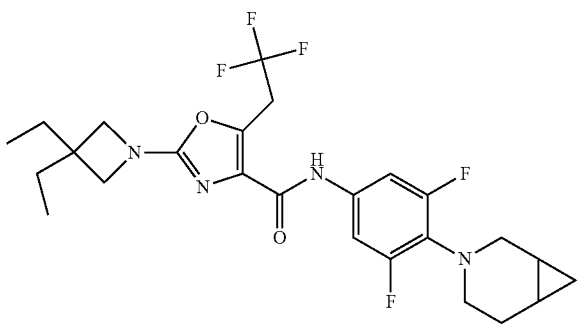 | N-(4-(3-azabicyclo[4.1.0]heptan-3-yl)-3,5-difluorophenyl)-2-(3,3-diethylazetidin-1-yl)-5-(2,2,2-trifluoroethyl)oxazole-4-carboxamide |
| 212 | 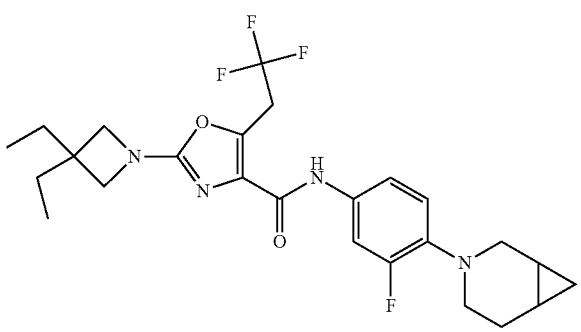 [SMILES: CCC1(CC)CN(c2nc(C(=O)Nc3ccc(N4CCC5CC5C4)c(F)c3)c(CC(F)(F)F)o2)C1] | N-(4-(3-azabicyclo[4.1.0]heptan-3-yl)-3-fluorophenyl)-2-(3,3-diethylazetidin-1-yl)-5-(2,2,2-trifluoroethyl)oxazole-4-carboxamide |
| 213 | 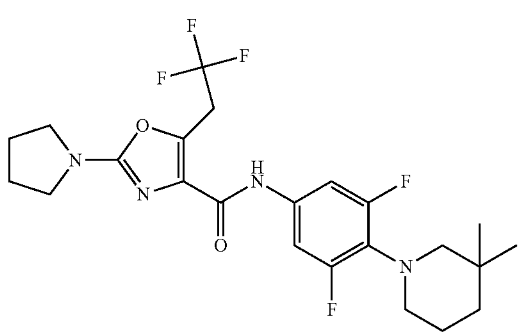 [SMILES: CC1(C)CCCN(c2c(F)cc(NC(=O)c3nc(N4CCCC4)oc3CC(F)(F)F)cc2F)C1] | N-(4-(3,3-dimethylpiperidin-1-yl)-3,5-difluorophenyl)-2-(pyrrolidin-1-yl)-5-(2,2,2-trifluoroethyl)oxazole-4-carboxamide |

-continued

| Ex. | Structures | Name |
|---|---|---|
| 214 | 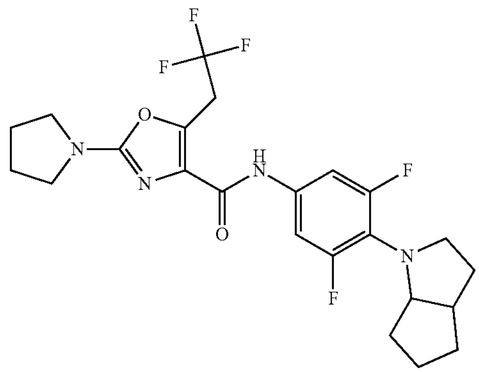 [SMILES: O=C(Nc1cc(F)c(N2CCC3CCCC32)c(F)c1)c1nc(N2CCCC2)oc1CC(F)(F)F] | N-(3,5-difluoro-4-(hexahydrocyclopenta[b]pyrrol-1(2H)-yl)phenyl)-2-(pyrrolidin-1-yl)-5-(2,2,2-trifluoroethyl)oxazole-4-carboxamide |
| 215 | 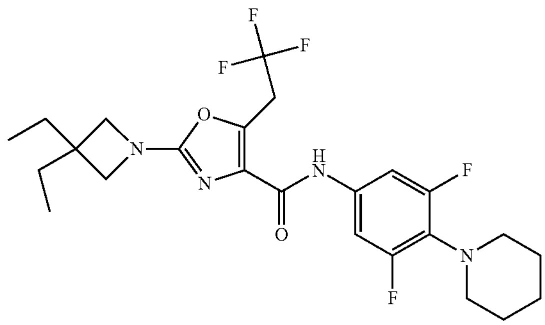 [SMILES: CCC1(CC)CN(c2nc(C(=O)Nc3cc(F)c(N4CCCCC4)c(F)c3)c(CC(F)(F)F)o2)C1] | 2-(3,3-diethylazetidin-1-yl)-N-(3,5-difluoro-4-(piperidin-1-yl)phenyl)-5-(2,2,2-trifluoroethyl)oxazole-4-carboxamide |
| 216 | 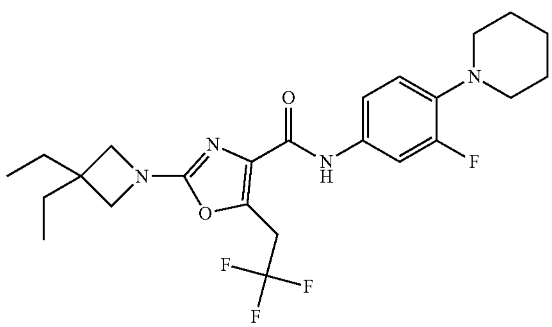 [SMILES: CCC1(CC)CN(c2nc(C(=O)Nc3ccc(N4CCCCC4)c(F)c3)c(CC(F)(F)F)o2)C1] | 2-(3,3-diethylazetidin-1-yl)-N-(3-fluoro-4-(piperidin-1-yl)phenyl)-5-(2,2,2-trifluoroethyl)oxazole-4-carboxamide |
| 217 | 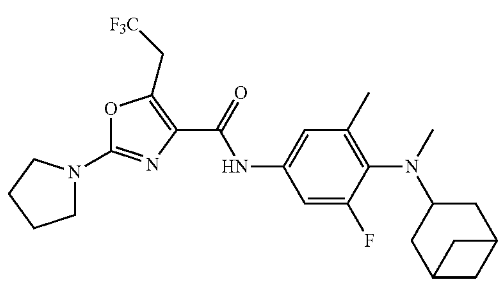 [SMILES: Cc1cc(NC(=O)c2nc(N3CCCC3)oc2CC(F)(F)F)cc(F)c1N(C)C1CC2CC(C2)C1] | N-(4-(bicyclo[3.1.1]heptan-3-yl(methyl)amino)-3-fluoro-5-methylphenyl)-2-(pyrrolidin-1-yl)-5-(2,2,2-trifluoroethyl)oxazole-4-carboxamide |
| 218 | 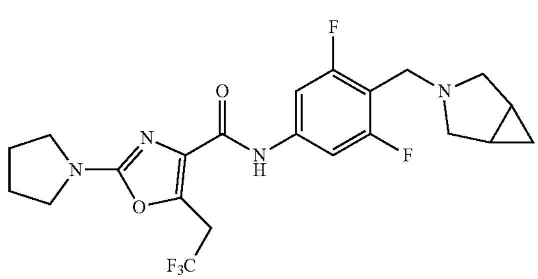 [SMILES: O=C(Nc1cc(F)c(CN2CC3CC3C2)c(F)c1)c1nc(N2CCCC2)oc1CC(F)(F)F] | N-(4-{3-azabicyclo [3.1.0]hexan-3-ylmethyl}-3,5-difluorophenyl)-2-(pyrrolidin-1-yl)-5-(2,2,2-trifluoroethyl)-1,3-oxazole-4-carboxamide |

| Ex. | Structures | Name |
| --- | --- | --- |
| 219 | 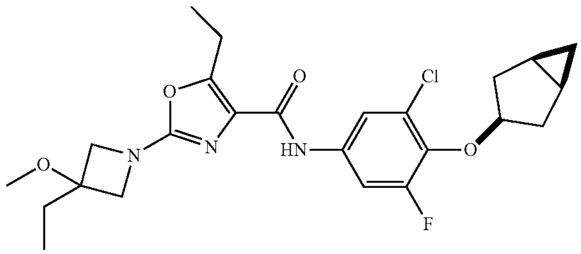 | N-(4-(cis-bicyclo[3.1.0]hexan-3-yloxy)-3-chloro-5-fluorophenyl)-5-ethyl-2-(3-ethyl-3-methoxyazetidin-1-yl)oxazole-4-carboxamide |
| 220 | 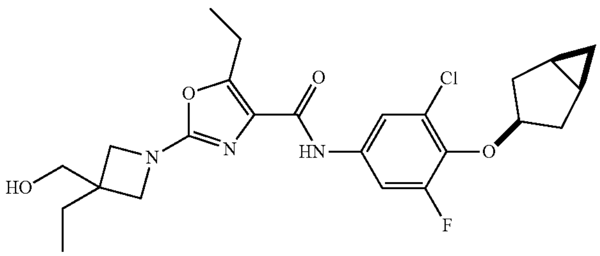 | N-(4-(cis-bicyclo[3.1.0]hexan-3-yloxy)-3-chloro-5-fluorophenyl)-5-ethyl-2-(3-ethyl-3-(hydroxymethyl)azetidin-1-yl)oxazole-4-carboxamide |
| 221 | 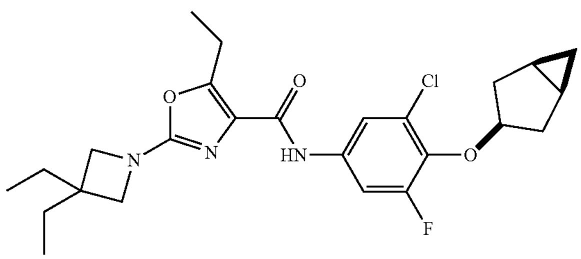 | N-(4-(cis-bicyclo[3.1.0]hexan-3-yloxy)-3-chloro-5-fluorophenyl)-2-(3,3-diethylazetidin-1-yl)-5-ethyloxazole-4-carboxamide |
| 222 | 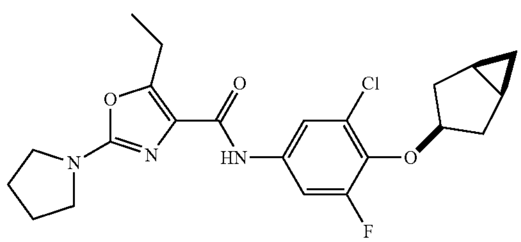 | N-(4-(cis-bicyclo[3.1.0]hexan-3-yloxy)-3-chloro-5-fluorophenyl)-5-ethyl-2-(pyrrolidin-1-yl)oxazole-4-carboxamide |
| 223 | 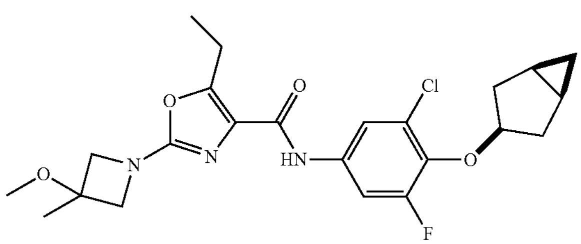 | N-(4-(cis-bicyclo[3.1.0]hexan-3-yloxy)-3-chloro-5-fluorophenyl)-5-ethyl-2-(3-methoxy-3-methylazetidin-1-yl)oxazole-4-carboxamide |
| 224 | 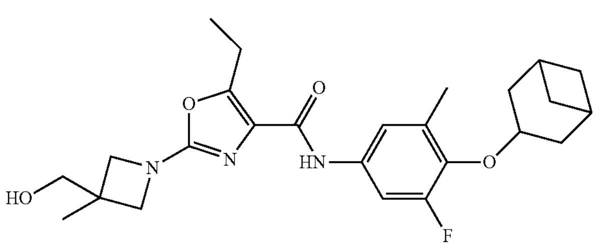 [SMILES: CCc1oc(N2CC(C)(CO)C2)nc1C(=O)Nc1cc(C)c(OC2CC3CC(C3)C2)c(F)c1] | N-(4-(bicyclo[3.1.1]heptan-3-yloxy)-3-fluoro-5-methylphenyl)-5-ethyl-2-(3-(hydroxymethyl)-3-methylazetidin-1-yl)oxazole-4-carboxamide |

-continued

| Ex. | Structures | Name |
|---|---|---|
| 225 | 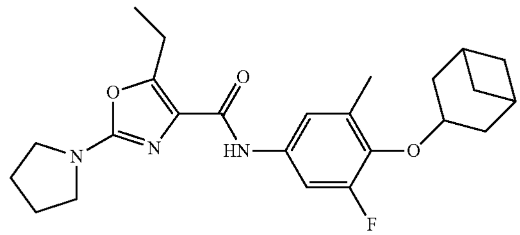 [SMILES: CCc1oc(N2CCCC2)nc1C(=O)Nc1cc(C)c(OC2CC3CC(C3)C2)c(F)c1] | N-(4-(bicyclo[3.1.1]heptan-3-yloxy)-3-fluoro-5-methylphenyl)-5-ethyl-2-(pyrrolidin-1-yl)oxazole-4-carboxamide |
| 226 | 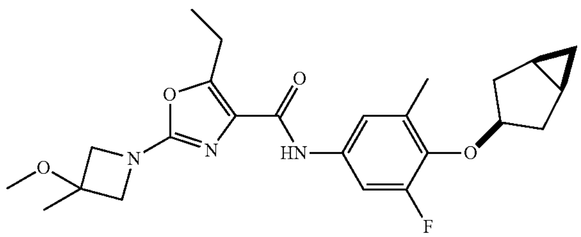 | N-(4-(cis-bicyclo[3.1.0]hexan-3-yloxy)-3-fluoro-5-methylphenyl)-5-ethyl-2-(3-methoxy-3-methylazetidin-1-yl)oxazole-4-carboxamide |
| 227 | 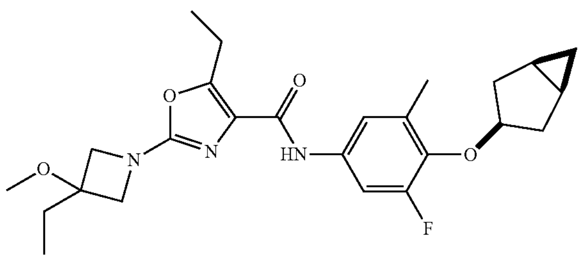 | N-(4-(cis-bicyclo[3.1.0]hexan-3-yloxy)-3-fluoro-5-methylphenyl)-5-ethyl-2-(3-ethyl-3-methoxyazetidin-1-yl)oxazole-4-carboxamide |
| 228 | 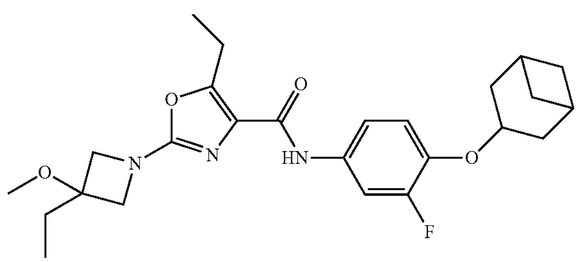 [SMILES: CCc1oc(N2CC(CC)(OC)C2)nc1C(=O)Nc1ccc(OC2CC3CC(C3)C2)c(F)c1] | N-(4-(bicyclo[3.1.1]heptan-3-yloxy)-3-fluorophenyl)-5-ethyl-2-(3-ethyl-3-methoxyazetidin-1-yl)oxazole-4-carboxamide |
| 229 | 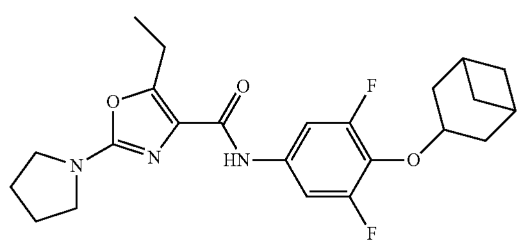 [SMILES: CCc1oc(N2CCCC2)nc1C(=O)Nc1cc(F)c(OC2CC3CC(C3)C2)c(F)c1] | N-(4-(bicyclo[3.1.1]heptan-3-yloxy)-3,5-difluorophenyl)-5-ethyl-2-(pyrrolidin-1-yl)oxazole-4-carboxamide |
| 230 | 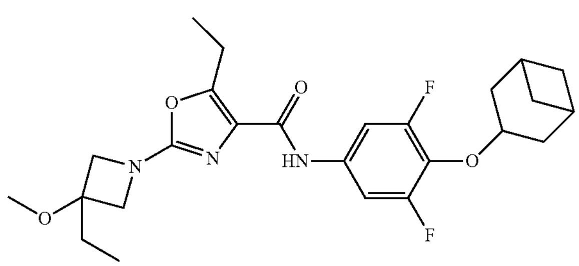 [SMILES: CCc1oc(N2CC(CC)(OC)C2)nc1C(=O)Nc1cc(F)c(OC2CC3CC(C3)C2)c(F)c1] | N-(4-(bicyclo[3.1.1]heptan-3-yloxy)-3,5-difluorophenyl)-5-ethyl-2-(3-ethyl-3-methoxyazetidin-1-yl)oxazole-4-carboxamide |

| Ex. | Structures | Name |
| --- | --- | --- |
| 231 | 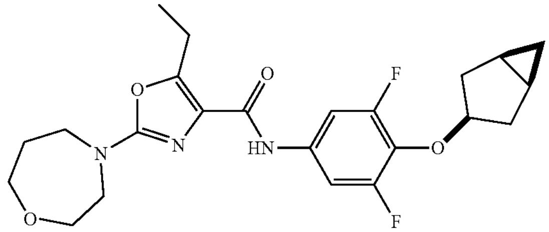 | N-(4-(cis-bicyclo[3.1.0]hexan-3-yloxy)-3,5-difluorophenyl)-5-ethyl-2-(1,4-oxazepan-4-yl)oxazole-4-carboxamide |
| 232 | 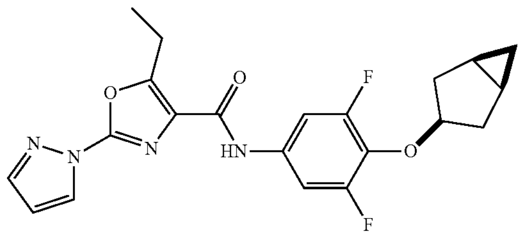 | N-(4-(cis-bicyclo[3.1.0]hexan-3-yloxy)-3,5-difluorophenyl)-5-ethyl-2-(1H-pyrazol-1-yl)oxazole-4-carboxamide |
| 233 | 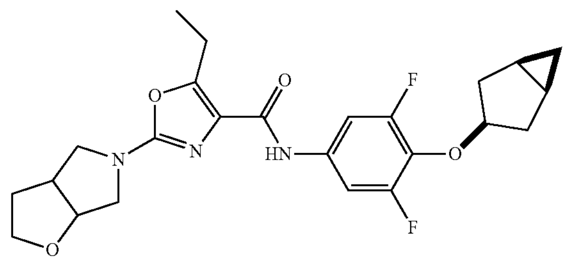 | N-(4-(cis-bicyclo[3.1.0]hexan-3-yloxy)-3,5-difluorophenyl)-5-ethyl-2-(hexahydro-5H-furo[2,3-c]pyrrol-5-yl)oxazole-4-carboxamide |
| 234 | 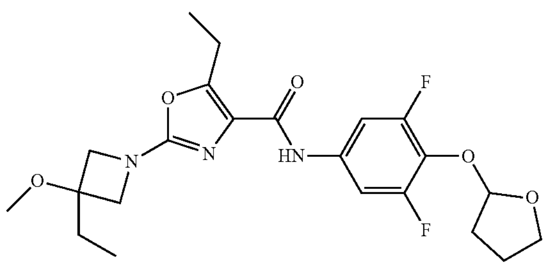 [SMILES: CCc1oc(N2CC(CC)(OC)C2)nc1C(=O)Nc1cc(F)c(OC2CCCO2)c(F)c1] | N-(3,5-difluoro-4-((tetrahydrofuran-3-yl)oxy)phenyl)-5-ethyl-2-(3-ethyl-3-methoxyazetidin-1-yl)oxazole-4-carboxamide |
| 235 | 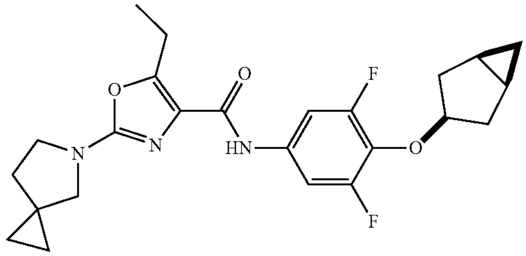 | N-(4-(cis-bicyclo[3.1.0]hexan-3-yloxy)-3,5-difluorophenyl)-5-ethyl-2-(5-azaspiro[2.4]heptan-5-yl)oxazole-4-carboxamide |
| 236 | 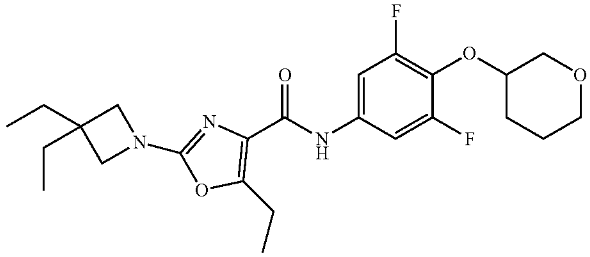 [SMILES: CCc1oc(N2CC(CC)(CC)C2)nc1C(=O)Nc1cc(F)c(OC2CCCOC2)c(F)c1] | 2-(3,3-diethylazetidin-1-yl)-N-(3,5-difluoro-4-((tetrahydro-2H-pyran-3-yl)oxy)phenyl)-5-ethyloxazole-4-carboxamide |

-continued

| Ex. | Structures | Name |
| --- | --- | --- |
| 237 | 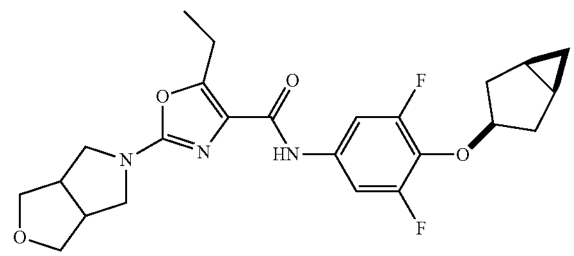 | N-(4-(cis-bicyclo[3.1.0]hexan-3-yloxy)-3,5-difluorophenyl)-5-ethyl-2-(tetrahydro-1H-furo[3,4-c]pyrrol-5(3H)-yl)oxazole-4-carboxamide |
| 238 | 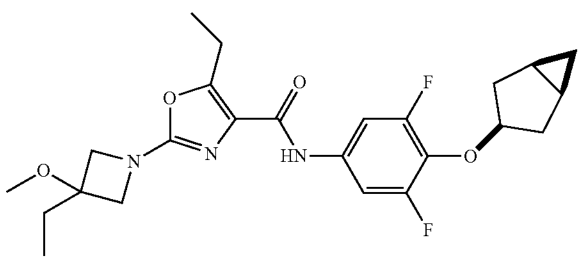 | N-(4-(cis-bicyclo[3.1.0]hexan-3-yloxy)-3,5-difluorophenyl)-5-ethyl-2-(3-ethyl-3-methoxyazetidin-1-yl)oxazole-4-carboxamide |
| 239 | 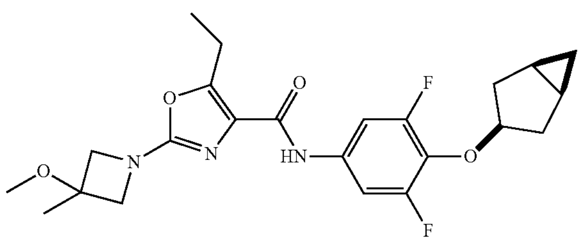 | N-(4-(cis-bicyclo[3.1.0]hexan-3-yloxy)-3,5-difluorophenyl)-5-ethyl-2-(3-methoxy-3-methylazetidin-1-yl)oxazole-4-carboxamide |
| 240 | 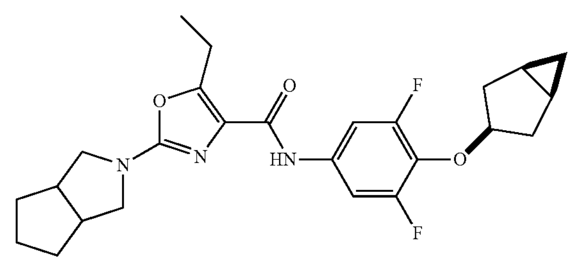 | N-(4-(cis-bicyclo[3.1.0]hexan-3-yloxy)-3,5-difluorophenyl)-5-ethyl-2-(hexahydrocyclopenta[c]pyrrol-2(1H)-yl)oxazole-4-carboxamide |
| 241 | 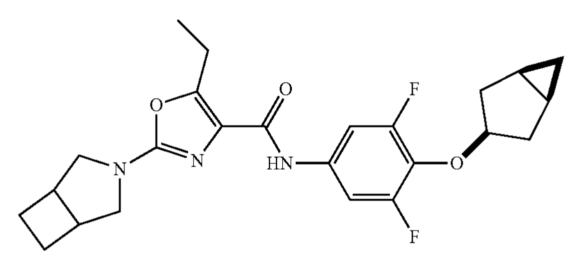 | N-(4-(cis-bicyclo[3.1.0]hexan-3-yloxy)-3,5-difluorophenyl)-2-(3-azabicyclo[3.2.0]heptan-3-yl)-5-ethyloxazole-4-carboxamide |
| 242 | 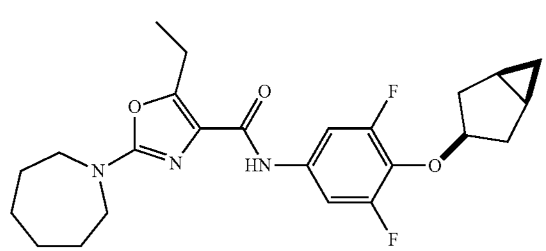 | 2-(azepan-1-yl)-N-(4-(cis-bicyclo[3.1.0]hexan-3-yloxy)-3,5-difluorophenyl)-5-ethyloxazole-4-carboxamide |

| Ex. | Structures | Name |
|---|---|---|
| 243 | 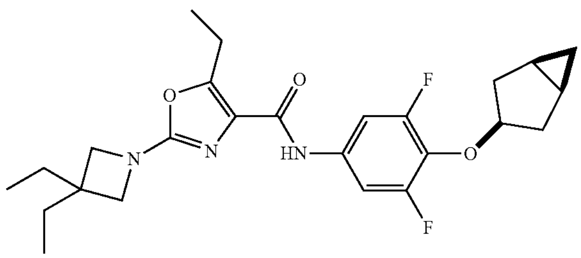 | N-(4-(cis-bicyclo[3.1.0]hexan-3-yloxy)-3,5-difluorophenyl)-2-(3,3-diethylazetidin-1-yl)-5-ethyloxazole-4-carboxamide |
| 244 | 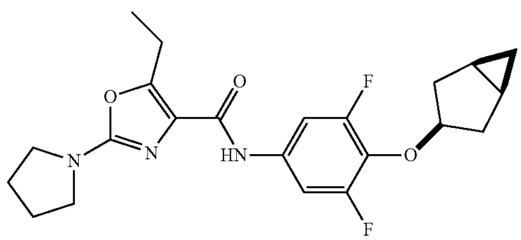 | N-(4-(cis-bicyclo[3.1.0]hexan-3-yloxy)-3,5-difluorophenyl)-5-ethyl-2-(pyrrolidin-1-yl)oxazole-4-carboxamide |
| 245 | 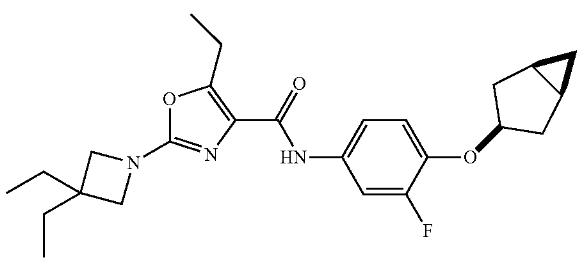 | N-(4-(cis-bicyclo[3.1.0]hexan-3-yloxy)-3-fluorophenyl)-2-(3,3-diethylazetidin-1-yl)-5-ethyloxazole-4-carboxamide |
| 246 | 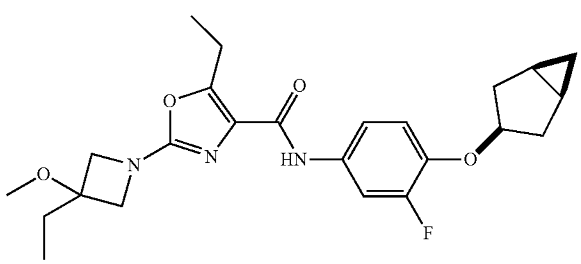 | N-(4-(cis-bicyclo[3.1.0]hexan-3-yloxy)-3-fluorophenyl)-5-ethyl-2-(3-ethyl-3-methoxyazetidin-1-yl)oxazole-4-carboxamide |
| 247 | 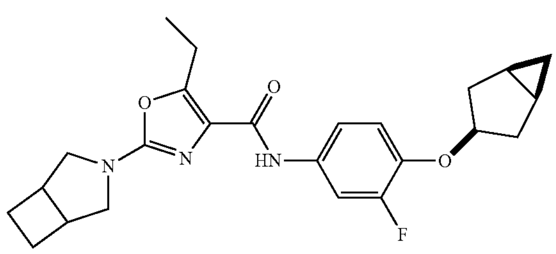 | N-(4-(cis-bicyclo[3.1.0]hexan-3-yloxy)-3-fluorophenyl)-2-(3-azabicyclo[3.2.0]heptan-3-yl)-5-ethyloxazole-4-carboxamide |
| 248 | 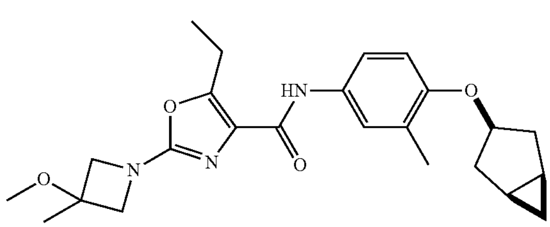 | N-(4-(cis-bicyclo[3.1.0]hexan-3-yloxy)-3-methylphenyl)-5-ethyl-2-(3-methoxy-3-methylazetidin-1-yl)oxazole-4-carboxamide |

| Ex. | Structures | Name |
|---|---|---|
| 249 | 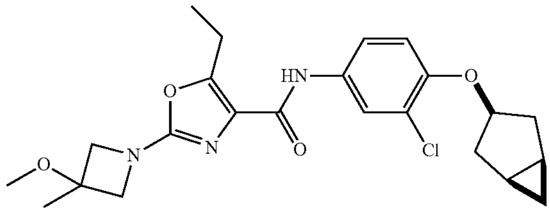 | N-(4-(cis-bicyclo[3.1.0]hexan-3-yloxy)-3-chlorophenyl)-5-ethyl-2-(3-methoxy-3-methylazetidin-1-yl)oxazole-4-carboxamide |
| 250 | 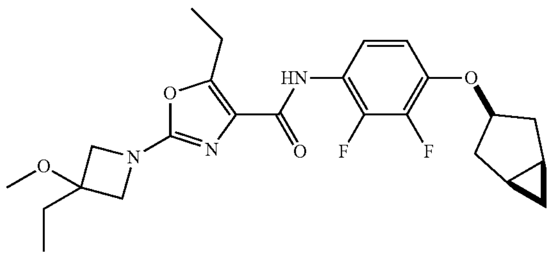 | N-(4-(cis-bicyclo[3.1.0]hexan-3-yloxy)-3-chlorophenyl)-5-ethyl-2-(3-methoxy-3-methylazetidin-1-yl)oxazole-4-carboxamide |
| 251 | 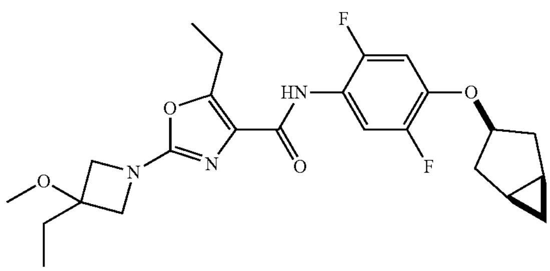 | N-(4-(cis-bicyclo[3.1.0]hexan-3-yloxy)-2,5-difluorophenyl)-5-ethyl-2-(3-ethyl-3-methoxyazetidin-1-yl)oxazole-4-carboxamide |
| 252 | 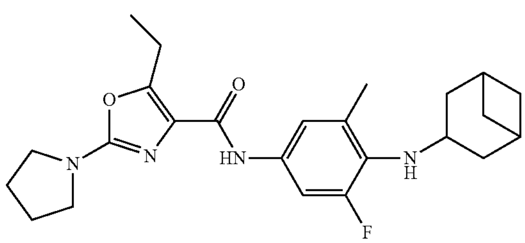 [SMILES: CCc1oc(N2CCCC2)nc1C(=O)Nc1cc(C)c(NC2CC3CC(C3)C2)c(F)c1] | N-(4-(bicyclo[3.1.1]heptan-3-ylamino)-3-fluoro-5-methylphenyl)-5-ethyl-2-(pyrrolidin-1-yl)oxazole-4-carboxamide |
| 253 | 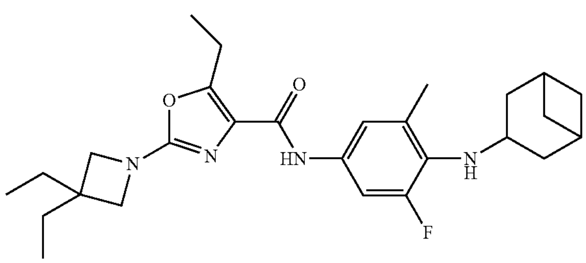 [SMILES: CCc1oc(N2CC(CC)(CC)C2)nc1C(=O)Nc1cc(C)c(NC2CC3CC(C3)C2)c(F)c1] | N-(4-(bicyclo[3.1.1]heptan-3-ylamino)-3-fluoro-5-methylphenyl)-2-(3,3-diethylazetidin-1-yl)-5-ethyloxazole-4-carboxamide |
| 254 | 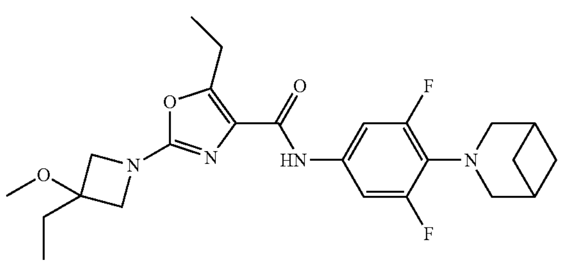 [SMILES: CCc1oc(N2CC(CC)(OC)C2)nc1C(=O)Nc1cc(F)c(N2CC3CC(C3)C2)c(F)c1] | N-(4-(3-azabicyclo[3.1.1]heptan-3-yl)-3,5-difluorophenyl)-5-ethyl-2-(3-ethyl-3-methoxyazetidin-1-yl)oxazole-4-carboxamide |

| Ex. | Structures | Name |
|---|---|---|
| 255 | 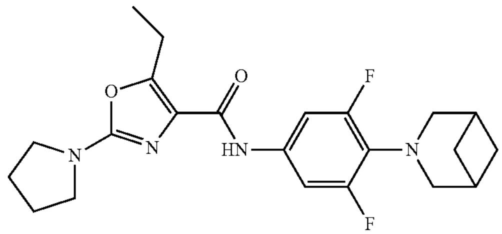 [SMILES: CCc1oc(N2CCCC2)nc1C(=O)Nc1cc(F)c(N2CC3CC(C3)C2)c(F)c1] | N-(4-(3-azabicyclo[3.1.1]heptan-3-yl)-3,5-difluorophenyl)-5-ethyl-2-(pyrrolidin-1-yl)oxazole-4-carboxamide |
| 256 | 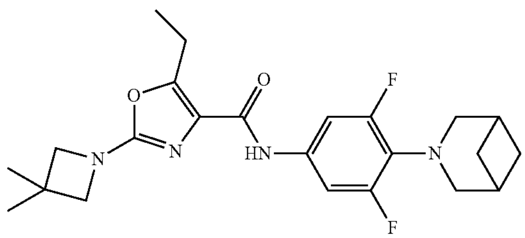 [SMILES: CCc1oc(N2CC(C)(C)C2)nc1C(=O)Nc1cc(F)c(N2CC3CC(C3)C2)c(F)c1] | N-(4-(3-azabicyclo[3.1.1]heptan-3-yl)-3,5-difluorophenyl)-2-(3,3-dimethylazetidin-1-yl)-5-ethyloxazole-4-carboxamide |
| 257 | 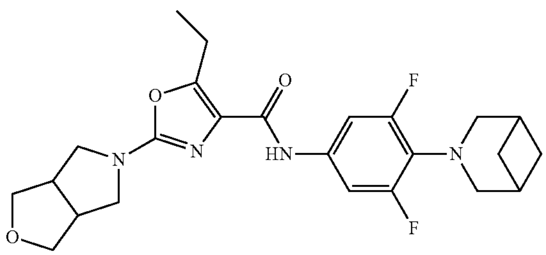 [SMILES: CCc1oc(N2CC3COCC3C2)nc1C(=O)Nc1cc(F)c(N2CC3CC(C3)C2)c(F)c1] | N-(4-(3-azabicyclo[3.1.1]heptan-3-yl)-3,5-difluorophenyl)-5-ethyl-2-(tetrahydro-1H-furo[3,4-c]pyrrol-5(3H)-yl)oxazole-4-carboxamide |
| 258 | 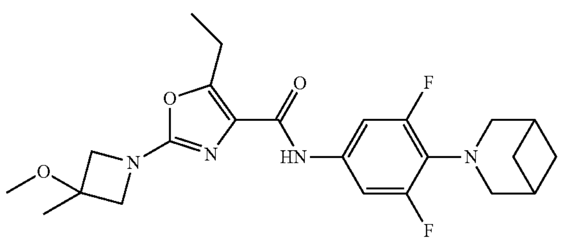 [SMILES: CCc1oc(N2CC(C)(OC)C2)nc1C(=O)Nc1cc(F)c(N2CC3CC(C3)C2)c(F)c1] | N-(4-(3-azabicyclo[3.1.1]heptan-3-yl)-3,5-difluorophenyl)-5-ethyl-2-(3-methoxy-3-methylazetidin-1-yl)oxazole-4-carboxamide |
| 259 | 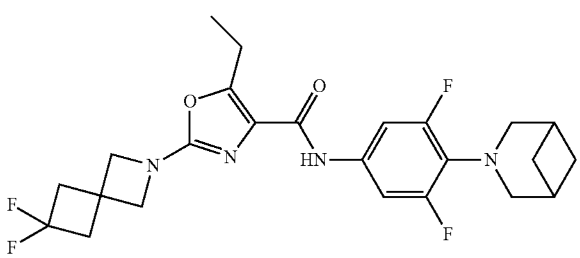 [SMILES: CCc1oc(N2CC3(C2)CC(F)(F)C3)nc1C(=O)Nc1cc(F)c(N2CC3CC(C3)C2)c(F)c1] | N-(4-(3-azabicyclo[3.1.1]heptan-3-yl)-3,5-difluorophenyl)-2-(6,6-difluoro-2-azaspiro[3.3]heptan-2-yl)-5-ethyloxazole-4-carboxamide |
| 260 | 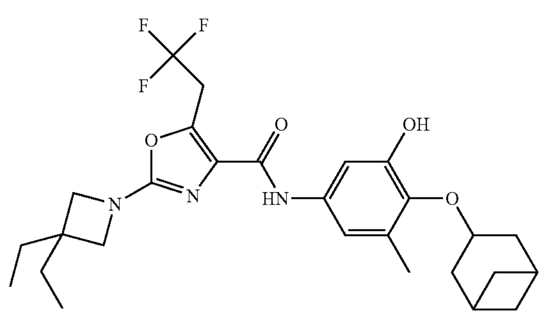 [SMILES: CCC1(CC)CN(c2nc(C(=O)Nc3cc(C)c(OC4CC5CC(C5)C4)c(O)c3)c(CC(F)(F)F)o2)C1] | N-(4-(bicyclo[3.1.1]heptan-3-yloxy)-3-hydroxy-5-methylphenyl)-2-(3,3-diethylazetidin-1-yl)-5-(2,2,2-trifluoroethyl)oxazole-4-carboxamide |

-continued

| Ex. | Structures | Name |
|---|---|---|
| 261 | 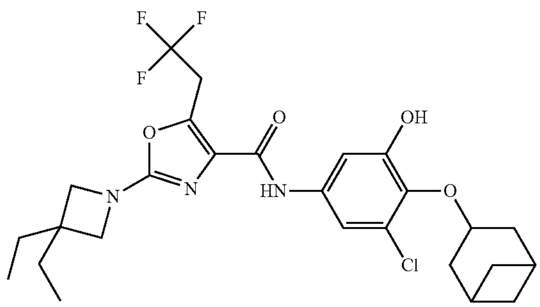 [SMILES: CCC1(CC)CN(c2nc(C(=O)Nc3cc(O)c(OC4CC5CC(C5)C4)c(Cl)c3)c(CC(F)(F)F)o2)C1] | N-(4-(bicyclo[3.1.1]heptan-3-yloxy)-3-chloro-5-hydroxyphenyl)-2-(3,3-diethylazetidin-1-yl)-5-(2,2,2-trifluoroethyl)oxazole-4-carboxamide |
| 262 | 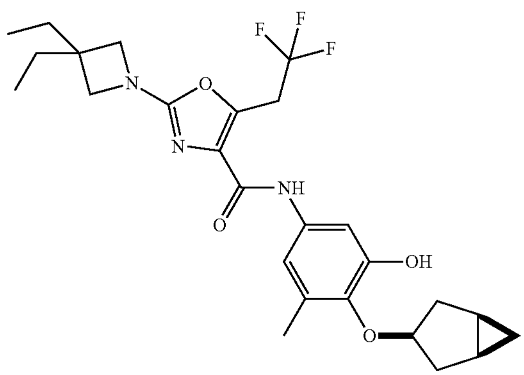 | N-(4-(cis-bicyclo[3.1.0]hexan-3-yloxy)-3-hydroxy-5-methylphenyl)-2-(3,3-diethylazetidin-1-yl)-5-(2,2,2-trifluoroethyl)oxazole-4-carboxamide |
| 263 | 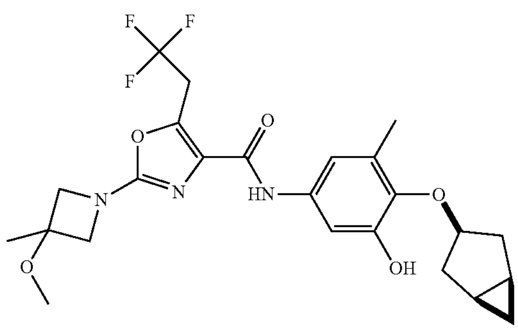 | N-(4-(cis-bicyclo[3.1.0]hexan-3-yloxy)-3-hydroxy-5-methylphenyl)-2-(3-methoxy-3-methylazetidin-1-yl)-5-(2,2,2-trifluoroethyl)oxazole-4-carboxamide |
| 264 | 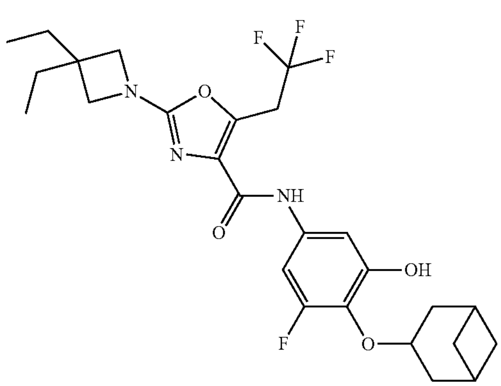 [SMILES: CCC1(CC)CN(c2nc(C(=O)Nc3cc(O)c(OC4CC5CC(C5)C4)c(F)c3)c(CC(F)(F)F)o2)C1] | N-(4-(bicyclo[3.1.1]heptan-3-yloxy)-3-fluoro-5-hydroxyphenyl)-2-(3,3-diethylazetidin-1-yl)-5-(2,2,2-trifluoroethyl)oxazole-4-carboxamide |

-continued

| Ex. | Structures | Name |
|---|---|---|
| 265 | 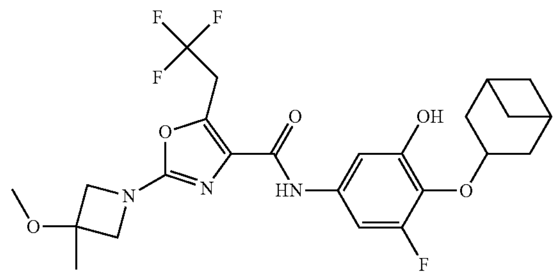 [SMILES: COC1(C)CN(c2nc(C(=O)Nc3cc(O)c(OC4CC5CC(C5)C4)c(F)c3)c(CC(F)(F)F)o2)C1] | N-(4-(bicyclo[3.1.1]heptan-3-yloxy)-3-fluoro-5-hydroxyphenyl)-2-(3-methoxy-3-methylazetidin-1-yl)-5-(2,2,2-trifluoroethyl)oxazole-4-carboxamide |
| 266 | 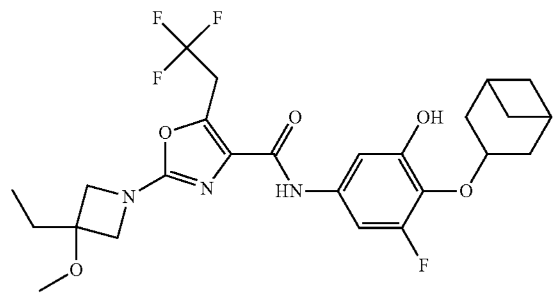 [SMILES: CCC1(OC)CN(c2nc(C(=O)Nc3cc(O)c(OC4CC5CC(C5)C4)c(F)c3)c(CC(F)(F)F)o2)C1] | N-(4-(bicyclo[3.1.1]heptan-3-yloxy)-3-fluoro-5-hydroxyphenyl)-2-(3-ethyl-3-methoxyazetidin-1-yl)-5-(2,2,2-trifluoroethyl)oxazole-4-carboxamide |
| 267 | 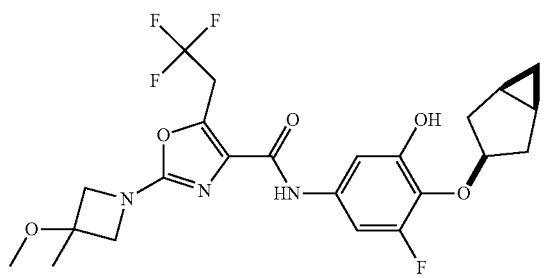 | N-(4-(cis-bicyclo[3.1.0]hexan-3-yloxy)-3-fluoro-5-hydroxyphenyl)-2-(3-methoxy-3-methylazetidin-1-yl)-5-(2,2,2-trifluoroethyl)oxazole-4-carboxamide |
| 268 | 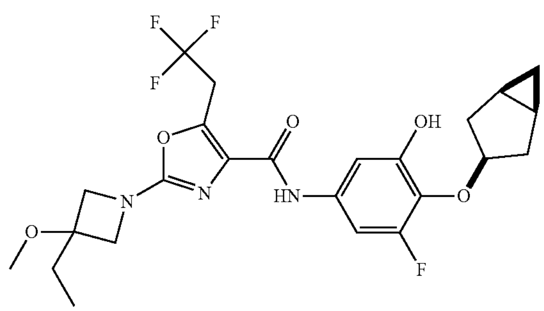 | N-(4-(cis-bicyclo[3.1.0]hexan-3-yloxy)-3-fluoro-5-hydroxyphenyl)-2-(3-ethyl-3-methoxyazetidin-1-yl)-5-(2,2,2-trifluoroethyl)oxazole-4-carboxamide |
| 269 | 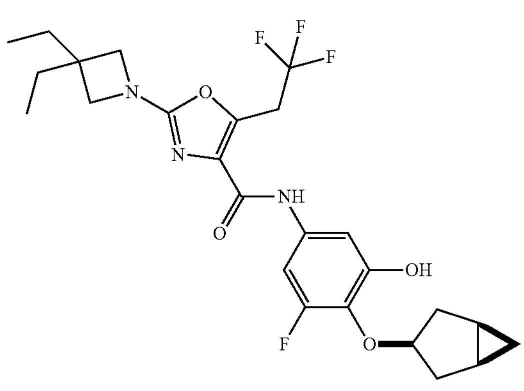 | N-(4-(cis-bicyclo[3.1.0]hexan-3-yloxy)-3-fluoro-5-hydroxyphenyl)-2-(3,3-diethylazetidin-1-yl)-5-(2,2,2-trifluoroethyl)oxazole-4-carboxamide |

| Ex. | Structures | Name |
|---|---|---|
| 270 | 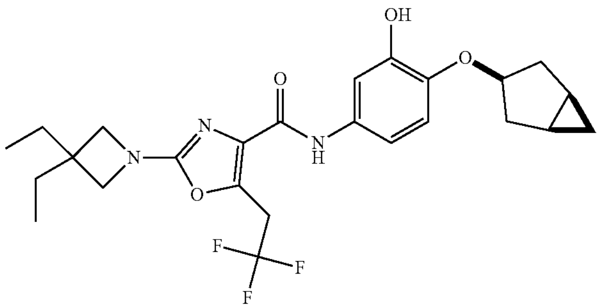 | N-(4-(cis-bicyclo[3.1.0]hexan-3-yloxy)-3-hydroxyphenyl)-2-(3,3-diethylazetidin-1-yl)-5-(2,2,2-trifluoroethyl)oxazole-4-carboxamide |
| 271 | 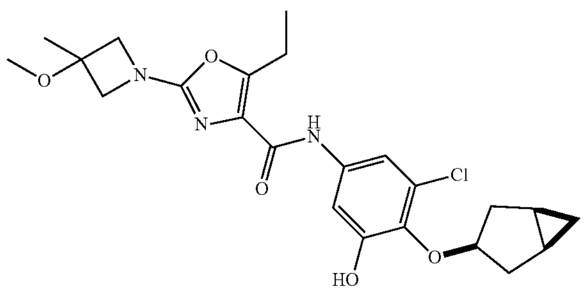 | N-(4-(cis-bicyclo[3.1.0]hexan-3-yloxy)-3-chloro-5-hydroxyphenyl)-5-ethyl-2-(3-methoxy-3-methylazetidin-1-yl)oxazole-4-carboxamide |
| 272 | 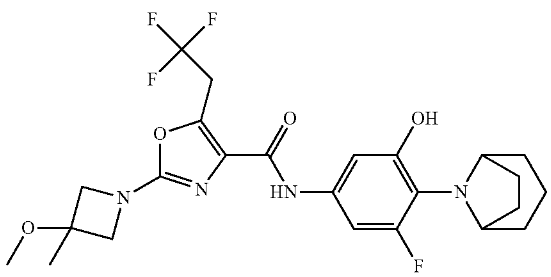 [SMILES: COC1(C)CN(c2nc(C(=O)Nc3cc(O)c(N4C5CCCC4CC5)c(F)c3)c(CC(F)(F)F)o2)C1] | N-(4-(8-azabicyclo[3.2.1]octan-8-yl)-3-fluoro-5-hydroxyphenyl)-2-(3-methoxy-3-methylazetidin-1-yl)-5-(2,2,2-trifluoroethyl)oxazole-4-carboxamide |
| 273 | 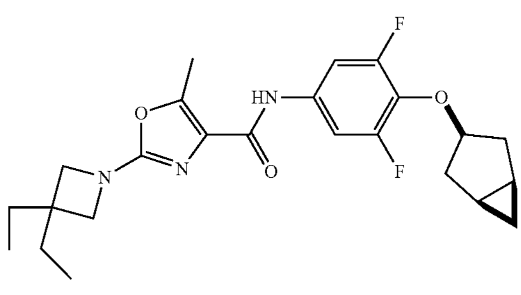 | N-(4-(cis-bicyclo[3.1.0]hexan-3-yloxy)-3,5-difluorophenyl)-2-(3,3-diethylazetidin-1-yl)-5-methyloxazole-4-carboxamide |
| 274 | 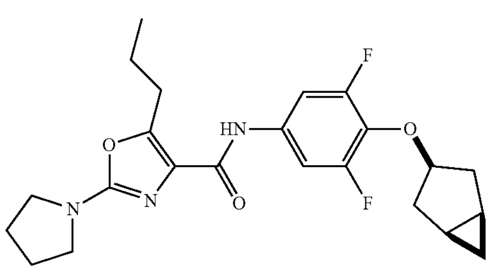 | N-(4-(cis-bicyclo[3.1.0]hexan-3-yloxy)-3,5-difluorophenyl)-5-propyl-2-(pyrrolidin-1-yl)oxazole-4-carboxamide |

| Ex. | Structures | Name |
|---|---|---|
| 275 | 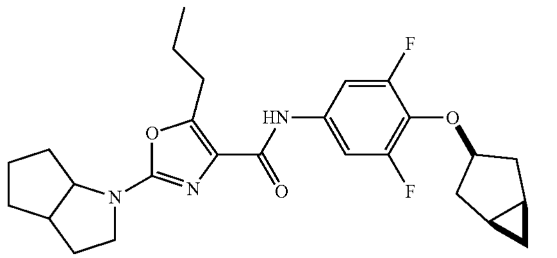 | N-(4-(cis-bicyclo[3.1.0]hexan-3-yloxy)-3,5-difluorophenyl)-2-(hexahydrocyclopenta[b]pyrrol-1(2H)-yl)-5-propyloxazole-4-carboxamide |
| 276 | 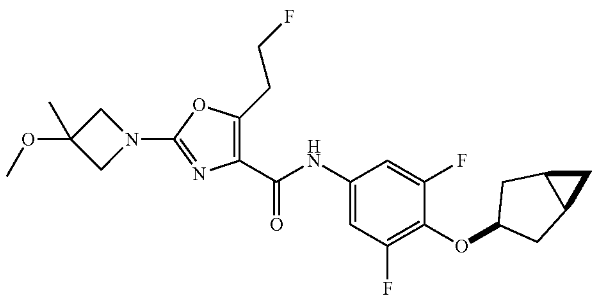 | N-(4-(cis-bicyclo[3.1.0]hexan-3-yloxy)-3,5-difluorophenyl)-5-(2-fluoroethyl)-2-(3-methoxy-3-methylazetidin-1-yl)oxazole-4-carboxamide |
| 277 | 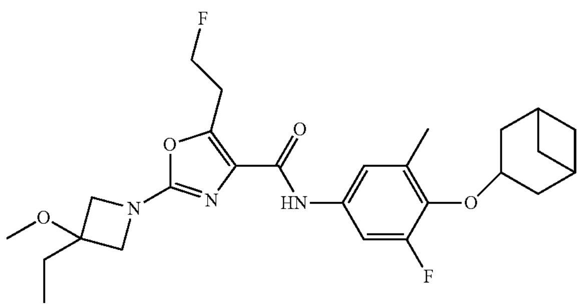 [SMILES: CCC1(OC)CN(c2nc(C(=O)Nc3cc(C)c(OC4CC5CC(C5)C4)c(F)c3)c(CCF)o2)C1] | N-(4-(bicyclo[3.1.1]heptan-3-yloxy)-3-fluoro-5-methylphenyl)-2-(3-ethyl-3-methoxyazetidin-1-yl)-5-(2-fluoroethyl)oxazole-4-carboxamide |
| 278 | 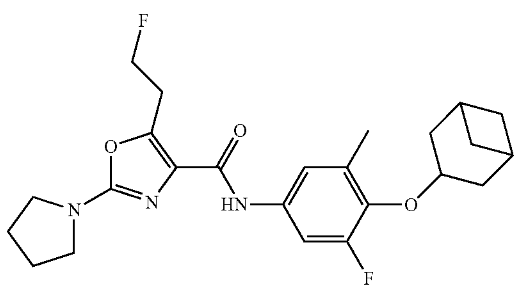 [SMILES: Cc1cc(NC(=O)c2nc(N3CCCC3)oc2CCF)cc(F)c1OC1CC2CC(C2)C1] | N-(4-(bicyclo[3.1.1]heptan-3-yloxy)-3-fluoro-5-methylphenyl)-5-(2-fluoroethyl)-2-(pyrrolidin-1-yl)oxazole-4-carboxamide |
| 279 | 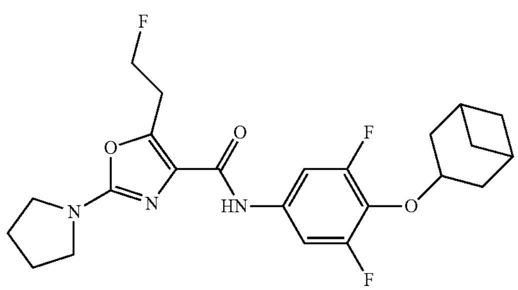 [SMILES: O=C(Nc1cc(F)c(OC2CC3CC(C3)C2)c(F)c1)c1nc(N2CCCC2)oc1CCF] | N-(4-(bicyclo[3.1.1]heptan-3-yloxy)-3,5-difluorophenyl)-5-(2-fluoroethyl)-2-(pyrrolidin-1-yl)oxazole-4-carboxamide |

-continued

| Ex. | Structures | Name |
|---|---|---|
| 280 | 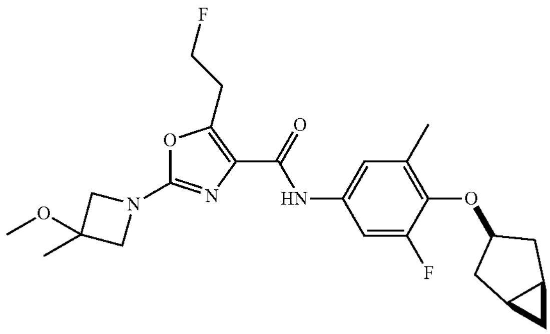 | N-(4-(cis-bicyclo[3.1.0]hexan-3-yloxy)-3-fluoro-5-methylphenyl)-5-(2-fluoroethyl)-2-(3-methoxy-3-methylazetidin-1-yl)oxazole-4-carboxamide |
| 281 | 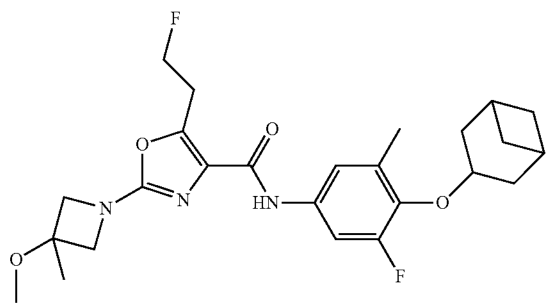 [SMILES: COC1(C)CN(c2nc(C(=O)Nc3cc(C)c(OC4CC5CC(C5)C4)c(F)c3)c(CCF)o2)C1] | N-(4-(bicyclo[3.1.1]heptan-3-yloxy)-3-fluoro-5-methylphenyl)-5-(2-fluoroethyl)-2-(3-methoxy-3-methylazetidin-1-yl)oxazole-4-carboxamide |
| 282 | 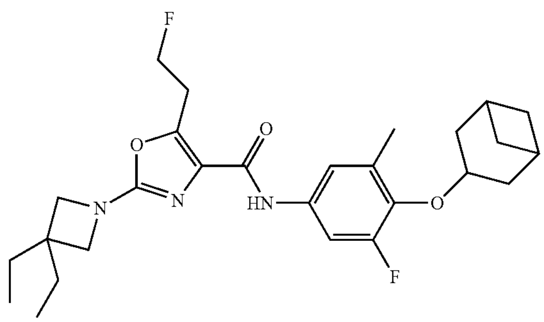 [SMILES: CCC1(CC)CN(c2nc(C(=O)Nc3cc(C)c(OC4CC5CC(C5)C4)c(F)c3)c(CCF)o2)C1] | N-(4-(bicyclo[3.1.1]heptan-3-yloxy)-3-fluoro-5-methylphenyl)-2-(3,3-diethylazetidin-1-yl)-5-(2-fluoroethyl)oxazole-4-carboxamide |
| 283 | 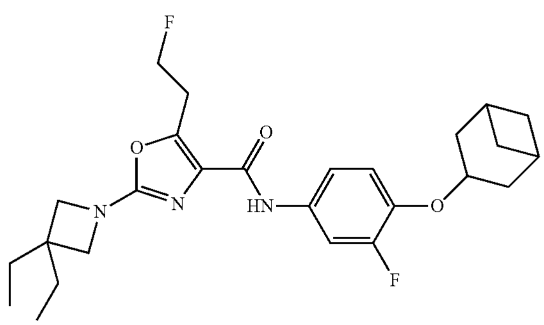 [SMILES: CCC1(CC)CN(c2nc(C(=O)Nc3ccc(OC4CC5CC(C5)C4)c(F)c3)c(CCF)o2)C1] | N-(4-(bicyclo[3.1.1]heptan-3-yloxy)-3-fluorophenyl)-2-(3,3-diethylazetidin-1-yl)-5-(2-fluoroethyl)oxazole-4-carboxamide |
| 284 | 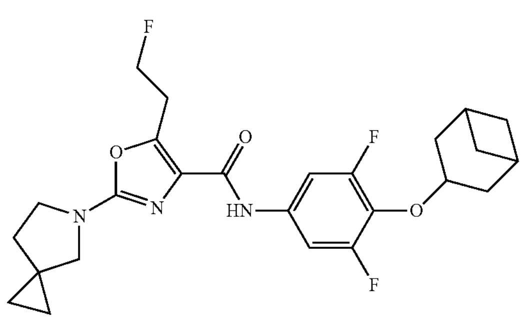 [SMILES: O=C(Nc1cc(F)c(OC2CC3CC(C3)C2)c(F)c1)c1nc(N2CCC3(CC3)C2)oc1CCF] | N-(4-(bicyclo[3.1.1]heptan-3-yloxy)-3,5-difluorophenyl)-5-(2-fluoroethyl)-2-(5-azaspiro[2.4]heptan-5-yl)oxazole-4-carboxamide |

| Ex. | Structures | Name |
|---|---|---|
| 285 | 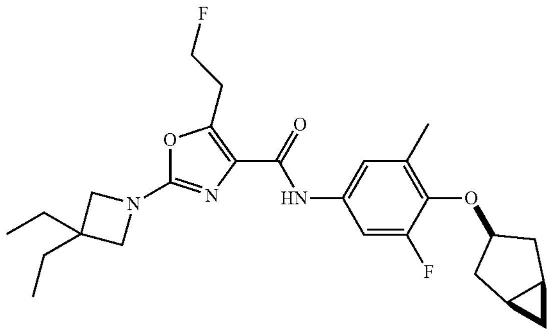 | N-(4-(cis-bicyclo[3.1.0]hexan-3-yloxy)-3-fluoro-5-methylphenyl)-2-(3,3-diethylazetidin-1-yl)-5-(2-fluoroethyl)oxazole-4-carboxamide |
| 286 | 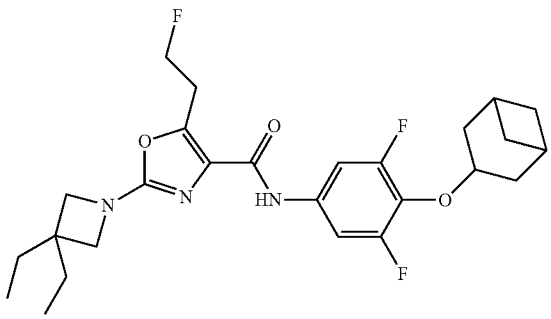 [SMILES: CCC1(CC)CN(c2nc(C(=O)Nc3cc(F)c(OC4CC5CC(C5)C4)c(F)c3)c(CCF)o2)C1] | N-(4-(bicyclo[3.1.1]heptan-3-yloxy)-3,5-difluorophenyl)-2-(3,3-diethylazetidin-1-yl)-5-(2-fluoroethyl)oxazole-4-carboxamide |
| 287 | 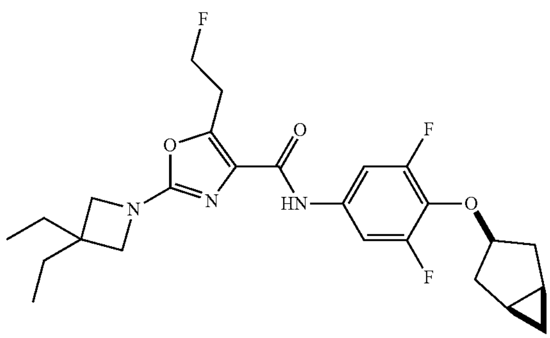 | N-(4-(cis-bicyclo[3.1.0]hexan-3-yloxy)-3,5-difluorophenyl)-2-(3,3-diethylazetidin-1-yl)-5-(2-fluoroethyl)oxazole-4-carboxamide |
| 288 | 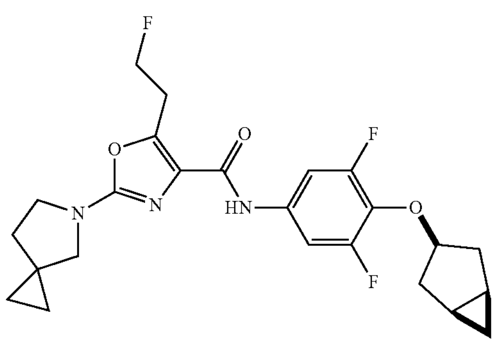 | N-(4-(cis-bicyclo[3.1.0]hexan-3-yloxy)-3,5-difluorophenyl)-5-(2-fluoroethyl)-2-(5-azaspiro[2.4]heptan-5-yl)oxazole-4-carboxamide |

-continued

| Ex. | Structures | Name |
| --- | --- | --- |
| 289 | 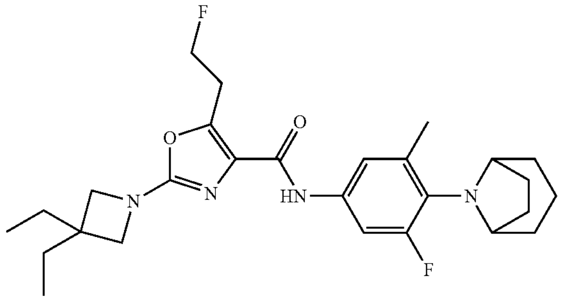 [SMILES: CCC1(CC)CN(c2nc(C(=O)Nc3cc(C)c(N4C5CCCC4CC5)c(F)c3)c(CCF)o2)C1] | N-(4-(8-azabicyclo[3.2.1]octan-8-yl)-3-fluoro-5-methylphenyl)-2-(3,3-diethylazetidin-1-yl)-5-(2-fluoroethyl)oxazole-4-carboxamide |
| 290 | 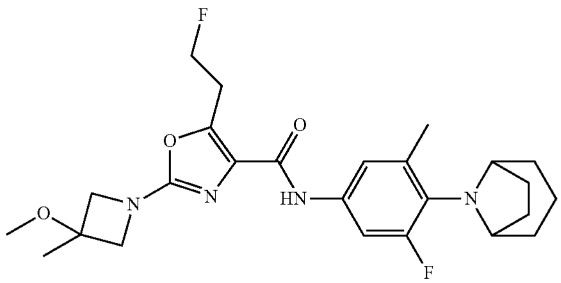 [SMILES: COC1(C)CN(c2nc(C(=O)Nc3cc(C)c(N4C5CCCC4CC5)c(F)c3)c(CCF)o2)C1] | N-(4-(bicyclo[3.1.1]heptan-3-yloxy)-3-fluoro-5-methylphenyl)-5-(2-fluoroethyl)-2-(3-methoxy-3-methylazetidin-1-yl)oxazole-4-carboxamide |
| 291 | 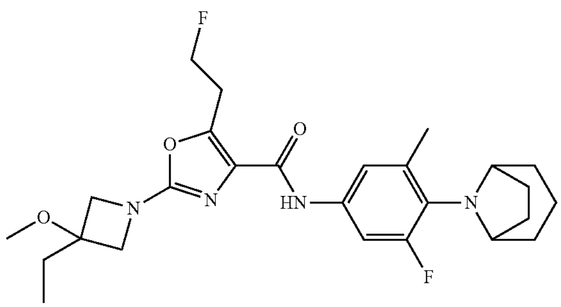 [SMILES: CCC1(OC)CN(c2nc(C(=O)Nc3cc(C)c(N4C5CCCC4CC5)c(F)c3)c(CCF)o2)C1] | N-(4-(8-azabicyclo[3.2.1]octan-8-yl)-3-fluoro-5-methylphenyl)-2-(3-ethyl-3-methoxyazetidin-1-yl)-5-(2-fluoroethyl)oxazole-4-carboxamide |
| 292 | 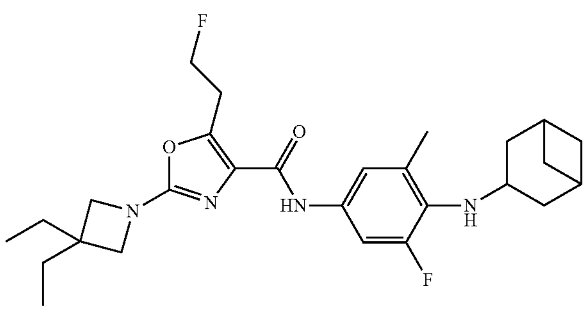 [SMILES: CCC1(CC)CN(c2nc(C(=O)Nc3cc(C)c(NC4CC5CC(C5)C4)c(F)c3)c(CCF)o2)C1] | N-(4-(bicyclo[3.1.1]heptan-3-ylamino)-3-fluoro-5-methylphenyl)-2-(3,3-diethylazetidin-1-yl)-5-(2-fluoroethyl)oxazole-4-carboxamide |
| 293 | 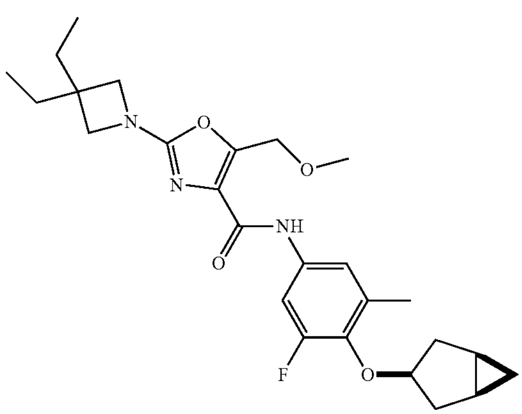 | N-(4-(cis-bicyclo[3.1.0]hexan-3-yloxy)-3-fluoro-5-methylphenyl)-2-(3,3-diethylazetidin-1-yl)-5-(methoxymethyl)oxazole-4-carboxamide |

-continued

| Ex. | Structures | Name |
|---|---|---|
| 294 | 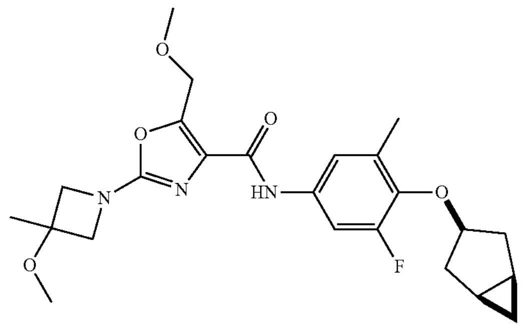 | N-(4-(cis-bicyclo[3.1.0]hexan-3-yloxy)-3-fluoro-5-methylphenyl)-2-(3-methoxy-3-methylazetidin-1-yl)-5-(methoxymethyl)oxazole-4-carboxamide |
| 295 | 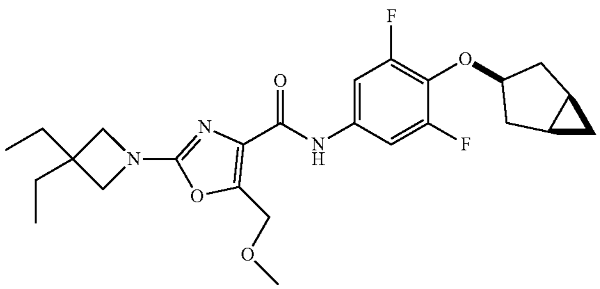 | N-(4-(cis-bicyclo[3.1.0]hexan-3-yloxy)-3,5-difluorophenyl)-2-(3,3-diethylazetidin-1-yl)-5-(methoxymethyl)oxazole-4-carboxamide |
| 296 | 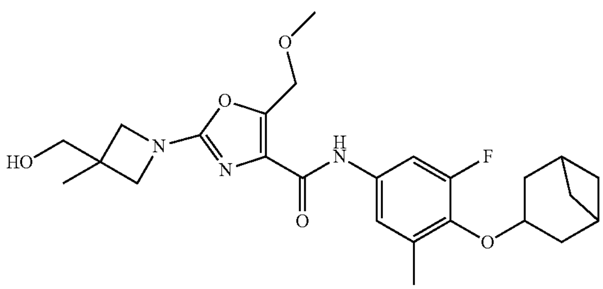 [SMILES: COCc1oc(N2CC(C)(CO)C2)nc1C(=O)Nc1cc(C)c(OC2CC3CC(C3)C2)c(F)c1] | N-(4-(bicyclo[3.1.1]heptan-3-yloxy)-3-fluoro-5-methylphenyl)-2-(3-(hydroxymethyl)-3-methylazetidin-1-yl)-5-(methoxymethyl)oxazole-4-carboxamide |
| 297 | 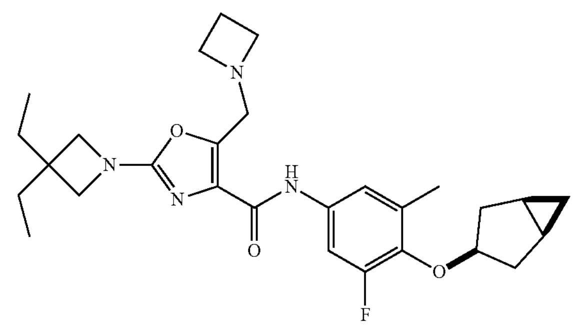 | 5-(azetidin-1-ylmethyl)-N-(4-(cis-bicyclo[3.1.0]hexan-3-yloxy)-3-fluoro-5-methylphenyl)-2-(3,3-diethylazetidin-1-yl)oxazole-4-carboxamide |
| 298 | 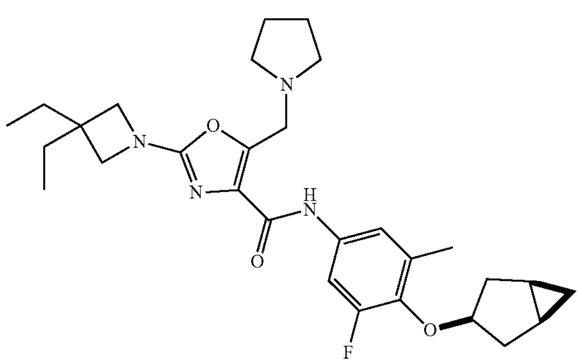 | N-(4-(cis-bicyclo[3.1.0]hexan-3-yloxy)-3-fluoro-5-methylphenyl)-2-(3,3-diethylazetidin-1-yl)-5-(pyrrolidin-1-ylmethyl)oxazole-4-carboxamide |

| Ex. | Structures | Name |
| --- | --- | --- |
| 299 | 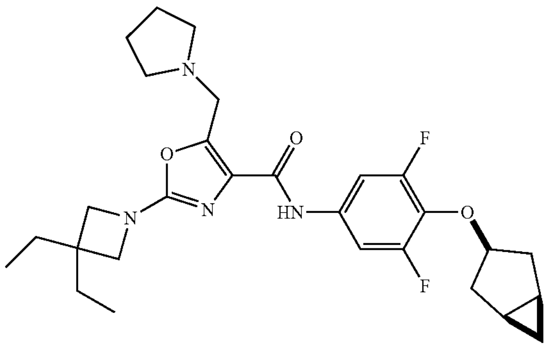 | N-(4-(cis-bicyclo[3.1.0]hexan-3-yloxy)-3,5-difluorophenyl)-2-(3,3-diethylazetidin-1-yl)-5-(pyrrolidin-1-ylmethyl)oxazole-4-carboxamide |
| 300 | 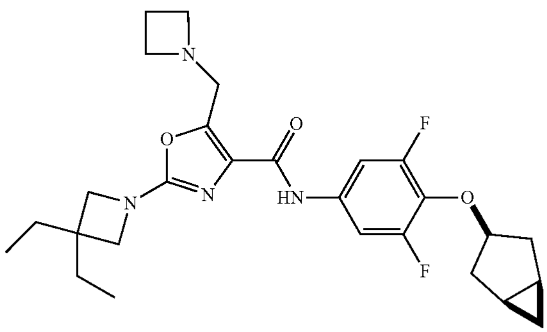 | 5-(azetidin-1-ylmethyl)-N-(4-(cis-bicyclo[3.1.0]hexan-3-yloxy)-3,5-difluorophenyl)-2-(3,3-diethylazetidin-1-yl)oxazole-4-carboxamide |
| 301 | 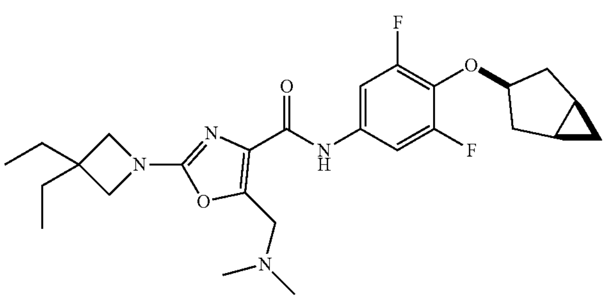 | N-(4-(cis-bicyclo[3.1.0]hexan-3-yloxy)-3,5-difluorophenyl)-2-(3,3-diethylazetidin-1-yl)-5-((dimethylamino)methyl)oxazole-4-carboxamide |
| 302 | 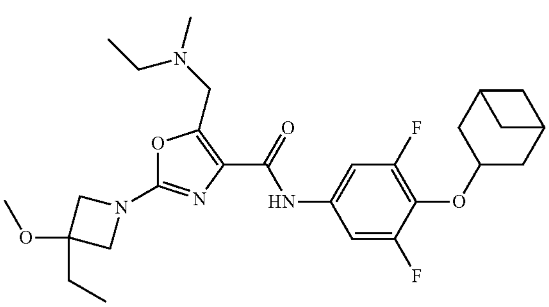 [SMILES: CCN(C)Cc1oc(N2CC(CC)(OC)C2)nc1C(=O)Nc1cc(F)c(OC2CC3CC(C3)C2)c(F)c1] | N-(4-(bicyclo[3.1.1]heptan-3-yloxy)-3,5-difluorophenyl)-5-((ethyl(methyl)amino)methyl)-2-(3-ethyl-3-methoxyazetidin-1-yl)oxazole-4-carboxamide |

| Ex. | Structures | Name |
|---|---|---|
| 303 | 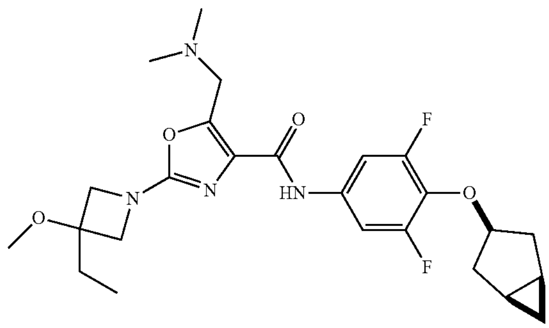 | N-(4-(cis-bicyclo[3.1.0]hexan-3-yloxy)-3,5-difluorophenyl)-5-((dimethylamino)methyl)-2-(3-ethyl-3-methoxyazetidin-1-yl)oxazole-4-carboxamide |
| 304 | 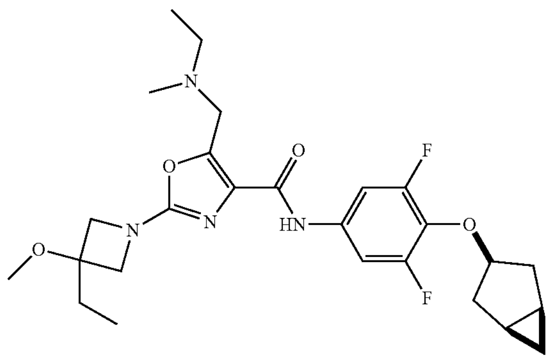 | N-(4-(cis-bicyclo[3.1.0]hexan-3-yloxy)-3,5-difluorophenyl)-5-((ethyl(methyl)amino)methyl)-2-(3-ethyl-3-methoxyazetidin-1-yl)oxazole-4-carboxamide |
| 305 | 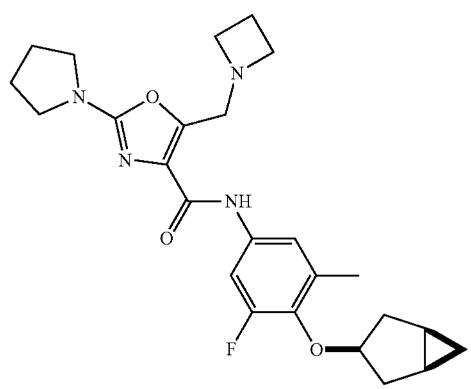 | 5-(azetidin-1-ylmethyl)-N-(4-(cis-bicyclo[3.1.0]hexan-3-yloxy)-3-fluoro-5-methylphenyl)-2-(pyrrolidin-1-yl)oxazole-4-carboxamide |
| 306 | 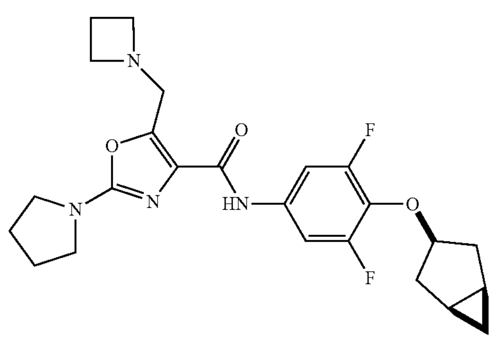 | 5-(azetidin-1-ylmethyl)-N-(4-(cis-bicyclo[3.1.0]hexan-3-yloxy)-3,5-difluorophenyl)-2-(pyrrolidin-1-yl)oxazole-4-carboxamide |

| Ex. | Structures | Name |
|---|---|---|
| 307 | 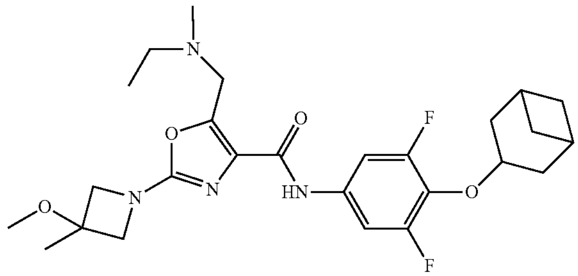 [SMILES: CCN(C)Cc1oc(N2CC(C)(OC)C2)nc1C(=O)Nc1cc(F)c(OC2CC3CC(C3)C2)c(F)c1] | N-(4-(bicyclo[3.1.1]heptan-3-yloxy)-3,5-difluorophenyl)-5-((ethyl(methyl)amino)methyl)-2-(3-methoxy-3-methylazetidin-1-yl)oxazole-4-carboxamide |
| 308 | 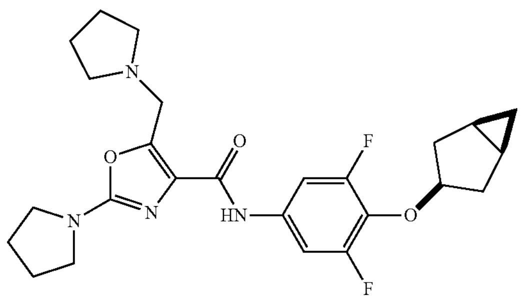 | N-(4-(cis-bicyclo[3.1.0]hexan-3-yloxy)-3,5-difluorophenyl)-2-(pyrrolidin-1-yl)-5-(pyrrolidin-1-ylmethyl)oxazole-4-carboxamide |
| 309 | 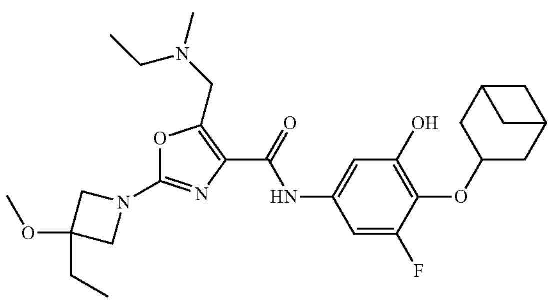 [SMILES: CCN(C)Cc1oc(N2CC(CC)(OC)C2)nc1C(=O)Nc1cc(O)c(OC2CC3CC(C3)C2)c(F)c1] | N-(4-(bicyclo[3.1.1]heptan-3-yloxy)-3-fluoro-5-hydroxyphenyl)-5-((ethyl(methyl)amino)methyl)-2-(3-ethyl-3-methoxyazetidin-1-yl)oxazole-4-carboxamide |
| 310 | 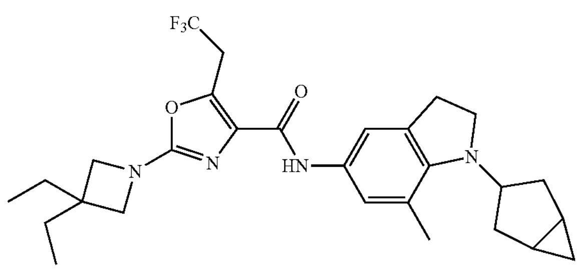 [SMILES: CCC1(CC)CN(c2nc(C(=O)Nc3cc(C)c4c(c3)CCN4C3CC4CC4C3)c(CC(F)(F)F)o2)C1] | N-(1-(bicyclo[3.1.0]hexan-3-yl)-7-methylindolin-5-yl)-2-(3,3-diethylazetidin-1-yl)-5-(2,2,2-trifluoroethyl)oxazole-4-carboxamide |
| 311 | 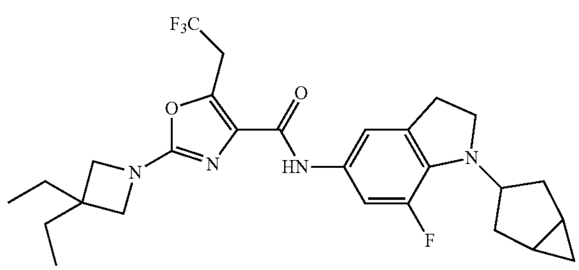 [SMILES: CCC1(CC)CN(c2nc(C(=O)Nc3cc(F)c4c(c3)CCN4C3CC4CC4C3)c(CC(F)(F)F)o2)C1] | N-(1-(bicyclo[3.1.0]hexan-3-yl)-7-fluoroindolin-5-yl)-2-(3,3-diethylazetidin-1-yl)-5-(2,2,2-trifluoroethyl)oxazole-4-carboxamide |

| Ex. | Structures | Name |
|---|---|---|
| 312 | 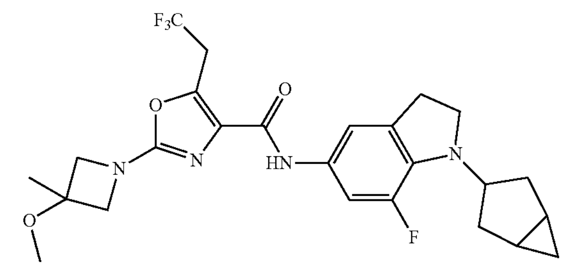 [SMILES: COC1(C)CN(c2nc(C(=O)Nc3cc(F)c4c(c3)CCN4C3CC4CC4C3)c(CC(F)(F)F)o2)C1] | N-(1-(bicyclo[3.1.0]hexan-3-yl)-7-fluoroindolin-5-yl)-2-(3-methoxy-3-methylazetidin-1-yl)-5-(2,2,2-trifluoroethyl)oxazole-4-carboxamide |
| 313 | 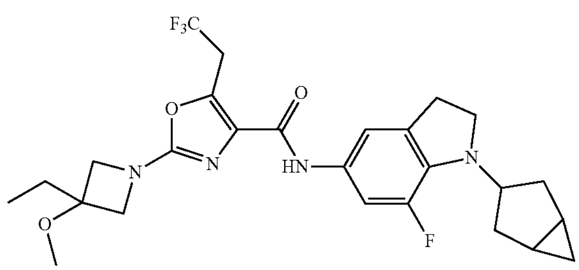 [SMILES: CCC1(OC)CN(c2nc(C(=O)Nc3cc(F)c4c(c3)CCN4C3CC4CC4C3)c(CC(F)(F)F)o2)C1] | N-(1-(bicyclo[3.1.0]hexan-3-yl)-7-fluoroindolin-5-yl)-2-(3-ethyl-3-methoxyazetidin-1-yl)-5-(2,2,2-trifluoroethyl)oxazole-4-carboxamide |
| 314 | 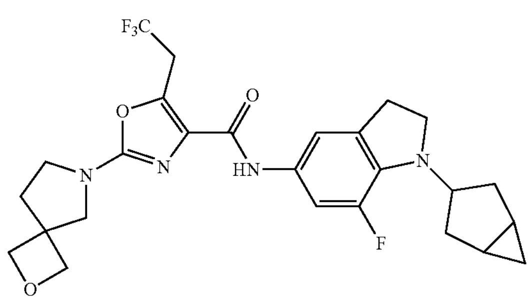 [SMILES: O=C(Nc1cc(F)c2c(c1)CCN2C1CC2CC2C1)c1nc(N2CCC3(COC3)C2)oc1CC(F)(F)F] | N-(1-(bicyclo[3.1.0]hexan-3-yl)-7-fluoroindolin-5-yl)-2-(2-oxa-6-azaspiro[3.4]octan-6-yl)-5-(2,2,2-trifluoroethyl)oxazole-4-carboxamide |
| 315 | 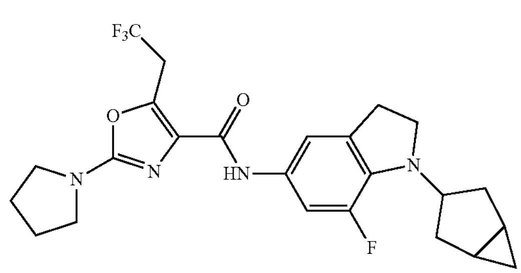 [SMILES: O=C(Nc1cc(F)c2c(c1)CCN2C1CC2CC2C1)c1nc(N2CCCC2)oc1CC(F)(F)F] | N-(1-(bicyclo[3.1.0]hexan-3-yl)-7-fluoroindolin-5-yl)-2-(pyrrolidin-1-yl)-5-(2,2,2-trifluoroethyl)oxazole-4-carboxamide |

| Ex. | Structures | Name |
|---|---|---|
| 316 | | N-(1-(bicyclo[3.1.0]hexan-3-yl)-7-fluoroindolin-5-yl)-2-(3,3-diethylazetidin-1-yl)-5-ethyloxazole-4-carboxamide | or a pharmaceutically acceptable salt, solvate, or stereoisomer thereof.

In some embodiments, the compound is selected from the group consisting of:

-continued
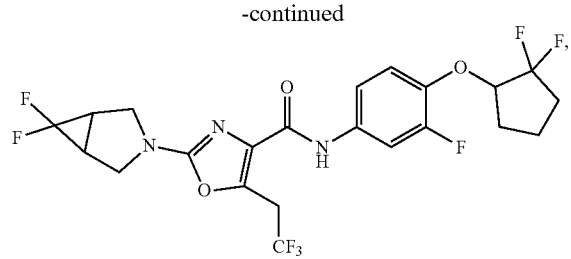
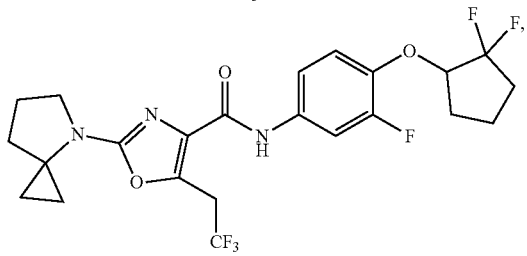
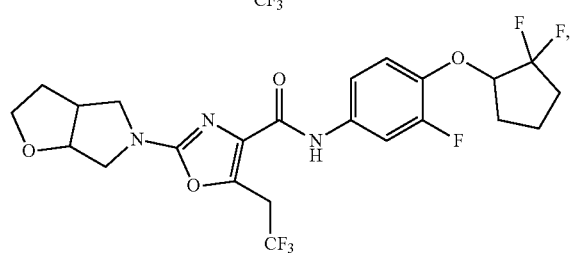
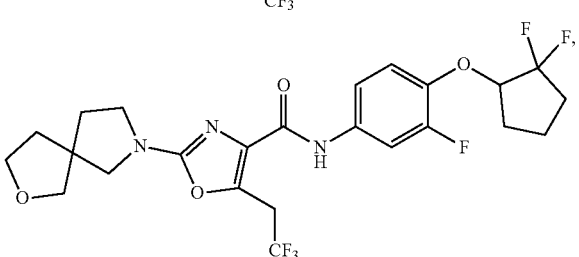
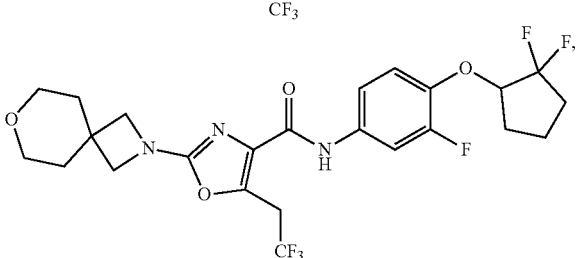
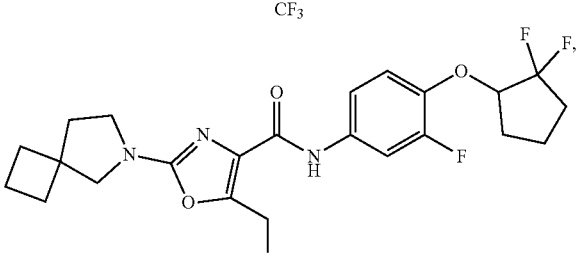
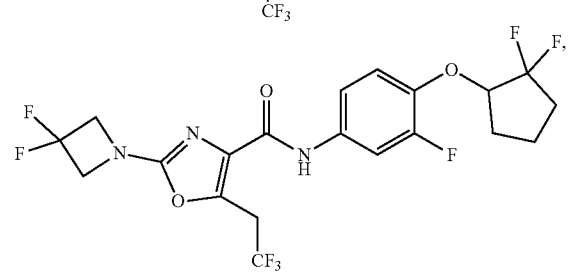
-continued
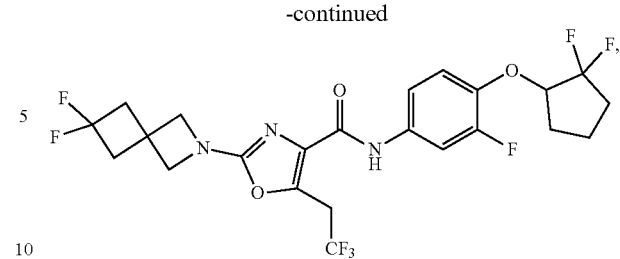
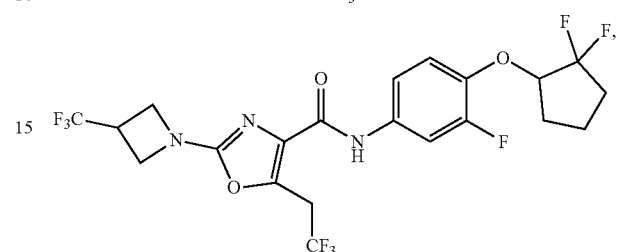
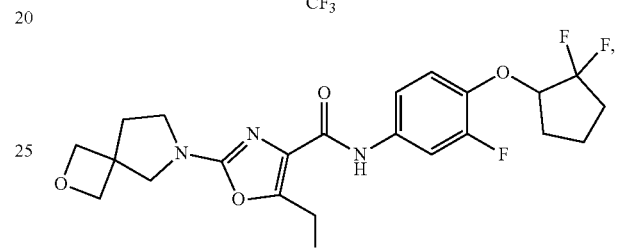
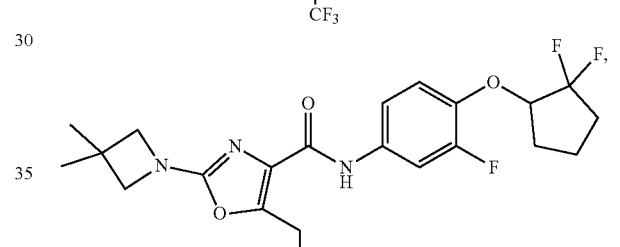
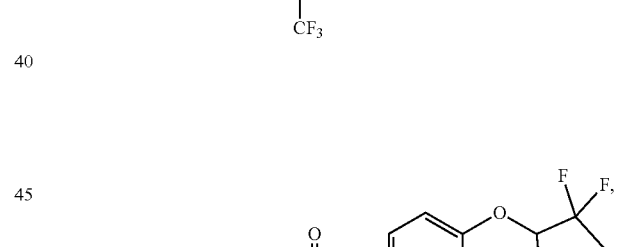
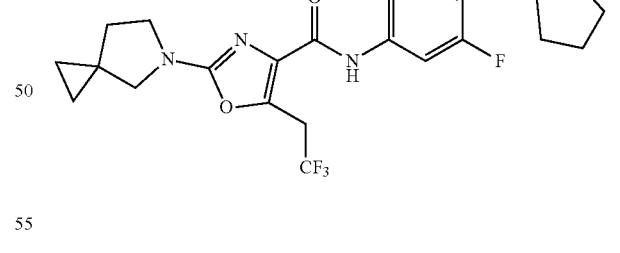
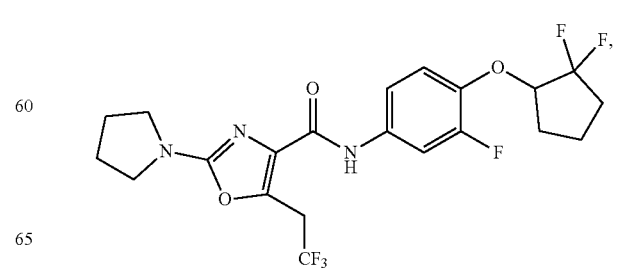

157
-continued
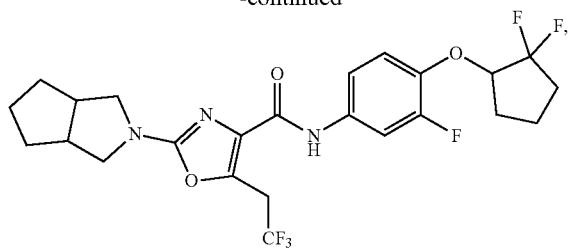
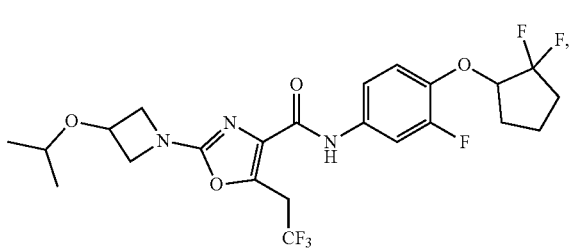
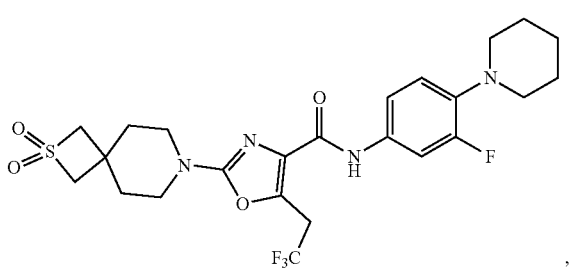
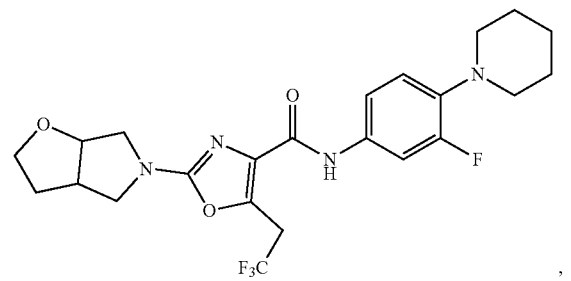
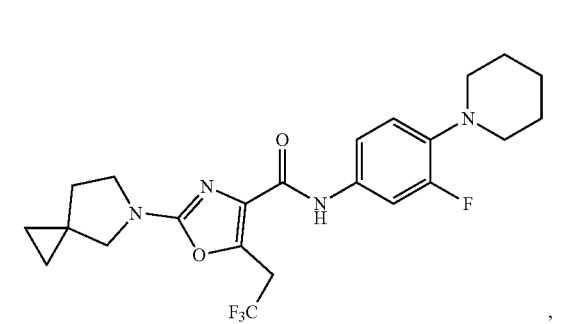
158
-continued
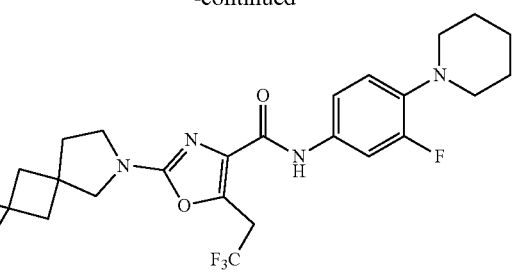
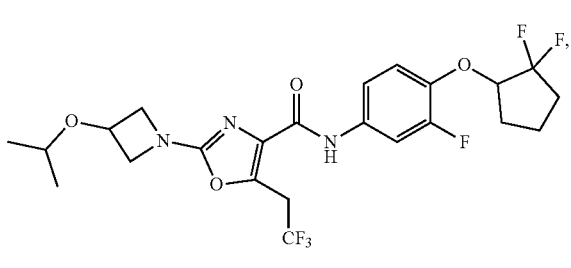
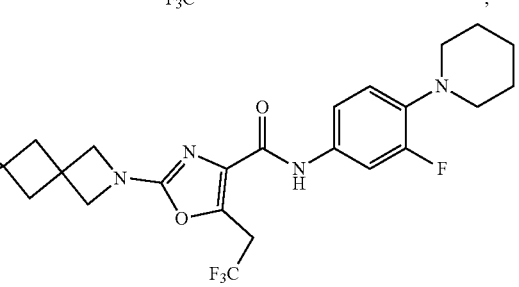
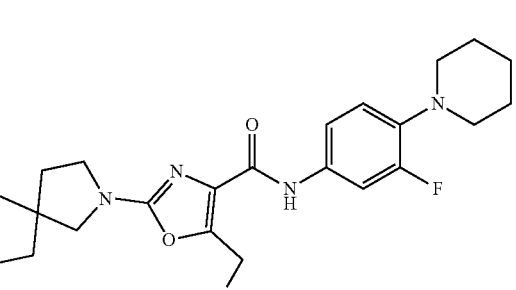
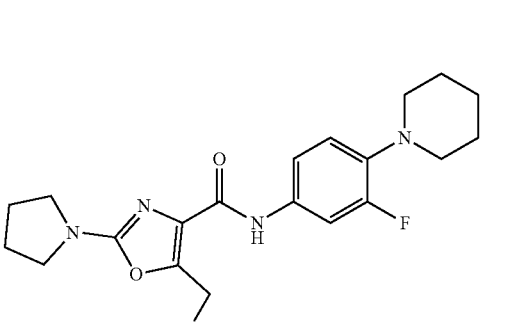

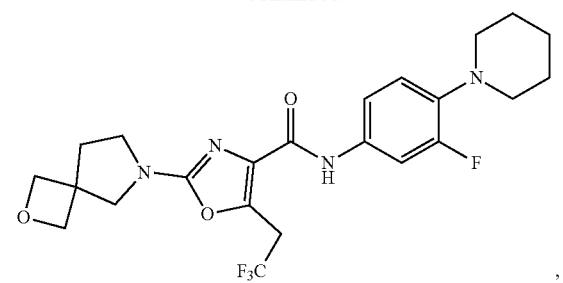
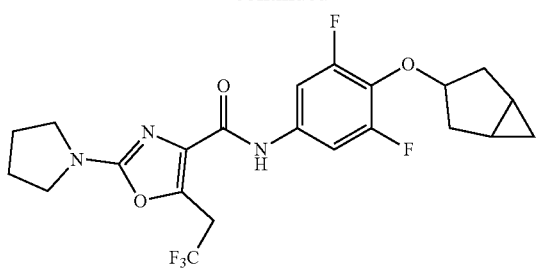
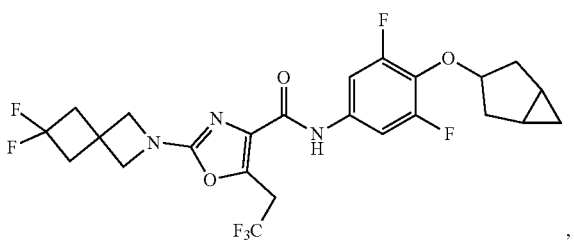
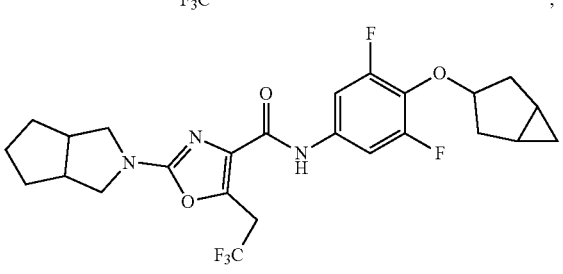
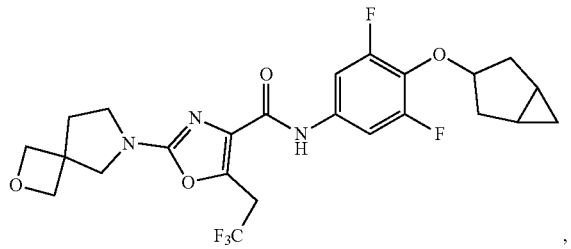
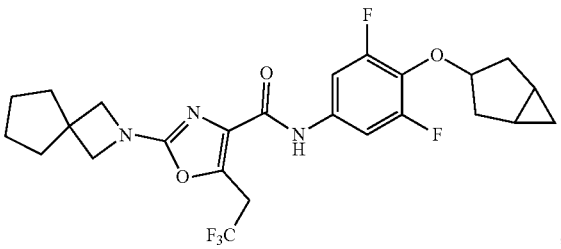
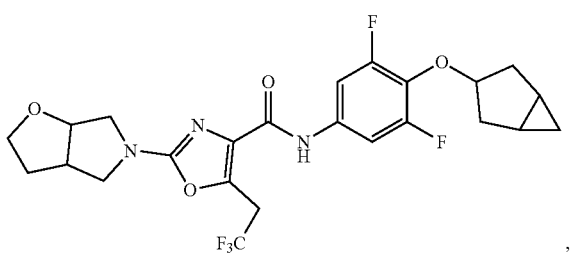
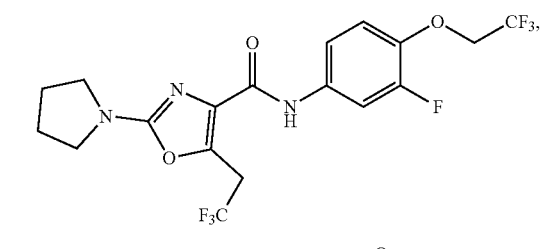
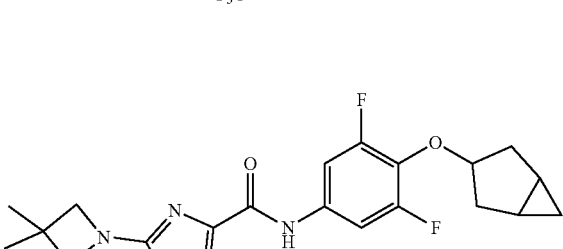
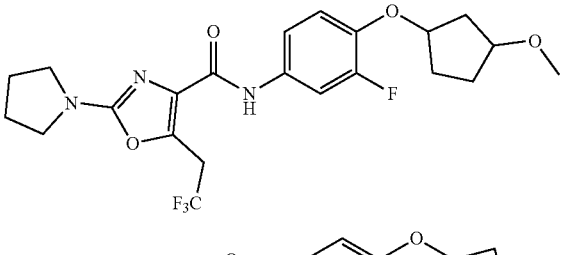
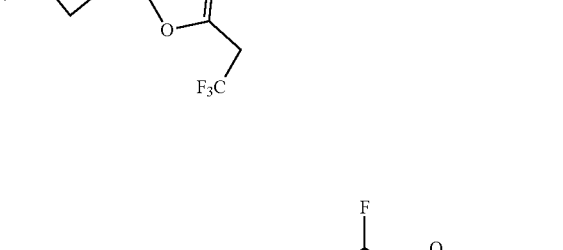
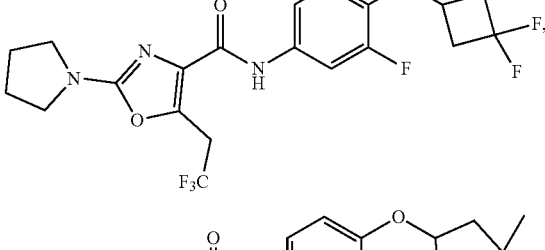
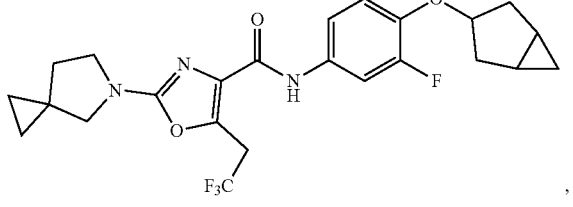
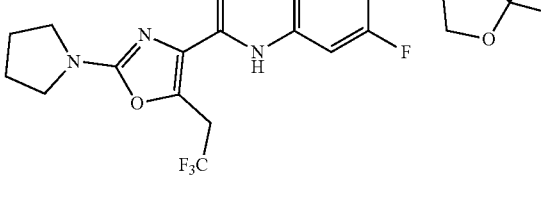

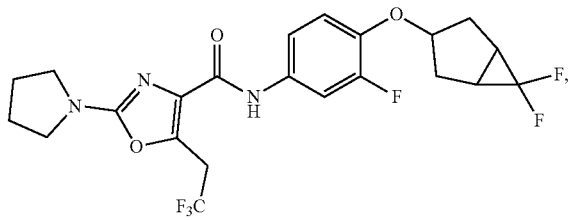
,
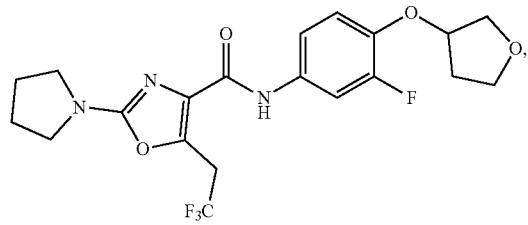
,
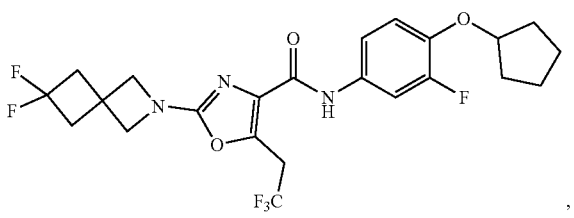
,
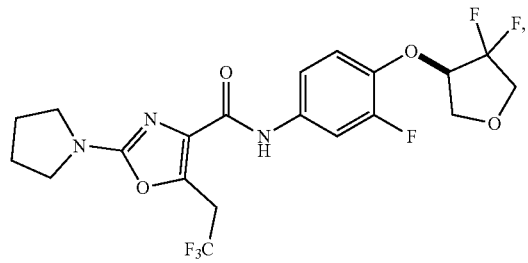
,
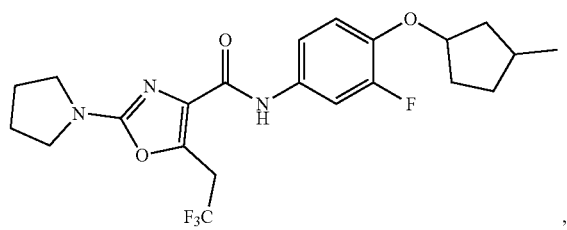
,
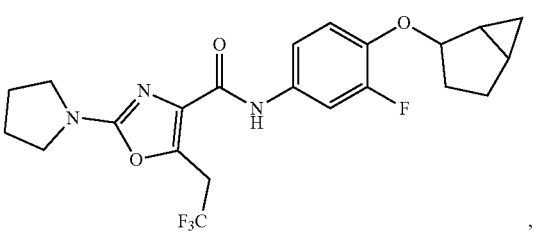
,
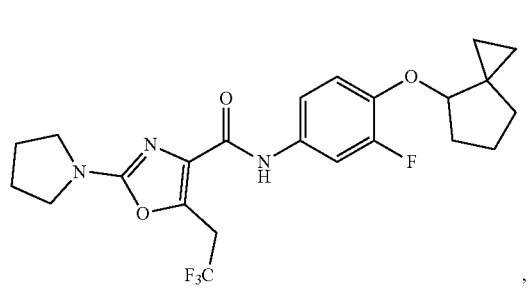
,
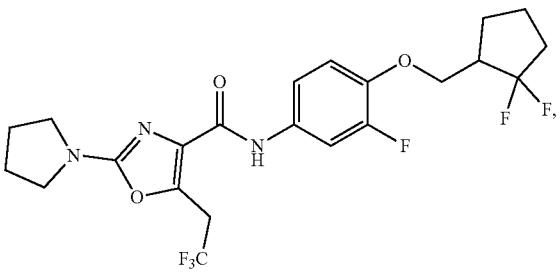
,
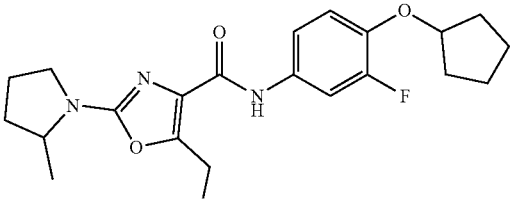
,
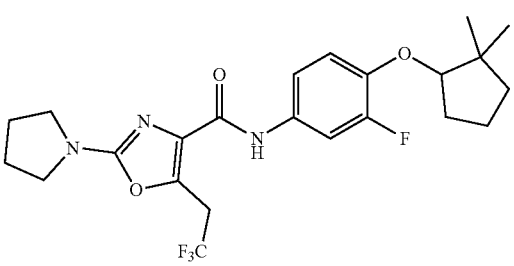
,
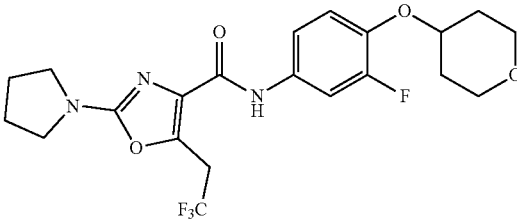
,
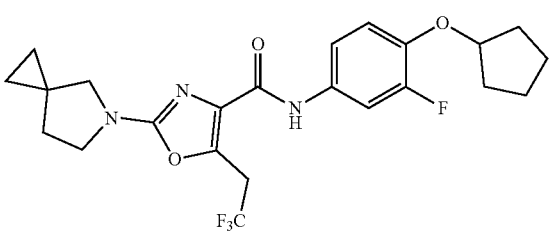
,
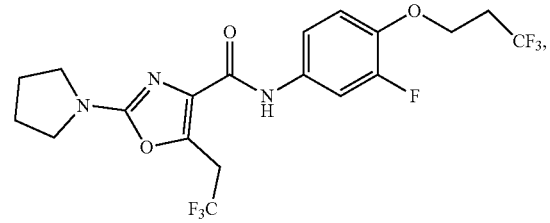
,
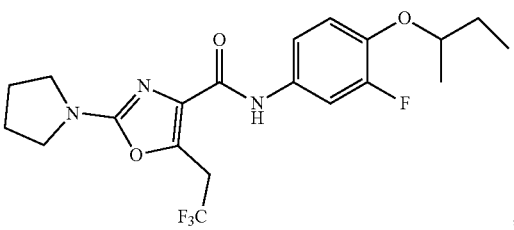
, -continued
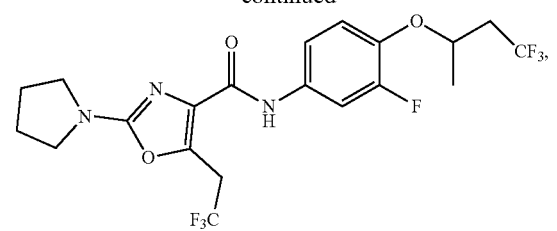
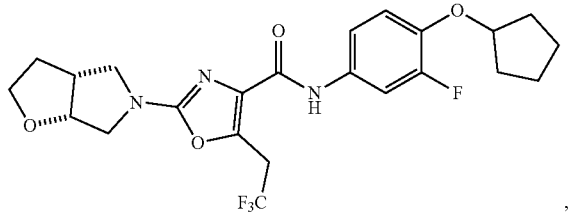
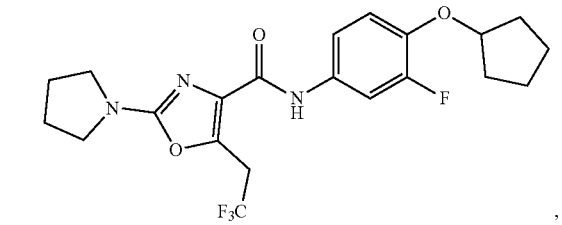
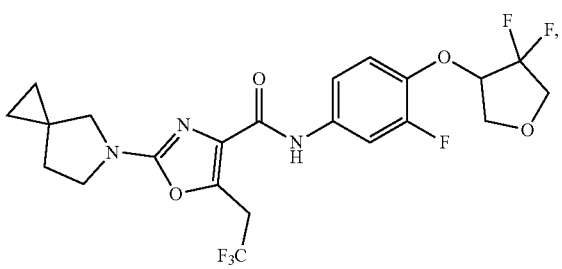
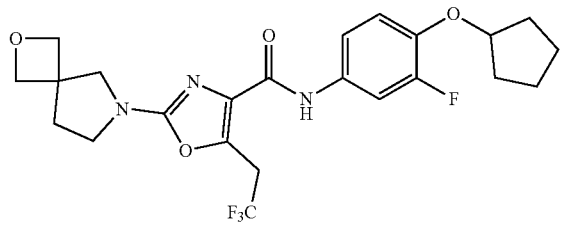
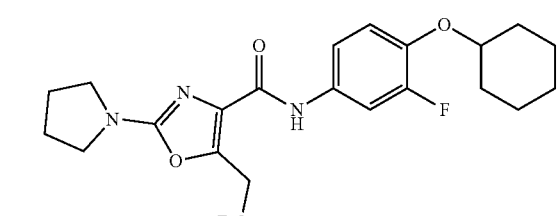
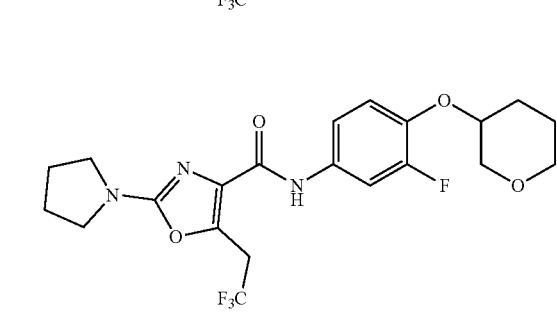
-continued
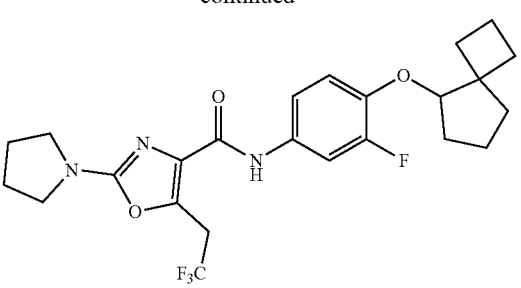
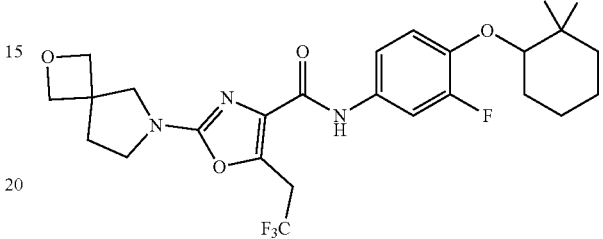
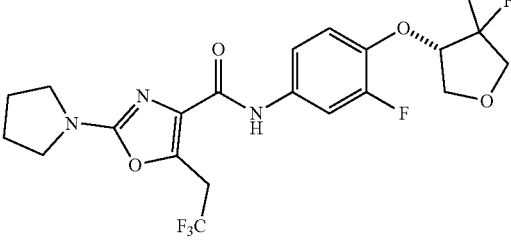
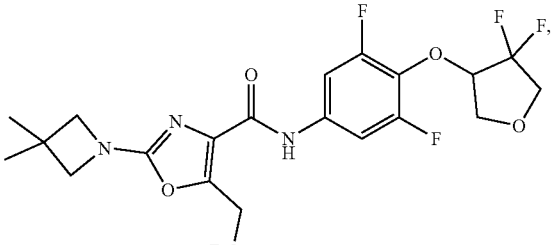
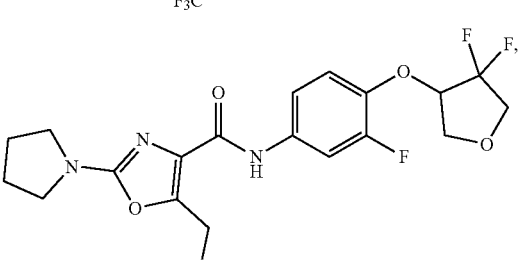
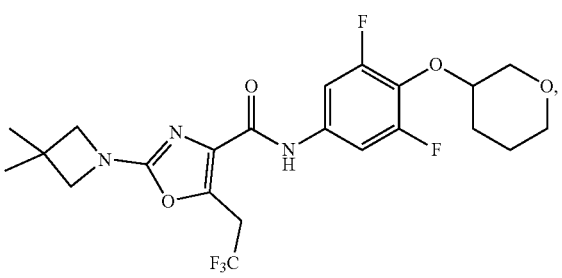

165
-continued
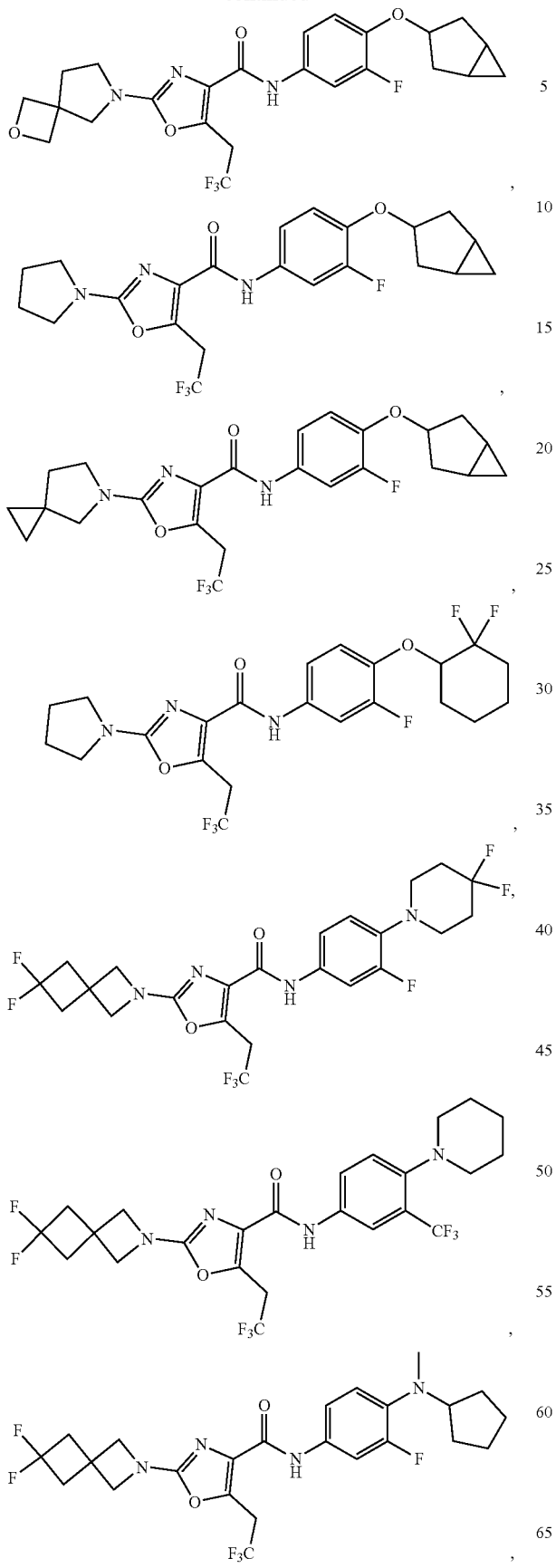
166
-continued
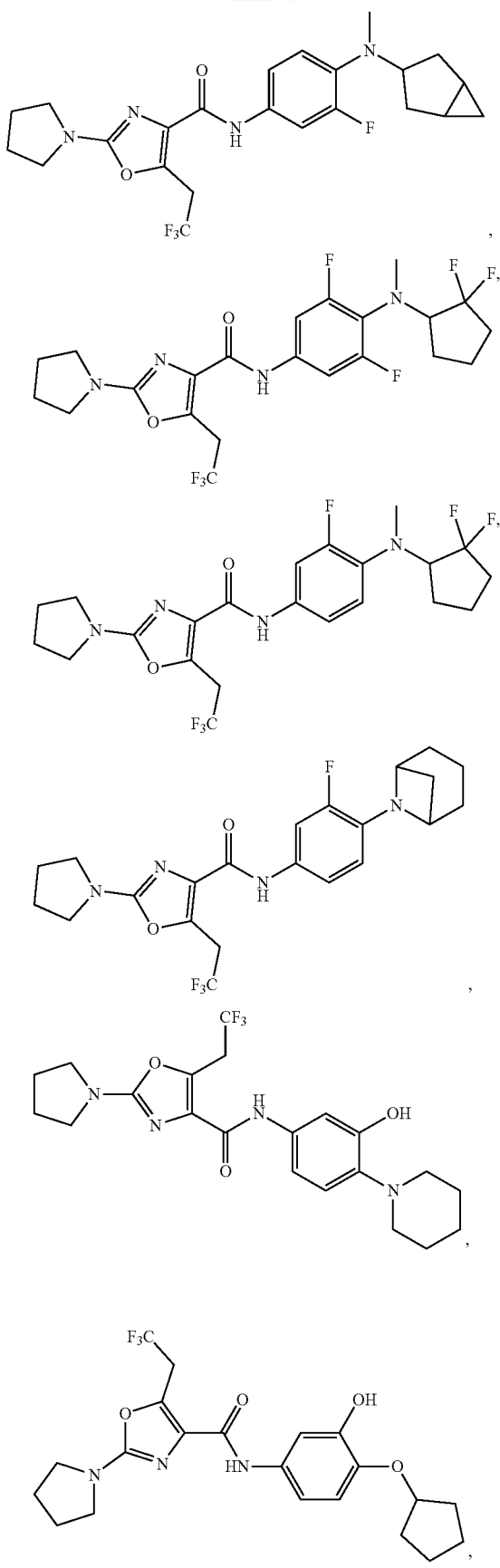

-continued
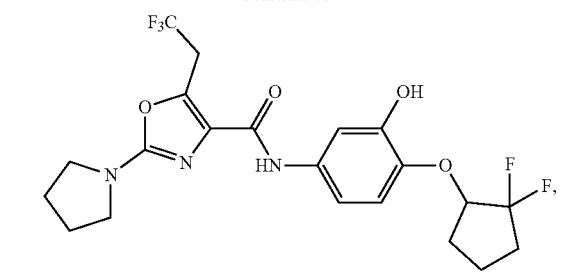
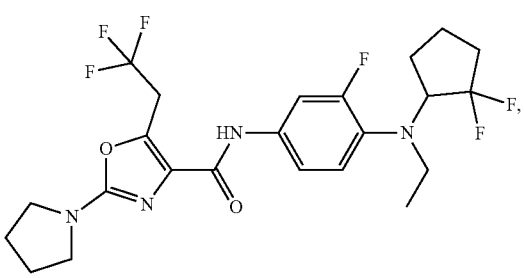
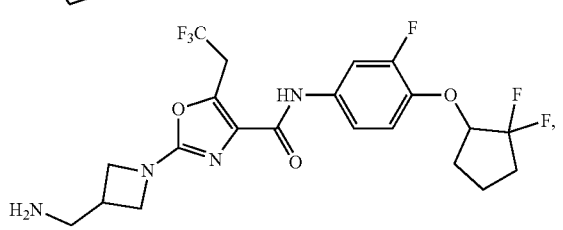
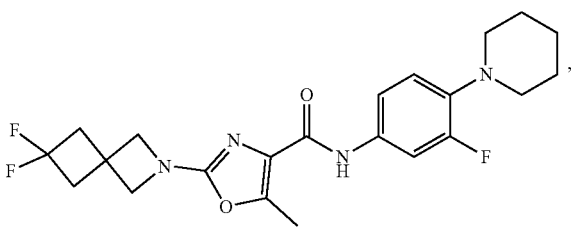
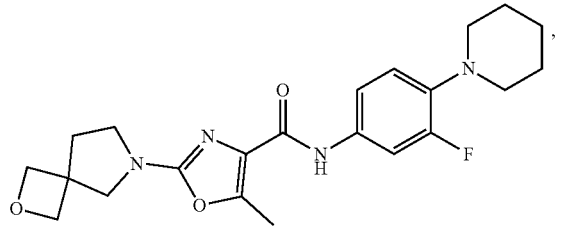
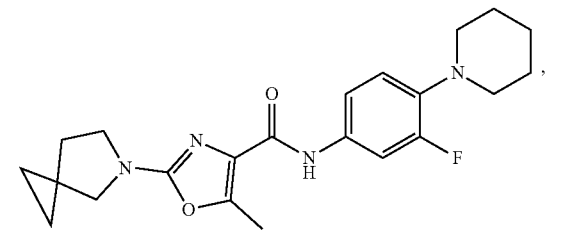
-continued
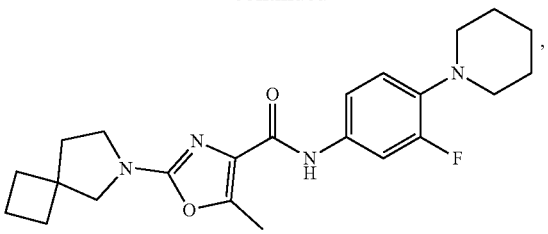
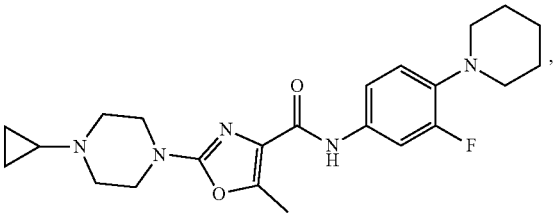
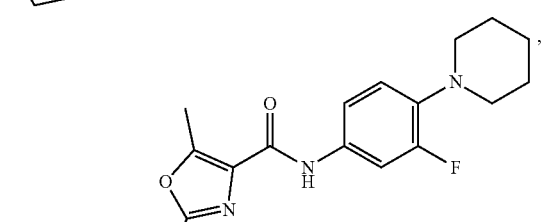
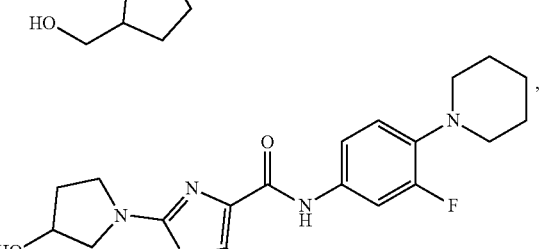
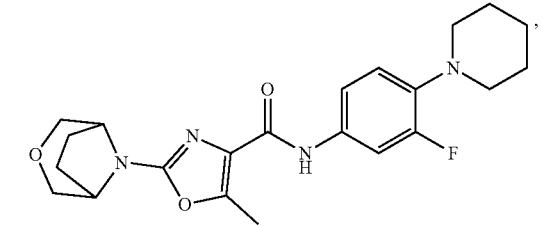

169
-continued
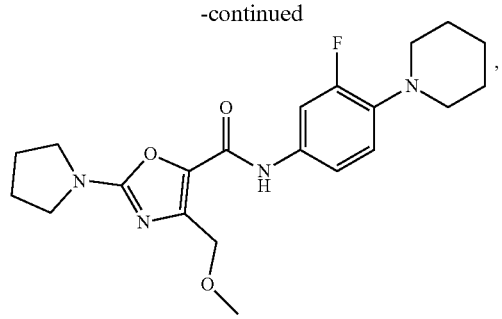
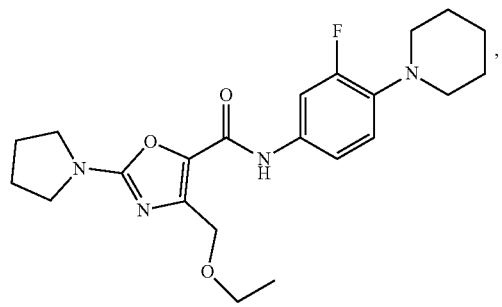
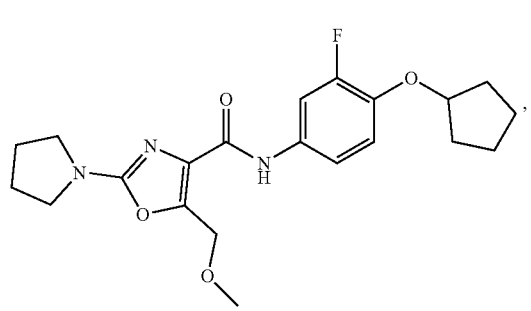
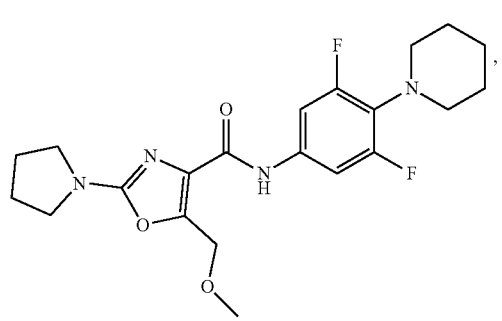
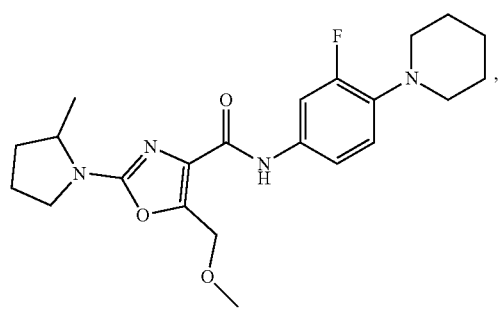
170
-continued
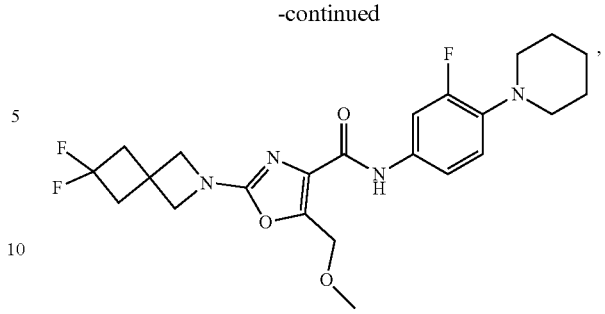
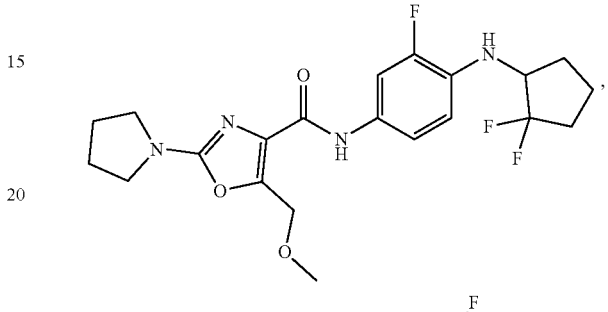
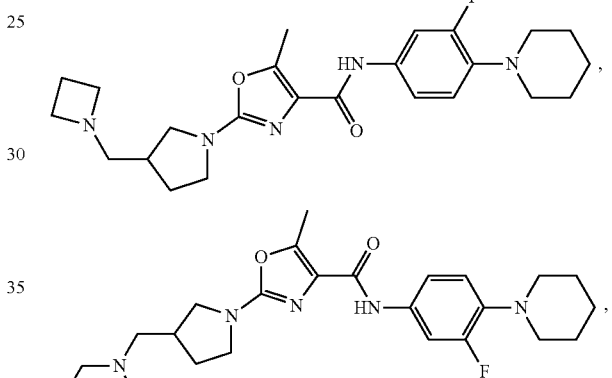
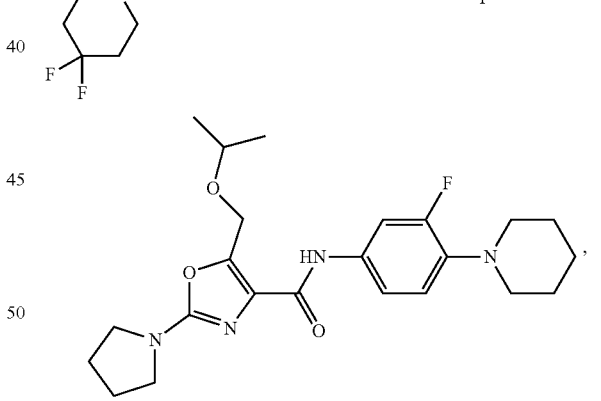
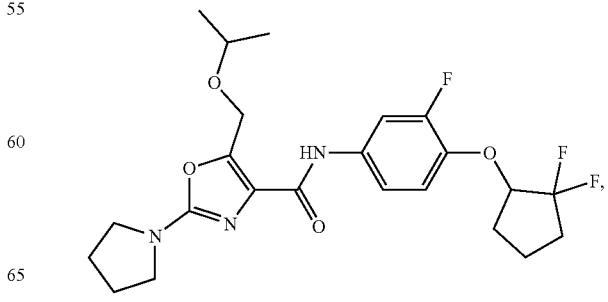

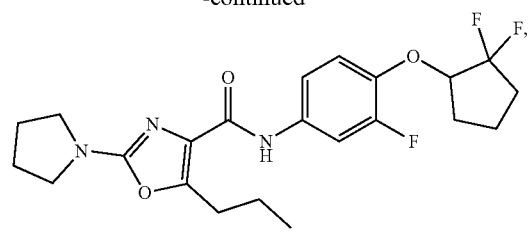
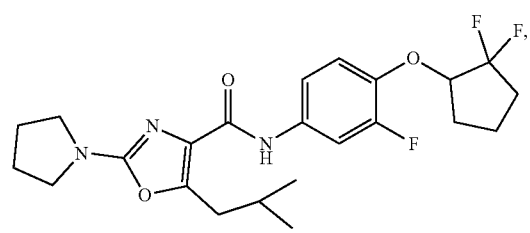
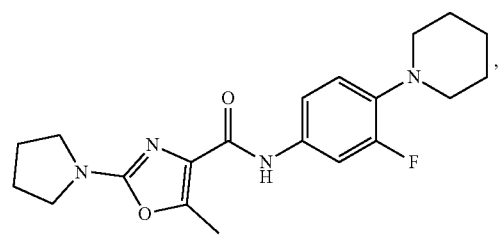
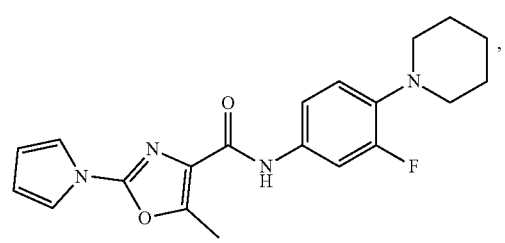
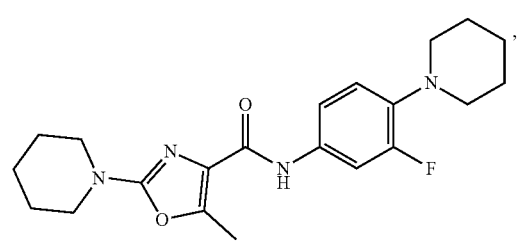
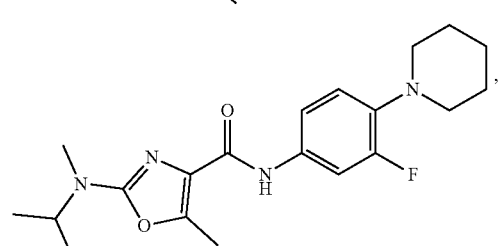
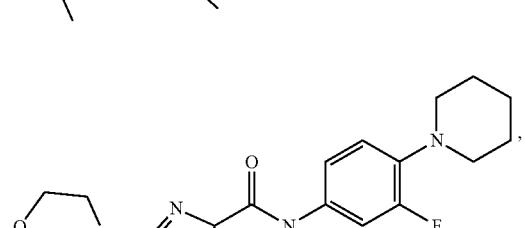
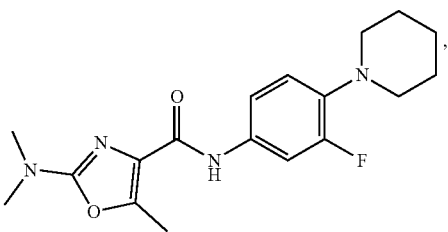
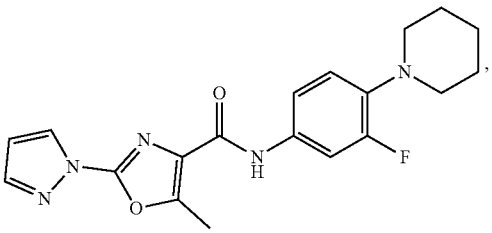
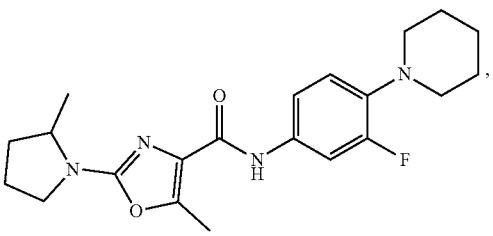
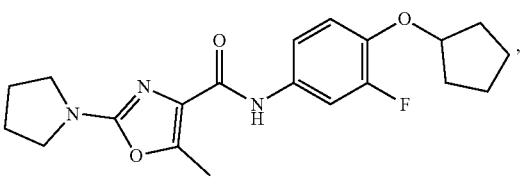
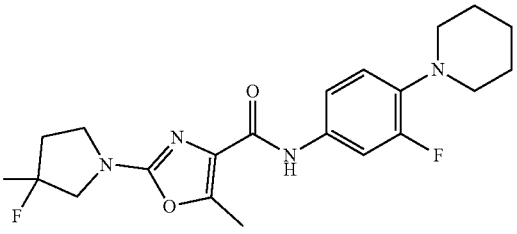
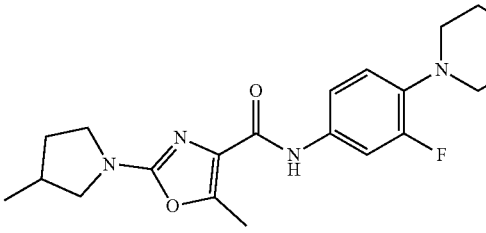
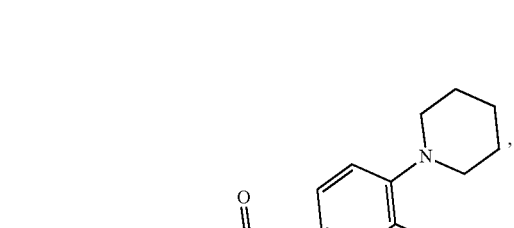
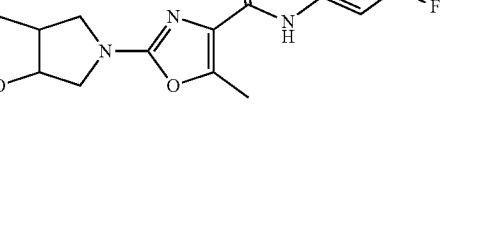

-continued
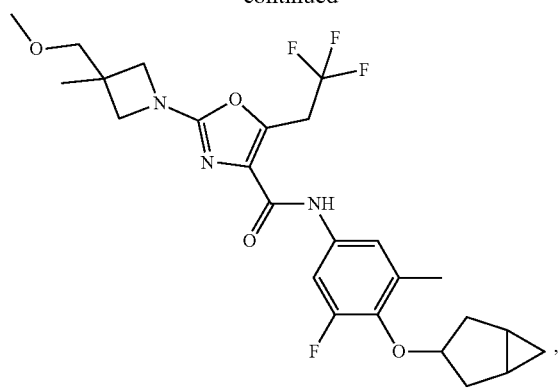
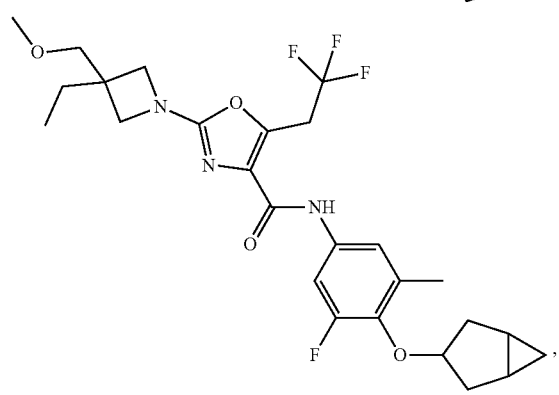
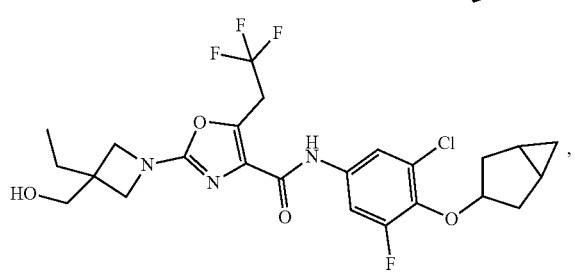
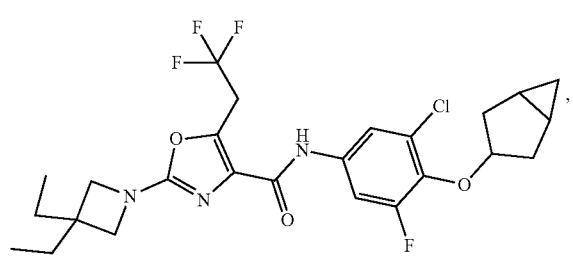
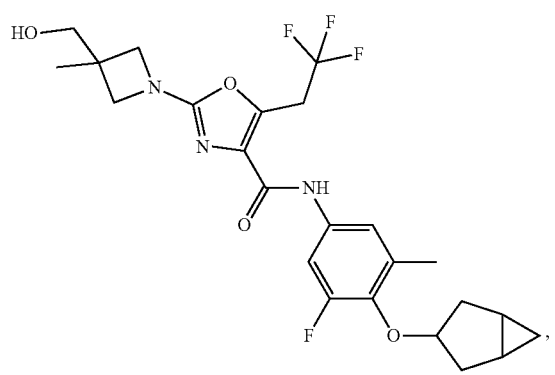
-continued
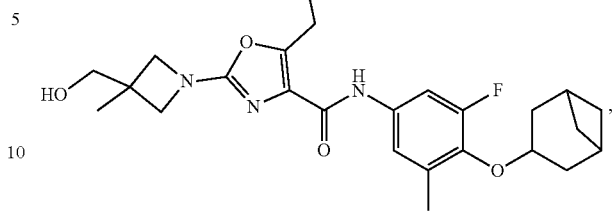
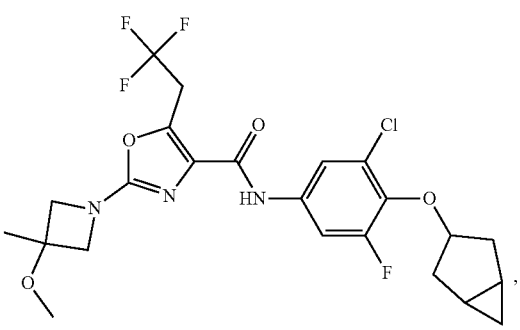
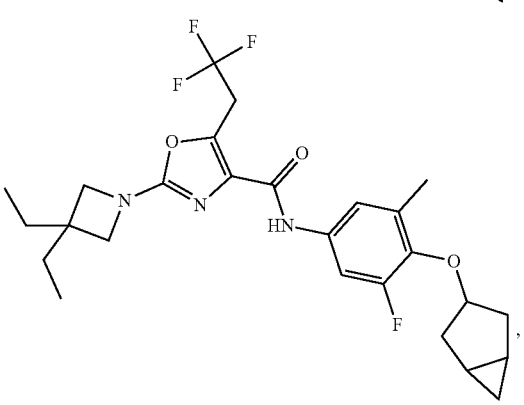
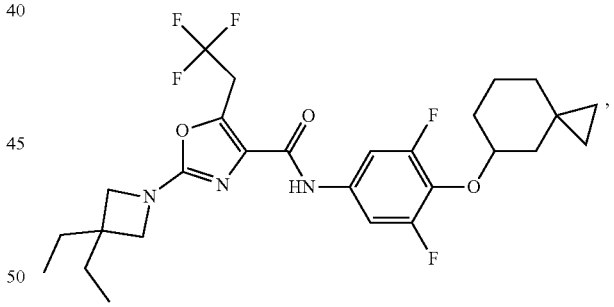
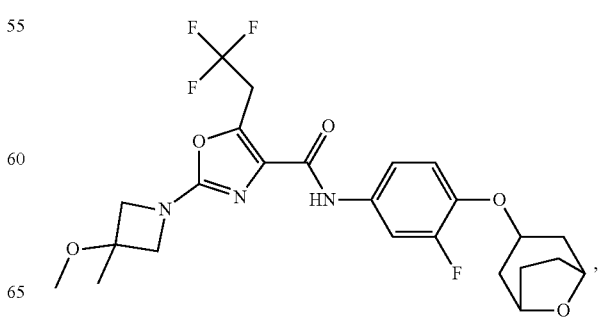

-continued
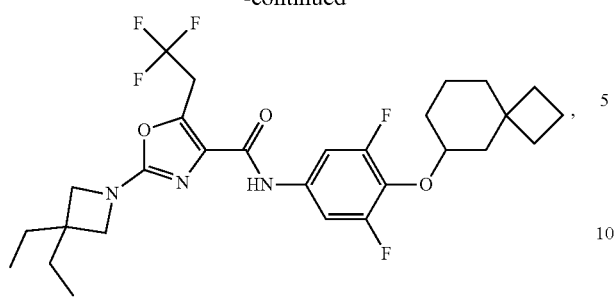
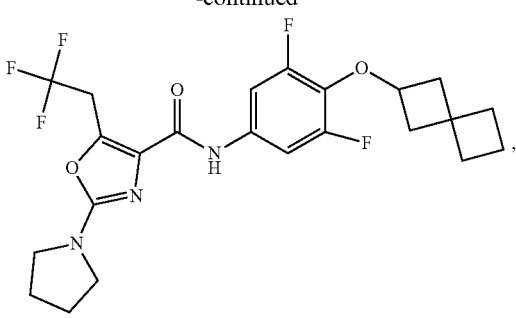
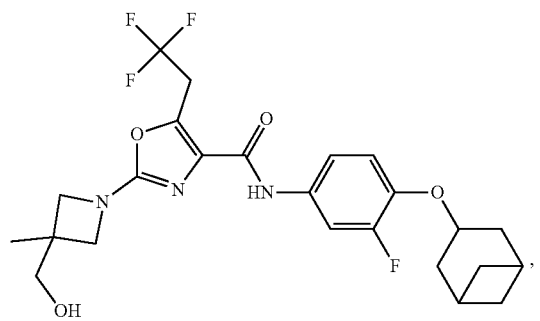
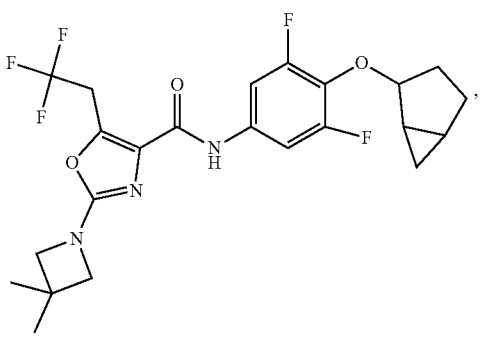
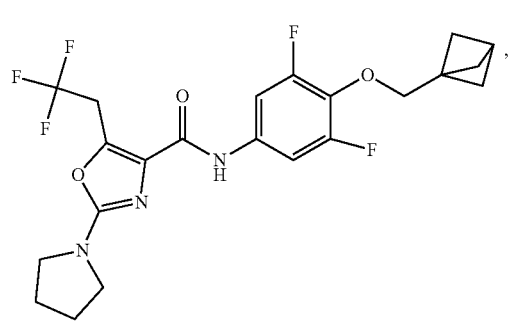
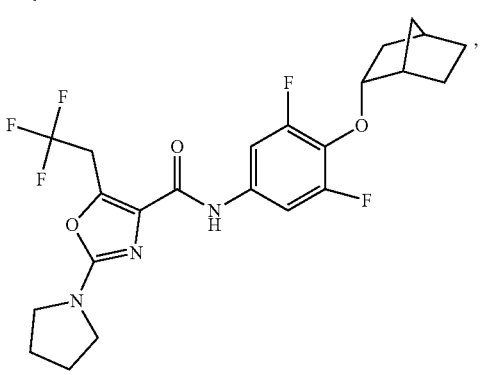
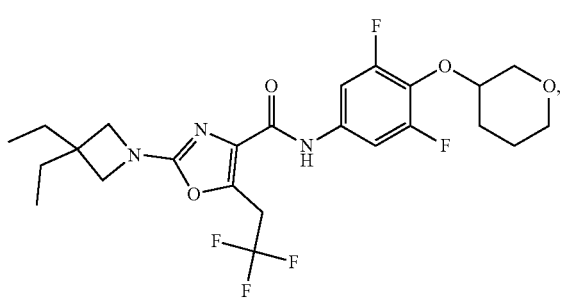
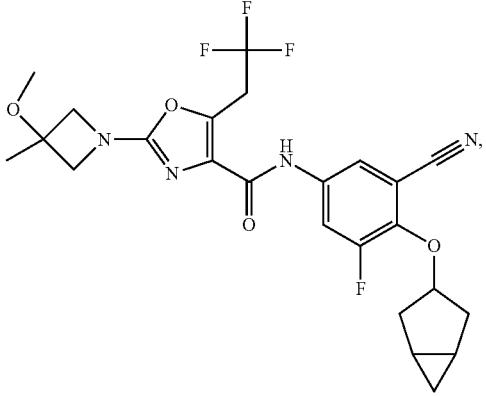 [SMILES: COC1(C)CN(c2nc(C(=O)Nc3ccc(OC4CC5CC5C4)c(C#N)c3)c(CC(F)(F)F)o2)C1]
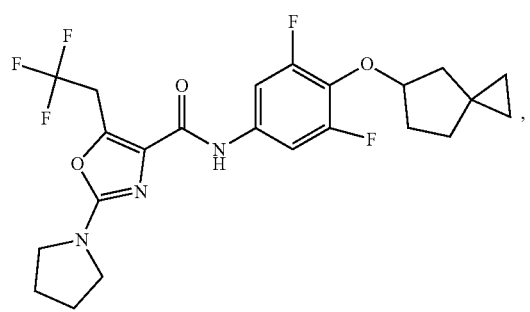
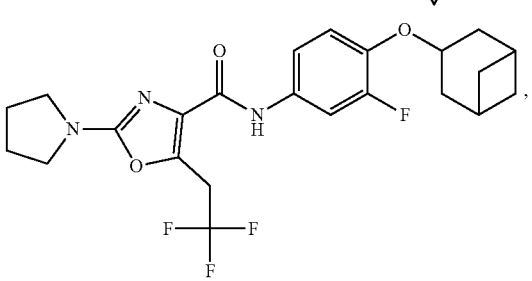

177
-continued
178
-continued
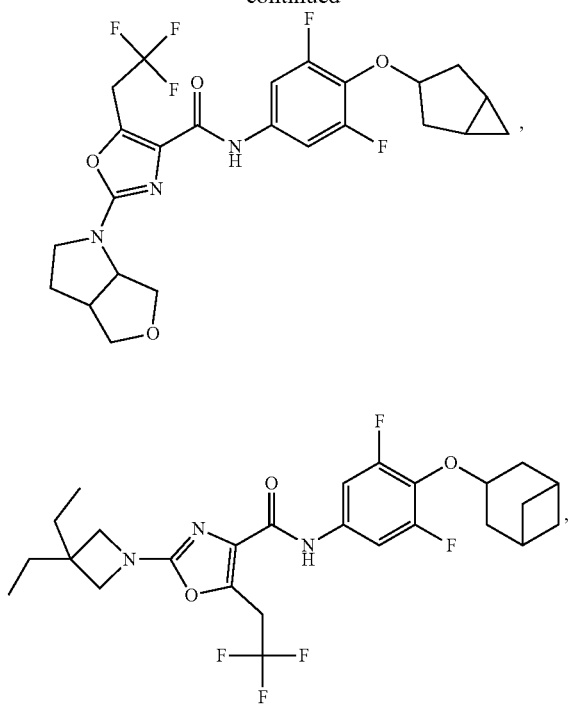
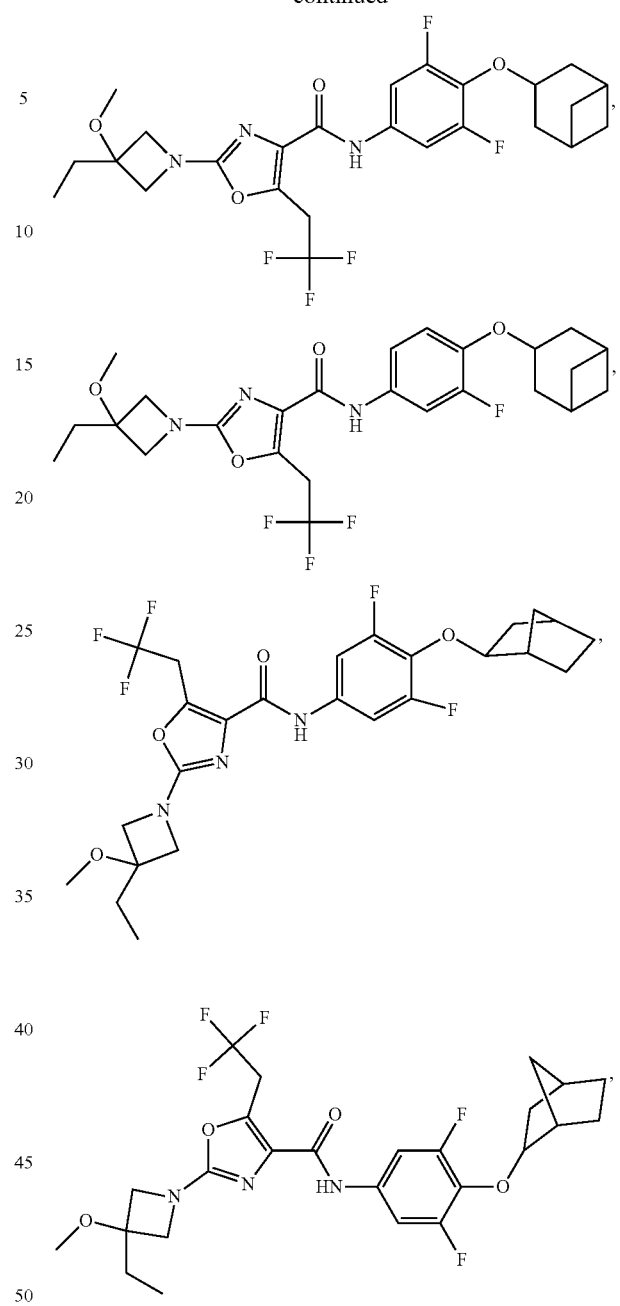
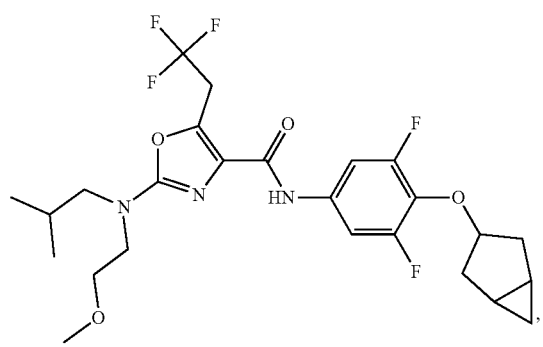
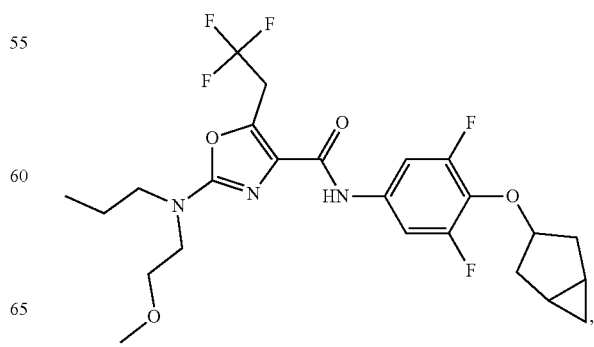

179
-continued
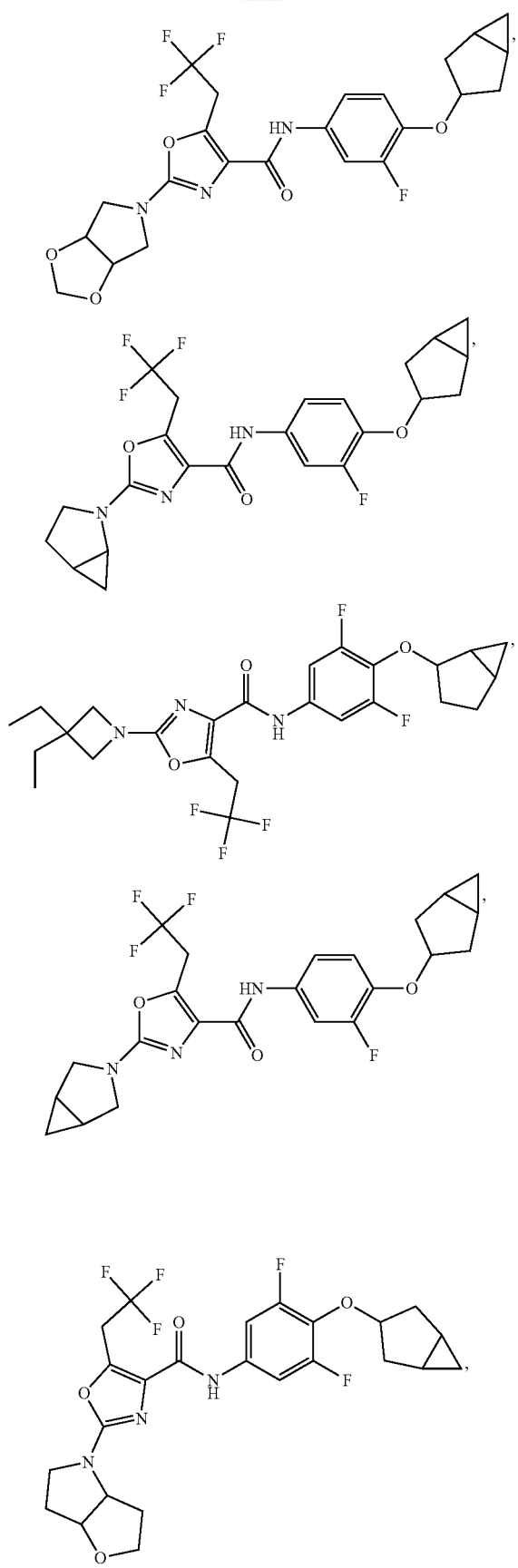
180
-continued
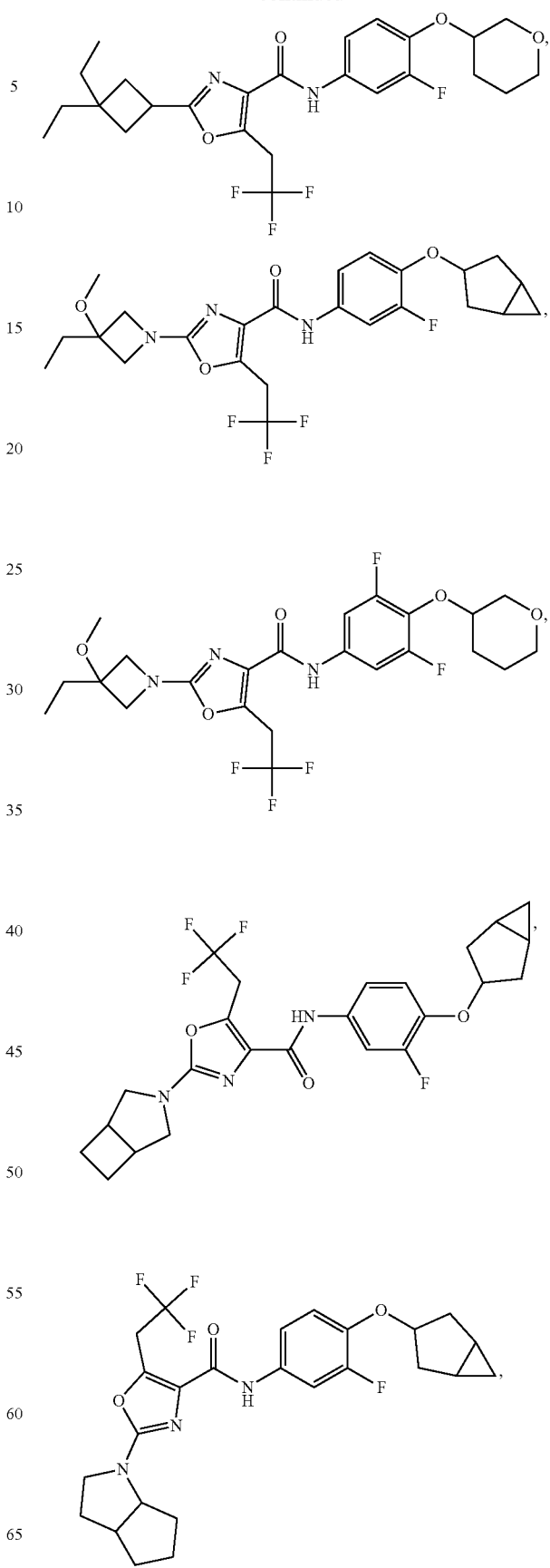

-continued
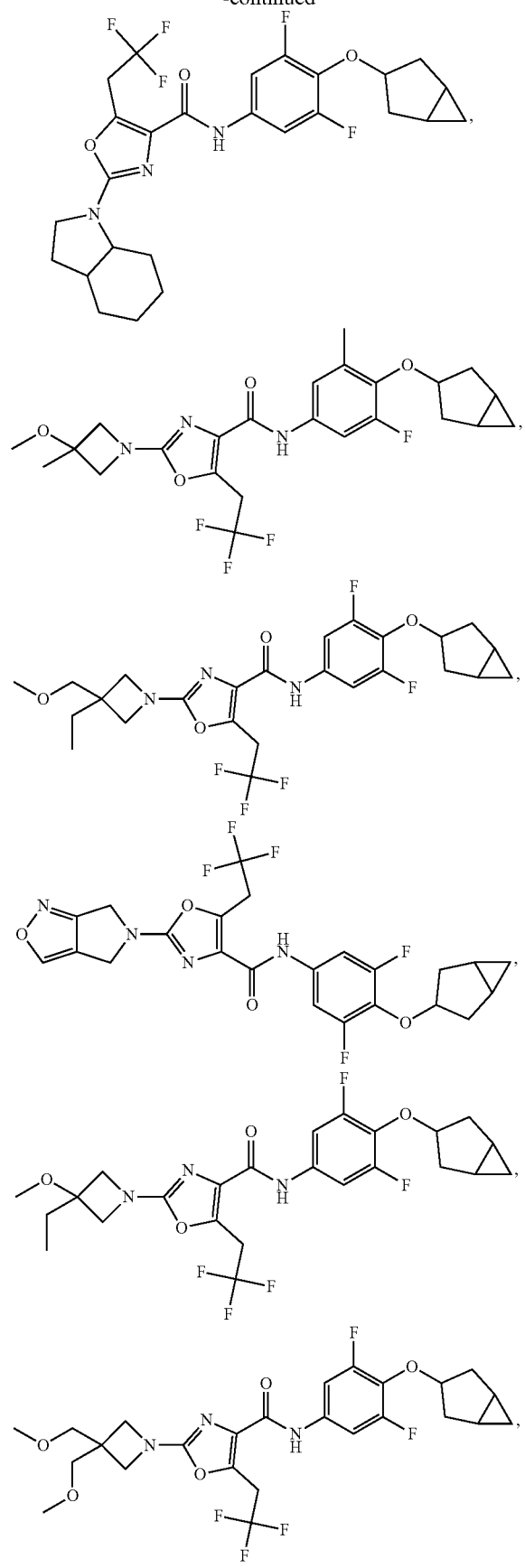
-continued
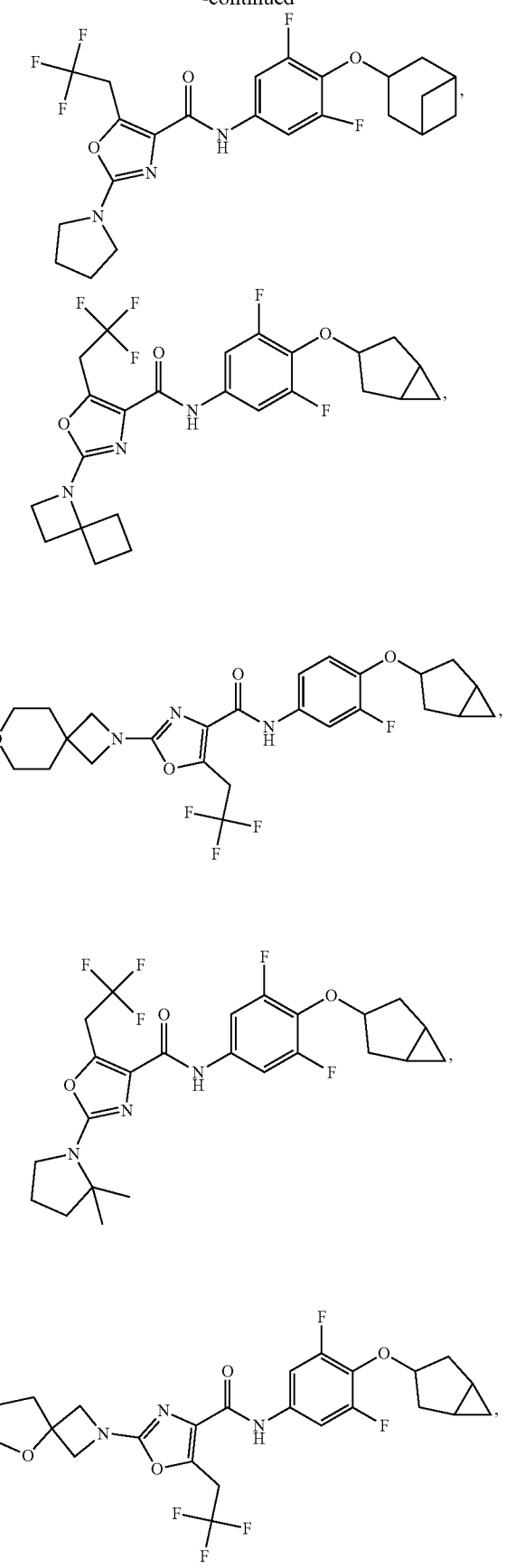

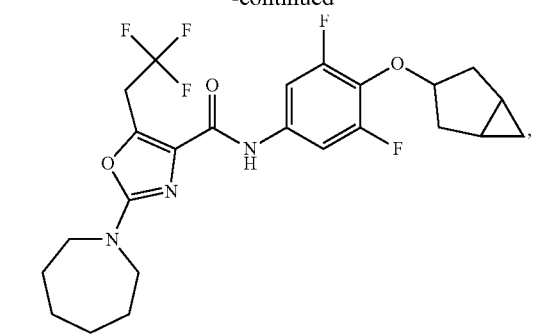
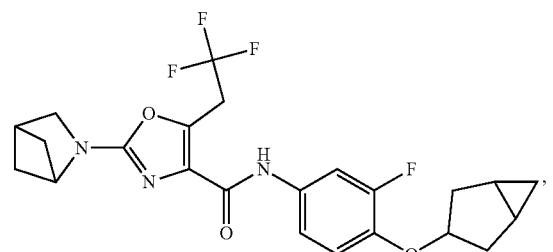
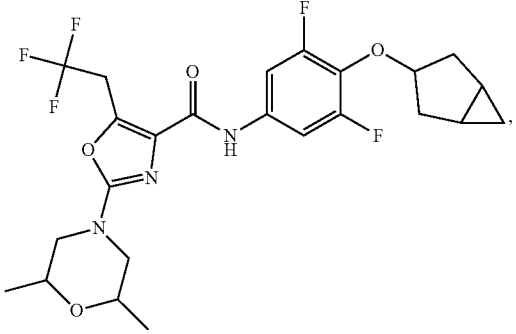
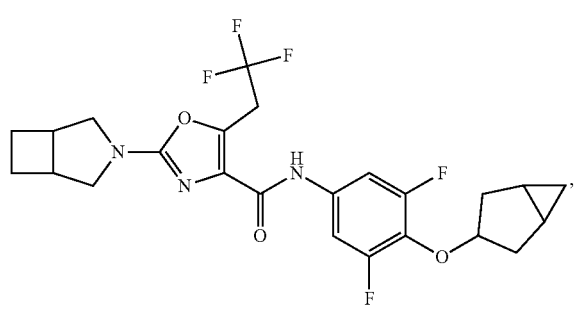
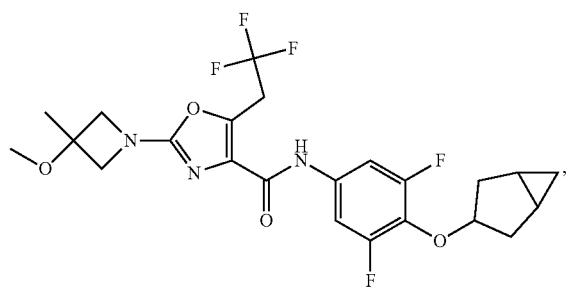
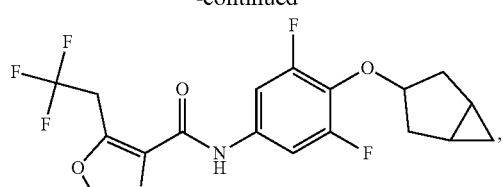
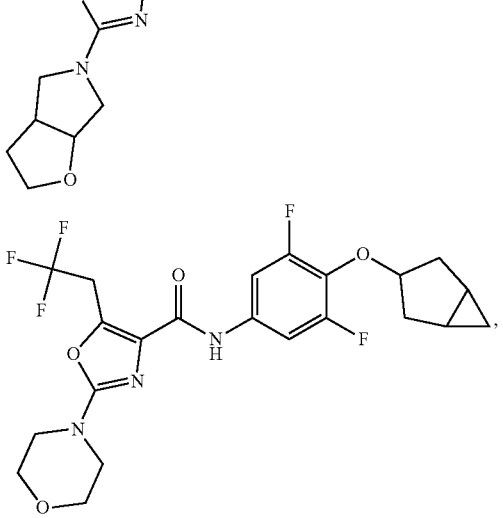
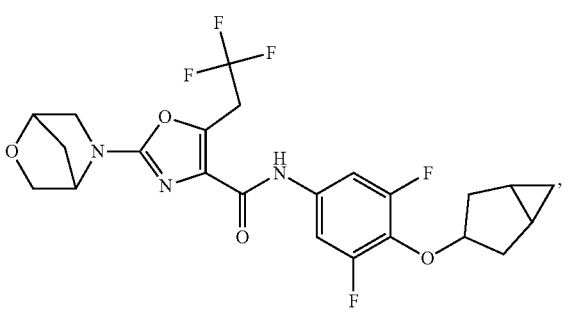
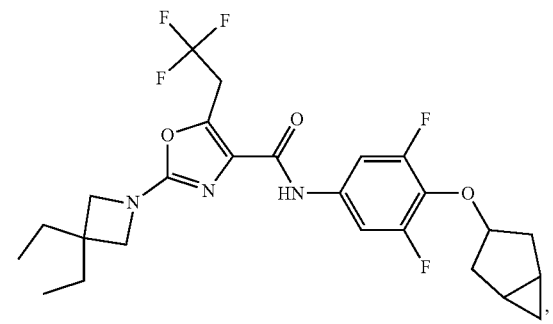
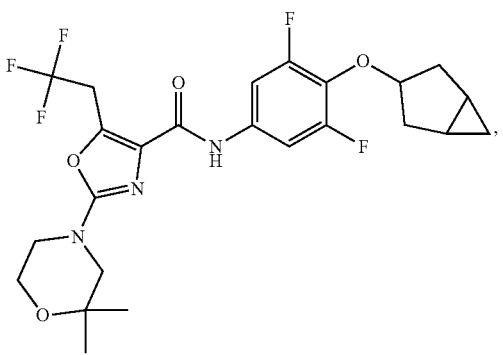

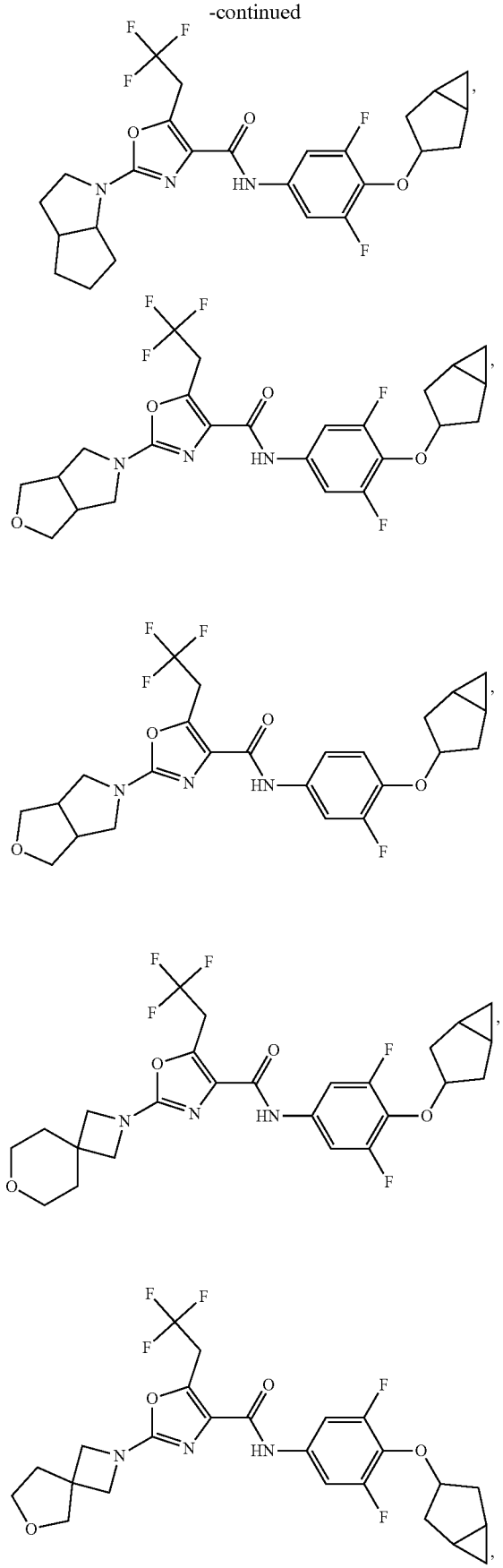
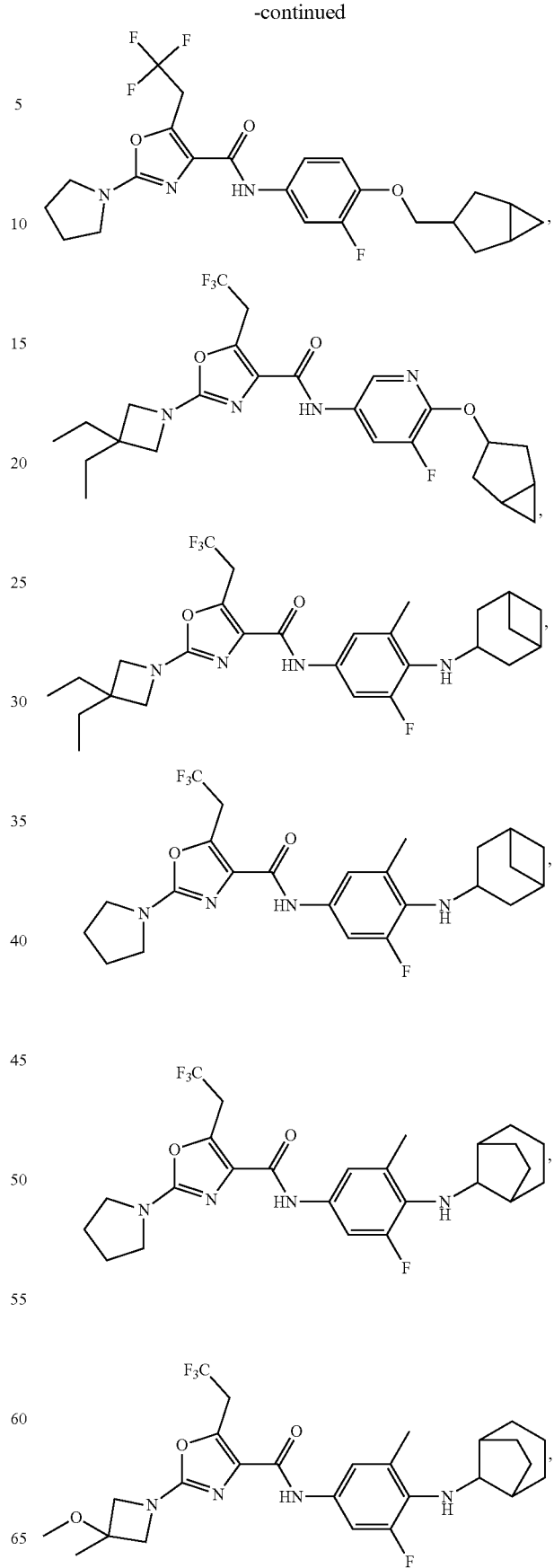

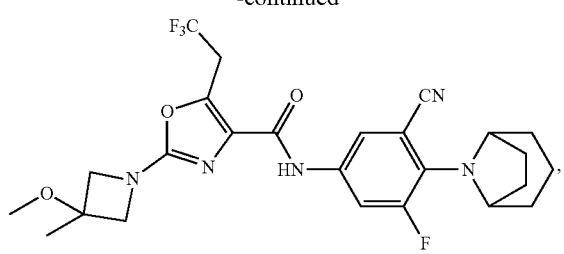
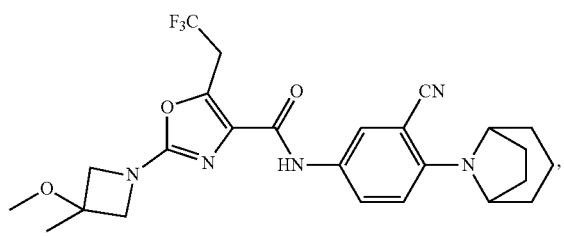
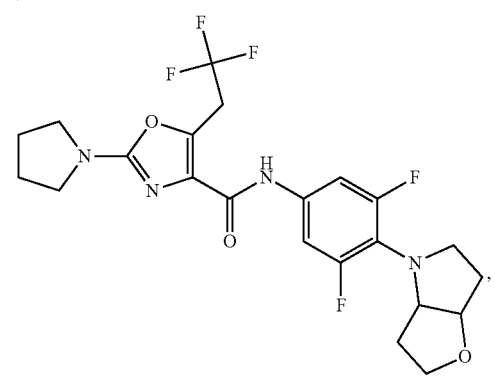
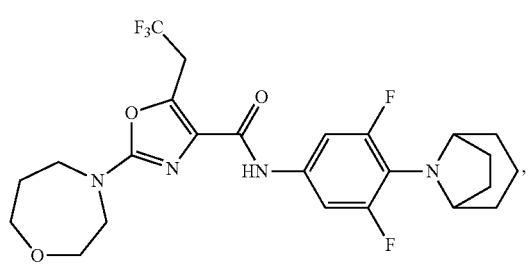
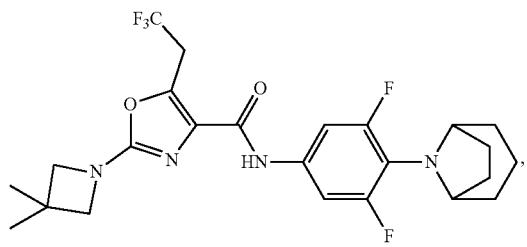
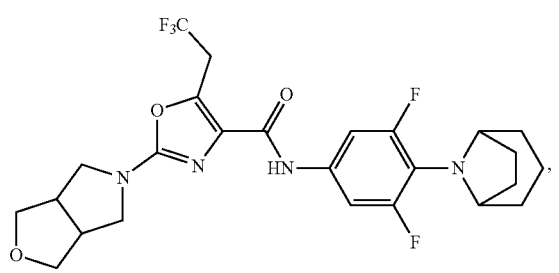
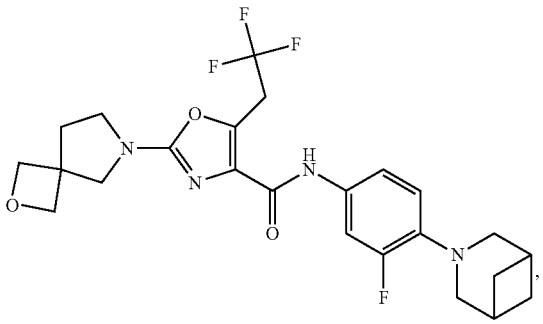
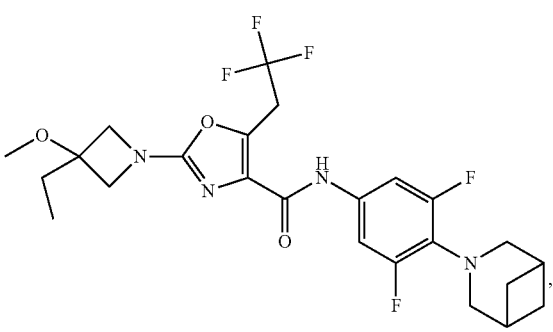
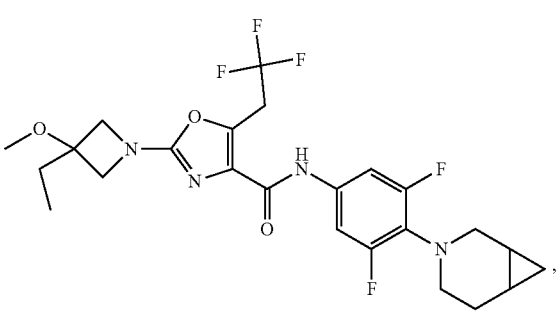
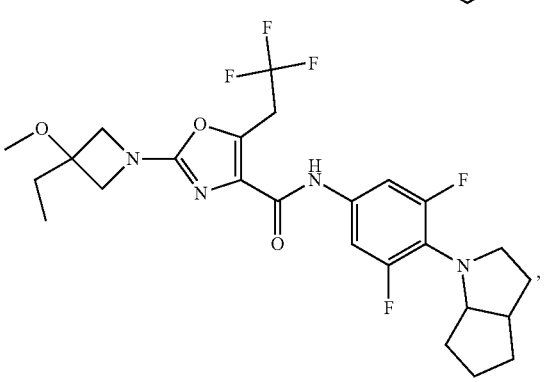
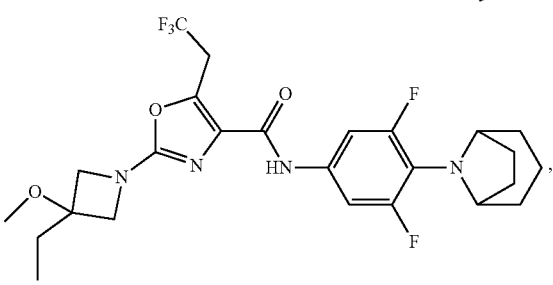

-continued
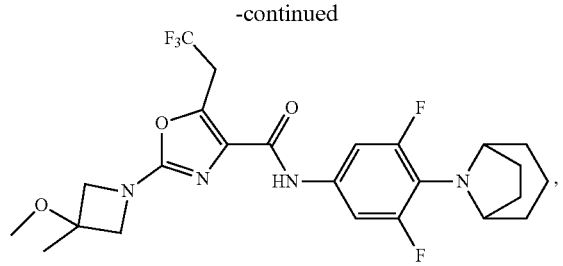
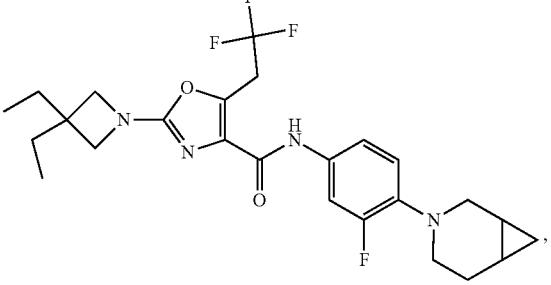
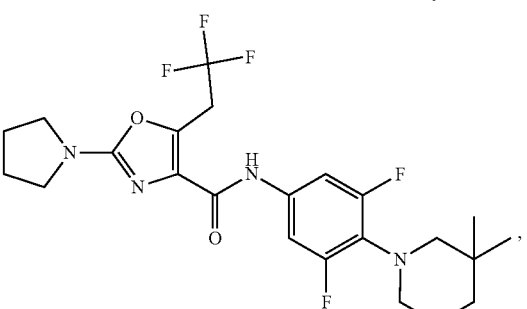
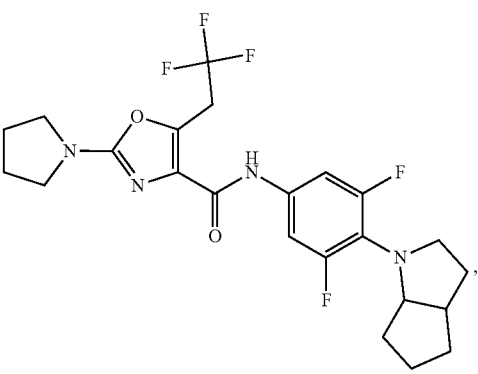
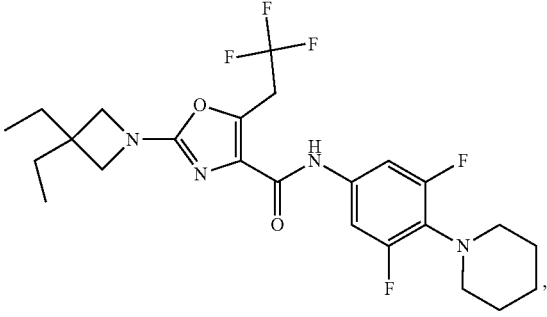
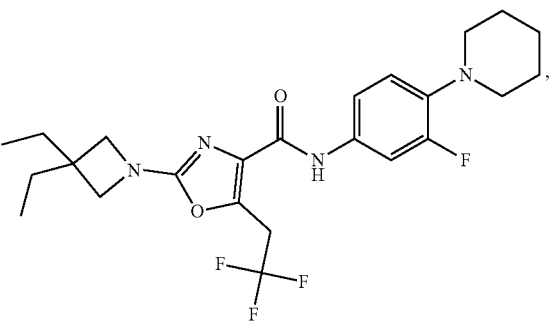

191
-continued
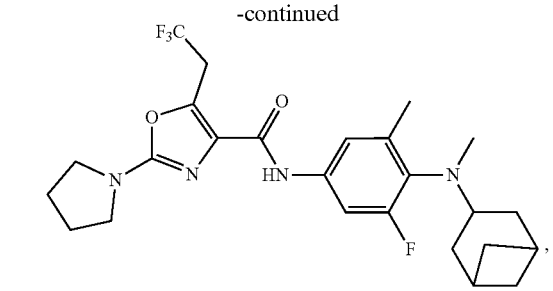
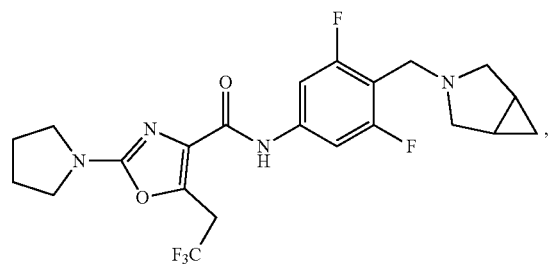
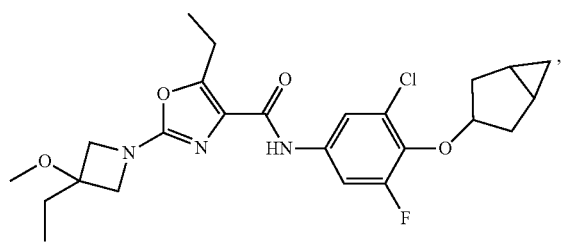
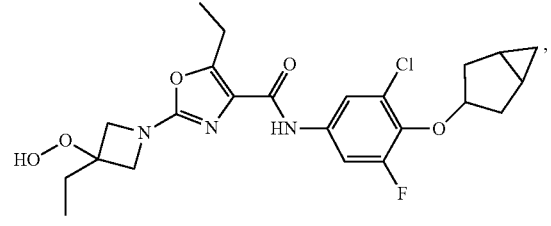
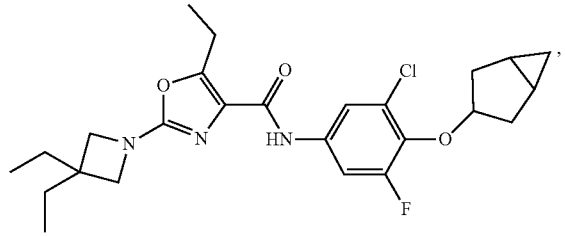
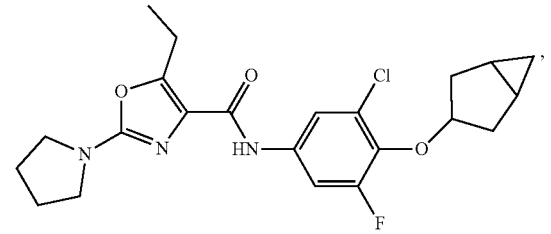
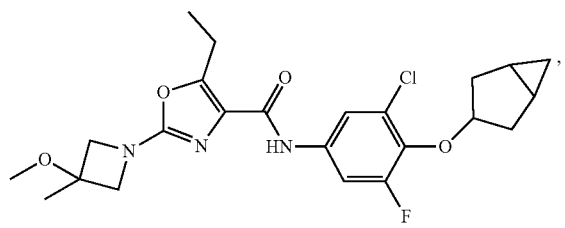
192
-continued
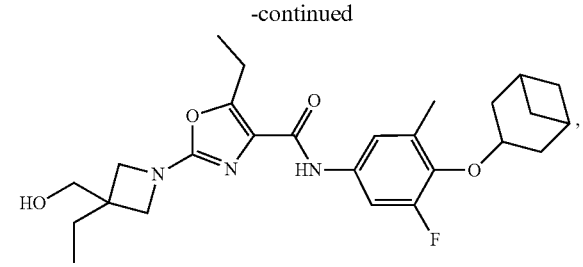
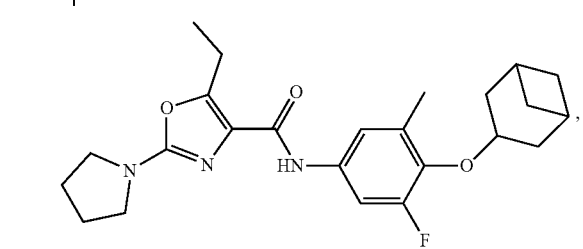
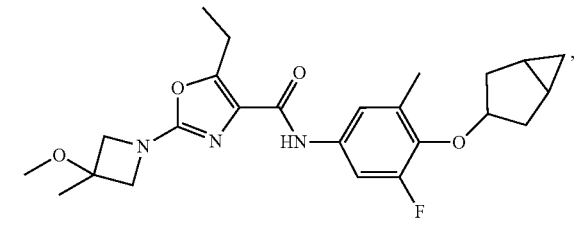
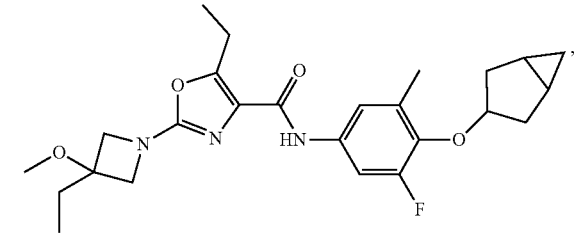
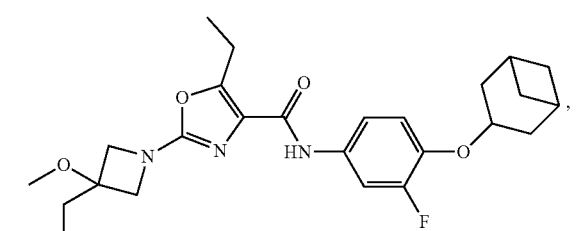
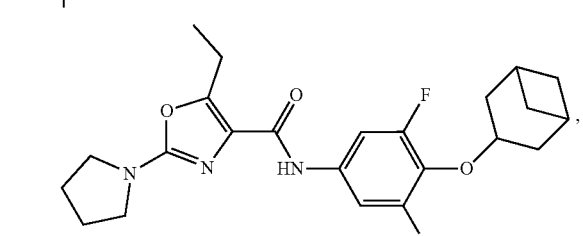
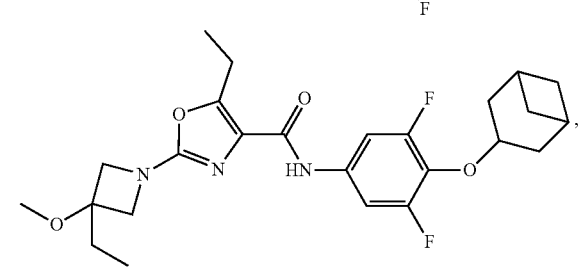

193
-continued
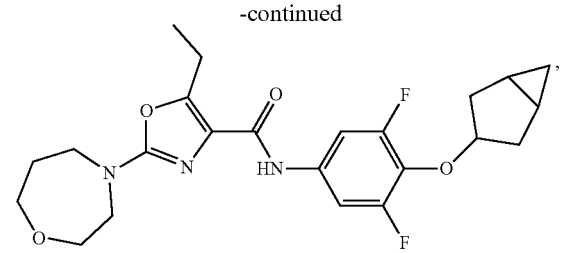
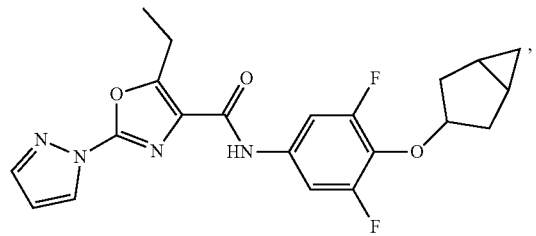
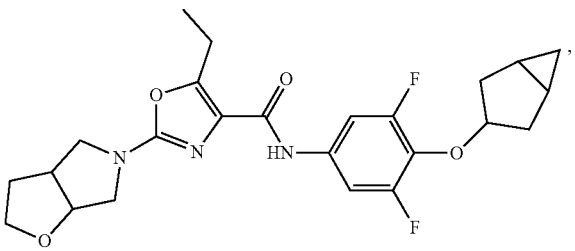
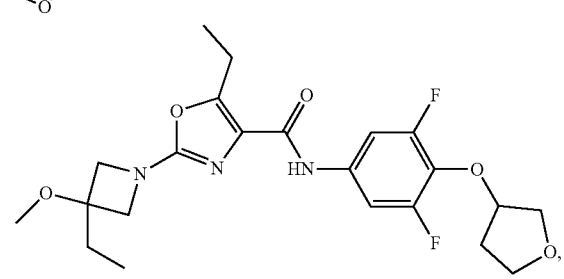
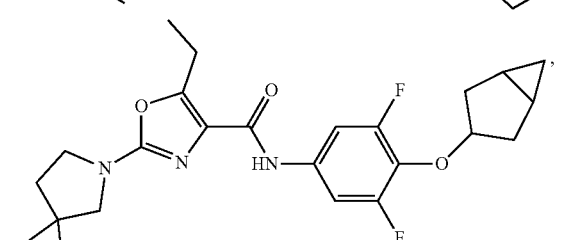

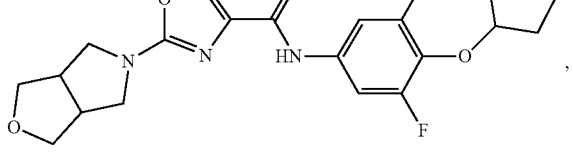
194
-continued
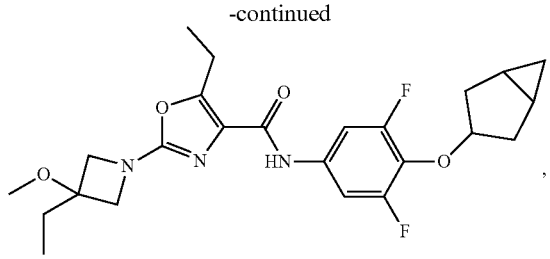
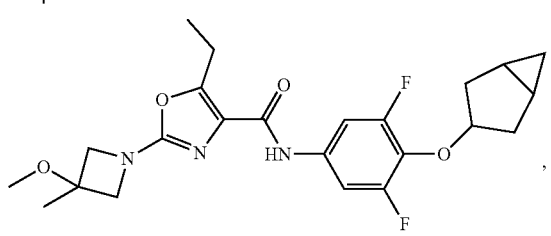
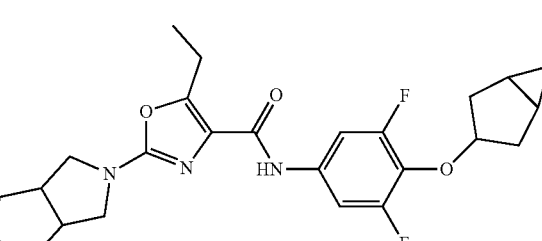
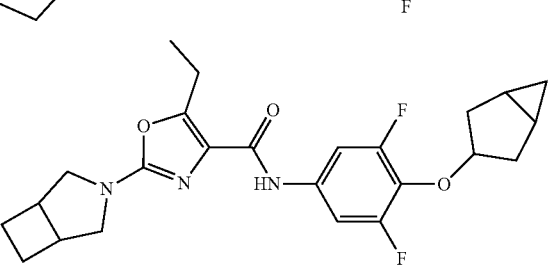
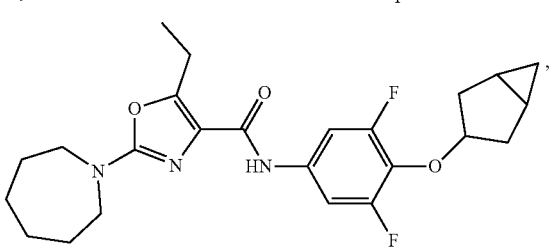
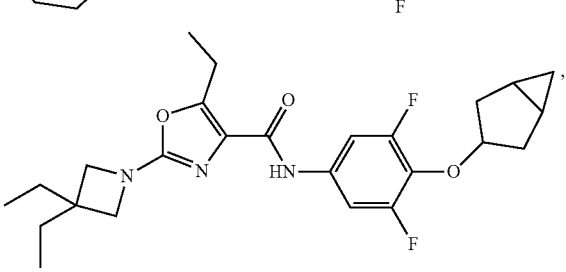
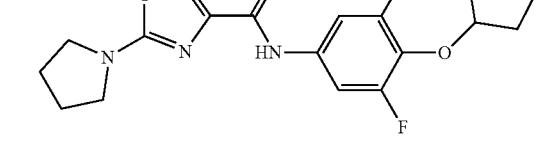

195
-continued
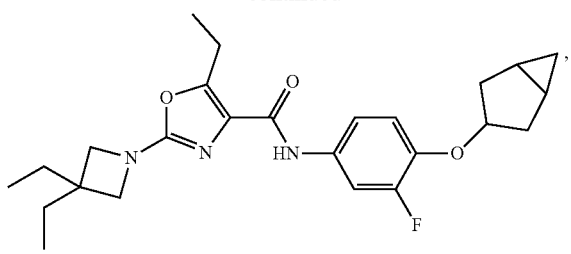
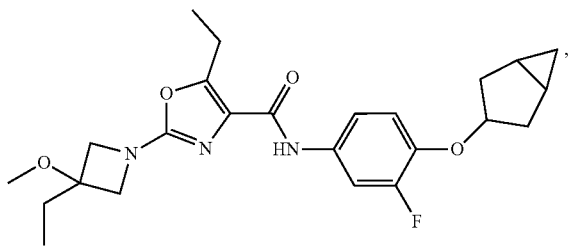
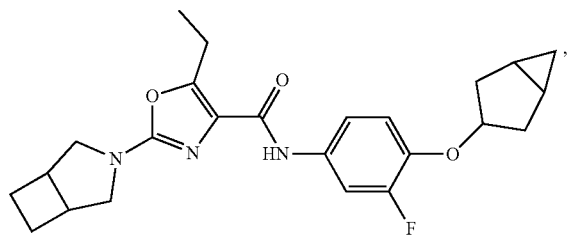
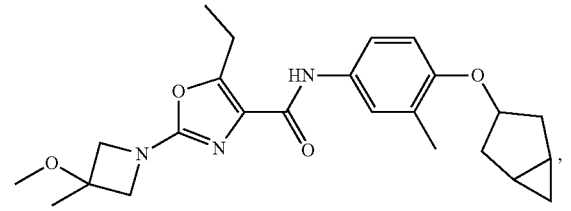
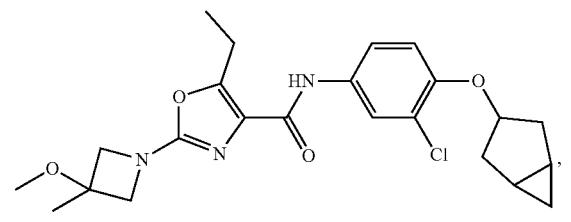
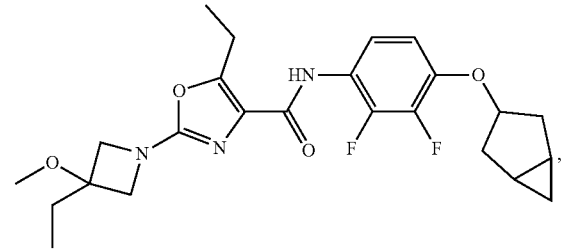
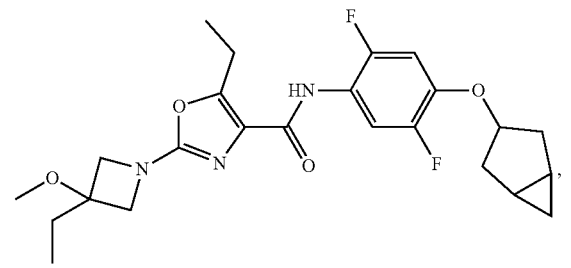
196
-continued
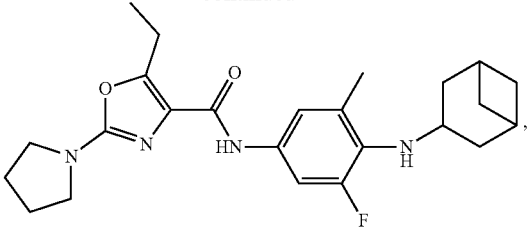
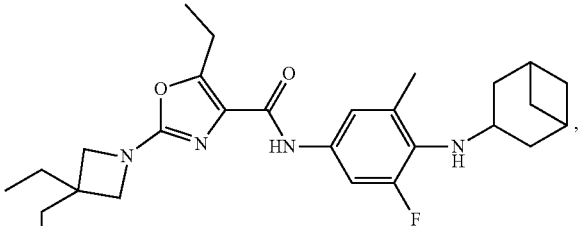
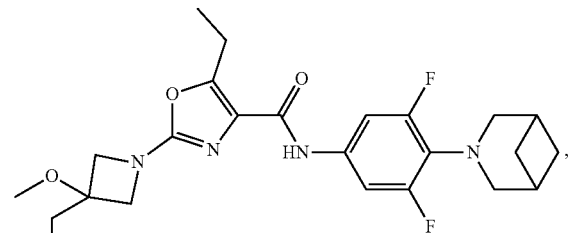
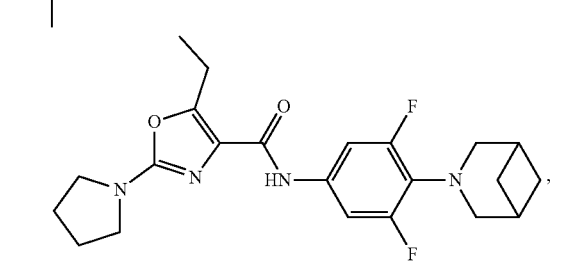
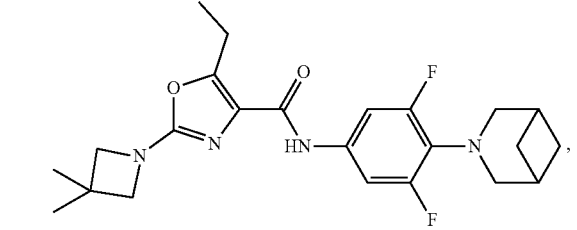
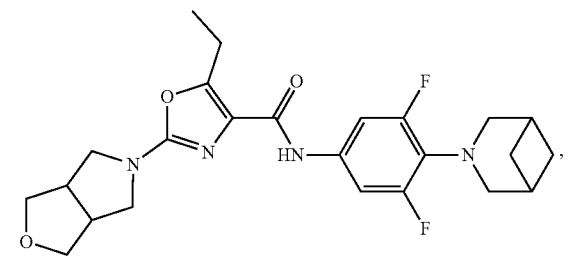
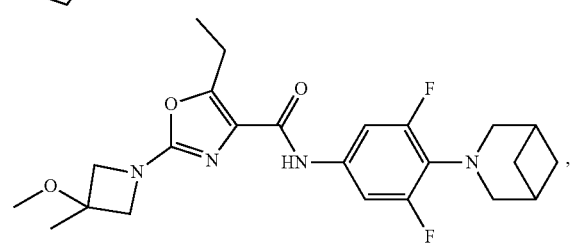

197
-continued
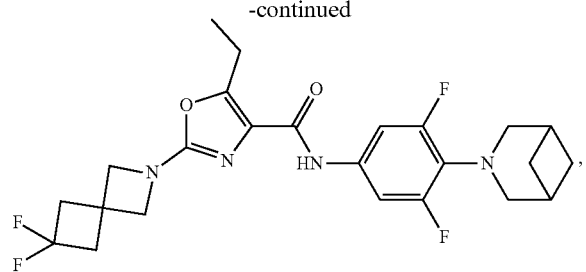
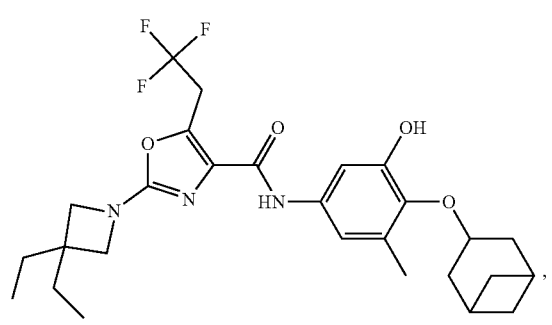
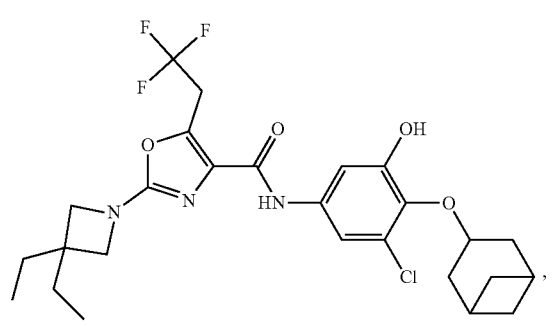
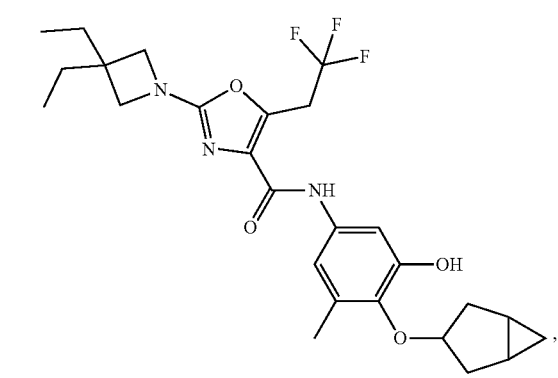
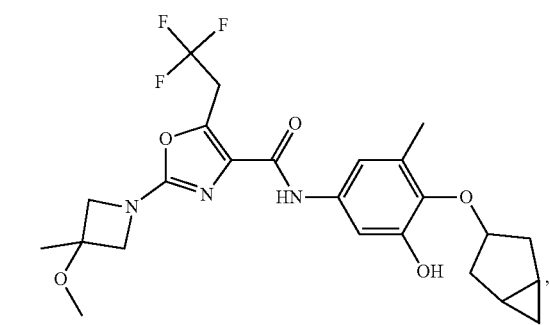
198
-continued
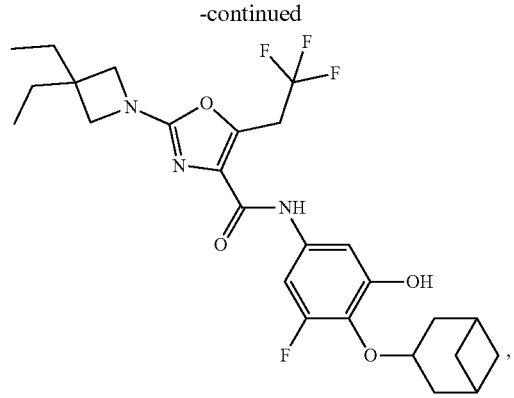
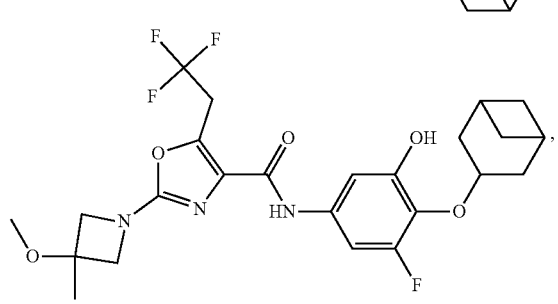
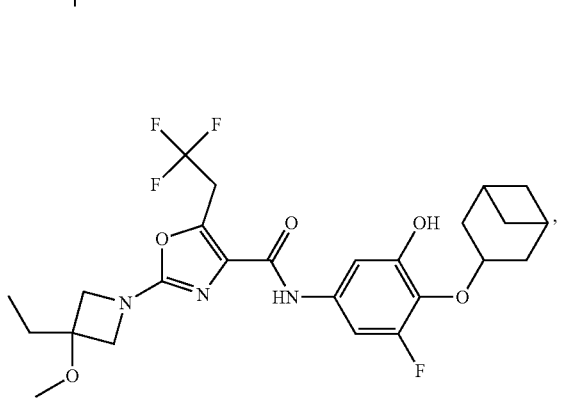
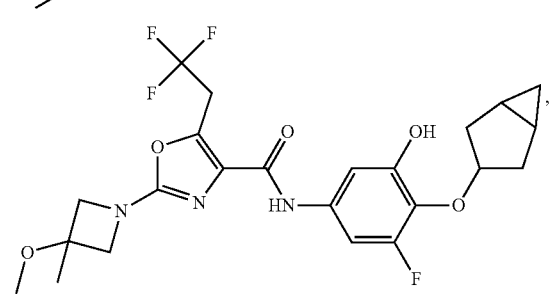
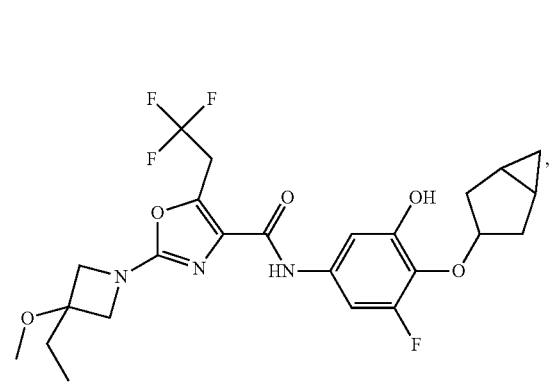

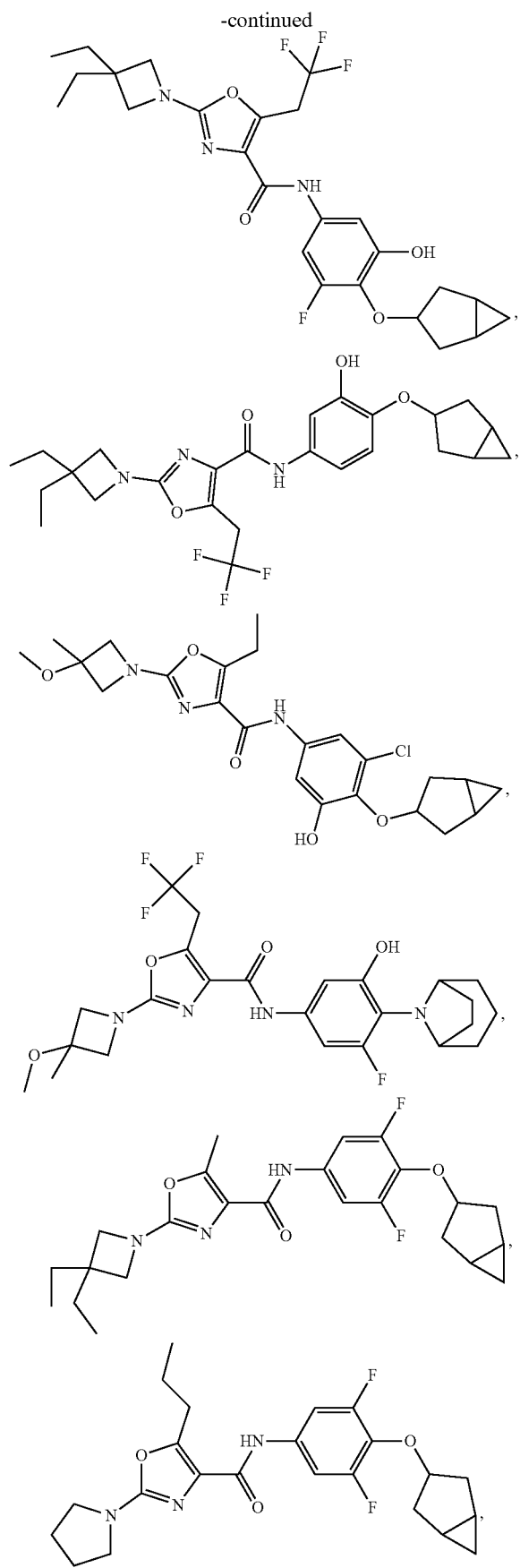

201
-continued
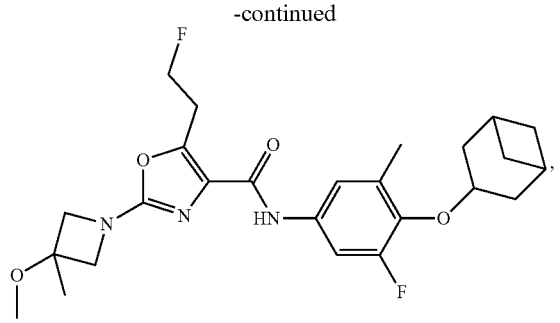
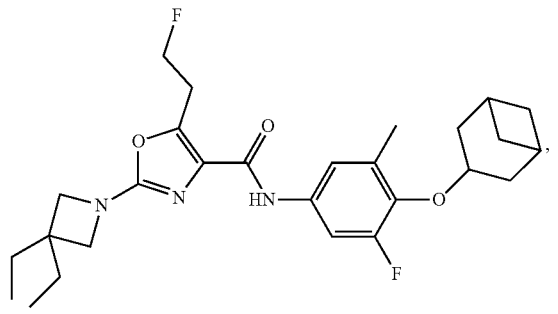
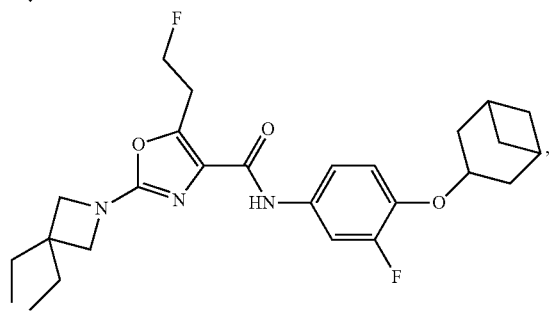
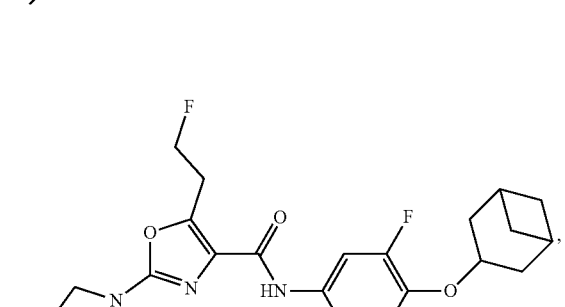
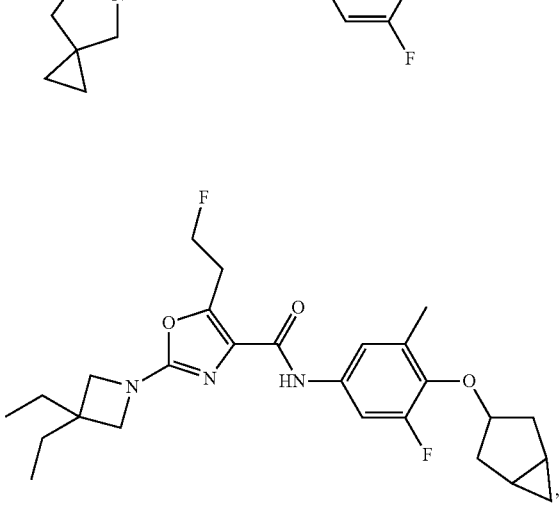
202
-continued
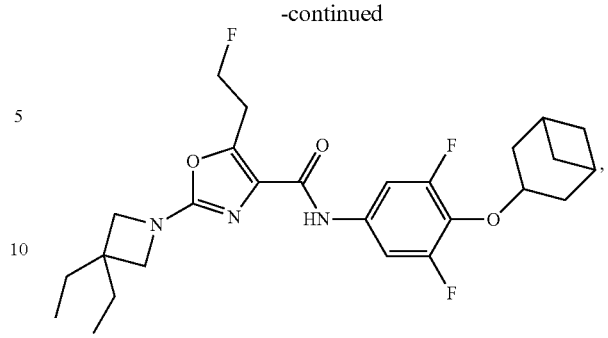
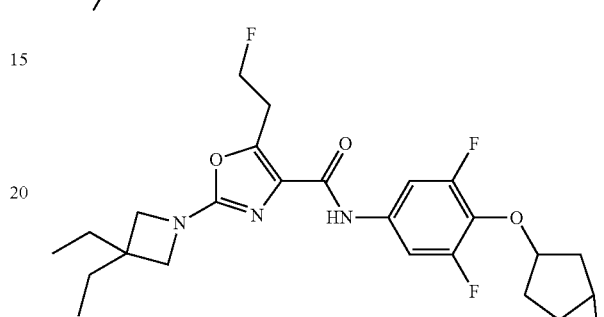
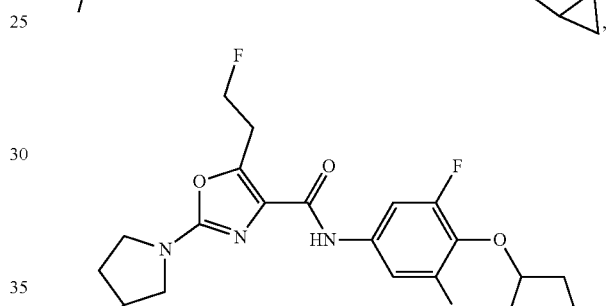
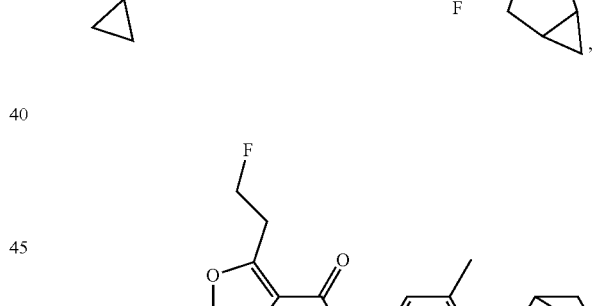
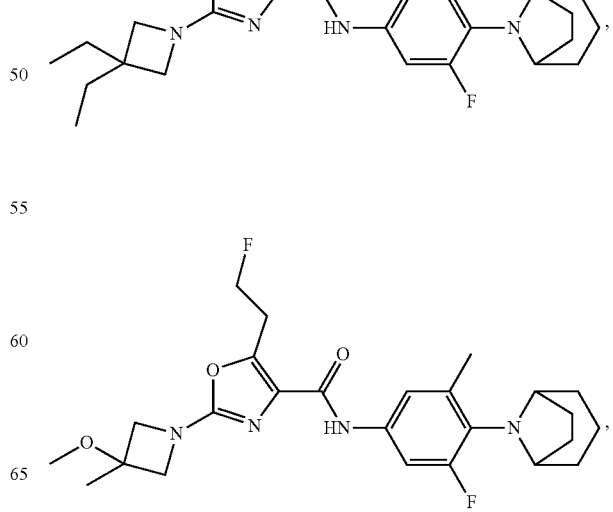

203
-continued
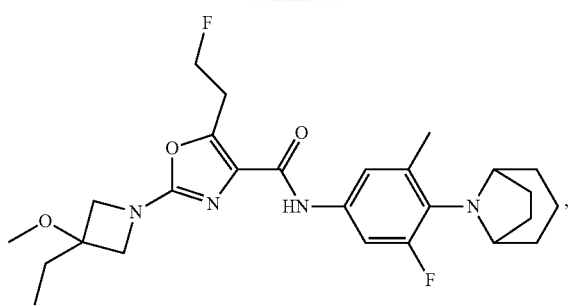
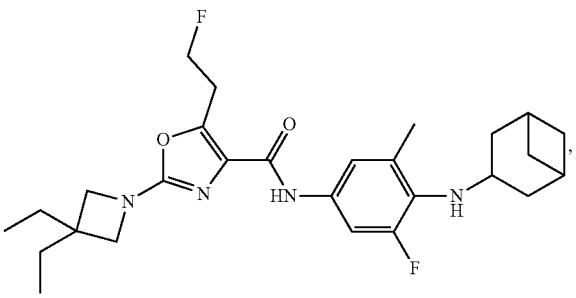
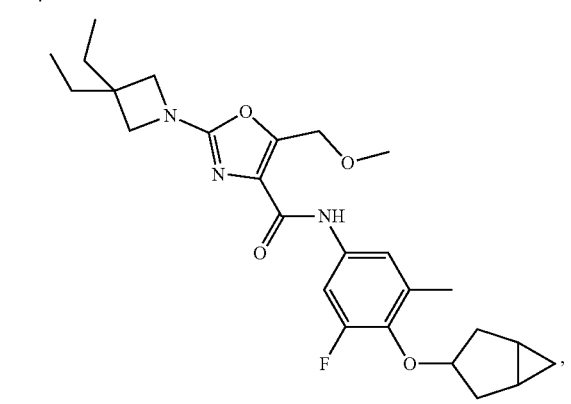
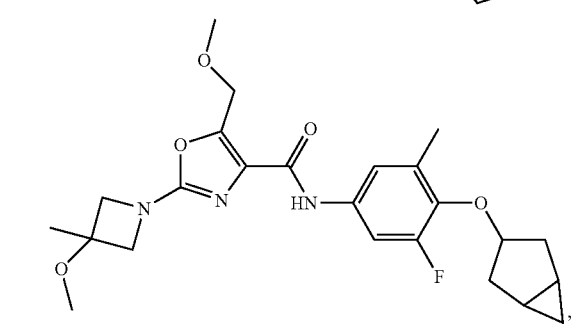
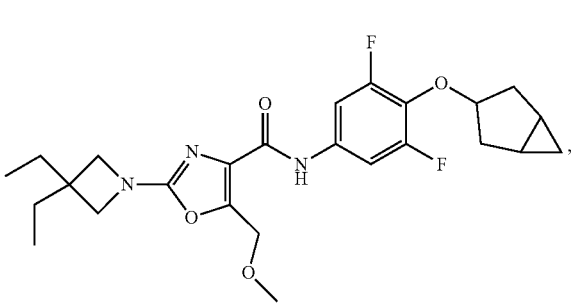
204
-continued
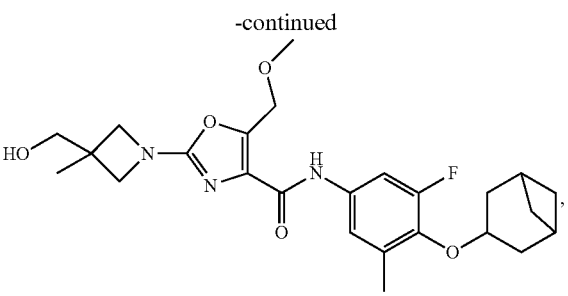
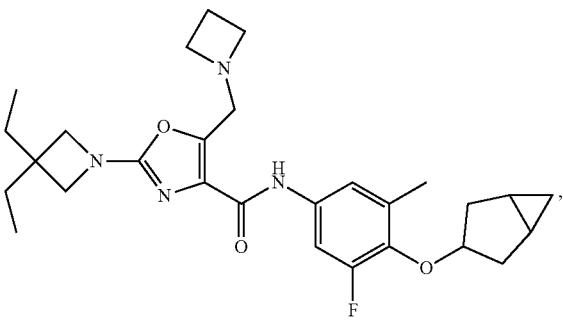
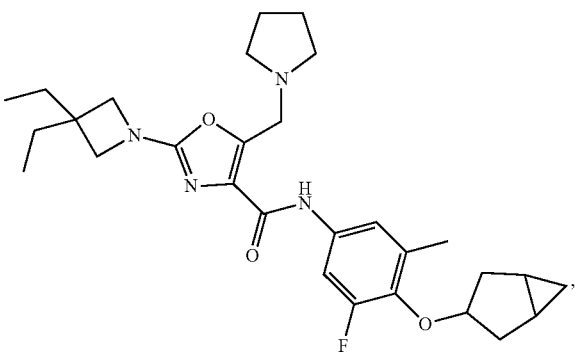
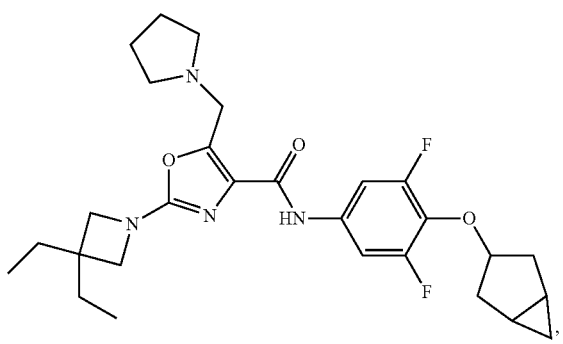
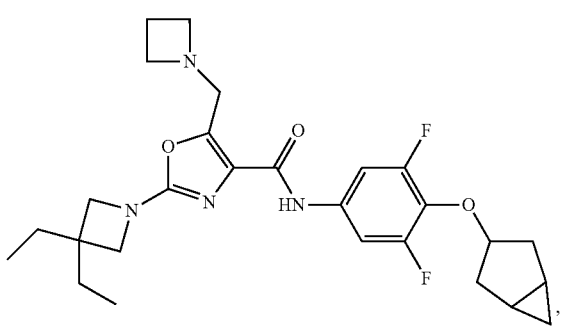

205
-continued
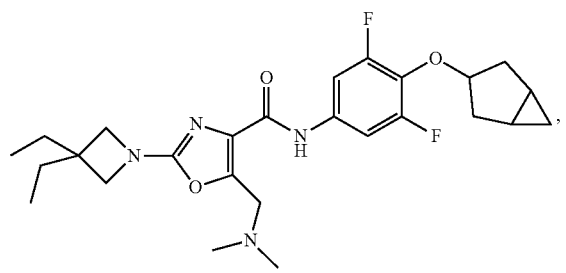
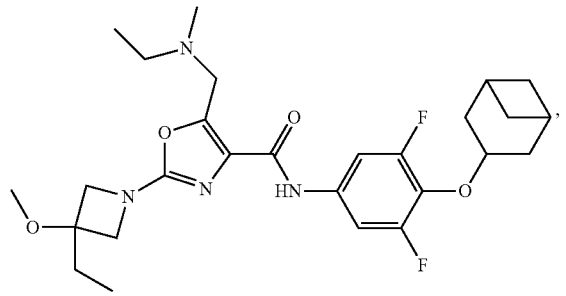
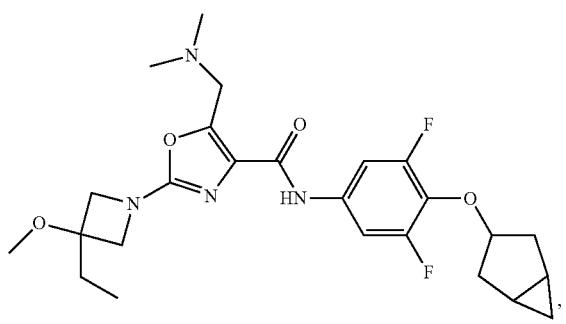
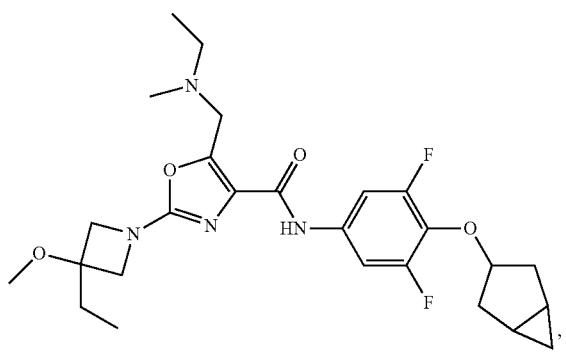
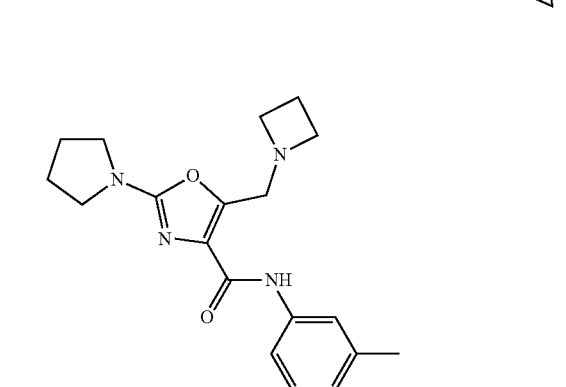
206
-continued
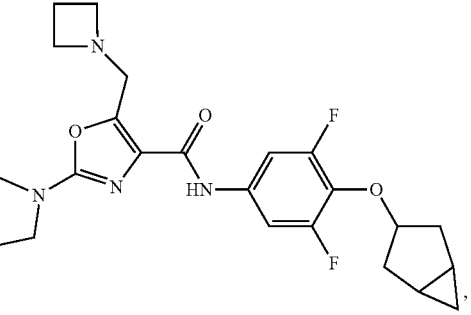
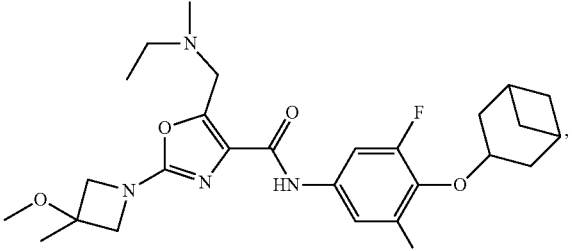
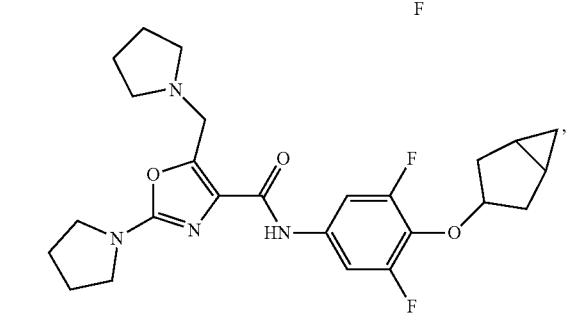
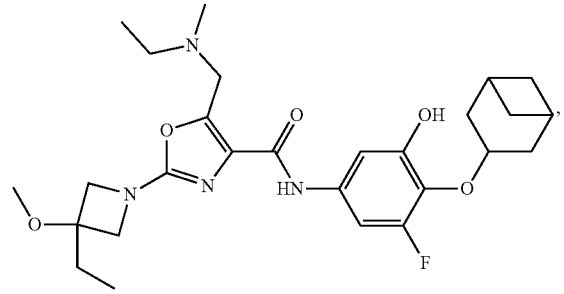
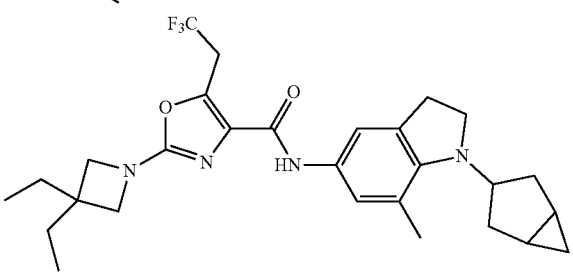
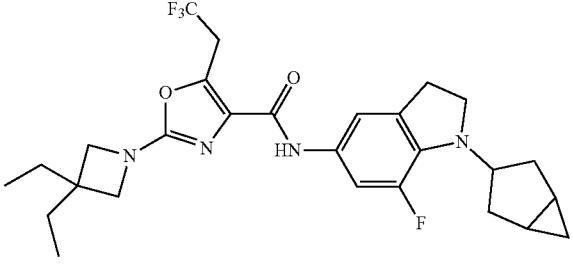

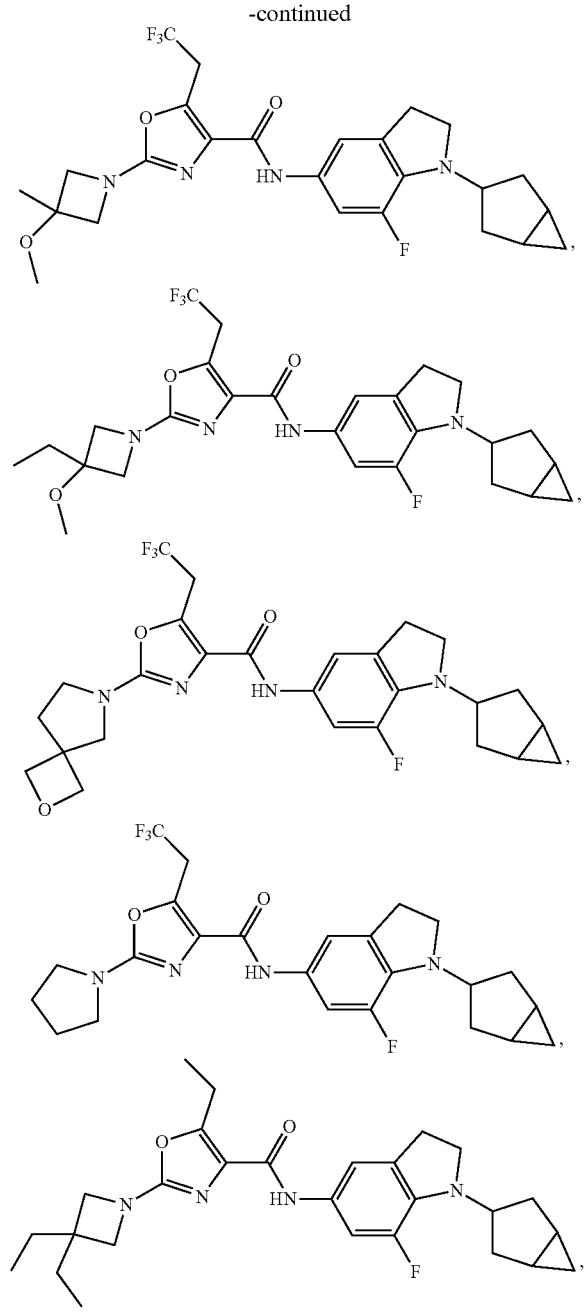

or a pharmaceutically acceptable salt, solvate, or stereoisomer thereof.

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center independently exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, but not limited to, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, gluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+ (C_1\text{-}C_4 \text{ alkyl})_4$ hydroxide, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and one or more adjacent double bonds. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Provided herein are methods for treating TRPML1-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. Certain embodiments provide therapeutic compositions comprising at least one compound disclosed herein in combination with one or more additional agents for the treatment of TRPML1-mediated disorders.

Also provided herein are compounds for use in the manufacture of a medicament for the treatment of a TRPML1 mediated disease. Further provided herein is a method of treatment of a disease mediated by TRPML1 activity, in a mammalian subject, which comprises administering a therapeutically effective amount of a compound disclosed herein.

TRPML1-mediated diseases include proliferative disorders such as cancers, inflammatory disorders, pain, neurodegenerative disorders, cognitive and psychiatric disorders, and other diseases as disclosed below.

TRPML1-mediated disorder or disease is aging, bone diseases, cardiovascular diseases, congenital developmental disorders, eye diseases, hematological and solid malignancies, infectious diseases, inflammatory diseases, liver diseases, metabolic diseases, neurological or neurodegenerative diseases, pancreatitis, renal diseases, skeletal muscle disorders, obesity, lysosomal storage diseases, hypertrophic cardiomyopathy, dilated cardiomyopathy, inclusion body myositis, Paget's disease, or pulmonary diseases.

In some embodiments, the TRPML1-mediated disorder or disease is Aicardi-Goutières syndrome, Alzheimer's disease, amyotrophic lateral sclerosis (ALS), ataxia-telangiectasia, autism spectrum disorders, Batten disease, bipolar disorder, cerebral ataxia, Charcot-Marie-Tooth variant diseases, Chronic Wasting disease, corticobasal degeneration, corticobasal syndrome, bovine spongiform encephalopathy, Creutzfeldt-Jacob disease, Danon disease, Duchenne muscular dystrophy, exotic ungulate encephalopathy, Fabre disease, Fatal Familial insomnia, Friedreich ataxia, Feline spongiform encephalopathy, Fragile X, frontal temporal dementia, Gaucher disease, Gerstmann-Straussler-Scheinker disease, Giant axonal neuropathy, GM1 and GM2 gangliosidosis, Huntington's disease, Infantile Refsum disease, JUNQ and IPOD, Krabbe's disease, Kuru, Leukoencephalopathy, Lewy Body dementia, locomotor ataxia, Lyme disease, Machado Joseph disease, major depressive disorder, MPS-III, mucolipidosis, multiple sulfatase deficiency, multiple systems atrophy, myofibrillar myopathies, myotonic dystrophy, Niemann-Pick disease, neuronal ceroid lipofuscinosis, Parkinson's disease, Parkinsonism, Pick's disease, polyglutamine diseases, Pompe disease, pontocerebellar hypoplasia, prion diseases, progressive nuclear palsy, progressive Supranuclear palsy, pyruvate dehydrogenase deficiency, Sandhoff disease, schizophrenia, scrapie, Shy-Drager syndrome, spinal muscular atrophy, spinocerebellar ataxias, sporadic familial insomnia, subacute degeneration of the spinal cord, subacute sclerosing panencephalitis, Tay-Sachs disease, transneuronal degeneration, tuberous Sclerosis, Spinocerebellar Ataxia's, or vascular dementia.

In some embodiments, the TRPML1-mediated disorder or disease is age-related macular degeneration, non-alcoholic steatohepatitis (NASH), non-alcoholic fatty liver disease (NAFLD), retinal cell degeneration in glaucoma, retinitis pigmentosa, acute kidney injury, atherosclerosis, Crohn's disease, diabetic nephropathy, female infertility, *H. pylori* infections, hypochlorhydria, pancreatitis, retinal detachment, type 2 diabetes mellitus, ulcerative colitis, or sarcopenia.

Compounds disclosed herein are useful for the treatment of neurodegenerative disorders of various origins such as Alzheimer's disease and other dementia conditions such as Lewy body dementia, fronto-temporal dementia and other taupathies; amyotrophic lateral sclerosis, multiple sclerosis, Parkinson's disease and other parkinsonian syndromes; Huntington's disease; HIV-induced neuroinflammation; essential tremors; other spinocerebellar degenerations, neuropathies such as Charcot-Marie-Tooth neuropathy and other TRPML1-mediated diseases such as Type IV mucolipidosis (MLIV). The compounds disclosed herein are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure, and atonic seizure, and for prevention and treatment of status epilepticus (SE).

The compounds disclosed herein are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behavior, delusional disorders, brief psychotic disorders, shared psychotic disorders, psychotic disorder due to a general medical condition, substance-induced psychotic disorders or a psychotic disorder not otherwise specified, anxiety disorders such as generalized anxiety disorder, panic disorders, post-traumatic stress disorder, impulse control disorders, phobic disorders, dissociative states. The compounds disclosed herein are also useful for the treatment of smoking addiction, drug addiction, or alcoholism. The compounds disclosed herein are particularly useful for the treatment of bipolar disorders, psychosis, anxiety, or addiction.

The compounds disclosed herein are useful in the prevention or treatment of neuroinflammation and CNS damage induced by HIV infection and of HIV-associated neurocognitive deficits. The compounds disclosed herein are useful in the prevention or treatment of neuropathic pain. Neuropathic pain syndromes include, and are not limited to: chemotherapy-induced peripheral neuropathy, diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds disclosed herein are also useful for the treatment of pain, including chronic pain. Chronic pain includes, and is not limited to, chronic pain caused by inflammation or an inflammatory-related condition, osteoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds disclosed herein are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis, or surgery (such as open heart or bypass surgery), post-operative pain, kidney stone pain, gallbladder pain, gallstone pain, obstetric pain, or dental pain.

The compounds disclosed herein are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds disclosed herein are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds disclosed herein are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis (NASH), non-alcoholic fatty liver disease (NAFLD), and liver transplant rejection.

The compounds disclosed herein inhibit inflammatory processes affecting all body systems. Therefore, they are useful in the treatment of inflammatory processes of the musculoskeletal system of which the following is a list of examples but it is not comprehensive of all target disorders: arthritic conditions such as ankylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinating disorders, encephalomyelitis, sarcoidosis, nephritic syndrome, Bechet's syndrome, polymyositis, gingivitis.

Compounds disclosed herein are also useful in the treatment of gastrointestinal (GI) tract disorders such as inflammatory bowel disorders (IBD) including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varioliforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); pancreatitis, emesis, diarrhea, visceral inflammation, and hypochlorhydria.

Compounds disclosed herein are also useful in the treatment of disorders of the genito-urinary tract such as overactive bladder, prostatitis (chronic bacterial and chronic nonbacterial prostatitis), prostadynia, interstitial cystitis, urinary incontinence, and benign prostatic hyperplasia, annexities, pelvic inflammation, bartholinities and vaginitis. In particular, overactive bladder and urinary incontinence.

Compounds disclosed herein are also useful in the treatment of renal disorders including diabetic nephropathy, renal allograft rejection, infectious renal diseases, IgA nephropathy, fibrotic kidney disease, lupus nephritis, glomerulonephritis, acute kidney injury, and renal carcinoma.

The compounds disclosed herein are also useful in the treatment of ophthalmic diseases such as retinitis, retinitis pigmentosa, retinopathies, uveitis, acute injury to the eye tissue, age-related macular degeneration, glaucoma, retinal cell degeneration in glaucoma, conjunctivitis, and retinal detachment.

The compounds disclosed herein are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds disclosed herein are also useful in the treatment of allergic dermatitis, hyper-responsiveness of the airway, chronic obstructive pulmonary disease (COPD), bronchitis, septic shock, Sjögren's syndrome, glomerulonephritis, atherosclerosis, growth, and metastases of malignant cells, myoblastic leukemia, diabetes (type 2 diabetes mellitus), meningitis, osteoporosis, burn injury, ischemic heart disease, stroke, peripheral vascular disease, varicose veins, glaucoma, and female infertility.

In some embodiments, the compounds and pharmaceutical compositions of the present disclosure are useful in the treatment or prevention of progression of cancer. In some embodiments, the cancer is a hematologic malignancy or solid tumor. Hematologic malignancies include leukemias, lymphomas, multiple myeloma, and subtypes thereof. Lymphomas can be classified various ways, often based on the underlying type of malignant cell, including Hodgkin's lymphoma (often cancers of Reed-Sternberg cells, but also sometimes originating in B cells; all other lymphomas are non-Hodgkin's lymphomas), B-cell lymphomas, T-cell lymphomas, mantle cell lymphomas, Burkitt's lymphoma, follicular lymphoma, and others as defined herein and known in the art.

B-cell lymphomas include, but are not limited to, diffuse large B-cell lymphoma (DLBCL), chronic lymphocytic leukemia (CLL)/small lymphocytic lymphoma (SLL), and others as defined herein and known in the art.

T-cell lymphomas include T-cell acute lymphoblastic leukemia/lymphoma (T-ALL), peripheral T-cell lymphoma (PTCL), T-cell chronic lymphocytic leukemia (T-CLL) Sezary syndrome, and others as defined herein and known in the art.

Leukemias include acute myeloid (or myelogenous) leukemia (AML), chronic myeloid (or myelogenous) leukemia (CML), acute lymphocytic (or lymphoblastic) leukemia (ALL), chronic lymphocytic leukemia (CLL) hairy cell leukemia (sometimes classified as a lymphoma) and others as defined herein and known in the art.

Plasma cell malignancies include lymphoplasmacytic lymphoma, plasmacytoma, and multiple myeloma.

Solid tumors include melanomas, neuroblastomas, gliomas or 5 carcinomas such as tumors of the brain, head and neck, breast, lung (e.g., non-small cell lung cancer, NSCLC), reproductive tract (e.g., ovary), upper digestive tract, pancreas, liver, renal system (e.g., kidneys), bladder, prostate and colorectum.

Besides being useful for human treatment, certain compounds and formulations disclosed herein may also be useful for veterinary treatment of companion animals, exotic animals, and farm animals, including mammals, rodents, and the like. More preferred animals include horses, dogs, and cats.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long-acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended-release formulation, or in the form of an intermediate-release formulation. In some embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds disclosed herein may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating a TRPML1-mediated disorder or disease using a compound disclosed herein, or a pharmaceutically acceptable salt, solvate, or stereoisomer thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

The following examples illustrate the present invention. Unless explicitly stated otherwise, all measurements (especially percentages and amounts) relate to the weight.

Preparation of intermediate ethyl 2-chloro-5-(2,2,2-trifluoroethyl)oxazole-4-carboxylate (VII)

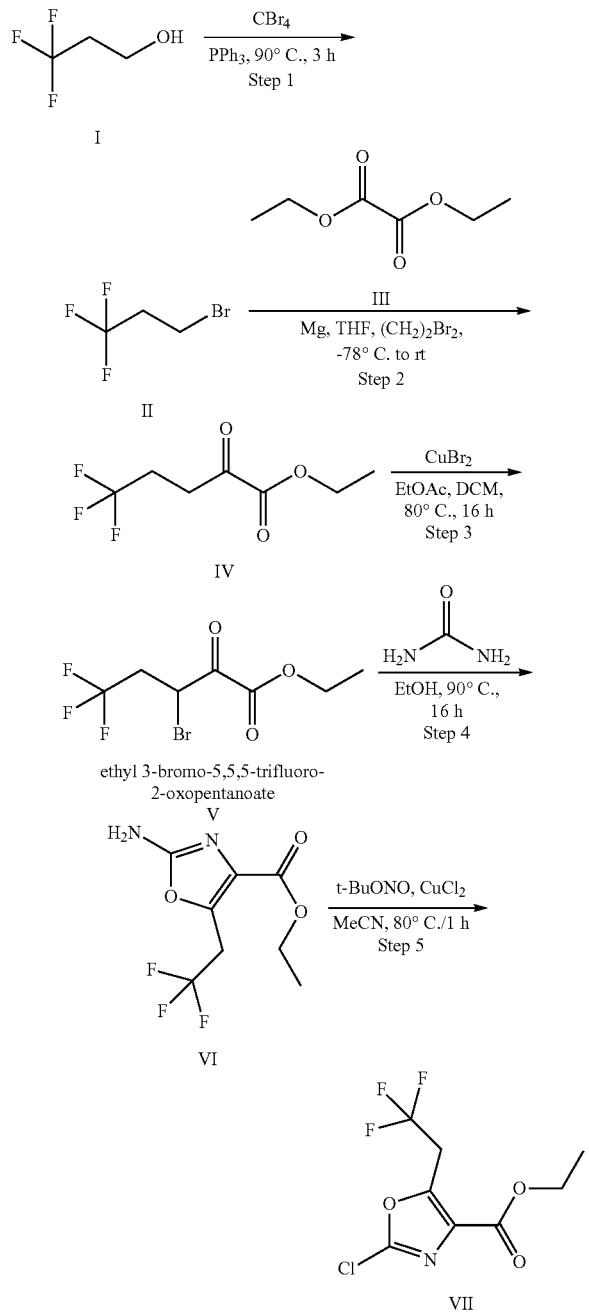

Step 1: Synthesis of 3-bromo-1,1,1-trifluoropropane: To the solid mixture of $CBr_4$ (45.43 g, 136.84 mmol) and $Ph_3P$ (35.85 g, 136.84 mmol) was added 3,3,3-trifluoropropan-1-ol (13.0 g, 114.03 mmol) at room temperature. Initiation of the reaction was indicated by vigorous exotherm while the solid reaction mass became liquid. The mixture was heated at 90° C. for 3 h under a condenser, circulating chilled (5–10° C.) water. Then the compound was distilled out using short path distillation to afford 3-bromo-1,1,1-trifluoropropane (15.5 g, 76.81%) as colorless liquid.

Step 2: Synthesis of ethyl 5,5,5-trifluoro-2-oxopentanoate: To the suspension of Mg turnings (2.87 g, 119.76 mmol) in THF (5 mL) was added catalytic amount of 1,2-dibromoethane and stirred until the effervescence started. As effervescence started, the solution of 3-bromo-1,1,1-trifluoropropane 2 (10 g, 59.88 mmol) in THF (50 mL) was added dropwise to the above hot suspension maintaining the temperature at about 50° C. and stirred at rt for 30 min more after completion of addition.

To a –78° C. solution of diethyloxalate (6.12 g, 41.91 mmol) in THF (50 mL) was added the above freshly prepared Grignard solution dropwise, and then it was allowed to warm up to room temperature gradually for 3 h when the reaction mixture became clear. After completion of the reaction [Monitored by TLC ($KMnO_4$ stain)] it was quenched with a saturated aqueous solution of $NH_4Cl$ (200 mL) and extracted with ethyl acetate (2×200 mL). The combined organic layers were washed with a brine solution, dried over anhydrous $Na_2SO_4$ and concentrated to afford the desired compound ethyl 5,5,5-trifluoro-2-oxopentanoate (6.2 g) as a brown gummy liquid (crude). It was directly used for the next step without further purification.

Step 3: Synthesis of ethyl 3-bromo-5,5,5-trifluoro-2-oxopentanoate: To the solution of ethyl 5,5,5-trifluoro-2-oxopentanoate (6.2 g, 31.31 mmol) in ethyl acetate (390 mL) and DCM (230 mL) was added $CuBr_2$ (24.44 g, 109.59 mmol), and the resultant reaction mixture was allowed to stir at 90° C. for 16 h. After completion [Monitored by TLC ($KMnO_4$ stain)], the reaction mixture was filtered through celite and the filtrate was concentrated to afford ethyl 3-bromo-5,5,5-trifluoro-2-oxopentanoate (8.6 g) as a brown gummy liquid (crude). It was used for next step directly without further purification.

Step 4: Synthesis of ethyl 2-amino-5-(2,2,2-trifluoroethyl)oxazole-4-carboxylate: To the stirred solution of ethyl 3-bromo-5,5,5-trifluoro-2-oxopentanoate (8.6 g, 31.04 mmol) in ethanol (100 mL) was added urea (7.45 g, 124.18 mmol) at room temperature and then it was refluxed for 16 h. After completion [Monitored by TLC, LC-MS], reaction mixture was concentrated to remove ethanol. The crude reaction mixture was then treated with saturated aqueous solution of $NaHCO_3$ (100 mL) and extracted with ethyl acetate (2×200 mL). Organic layer was dried over anhydrous $Na_2SO_4$ and concentrated under reduced pressure. The crude residue thus obtained was triturated with 50% ether/pentane, the resultant precipitate was filtered through sintered glass funnel and dried under vacuum to afford ethyl 2-amino-5-(2,2,2-trifluoroethyl)oxazole-4-carboxylate (VI) (2.9 g, 39.2%) as off-white solid.

Step 5: Synthesis of ethyl 2-chloro-5-(2,2,2-trifluoroethyl)oxazole-4-carboxylate: A suspension of $CuCl_2$ (1.72 g, 12.86 mmol) and t-BuONO (2.10 g, 20.42 mmol) in 60 mL of acetonitrile was stirred at 70° C. for 15 min. A suspension of ethyl 2-amino-5-(2,2,2-trifluoroethyl)oxazole-4-carboxylate in acetonitrile (90 mL) was then added to the hot reaction mixture dropwise. After addition, the reaction mixture was allowed to stir at 75° C. for 1 h. After completion [Monitored by TLC], the reaction mixture was concentrated to remove acetonitrile and diluted with ethyl acetate (200 mL) and water (100 mL). Reaction mixture was filtered through a celite bed and the organic layer was separated, dried over anhydrous sodium sulfate, and concentrated under reduced pressure. The crude material was purified by flash column chromatography using 10% EtOAc-hexane as an eluent to afford ethyl 2-chloro-5-(2,2,2-trifluoroethyl) oxazole-4-carboxylate (VII) as a pale yellow liquid (1.9 g, 58.5%).

Preparation of 4-((2,2-difluorocyclopentyl)oxy)-3-fluoroaniline

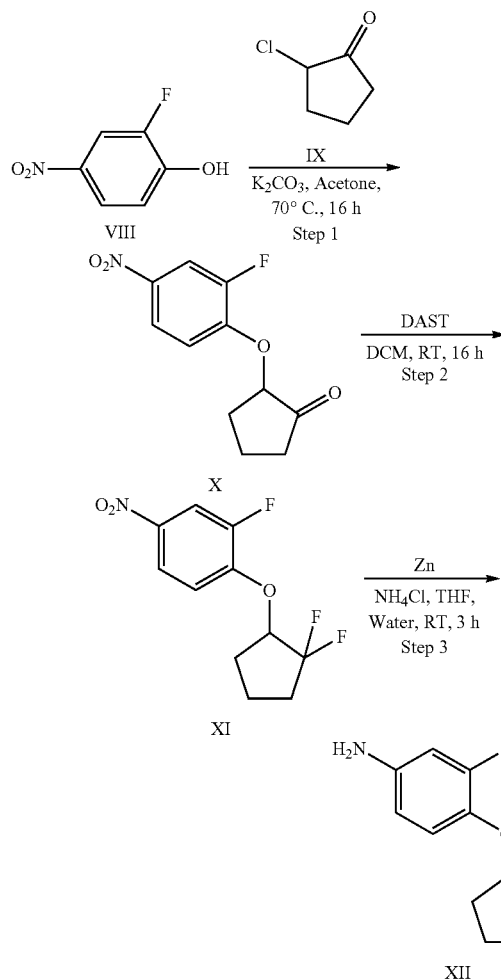

Step 1: Synthesis of 2-(2-fluoro-4-nitrophenoxy)cyclopentan-1-one: To a stirred suspension of 2-fluoro-4-nitrophenol (2.0 g, 63.69 mmol) and potassium carbonate (5.2 g, 38.21 mmol) in acetone (20 mL) was added 2-chlorocyclopentan-1-one (2.4 g, 12.74 mmol) and resultant reaction mixture was allowed to stir at 70° C. for 8 h. The reaction was then concentrated under vacuum to remove acetone, crude material was diluted with ethyl acetate (200 mL) and washed with brine (50 mL). The organic layer was dried over anhydrous sodium sulfate and concentrated under reduced pressure. The resultant crude was purified by flash column chromatography using 10% EtOAc/hexane as eluent to afford 2-(2-fluoro-4-nitrophenoxy)cyclopentan-1-one (X) (1.2 g, 39.38%) as a yellow liquid.

Step 2: Synthesis of 1-((2,2-difluorocyclopentyl)oxy)-2-fluoro-4-nitrobenzene: To a stirred solution of 2-(2-fluoro-4-nitrophenoxy)cyclopentan-1-one (X) (0.7 g, 2.93 mmol) in DCM (20 mL) was added DAST (2.36 g, 14.64 mmol) dropwise at 0° C., after addition the reaction mixture was allowed to stir at rt for 16 h. After completion [Monitored by LC-MS], the reaction mixture was quenched with sat. sodium bicarbonate solution and extracted with DCM (100 mL). The organic layer was separated, dried over sodium sulfate, and concentrated under reduced pressure. The resultant crude was purified by flash column chromatography using 10% EtOAc-hexane as eluent to afford 1-((2,2-difluorocyclopentyl)oxy)-2-fluoro-4-nitrobenzene (0.42 g, 54.9%) as yellow liquid.

Step 3: Synthesis of 4-((2,2-difluorocyclopentyl)oxy)-3-fluoroaniline: To a stirred solution of 1-((2,2-difluorocyclopentyl)oxy)-2-fluoro-4-nitrobenzene (460 mg, 1.99 mmol) in 10 mL of 1.4 dioxane:water (5:1) was added zinc dust and ammonium chloride (633 mg, 11.91 mmol) at 0° C. The resultant reaction mixture was allowed to stir at room temperature for 3 h. After completion [Monitored by LC-MS], reaction mixture was filtered through a glass sintered. The filtrate was dried over anhydrous Na2SO4, concentrated under reduced pressure and resultant crude was purified by combiflash column chromatography using 10% EtOAc-hexane to afford the 4-((2,2-difluorocyclopentyl)oxy)-3-fluoroaniline (255 mg, 62.58%) as a brown sticky liquid. General Scheme for Preparation of Examples 1-24.

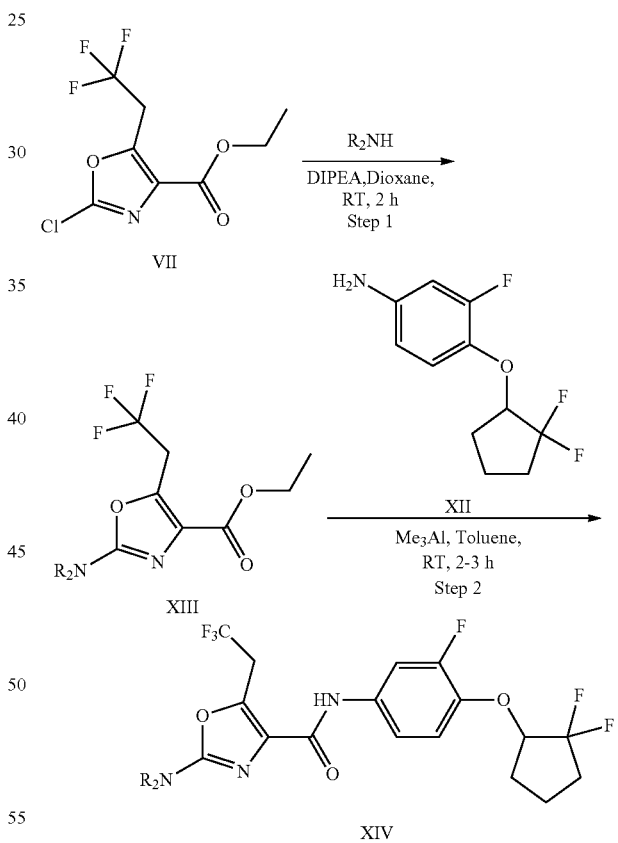

Step 1: To a stirred solution of intermediate (VII) (1.0 eq.) and DIPEA (3.0 equiv) in dioxane (3 mL/g VII) was added R₂NH (1.1 eq.) and the resultant reaction mixture was allowed to stir at room temperature for 2 h. After completion of the reaction [Monitored by TLC], the reaction mixture was concentrated under reduced pressure to remove dioxane. Resultant crude was purified through flash column chromatography to provide intermediates of structure XIII.

Step 2: To a stirred solution of XIII (1.0 eq) and 4-((2,2-difluorocyclopentyl)oxy)-3-fluoroaniline (XII) (0.8 eq) in dry toluene (30 mL/g XIII), trimethylaluminum (1 M in toluene, 4.0 eq) was added dropwise at 0° C., and the resultant reaction mixture was allowed to stir at rt for 2 h. After completion [Monitored with TLC/LCMS], the reaction mixture was quenched with saturated ammonium chloride solution and partitioned with EtOAc. The organic layer was separated, dried over anhydrous sodium sulfate, and concentrated under reduced pressure. The resultant crude was purified by flash column chromatography to afford products of general structure XIV.

All amines (R₂NH) used in the synthesis of products (XIV) were purchased from chemical providers.

Example 1

The title compound was prepared as described in the general scheme above utilizing isoindoline as the amine in step 1 affording N-{4-[(2,2-difluorocyclopentyl)oxy]-3-fluorophenyl}-2-(2,3-dihydro-1H-isoindol-2-yl)-5-(2,2,2-trifluoroethyl)-1,3-oxazole-4-carboxamide (20 mg, 19%).

Example 2

The title compound was prepared as described in the general scheme above utilizing 3-cyanoazetidine as the amine in step 1 affording 2-(3-cyanoazetidin-1-yl)-N-{4-[(2,2-difluorocyclopentyl)oxy]-3-fluorophenyl}-5-(2,2,2-trifluoroethyl)-1,3-oxazole-4-carboxamide (45 mg, 17%).

Example 3

The title compound was prepared as described in the general scheme above utilizing 3-(hydroxymethyl)pyrrolidine as the amine in step 1 affording N-(4-((2,2-difluorocyclopentyl)oxy)-3-fluorophenyl)-2-(3-(hydroxymethyl)pyrrolidin-1-yl)-5-(2,2,2-trifluoroethyl)oxazole-4-carboxamide (20 mg, 19.5%).

Example 4

The title compound was prepared as described in the general scheme above utilizing 2,2-dimethylmorpholine as the amine in step 1 affording N-{4-[(2,2-difluorocyclopentyl)oxy]-3-fluorophenyl}-2-(2,2-dimethylmorpholin-4-yl)-5-(2,2,2-trifluoroethyl)-1,3-oxazole-4-carboxamide (20 mg, 13%).

Example 5

The title compound was prepared as described in the general scheme above utilizing indoline as the amine in step 1 affording N-(4-((2,2-difluorocyclopentyl)oxy)-3-fluorophenyl)-2-(indolin-1-yl)-5-(2,2,2-trifluoroethyl)oxazole-4-carboxamide (14 mg, 45.3%).

Example 6

The title compound was prepared as described in the general scheme above utilizing morpholine as the amine in step 1 affording N-(4-((2,2-difluorocyclopentyl)oxy)-3-fluorophenyl)-2-morpholino-5-(2,2,2-trifluoroethyl)oxazole-4-carboxamide (23 mg, 15.95%).

Example 7

The title compound was prepared as described in the general scheme above utilizing 3-(methoxymethyl)pyrrolidine as the amine in step 1 affording N-(4-((2,2-difluorocyclopentyl)oxy)-3-fluorophenyl)-2-(3-(methoxymethyl)pyrrolidin-1-yl)-5-(2,2,2-trifluoroethyl)oxazole-4-carboxamide (30 mg, 11%).

Example 8

The title compound was prepared as described in the general scheme above utilizing 3-methoxyazetidine as the amine in step 1 affording N-(4-((2,2-difluorocyclopentyl)oxy)-3-fluorophenyl)-2-(3-methoxyazetidin-1-yl)-5-(2,2,2-trifluoroethyl)oxazole-4-carboxamide (20 mg, 10.41%).

Example 9

The title compound was prepared as described in the general scheme above utilizing 7-azabicyclo[2.2.1]heptane as the amine in step 1 affording 2-{7-azabicyclo[2.2.1]heptan-7-yl}-N-{4-[(2,2-difluorocyclopentyl)oxy]-3-fluorophenyl}-5-(2,2,2-trifluoroethyl)oxazole-4-carboxamide (12 mg, 16%).

Example 10

The title compound was prepared as described in the general scheme above utilizing 6,6-difluoro-3-azabicyclo[3.1.0]hexane as the amine in step 1 affording 2-{6,6-difluoro-3-azabicyclo[3.1.0]hexan-3-yl}-N-{4-[(2,2-difluorocyclopentyl)oxy]-3-fluorophenyl}-5-(2,2,2-trifluoroethyl)oxazole-4-carboxamide (30 mg, 22%).

Example 11

The title compound was prepared as described in the general scheme above utilizing 4-azaspiro[2.4]heptane as the amine in step 1 affording N-(4-((2,2-difluorocyclopentyl)oxy)-3-fluorophenyl)-2-(4-azaspiro[2.4]heptan-4-yl)-5-(2,2,2-trifluoroethyl)oxazole-4-carboxamide (18 mg, 19%).

Example 12

The title compound was prepared as described in the general scheme above utilizing hexahydro-2H-furo[2,3-c]pyrrole as the amine in step 1 affording N-(4-((2,2-difluorocyclopentyl)oxy)-3-fluorophenyl)-2-(hexahydro-5H-furo[2,3-c]pyrrol-5-yl)-5-(2,2,2-trifluoroethyl)oxazole-4-carboxamide (8 mg, 26%).

Example 13

The title compound was prepared as described in the general scheme above utilizing 2-oxa-7-azaspiro[4.4]nonane as the amine in step 1 affording N-(4-((2,2-difluorocyclopentyl)oxy)-3-fluorophenyl)-2-(2-oxa-7-azaspiro[4.4]nonan-7-yl)-5-(2,2,2-trifluoroethyl)oxazole-4-carboxamide (30 mg, 20.66%).

Example 14

The title compound was prepared as described in the general scheme above utilizing 7-oxa-2-azaspiro[3.5]nonane as the amine in step 1 affording N-(4-((2,2-difluorocyclopentyl)oxy)-3-fluorophenyl)-2-(7-oxa-2-azaspiro[3.5]nonan-2-yl)-5-(2,2,2-trifluoroethyl)oxazole-4-carboxamide (20 mg, 22%).

Example 15

The title compound was prepared as described in the general scheme above utilizing 6-azaspiro[3.4]octane as the amine in step 1 affording N-(4-((2,2-difluorocyclopentyl)oxy)-3-fluorophenyl)-2-(6-azaspiro[3.4]octan-6-yl)-5-(2,2,2-trifluoroethyl)oxazole-4-carboxamide (20 mg, 18.33%).

Example 16

The title compound was prepared as described in the general scheme above utilizing 3,3-difluoroazetidine as the amine in step 1 affording 2-(3,3-difluoroazetidin-1-yl)-N-{4-[(2,2-difluorocyclopentyl)oxy]-3-fluorophenyl}-5-(2,2,2-trifluoroethyl)oxazole-4-carboxamide (40 mg, 17%).

Example 17

The title compound was prepared as described in the general scheme above utilizing 6,6-difluoro-2-azaspiro[3.3]heptane as the amine in step 1 affording 2-(6,6-difluoro-2-azaspiro[3.3]heptan-2-yl)-N-(4-((2,2-difluorocyclopentyl)oxy)-3-fluorophenyl)-5-(2,2,2-trifluoroethyl)oxazole-4-carboxamide (70 mg, 50%).

Example 18

The title compound was prepared as described in the general scheme above utilizing 3-trifluoromethylazetidine as the amine in step 1 affording N-(4-((2,2-difluorocyclopentyl)oxy)-3-fluorophenyl)-5-(2,2,2-trifluoroethyl)-2-(3-(trifluoromethyl)azetidin-1-yl)oxazole-4-carboxamide (70 mg, 50%).

Example 19

The title compound was prepared as described in the general scheme above utilizing 2-oxa-6-azaspiro[3.4]octane as the amine in step 1 affording N-{4-[(2,2-difluorocyclopentyl)oxy]-3-fluorophenyl}-2-{2-oxa-6-azaspiro[3.4]octan-6-yl}-5-(2,2,2-trifluoroethyl)oxazole-4-carboxamide (45 mg, 29%).

Example 20

The title compound was prepared as described in the general scheme above utilizing 3,3-dimethylazetidine as the amine in step 1 affording N-(4-((2,2-difluorocyclopentyl)oxy)-3-fluorophenyl)-2-(3,3-dimethylazetidin-1-yl)-5-(2,2,2-trifluoroethyl)oxazole-4-carboxamide (30 mg, 23%).

Example 21

The title compound was prepared as described in the general scheme above utilizing 5-azaspiro[2.4]heptane as the amine in step 1 affording N-(4-((2,2-difluorocyclopentyl)oxy)-3-fluorophenyl)-2-(5-azaspiro[2.4]heptan-5-yl)-5-(2,2,2-trifluoroethyl)oxazole-4-carboxamide (20 mg, 14.4%).

Example 22

The title compound was prepared as described in the general scheme above utilizing pyrrolidine as the amine in step 1 affording N-{4-[(2,2-difluorocyclopentyl)oxy]-3-fluorophenyl}-2-(pyrrolidin-1-yl)-5-(2,2,2-trifluoroethyl)oxazole-4-carboxamide (60 mg, 51%).

Example 23

The title compound was prepared as described in the general scheme above utilizing octahydrocyclopenta[c]pyrrole as the amine in step 1 affording N-(4-((2,2-difluorocyclopentyl)oxy)-3-fluorophenyl)-2-(hexahydrocyclopenta[c]pyrrol-2(1H)-yl)-5-(2,2,2-trifluoroethyl)oxazole-4-carboxamide (11 mg, 15.68%).

Example 24

The title compound was prepared as described in the general scheme above utilizing 3-isopropylazetidine as the amine in step 1 affording N-{4-[(2,2-difluorocyclopentyl)oxy]-3-fluorophenyl}-2-[3-(propan-2-yloxy)azetidin-1-yl]-5-(2,2,2-trifluoroethyl)oxazole-4-carboxamide (40 mg, 32%).

General Scheme for Preparation of Examples 25-33.

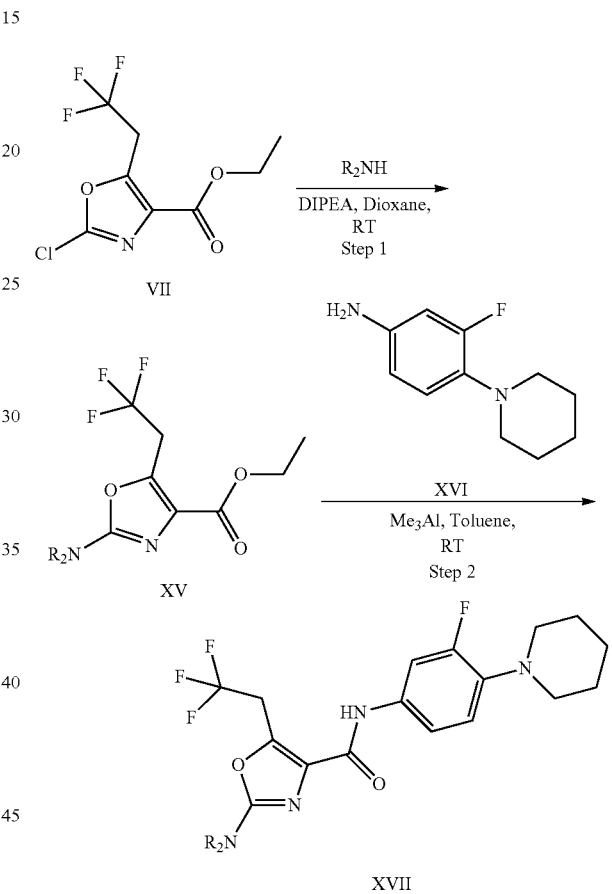

Step 1: To a stirred solution of intermediate VII (1.0 eq.) and DIPEA (3.0 equiv) in dioxane (3 mL/g) was added the amine compound (1.1 eq.) and the resultant reaction mixture was allowed to stir at room temperature for 2 h. After completion [Monitored with TLC or LCMS], the reaction mixture was concentrated under reduced pressure to remove dioxane. The resultant crude was subjected to flash column chromatography to provide XV.

Step 2: To a stirred solution of XV (1.0 eq) in dry toluene (30 mL/g), 3-fluoro-4-(piperidin-1-yl)aniline (XVI) (0.8 eq) was added followed by dropwise addition of trimethylaluminum (1 M in toluene, 4.0 eq) at 0° C. and the resultant reaction mixture was allowed to stir at rt for 2 h. After completion [Monitored with TLC/or LCMS], the reaction mixture was quenched with saturated ammonium chloride solution and partitioned with EtOAc. The organic layer was separated, dried over anhydrous sodium sulfate, and concentrated under reduced pressure. The resultant crude was purified by flash column chromatography to afford examples of the general structure XVII.

All amines used as starting materials were purchased from commercial sources

Example 25

The title compound was prepared as described in the general scheme above utilizing 2-thia-7-azaspiro[3,5]nonane-2,2-dioxide as the amine in step 1 affording 2-(2,2-dioxo-2-thia-7-azaspiro[3.5]nonan-7-yl)-N-[3-fluoro-4-(piperidin-1-yl)phenyl]-5-(2,2,2-trifluoroethyl) oxazole-4-carboxamide (20 mg, 13%).

Example 26

The title compound was prepared as described in the general scheme above utilizing (3aR,6aR)-hexahydro-2H-furo[2,3-c]pyrrole as the amine in step 1 affording 2-[(3aR,6aR)-hexahydro-5H-furo[2,3-c]pyrrol-5-yl]-N-[3-fluoro-4-(piperidin-1-yl)phenyl]-5-(2,2,2-trifluoroethyl)oxazole-4-carboxamide (16 mg, 22%).

Example 27

The title compound was prepared as described in the general scheme above utilizing 5-azaspiro[2.4]heptane as the amine in step 1 affording 2-{5-azaspiro[2.4]heptan-5-yl}-N-[3-fluoro-4-(piperidin-1-yl)phenyl]-5-(2,2,2-trifluoroethyl)-1,3-oxazole-4-carboxamide (30 mg, 32%).

Example 28

The title compound was prepared as described in the general scheme above utilizing 2,2-difluoro-6-azaspiro[3.4]octane as the amine in step 1 affording 2-(2,2-difluoro-6-azaspiro[3.4]octan-6-yl)-N-(3-fluoro-4-(piperidin-1-yl)phenyl)-5-(2,2,2-trifluoroethyl)oxazole-4-carboxamide (20 mg, 11.88%).

Example 29

The title compound was prepared as described in the general scheme above utilizing 2-methylpyrrolidine as the amine in step 1 affording N-(3-fluoro-4-(piperidin-1-yl)phenyl)-2-(2-methylpyrrolidin-1-yl)-5-(2,2,2-trifluoroethyl)oxazole-4-carboxamide (12 mg, 13.47%).

Example 30

The title compound was prepared as described in the general scheme above utilizing 6,6-difluoro-2-azaspiro[3.3]heptane as the amine in step 1 affording 2-{6,6-difluoro-2-azaspiro[3.3]heptan-2-yl}-N-[3-fluoro-4-(piperidin-1-yl)phenyl]-5-(2,2,2-trifluoroethyl)oxazole-4-carboxamide (18 mg, 31%).

Example 31

The title compound was prepared as described in the general scheme above utilizing 2-oxa-7-azaspiro[4.4]nonane as the amine in step 1 affording N-(3-fluoro-4-(piperidin-1-yl)phenyl)-2-(2-oxa-7-azaspiro[4.4]nonan-7-yl)-5-(2,2,2-trifluoroethyl)oxazole-4-carboxamide (35 mg, 27%).

Example 32

The title compound was prepared as described in the general scheme above utilizing pyrrolidine as the amine in step 1 affording N-(3-fluoro-4-(piperidin-1-yl)phenyl)-2-(pyrrolidin-1-yl)-5-(2,2,2-trifluoroethyl)oxazole-4-carboxamide (9 mg, 21%).

Example 33

The title compound was prepared as described in the general scheme above utilizing 2-oxa-6-azaspiro[3.4]octane as the amine in step 1 affording N-(3-fluoro-4-(piperidin-1-yl)phenyl)-2-(2-oxa-6-azaspiro[3.4]octan-6-yl)-5-(2,2,2-trifluoroethyl)oxazole-4-carboxamide (28 mg, 24.23%).

Preparation of 4-(cis-bicyclo[3.1.0]hexan-3-yloxy)-3,5-difluoroaniline] (XXI)

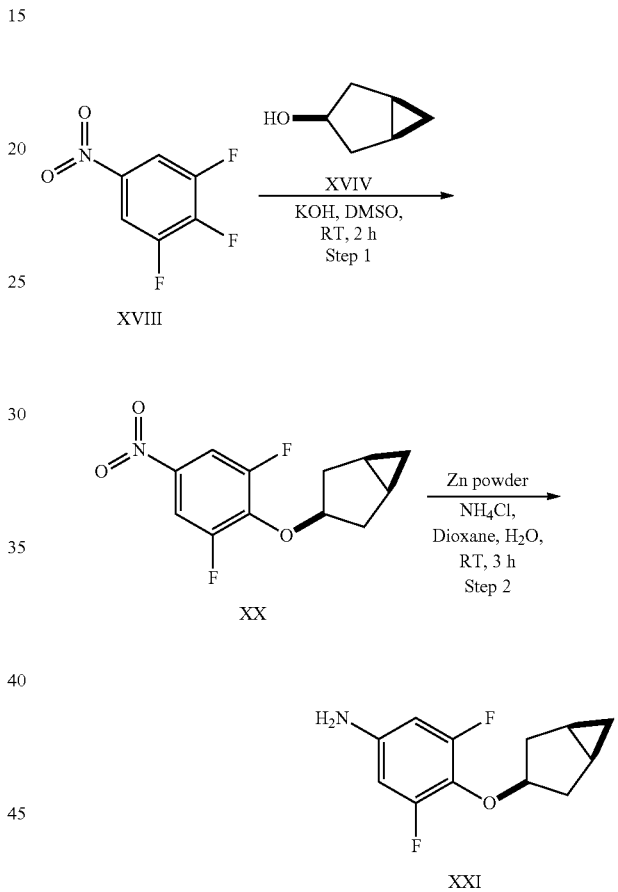

Step 1: To a stirred solution of 1,2,3-trifluoro-5-nitrobenzene (500 mg, 3.14 mmol), KOH dust (547 mg, 9.43 mmol) in DMSO (5 mL) was added bicyclo[3.1.0]hexan-3-ol and stirred for 2 h at RT. After completion [Monitored by TLC], reaction mixture was partitioned between EtOAc (100 mL) and water (50 mL). The organic layer was separated, dried over anhydrous sodium sulfate, and concentrated under reduced pressure. The resultant crude (XX) was purified through flash column chromatography using 5% EtOAc in hexane as an eluent to afford 3-(2,6-difluoro-4-nitrophenoxy)bicyclo[3.1.0]hexane (XX, 530 mg, 66.04%).

Step 2: To a stirred solution of 3-(2,6-difluoro-4-nitrophenoxy)bicyclo[3.1.0]hexane (XX) (500 mg, 1.97 mmol) in 10 mL of 1,4 dioxane:water (5:1) was added zinc dust (639 mg, 9.84 mmol) along with ammonium chloride (637 mg, 11.81 mmol) at 0° C. It was then stirred for 3 h at rt. After completion [Monitored by TLC], the reaction mixture was filtered through a glass sintered filter. The filtrate was dried over anhydrous sodium sulfate and concentrated under reduced pressure. The resultant crude (XXI) was purified by flash column chromatography using 10% EtOAc in hexane to afford 4-(cis-bicyclo[3.1.0]hexan-3-yloxy)-3,5-difluoroaniline (XXI) (400 mg, 90.22%).

General Scheme for Preparation of Examples 34-41.

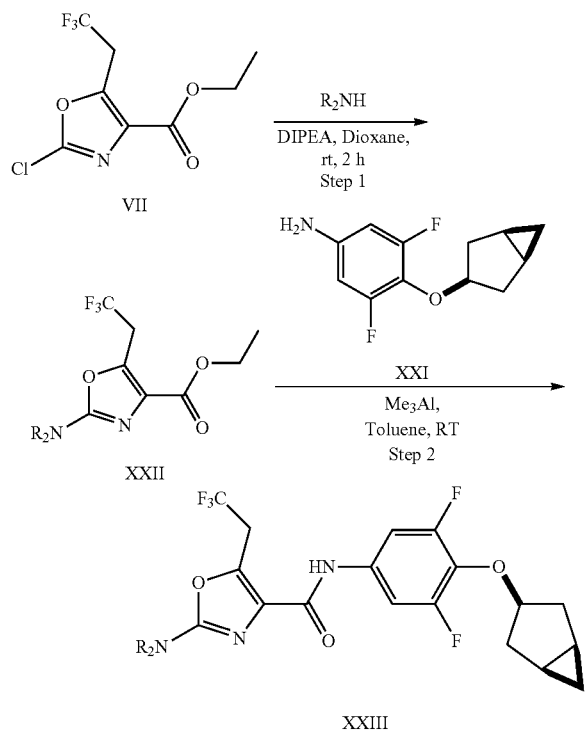

Step 1: To a stirred solution of intermediate (VII) (1.0 eq.) and DIPEA (3.0 equiv) in dioxane (3 mL/mmol) was added amine of general formula R$_2$NH (1.1 eq.), and the resultant reaction mixture was allowed to stir at room temperature for 2 h. After completion [Monitored by TLC], the reaction mixture was concentrated under reduced pressure to remove dioxane. Resultant crude was purified through flash column chromatography to provide intermediates of general formula XXII.

Step 2: To a stirred solution of XXII (1.0 eq) in dry toluene (30 mL/g), 4-(cis-bicyclo[3.1.0]hexan-3-yloxy)-3,5-difluoroaniline (XXI) (0.8 eq) was added, followed by dropwise addition of trimethylaluminum (2 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. The organic layer was separated, dried over anhydrous sodium sulfate, and concentrated under reduced pressure. The resultant crude XXIII was purified by flash column chromatography to afford example with the general formula XXIII.

All amines used as starting materials were purchased from commercial suppliers.

Example 34

The title compound was prepared as described in the general scheme above utilizing 6,6-difluoro-2-azaspiro[3.3]heptane as the amine in step 1 affording N-(4-(cis-bicyclo[3.1.0]hexan-3-yloxy)-3,5-difluorophenyl)-2-(6,6-difluoro-2-azaspiro[3.3]heptan-2-yl)-5-(2,2,2-trifluoroethyl)oxazole-4-carboxamide (25 mg, 16.59%).

Example 35

The title compound was prepared as described in the general scheme above utilizing 2-oxa-6-azaspiro[3.4]octane as the amine in step 1 affording N-(4-{cis-bicyclo[3.1.0]hexan-3-yloxy}-3,5-difluorophenyl)-2-{2-oxa-6-azaspiro[3.4]octan-6-yl}-5-(2,2,2-trifluoroethyl)oxazole-4-carboxamide (50 mg 30%).

Example 36

The title compound was prepared as described in the general scheme above utilizing hexahydro-2H-furo[2,3-c]pyrrole as the amine in step 1 affording N-(4-{cis-bicyclo[3.1.0]hexan-3-yloxy}-3,5-difluorophenyl)-2-{hexahydro-5H-furo[2,3-c]pyrrol-5-yl}-5-(2,2,2-trifluoroethyl)oxazole-4-carboxamide (40 mg, 26%).

Example 37

The title compound was prepared as described in the general scheme above utilizing 3,3-dimethylazetidine as the amine in step 1 affording N-(4-{cis-bicyclo[3.1.0]hexan-3-yloxy}-3,5-difluorophenyl)-2-(3,3-dimethylazetidin-1-yl)-5-(2,2,2-trifluoroethyl)oxazole-4-carboxamide (18 mg, 11%).

Example 38

The title compound was prepared as described in the general scheme above utilizing 5-azaspiro[2.4]heptane as the amine in step 1 affording N-(4-{cis-bicyclo[3.1.0]hexan-3-yloxy}-3,5-difluorophenyl)-2-{hexahydro-2H-furo[2,3-c]pyrrol-5-yl}-5-(2,2,2-trifluoroethyl)-1,3-oxazole-4-carboxamide (49 mg, 33%).

Example 39

The title compound was prepared as described in the general scheme above utilizing pyrrolidine as the amine in step 1 affording N-(4-(cis-bicyclo[3.1.0]hexan-3-yloxy)-3,5-difluorophenyl)-2-(pyrrolidin-1-yl)-5-(2,2,2-trifluoroethyl)oxazole-4-carboxamide (15 mg, 10.93%).

Example 40

The title compound was prepared as described in the general scheme above utilizing octahydrocyclopenta[c]pyrrole as the amine in step 1 affording N-(4-{cis-bicyclo[3.1.0]hexan-3-yloxy}-3,5-difluorophenyl)-2-{octahydrocyclopenta[c]pyrrol-2-yl}-5-(2,2,2-trifluoroethyl)oxazole-4-carboxamide (15 mg, 10.93%)

Example 41

The title compound was prepared as described in the general scheme above utilizing 2-azaspiro[3.4]octane as the amine in step 1 affording N-(4-(cis-bicyclo[3.1.0]hexan-3-yloxy)-3,5-difluorophenyl)-2-(2-azaspiro[3.4]octan-2-yl)-5-(2,2,2-trifluoroethyl)oxazole-4-carboxamide (70 mg, 45.4%).

General Conditions for Preparation of Example of the General Formula Specified by Structure XXIX Examples 42-76

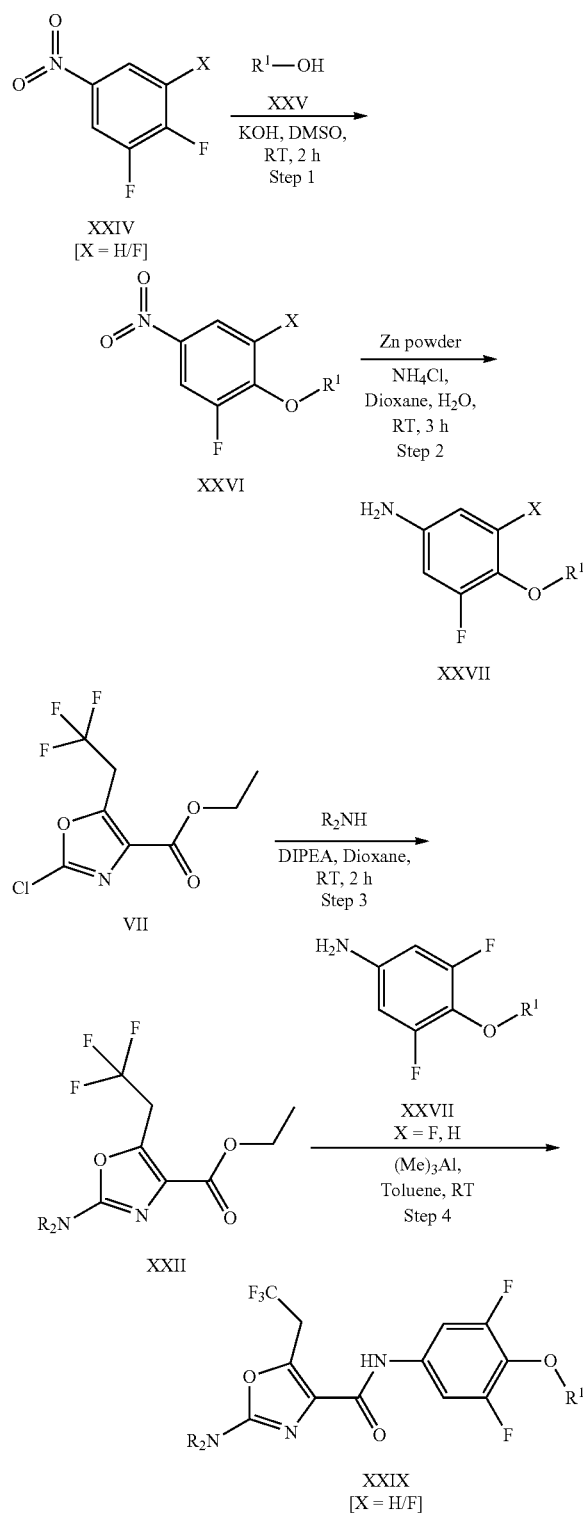

column chromatography using EtOAc in hexane as an eluent to afford desired product (XXVI).

Step 2: To a stirred solution of (XXVI) (2 mmol) in 10 mL of 1,4 dioxane:water (5:1) was added zinc dust (639 mg, 9.84 mmol) along with ammonium chloride (637 mg, 11.81 mmol) at 0° C. It was then stirred for 3 h at rt. After completion [Monitored by TLC], the reaction mixture was filtered through a glass sintered filter. The filtrate was dried over anhydrous sodium sulfate and concentrated under reduced pressure. The resultant crude (XXVII) was purified by flash column chromatography using 10% EtOAc in hexane to afford the pure (XXVII).

Step 3: To a stirred solution of intermediate (VII) (1.0 eq.) and DIPEA (3.0 equiv) in dioxane (3 mL/mmol) was added amine of general formula $R_2NH$ (1.1 eq.) and the resultant reaction mixture was allowed to stir at room temperature for 2 h. After completion [Monitored by TLC], the reaction mixture was concentrated under reduced pressure to remove dioxane. The resultant crude was purified through flash column chromatography to provide intermediates of general formula XXII.

Step 4: To a stirred solution of XXII (1.0 eq) in dry toluene (30 mL/g), compound XXVII from step 2 (0.8 eq) was added, followed by dropwise addition of trimethylaluminum (2 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. The resultant crude XXIX was purified by flash column chromatography to afford examples with the general formula XXIX.

All the alcohol used as starting materials were purchased from commercial suppliers.

All amines used in step 3 of the above procedure were purchased from commercial suppliers.

Example 42

The above referenced compound was synthesized utilizing the procedures as described in the general scheme above using 2,2,2-trifluoroethanol as the alcohol in step 1 and pyrrolidine as the amine in step 4, to provide N-(3-fluoro-4-(2,2,2-trifluoroethoxy)phenyl)-2-(pyrrolidin-1-yl)-5-(2,2,2-trifluoroethyl)oxazole-4-carboxamide (19 mg, 16%).

Example 43

The above referenced compound was synthesized utilizing the procedures as described in the general scheme above using 3-methoxycyclopentanol as the alcohol in step 1 and pyrrolidine as the amine in step 4, to provide N-{3-fluoro-4-[(3-methoxycyclopentyl)oxy]phenyl}-2-(pyrrolidin-1-yl)-5-(2,2,2-trifluoroethyl)oxazole-4-carboxamide (30 mg, 24%).

Example 44

The above referenced compound was synthesized utilizing the procedures as described in the general scheme above using 3,3-difluorocyclobutanol as the alcohol in step 1 and pyrrolidine as the amine in step 4, to provide N-[4-(3,3-difluorocyclobutoxy)-3-fluorophenyl]-2-(pyrrolidin-1-yl)-5-(2,2,2-trifluoroethyl)oxazole-4-carboxamide (30 mg, 45%).

Step 1. To a stirred solution of XXIV (1.0 eq) and XXV (1.2 eq) in DMSO (3 mL/mmol), was added KOH (3.0 eq). The reaction was stirred for 2 h at RT. After completion [Monitored by TLC], the resultant reaction mixture was partitioned between EtOAc and water. The organic layer was dried over anhydrous sodium sulfate and concentrated under reduced pressure. The crude was purified through flash

Example 45

The above referenced compound was synthesized utilizing the procedures as described in the general scheme above using 5,5-dimethyltetrahydrofuran-3-ol as the alcohol in step 1 and pyrrolidine as the amine in step 4, to provide N-{4-[(5,5-dimethyloxolan-3-yl)oxy]-3-fluorophenyl}-2-(pyrrolidin-1-yl)-5-(2,2,2-trifluoroethyl)oxazole-4-carboxamide (20 mg, 16%).

Example 46

The above referenced compound was synthesized utilizing the procedures as described in the general scheme above using 6,6-difluorobicyclo[3.1.0]hexan-3-ol as the alcohol in step 1 and pyrrolidine as the amine in step 4, to provide N-[4-({6,6-difluorobicyclo[3.1.0]hexan-3-yl}oxy)-3-fluorophenyl]-2-(pyrrolidin-1-yl)-5-(2,2,2-trifluoroethyl)oxazole-4-carboxamide (30 mg, 22%).

Example 47

The above referenced compound was synthesized utilizing the procedures as described in the general scheme above using tetrahydrofuran-3-ol as the alcohol in step 1 and pyrrolidine as the amine in step 4, to provide N-[3-fluoro-4-(oxolan-3-yloxy)phenyl]-2-(pyrrolidin-1-yl)-5-(2,2,2-trifluoroethyl)oxazol-4-carboxamide (30 mg, 36%).

Example 48

The above referenced compound was synthesized utilizing the procedures as described in the general scheme above using cyclopentanol as the alcohol in step 1 and 6,6-difluoro-2-azaspiro[3.3]heptane as the amine in step 4, to provide N-[4-(cyclopentyloxy)-3-fluorophenyl]-2-{6,6-difluoro-2-azaspiro[3.3]heptan-2-yl}-5-(2,2,2-trifluoroethyl)oxazole-4-carboxamide (30 mg, 36%).

Example 49

The above referenced compound was synthesized utilizing the procedures as described in the general scheme above using 4,4-difluorotetrahydrofuran-3-ol as the alcohol in step 1 and pyrrolidine as the amine in step 4, to provide the racemic title compound. Chiral separation was conducted on an Agilent 1200 series instrument. Column: CHIRALPAK IG (250×21 mm) 5 µm particle size. This separation was conducted at ambient temperature and a flow rate of 21.0 mL/min. The mobile phase was a mixture of 70% Hexane and 30% EtOH, held as an isocratic mixture for 40 min with wavelength of 280 nm. Separation provided enantiomerically pure (R)—N-(4-((4,4-difluorotetrahydrofuran-3-yl)oxy)-3-fluorophenyl)-2-(pyrrolidin-1-yl)-5-(2,2,2-trifluoroethyl)oxazole-4-carboxamide (15 mg, 29%).

Example 50

The above referenced compound was synthesized utilizing the procedures as described in the general scheme above using 3-methylcyclopentanol as the alcohol in step 1 and pyrrolidine as the amine in step 4, to provide N-(3-fluoro-4-((3-methylcyclopentyl)oxy)phenyl)-2-(pyrrolidin-1-yl)-5-(2,2,2-trifluoroethyl)oxazole-4-carboxamide (20 mg, 16.03%).

Example 51

The above referenced compound was synthesized utilizing the procedures as described in the general scheme above using bicyclo[3.1.0]hexan-2-ol as the alcohol in step 1 and pyrrolidine as the amine in step 4, to provide N-(4-{bicyclo[3.1.0]hexan-2-yloxy}-3-fluorophenyl)-2-(pyrrolidin-1-yl)-5-(2,2,2-trifluoroethyl)oxazole-4-carboxamide (20 mg, 16.03%).

Example 52

The above referenced compound was synthesized utilizing the procedures as described in the general scheme above using spiro[2.4]heptan-4-ol as the alcohol in step 1 and pyrrolidine as the amine in step 4, to provide N-(3-fluoro-4-(spiro[2.4]heptan-4-yloxy)phenyl)-2-(pyrrolidin-1-yl)-5-(2,2,2-trifluoroethyl)oxazole-4-carboxamide (8 mg, 14.28%).

Example 53

The above referenced compound was synthesized utilizing the procedures as described in the general scheme above using (2,2-difluorocyclopentyl)methanol as the alcohol in step 1 and pyrrolidine as the amine in step 4, to provide N-{4-[(2,2-difluorocyclopentyl)methoxy]-3-fluorophenyl}-2-(pyrrolidin-1-yl)-5-(2,2,2-trifluoroethyl)oxazole-4-carboxamide (30 mg, 25%).

Example 54

The above referenced compound was synthesized utilizing the procedures as described in the general scheme above using cyclopentanol as the alcohol in step 1 and 2-methylpyrrolidine as the amine in step 4, to provide N-(4-(cyclopentyloxy)-3-fluorophenyl)-2-(2-methylpyrrolidin-1-yl)-5-(2,2,2-trifluoroethyl)oxazole-4-carboxamide (18 mg, 20%).

Example 55

The above referenced compound was synthesized utilizing the procedures as described in the general scheme above using 2,2-dimethylcyclopentanol as the alcohol in step 1 and pyrrolidine as the amine in step 4, to provide N-(4-((2,2-dimethylcyclopentyl)oxy)-3-fluorophenyl)-2-(pyrrolidin-1-yl)-5-(2,2,2-trifluoroethyl)oxazole-4-carboxamide (12 mg, 14.2%).

Example 56

The above referenced compound was synthesized utilizing the procedures as described in the general scheme above using tetrahydro-2H-pyran-4-ol as the alcohol in step 1 and pyrrolidine as the amine in step 4, to provide N-[3-fluoro-4-(oxan-4-yloxy)phenyl]-2-(pyrrolidin-1-yl)-5-(2,2,2-trifluoroethyl)oxazole-4-carboxamide (47 mg, 37%).

Example 57

The above referenced compound was synthesized utilizing the procedures as described in the general scheme above using cyclopentanol as the alcohol in step 1 and 5-azaspiro[2.4]heptane as the amine in step 4, to provide N-(4-(cyclopentyloxy)-3-fluorophenyl)-2-(5-azaspiro[2.4]heptan-5-yl)-5-(2,2,2-trifluoroethyl)oxazole-4-carboxamide (25 mg, 26%).

Example 58

The above referenced compound was synthesized utilizing the procedures as described in the general scheme above using 3,3,3-trifluoropropanol as the alcohol in step 1 and pyrrolidine as the amine in step 4, to provide N-(3-fluoro-4-(3,3,3-trifluoropropoxy)phenyl)-2-(pyrrolidin-1-yl)-5-(2,2,2-trifluoroethyl)oxazole-4-carboxamide (40 mg, 31%).

Example 59

The above referenced compound was synthesized utilizing the procedures as described in the general scheme above using 2-butanol as the alcohol in step 1 and pyrrolidine as the amine in step 4, to provide N-(4-(sec-butoxy)-3-fluorophenyl)-2-(pyrrolidin-1-yl)-5-(2,2,2-trifluoroethyl)oxazole-4-carboxamide (30 mg, 26%).

Example 60

The above referenced compound was synthesized utilizing the procedures as described in the general scheme above using 4,4,4-trifluorobutan-2-ol as the alcohol in step 1 and pyrrolidine as the amine in step 4, to provide N-(3-fluoro-4-((4,4,4-trifluorobutan-2-yl)oxy)phenyl)-2-(pyrrolidin-1-yl)-5-(2,2,2-trifluoroethyl) oxazole-4-carboxamide (17 mg, 12.85%).

Example 61

The above referenced compound was synthesized utilizing the procedures as described in the general scheme above using cyclopentanol as the alcohol in step 1 and (3aR,6aR)-hexahydro-2H-furo[2,3-c]pyrrole as the amine in step 4, to provide N-(4-(cyclopentyloxy)-3-fluorophenyl)-2-((3aR,6aR)-hexahydro-5H-furo[2,3-c]pyrrol-5-yl)-5-(2,2,2-trifluoroethyl)oxazole-4-carboxamide (25 mg, 21.59%)

Example 62

The above referenced compound was synthesized utilizing the procedures as described in the general scheme above using cyclopentanol as the alcohol in step 1 and pyrrolidine as the amine in step 4, to provide N-[4-(cyclopentyloxy)-3-fluorophenyl]-2-(pyrrolidin-1-yl)-5-(2,2,2-trifluoroethyl) oxazole-4-carboxamide (40 mg, 30%).

Example 63

The above referenced compound was synthesized utilizing the procedures as described in the general scheme above using 4,4-difluorotetrahydrofuran-3-ol as the alcohol in step 1 and 5-azaspiro[2.4]heptane as the amine in step 4, to provide N-(4-((4,4-difluorotetrahydrofuran-3-yl)oxy)-3-fluorophenyl)-2-(5-azaspiro[2.4]heptan-5-yl)-5-(2,2,2-trifluoroethyl)oxazole-4-carboxamide (20 mg, 20.97%).

Example 64

The above referenced compound was synthesized utilizing the procedures as described in the general scheme above using cyclopentanol as the alcohol in step 1 and 2-oxa-6-azaspiro[3.4]octane as the amine in step 4, to provide N-(4-(cyclopentyloxy)-3-fluorophenyl)-2-(2-oxa-6-azaspiro[3.4]octan-6-yl)-5-(2,2,2-trifluoroethyl)oxazole-4-carboxamide (40 mg, 34.54%).

Example 65

The above referenced compound was synthesized utilizing the procedures as described in the general scheme above using cyclohexanol as the alcohol in step 1 and pyrrolidine as the amine in step 4, to provide N-(4-(cyclohexyloxy)-3-fluorophenyl)-2-(pyrrolidin-1-yl)-5-(2,2,2-trifluoroethyl)oxazole-4-carboxamide (24 mg, 18.62%).

Example 66

The above referenced compound was synthesized utilizing the procedures as described in the general scheme above using tetrahydro-2H-pyran-3-ol as the alcohol in step 1 and pyrrolidine as the amine in step 4, to provide N-[3-fluoro-4-(oxan-3-yloxy)phenyl]-2-(pyrrolidin-1-yl)-5-(2,2,2-trifluoroethyl)oxazole-4-carboxamide (25 mg, 31%).

Example 67

The above referenced compound was synthesized utilizing the procedures as described in the general scheme above using spiro[3.4]octan-5-ol as the alcohol in step 1 and pyrrolidine as the amine in step 4, to provide N-(3-fluoro-4-{spiro[3.4]octan-5-yloxy}phenyl)-2-(pyrrolidin-1-yl)-5-(2,2,2-trifluoroethyl)oxazole-4-carboxamide (25 mg, 31%).

Example 68

The above referenced compound was synthesized utilizing the procedures as described in the general scheme above using 2,2-difluorocyclohexanol as the alcohol in step 1 and 2-oxa-6-azaspiro[3.4]octane as the amine in step 4, to provide N-(4-((2,2-difluorocyclohexyl)oxy)-3-fluorophenyl)-2-(2-oxa-6-azaspiro[3.4]octan-6-yl)-5-(2,2,2-trifluoroethyl)oxazole-4-carboxamide (16 mg, 14%).

Example 69

The above referenced compound was synthesized utilizing the procedures as described in the general scheme above using 4,4-difluorotetrahydrofuran-3-ol as the alcohol in step 1 and pyrrolidine as the amine in step 4, to provide the racemic title compound. Chiral separation was conducted on an Agilent 1200 series instrument. Column: CHIRALPAK IG (250×21 mm) 5 μm particle size. This separation was conducted at ambient temperature and a flow rate of 21.0 mL/min. The mobile phase was a mixture of 70% Hexane and 30% EtOH, held as an isocratic mixture for 40 min with a wavelength of 280 nm. Separation provided enantiomerically pure (S)—N-(4-((4,4-difluorotetrahydrofuran-3-yl)oxy)-3-fluorophenyl)-2-(pyrrolidin-1-yl)-5-(2,2,2-trifluoroethyl)oxazole-4-carboxamide (30 mg, 29%).

Example 70

The above referenced compound was synthesized utilizing the procedures as described in the general scheme above using 4,4-difluorotetrahydrofuran-3-ol as the alcohol in step 1 and 3,3-dimethylazetidine as the amine in step 4, to provide N-{4-[(4,4-difluorotetrahydrofuran-3-yl)oxy]-3,5-difluorophenyl}-2-(3,3-dimethylazetidin-1-yl)-5-(2,2,2-trifluoroethyl)oxazole-4-carboxamide (50 mg, 30%).

Example 71

The above referenced compound was synthesized utilizing the procedures as described in the general scheme above using 4,4-difluorotetrahydrofuran-3-ol as the alcohol in step 1 and pyrrolidine as the amine in step 4, to provide the racemic title compound N-(4-((4,4-difluorotetrahydrofuran- 3-yl)oxy)-3-fluorophenyl)-2-(pyrrolidin-1-yl)-5-(2,2,2-trifluoroethyl)oxazole-4-carboxamide (30 mg, 36%).

Example 72

The above referenced compound was synthesized utilizing the procedures as described in the general scheme above using tetrahydro-2H-pyran-3-ol as the alcohol in step 1 and 3,3-dimethylazetidine as the amine in step 4, to provide the racemic title compound N-(3,5-difluoro-4-((tetrahydro-2H-pyran-3-yl)oxy)phenyl)-2-(3,3-dimethylazetidin-1-yl)-5-(2,2,2-trifluoroethyl)oxazole-4-carboxamide (30 mg, 22%).

Example 73

The above referenced compound was synthesized utilizing the procedures as described in the general scheme above using cis-bicyclo[3.1.0]hexan-3-ol as the alcohol in step 1 and 2-oxa-6-azaspiro[3.4]octane as the amine in step 4, to provide N-(4-{cis-bicyclo[3.1.0]hexan-3-yloxy}-3-fluorophenyl)-2-{2-oxa-6-azaspiro[3.4]octan-6-yl}-5-(2,2,2-trifluoroethyl)oxazole-4-carboxamide (40 mg, 30%).

Example 74

The above referenced compound was synthesized utilizing the procedures as described in the general scheme above using cis-bicyclo[3.1.0]hexan-3-ol as the alcohol in step 1 and pyrrolidine as the amine in step 4, to provide N-(4-{cis-bicyclo[3.1.0]hexan-3-yloxy}-3-fluorophenyl)-2-(pyrrolidin-1-yl)-5-(2,2,2-trifluoroethyl)oxazole-4-carboxamide (60 mg, 77%).

Example 75

The above referenced compound was synthesized utilizing the procedures as described in the general scheme above using cis-bicyclo[3.1.0]hexan-3-ol as the alcohol in step 1 and 5-azaspiro[2.4]heptane as the amine in step 4, to provide 2-{5-azaspiro[2.4]heptan-5-yl}-N-(4-{cis-bicyclo[3.1.0]hexan-3-yloxy}-3-fluorophenyl)-5-(2,2,2-trifluoroethyl)oxazole-4-carboxamide (25 mg, 21%).

Example 76

The above referenced compound was synthesized utilizing the procedures as described in the general scheme above using 2,2-difluorocyclohexanol as the alcohol in step 1 and pyrrolidine as the amine in step 4, to provide N-{4-[(2,2-difluorocyclohexyl)oxy]-3-fluorophenyl}-2-(pyrrolidin-1-yl)-5-(2,2,2-trifluoroethyl)oxazole-4-carboxamide (30 mg, 36%).

General Procedure for the Synthesis of Examples of General Structure XXXV (Examples 77-83).

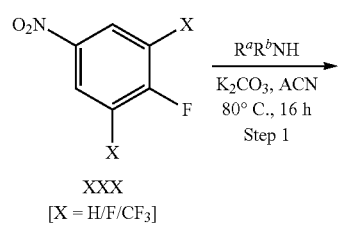

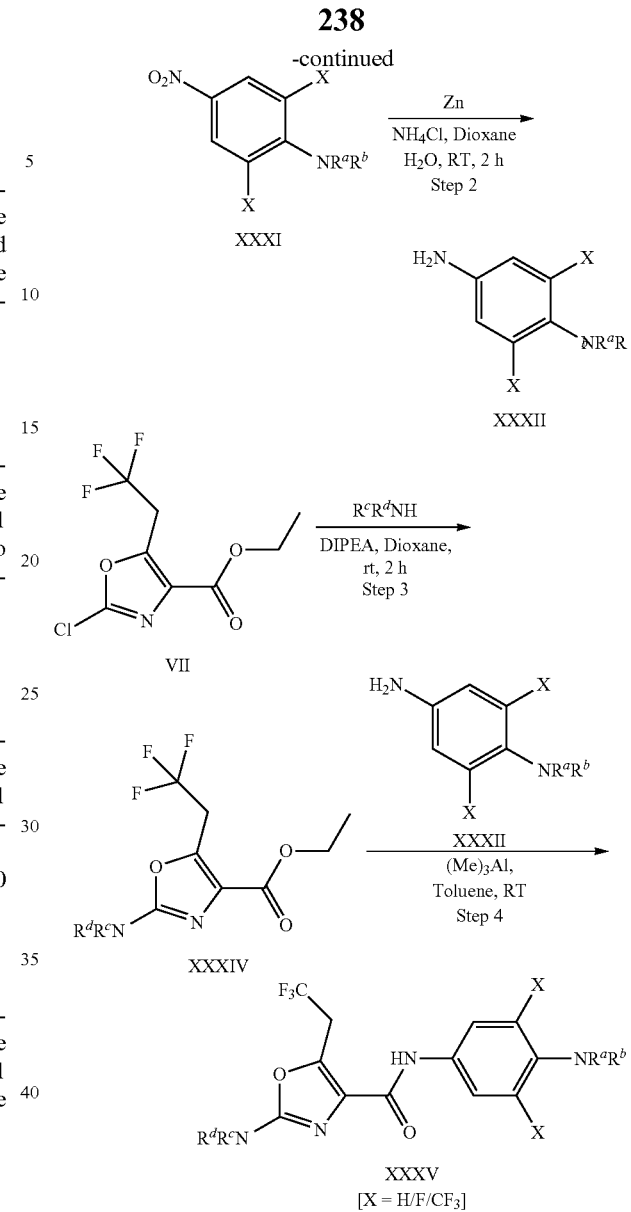

Step 1: To a stirred solution of compound (XXX) (1.0 eq) and potassium carbonate (2.0 eq) in acetonitrile (3 mL/mmol) was added amine $R^aR^bNH$ (1.1 eq). The reaction mass was heated at 80° C. for 16 h. After completion [Monitored by TLC or LC-MS], the reaction mixture was concentrated to remove the volatiles. The crude reaction mixture was then diluted with EtOAc and washed with brine. The organic layer was separated, dried over anhydrous sodium sulfate, and concentrated under reduced pressure. The crude material was purified through flash column chromatography using EtOAc/hexane as eluent to afford the intermediate compound XXXI.

Step 2: To a stirred solution of compound XXXI in 1,4 dioxane:water (5:1) was added zinc dust (5.0 eq) followed by ammonium chloride (6.0 eq) at 0° C. The reaction mixture was then stirred for 3 h at rt. After completion [Monitored by TLC], the reaction mixture was filtered through a sintered glass filter. The filtrate was dried over anhydrous $Na_2SO_4$, concentrated under reduced pressure, and purified through flash column chromatography using EtOAc-hexane as eluent to afford intermediate compound XXXII.

Step 3: To a stirred solution of compound VII (1.0 eq.) in dioxane (3 mL/g) was added amine $R^cR_dNH$ (1.1 eq.) and DIPEA (3.0 equiv), the resultant reaction mixture was allowed to stir at room temperature for 2 h. After completion [Monitored by TLC], the reaction mixture was concentrated under reduced pressure to remove dioxane. The resultant crude was purified through flash column chromatography using EtOAc-Hexane as eluent to provide XXXIV.

Step 4: To a stirred solution of XXXIV (1.0 eq) in dry toluene (30 mL/g), XXXII (0.8 eq) was added followed by dropwise addition of trimethylaluminum (1 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. The organic layer was separated, dried over anhydrous sodium sulfate, and concentrated under reduced pressure. The resulting crude product was purified by flash column chromatography to afford XXXV.

All the amines used as starting materials were purchased from commercial suppliers.

Example 77

The above referenced compound was synthesized utilizing the procedures as described in the general scheme above wherein compound XXX was 3,4-difluoronitrobenzene, using 4,4-difluoropiperidine as the amine in step 1 and 6,6-difluoro-2-azaspiro[3.3]heptane as the amine in step 4, to provide 2-{6,6-difluoro-2-azaspiro[3.3]heptan-2-yl}-N-[4-(4,4-difluoropiperidin-1-yl)-3-fluorophenyl]-5-(2,2,2-trifluoroethyl)oxazole-4-carboxamide (58 mg, 48%).

Example 78

The above referenced compound was synthesized utilizing the procedures as described in the general scheme above wherein compound XXX was 4-fluoro-3-trifluoromethylnitrobenzene, using piperidine as the amine in step 1 and 6,6-difluoro-2-azaspiro[3.3]heptane as the amine in step 4, to provide 2-{6,6-difluoro-2-azaspiro[3.3]heptan-2-yl}-N-[4-(piperidin-1-yl)-3-(trifluoromethyl)phenyl]-5-(2,2,2-trifluoroethyl)oxazole-4-carboxamide (45 mg, 29%).

Example 79

The above referenced compound was synthesized utilizing the procedures as described in the general scheme above wherein compound XXX was 3,4-difluoronitrobenzene, using N-methylcyclopentanamine as the amine in step 1 and 6,6-difluoro-2-azaspiro[3.3]heptane as the amine in step 4, to provide N-{4-[cyclopentyl(methyl)amino]-3-fluorophenyl}-2-{6,6-difluoro-2-azaspiro[3.3]heptan-2-yl}-5-(2,2,2-trifluoroethyl)oxazole-4-carboxamide (64 mg, 33%).

Example 80

The above referenced compound was synthesized utilizing the procedures as described in the general scheme above wherein compound XXX was 3,4-difluoronitrobenzene, using N-methylbicyclo[3.1.0]hexan-3-amine as the amine in step 1 and pyrrolidine as the amine in step 4, to provide N-(4-{bicyclo[3.1.0]hexan-3-yl(methyl)amino}-3-fluorophenyl)-2-(pyrrolidin-1-yl)-5-(2,2,2-trifluoroethyl)oxazole-4-carboxamide (30 mg, 18%).

Example 81

The above referenced compound was synthesized utilizing the procedures as described in the general scheme above wherein compound XXX was 3,4,5-trifluoronitrobenzene, using 2,2-difluoro-N-methylcyclopentan-1-amine as the amine in step 1 and pyrrolidine as the amine in step 4, to provide N-{4-[(2,2-difluorocyclopentyl)(methyl)amino]-3,5-difluorophenyl}-2-(pyrrolidin-1-yl)-5-(2,2,2-trifluoroethyl)oxazole-4-carboxamide (30 mg, 18%).

Example 82

The above referenced compound was synthesized utilizing the procedures as described in the general scheme above wherein compound XXX was 3,4-difluoronitrobenzene, using 2,2-difluoro-N-methylcyclopentan-1-amine as the amine in step 1 and pyrrolidine as the amine in step 4, to provide N-{4-[(2,2-difluorocyclopentyl)(methyl)amino]-3-fluorophenyl}-2-(pyrrolidin-1-yl)-5-(2,2,2-trifluoroethyl)oxazole-4-carboxamide (25 mg, 21%).

Example 83

The above referenced compound was synthesized utilizing the procedures as described in the general scheme above wherein compound XXX was 3,4-difluoronitrobenzene, using 6-azabicyclo[3.1.1]heptane as the amine in step 1 and pyrrolidine as the amine in step 4, to provide N-(4-{6-azabicyclo[3.1.1]heptan-6-yl}-3-fluorophenyl)-2-(pyrrolidin-1-yl)-5-(2,2,2-trifluoroethyl)oxazole-4-carboxamide (16 mg, 12%).

Example 84

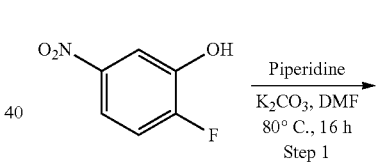

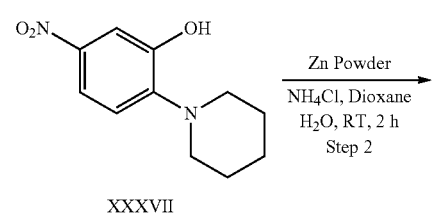

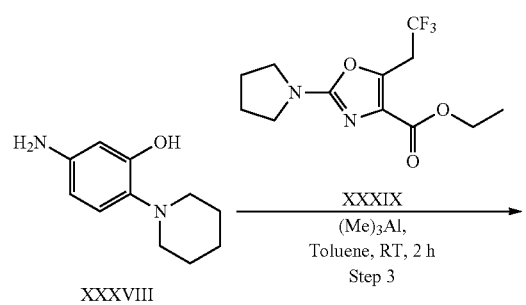

-continued

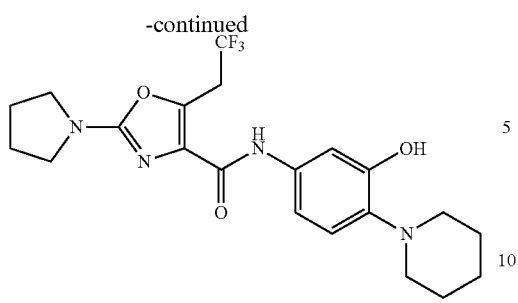

Example 84

Step 1: Synthesis of 5-nitro-2-(piperidin-1-yl)phenol: To a stirred suspension of 2-fluoro-5-nitrophenol (0.8 g, 5.10 mmol) and potassium carbonate (2.1 g, 15.30 mmol) in DMF (5 mL) was added piperidine (0.86 g, 10.2 mmol), the reaction is allowed to stir at 80° C. for 16 h. After completion [Monitored by TLC], the reaction mixture was diluted with ethyl acetate (20 mL) and washed with water (2×30 mL). The organic layer was separated, dried over anhydrous sodium sulfate, and concentrated under reduced pressure. The crude was purified through flash column chromatography using 10% ethyl acetate in hexane to afford 5-nitro-2-(piperidin-1-yl)phenol (0.85 g, 75%) as a yellow liquid.

Step 2: Synthesis of 5-amino-2-(piperidin-1-yl)phenol: To a stirred solution of 5-nitro-2-(piperidin-1-yl)phenol (XXXVII) (200 mg, 0.90 mmol) in 10 mL of 1,4 dioxane:water (5:1) was added zinc dust (292 mg, 4.5 mmol) along with ammonium chloride (287 mg, 5.4 mmol) at 0° C. It was then stirred for 3 h at rt. After completion [Monitored by LC-MS], the reaction mixture was filtered through a sintered glass filter. The filtrate was dried over anhydrous $Na_2SO_4$, concentrated, and purified through flash column chromatography using 15% ethyl acetate in hexane to afford 5-amino-2-(piperidin-1-yl)phenol (55 mg, 31.75%).

Step 3: Synthesis of N-(3-hydroxy-4-(piperidin-1-yl)phenyl)-2-(pyrrolidin-1-yl)-5-(2,2,2-trifluoroethyl)oxazole-4-carboxamide. To a stirred solution of XXXVIII (38 mg, 0.185 mmol) in dry toluene (5 mL), XXXIX (60 mg, 0.205 mmol) was added followed by dropwise addition of trimethylaluminum (2 M in toluene, 0.4 mL, 0.80 mmol) at 0° C. and the resultant reaction mixture was allowed to stir at rt for 2 h. After completion [Monitored with TLC], the reaction mixture was quenched with saturated ammonium chloride solution and partitioned with EtOAc. The organic layer was separated, dried over anhydrous sodium sulfate, and concentrated under reduced pressure. The resultant crude was purified by flash column chromatography to afford N-(3-hydroxy-4-(piperidin-1-yl)phenyl)-2-(pyrrolidin-1-yl)-5-(2,2,2-trifluoroethyl)oxazole-4-carboxamide (10 mg, 11%).

Example 85

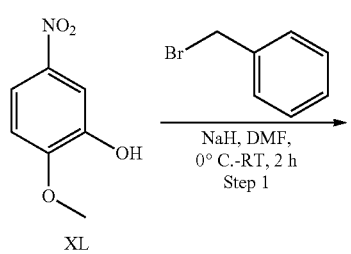

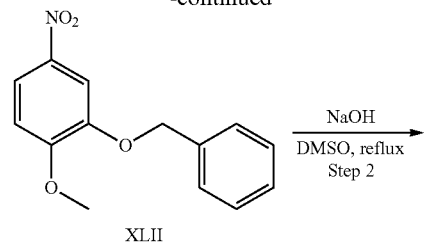

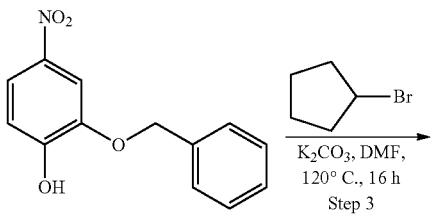

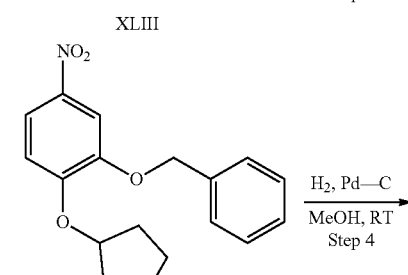

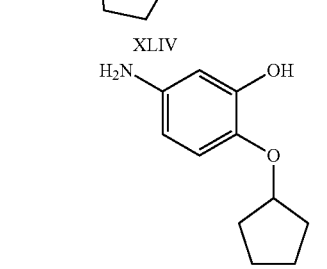

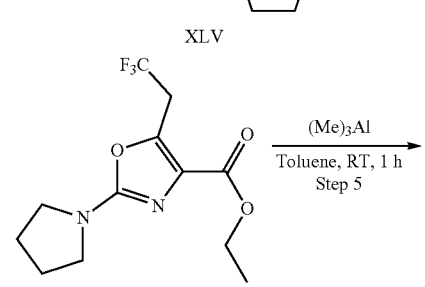

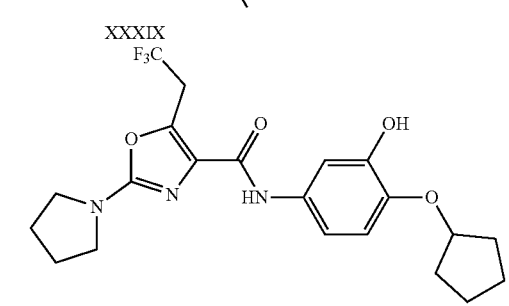

Example 85

Step 1: To a stirred solution of 2-methoxy-5-nitrophenol (XL) (500 mg, 2.95 mmol) in DMF (10 mL) were added $K_2CO_3$ (407 mg, 2.95 mmol), and benzyl bromide (505 mg, 2.95 mmol) and stirred at RT for 16 h. After completion

[Monitored with TLC], the reaction mixture was diluted with cold water [20 mL] and extracted with EtOAc [20 mL×2]. The organic part was separated, dried over sodium sulfate, and concentrated under reduced pressure. The resultant crude was purified by flash column chromatography using 2-5% EtOAc-Hexane as eluting solvent to afford 2-(benzyloxy)-1-methoxy-4-nitrobenzene (XLII) (475 mg, 62%) as pale yellow solid.

Step 2: To a stirred solution of compound XLII (475 mg, 1.83 mmol) in DMSO (10 mL) was added 10 N NaOH solution (0.5 mL) and stirred at 100° C. for 5 h. After completion [Monitored with TLC], the reaction mixture was acidified with 1 N HCl solution (~2 mL), extracted with EtOAc [20 mL×2]. The organic part was separated, dried over sodium sulfate, and concentrated under reduced pressure. The resultant crude was purified by flash column chromatography using 2-5% EtOAc-Hexane as eluting solvent to afford 2-(benzyloxy)-4-nitrophenol (XLIII) (360 mg, 80%).

Step 3: To a stirred solution of XLIII (360 mg, 1.46 mmol) in DMF (8 mL) were added bromocyclopentane (218.89 mg, 1.46 mmol), K₂CO₃ and stirred at 120° C. for 16 h. After completion [Monitored with TLC], the reaction mixture was diluted with cold water [20 mL] and extracted with EtOAc [20 mL×2]. The organic part was separated, dried over sodium sulfate, and concentrated under reduced pressure. The resultant crude was purified by flash column chromatography using 15% EtOAc-Hexane to afford 2-(benzyloxy)-1-(cyclopentyloxy)-4-nitrobenzene (XLIV) (300 mg, 65%).

Step 4: To a stirred solution of XLIV (150 mg, 0.47 mmol) in ethanol (4 mL) was added Pd/C (20%) (~80 mg) and stirred under a hydrogen atmosphere for 1 h. After completion [Monitored with TLC], the reaction mixture was filtered through celite and concentrated under reduced pressure. The residue was then purified by flash column chromatography using 50% EtOAc-Hexane to afford 5-amino-2-(cyclopentyloxy)phenol XLV (60 mg, 64%) as brown solid.

Step 5: To a stirred solution of XXXIX (100 mg, 0.34 mmol) in dry toluene (4 mL) was added 5-amino-2-(cyclopentyloxy)phenol (66 mg, 0.34 mmol) followed by dropwise addition of trimethylaluminum (2 M in toluene, 0.68 mL, 1.36 mmol) at 0° C. and the resultant reaction mixture was allowed to stir at room temperature for 2 h. After completion [Monitored with TLC], the reaction mixture was quenched with saturated ammonium chloride solution (10 mL) and partitioned with EtOAc [30 mL×2]. The organic layer was separated, dried over sodium sulfate, and concentrated under reduced pressure. The resultant crude product was purified by flash column chromatography using 35% EtOAc-Hexane as eluting solvent to afford N-(4-(cyclopentyloxy)-3-hydroxyphenyl)-2-(pyrrolidin-1-yl)-5-(2,2,2-trifluoroethyl)oxazole-4-carboxamide (20 mg, 13%).

Example 86

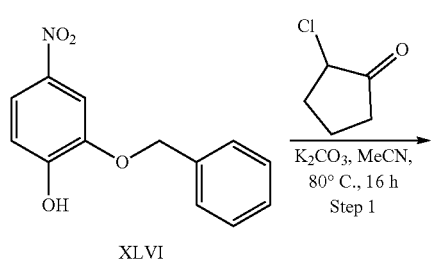

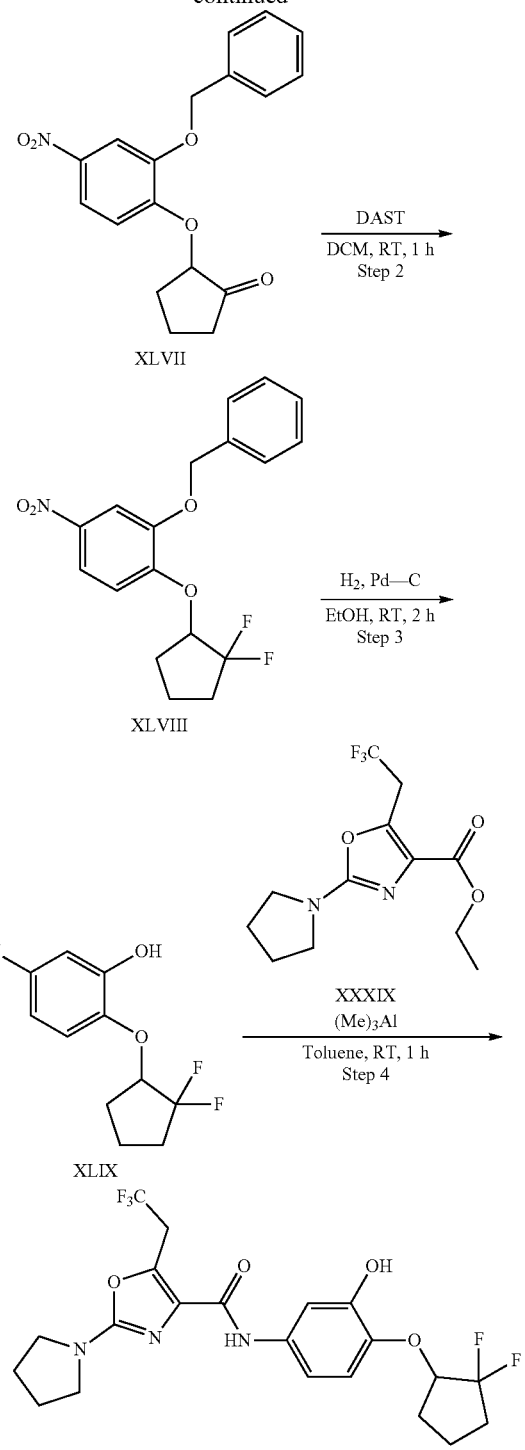

Example 86

Step 1: To a stirred solution of 2-(benzyloxy)-4-nitrophenol (XLVI) (600 mg, 2.44 mmol) in Acetone (8 mL) was added K₂CO₃ (1 g, 7.34 mmol), chlorocyclopentanone (319 mg, 2.69 mmol) and stirred at 80° C. for 16 h. After completion [Monitored with TLC], the reaction mixture was concentrated under reduced pressure to provide crude XLVII. The resultant crude material was purified by flash column chromatography using Silica gel under gradient elution of 0-50% EtOAc-Hexane to afford 2-[2-(benzyloxy)-4-nitrophenoxy]cyclopentan-1-one XLVII (293 mg, 37%).

Step 2: To a stirred solution of 2-[2-(benzyloxy)-4-nitrophenoxy]cyclopentan-1-one (XLVII) (293 mg, 0.89 mmol) in DCM (5 mL) was added DAST (720 mg, 4.47 mmol) at 0° C. and stirred at RT for 1 h. After completion [Monitored with TLC], the reaction mixture was quenched with saturated NH$_4$Cl solution (~20 mL), extracted with EtOAc [20 mL×2]. The organic part was separated, dried over sodium sulfate, and concentrated under reduced pressure to get the crude XLVIII. The resultant crude material was purified by flash column chromatography using Silica gel under gradient elution of 10% EtOAc-Hexane to afford 2-(benzyloxy)-1-[(2,2-difluorocyclopentyl)oxy]-4-nitrobenzene XLVIII (233 mg, 75%).

Step 3: To a stirred solution of 2-(benzyloxy)-1-[(2,2-difluorocyclopentyl)oxy]-4-nitrobenzene XLVIII (100 mg, 0.66 mmol) in THF:EtOH (4 mL) was added Pd/C (~80 mg) and stirred under a hydrogen atmosphere for 16 h. After completion [Monitored with TLC], the reaction mixture was filtered and concentrated under reduced pressure to get the crude XLIX. The resultant crude material was purified by flash column chromatography using Silica gel under gradient elution of 30-40% EtOAc-Hexane to afford 5-amino-2-[(2,2-difluorocyclopentyl)oxy]phenol XLIX (80 mg, 52%) as a brown viscous liquid.

Step 4: Trimethylaluminum (2 Min toluene, 0.5 mL, 1.0 mmol) was added dropwise to a stirred solution of ethyl 2-(pyrrolidin-1-yl)-5-(2,2,2-trifluoroethyl)oxazole-4-carboxylate XXXIX (70 mg, 0.24 mmol) and 5-amino-2-[(2,2-difluorocyclopentyl)oxy]phenol XLIX (55 mg, 0.24 mmol) at 0° C. The resultant reaction mixture was allowed to stir at room temperature for 2 h. After completion [Monitored with TLC], reaction mixture was quenched with saturated ammonium chloride solution (10 mL) and partitioned with EtOAc [30 mL×2]. The organic layer was separated, dried over sodium sulfate, and concentrated under reduced pressure. The resultant crude material was purified by flash column chromatography using 35% EtOAc-Hexane as eluting solvent to afford N-{4-[(2,2-difluorocyclopentyl)oxy]-3-hydroxyphenyl}-2-(pyrrolidin-1-yl)-5-(2,2,2-trifluoroethyl)-1,3-oxazole-4-carboxamide Example 86 (20 mg, 18%).

Example 87

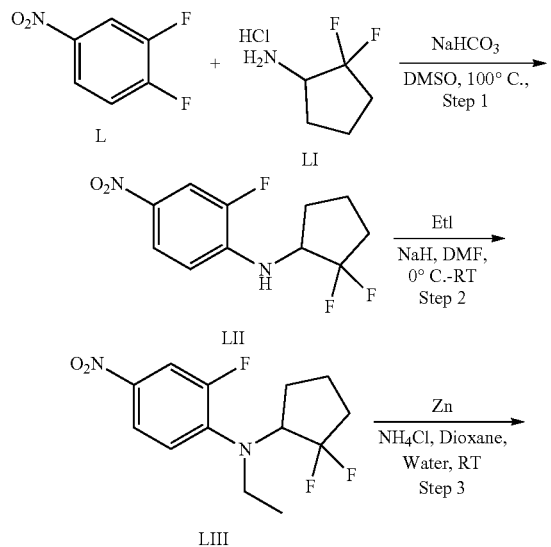

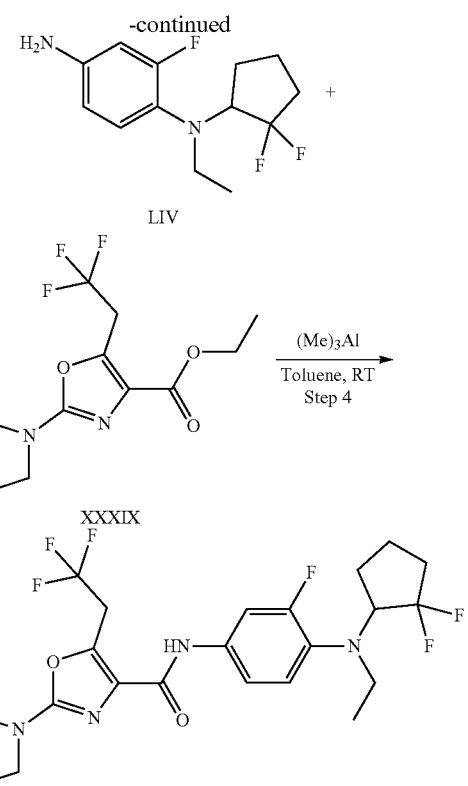

Example 87

Step 1: To a stirred solution of 1,2-difluoro-4-nitrobenzene (500 mg, 3.14 mmol) in DMSO (5 ml) was added NaHCO$_3$ (924 mg, 11.0 mmol) & 2,2-difluorocyclopentan-1-amine hydrochloride (495 mg, 3.14 mmol) the mixture was heated to 100° C. (sealed tube) and stirred for 20 h. After completion [Monitored with TLC], the reaction mixture was concentrated and diluted with water [20 mL] and extracted with EtOAc [2×30 mL]. The combined organic layers were separated, dried over sodium sulfate, and concentrated under reduced pressure. The resultant crude material was purified by flash column chromatography using 0-6% EtOAc in Hexane as eluent to afford desired product N-(2,2-difluorocyclopentyl)-2-fluoro-4-nitroaniline LII (500 mg, 61%) as a yellow gummy liquid.

Step 2: To a stirred solution of N-(2,2-difluorocyclopentyl)-2-fluoro-4-nitroaniline (300 mg, 1.15 mmol) in DMF (5 mL) was added NaH (92 mg, 2.3 mmol) at 0° C. stirred for 30 min. Ethyl iodide (0.186 mL, 2.30 mmol) was then added and the mixture was allowed to warm to RT while stirring for 16 h. After completion [Monitored with TLC], the reaction mixture was concentrated and diluted with water [20 mL] and extracted with EtOAc [2×30 mL]. The resultant crude material was purified by flash column chromatography using 10% EtOAc in Hexane as eluent to afford desired product N-(2,2-difluorocyclopentyl)-N-ethyl-2-fluoro-4-nitroaniline LIII (160 mg, 48%) as a yellow solid.

Step 3: To a stirred solution of N-(2,2-difluorocyclopentyl)-N-ethyl-2-fluoro-4-nitroaniline LIII (160 mg, 0.55 mmol) in dioxane (6 mL) were added NH$_4$Cl·H$_2$O (300 mg, 5.55 mmol) and Zn dust (361 mg, 5.55 mmol) and stirred for 6 h. After completion [Monitored with TLC], the reaction mixture was filtered through celite and washed with EtOAc. The filtrate was concentrated and purified by flash column chromatography using 30% EtOAc in Hexane as eluent to afford desired product N1-(2,2-difluorocyclopentyl)-N1-ethyl-2-fluorobenzene-1,4-diamine LIV (110 mg, 77%) as a brown liquid.

Step 4: To a stirred solution of ethyl 2-(pyrrolidin-1-yl)-5-(2,2,2-trifluoroethyl)oxazole-4-carboxylate XXXIX (75 mg, 0.25 mmol) in dry toluene (3 mL) was added N1-(2,2-difluorocyclopentyl)-N1-ethyl-2-fluorobenzene-1,4-diamine (53 mg, 0.20 mmol) followed by dropwise addition of trimethyl aluminum (2 M in toluene, 0.5 mL, 1.0 mmol) at 0° C. and the resultant reaction mixture was allowed to stir at room temperature for 2 h. After completion [Monitored with TLC], the reaction mixture was quenched with saturated ammonium chloride solution (10 mL) and partitioned with EtOAc [30 mL×2]. The organic layer was separated, dried over sodium sulfate, and concentrated under reduced pressure. The resultant crude material was purified by flash column chromatography using 20% EtOAc-Hexane as eluting solvent to afford N-(4-((2,2-difluorocyclopentyl)(ethyl)amino)-3-fluorophenyl)-2-(pyrrolidin-1-yl)-5-(2,2,2-trifluoroethyl)oxazole-4-carboxamide Example 87 (26 mg, 20%).

Example 88

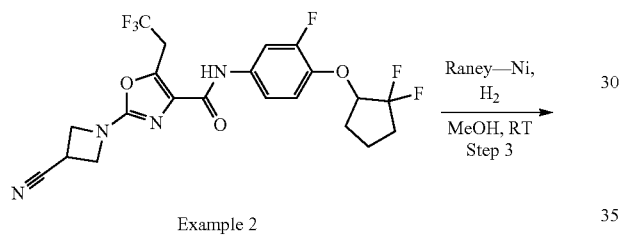

Example 2

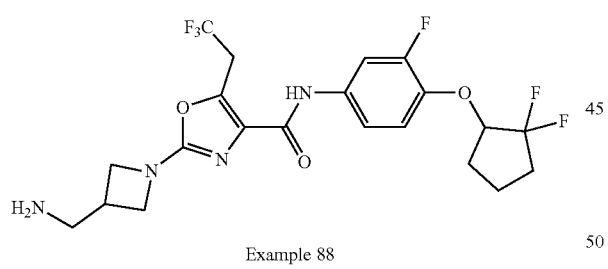

Example 88

To a stirred solution of 2-(3-(aminomethyl)azetidin-1-yl)-N-(4-((2,2-difluorocyclopentyl)oxy)-3-fluorophenyl)-5-(2,2,2-trifluoroethyl)oxazole-4-carboxamide (Example 2) (70 mg, 0.14 mmol) in MeOH (3 mL) was added Raney Ni and stirred at RT for 3 h under Hydrogen at 1 atm. After completion [Monitored with TLC], the reaction mixture was filtered through celite and concentrated to get the crude product. The crude residue was dissolved in DCM (3 mL) and purified by column chromatography using Silica gel under gradient elution of 0-5% MeOH-DCM to afford 2-[3-(aminomethyl)azetidin-1-yl]-N-{4-[(2,2-difluorocyclopentyl)oxy]-3-fluorophenyl}-5-(2,2,2-trifluoroethyl)oxazole-4-carboxamide Example 88 (22 mg, 710%).

Preparation of Intermediate Ethyl 2-Chloro-5-Methyloxazole-4-Carboxylate (LXI)

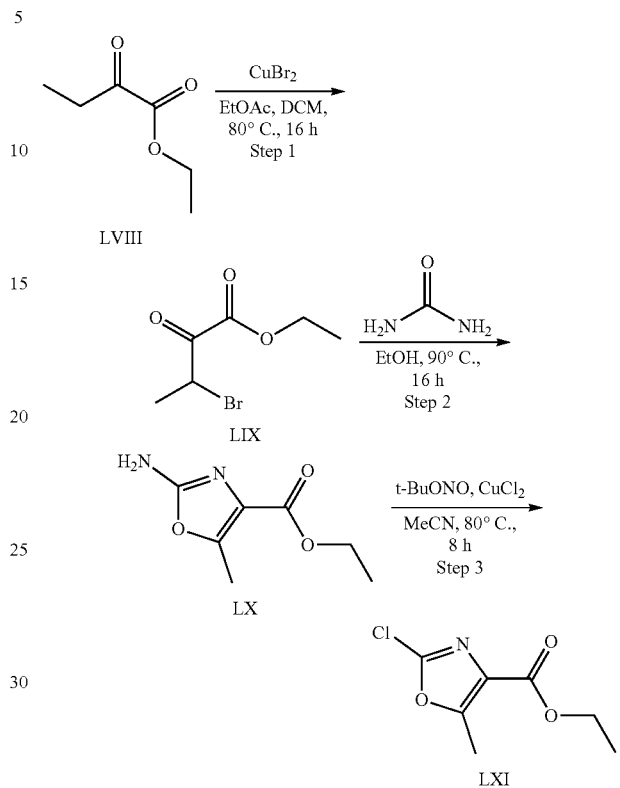

Step 1: To the stirred solution of ethyl 2-oxobutanoate (16.0 g, 123.07 mmol) in EtOAc (1000 mL) and DCM (600 mL) was added CuBr$_2$ (109.78 g, 492.30 mmol) at room temperature. The mixture was then heated at 90° C. for 16 h. After completion [Monitored with TLC], the reaction mixture was filtered through celite and the filtrate was concentrated to afford ethyl 3-bromo-2-oxobutanoate (LIX) (25.0 g) as a brown gummy liquid (crude). It was used for next step without further purification.

Step 2: To the solution of ethyl 3-bromo-2-oxobutanoate (25.0 g, 120.19 mmol) in ethanol (200 mL) was added urea (28.84 g, 480.76 mmol) at room temperature and allowed to stir at 80° C. for 24 h. After completion [Monitored with TLC], the reaction mixture was concentrated to remove ethanol. The crude mass was then treated with a saturated aqueous solution of NaHCO$_3$ (200 mL) and extracted with EtOAc (2×300 mL). The organic part was dried over anhydrous Na$_2$SO$_4$ and concentrated under reduced pressure. The crude product was triturated with Et$_2$O, the resultant precipitate was filtered through a sintered glass filter and dried under vacuum to afford pure ethyl 2-amino-5-methyloxazole-4-carboxylate (LX) (13.6 g) as off-white solid.

Step 3: A suspension of CuCl$_2$ (6.51 g, 48.47 mmol) and tert-butylnitrite (7.75 g, 75.29 mmol) in acetonitrile (80 mL) was heated to 70° C. and stirred for 15 min. Then a suspension of ethyl 2-amino-5-methyloxazole-4-carboxylate (LX) (8.0 g, 47.05 mmol) in acetonitrile (120 mL) was added dropwise to the reaction mixture at 70° C. and allowed to stir at room temperature for 16 h. After completion [Monitored with TLC], the reaction mixture was concentrated to remove volatiles and then diluted with ethyl acetate (250 mL) and water (250 mL), the resultant suspension was filtered through a sintered glass filter. The organic layer was separated, dried over anhydrous Na₂SO₄, and concentrated under reduced pressure. The resulting crude material was purified by silica gel flash column using 5% EtOAc-hexane as eluent to afford ethyl 2-chloro-5-methyl-oxazole-4-carboxylate (LXI) (5.6 g, 62.77%).

General Procedure for the Synthesis of Examples of General Structure LXIII (Examples 89-90).

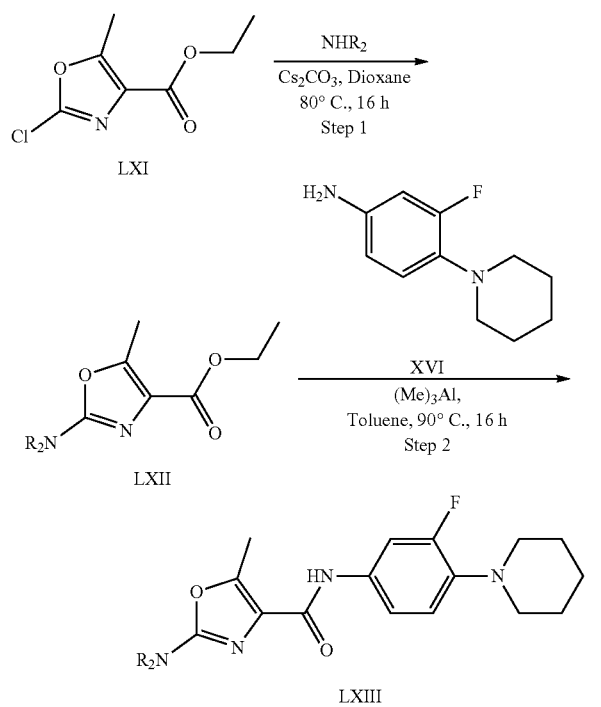

Step 1: To a stirred solution of amine/amine salt (1.2 eq.) and Cs₂CO₃ (3.0 equiv) in dioxane (30 mL/g) was added ethyl 2-chloro-5-methyloxazole-4-carboxylate (LXI) (1.0 eq.) and the resultant reaction mixture was allowed to stir at room 80° C. for 16 h. After completion [monitored with TLC], the reaction mixture was filtered through a sintered glass filter and the filtrate was concentrated under reduced pressure. The resultant crude was purified by column chromatography to provide LXII.

Step 2: To a stirred solution of LXII (1.0 eq) in dry toluene (10 mL/mmol), 3-fluoro-4-(piperidin-1-yl)aniline (XVI) (0.8 eq) was added followed by dropwise addition of trimethylaluminum (1 Min toluene, 4.0 eq) at 0° C. and the resultant reaction mixture was allowed to stir at 90° C. for 16 h. After completion [Monitored with TLC/LCMS], the reaction mixture was quenched with saturated ammonium chloride solution and partitioned with EtOAc. The organic layer was separated, dried over anhydrous sodium sulfate, and concentrated under reduced pressure. The resultant crude material was purified by flash column chromatography to afford examples of the general structure LXIII.

All the amines used as starting materials were purchased from commercial providers.

Example 89

The above referenced compound was synthesized utilizing the procedures outlined in the scheme above wherein the amine in step 1 is 6,6-difluoro-2-azaspiro[3.3]heptane to provide, 2-(6,6-difluoro-2-azaspiro[3.3]heptan-2-yl)-N-(3-fluoro-4-(piperidin-1-yl)phenyl)-5-methyloxazole-4-carboxamide (25 mg, 19.39%).

Example 90

The above referenced compound was synthesized utilizing the procedures outlined in the scheme above wherein the amine in step 1 is 2-oxa-6-azaspiro[3.4]octane to provide, N-(3-fluoro-4-(piperidin-1-yl)phenyl)-5-methyl-2-(2-oxa-6-azaspiro[3.4]octan-6-yl)oxazole-4-carboxamide (54 mg, 43.4%).

Preparation of intermediate 2-chloro-N-(3-fluoro-4-(piperidin-1-yl)phenyl)-5-methyloxazole-4-carboxamide (LXVI)

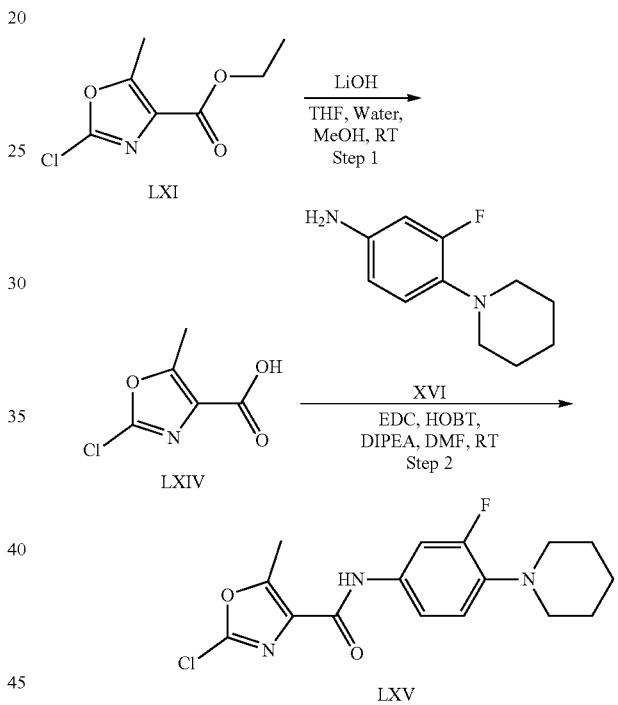

Step 1: To the solution of ethyl 2-chloro-5-methyloxazole-4-carboxylate (2.9 g, 15.4 mmol) in THF (4 mL) was added the solution of LiOH·H₂O (0.96 g, 23 mmol) in water (2 mL) at 0° C. and then it was stirred for 3 h at RT. After completion [Monitored with LC-MS], the reaction mixture was acidified with aqueous HCl (1 N) and partitioned between EtOAc (100 mL) and water (50 mL). The organic layer was separated, dried over sodium sulfate, and concentrated under reduced pressure to afford 2.4 g of 2-chloro-5-methyloxazole-4-carboxylic acid (LXIV) as off white solid (96%).

Step 2: To a stirred solution of 2-chloro-5-methyloxazole-4-carboxylic acid (0.82 g, 5.09 mmol) and 3-fluoro-4-(piperidin-1-yl)aniline (1 g, 5.6 mmol) in DMF (3 mL) was added DIPEA (1.9 g, 15.28 mmol), EDC (1.7 g, 9.16 mmol), HOBT (1.2 g, 9.6 mmol) and the resultant reaction mixture was allowed to stir at room temperature for 16 h. After completion [monitored with LC-MS], the reaction mixture was partitioned between EtOAc (50 mL) and water (200 mL). The organic layer was separated, dried over sodium sulfate, and concentrated under reduced pressure. The resultant crude was purified using silica flash column chromatography using 10% EtOAc-hexane as eluent to afford 2-chloro-N-(3-fluoro-4-(piperidin-1-yl)phenyl)-5-methyloxazole-4-carboxamide (LXV) (0.47 g, 27.3%).

Preparation of Examples with the General Structure LXVI

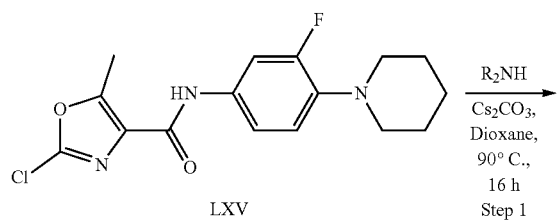
LXV

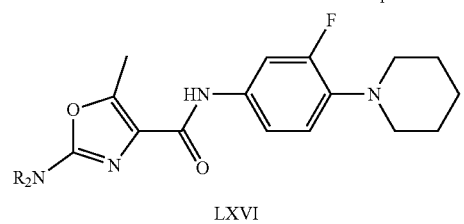
LXVI

Step 1: To the suspension of 2-chloro-N-(3-fluoro-4-(piperidin-1-yl)phenyl)-5-methyloxazole-4-carboxamide (LXV) and Cs$_2$CO$_3$ (1.5 eq) in dioxane was added amine (2 eq) then it was heated at 90° C. for 16 h. After completion (monitored by LC-MS), the reaction mixture was filtered through a sintered glass frit. The organic layer was separated and concentrated under reduced pressure. The resultant crude was purified by silica flash column chromatography under gradient elution of EtOAc-hexane or MeOH-DCM to afford examples with the general structure LXVI.

Example 91

The above referenced compound was synthesized utilizing the procedures outlined in the scheme above wherein the amine in step 1 is 5-azaspiro[2.4]heptane to provide, N-(3-fluoro-4-(piperidin-1-yl)phenyl)-5-methyl-2-(5-azaspiro[2.4]heptan-5-yl)oxazole-4-carboxamide (30 mg, 25%).

Example 92

The above referenced compound was synthesized utilizing the procedures outlined in the scheme above wherein the amine in step 1 is 6-azaspiro[3.4]octane to provide, N-(3-fluoro-4-(piperidin-1-yl)phenyl)-5-methyl-2-(6-azaspiro[3.4]octan-6-yl)oxazole-4-carboxamide (70 mg, 56%).

Example 93

The above referenced compound was synthesized utilizing the procedures outlined in the scheme above wherein the amine in step 1 is pyrrolidin-2-ylmethanol to provide, N-(3-fluoro-4-(piperidin-1-yl)phenyl)-2-(2-(hydroxymethyl)pyrrolidin-1-yl)-5-methyloxazole-4-carboxamide (20 mg, 24%).

Example 94

The above referenced compound was synthesized utilizing the procedures outlined in the scheme above wherein the amine in step 1 is 1-cyclopropylpiperazine to provide, 2-(4-cyclopropylpiperazin-1-yl)-N-(3-fluoro-4-(piperidin-1-yl)phenyl)-5-methyloxazole-4-carboxamide (20 mg, 23%).

Example 95

The above referenced compound was synthesized utilizing the procedures outlined in the scheme above wherein the amine in step 1 is 1-oxaspiro[4.4]nonan-6-amine to provide, 2-((1-oxaspiro[4.4]nonan-6-yl)amino)-N-(3-fluoro-4-(piperidin-1-yl)phenyl)-5-methyloxazole-4-carboxamide (30 mg, 23%).

Example 96

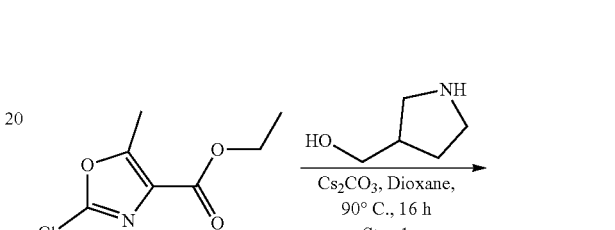
LXI

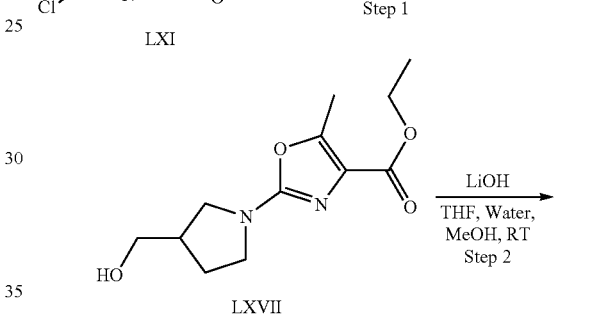
LXVII

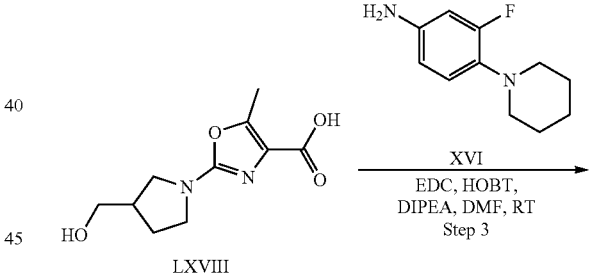
LXVIII

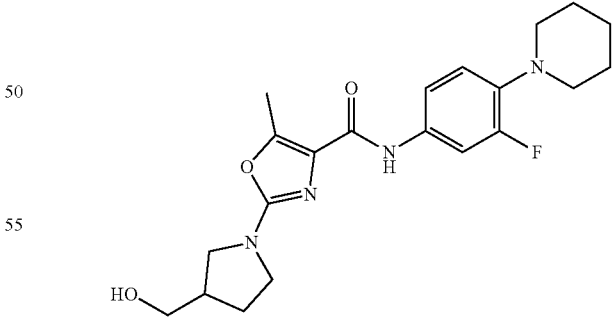
Example 96

Step 1: To the suspension of ethyl 2-chloro-5-methyloxazole-4-carboxylate (200 mg, 1.05 mmol) and Cs$_2$CO$_3$ (687 mg, 2.11 mmol) in dioxane was added pyrrolidin-3-ylmethanol (128 mg, 1.26 mmol) then it was heated at 90° C. for 16 h. After completion [monitored by LC-MS], the reaction mixture was filtered through a sintered glass filter. The organic layer was separated, concentrated under reduced pressure. The resultant crude material was purified by silica flash column chromatography using 30% EtOAc-hexane to afford ethyl 2-(3-(hydroxymethyl)pyrrolidin-1-yl)-5-methyloxazole-4-carboxylate LXVH as a light yellow solid (90 mg, 33%).

Step 2: To the solution of ethyl 2-(3-(hydroxymethyl)pyrrolidin-1-yl)-5-methyloxazole-4-carboxylate (90 mg, 0.35 mmol) in THF (5 mL) was added the solution of LiOH·H₂O (27 mg, 0.7 mmol) in water (1 mL) at 0° C. and then it was stirred for 3 h at RT. After completion [Monitored with LC-MS], the reaction mixture was acidified with aqueous HCl (1 N) and partitioned between EtOAc (50 mL) and water (25 mL). The organic layer was separated, dried over sodium sulfate, and concentrated under reduced pressure to afford 2-(3-(hydroxymethyl)pyrrolidin-1-yl)-5-methyloxazole-4-carboxylic acid as an off white solid (LXVIII) (77 mg, 96%).

Step 3: To a stirred solution of solution of 2-(3-(hydroxymethyl)pyrrolidin-1-yl)-5-methyloxazole-4-carboxylic acid (77 mg, 0.34 mmol) and 3-fluoro-4-(piperidin-1-yl)aniline (72 mg, 0.37 mmol) in DMF (3 mL) was added DIPEA (0.13 mL, 1 mmol), EDC (98 mg, 0.51 mmol) and HOBT (68 mg 0.51 mmol) and the resultant reaction mixture was allowed to stir at room temperature for 16 h. After completion [monitored with LC-MS], the reaction mixture was partitioned between EtOAc (30 mL) and water (100 mL). The organic layer was separated, dried over sodium sulfate, and concentrated under reduced pressure. The resultant crude was purified using silica flash column chromatography using 30% EtOAc-hexane as eluent to afford N-(3-fluoro-4-(piperidin-1-yl)phenyl)-2-(3-(hydroxymethyl)pyrrolidin-1-yl)-5-methyloxazole-4-carboxamide (Example 96) (50 mg, 36%).

The amines were obtained from commercial suppliers.

Example 97

The above referenced compound was synthesized utilizing the procedures outlined in the scheme above wherein the amine in step 1 is 3-hydroxy-pyrrolidine to provide, N-(3-fluoro-4-(piperidin-1-yl)phenyl)-2-(3-hydroxypyrrolidin-1-yl)-5-methyloxazole-4-carboxamide (35 mg, 20%).

Example 98

The above referenced compound was synthesized utilizing the procedures outlined in the scheme above wherein the amine in step 1 is 3-oxa-8-azabicyclo[3.2.1]octane to provide, 2-(3-oxa-8-azabicyclo[3.2.1]octan-8-yl)-N-(3-fluoro-4-(piperidin-1-yl)phenyl)-5-methyloxazole-4-carboxamide (90 mg, 43%).

Preparation of Examples with the General Formula LXXIV (Examples 99-104)

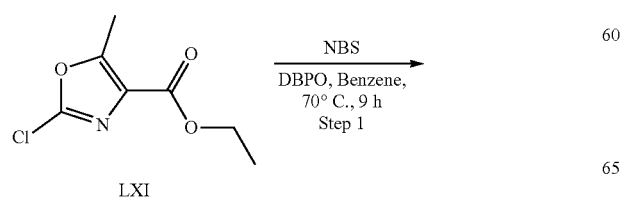

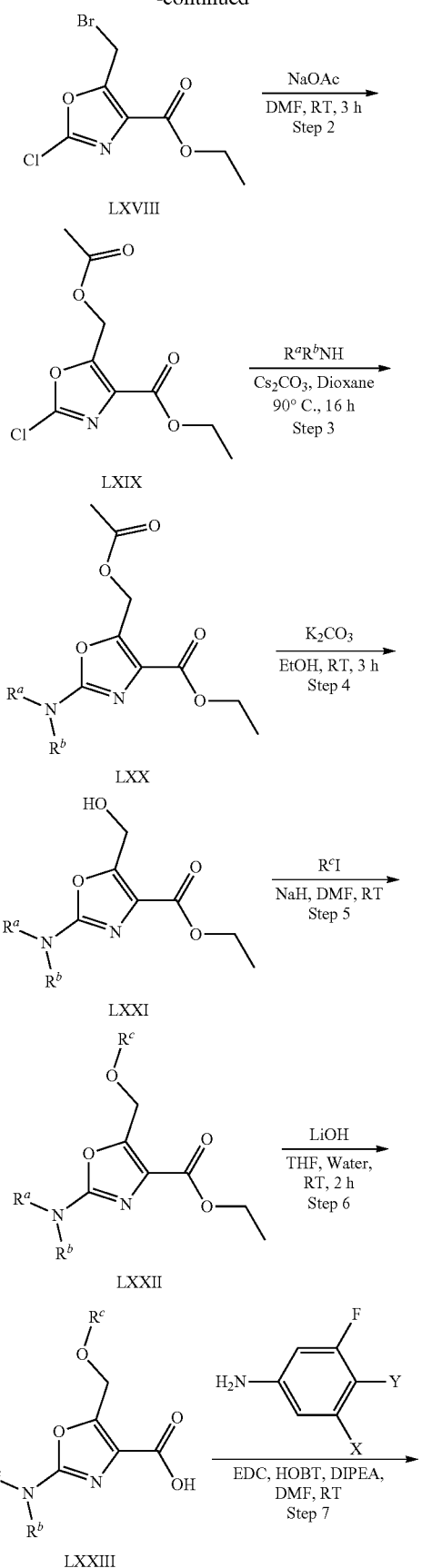

-continued

LXXIV

R$^c$ = Me, Et
X = H, F
Y =

Step 1: To the mixture of ethyl 2-chloro-5-methyloxazole-4-carboxylate (LXI) (4.4 g, 23.21 mmol) in benzene was added NBS (6.16 g, 34.82 mmol) and DBPO (1.12 g, 4.64 mmol) and then it was heated at 70° C. for 9 h. After completion of the reaction [Monitored by TLC], the reaction mixture was filtered and the filtrate was concentrated to get the crude product. The crude material was purified through silica flash column chromatography using 5% ethyl acetate in hexane as an eluent to afford ethyl 5-(bromomethyl)-2-chlorooxazole-4-carboxylate (LXVIII) (4.6 g, 73%) as a light yellow liquid.

Step 2: To the solution of ethyl 5-(bromomethyl)-2-chlorooxazole-4-carboxylate (5.5 g, 20.52 mmol) in DMF (50 mL) was added Sodium acetate (3.36 g, 41.04 mmol) at rt and then it was stirred for 3 h at rt. After completion of reaction [Monitored by TLC], the reaction mixture was filtered and filtrate was diluted with ethyl acetate and washed with water, concentrated to get the crude substance which was purified through silica gel flash column chromatography using 10% EtOAc/Hexane as an eluent to afford ethyl 5-(acetoxymethyl)-2-chlorooxazole-4-carboxylate (LXIX) (3.3 g, 64.94%) as a light yellow liquid.

Step 3: To the suspension of ethyl 5-(acetoxymethyl)-2-chlorooxazole-4-carboxylate (1.2 g, 4.85 mmol) and Cs$_2$CO$_3$ (3.16 g, 9.71 mmol) in dioxane (15 mL) was added an amine (7.29 mmol) the resulting mixture was heated at 90° C. for 16 h. After completion of reaction [Monitored by TLC], the reaction mixture was filtered and the filtrate was concentrated and purified through silica gel column chromatography using 30% EtOAc in Hexane as an eluent to afford intermediate LXX (0.51 g, 37.19%) as a liquid.

Step 4: To a suspension of LXX in EtOH (15 mL) was added K$_2$CO$_3$ (1.34 g, 9.71 mmol) and then it was stirred at for 2 h at RT. After completion of the reaction [Monitored by TLC], the reaction mixture was filtered and the filtrate was concentrated and purified through silica gel column chromatography using 80% EtOAc in Hexane as an eluent to afford intermediate LXXI (0.71 g, 60.83%) as an off-white solid.

Step 5: To a stirred solution of LXXI (1.0 eq) in DMF (5 mL/mmol) was added NaH (2.0 eq) portion-wise under ice cold conditions. After 15 minutes, R$^c$I (3.0 eq) was added to it and the reaction mixture was stirred for 2 hours at room temperature. After completion [Monitored with TLC], the reaction mixture was quenched with saturated ammonium chloride solution and partitioned with EtOAc. The organic layer was separated, dried over anhydrous sodium sulfate, and concentrated under reduced pressure to get the crude product. The resultant crude material was purified by silica gel flash column chromatography using EtOAc-Hexane as eluting solvent to afford LXXII as an off-white solid.

Step 6: To the solution of LXXII (1 eq) in THF (5 mL) was added the solution of LiOH·H$_2$O (3 eq) in water (1 mL) at 0° C. and then it was stirred for 3 h at RT. After completion [Monitored with LC-MS], the reaction mixture was acidified with aqueous HCl (1 N) and partitioned between EtOAc and water. The organic layer was separated, dried over sodium sulfate, and concentrated under reduced pressure to afford acid products of structure LXXIII.

Step 7: To a stirred solution of LXXIII (0.18 mmol) and the appropriate fluoro aniline (1 eq) in DMF (3 mL) was added DIPEA (0.057 mL, 0.56 mmol), EDC (54 mg, 0.28 mmol) and HOBT (38 mg, 0.28 mmol) and the resultant reaction mixture was allowed to stir at room temperature for 16 h. After completion (monitored with LC-MS), the reaction mixture was partitioned between EtOAc (50 mL) and water (100 mL). The organic layer was separated, dried over sodium sulfate, and concentrated under reduced pressure. The resultant crude product was purified using silica gel flash column chromatography using 10% EtOAc-hexane as eluent to afford pure final products of general formula LXXIV.

All the amines used as starting materials were purchased from commercial providers.

Example 99

The above compound was synthesized by the general procedure outlined in the scheme above utilizing pyrrolidine as the amine in step 3, iodomethane in step 5, and 3-fluoro-4-(piperidin-1-yl)aniline in step 7 affording N-[3-fluoro-4-(piperidin-1-yl)phenyl]-5-(methoxymethyl)-2-(pyrrolidin-1-yl) oxazole-4-carboxamide (15 mg, 15%).

Example 100

The above compound was synthesized by the general procedure outlined in the scheme above utilizing pyrrolidine as the amine in step 3, iodoethane in step 5, and 3-fluoro-4-(piperidin-1-yl)aniline in step 7 affording 5-(ethoxymethyl)-N-[3-fluoro-4-(piperidin-1-yl)phenyl]-2-(pyrrolidin-1-yl)oxazole-4-carboxamide (19 mg, 24.3%).

Example 101

The above compound was synthesized by the general procedure outlined in the scheme above utilizing pyrrolidine as the amine in step 3, iodomethane in step 5, and 4-(cyclopentyloxy)-3-fluoroaniline in step 7 affording N-[4-(cyclopentyloxy)-3-fluorophenyl]-5-(methoxymethyl)-2-(pyrrolidin-1-yl)oxazole-4-carboxamide (19 mg, 24.3%).

Example 102

The above compound was synthesized by the general procedure outlined in the scheme above utilizing pyrrolidine as the amine in step 3, iodomethane in step 5, and 3,5-difluoro-4-(piperidin-1-yl)aniline in step 7 affording N-[3,5-difluoro-4-(piperidin-1-yl)phenyl]-5-(methoxymethyl)-2-(pyrrolidin-1-yl) oxazole-4-carboxamide (32 mg, 19%).

Example 103

The above compound was synthesized by the general procedure outlined in the scheme above utilizing 2-methylpyrrolidine as the amine in step 3, iodomethane in step 5, and 3-fluoro-4-(piperidin-1-yl)aniline in step 7 affording N-(3-fluoro-4-(piperidin-1-yl)phenyl)-5-(methoxymethyl)-2-(2-methylpyrrolidin-1-yl)oxazole-4-carboxamide (80 mg, 23%).

Example 104

The above compound was synthesized by the general procedure outlined in the scheme above utilizing 2-6,6-difluoro-2-azaspiro[3.3]heptane as the amine in step 3, iodomethane in step 5, and 3-fluoro-4-(piperidin-1-yl)aniline in step 7 affording 2-{6,6-difluoro-2-azaspiro[3.3]heptan-2-yl}-N-[3-fluoro-4-(piperidin-1-yl)phenyl]-5-(methoxymethyl)oxazole-4-carboxamide (10 mg, 7%).

Example 105

The above compound was synthesized by the general procedure outlined in the scheme above utilizing pyrrolidine as the amine in step 3, iodomethane in step 5, and 4-((2,2-difluorocyclopentyl)oxy)-3-fluoroaniline in step 7 affording N-(4-((2,2-difluorocyclopentyl)oxy)-3-fluorophenyl)-5-(methoxymethyl)-2-(pyrrolidin-1-yl)oxazole-4-carboxamide (12 mg, 9.9%).

Example 106

Step 1. To a stirred solution of t-butyl-3-formylpyrrolidine-1-carboxylate (100 mg, 0.503 mmol) and azetidine (34 mg, 0.603 mmol) in methanol was added 1 drop of acetic acid. The reaction was stirred at room temperature for 3 h. Then sodium cyanoborohydride (62 mg, 1.0 mmol) was added to the reaction mixture at 0° C. and allowed to stir for overnight. After completion of reaction [Monitored GCMS], the reaction mass was concentrated to remove methanol. The crude material was diluted with DCM and washed with saturated aqueous solution of sodium bicarbonate. The organic layer was dried over anhydrous sodium sulfate and concentrated and purified by silica gel chromatography to afford t-butyl 3-(azetidin-1-ylmethyl)pyrrolidine-1-carboxylate LXXVI (90 mg, 74.5%) as a sticky liquid.

Step 2: To a stirred solution oft-butyl 3-(azetidin-1-ylmethyl)pyrrolidine-1-carboxylate (90 mg, 0.38 mmol) in 1,4-dioxane (1 mL) was added HCl in 1,4 dioxane (4 M, 1.0 mL, 4.0 mmol) at 0° C. and then stirred for 3 h at room temperature. The reaction mixture then concentrated to afford crude 3-(azetidin-1-ylmethyl)pyrrolidine hydrochloride (LXXVII) (60 mg) as a gummy liquid which was used as is in Step 3.

Step 3: To a stirred solution of LXXVII (60 mg, 0.34 mmol) in dioxane was added cesium carbonate (328 mg, 1.023 mmol) followed by intermediate LXV (80 mg, 0.239 mol) and the mixture was heated at 90° C. for 6 h. After completion of reaction [Monitored by LC-MS], the reaction mass was then filtered & the filtrate was evaporated to afford the crude product. The crude material was purified by silica gel chromatography using 5% MeOH in DCM to afford 2-(3-(azetidin-1-ylmethyl)pyrrolidin-1-yl)-N-(3-fluoro-4-(piperidin-1-yl)phenyl)-5-methyloxazole-4-carboxamide (Example 106) (30 mg, 20%).

Example 107

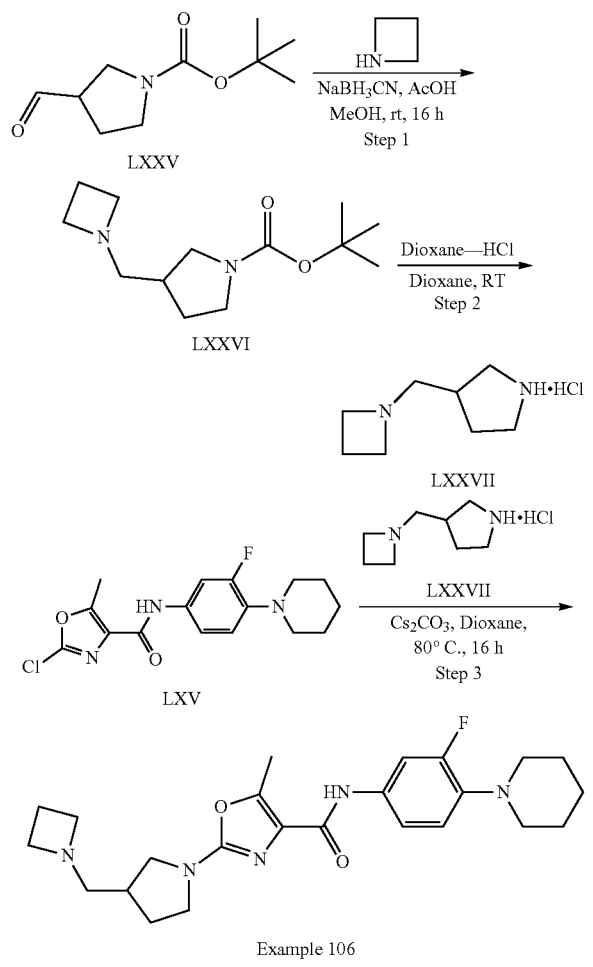

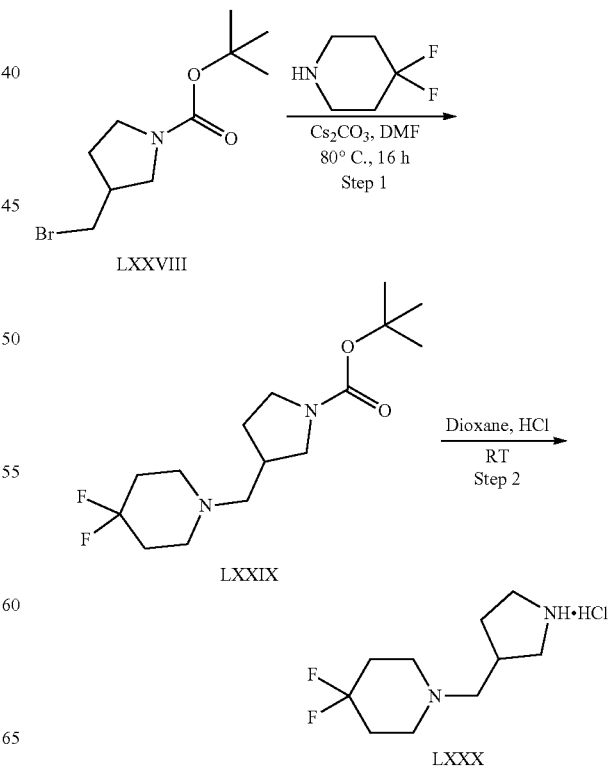

-continued

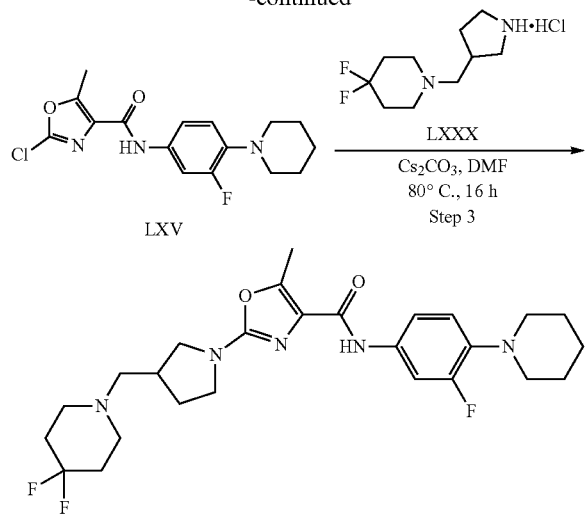

Example 107

Step 1. To a stirred solution of tert-butyl 3-(bromomethyl) pyrrolidine-1-carboxylate (100 mg, 0.38 mmol) and 4,4-difluoropiperidine (46 mg, 0.38 mmol) in DMF (3 mL) was added cesium carbonate (365 mg, 1.141 mmol). Then the reaction was heated at 80° C. After completion of reaction [Monitored by TLC], the reaction mass was filtered. The filtrate was diluted with ethyl acetate (10 mL) and washed with water (2×20 mL). The organics were concentrated to provide crude product which was purified through silica gel column chromatography using 55% EtOAc-Hexane as an eluent to afford tert-butyl 3-((4,4-difluoropiperidin-1-yl) methyl)pyrrolidine-1-carboxylate (LXXIX) (110 mg, 95%).

Step 2: To a stirred solution of tert-butyl-3-((4,4-difluoropiperidin-1-yl)methyl)pyrrolidine-1-carboxylate (100 mg, 0.33 mmol) in 1,4-dioxane (2 mL) was added HCl in 1,4-dioxane (4 M, 1.0 mL, 4.0 mmol) at 0° C. and then stirred for 3 h at room temperature. The reaction mixture then concentrated to afford 4,4-difluoro-1-(pyrrolidin-3-yl-methyl)piperidine hydrochloride LXXX (68 mg) as a gummy liquid, and was used crude in the following step.

Step 3: To a stirred solution of 4,4-difluoro-1-(pyrrolidin-3-ylmethyl)piperidine hydrochloride LXXX (68 mg, 0.29 mmol) and cesium carbonate (235 mg, 0.712 mmol) in dioxane (5 mL) was added 2-amino-N-(3-fluoro-4-(piperidin-1-yl)phenyl)-5-methyloxazole-4-carboxamide LXV (80 mg, 0.24 mmol) and the reaction mixture was heated at 90° C. for 6 h. After completion of the reaction [Monitored by LC-MS], the reaction mass was then filtered and the filtrate was evaporated to get the crude product. The crude was purified by silica gel chromatography utilizing 70% ethyl acetate in hexane as an eluent to afford 2-(3-((4,4-difluoropiperidin-1-yl)methyl)pyrrolidin-1-yl)-N-(3-fluoro-4-(piperidin-1-yl)phenyl)-5-methyloxazole-4-carboxamide (Example 107) (30 mg, 20%).

Example 108 & 109

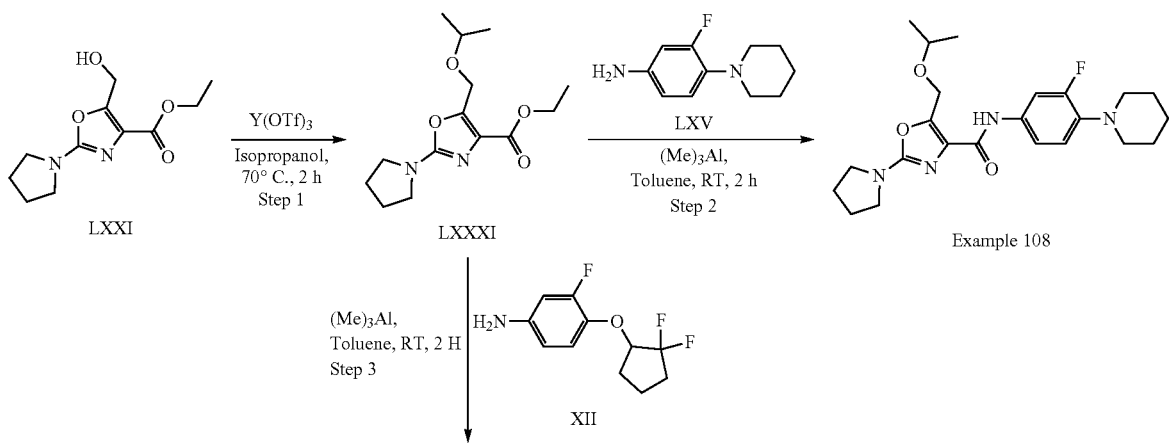

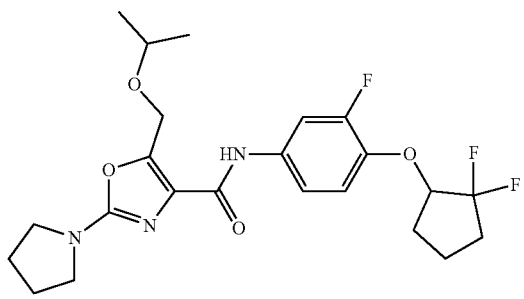

Example 109

Step 1: To the solution of ethyl 5-(hydroxymethyl)-2-(pyrrolidin-1-yl)oxazole-4-carboxylate (200 mg, 0.83 mmol) in isopropanol (2 mL) was added Yttrium triflate (45 mg, 0.083 mmol) at rt and the mixture was allowed to stir at 70° C. for 2 h. After completion [Monitored with TLC], the reaction mixture was quenched with saturated solution of NaHCO₃ and extracted with ethyl acetate. The combined organic layer was dried over anhydrous Na₂SO₄ and concentrated to afford the crude product. The crude was purified through silica gel flash column chromatography using ethyl acetate to afford ethyl 5-(isopropoxymethyl)-2-(pyrrolidin-1-yl)oxazole-4-carboxylate LXXXI (22 mg, 9.3%) as solid.

Step 2: To a stirred solution of ethyl 5-(isopropoxymethyl)-2-(pyrrolidin-1-yl)oxazole-4-carboxylate LXXXI (60 mg, 0.19 mmol) and 3-fluoro-4-(piperidin-1-yl)aniline LXV (38 mg, 0.17 mmol) in dry toluene (3 mL) was added trimethyl aluminum (0.4 mL, 0.80 mmol) at 0° C. and the resultant reaction mixture was allowed to stir at room temperature for 2 h. After completion [Monitored with TLC], the reaction mixture was quenched with saturated ammonium chloride solution (10 mL) and partitioned with EtOAc [10 mL×2]. The organic layer was dried over anhydrous sodium sulfate and concentrated under reduced pressure. The resultant crude material was purified by silica gel column chromatography using 20-30% EtOAc-Hexane as eluting solvent to afford N-(3-fluoro-4-(piperidin-1-yl)phenyl)-5-(isopropoxymethyl)-2-(pyrrolidin-1-yl)oxazole-4-carboxamide (Example 108) (15 mg, 17%) as an off-white solid.

Step 3: To a stirred solution of ethyl 5-(isopropoxymethyl)-2-(pyrrolidin-1-yl)oxazole-4-carboxylate LXXXI (50 mg, 0.177 mmol) and 4-((2,2-difluorocyclopentyl)oxy)-3-fluoroaniline XII (31 mg, 0.16 mmol) in dry toluene (3 mL) was added trimethyl aluminum (0.35 mL, 0.70 mmol) at 0° C. and the resultant reaction mixture was allowed to stir at room temperature for 2 h. After completion [Monitored with TLC], the reaction mixture was quenched with saturated ammonium chloride solution (10 mL) and partitioned with EtOAc [10 mL×2]. The organic layer was dried over anhydrous sodium sulfate and concentrated under reduced pressure. The resultant crude material was purified by silica gel column chromatography using 20-30% EtOAc-Hexane as eluting solvent to afford N-(3-fluoro-4-(piperidin-1-yl)phenyl)-5-(isopropoxymethyl)-2-(pyrrolidin-1-yl)oxazole-4-carboxamide (Example 109) (20 mg, 26.2%).

General Scheme for the Synthesis of Example 110 and 111

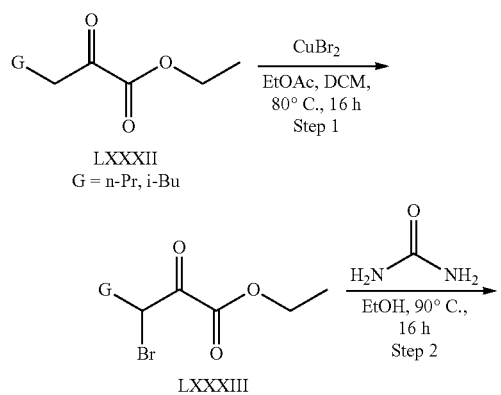

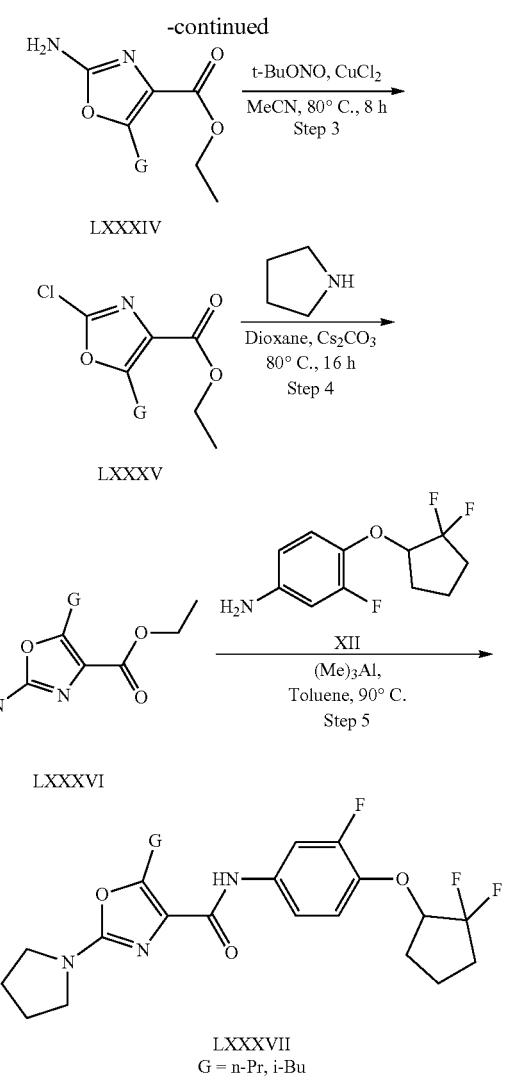

Step 1. To the stirred solution of LXXXII (1 eq) in ethyl acetate and DCM (6:4 ratio) was added CuBr₂ (3.5 eq) at room temperature. The mixture was then heated at 90° C. for 16 h. After completion of the reaction [Monitored with TLC], the reaction mixture was filtered through celite and the filtrate was concentrated to afford crude LXXXIII as a brown gummy liquid (as crude). It was used for the next step directly without any further purification.

Step 2: To the solution of LXXXIII (1 eq) in ethanol (200 mL) was added urea (4 eq) at room temperature and the mixture was then refluxed for 24 h. After completion of reaction [Monitored with TLC], the reaction mixture was concentrated to remove ethanol. The crude mass was then treated with saturated aqueous solution of NaHCO₃ and extracted with ethyl acetate. The organics were dried over anhydrous sodium sulfate and concentrated to afford crude product. The crude material was purified by trituration with ether. The solids were filtered and dried to afford LXXXIV as off-white solid.

Step 3: A suspension of CuCl₂ (1.6 eq) and tert-butylnitrite (1.05 eq) in acetonitrile (80 mL) was heated to 70° C. and stirred for 15 min a suspension of LXXXIV (1 eq) in acetonitrile (120 mL) was then added dropwise to the above reaction mixture at 70° C. The reaction was stirred at 70° C. for 16 hours. After completion of the reaction [Monitored with TLC], the reaction mixture was concentrated to remove volatiles and then diluted with ethyl acetate (250 mL) and water (250 mL), and filtered through celite. The organic layer was separated out and dried over anhydrous Na₂SO₄, concentrated to provide crude product. The crude material was purified through silica gel column chromatography using 5% ethyl acetate in hexane to afford LXXXV (5.6 g, 62.77%) as a colorless liquid.

Step 4: To a stirred solution of pyrrolidine (1.2 eq.) and Cs₂CO₃ (3.0 equiv) in dioxane (30 mL/g) was added LXXXV (1.0 eq.) and resultant reaction mixture was allowed to stir at 80° C. for 16 h. After completion of reaction [monitored with TLC], the reaction mixture was filtered and the filtrate was concentrated under reduced pressure to remove volatiles. The resultant crude material was purified through silica gel column chromatography to provide LXXXVI.

Step 5: To a stirred solution of LXXXVI (1.0 eq) in dry toluene (10 mL) is added 4-((2,2-difluorocyclopentyl)oxy)-3-fluoroaniline XII (0.8 eq) followed by cooling to 0° C. and dropwise addition of trimethylaluminum (1 M in toluene, 4.0 eq) and the resultant reaction mixture was heated to 90° C. for 16 h. After completion [Monitored with TLC], the reaction mixture was quenched with saturated ammonium chloride solution and partitioned with EtOAc. The organic layer was separated, dried over anhydrous sodium sulfate, and concentrated under reduced pressure. The resultant crude product was purified by Silica gel column chromatography to afford LXXXVII.

Example 110

The above referenced compound was synthesized utilizing the general procedures outlined in the scheme above using ethyl 2-oxohexanoate as the keto-ester in step 1 to afford N-(4-((2,2-difluorocyclopentyl)oxy)-3-fluorophenyl)-5-propyl-2-(pyrrolidin-1-yl)oxazole-4-carboxamide (20 mg, 17% Example 111

The above referenced compound was synthesized utilizing the general procedures outlined in the scheme above using ethyl 5-methyl-2-oxohexanoate as the keto-ester in step 1 to afford N-(4-((2,2-difluorocyclopentyl)oxy)-3-fluorophenyl)-5-isobutyl-2-(pyrrolidin-1-yl)oxazole-4-carboxamide (25 mg, 31%).

General Scheme for the Synthesis of Examples 112 to 123.

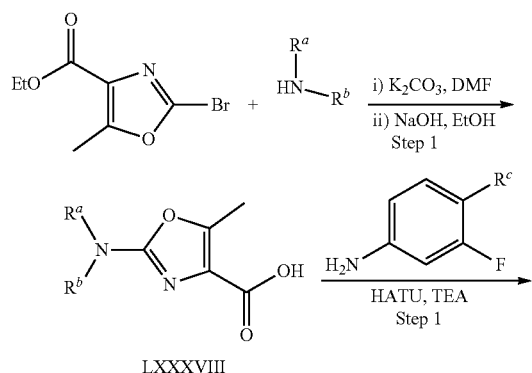

LXXXVIII

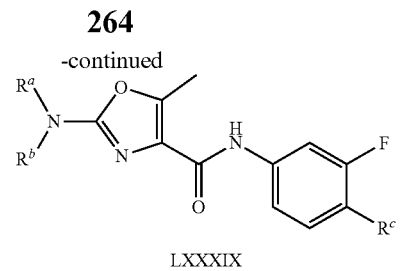

LXXXIX

Step 1. To a mixture of the commercially available ethyl 2-bromo-5-methyloxazole-4-carboxylate (1 eq.) in DMF, K₂CO₃ (1 eq.) and the commercially available amine (1.2 eq.) were added. The resulting solution was heated to 90° C. and vigorously stirred for 12 hrs. The mixture was cooled to rt and filtered-off. The filtrate was concentrated under reduced pressure and treated with a solution of NaOH 0.1 M in EtOH (2 eq.). Upon completion of the reaction, HCl (2 M aq. solution) was added, and the material was extracted in EtOAc. The organic layers were combined, dried over Na₂SO₄, filtered, and evaporated under reduced pressure, to obtain the intermediate LXXVIII, which was used for the next step without purification.

Step 2. To a solution of the carboxylic acid derivative LXXXVIII (1 eq.) in DCM, HATU (1.2 eq.) and TEA (3 eq.) were added. The solution was stirred for 10 min before adding the opportune commercially available aniline (1.2 eq.). The reaction was stirred at rt for 12 hrs. After evaporation of the solvents under reduced pressure, purification via the below described methods provided Examples of the general structure LXXXIX.

Amine derivatives from commercial suppliers.

Example 112

The title compound was prepared according to general procedure shown in the scheme above utilizing pyrrolidine as the amine in step 1 and commercially available aniline CAS: 85983-56-8 in step 2. Purification was by HPLC (linear gradient, H₂O 30% to 80% in CH₃CN) to afford N-(3-fluoro-4-(piperidin-1-yl)phenyl)-5-methyl-2-(pyrrolidin-1-yl)oxazole-4-carboxamide (32%).

Example 113

The title compound was prepared according to general procedure shown in the scheme above utilizing pyrrole as the amine in step 1 and commercially available aniline CAS: 85983-56-8 in step 2. Purification was performed by silica gel column chromatography, eluting with EtOAc 0% to 30% in n-hexaneto afford N-(3-fluoro-4-(piperidin-1-yl)phenyl)-5-methyl-2-(1H-pyrrol-1-yl)oxazole-4-carboxamide (50%).

Example 114

The title compound was prepared according to general procedure shown in the scheme above utilizing piperidine as the amine in step 1 and the commercially available aniline CAS: 85983-56-8 in step 2. Purification was performed by HPLC (linear gradient, H₂O 30% to 95% in CH₃CN) to affordN-(3-fluoro-4-(piperidin-1-yl)phenyl)-5-methyl-2-(piperidin-1-yl)oxazole-4-carboxamide (41%).

Example 115

The title compound was prepared according to general procedure shown in the scheme above utilizing isopropylmethylamine as the amine in step 1 and commercially available aniline CAS: 85983-56-8 in step 2. Purification was performed by HPLC (linear gradient linear gradient, H₂O 30% to 95%) to afford N-(3-fluoro-4-(piperidin-1-yl)phenyl)-2-(isopropyl(methyl)amino)-5-methyloxazole-4-carboxamide (37%).

Example 116

The title compound was prepared according to general procedure shown in the scheme above utilizing morpholine as the amine in step 1, and commercially available aniline CAS: 85983-56-8 in step 2. Purification was performed by silica gel column chromatography, eluting with EtOAc 0% to 30% in n-hexane to afford N-(3-fluoro-4-(piperidin-1-yl)phenyl)-5-methyl-2-morpholinooxazole-4-carboxamide (Y=42%).

Example 117

The title compound was prepared according to general procedure shown in the scheme above utilizing dimethylamine as the amine in step 1, and commercially available aniline CAS: 85983-56-8 in step 2. Purification was performed by silica gel column chromatography, eluting with EtOAc 0% to 30% in n-hexane to afford 2-(dimethylamino)-N-(3-fluoro-4-(piperidin-1-yl)phenyl)-5-methyloxazole-4-carboxamide (52%).

Example 118

The title compound was prepared according to general procedure shown in the scheme above utilizing pyrazole as the amine in step 1, and commercially available aniline CAS: 85983-56-8 in step 2. Purification was performed by silica gel column chromatography, eluting with EtOAc 0% to 30% in n-hexane to afford N-(3-fluoro-4-(piperidin-1-yl)phenyl)-5-methyl-2-(1H-pyrazol-1-yl)oxazole-4-carboxamide (48%).

Example 119

The title compound was prepared according to general procedure shown in the scheme above utilizing 2-methylpyrrolidine as the amine in step 1, and commercially available aniline CAS: 85983-56-8 in step 2. Purification was performed by HPLC (linear gradient linear gradient, H₂O 30% to 95%) to afford N-(3-fluoro-4-(piperidin-1-yl)phenyl)-5-methyl-2-(2-methylpyrrolidin-1-yl)oxazole-4-carboxamide (38%).

Example 120

The title compound was prepared according to general procedure shown in the scheme above utilizing pyrrolidine as the amine in step 1, and commercially available aniline CAS: 1039868-84-2 in step 2. Purification was performed by HPLC (linear gradient linear gradient, H₂O 30% to 80%) to afford N-(4-(cyclopentyloxy)-3-fluorophenyl)-5-methyl-2-(pyrrolidin-1-yl)oxazole-4-carboxamide (55%).

Example 121

The title compound was prepared according to general procedure shown in the scheme above utilizing 3,3-difluoropyrrolidine as the amine in step 1, and commercially available aniline CAS: 85983-56-8 in step 2. Purification was performed by HPLC (linear gradient, H₂O 30% to 95%) to afford 2-(3,3-difluoropyrrolidin-1-yl)-N-(3-fluoro-4-(piperidin-1-yl)phenyl)-5-methyloxazole-4-carboxamide (67%).

Example 122

The title compound was prepared according to general procedure shown in the scheme above utilizing 3-methylpyrrolidine as the amine in step 1, and commercially available aniline CAS: 85983-56-8 in step 2. Purification was performed by HPLC (linear gradient, H₂O 30% to 95%) to afford N-(3-fluoro-4-(piperidin-1-yl)phenyl)-5-methyl-2-(3-methylpyrrolidin-1-yl)oxazole-4-carboxamide (38%).

Example 123

The title compound was prepared according to general procedure shown in the scheme above utilizing (3aR,6aR)-hexahydro-2H-furo[2,3-c]pyrrole as the amine in step 1, and commercially available aniline CAS: 85983-56-8 in step 2. Purification was performed by HPLC (linear gradient, H₂O 30% to 95%) to afford N-(3-fluoro-4-(piperidin-1-yl)phenyl)-2-((3aR,6aR)-hexahydro-5H-furo[2,3-c]pyrrol-5-yl)-5-methyloxazole-4-carboxamide (36%).

General Conditions for Preparation of Example of the General Formula Specified by Structure XCV (Examples 124-190):

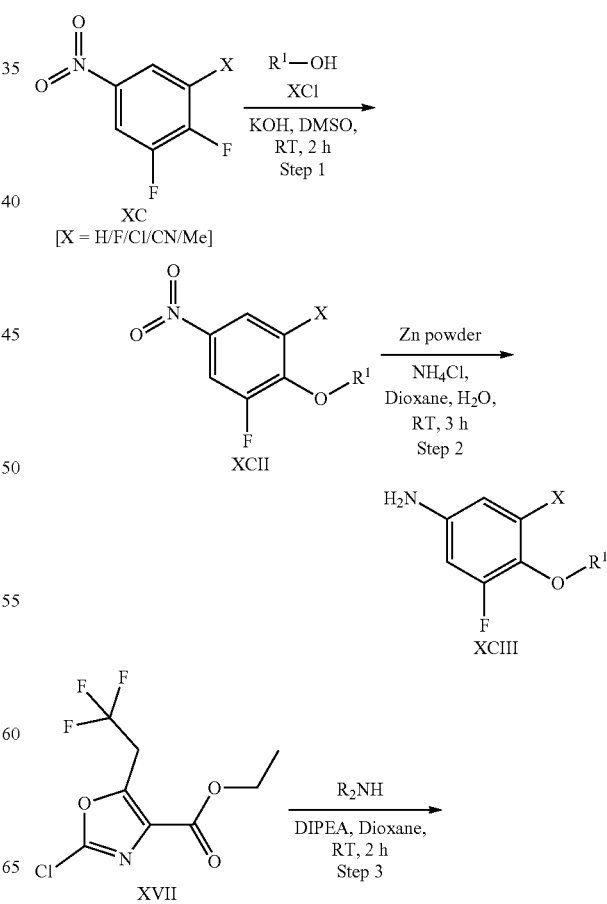

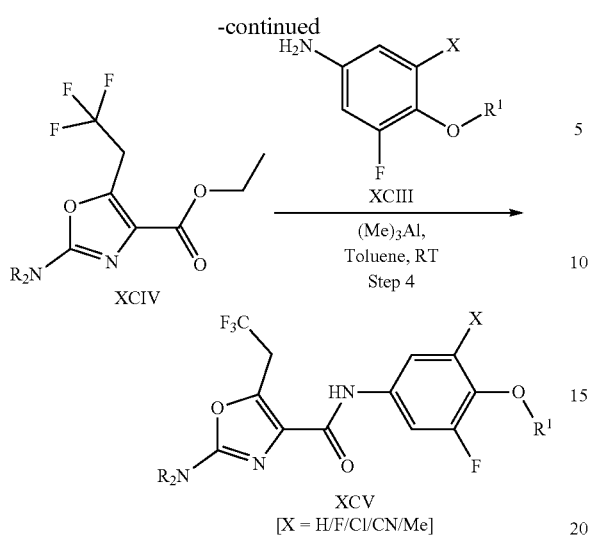

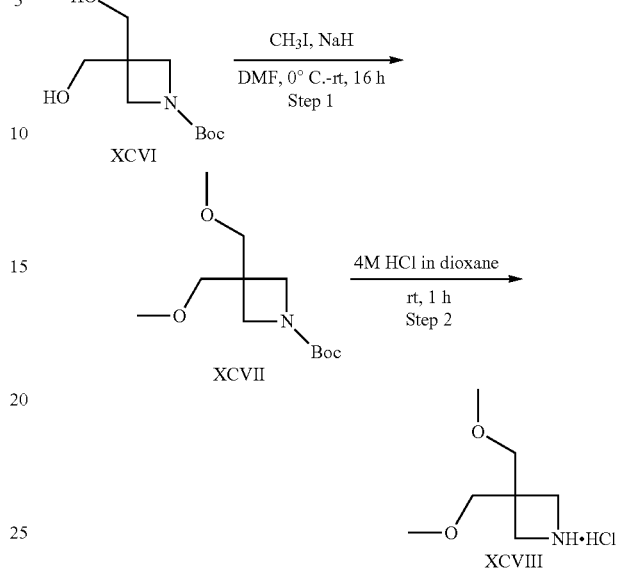

Synthesis of amine (R₂NH)

Step 1. To a stirred solution of XC (1.0 eq) and XCI (1.2 eq) in DMSO (3 mL/mmol), was added KOH (3.0 eq). The reaction was stirred for 2 h at RT. After completion [Monitored by TLC], the resultant reaction mixture was partitioned between EtOAc and water. The organic layer was dried over anhydrous sodium sulfate and concentrated under reduced pressure. The crude was purified through flash column chromatography using EtOAc in hexane as an eluent to afford desired product XCII.

Step 2: To a stirred solution of XCII (1.0 eq) in (3 mL/mmol), of 1,4 dioxane: water (5:1) was added zinc dust (5.0 eq) along with ammonium chloride (6.0 eq) at 0° C. It was then stirred for 3 h at rt. After completion [Monitored by TLC], the reaction mixture was filtered through a glass sintered filter. The filtrate was dried over anhydrous sodium sulfate and concentrated under reduced pressure. The resultant crude was purified by flash column chromatography to afford the pure XCIII.

Step 3: To a stirred solution of intermediate, XVII (1.0 eq.) and DIPEA (3.0 eq) in dioxane (3 mL/mmol) was added amine of general formula R₂NH (1.1 eq.) and the resultant reaction mixture was allowed to stir at room temperature for 2 h. After completion [Monitored by TLC], the reaction mixture was concentrated under reduced pressure to remove dioxane. The resultant crude was purified through flash column chromatography to provide intermediates of general formula XCIV.

Step 4: To a stirred solution of XCIV (1.0 eq) in dry toluene (30 mL/g), compound XCIII (0.8 eq) from step 2 was added, followed by dropwise addition of trimethylaluminum (2 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography to afford examples with the general formula XCV.

All amines used as starting materials were purchased from commercial suppliers.

Step 1: To a stirred solution of tert-butyl 3,3-bis(hydroxymethyl)azetidine-1-carboxylate XCVI (300 mg, 1.38 mmol) in DMF (5 mL) at 0° C., NaH (221.19 mg, 5.52 mmol, 60% in oil) was added. After 20 min. of stirring, CH₃I (783 mg, 5.53 mmol) was added into the reaction mixture and was stirred at room temperature for 16 h. After completion [Monitored by TLC], the resultant reaction mixture was quenched with sat. NH₄Cl solution and was partitioned between EtOAc and water. The organic layer was dried over anhydrous sodium sulfate and concentrated under reduced pressure. The crude was purified through flash column chromatography using EtOAc in hexane as an eluent to afford desired product tert-butyl 3,3-bis(methoxymethyl)azetidine-1-carboxylate, XCVII (245 mg, 72%) as colorless oil.

Step 2: Tert-butyl 3,3-bis(methoxymethyl)azetidine-1-carboxylate XCVII (490 mg, 1.99 mmol) was dissolved in 4 N HCl dioxane solution (5 mL) and was stirred at room temperature for 1 h. The reaction mixture was concentrated in vacuum, triturated with diethyl ether, and dried to afford the desired compound 3,3-bis(methoxymethyl)azetidine hydrochloride, XCVIII (300 mg, 83%) as a colorless gummy liquid.

All the alcohols used as starting materials were purchased from commercial suppliers

Synthesis of spiro[3.5]nonan-6-ol

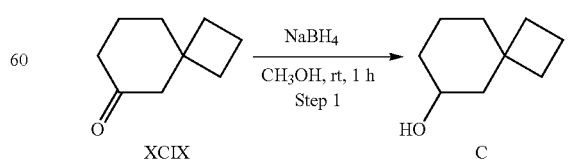

To a stirred solution of spiro[3.5]nonan-6-one, XCIX (100 mg, 0.72 mmol) in CH₃OH (5 mL), NaBH₄ (82.4 mg, 2.17 mmol) was added under ice cold condition and the reaction mixture was stirred at room temperature for 1 h. After completion, the reaction was quenched with acetone and concentrated under vacuum to afford the crude. Then, the crude was partitioned between EtOAc and water. The organic layer was separated and dried over anhydrous sodium sulfate and concentrated under reduced pressure to afford desired alcohol spiro[3.5]nonan-6-ol, C (90 mg, 89%) as pale yellow solid.

Example 124

The above referenced compound was synthesized utilizing the procedures outlined in the scheme above using 1,2-difluoro-3-methyl-5-nitrobenzene as compound XC and cis-bicyclo[3.1.0]hexan-3-ol as the alcohol in step 1 and 3-(methoxymethyl)-3-methylazetidine as the amine in step 3, to provide N-(4-(cis-bicyclo[3.1.0]hexan-3-yloxy)-3-fluoro-5-methylphenyl)-2-(3-(methoxymethyl)-3-methylazetidin-1-yl)-5-(2,2,2-trifluoroethyl)oxazole-4-carboxamide (35 mg, 23%).

Example 125

The above referenced compound was synthesized utilizing the procedures outlined in the scheme above using 1,2-difluoro-3-methyl-5-nitrobenzene as compound XC and cis-bicyclo[3.1.0]hexan-3-ol as the alcohol in step 1 and 3-(methoxymethyl)-3-ethylazetidine as the amine in step 3, to provide N-(4-(cis-bicyclo[3.1.0]hexan-3-yloxy)-3-fluoro-5-methylphenyl)-2-(3-(methoxymethyl)-3-ethylazetidin-1-yl)-5-(2,2,2-trifluoroethyl)oxazole-4-carboxamide (40 mg, 26%).

Example 126

The above referenced compound was synthesized utilizing the procedures outlined in the scheme above using 1-chloro-2,3-difluoro-5-nitrobenzene as compound XC and cis-bicyclo[3.1.0]hexan-3-ol as the alcohol in step 1 and (3-ethylazetidin-3-yl)methanol hydrochloride as the amine in step 3, to provide N-(4-(cis-bicyclo[3.1.0]hexan-3-yloxy)-3-chloro-5-fluorophenyl)-2-(3-ethyl-3-(hydroxymethyl)azetidin-1-yl)-5-(2,2,2-trifluoroethyl)oxazole-4-carboxamide (55 mg, 43%).

Example 127

The above referenced compound was synthesized utilizing the procedures outlined in the scheme above using 1-chloro-2,3-difluoro-5-nitrobenzene as compound XC and cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3-chloro-5-fluorophenyl)-2-(3,3-diethylazetidin-1-yl)-5-(2,2,2-trifluoroethyl)oxazole-4-carboxamide (50 mg, 31%).

Example 128

The above referenced compound was synthesized utilizing the procedures outlined in the scheme above using 1,2-difluoro-3-methyl-5-nitrobenzene as compound XC and cis-bicyclo[3.1.0]hexan-3-ol as the alcohol in step 1 and (3-methylazetidin-3-yl)methanol as the amine in step 3, to provide N-(4-(cis-bicyclo[3.1.0]hexan-3-yloxy)-3-fluoro-5-methylphenyl)-2-(3-(methoxymethyl)-3-methylazetidin-1-yl)-5-(2,2,2-trifluoroethyl)oxazole-4-carboxamide (40 mg, 39%).

Example 129

The above referenced compound was synthesized utilizing the procedures outlined in the scheme above using 1,2-difluoro-3-methyl-5-nitrobenzene as compound XC and bicyclo[3.1.1]heptan-3-ol as the alcohol in step 1 and (3-methylazetidin-3-yl)methanol as the amine in step 3, to provide N-(4-(bicyclo[3.1.1]heptan-3-yloxy)-3-fluoro-5-methylphenyl)-2-(3-(hydroxymethyl)-3-methylazetidin-1-yl)-5-(2,2,2-trifluoroethyl)oxazole-4-carboxamide (20 mg, 12%).

Example 130

The above referenced compound was synthesized utilizing the procedures outlined in the scheme above using 1-chloro-2,3-difluoro-5-nitrobenzene as compound XC and cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-chloro-5-fluorophenyl)-2-(3-methoxy-3-methylazetidin-1-yl)-5-(2,2,2-trifluoroethyl)oxazole-4-carboxamide (45 mg, 28%).

Example 131

The above referenced compound was synthesized utilizing the procedures outlined in the scheme above using 1,2-difluoro-3-methyl-5-nitrobenzene as compound XC and cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3-fluoro-5-methylphenyl)-2-(3,3-diethylazetidin-1-yl)-5-(2,2,2-trifluoroethyl)oxazole-4-carboxamide (13 mg, 9%).

Example 132

The above referenced compound was synthesized utilizing the procedures outlined in the scheme above using 1,2,3-trifluoro-5-nitrobenzene as compound XC and spiro[2.5]octan-5-ol as the alcohol in step 1 and 3,3-diethylazetidine hydrochloride as the amine in step 3, to provide 2-(3,3-diethylazetidin-1-yl)-N-(3,5-difluoro-4-(spiro[2.5]octan-5-yloxy)phenyl)-5-(2,2,2-trifluoroethyl)oxazole-4-carboxamide (70 mg, 46%).

Example 133

The above referenced compound was synthesized utilizing the procedures outlined in the scheme above using 1,2-difluoro-4-nitrobenzene as compound XC and 3-oxabicyclo[3.2.1]octan-8-ol as the alcohol in step 1 and 3-methoxy-3-methylazetidine hydrochloride as the amine in step 3, to provide N-(4-((8-oxabicyclo[3.2.1]octan-3-yl)oxy)-3-fluorophenyl)-2-(3-methoxy-3-methylazetidin-1-yl)-5-(2,2,2-trifluoroethyl)oxazole-4-carboxamide (60 mg, 21%).

Example 134

The above referenced compound was synthesized utilizing the procedures outlined in the scheme above using 1,2,3-trifluoro-5-nitrobenzene as compound XC and spiro

[3.5]nonan-6-ol, as the alcohol in step 1 and 3,3-diethylazetidine hydrochloride as the amine in step 3, to provide 2-(3,3-diethylazetidin-1-yl)-N-(3,5-difluoro-4-(spiro[3.5]nonan-6-yloxy)phenyl)-5-(2,2,2-trifluoroethyl)oxazole-4-carboxamide (60 mg, 41%).

Example 135

The above referenced compound was synthesized utilizing the procedures outlined in the scheme above using 1,2-difluoro-4-nitrobenzene as compound XC and bicyclo[3.1.1]heptan-3-ol as the alcohol in step 1 and (3-methylazetidin-3-yl)methanol as the amine in step 3, to provide N-(4-(bicyclo[3.1.1]heptan-3-yloxy)-3-fluorophenyl)-2-(3-(hydroxymethyl)-3-methylazetidin-1-yl)-5-(2,2,2-trifluoroethyl)oxazole-4-carboxamide (55 mg, 32.36%).

Example 136

The above referenced compound was synthesized utilizing the procedures outlined in the scheme above using 1,2,3-trifluoro-5-nitrobenzene as compound XC and bicyclo[1.1.1]pentan-1-ylmethanol as the alcohol in step 1 and pyrrolidine as the amine in step 3, to provide N-(4-(bicyclo[1.1.1]pentan-1-ylmethoxy)-3,5-difluorophenyl)-2-(pyrrolidin-1-yl)-5-(2,2,2-trifluoroethyl)oxazole-4-carboxamide (30 mg, 18.6%).

Example 137

The above referenced compound was synthesized utilizing the procedures outlined in the scheme above using 1,2,3-trifluoro-5-nitrobenzene as compound XC and tetrahydro-2H-pyran-3-ol as the alcohol in step 1 and 3,3-diethylazetidine hydrochloride as the amine in step 3, to provide 2-(3,3-diethylazetidin-1-yl)-N-(3,5-difluoro-4-((tetrahydro-2H-pyran-3-yl)oxy)phenyl)-5-(2,2,2-trifluoroethyl)oxazole-4-carboxamide (50 mg, 37.97%).

Example 138

The above referenced compound was synthesized utilizing the procedures outlined in the scheme above using 1,2,3-trifluoro-5-nitrobenzene as compound XC and spiro[2.4]heptan-5-ol as the alcohol in step 1 and pyrrolidine as the amine in step 3, to provide N-(3,5-difluoro-4-(spiro[2.4]heptan-5-yloxy)phenyl)-2-(pyrrolidin-1-yl)-5-(2,2,2-trifluoroethyl)oxazole-4-carboxamide (14 mg, 7.02%).

Example 139

The above referenced compound was synthesized utilizing the procedures outlined in the scheme above using 1,2,3-trifluoro-5-nitrobenzene as compound XC and spiro[3.3]heptan-2-ol as the alcohol in step 1 and pyrrolidine as the amine in step 3, to provide N-(3,5-difluoro-4-(spiro[3.3]heptan-2-yloxy)phenyl)-2-(pyrrolidin-1-yl)-5-(2,2,2-trifluoroethyl)oxazole-4-carboxamide (21 mg, 13.48%).

Example 140

The above referenced compound was synthesized utilizing the procedures outlined in the scheme above using 1,2-difluoro-4-nitrobenzene as compound XC and bicyclo[3.1.0]hexan-2-ol as the alcohol in step 1 and 3,3-dimethylazetidine hydrochloride as the amine in step 3, to provide N-(4-(bicyclo[3.1.0]hexan-2-yloxy)-3-fluorophenyl)-2-(3,3-dimethylazetidin-1-yl)-5-(2,2,2-trifluoroethyl)oxazole-4-carboxamide (50 mg, 29.77%).

Example 141

The above referenced compound was synthesized utilizing the procedures outlined in the scheme above using 1,2,3-trifluoro-5-nitrobenzene as compound XC and bicyclo[2.2.1]heptan-2-ol as the alcohol in step 1 and pyrrolidine as the amine in step 3, to provide N-(4-(bicyclo[2.2.1]heptan-2-yloxy)-3,5-difluorophenyl)-2-(pyrrolidin-1-yl)-5-(2,2,2-trifluoroethyl)oxazole-4-carboxamide (17 mg, 10.23%).

Example 142

The above referenced compound was synthesized utilizing the procedures outlined in the scheme above using 2,3-difluoro-5-nitrobenzonitrile as compound XC and cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-cyano-5-fluorophenyl)-2-(3-methoxy-3-methylazetidin-1-yl)-5-(2,2,2-trifluoroethyl)oxazole-4-carboxamide (27 mg, 48%).

Example 143

The above referenced compound was synthesized utilizing the procedures outlined in the scheme above using 1,2-difluoro-4-nitrobenzene as compound XC and bicyclo[3.1.1]heptan-3-ol as the alcohol in step 1 and pyrrolidine as the amine in step 3, to provide N-(4-(bicyclo[3.1.1]heptan-3-yloxy)-3-fluorophenyl)-2-(pyrrolidin-1-yl)-5-(2,2,2-trifluoroethyl)oxazole-4-carboxamide (20 mg, 12%).

Example 144

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and hexahydro-1H-furo[3,4-b]pyrrole as the amine in step 3, to provide N-(4-(cis-bicyclo[3.1.0]hexan-3-yloxy)-3,5-difluorophenyl)-2-(hexahydro-1H-furo[3,4-b]pyrrol-1-yl)-5-(2,2,2-trifluoroethyl)oxazole-4-carboxamide (40 mg, 29%).

Example 145

The above referenced compound was synthesized utilizing the procedures outlined in the scheme above using 1,2,3-trifluoro-5-nitrobenzene as compound XC and bicyclo[3.1.1]heptan-3-ol as the alcohol in step 1 and 3,3-diethylazetidine hydrochloride as the amine in step 3, to provide N-(4-(bicyclo[3.1.1]heptan-3-yloxy)-3,5-difluorophenyl)-2-(3,3-diethylazetidin-1-yl)-5-(2,2,2-trifluoroethyl)oxazole-4-carboxamide (28 mg, 17.7%).

Example 146

The above referenced compound was synthesized utilizing the procedures outlined in the scheme above using 2-fluoro-5-nitrobenzonitrile as compound XC and cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-cyano-

273 phenyl)-2-(3-methoxy-3-methylazetidin-1-yl)-5-(2,2,2-trifluoroethyl)oxazole-4-carboxamide (20 mg, 6%).

Example 147

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and N-(2-methoxyethyl)-2-methylpropan-1-amine as the amine in step 3, to provide N-(4-(cis-bicyclo[3.1.0]hexan-3-yloxy)-3,5-difluorophenyl)-2-(isobutyl(2-methoxyethyl)amino)-5-(2,2,2-trifluoroethyl)oxazole-4-carboxamide (25 mg, 16%).

Example 148

The above referenced compound was synthesized utilizing the procedures outlined in the scheme above using 1,2,3-trifluoro-5-nitrobenzene as compound XC and bicyclo[3.1.1]heptan-3-ol as the alcohol in step 1 and 3-ethyl-3-methoxyazetidine as the amine in step 3, to provide N-(4-(bicyclo[3.1.1]heptan-3-yloxy)-3,5-difluorophenyl)-2-(3-ethyl-3-methoxyazetidin-1-yl)-5-(2,2,2-trifluoroethyl)oxazole-4-carboxamide (15 mg, 10%).

Example 149

The above referenced compound was synthesized utilizing the procedures outlined in the scheme above using 1,2-difluoro-4-nitrobenzene as compound XC and bicyclo[3.1.1]heptan-3-ol as the alcohol in step 1 and 3-ethyl-3-methoxyazetidine as the amine in step 3, to provide N-(4-(bicyclo[3.1.1]heptan-3-yloxy)-3-fluorophenyl)-2-(3-ethyl-3-methoxyazetidin-1-yl)-5-(2,2,2-trifluoroethyl)oxazole-4-carboxamide (50 mg, 33%).

Example 150

The above referenced compound was synthesized utilizing the procedures outlined in the scheme above using 1,2,3-trifluoro-5-nitrobenzene as compound XC and bicyclo[2.2.1]heptan-2-ol as the alcohol in step 1 and 3-ethyl-3-methoxyazetidine as the amine in step 3, to provide N-(4-(bicyclo[2.2.1]heptan-2-yloxy)-3,5-difluorophenyl)-2-(3-ethyl-3-methoxyazetidin-1-yl)-5-(2,2,2-trifluoroethyl)oxazole-4-carboxamide (30 mg, 19%).

Example 151

The above referenced compound was synthesized utilizing the procedures outlined in the scheme above using 1,2,3-trifluoro-5-nitrobenzene as compound XC and (1S,4R)-bicyclo[2.2.1]heptan-2-ol as the alcohol in step 1 and 3-ethyl-3-methoxyazetidine as the amine in step 3, to provide N-(4-(((1S,4R)-bicyclo[2.2.1]heptan-2-yl)oxy)-3,5-difluorophenyl)-2-(3-ethyl-3-methoxyazetidin-1-yl)-5-(2,2,2-trifluoroethyl)oxazole-4-carboxamide (15 mg, 10%).

Example 152

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and N-(2-methoxyethyl)propan-1-amine as the amine in step 3, to provide N-(4-(cis-bicyclo[3.1.0]hexan-3-yloxy)-3,5-difluo-

274 rophenyl)-2-((2-methoxyethyl)(propyl)amino)-5-(2,2,2-trifluoroethyl)oxazole-4-carboxamide (45 mg, 29%).

Example 153

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and tetrahydro-4H-[1,3]dioxolo[4,5-c]pyrrole as the amine in step 3, to provide N-(4-(cis-bicyclo[3.1.0]hexan-3-yloxy)-3-fluorophenyl)-2-(tetrahydro-5H-[1,3]dioxolo[4,5-c]pyrrol-5-yl)-5-(2,2,2-trifluoroethyl)oxazole-4-carboxamide (36 mg, 22%).

Example 154

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and 2-azabicyclo[3.1.0]hexane as the amine in step 3, to provide 2-(2-azabicyclo[3.1.0]hexan-2-yl)-N-(4-(cis-bicyclo[3.1.0]hexan-3-yloxy)-3-fluorophenyl)-5-(2,2,2-trifluoroethyl)oxazole-4-carboxamide (20 mg, 10%).

Example 155

The above referenced compound was synthesized utilizing the procedures outlined in the scheme above using 1,2,3-trifluoro-5-nitrobenzene as compound XC and bicyclo[3.1.0]hexan-2-ol as the alcohol in step 1 and 3,3-diethylazetidine hydrochloride as the amine in step 3, to provide N-(4-(bicyclo[3.1.0]hexan-2-yloxy)-3,5-difluorophenyl)-2-(3,3-diethylazetidin-1-yl)-5-(2,2,2-trifluoroethyl)oxazole-4-carboxamide (50 mg, 27%).

Example 156

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and 3-azabicyclo[3.1.0]hexane as the amine in step 3, to provide 2-(3-azabicyclo[3.1.0]hexan-3-yl)-N-(4-(cis-bicyclo[3.1.0]hexan-3-yloxy)-3-fluorophenyl)-5-(2,2,2-trifluoroethyl)oxazole-4-carboxamide (20 mg, 24%).

Example 157

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and N-(2-methoxyethyl)propan-1-amine as the amine in step 3, to provide hexahydro-2H-furo[3,2-b]pyrrole (35 mg, 38%).

Example 158

The above referenced compound was synthesized utilizing the procedures outlined in the scheme above using 1,2-difluoro-4-nitrobenzene as compound XC and tetrahydro-2H-pyran-3-ol as the alcohol in step 1 and 3,3-diethylazetidine hydrochloride as the amine in step 3, to provide 2-(3,3-diethylazetidin-1-yl)-N-(3-fluoro-4-((tetrahydro-2H-pyran-3-yl)oxy)phenyl)-5-(2,2,2-trifluoroethyl) oxazole-4-carboxamide (50 mg, 22%).

Example 159

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and 3-methoxy-3-ethylazetidine as the amine in step 3, to provide N-(4-(cis-bicyclo[3.1.0]hexan-3-yloxy)-3-fluorophenyl)-2-(3-ethyl-3-methoxyazetidin-1-yl)-5-(2,2,2-trifluoroethyl) oxazole-4-carboxamide (52 mg, 35%).

Example 160

The above referenced compound was synthesized utilizing the procedures outlined in the scheme above using 1,2,3-trifluoro-5-nitrobenzene as compound XC and tetrahydro-2H-pyran-3-ol as the alcohol in step 1 and 3-methoxy-3-ethylazetidine as the amine in step 3, to provide N-(3,5-difluoro-4-((tetrahydro-2H-pyran-3-yl)oxy) phenyl)-2-(3-ethyl-3-methoxyazetidin-1-yl)-5-(2,2,2-trifluoroethyl)oxazole-4-carboxamide (52 mg, 33%).

Example 161

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and 3-azabicyclo[3.2.0]heptane as the amine in step 3, to provide N-(4-(cis-bicyclo[3.1.0]hexan-3-yloxy)-3-fluorophenyl)-2-(3-azabicyclo[3.2.0]heptan-3-yl)-5-(2,2,2-trifluoroethyl) oxazole-4-carboxamide (50 mg, 37.37%).

Example 162

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and octahydrocyclopenta[b]pyrrole as the amine in step 3, to provide N-(4-(cis-bicyclo[3.1.0]hexan-3-yloxy)-3-fluorophenyl)-2-(hexahydrocyclopenta[b]pyrrol-1(2H)-yl)-5-(2,2,2-trifluoroethyl)oxazole-4-carboxamide (18 mg, 10%).

Example 163

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and octahydro-1H-indole as the amine in step 3, to provide N-(4-(cis-bicyclo[3.1.0]hexan-3-yloxy)-3,5-difluorophenyl)-2-(octahydro-1H-indol-1-yl)-5-(2,2,2-trifluoroethyl)oxazole-4-carboxamide (17 mg, 11.21%).

Example 164

The above referenced compound was synthesized utilizing the procedures outlined in the scheme above using 1,2-difluoro-3-methyl-5-nitrobenzene as compound XC and cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-fluoro-5-methylphenyl)-2-(3-methoxy-3-methylazetidin-1-yl)-5-(2,2,2-trifluoroethyl)oxazole-4-carboxamide (25 mg, 10.79%).

Example 165

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3-(methoxymethyl)-3-ethylazetidine as the amine in step 3, to provide N-(4-(cis-bicyclo[3.1.0]hexan-3-yloxy)-3,5-difluorophenyl)-2-(3-ethyl-3-(methoxymethyl)azetidin-1-yl)-5-(2,2,2-trifluoroethyl)oxazole-4-carboxamide (40 mg, 26%).

Example 166

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 5,6-dihydro-4H-pyrrolo[3,4-c]isoxazole as the amine in step 3, to provide N-(4-(cis-bicyclo[3.1.0]hexan-3-yloxy)-3,5-difluorophenyl)-2-(4H-pyrrolo[3,4-c]isoxazol-5(6H)-yl)-5-(2,2,2-trifluoroethyl)oxazole-4-carboxamide (40 mg, 52%).

Example 167

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3-methoxy-3-ethylazetidine as the amine in step 3, to provide N-(4-(cis-bicyclo[3.1.0]hexan-3-yloxy)-3,5-difluorophenyl)-2-(3-ethyl-3-methoxyazetidin-1-yl)-5-(2,2,2-trifluoroethyl)oxazole-4-carboxamide (60 mg, 30%).

Example 168

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3,3-bis(methoxymethyl)azetidine hydrochloride as the amine in step 3, to provide N-(4-(cis-bicyclo[3.1.0]hexan-3-yloxy)-3,5-difluorophenyl)-2-(3,3-bis(methoxymethyl)azetidin-1-yl)-5-(2,2,2-trifluoroethyl)oxazole-4-carboxamide (45 mg, 30%).

Example 169

The above referenced compound was synthesized utilizing the procedures outlined in the scheme above using 1,2,3-trifluoro-5-nitrobenzene as compound XC and bicyclo[3.1.1]heptan-3-ol as the alcohol in step 1 and pyrrolidine as the amine in step 3, to provide N-(4-(bicyclo[3.1.1]heptan-3-yloxy)-3,5-difluorophenyl)-2-(pyrrolidin-1-yl)-5-(2,2,2-trifluoroethyl)oxazole-4-carboxamide (25 mg, 11.58%).

Example 170

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 1-azaspiro[3.3]heptane as the amine in step 3, to provide N-(4-(cis-bicyclo[3.1.0]hexan-3-yloxy)-3,5-difluorophenyl)-2-(1-azaspiro[3.3]heptan-1-yl)-5-(2,2,2-trifluoroethyl) oxazole-4-carboxamide (25 mg, 17.76%).

Example 171

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and 7-oxa-2-azaspiro[3.5]nonane as the amine in step 3, to provide N-(4-(cis-bicyclo[3.1.0]hexan-3-yloxy)-3-fluorophenyl)-2-(7-oxa-2-azaspiro[3.5]nonan-2-yl)-5-(2,2,2-trifluoroethyl) oxazole-4-carboxamide (70 mg, 45.58%).

Example 172

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 2,2-dimethylpyrrolidine as the amine in step 3, to provide N-(4-(cis-bicyclo[3.1.0]hexan-3-yloxy)-3,5-difluorophenyl)-2-(2,2-dimethylpyrrolidin-1-yl)-5-(2,2,2-trifluoroethyl)oxazole-4-carboxamide (15 mg, 19.2%).

Example 173

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 5-oxa-2-azaspiro[3.4]octane as the amine in step 3, to provide N-(4-(cis-bicyclo[3.1.0]hexan-3-yloxy)-3,5-difluorophenyl)-2-(5-oxa-2-azaspiro[3.4]octan-2-yl)-5-(2,2,2-trifluoroethyl)oxazole-4-carboxamide (18 mg, 21.3%).

Example 174

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and azepane as the amine in step 3, to provide 2-(azepan-1-yl)-N-(4-(cis-bicyclo[3.1.0]hexan-3-yloxy)-3,5-difluorophenyl)-5-(2,2,2-trifluoroethyl)oxazole-4-carboxamide (30 mg, 19.23%).

Example 175

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 2-azabicyclo[2.1.1]hexane as the amine in step 3, to provide 2-(2-azabicyclo[2.1.1]hexan-2-yl)-N-(4-(cis-bicyclo[3.1.0]hexan-3-yloxy)-3,5-difluorophenyl)-5-(2,2,2-trifluoroethyl) oxazole-4-carboxamide (32 mg, 28%).

Example 176

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 2,6-dimethylmorpholine as the amine in step 3, to provide N-(4-(cis-bicyclo[3.1.0]hexan-3-yloxy)-3,5-difluorophenyl)-2-(2,6-dimethylmorpholino)-5-(2,2,2-trifluoroethyl) oxazole-4-carboxamide (50 mg, 32.6%).

Example 177

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3-azabicyclo[3.2.0]heptane as the amine in step 3, to provide N-(4-(cis-bicyclo[3.1.0]hexan-3-yloxy)-3,5-difluorophenyl)-2-(3-azabicyclo[3.2.0]heptan-3-yl)-5-(2,2,2-trifluoroethyl)oxazole-4-carboxamide (30 mg, 19.18%).

Example 178

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3,5-difluorophenyl)-2-(3-methoxy-3-methylazetidin-1-yl)-5-(2,2,2-trifluoroethyl)oxazole-4-carboxamide (6.0 g, 38.65%).

Example 179

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and (3aR,6aR)-hexahydro-2H-furo[2,3-c]pyrrole as the amine in step 3, to provide N-(4-(cis-bicyclo[3.1.0]hexan-3-yloxy)-3,5-difluorophenyl)-2-((3aR,6aR)-hexahydro-5H-furo[2,3-c]pyrrol-5-yl)-5-(2,2,2-trifluoroethyl)oxazole-4-carboxamide (27 mg, 17.56%).

Example 180

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and (3aS,6aS)-hexahydro-2H-furo[2,3-c]pyrrole as the amine in step 3, to provide N-(4-(cis-bicyclo[3.1.0]hexan-3-yloxy)-3,5-difluorophenyl)-2-((3aS,6aS)-hexahydro-5H-furo[2,3-c]pyrrol-5-yl)-5-(2,2,2-trifluoroethyl)oxazole-4-carboxamide (32 mg, 20.82%).

Example 181

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and morpholine as the amine in step 3, to provide N-(4-(cis-bicyclo[3.1.0]hexan-3-yloxy)-3,5-difluorophenyl)-2-morpholino-5-(2,2,2-trifluoroethyl)oxazole-4-carboxamide (38 mg, 40%).

Example 182

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 2-oxa- 5-azabicyclo[2.2.1]heptane as the amine in step 3, to provide 2-(2-oxa-5-azabicyclo[2.2.1]heptan-5-yl)-N-(4-(cis-bicyclo[3.1.0]hexan-3-yloxy)-3,5-difluorophenyl)-5-(2,2,2-trifluoroethyl)oxazole-4-carboxamide (19 mg, 18.2%).

Example 183

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3,5-difluorophenyl)-2-(3,3-diethylazetidin-1-yl)-5-(2,2,2-trifluoroethyl)oxazole-4-carboxamide (22 mg, 15.9%).

Example 184

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 2,2-dimethylmorpholine as the amine in step 3, to provide N-(4-(cis-bicyclo[3.1.0]hexan-3-yloxy)-3,5-difluorophenyl)-2-(2,2-dimethylmorpholino)-5-(2,2,2-trifluoroethyl)oxazole-4-carboxamide (16 mg, 11.6%).

Example 185

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and octahydrocyclopenta[b]pyrrole as the amine in step 3, to provide N-(4-(cis-bicyclo[3.1.0]hexan-3-yloxy)-3,5-difluorophenyl)-2-(hexahydrocyclopenta[b]pyrrol-1(2H)-yl)-5-(2,2,2-trifluoroethyl)oxazole-4-carboxamide (25 mg, 17%).

Example 186

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and hexahydro-1H-furo[3,4-c]pyrrole as the amine in step 3, to provide N-(4-(cis-bicyclo[3.1.0]hexan-3-yloxy)-3,5-difluorophenyl)-2-(tetrahydro-1H-furo[3,4-c]pyrrol-5(3H)-yl)-5-(2,2,2-trifluoroethyl)oxazole-4-carboxamide (60 mg, 39%).

Example 187

The above referenced compound was synthesized utilizing the procedures outlined in the scheme above using 1,2-difluoro-4-nitrobenzene as compound XC and cis-bicyclo[3.1.0]hexan-3-ol as the alcohol in step 1 and hexahydro-2H-furo[2,3-c]pyrrole as the amine in step 3, to provide N-(4-(cis-bicyclo[3.1.0]hexan-3-yloxy)-3-fluorophenyl)-2-(hexahydro-5H-furo[2,3-c]pyrrol-5-yl)-5-(2,2,2-trifluoroethyl)oxazole-4-carboxamide (30 mg, 26.96%).

Example 188

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 7-oxa-2-azaspiro[3.5]nonane as the amine in step 3, to provide N-(4-(cis-bicyclo[3.1.0]hexan-3-yloxy)-3,5-difluorophenyl)-2-(7-oxa-2-azaspiro[3.5]nonan-2-yl)-5-(2,2,2-trifluoroethyl)oxazole-4-carboxamide (60 mg, 39.58%).

Example 189

The above referenced compound was synthesized utilizing the procedures outlined in the scheme above using 1,2,3-trifluoro-5-nitrobenzene as compound XC and cis-bicyclo[3.1.0]hexan-3-ol as the alcohol in step 1 and 6-oxa-2-azaspiro[3.4]octane as the amine in step 3, to provide N-(4-(cis-bicyclo[3.1.0]hexan-3-yloxy)-3,5-difluorophenyl)-2-(6-oxa-2-azaspiro[3.4]octan-2-yl)-5-(2,2,2-trifluoroethyl)oxazole-4-carboxamide (65 mg, 44%).

Example 190

The above referenced compound was synthesized utilizing the procedures outlined in the scheme above using 1,2-difluoro-4-nitrobenzene as compound XC and bicyclo[3.1.0]hexan-3-ylmethanol as the alcohol in step 1 and pyrrolidine as the amine in step 3, to provide N-(4-(bicyclo[3.1.0]hexan-3-ylmethoxy)-3-fluorophenyl)-2-(pyrrolidin-1-yl)-5-(2,2,2-trifluoroethyl)oxazole-4-carboxamide (25 mg, 15.62%).

Example 191

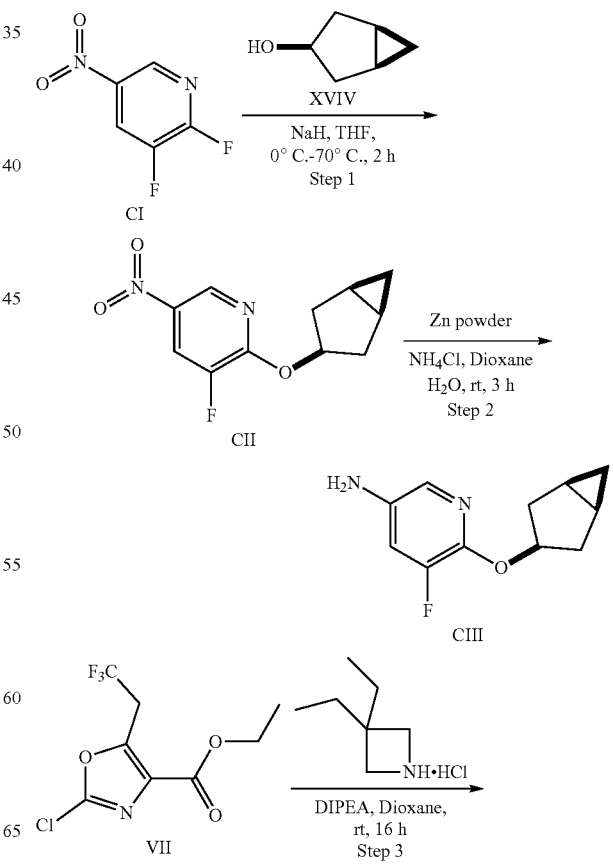

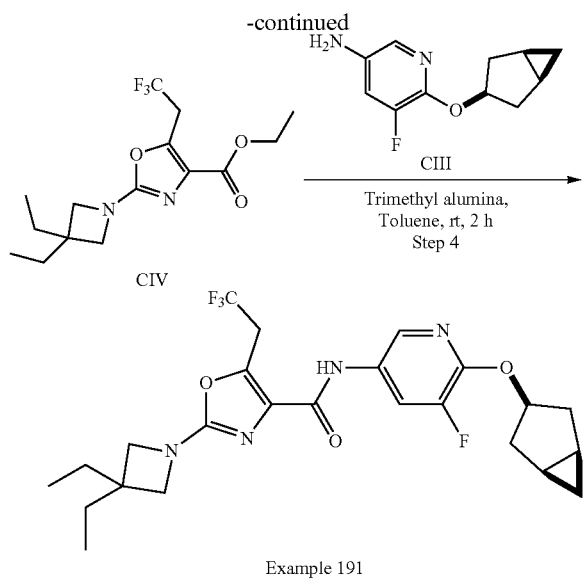

Example 191

Step 1: To a stirred solution of bicyclo[3.1.0]hexan-3-ol, XVIV (300 mg, 3.12 mmol), NaH (300 mg, 9.37 mmol) in THF (6 mL) was added 2,3-difluoro-5-nitropyridine, CI (500 mg, 3.12 mmol) under ice cold condition and then it was allowed to stir for 3 h at 70° C. After completion [Monitored by TLC], reaction mixture was partitioned between EtOAc and saturated aqueous solution of NH₄Cl. The organic layer was separated, dried over anhydrous sodium sulfate, and concentrated under reduced pressure. The resultant crude was purified through flash column chromatography using 5% EtOAc in hexane as an eluent as an eluent to afford 2-(cis-bicyclo[3.1.0]hexan-3-yloxy)-3-fluoro-5-nitropyridine, CH (295 mg, 39%) as light-yellow oily liquid.

Step 2: To a stirred solution of 2-(cis-bicyclo[3.1.0]hexan-3-yloxy)-3-fluoro-5-nitropyridine, CH (295 mg, 1.23 mmol) in 1,4 dioxane: water (6 mL, 5:1) was added zinc dust (550 mg, 8.66 mmol) along with ammonium chloride (463.7 mg, 8.66 mmol) at 0° C. It was then stirred for 3 h at rt. After completion [Monitored by TLC], reaction mixture was filtered through a glass sintered. The filtrate was dried over anhydrous sodium sulfate, and concentrated under reduced pressure. The resultant crude was purified by flash column chromatography using 10% EtOAc in hexane as an eluent to afford 6-(cis-bicyclo[3.1.0]hexan-3-yloxy)-5-fluoropyridin-3-amine, CHI (180 mg, 69%) as brown solid.

Step 3: To a stirred solution of ethyl 2-chloro-5-(2,2,2-trifluoroethyl)oxazole-4-carboxylate, VII (500 mg. 1.95 mmol.) and DIPEA (1.77 mL, 9.72 mmol) in dioxane (6 mL) was added compound 6 (306 mg, 2.04 mmol) and the resultant reaction mixture was allowed to stir at room temperature for 16 h. After completion [Monitored by TLC], reaction mixture was concentrated under reduced pressure to remove dioxane. Resultant crude was purified through flash column chromatography 20% EtOAc in hexane as an eluent to provide ethyl 2-(3,3-diethylazetidin-1-yl)-5-(2,2,2-trifluoroethyl)oxazole-4-carboxylate, CIV (480 mg, 74%).

Step 4: To a stirred solution of ethyl 2-(3,3-diethylazetidin-1-yl)-5-(2,2,2-trifluoroethyl)oxazole-4-carboxylate, CIV (100 mg, 0.29 mmol) in dry toluene (5 mL), 6-(cis-bicyclo[3.1.0]hexan-3-yloxy)-5-fluoropyridin-3-amine, CIII (50 mg, 0.23 mmol) was added, followed by dropwise addition of trimethyl alumina (0.6 mL, 1.2 mmol) at rt and the resultant reaction mixture was allowed to stir at rt for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 15% EtOAc in hexane as an eluent to afford N-(6-(cis-bicyclo[3.1.0]hexan-3-yloxy)-5-fluoropyridin-3-yl)-2-(3,3-diethylazetidin-1-yl)-5-(2,2,2-trifluoroethyl)oxazole-4-carboxamide, Example 191 (60 mg, 31%).

General Procedure for the Synthesis of Examples of General Structure CIX (Examples 192-216).

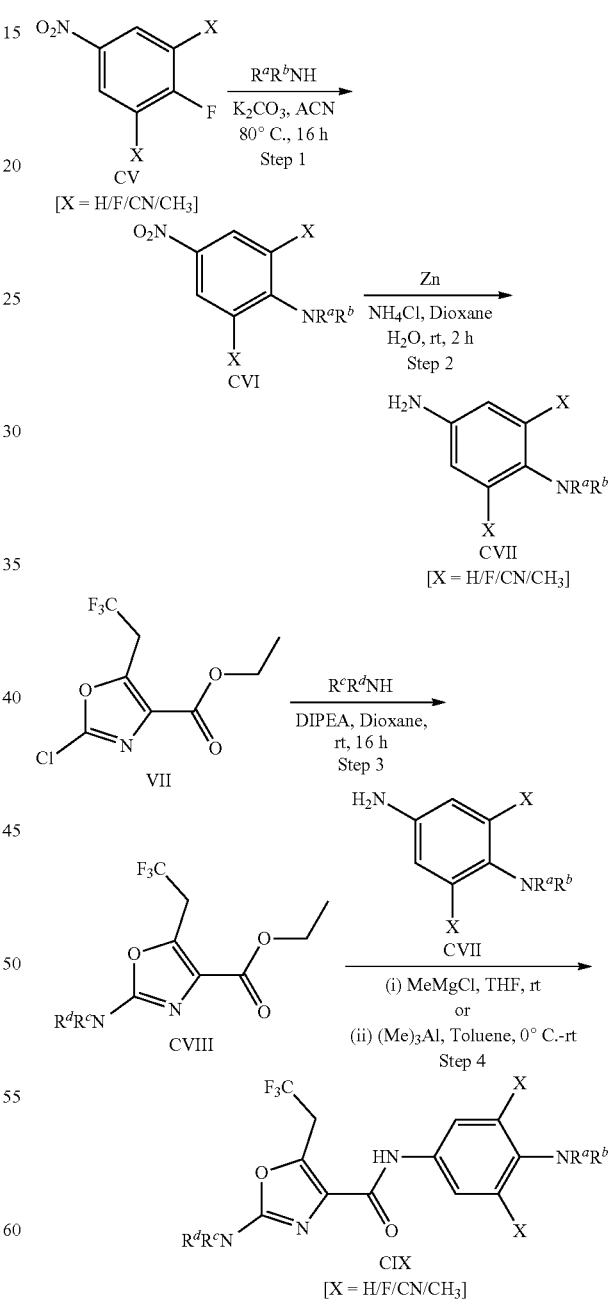

Step 1: To a stirred suspension of fluoro-nitrobenzene CV (1.0 eq.) and K₂CO₃ (3.0 equiv) in CH₃CN (3 mL/g CV) was added RᵃRᵇNH (1.2 eq.) and the resultant reaction mixture was allowed to stir at 80° C. in a sealed tube for 16 h. After completion of reaction [Monitored by TLC], the reaction mixture was concentrated under reduced pressure to remove CH$_3$CN. Resultant crude was purified through flash column chromatography to provide intermediates of structure CVI.

Step 2: To a stirred solution of compound CVI in 1,4 dioxane:water (5:1) was added zinc dust (5.0 eq) followed by ammonium chloride (6.0 eq) at 0° C. It was then stirred for 2 h at rt. After completion [Monitored by TLC], the reaction mixture was filtered through a sintered glass. The filtrate was dried over anhydrous Na$_2$SO$_4$, concentrated under reduced pressure and purified through flash column chromatography using EtOAc-hexane as eluent to afford intermediate compound CVII.

Step 3: To a stirred solution of intermediate VII (1.0 eq.) and DIPEA (3.0 equiv) in dioxane (3 mL/mmol) was added R$^c$R$^d$NH (1.1 eq.) and resultant reaction mixture was allowed to stir at room temperature for 16 h. After completion [Monitored by TLC], reaction mixture was concentrated under reduced pressure to remove dioxane. Resultant crude was purified through combiflash column chromatography using EtOAc-Hexane as eluent to provide CVIII.

Step 4: To a stirred solution of CVIII (1.0 eq.) and CVII (1.0 eq.) in dry THF (30 mL/g), was added MeMgCl (3 M in THF, 2.4 eq) dropwise and was stirred for 1 h at room temperature. The reaction was monitored by TLC. After completion reaction mixture was quenched with 1 N HCl, extracted with EtOAc and washed with water. Organic layer was separated, dried over anhydrous sodium sulfate, and concentrated under reduced pressure. Resultant crude was purified by combiflash column chromatography to afford desired compound CIX. Example 192 to Example 195 were synthesized following condition (ii): To a stirred solution of CVIII (1.0 eq) and amine CVII (0.8 eq) in dry toluene (30 mL/g CVI), trimethylaluminum (2 M in toluene, 4.0 eq) was added dropwise at 0° C., and the resultant reaction mixture was allowed to stir at rt. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography to afford products of general structure CIX.

All amines used as starting materials were purchased from chemical providers.

Example 192

The above referenced compound was synthesized utilizing the procedures outlined in the scheme above wherein compound CV was 1,2-difluoro-3-methyl-5-nitrobenzene, using bicyclo[3.1.1]heptan-3-amine as the amine in step 1 [Reaction temperature & time 120° C. & 48 h] and 3,3-diethylazetidine hydrochloride as the amine in step 3, to provide N-(4-(bicyclo[3.1.1]heptan-3-ylamino)-3-fluoro-5-methylphenyl)-2-(3,3-diethylazetidin-1-yl)-5-(2,2,2-trifluoroethyl)oxazole-4-carboxamide (25 mg, 13.3%).

Example 193

The above referenced compound was synthesized utilizing the procedures outlined in the scheme above wherein compound CV was 1,2-difluoro-3-methyl-5-nitrobenzene, using bicyclo[3.1.1]heptan-3-amine as the amine in step 1 [Reaction temperature & time 120° C. & 48 h] and pyrrolidine as the amine in step 3, to provide N-(4-(bicyclo[3.1.1]heptan-3-ylamino)-3-fluoro-5-methylphenyl)-2-(pyrrolidin-1-yl)-5-(2,2,2-trifluoroethyl)oxazole-4-carboxamide (10 mg, 5.42%).

Example 194

The above referenced compound was synthesized utilizing the procedures outlined in the scheme above wherein compound CV was 1,2-difluoro-3-methyl-5-nitrobenzene, using bicyclo[3.2.1]octan-8-amine as the amine in step 1 and pyrrolidine as the amine in step 3, to provide N-(4-(bicyclo[3.2.1]octan-8-ylamino)-3-fluoro-5-methylphenyl)-2-(pyrrolidin-1-yl)-5-(2,2,2-trifluoroethyl)oxazole-4-carboxamide (25 mg, 25.48%).

Example 195

The above referenced compound was synthesized utilizing the procedures outlined in the scheme above wherein compound CV was 1,2-difluoro-3-methyl-5-nitrobenzene, using bicyclo[3.2.1]octan-8-amine as the amine in step 1 and 3-methoxy-3-methylazetidine hydrochloride as the amine in step 3, to provide N-(4-(bicyclo[3.2.1]octan-8-ylamino)-3-fluoro-5-methylphenyl)-2-(3-methoxy-3-methylazetidin-1-yl)-5-(2,2,2-trifluoroethyl)oxazole-4-carboxamide (15 mg, 10.52%).

Example 196

The above referenced compound was synthesized utilizing the procedures outlined in the scheme above wherein compound CV was 2,3-difluoro-5-nitrobenzonitrile, using 8-azabicyclo[3.2.1]octane as the amine in step 1 and 3-methoxy-3-methylazetidine hydrochloride as the amine in step 3, to provide N-(4-(8-azabicyclo[3.2.1]octan-8-yl)-3-cyano-5-fluorophenyl)-2-(3-methoxy-3-methylazetidin-1-yl)-5-(2,2,2-trifluoroethyl)oxazole-4-carboxamide (77 mg, 28.84%).

Example 197

The above referenced compound was synthesized utilizing the procedures outlined in the scheme above wherein compound CV was 2-fluoro-5-nitrobenzonitrile, using 8-azabicyclo[3.2.1]octane as the amine in step 1 and 3-methoxy-3-methylazetidine hydrochloride as the amine in step 3, to provide N-(4-(8-azabicyclo[3.2.1]octan-8-yl)-3-cyanophenyl)-2-(3-methoxy-3-methylazetidin-1-yl)-5-(2,2,2-trifluoroethyl)oxazole-4-carboxamide (30 mg, 19.19%).

Example 198

The above referenced compound was synthesized utilizing the procedures outlined in the scheme above wherein compound CV was 1,2,3-trifluoro-5-nitrobenzene, using hexahydro-2H-furo[3,2-b]pyrrole as the amine in step 1 and pyrrolidine as the amine in step 3, to provide N-(3,5-difluoro-4-(hexahydro-4H-furo[3,2-b]pyrrol-4-yl)phenyl)-2-(pyrrolidin-1-yl)-5-(2,2,2-trifluoroethyl)oxazole-4-carboxamide (20 mg, 15%).

Example 199

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and 1,4-

285 oxazepane as the amine in step 3, to provide N-(4-(8-azabicyclo[3.2.1]octan-8-yl)-3,5-difluorophenyl)-2-(1,4-oxazepan-4-yl)-5-(2,2,2-trifluoroethyl)oxazole-4-carboxamide (20 mg, 12.53%).

Example 200

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and 3,3-dimethylazetidine hydrochloride as the amine in step 3, to provide N-(4-(8-azabicyclo[3.2.1]octan-8-yl)-3,5-difluorophenyl)-2-(3,3-dimethylazetidin-1-yl)-5-(2,2,2-trifluoroethyl)oxazole-4-carboxamide (30 mg, 18.43%).

Example 201

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and hexahydro-1H-furo[3,4-c]pyrrole as the amine in step 3, to provide N-(4-(8-azabicyclo[3.2.1]octan-8-yl)-3,5-difluorophenyl)-2-(tetrahydro-1H-furo[3,4-c]pyrrol-5(3H)-yl)-5-(2,2,2-trifluoroethyl)oxazole-4-carboxamide (50 mg, 31.75%).

Example 202

The above referenced compound was synthesized utilizing the procedures outlined in the scheme above wherein compound CV was 3,4-difluoronitrobenzene, using 3-azabicyclo[3.1.1]heptane as the amine in step 1 and 2-oxa-6-azaspiro[3.4]octane as the amine in step 3, to provide N-(4-(3-azabicyclo[3.1.1]heptan-3-yl)-3-fluorophenyl)-2-(2-oxa-6-azaspiro[3.4]octan-6-yl)-5-(2,2,2-trifluoroethyl)oxazole-4-carboxamide (20 mg, 17%).

Example 203

The above referenced compound was synthesized utilizing the procedures outlined in the scheme above wherein compound CV was 1,2,3-trifluoro-5-nitrobenzene, using 3-azabicyclo[3.1.1]heptane as the amine in step 1 and 3-ethyl-3-methoxyazetidine as the amine in step 3, to provide N-(4-(3-azabicyclo[3.1.1]heptan-3-yl)-3,5-difluorophenyl)-2-(3-ethyl-3-methoxyazetidin-1-yl)-5-(2,2,2-trifluoroethyl)oxazole-4-carboxamide (25 mg, 11.66%).

Example 204

The above referenced compound was synthesized utilizing the procedures outlined in the scheme above wherein compound CV was 1,2,3-trifluoro-5-nitrobenzene, using 3-azabicyclo[4.1.0]heptane as the amine in step 1 and 3-ethyl-3-methoxyazetidine as the amine in step 3, to provide N-(4-(3-azabicyclo[4.1.0]heptan-3-yl)-3,5-difluorophenyl)-2-(3-ethyl-3-methoxyazetidin-1-yl)-5-(2,2,2-trifluoroethyl)oxazole-4-carboxamide (30 mg, 19.61%).

Example 205

The above referenced compound was synthesized utilizing the procedures outlined in the scheme above wherein compound CV was 1,2,3-trifluoro-5-nitrobenzene, using octahydrocyclopenta[b]pyrrole as the amine in step 1 and 3-ethyl-3-methoxyazetidine as the amine in step 3, to provide N-(3,5-difluoro-4-(hexahydrocyclopenta[b]pyrrol-1(2H)-yl)phenyl)-2-(3-ethyl-3-methoxy azetidin-1-yl)-5-(2,2,2-trifluoroethyl)oxazole-4-carboxamide (12 mg, 7.64%).

286

Example 206

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and 3-ethyl-3-methoxyazetidine as the amine in step 3, to provide N-(4-(8-azabicyclo[3.2.1]octan-8-yl)-3,5-difluorophenyl)-2-(3-ethyl-3-methoxyazetidin-1-yl)-5-(2,2,2-trifluoroethyl)oxazole-4-carboxamide (60 mg, 42.41%).

Example 207

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and 3-methoxy-3-methylazetidine hydrochloride as the amine in step 3, to provide N-(4-(8-azabicyclo[3.2.1]octan-8-yl)-3,5-difluorophenyl)-2-(3-methoxy-3-methylazetidin-1-yl)-5-(2,2,2-trifluoroethyl)oxazole-4-carboxamide (50 mg, 64.58%).

Example 208

The above referenced compound was synthesized utilizing the procedures outlined in the scheme above wherein compound CV was 1,2,3-trifluoro-5-nitrobenzene, using 3-azabicyclo[3.1.1]heptane as the amine in step 1 and 2-oxa-6-azaspiro[3.4]octane as the amine in step 3, to provide N-(4-(3-azabicyclo[3.1.1]heptan-3-yl)-3,5-difluorophenyl)-2-(2-oxa-6-azaspiro[3.4]octan-6-yl)-5-(2,2,2-trifluoroethyl)oxazole-4-carboxamide (30 mg, 19.56%).

Example 209

The above referenced compound was synthesized utilizing the procedures outlined in the scheme above wherein compound CV was 1,2,3-trifluoro-5-nitrobenzene, using 3-azabicyclo[3.1.1]heptane as the amine in step 1 and pyrrolidine as the amine in step 3, to provide N-(4-(3-azabicyclo[3.1.1]heptan-3-yl)-3,5-difluorophenyl)-2-(pyrrolidin-1-yl)-5-(2,2,2-trifluoroethyl)oxazole-4-carboxamide (25 mg, 22.17%).

Example 210

The above referenced compound was synthesized utilizing the procedures outlined in the scheme above wherein compound CV was 1,2,3-trifluoro-5-nitrobenzene, using 8-azabicyclo[3.2.1]octane as the amine in step 1 and pyrrolidine as the amine in step 3, to provide N-(4-(8-azabicyclo[3.2.1]octan-8-yl)-3,5-difluorophenyl)-2-(pyrrolidin-1-yl)-5-(2,2,2-trifluoroethyl)oxazole-4-carboxamide (90 mg, 72.39%).

Example 211

The above referenced compound was synthesized utilizing the procedures outlined in the scheme above wherein compound CV was 1,2,3-trifluoro-5-nitrobenzene, using 3-azabicyclo[4.1.0]heptane as the amine in step 1 and 3,3-diethylazetidine hydrochloride as the amine in step 3, to provide N-(4-(3-azabicyclo[4.1.0]heptan-3-yl)-3,5-difluorophenyl)-2-(3,3-diethylazetidin-1-yl)-5-(2,2,2-trifluoroethyl) oxazole-4-carboxamide (36 mg, 16.76%).

Example 212

The above referenced compound was synthesized utilizing the procedures outlined in the scheme above wherein compound CV was 3,4-difluoronitrobenzene, using 3-azabicyclo[4.1.0]heptane as the amine in step 1 and 3,3-diethylazetidine hydrochloride as the amine in step 3, to provide N-(4-(3-azabicyclo[4.1.0]heptan-3-yl)-3-fluorophenyl)-2-(3,3-diethylazetidin-1-yl)-5-(2,2,2-trifluoroethyl)oxazole-4-carboxamide (13 mg, 8.78%).

Example 213

The above referenced compound was synthesized utilizing the procedures outlined in the scheme above wherein compound CV was 1,2,3-trifluoro-5-nitrobenzene, using 3,3-dimethylpiperidine as the amine in step 1 and pyrrolidine as the amine in step 3, to provide N-(4-(3,3-dimethylpiperidin-1-yl)-3,5-difluorophenyl)-2-(pyrrolidin-1-yl)-5-(2,2,2-trifluoroethyl)oxazole-4-carboxamide (30 mg, 15%).

Example 214

The above referenced compound was synthesized utilizing the procedures outlined in the scheme above wherein compound CV was 1,2,3-trifluoro-5-nitrobenzene, using octahydrocyclopenta[b]pyrrole as the amine in step 1 and pyrrolidine as the amine in step 3, to provide N-(3,5-difluoro-4-(hexahydrocyclopenta[b]pyrrol-1(2H)-yl)phenyl)-2-(pyrrolidin-1-yl)-5-(2,2,2-trifluoroethyl)oxazole-4-carboxamide (30 mg, 23%).

Example 215

The above referenced compound was synthesized utilizing the procedures outlined in the scheme above wherein compound CV was 1,2,3-trifluoro-5-nitrobenzene, using piperidine as the amine in step 1 and 3,3-diethylazetidine hydrochloride as the amine in step 3, to provide 2-(3,3-diethylazetidin-1-yl)-N-(3,5-difluoro-4-(piperidin-1-yl)phenyl)-5-(2,2,2-trifluoroethyl)oxazole-4-carboxamide (16 mg, 21.35%).

Example 216

The above referenced compound was synthesized utilizing the procedures outlined in the scheme above wherein compound CV was 3,4-difluoronitrobenzene, using piperidine as the amine in step 1 and 3,3-diethylazetidine hydrochloride as the amine in step 3, to provide 2-(3,3-diethylazetidin-1-yl)-N-(3-fluoro-4-(piperidin-1-yl)phenyl)-5-(2,2,2-trifluoroethyl)oxazole-4-carboxamide (38 mg, 26.3%).

Example 217

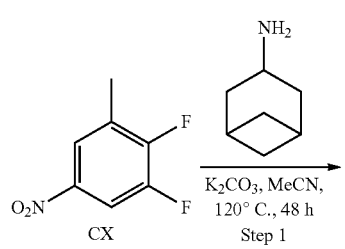

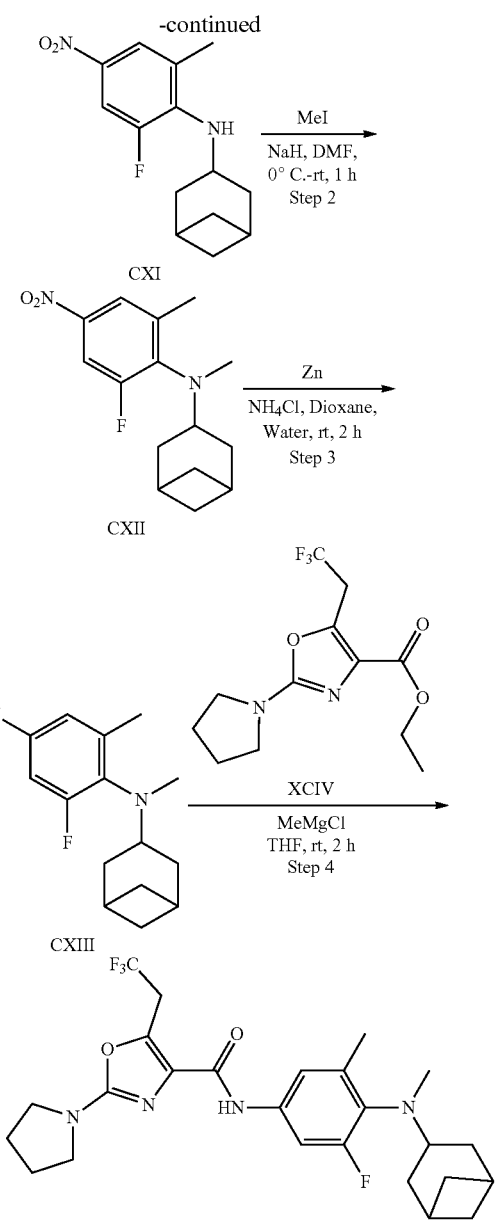

Example 217

Step 1: To a stirred suspension of 1,2-difluoro-3-methyl-5-nitrobenzene CX (281 mg, 1.62 mmol), $K_2CO_3$ (748 mg, 5.42 mmol) in $CH_3CN$ (10 mL) was added bicyclo[3.1.1]heptan-3-amine (150 mg, 1.35 mmol) and the resultant reaction mixture was allowed to stir at 120° C. for 48 h in a sealed tube. After completion of the reaction [Monitored by TLC], the reaction mixture was concentrated under reduced pressure to remove $CH_3CN$. Resultant crude was purified through combi flash column chromatography 5% EtOAc in hexane as an eluent to provide intermediates N-(2-fluoro-6-methyl-4-nitrophenyl)bicyclo[3.1.1]heptan-3-amine CXI (250 mg, 69.8%) as pale yellow solid.

Step 2: To a stirred ice cold solution of CXI (100 mg, 0.378 mmol) in DMF (3 mL) was added NaH (45 mg, 1.1 mmol) under nitrogen atmosphere. Then MeI (107 mg, 0.757 mmol) was added to it at 0° C. and stirred for 1 h at room temperature. After completion [Monitored with TLC], reaction mixture quenched with aq $NH_4Cl$ (5 mL), extracted by EtOAc and was concentrated under reduced pressure. Then resultant crude was purified by column chromatography 5% EtOAc in hexane as an eluent to afford N-(2-fluoro-6-methyl-4-nitrophenyl)-N-methylbicyclo[3.1.1]heptan-3-amine, CXII (80 mg, 76%) as colorless oil.

Step 3: To a stirred solution of CXII (80 mg, 0.287 mmol) in 1,4 dioxane (8 mL) was added zinc dust (190 mg, 2.84 mmol) in ice-cold condition, followed by addition of ammonium chloride (153 mg, 2.84 mmol) dissolved in water (3 mL). The reaction mixture was stirred at rt for 2 h. After completion [Monitored by TLC], the reaction mixture was filtered through celite bed. The filtrate was evaporated and the residue was partitioned between EtOAc and water. The organic layer was separated, dried over anhydrous sodium sulfate, and concentrated under reduced pressure. The resultant crude was purified through flash column chromatography 30% EtOAc in hexane as an eluent to provide N1-(bicyclo[3.1.1]heptan-3-yl)-2-fluoro-N1,6-dimethylbenzene-1,4-diamine CXIII (60 mg, 84%) as colorless oil.

Step 4: To a stirred solution of amine CXIII (60 mg, 0.256 mmol) and XCIV (90 mg, 0.307 mmol) in dry THF (5 mL), was added MeMgCl (0.26 mL, 3 M in THF) dropwise and was stirred for 2 h at rt. The reaction was monitored by TLC. After completion, the reaction mixture was quenched with 1 N HCl and extracted with EtOAc and washed with water. The organic layer was separated, dried over anhydrous sodium sulfate, and concentrated under reduced pressure. The resultant crude was purified by combiflash column chromatography using 20% EtOAc in hexane as an eluent to afford N-(4-(bicyclo[3.1.1]heptan-3-yl(methyl)amino)-3-fluoro-5-methylphenyl)-2-(pyrrolidin-1-yl)-5-(2,2,2-trifluoroethyl)oxazole-4-carboxamide, Example 217 (32 mg, 25.27%).

Example 218

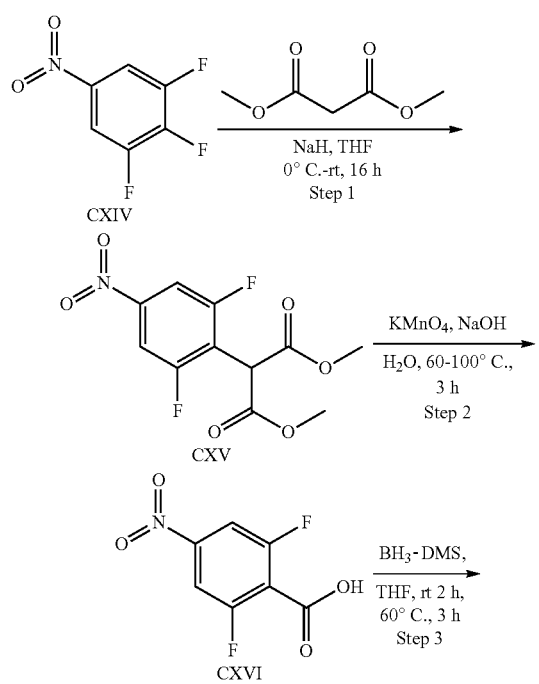

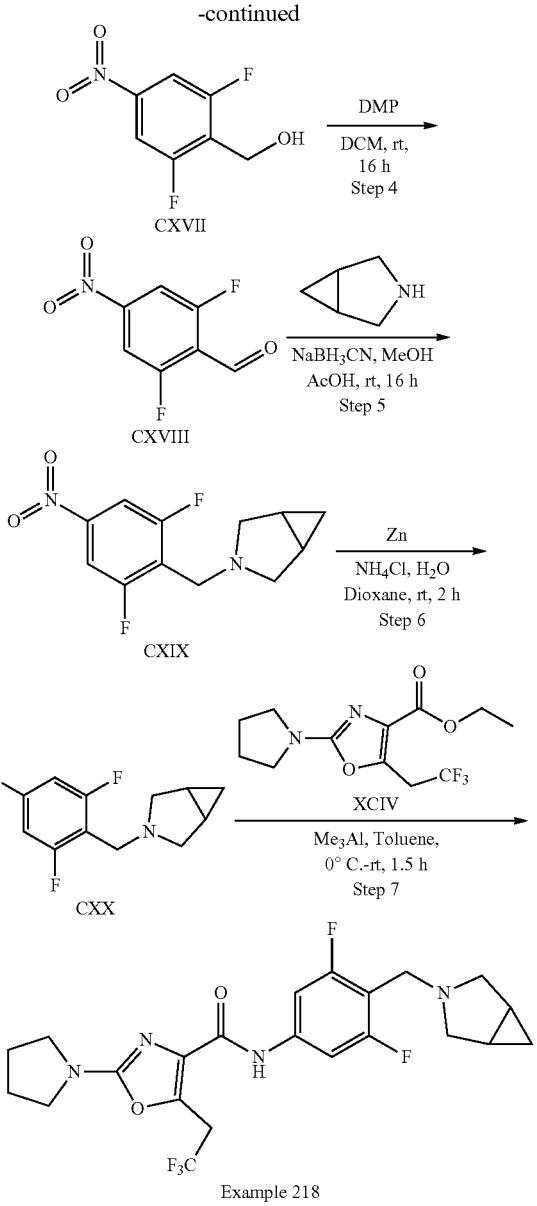

Example 218

Step 1: To a stirred solution of dimethyl malonate (2.5 mL, 22.599 mmol) in THF (20 mL), NaH (1.50 gm, 22.599 mmol, 60% in oil) was added portion wise under ice cold condition. The resultant reaction mixture was stirred at 0° C. for 1 h. Then solution of 3,4,5 trifluoro nitro benzene, CXIV (2.0 g, 11.299 mmol) in THF (5 mL) was added to it and the reaction mass was allowed to stir at rt for 16 h. After completion [Monitored by TLC], resultant reaction mixture was partitioned between EtOAc and water. Organic layer was dried over anhydrous sodium sulfate and concentrated under reduced pressure. The crude was purified through flash column chromatography using 15% EtOAc in hexane as an eluent to afford dimethyl 2-(2,6-difluoro-4-nitrophenyl) malonate, CXV (3.0 g, 91%) as a colorless liquid.

Step 2: To a stirred solution of dimethyl 2-(2,6-difluoro-4-nitrophenyl)malonate, CXV (3.0 g, 10.381 mmol) in 0.5 N aq NaOH (84 mL) was added solid KMnO₄ (8.2 g, 51.903 mmol) portion wise at 50° C. The resultant mixture was refluxed at 100° C. for 3 h. Then it was filtered through celite bed under hot condition. The bed was washed with hot water. The aqueous layer was acidified with conc. HCl up to pH 1 followed by extraction with ethyl acetate. Then combined organic layer was washed with water and brine solution, and dried over anhydrous $Na_2SO_4$ and concentrated under vacuum to afford 2,6-difluoro-4-nitrobenzoic acid, CXVI (1.3 gm) as crude.

Step 3: To a stirred solution of 2,6-difluoro-4-nitrobenzoic acid, CXVI (1.3 g, 6.40 mmol) in THF (27 mL) was added borane-DMS complex (3.6 mL, 38.42 mmol) under ice cold condition. After stirring at room temperature for 2 h, again Borane-DMS complex (1.82 mL, 19.22 mmol) was added to the reaction mixture and heated at 60° C. for 3 h. After completion [Monitored by TLC], the resultant reaction mixture was quenched with MeOH dropwise at 0° C. and stirred at room temperature for 30 minutes. The reaction mass was then concentrated, and the crude was purified through flash column chromatography using 15% EtOAc in hexane as an eluent to afford 2,6-difluoro-4-nitrophenyl) methanol, CXVII (1.0 gm, 82%) as a colorless liquid.

Step 4: To an ice cool solution of 2,6-difluoro-4-nitrophenyl)methanol, CXVII (500 mg, 2.64 mmol) in DCM, Dess-Martin periodinane (2.46 gm, 5.82 mmol) was added and the reaction mixture was allowed to stir at room temperature for 3 h. After TLC analysis another portion of Dess-Martin periodinane (1.122 gm, 2.64 mmol) was added and reaction mixture was stirred at room temperature for additional 13 h. After completion [Monitored by TLC], the resultant reaction mixture was quenched with sat aqueous $NaHCO_3$ solution and 10% aqueous sodium thiosulfate solution and then extracted with DCM. The organic layer was washed with brine solution dried over $Na_2SO_4$ and concentrated to get the crude. the crude was purified through flash column chromatography using 10% EtOAc in hexane as an eluent to afford 2,6-difluoro-4-nitrobenzaldehyde, CXVIII (240 mg, 48%) as a semi-solid.

Step 5: To a solution of 3-azabicyclo[3.1.0]hexane (244 mg, 2.94 mmol) in methanol (20 mL) DIPEA (864 mg, 6.68 mmol) was added and stirred for 15 min rt. Then 2,6-difluoro-4-nitrobenzaldehyde, CXVIII (500 mg, 2.67 mmol) followed by the addition of acetic acid (513.36 mg, 8.556 mmol) were added to it and allowed to stir at room temperature for 16 h. Then sodium cyanoborohydride (420 mg, 6.68 mmol) was added to the reaction mass at 0° C. and stirred for additional 6 h at rt. After completion [Monitored by TLC], the resultant reaction mixture was quenched with $NaHCO_3$ solution and diluted with DCM. The combined organic layer was washed with brine solution and dried over anhydrous sodium sulfate, concentrated to get crude material which was purified through combi flash column chromatography using 50% EtOAc in hexane as an eluent to afford 3-(2,6-difluoro-4-nitrobenzyl)-3-azabicyclo[3.1.0]hexane, CXIX (260 mg, 38.5) as an off-white solid.

Step 6: To a solution of 3-[(2,6-difluoro-4-nitrophenyl)methyl]-3-azabicyclo[3.1.0]hexane, CXIX (240 mg, 0.95 mmol) in dioxane were added aqua solution of $NH_4Cl$ (715 mg, 13.23 mmol) and Zn dust (860 mg, 13.29 mmol) and then it was allowed to stir at room temperature for 1.5 h. After completion [Monitored by TLC], the resultant reaction mixture was filtered through celite bed and the filtrate was diluted with ethyl acetate and washed with water. The organic layer was dried over sodium sulfate, concentrated to get crude material which was purified through combi flash column using 60% EtOAc in hexane as an eluent chromatography to afford 4-{3-azabicyclo[3.1.0]hexan-3-ylmethyl}-3,5-difluoroaniline, CXX (150 mg, 70.5%) as an off white solid.

Step 7: To an ice cool solution of ethyl 2-(pyrrolidin-1-yl)-5-(2,2,2-trifluoroethyl)oxazole-4-carboxylate, XCIV (125.14 mg, 0.429 mmol) in toluene and 4-{3-azabicyclo[3.1.0]hexan-3-ylmethyl}-3,5-difluoroaniline, CXX (80 mg, 0.357 mmol) in toluene was added trimethyl alumina (2 M in toluene, 0.80 mL, 1.60 mmol) and stirred for 1.5 h at rt. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 40% EtOAc in hexane as an eluent to afford N-(4-{3-azabicyclo [3.1.0] hexan-3-ylmethyl}-3,5-difluorophenyl)-2-(pyrrolidin-1-yl)-5-(2,2,2-trifluoroethyl)-1,3-oxazole-4-carboxamide, Example 218 (32 mg, 19%).

Preparation of Intermediate ethyl
2-chloro-5-ethyloxazole-4-carboxylate (CXXV)

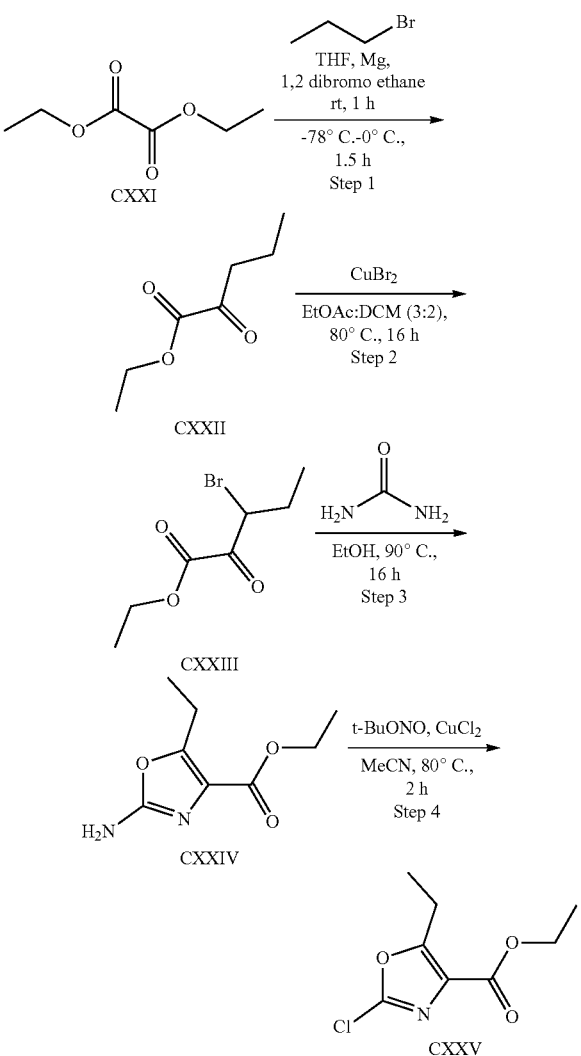

Step 1: To a stirred suspension of Mg (25 g, 1033.05 mmol) in THF (20 mL) was slowly added 1,2-dibromoethane (1.5 mL) under nitrogen atmosphere, followed by slow addition of 1-bromopropane (50 g, 413.22 mmol) dissolved in THF (600 mL) [Exotherm was neutralized by normal water bath] and stirred for 1 h at room temperature. Resultant Grignard solution was slowly added to a stirred solution of diethyl oxalate, CXXI (45.11 mL, 330.58 mmol) in THF (700 mL) maintaining the external temperature at −78° C. and allowed to gradually warm the mixture up to 0° C. After 1.5 h of stirring [Monitored by TLC 10% EtOAc/Hexane, Rf–0.2, (KMnO₄ active)], the reaction mixture reaction was quenched by saturated ammonium chloride solution and was extracted by EtOAc (2×500 mL). The organic layer was washed by brine solution (lx 300 mL), dried over sodium sulfate, and concentrated under reduced pressure. Resultant crude was purified by column chromatography using silica gel (100-200 mesh) under gradient elution of 10% EtOAc/Hexane to afford ethyl 2-oxopentanoate, CXXII (42 g, 70.5%) as a light brown liquid.

Step 2: To a stirred solution of ethyl 2-oxopentanoate, CXXII (150 g, 1041.67 mmol) in EtOAc:DCM mixture (6000 mL, 3:2) was added CuBr₂ (464.58 g, 2083.33 mmol) and reaction mixture was heated to 80° C. for 16 h. After completion [monitored by TLC (20% EtOAc/Hexane), Rf–0.3 (KMnO₄ active)], reaction was filtered through sintered funnel and the filtrate was dried over sodium sulfate and concentrated under reduced pressure to obtain crude compound. The crude was purified by column chromatography using silica (100-200 mesh) under gradient elution of 20% EtOAc/Hexane to afford ethyl 3-bromo-2-oxopentanoate, CXXIII as a brown liquid (160 g, 68.86%).

Step 3: To a stirred solution of ethyl 3-bromo-2-oxopentanoate, CXXIII (330 g, 1479.82 mmol) in ethanol (6600 mL) was added urea (266.37 g, 4439.46 mmol). The reaction was heated to 90° C. for 16 h. After completion [Monitored by TLC 20% EtOAc/Hexane, Rf–0.1], reaction mixture was concentrated under reduced pressure. Resultant crude was diluted with ethyl acetate (1000 mL), washed by saturated solution of NaHCO₃ (1×500 mL) and brine solution (1×300 mL). The organic part was dried over sodium sulfate and concentrated under reduced pressure to obtain crude compound. The crude was triturated by 70% n-pentane in diethyl ether solution three times [first with ~300 mL (70% pentane-Ether), followed by ~150 mL of same solvent twice], to get pure ethyl 2-amino-5-ethyloxazole-4-carboxylate, CXXIV as an off white solid (170 g, 62.37%).

Step 4: To a stirred solution of CuCl₂ (111.42 g, 831.52 mmol) in acetonitrile (4000 mL) was added tert-Butyl nitrite (158.17 mL, 1320.65 mmol) heated to 60° C. for 30 min. Then into the solution, ethyl-2-amino-5-ethyloxazole-4-carboxylate, CXXIV (150 g, 815.22 mmol) dissolved in acetonitrile (2000 mL) was added and the reaction mixture was heated to 80° C. and stirred for 2 h. After completion [monitored by TLC (40% EtOAc/Hexane, Rf–0.7)], reaction mixture was concentrated under reduced pressure. The mixture was diluted in EtOAc (2000 mL) and water (1000 mL) and filtered through celite bed. The organic part was separated and washed by brine solution (lx 500 mL), dried over sodium sulfate, and concentrated under reduced pressure. The resultant crude was purified by column chromatography using silica (100-200 mesh) under gradient elution of 0-10% EtOAc/Hexane to afford ethyl 2-chloro-5-ethyloxazole-4-carboxylate, CXXV as a colorless liquid (115 g, 69.52%).

General Conditions for Preparation of Example of the General Formula Specified by Structure CXXXI (Examples 219-247):

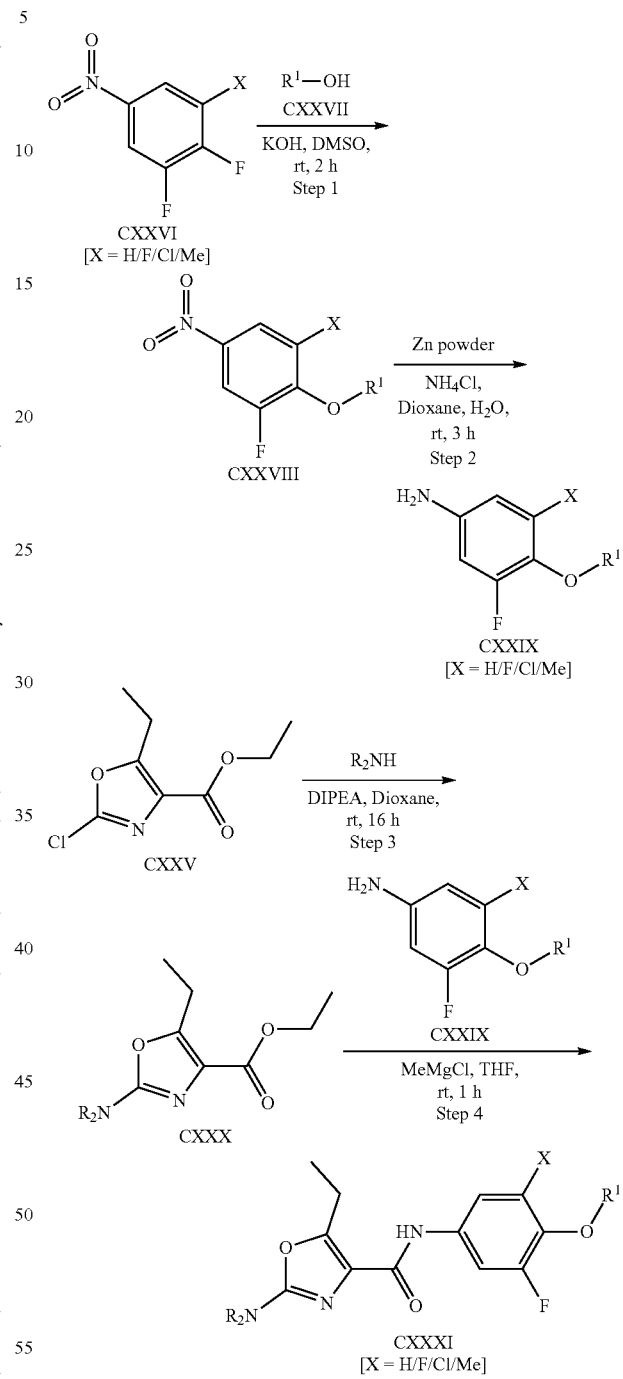

Step 1. To a stirred solution of CXXVI (1.0 eq) and CXXVII (1.2 eq) in DMSO (3 mL/mmol), was added KOH (3.0 eq). The reaction was stirred for 2 h at rt. After completion [Monitored by TLC], the resultant reaction mixture was partitioned between EtOAc and water. Organic layer was dried over anhydrous sodium sulfate and concentrated under reduced pressure. The crude was purified through flash column chromatography using EtOAc in hexane as an eluent to afford desired product CXXVIII.

Step 2: To a stirred solution of CXXVIII (1 eq.)) in 20 mL/g CXXVIII 1,4 dioxane:water (5:1) was added zinc dust (7 eq.) along with ammonium chloride (7 eq.) at 0° C. It was then stirred for 3 h at rt. After completion [Monitored by TLC], reaction mixture was filtered through a glass sintered. The filtrate was dried over anhydrous sodium sulfate and concentrated under reduced pressure. The resultant crude was purified by flash column chromatography using EtOAc in hexane to afford the pure CXXIX.

Step 3: To a stirred solution of CXXV (1.0 eq.) and DIPEA (3.0 equiv) in dioxane (3 mL/mmol) was added R₂NH (1.1 eq.) and resultant reaction mixture was allowed to stir at room temperature for 16 h. After completion [Monitored by TLC], reaction mixture was concentrated under reduced pressure to remove dioxane. The resultant crude was purified by flash column chromatography using EtOAc in hexane to afford the pure CXXX.

Step 4: To a stirred solution of CXXX (1.0 eq.) and CXXIX (1.0 eq.) in dry THF (30 mL/g), was added MeMgCl (3 M in THF, 2.4 eq) dropwise and was stirred for 1 h at RT. The reaction was monitored by TLC. After completion reaction mixture was quenched with 1 N HCl and extracted with EtOAc and washed with water. Organic layer was separated, dried over anhydrous sodium sulfate, and concentrated under reduced pressure. Resultant crude was purified by combiflash column chromatography to afford examples of the general structure CXXXI.

All the alcohol and amines used as starting materials were purchased from commercial suppliers.

Example 219

The above referenced compound was synthesized utilizing the procedures outlined in the scheme above wherein compound CXXVI was 1-chloro-2,3-difluoro-5-nitrobenzene, using cis-bicyclo[3.1.0]hexan-3-ol as the alcohol in step 1 and 3-ethyl-3-methoxyazetidine as the amine in step 3, to provide N-(4-(cis-bicyclo[3.1.0]hexan-3-yloxy)-3-chloro-5-fluorophenyl)-5-ethyl-2-(3-ethyl-3-methoxyazetidin-1-yl)oxazole-4-carboxamide (25 mg, 12.29%).

Example 220

The above referenced compound was synthesized utilizing the procedures outlined in the scheme above wherein compound CXXVI was 1-chloro-2,3-difluoro-5-nitrobenzene, using cis-bicyclo[3.1.0]hexan-3-ol as the alcohol in step 1 and (3-ethylazetidin-3-yl)methanol hydrochloride as the amine in step 3, to provide N-(4-(cis-bicyclo[3.1.0]hexan-3-yloxy)-3-chloro-5-fluorophenyl)-5-ethyl-2-(3-ethyl-3-(hydroxymethyl)azetidin-1-yl)oxazole-4-carboxamide (30 mg, 11.8%).

Example 221

The above referenced compound was synthesized utilizing the procedures outlined in the scheme above wherein compound CXXVI was 1-chloro-2,3-difluoro-5-nitrobenzene, using cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3-chloro-5-fluorophenyl)-2-(3,3-diethylazetidin-1-yl)-5-ethyloxazole-4-carboxamide 94 mg, 47.59%).

Example 222

The above referenced compound was synthesized utilizing the procedures outlined in the scheme above wherein compound CXXVI was 1-chloro-2,3-difluoro-5-nitrobenzene, using cis-bicyclo[3.1.0]hexan-3-ol as the alcohol in step 1 and pyrrolidine as the amine in step 3, to provide N-(4-(cis-bicyclo[3.1.0]hexan-3-yloxy)-3-chloro-5-fluorophenyl)-5-ethyl-2-(pyrrolidin-1-yl)oxazole-4-carboxamide (40 mg, 22.22%).

Example 223

The above referenced compound was synthesized utilizing the procedures outlined in the scheme above wherein compound CXXVI was 1-chloro-2,3-difluoro-5-nitrobenzene, using cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-chloro-5-fluorophenyl)-5-ethyl-2-(3-methoxy-3-methylazetidin-1-yl)oxazole-4-carboxamide (45 mg, 23.38%).

Example 224

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and (3-methylazetidin-3-yl)methanol as the amine in step 3, to provide N-(4-(bicyclo[3.1.1]heptan-3-yloxy)-3-fluoro-5-methylphenyl)-5-ethyl-2-(3-(hydroxymethyl)-3-methylazetidin-1-yl)oxazole-4-carboxamide (30 mg, 17.57%).

Example 225

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and pyrrolidine as the amine in step 3, to provide N-(4-(bicyclo[3.1.1]heptan-3-yloxy)-3-fluoro-5-methylphenyl)-5-ethyl-2-(pyrrolidin-1-yl)oxazole-4-carboxamide (15 mg, 16.71%).

Example 226

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-fluoro-5-methylphenyl)-5-ethyl-2-(3-methoxy-3-methylazetidin-1-yl)oxazole-4-carboxamide (20 mg, 20.14%).

Example 227

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3-ethyl-3-methoxyazetidine as the amine in step 3, to provide N-(4-(cis-bicyclo[3.1.0]hexan-3-yloxy)-3-fluoro-5-methylphenyl)-5-ethyl-2-(3-ethyl-3-methoxyazetidin-1-yl)oxazole-4-carboxamide (15 mg, 10.28%).

Example 228

The above referenced compound was synthesized utilizing the procedures outlined in the scheme above wherein

297 compound CXXVI was 1,2-difluoro-4-nitrobenzene, using bicyclo[3.1.1]heptan-3-ol as the alcohol in step 1 and 3-ethyl-3-methoxyazetidine as the amine in step 3, to provide N-(4-(bicyclo[3.1.1]heptan-3-yloxy)-3-fluorophenyl)-5-ethyl-2-(3-ethyl-3-methoxyazetidin-1-yl)oxazole-4-carboxamide (18 mg, 10.58%).

Example 229

The above referenced compound was synthesized utilizing the procedures outlined in the scheme above wherein compound CXXVI was 3,4,5-trifluoronitrobenzene, using bicyclo[3.1.1]heptan-3-ol as the alcohol in step 1 and pyrrolidine as the amine in step 3, to provide N-(4-(bicyclo[3.1.1]heptan-3-yloxy)-3,5-difluorophenyl)-5-ethyl-2-(pyrrolidin-1-yl)oxazole-4-carboxamide (23 mg, 12.7%).

Example 230

The above referenced compound was synthesized utilizing the procedures outlined in the scheme above wherein compound CXXVI was 3,4,5-trifluoronitrobenzene, using bicyclo[3.1.1]heptan-3-ol as the alcohol in step 1 and 3-ethyl-3-methoxyazetidine as the amine in step 3, to provide N-(4-(bicyclo[3.1.1]heptan-3-yloxy)-3,5-difluorophenyl)-5-ethyl-2-(3-ethyl-3-methoxyazetidin-1-yl)oxazole-4-carboxamide (20 mg, 11.87%).

Example 231

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 1,4-oxazepane as the amine in step 3, to provide N-(4-(cis-bicyclo[3.1.0]hexan-3-yloxy)-3,5-difluorophenyl)-5-ethyl-2-(1,4-oxazepan-4-yl)oxazole-4-carboxamide (12 mg, 6%).

Example 232

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 1H-pyrazole as the amine in step 3, to provide N-(4-(cis-bicyclo[3.1.0]hexan-3-yloxy)-3,5-difluorophenyl)-5-ethyl-2-(1H-pyrazol-1-yl)oxazole-4-carboxamide (60 mg, 30.96%).

Example 233

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and hexahydro-2H-furo[2,3-c]pyrrole as the amine in step 3, to provide N-(4-(cis-bicyclo[3.1.0]hexan-3-yloxy)-3,5-difluorophenyl)-5-ethyl-2-(hexahydro-5H-furo[2,3-c]pyrrol-5-yl)oxazole-4-carboxamide (30 mg, 18.3%).

Example 234

The above referenced compound was synthesized utilizing the procedures outlined in the scheme above wherein compound CXXVI was 3,4,5-trifluoronitrobenzene, using tetrahydrofuran-3-ol as the alcohol in step 1 and 3-ethyl-3-methoxyazetidine as the amine in step 3, to provide N-(3,5-difluoro-4-((tetrahydrofuran-3-yl)oxy)phenyl)-5-ethyl-2-(3-ethyl-3-methoxyazetidin-1-yl)oxazole-4-carboxamide (30 mg, 18.74%).

Example 235

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 5-azaspiro[2.4]heptane as the amine in step 3, to provide N-(4-(cis-bicyclo[3.1.0]hexan-3-yloxy)-3,5-difluorophenyl)-5-ethyl-2-(5-azaspiro[2.4]heptan-5-yl)oxazole-4-carboxamide (20 mg, 11.91%).

Example 236

The above referenced compound was synthesized utilizing the procedures outlined in the scheme above wherein compound CXXVI was 3,4,5-trifluoronitrobenzene, using tetrahydro-2H-pyran-3-ol as the alcohol in step 1 and 3,3-diethylazetidine hydrochloride as the amine in step 3, to provide 2-(3,3-diethylazetidin-1-yl)-N-(3,5-difluoro-4-((tetrahydro-2H-pyran-3-yl)oxy)phenyl)-5-ethyloxazole-4-carboxamide (22 mg, 14.77%).

Example 237

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and hexahydro-1H-furo[3,4-c]pyrrole as the amine in step 3, to provide N-(4-(cis-bicyclo[3.1.0]hexan-3-yloxy)-3,5-difluorophenyl)-5-ethyl-2-(tetrahydro-1H-furo[3,4-c]pyrrol-5(3H)-yl)oxazole-4-carboxamide (30 mg, 16.64%).

Example 238

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3-ethyl-3-methoxyazetidine as the amine in step 3, to provide N-(4-(cis-bicyclo[3.1.0]hexan-3-yloxy)-3,5-difluorophenyl)-5-ethyl-2-(3-ethyl-3-methoxyazetidin-1-yl)oxazole-4-carboxamide (40 mg, 27.16%).

Example 239

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3,5-difluorophenyl)-5-ethyl-2-(3-methoxy-3-methylazetidin-1-yl)oxazole-4-carboxamide (2.7 g, 53.9%).

Example 240

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and octahydrocyclopenta[c]pyrrole as the amine in step 3, to provide N-(4-(cis-bicyclo[3.1.0]hexan-3-yloxy)-3,5-difluororophenyl)-5-ethyl-2-(hexahydrocyclopenta[c]pyrrol-2(1H)-yl)oxazole-4-carboxamide (18 mg, 10.95%).

Example 241

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3-azabicyclo[3.2.0]heptane as the amine in step 3, to provide N-(4-(cis-bicyclo[3.1.0]hexan-3-yloxy)-3,5-difluorophenyl)-2-(3-azabicyclo[3.2.0]heptan-3-yl)-5-ethyloxazole-4-carboxamide (25 mg, 24.8%).

Example 242

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and azepane as the amine in step 3, to provide 2-(azepan-1-yl)-N-(4-(cis-bicyclo[3.1.0]hexan-3-yloxy)-3,5-difluorophenyl)-5-ethyloxazole-4-carboxamide (30 mg, 14.93%).

Example 243

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3,5-difluorophenyl)-2-(3,3-diethylazetidin-1-yl)-5-ethyloxazole-4-carboxamide (10 mg, 10.16%).

Example 244

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and pyrrolidine as the amine in step 3, to provide N-(4-(cis-bicyclo[3.1.0]hexan-3-yloxy)-3,5-difluorophenyl)-5-ethyl-2-(pyrrolidin-1-yl)oxazole-4-carboxamide (1.17 g, 38.12%).

Example 245

The above referenced compound was synthesized utilizing the procedures outlined in the scheme above wherein compound CXXVI was 1,2-difluoro-4-nitrobenzene, using cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3-fluorophenyl)-2-(3,3-diethylazetidin-1-yl)-5-ethyloxazole-4-carboxamide (24 mg, 10.15%).

Example 246

The above referenced compound was synthesized utilizing the procedures outlined in the scheme above wherein compound CXXVI was 1,2-difluoro-4-nitrobenzene, using cis-bicyclo[3.1.0]hexan-3-ol as the alcohol in step 1 and 3-ethyl-3-methoxyazetidine as the amine in step 3, to provide N-(4-(cis-bicyclo[3.1.0]hexan-3-yloxy)-3-fluorophenyl)-5-ethyl-2-(3-ethyl-3-methoxyazetidin-1-yl)oxazole-4-carboxamide (27 mg, 17.19%).

Example 247

The above referenced compound was synthesized utilizing the procedures outlined in the scheme above wherein compound CXXVI was 1,2-difluoro-4-nitrobenzene, using cis-bicyclo[3.1.0]hexan-3-ol as the alcohol in step 1 and 3-azabicyclo[3.2.0]heptane as the amine in step 3, to provide N-(4-(cis-bicyclo[3.1.0]hexan-3-yloxy)-3-fluorophenyl)-2-(3-azabicyclo[3.2.0]heptan-3-yl)-5-ethyloxazole-4-carboxamide (25 mg, 25.85%).

Example 248

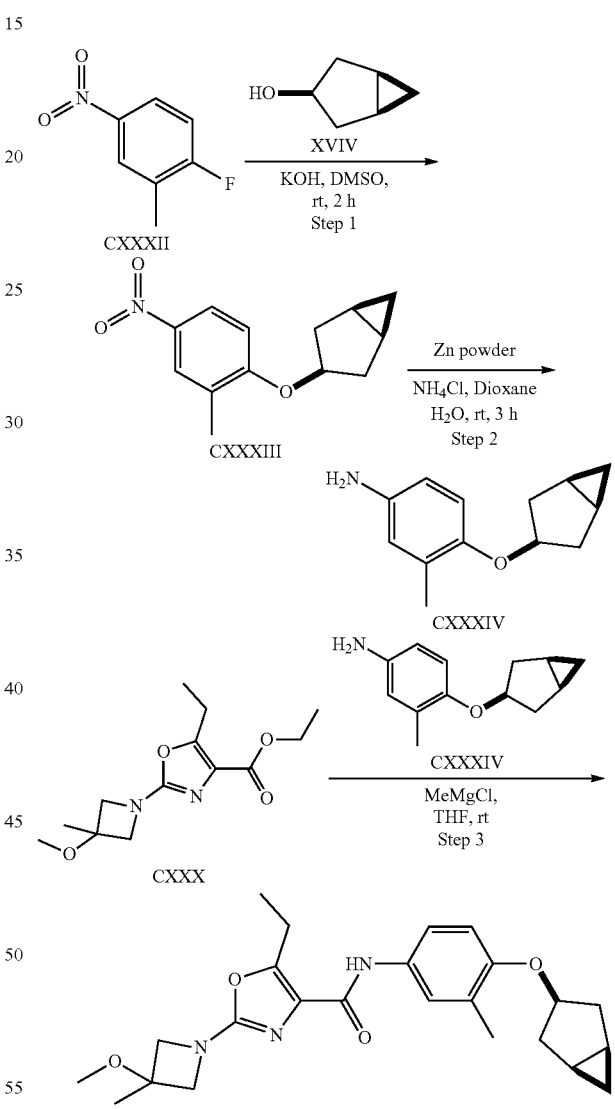

Example 248

Step 1: To a stirred solution of bicyclo[3.1.0]hexan-3-ol, XVIV (285 mg, 2.90 mmol), KOH dust (331 mg, 5.80 mmol) in DMSO (5 mL) was added 1-fluoro-2-methyl-4-nitrobenzene, CXXXII (300 mg, 1.94 mmol) and stirred for 2.5 h at RT. After completion [Monitored by TLC], reaction mixture was partitioned between EtOAc (10 mL) and water (2×30 mL). The organic layer was separated, dried over anhydrous sodium sulfate, and concentrated under reduced pressure. The resultant crude was purified through flash column chromatography using 5% EtOAc in hexane as an eluent to afford 3-(2-methyl-4-nitrophenoxy)bicyclo[3.1.0]hexane, CXXXIII (300 mg, 66%) as light-yellow oily liquid.

Step 2: To a stirred solution of 3-(2-methyl-4-nitrophenoxy)bicyclo[3.1.0]hexane, CXXXIII (200 mg, 0.86 mmol) in 1,4 dioxane: water (6 mL, 5:1) was added zinc dust (280 mg, 4.23 mmol) along with ammonium chloride (230 mg, 4.23 mmol) at 0° C. It was then stirred for 3 h at rt. After completion [Monitored by TLC], reaction mixture was filtered through a glass sintered filter. The filtrate was dried over anhydrous sodium sulfate and concentrated under reduced pressure. The resultant crude was purified by flash column chromatography using 10% EtOAc in hexane to afford 4-(cis-bicyclo[3.1.0]hexan-3-yloxy)-3-methylaniline, CXXXIV (140 mg, 80%) as off white solid.

Step 3: To a stirred solution of ethyl 5-ethyl-2-(3-methoxy-3-methylazetidin-1-yl)oxazole-4-carboxylate, CXXX (150 mg, 0.449 mmol) in dry THF (5 mL), 4-(cis-bicyclo[3.1.0]hexan-3-yloxy)-3-methylaniline, CXXXIV (75 mg, 0.36 mmol) was added, followed by dropwise addition of MeMgCl (3 M in THF, 0.4 mL, 1.20 mmol) at rt and the resultant reaction mixture was allowed to stir at rt for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 10% EtOAc in hexane to afford N-(4-(cis-bicyclo[3.1.0]hexan-3-yloxy)-3-methylphenyl)-5-ethyl-2-(3-methoxy-3-methylazetidin-1-yl)oxazole-4-carboxamide, Example 248 (47.3 mg, 31%).

Example 249

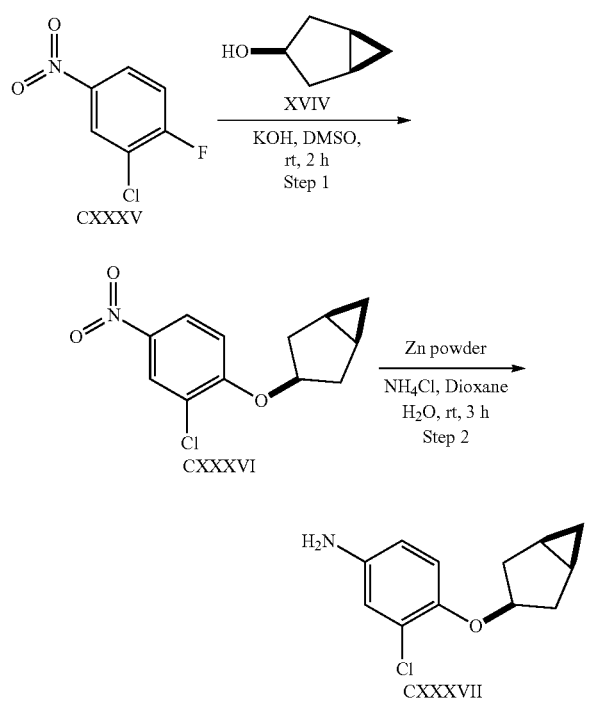

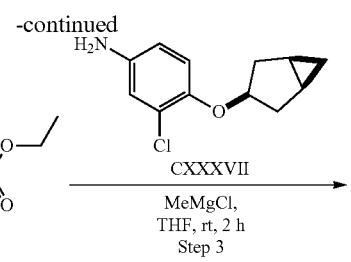

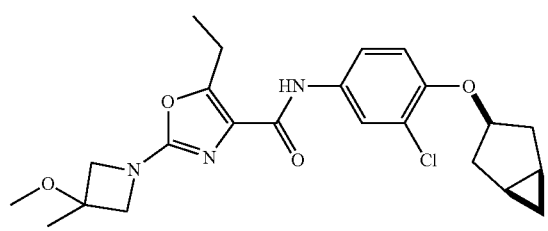

Example 249

Step 1: To a stirred solution of bicyclo[3.1.0]hexan-3-ol, XVIV (135 mg, 1.37 mmol), KOH dust (192 mg, 3.429 mmol) in DMSO (3 mL) was added CXXXV (200 mg, 1.143 mmol) and stirred for 2 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using 5% EtOAc in hexane as an eluent to afford 3-(2-chloro-4-nitrophenoxy)bicyclo[3.1.0]hexane, CXXXVI (170 mg, 56%) as light-yellow oil.

Step 2: To a stirred solution of 3-(2-chloro-4-nitrophenoxy)bicyclo[3.1.0]hexane, CXXXVI (410 mg, 1.62 mmol) in 1,4 dioxane: water (6 mL, 5:1) was added zinc dust (737 mg, 11.34 mmol) along with ammonium chloride (700 mg, 12.97 mmol) at 0° C. It was then stirred for 3 h at rt. After completion [Monitored by TLC], reaction mixture was filtered through a glass sintered filter. The filtrate was dried over anhydrous sodium sulfate and concentrated under reduced pressure. The resultant crude was purified by flash column chromatography using 10% EtOAc in hexane to afford 4-(cis-bicyclo[3.1.0]hexan-3-yloxy)-3-chloroaniline, CXXXVII (350 mg, 96%) as off white solid.

Step 3: To a stirred solution of ethyl 5-ethyl-2-(3-methoxy-3-methylazetidin-1-yl)oxazole-4-carboxylate, CXXX (150 mg, 0.559 mmol) in dry THF (5 mL), 4-(cis-bicyclo[3.1.0]hexan-3-yloxy)-3-chloroaniline, CXXXVII (99.834 mg, 0.448 mmol) was added, followed by dropwise addition of MeMgCl (3 M in THF, 0.5 mL, 1.39 mmol) at rt and the resultant reaction mixture was allowed to stir at rt for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 5-10% EtOAc in hexane to afford N-(4-(cis-bicyclo[3.1.0]hexan-3-yloxy)-3-chlorophenyl)-5-ethyl-2-(3-methoxy-3-methylazetidin-1-yl)oxazole-4-carboxamide, Example 249 (30 mg, 12%).

Example 250

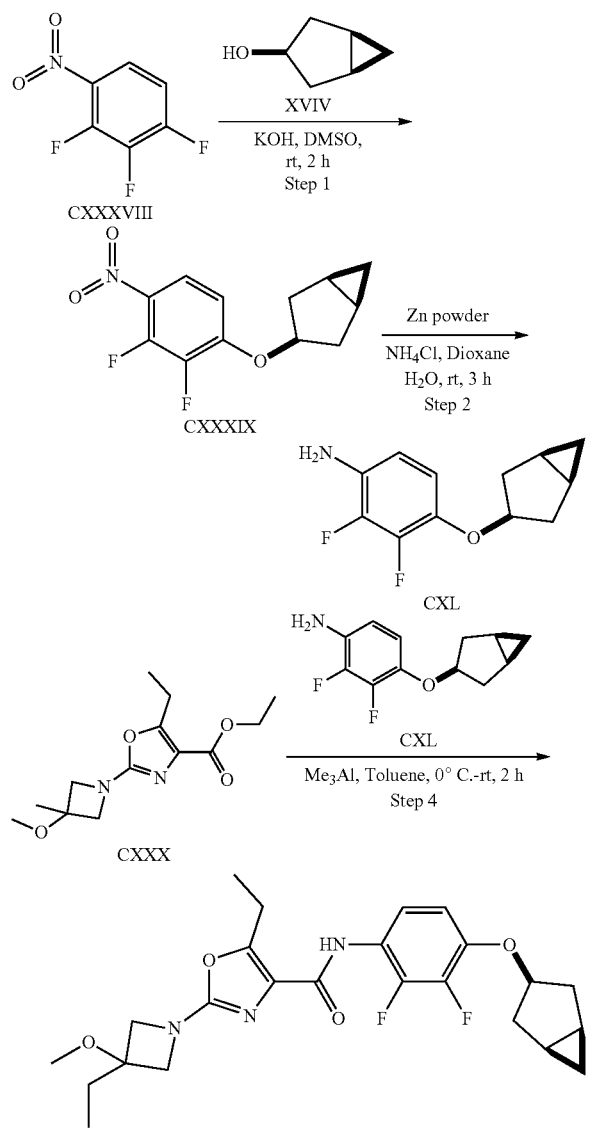

Example 250

Step 1: To a stirred solution of bicyclo[3.1.0]hexan-3-ol, XVIV (609 mg, 6.21 mmol), KOH dust (950 mg, 16.94 mmol) in DMSO (5 mL) was added 1,2,3-trifluoro-4-nitrobenzene, CXXXVIII (1000 mg, 5.64 mmol) and stirred for 2 h at rt. After completion [Monitored by TLC], reaction mixture was partitioned between EtOAc (10 mL) and Water (2×30 mL). The organic layer was separated, dried over anhydrous sodium sulfate, and concentrated under reduced pressure. The resultant crude was purified through flash column chromatography using 5% EtOAc in hexane as an eluent to afford 3-(2,3-difluoro-4-nitrophenoxy)bicyclo[3.1.0]hexane, CXXXIX (100 mg, 28%) as light-yellow oily liquid.

Step 2: To a stirred solution of 3-(2,3-difluoro-4-nitrophenoxy)bicyclo[3.1.0]hexane, CXXXIX (200 mg, 0.78 mmol) in 1,4 dioxane: water (6 mL, 5:1) was added zinc dust (410 mg, 6.27 mmol) along with ammonium chloride (336 mg, 6.27 mmol) at 0° C. It was then stirred for 3 h at rt. After completion [Monitored by TLC], reaction mixture was filtered through a glass sintered filter. The filtrate was dried over anhydrous sodium sulfate and concentrated under reduced pressure. The resultant crude was purified by flash column chromatography using 10% EtOAc in hexane to afford 4-(cis-bicyclo[3.1.0]hexan-3-yloxy)-2,3-difluoroaniline, CXL (120 mg, 68%) as off white solid.

Step 3: To a stirred solution of 4-(cis-bicyclo[3.1.0]hexan-3-yloxy)-2,3-difluoroaniline, CXL (7, 60 mg, 0.21 mmol) in dry toluene (3 mL), ethyl 5-ethyl-2-(3-methoxy-3-methylazetidin-1-yl)oxazole-4-carboxylate, CXXX (72 mg, 0.32 mmol) was added, followed by dropwise addition of Me$_3$Al (2 M in toluene, 0.42 mL, 0.84 mmol) at 0° C. and the resultant reaction mixture was allowed to stir at rt for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 20% EtOAc in hexane to afford N-(4-(cis-bicyclo[3.1.0]hexan-3-yloxy)-3-chlorophenyl)-5-ethyl-2-(3-methoxy-3-methylazetidin-1-yl)oxazole-4-carboxamide, Example 250 (40 mg, 41%).

Example 251

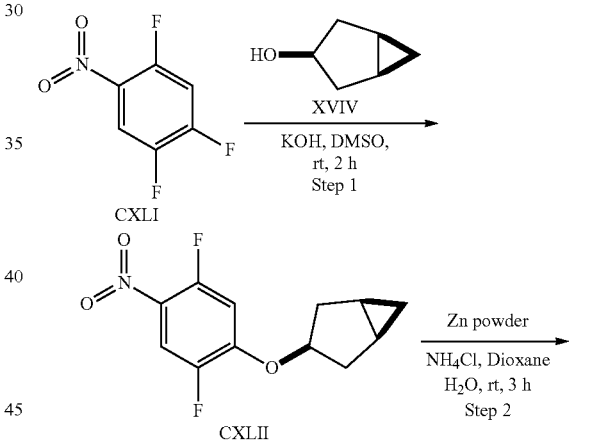

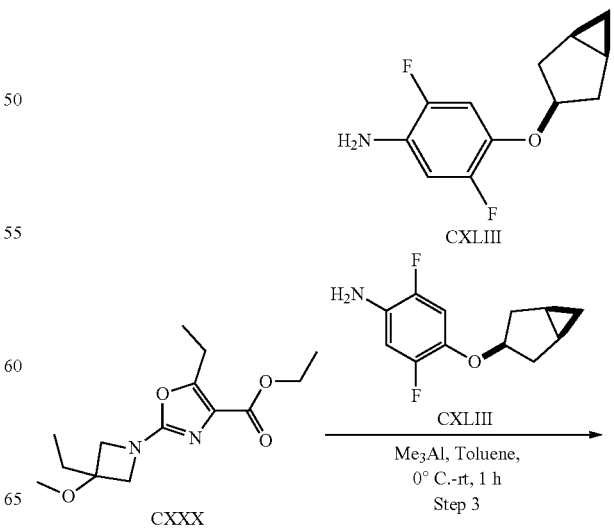

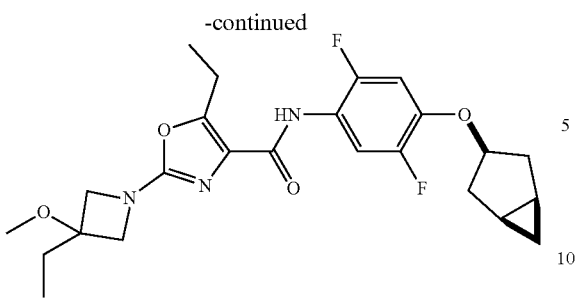

Example 251

Step 1: To a stirred solution of bicyclo[3.1.0]hexan-3-ol, XVIV (332.25 mg, 3.39 mmol), KOH dust (474.31 mg, 8.47 mmol) in DMSO (5 mL) was added 1,2,4-trifluoro-5-nitrobenzene, CXLI (500 mg, 2.82 mmol) and stirred for 2 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using 5% EtOAc in hexane as an eluent to afford 3-(2,5-difluoro-4-nitrophenoxy)bicyclo[3.1.0]hexane, CXLII (255 mg, 41%) as light-yellow oily liquid.

Step 2: To a stirred solution of 3-(2,5-difluoro-4-nitrophenoxy)bicyclo[3.1.0]hexane, CXLII (300 mg, 1.176 mmol) in 1,4 dioxane: water (6 mL, 5:1) was added zinc dust (535 mg, 8.23 mmol) along with ammonium chloride (508 mg, 9.41 mmol) at 0° C. It was then stirred for 3 h at rt. After completion [Monitored by TLC], reaction mixture was filtered through a glass sintered filter. The filtrate was dried over anhydrous sodium sulfate and concentrated under reduced pressure. The resultant crude was purified by flash column chromatography using 10% EtOAc in hexane to afford 4-(cis-bicyclo[3.1.0]hexan-3-yloxy)-2,5-difluoroaniline, CXLIII (220 mg, 83%) as brown gummy liquid.

Step 3: To a stirred solution of ethyl 5-ethyl-2-(3-ethyl-3-methoxyazetidin-1-yl)oxazole-4-carboxylate, CXXX (100 mg, 0.354 mmol) in dry toluene (5 mL), 4-(cis-bicyclo[3.1.0]hexan-3-yloxy)-2,5-difluoroaniline, CXLIII (64 mg, 0.284 mmol) was added, followed by dropwise addition of trimethyl aluminum (2 M in toluene, 0.7 mL, 1.418 mmol) at 0° C. and the resultant reaction mixture was allowed to stir at rt for 1 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 5-10% EtOAc in hexane to afford N-(4-(cis-bicyclo[3.1.0]hexan-3-yloxy)-2,5-difluorophenyl)-5-ethyl-2-(3-ethyl-3-methoxyazetidin-1-yl)oxazole-4-carboxamide, Example 251 (15 mg, 9.2%).

General Procedure for the Synthesis of Examples of General Structure CLVII (Examples 252-259).

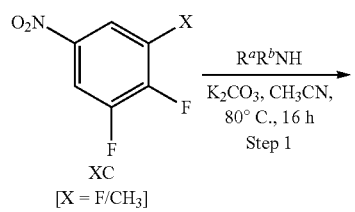

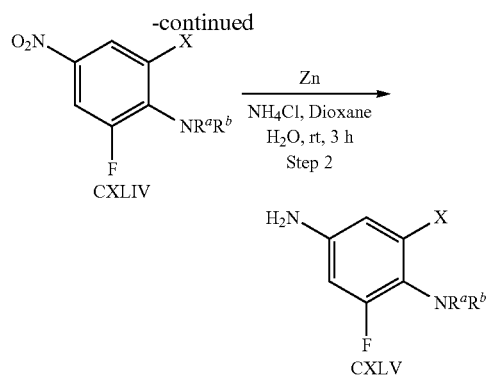

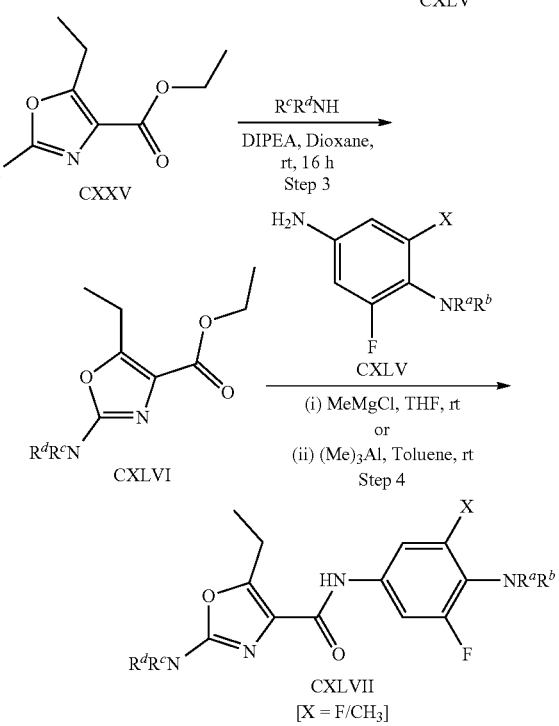

Step 1: To a stirred solution of fluoro-nitrobenzene XC (1.0 eq.) in a sealed tube and $K_2CO_3$ (3.0 equiv) in $CH_3CN$ (3 mL/g VII) was added $R^aR^bNH$ (1.2 eq.) and the resultant reaction mixture was allowed to stir at 80° C. for 16 h. After completion of reaction [Monitored by TLC], the reaction mixture was concentrated under reduced pressure to remove $CH_3CN$. Resultant crude was purified through flash column chromatography to provide intermediates of structure CXLIV.

Step 2: To a stirred solution of compound CXLIV in 1,4 dioxane:water (5:1) was added zinc dust (7.0 eq) followed by with ammonium chloride (7.0 eq) at 0° C. It was then stirred for 3 h at rt. After completion [Monitored by TLC], the reaction mixture was filtered through a sintered glass filter. The filtrate was dried over anhydrous $Na_2SO_4$, concentrated under reduced pressure and purified through flash column chromatography using EtOAc-hexane as eluent to afford intermediate compound CXLV.

Step 3: To a stirred solution of CXXV (1.0 eq.) and DIPEA (3.0 equiv) in dioxane (3 mL/mmol) was added $R^cR^DNH$ (1.1 eq.), and the resultant reaction mixture was allowed to stir at room temperature for 16 h. After completion [Monitored by TLC], reaction mixture was concentrated under reduced pressure to remove dioxane. Resultant crude was purified through combiflash column chromatography using EtOAc-hexane as eluent to afford intermediate compound CXLVI.

Step 4, To a stirred solution of CXLVI (1.0 eq.) and CXLV (1.0 eq.) in dry THF (30 mL/g), was added MeMgCl (3 M in THF, 2.4 eq) dropwise and was stirred for 1 h at RT. The reaction was monitored by TLC. After completion reaction mixture was quenched with 1 N HCl and extracted with EtOAc and washed with water. Organic layer was separated, dried over anhydrous sodium sulfate, and concentrated under reduced pressure. Resultant crude was purified by combiflash column chromatography to afford desired compound. Example 252 and Example 253 were synthesized following condition (ii) as follows: To a stirred solution of CXLVI (1.0 eq) and amine CXLV (0.8 eq) in dry toluene (30 mL/g CXLVI), trimethylaluminum (2 M in toluene, 4.0 eq) dropwise at 0° C., and the resultant reaction mixture was allowed to stir at rt. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography to afford products of general structure CXLVII.

All amines used as starting materials for Step 1 were purchased from chemical providers.

Example 252

The above referenced compound was synthesized utilizing the procedures outlined in the scheme above wherein compound XC was 1,2-difluoro-3-methyl-5-nitrobenzene, using bicyclo[3.1.1]heptan-3-amine as the amine in step 1 and pyrrolidine as the amine in step 3, to provide N-(4-(bicyclo[3.1.1]heptan-3-ylamino)-3-fluoro-5-methylphenyl)-5-ethyl-2-(pyrrolidin-1-yl)oxazole-4-carboxamide (25 mg, 13.89%).

Example 253

The above referenced compound was synthesized utilizing the procedures outlined in the scheme above wherein compound XC was 1,2-difluoro-3-methyl-5-nitrobenzene, using bicyclo[3.1.1]heptan-3-amine as the amine in step 1 and 3,3-diethylazetidine hydrochloride as the amine in step 3, to provide N-(4-(bicyclo[3.1.1]heptan-3-ylamino)-3-fluoro-5-methylphenyl)-2-(3,3-diethylazetidin-1-yl)-5-ethyloxazole-4-carboxamide (31 mg, 22%).

Example 254

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and 3-ethyl-3-methoxyazetidine as the amine in step 3, to provide N-(4-(3-azabicyclo[3.1.1]heptan-3-yl)-3,5-difluorophenyl)-5-ethyl-2-(3-ethyl-3-methoxyazetidin-1-yl)oxazole-4-carboxamide (10 mg, 8.76%).

Example 255

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and pyrrolidine as the amine in step 3, to provide N-(4-(3-azabicyclo[3.1.1]heptan-3-yl)-3,5-difluorophenyl)-5-ethyl-2-(pyrrolidin-1-yl)oxazole-4-carboxamide (40 mg, 19.05%).

Example 256

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and 3,3-dimethylazetidine hydrochloride as the amine in step 3, to provide N-(4-(3-azabicyclo[3.1.1]heptan-3-yl)-3,5-difluorophenyl)-2-(3,3-dimethylazetidin-1-yl)-5-ethyloxazole-4-carboxamide (21 mg, 10%).

Example 257

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and hexahydro-1H-furo[3,4-c]pyrrole as the amine in step 3, to provide N-(4-(3-azabicyclo[3.1.1]heptan-3-yl)-3,5-difluorophenyl)-5-ethyl-2-(tetrahydro-1H-furo[3,4-c]pyrrol-5(3H)-yl)oxazole-4-carboxamide (70 mg, 47.55%).

Example 258

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and 3-methoxy-3-methylazetidine hydrochloride as the amine in step 3, to provide N-(4-(3-azabicyclo[3.1.1]heptan-3-yl)-3,5-difluorophenyl)-5-ethyl-2-(3-methoxy-3-methylazetidin-1-yl)oxazole-4-carboxamide (15 mg, 9%).

Example 259

The above referenced compound was synthesized utilizing the procedures outlined in the scheme above wherein compound XC was 1,2,3-trifluoro-5-nitrobenzene, using 3-azabicyclo[3.1.1]heptane as the amine in step 1 and 6,6-difluoro-2-azaspiro[3.3]heptane 2,2,2-trifluoroacetate as the amine in step 3, to provide N-(4-(3-azabicyclo[3.1.1]heptan-3-yl)-3,5-difluorophenyl)-2-(6,6-difluoro-2-azaspiro[3.3]heptan-2-yl)-5-ethyloxazole-4-carboxamide (65 mg, 42.9%).

General Procedure for the Synthesis of Examples of General Structure CLII (Examples 260-270).

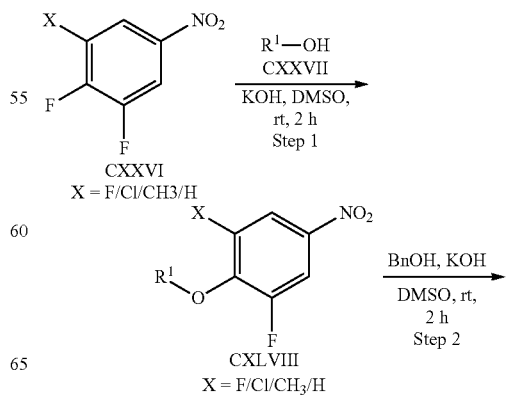

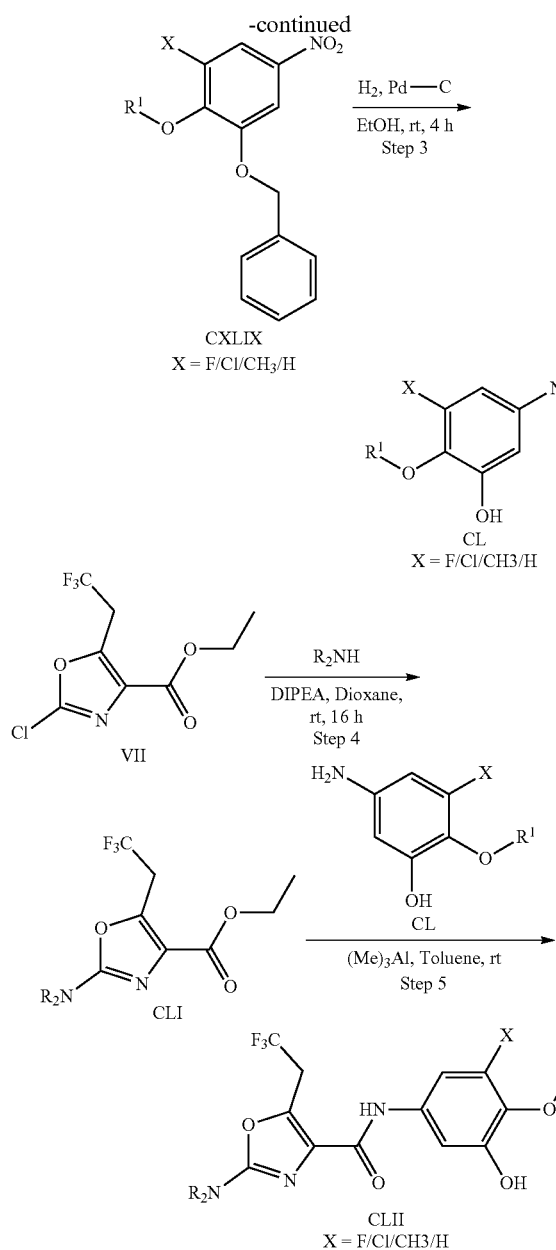

Step 1. To a stirred solution of CXXVI (1.0 eq) and CXXVII (1.2 eq) in DMSO (3 mL/mmol), was added KOH (3.0 eq). The reaction was stirred for 2 h at RT. After completion [Monitored by TLC], the resultant reaction mixture was partitioned between EtOAc and water. Organic layer was dried over anhydrous sodium sulfate and concentrated under reduced pressure. The crude was purified through flash column chromatography using EtOAc in hexane as an eluent to afford desired product CXLVIII.

Step 2: To a stirred solution of CXLVIII (1.0 eq.) and KOH dust (3.0 eq.) in DMSO (10 mL/g CXLVIII) was added BnOH (1.2 eq.) and stirred for 2 h at rt. After completion [Monitored by TLC], reaction mixture was partitioned between EtOAc and water. Organic layer was separated, dried over anhydrous sodium sulfate, and concentrated under reduced pressure. The resultant crude was purified through silica column chromatography to afford product of general structure CXLIX.

Step 3: To a stirred solution of CXLIX (1.0 eq) in ethanol (20 mL/g CXLIX) was added 20% Pd/C (by wt %) and stirred under hydrogen atmosphere at rt for 4 h. After completion [Monitored with TLC], the reaction mixture was filtered through celite, concentrated under reduced pressure. The residue was then purified by flash column chromatography to afford amine, CL.

Step 4: To a stirred solution of VII (1.0 eq.) and DIPEA (3.0 equiv) in dioxane (3 mL/mmol) was added $R_2NH$ (1.1 eq.) and resultant reaction mixture was allowed to stir at room temperature for 16 h. After completion [Monitored by TLC], reaction mixture was concentrated under reduced pressure to remove dioxane. Resultant crude was purified through combiflash column chromatography to afford product of general structure CLI.

Step 5: To a stirred solution of CLI (1.0 eq) and amine CL (0.8 eq) in dry toluene (30 mL/g CLI), trimethylaluminum (2 M in toluene, 4.0 eq) dropwise at 0° C., and the resultant reaction mixture was allowed to stir at rt. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography to afford products of general structure CLII.

All amines and alcohols used as starting materials were purchased from chemical providers.

Example 260

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and 3,3-diethylazetidine hydrochloride as the amine in step 4, to provide N-(4-(bicyclo[3.1.1]heptan-3-yloxy)-3-hydroxy-5-methylphenyl)-2-(3,3-diethylazetidin-1-yl)-5-(2,2,2-trifluoroethyl)oxazole-4-carboxamide (115 mg, 64.2%).

Example 261

The above referenced compound was synthesized utilizing the procedures outlined in the scheme above wherein compound CXXVI was 1-chloro-2,3-difluoro-5-nitrobenzene, using bicyclo[3.1.1]heptan-3-ol as the alcohol in step 1 and 3,3-diethylazetidine hydrochloride as the amine in step 4, to provide N-(4-(bicyclo[3.1.1]heptan-3-yloxy)-3-chloro-5-hydroxyphenyl)-2-(3,3-diethylazetidin-1-yl)-5-(2,2,2-trifluoroethyl)oxazole-4-carboxamide (33 mg, 20.35%).

Example 262

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3,3-diethylazetidine hydrochloride as the amine in step 4, to provide N-(4-(cis-bicyclo[3.1.0]hexan-3-yloxy)-3-hydroxy-5-methylphenyl)-2-(3,3-diethylazetidin-1-yl)-5-(2,2,2-trifluoroethyl)oxazole-4-carboxamide (40 mg, 28.77%).

Example 263

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3-methoxy-3-methylazetidine hydrochloride as the amine in step 4, to provide N-(4-(cis-bicyclo[3.1.0]hexan-3-yloxy)-3-hydroxy-5-methylphenyl)-2-(3-methoxy-3-methylazetidin-1-yl)-5-(2,2,2-trifluoroethyl)oxazole-4-carboxamide (60 mg, 53%).

Example 264

The above referenced compound was synthesized utilizing the procedures outlined in the scheme above wherein compound CXXVI was 1,2,3-trifluoro-5-nitrobenzene, using bicyclo[3.1.1]heptan-3-ol as the alcohol in step 1 and 3,3-diethylazetidine hydrochloride as the amine in step 4, to provide N-(4-(bicyclo[3.1.1]heptan-3-yloxy)-3-fluoro-5-hydroxyphenyl)-2-(3,3-diethylazetidin-1-yl)-5-(2,2,2-trifluoroethyl)oxazole-4-carboxamide (39 mg, 24.8%).

Example 265

The above referenced compound was synthesized utilizing the procedures outlined in the scheme above wherein compound CXXVI was 1,2,3-trifluoro-5-nitrobenzene, using bicyclo[3.1.1]heptan-3-ol as the alcohol in step 1 and 3-methoxy-3-methylazetidine hydrochloride as the amine in step 4, to provide N-(4-(bicyclo[3.1.1]heptan-3-yloxy)-3-fluoro-5-hydroxyphenyl)-2-(3-methoxy-3-methylazetidin-1-yl)-5-(2,2,2-trifluoroethyl)oxazole-4-carboxamide (15 mg, 9.41%).

Example 266

The above referenced compound was synthesized utilizing the procedures outlined in the scheme above wherein compound CXXVI was 1,2,3-trifluoro-5-nitrobenzene, using bicyclo[3.1.1]heptan-3-ol as the alcohol in step 1 and 3-ethyl-3-methoxyazetidine as the amine in step 4, to provide N-(4-(bicyclo[3.1.1]heptan-3-yloxy)-3-fluoro-5-hydroxyphenyl)-2-(3-ethyl-3-methoxyazetidin-1-yl)-5-(2,2,2-trifluoroethyl)oxazole-4-carboxamide (15 mg, 15.93%).

Example 267

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3-methoxy-3-methylazetidine hydrochloride as the amine in step 4, to provide N-(4-(cis-bicyclo[3.1.0]hexan-3-yloxy)-3-fluoro-5-hydroxyphenyl)-2-(3-methoxy-3-methylazetidin-1-yl)-5-(2,2,2-trifluoroethyl)oxazole-4-carboxamide (20 mg, 12.9%).

Example 268

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3-ethyl-3-methoxyazetidine as the amine in step 4, to provide N-(4-(cis-bicyclo[3.1.0]hexan-3-yloxy)-3-fluoro-5-hydroxyphenyl)-2-(3-ethyl-3-methoxyazetidin-1-yl)-5-(2,2,2-trifluoroethyl)oxazole-4-carboxamide (30 mg, 19.13%).

Example 269

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3,3-diethylazetidine hydrochloride as the amine in step 4, to provide N-(4-(cis-bicyclo[3.1.0]hexan-3-yloxy)-3-fluoro-5-hydroxyphenyl)-2-(3,3-diethylazetidin-1-yl)-5-(2,2,2-trifluoroethyl)oxazole-4-carboxamide (60 mg, 32.66%).

Example 270

The above referenced compound was synthesized utilizing the procedures outlined in the scheme above wherein compound CXXVI was 1,2-difluoro-4-nitrobenzene, using cis-bicyclo[3.1.0]hexan-3-ol as the alcohol in step 1 and 3,3-diethylazetidine hydrochloride as the amine in step 4, to provide N-(4-(cis-bicyclo[3.1.0]hexan-3-yloxy)-3-hydroxyphenyl)-2-(3,3-diethylazetidin-1-yl)-5-(2,2,2-trifluoroethyl)oxazole-4-carboxamide (20 mg, 13%).

Example 271

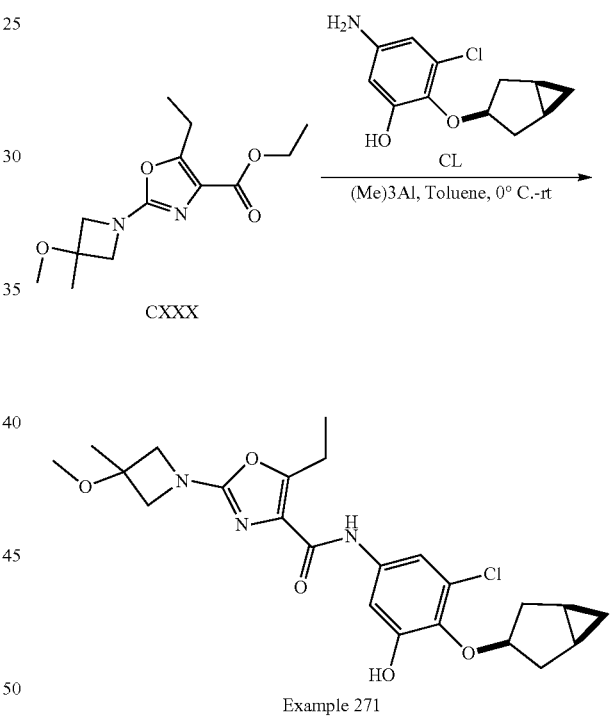

Example 271

To a stirred solution of CXXX (145 mg, 0.54 mmol) and amine CL (90.14 mg, 0.38 mmol) in dry toluene (5 mL), trimethylaluminum (1 mL, 2 M in toluene) dropwise at 0° C., and the resultant reaction mixture was allowed to stir at rt for 2 h. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography using 5-10% EtOAc in hexane as an eluent to afford N-(4-(cis-bicyclo[3.1.0]hexan-3-yloxy)-3-chloro-5-hydroxyphenyl)-5-ethyl-2-(3-methoxy-3-methylazetidin-1-yl)oxazole-4-carboxamide, Example 271 (29 mg, 11.6%).

Example 272

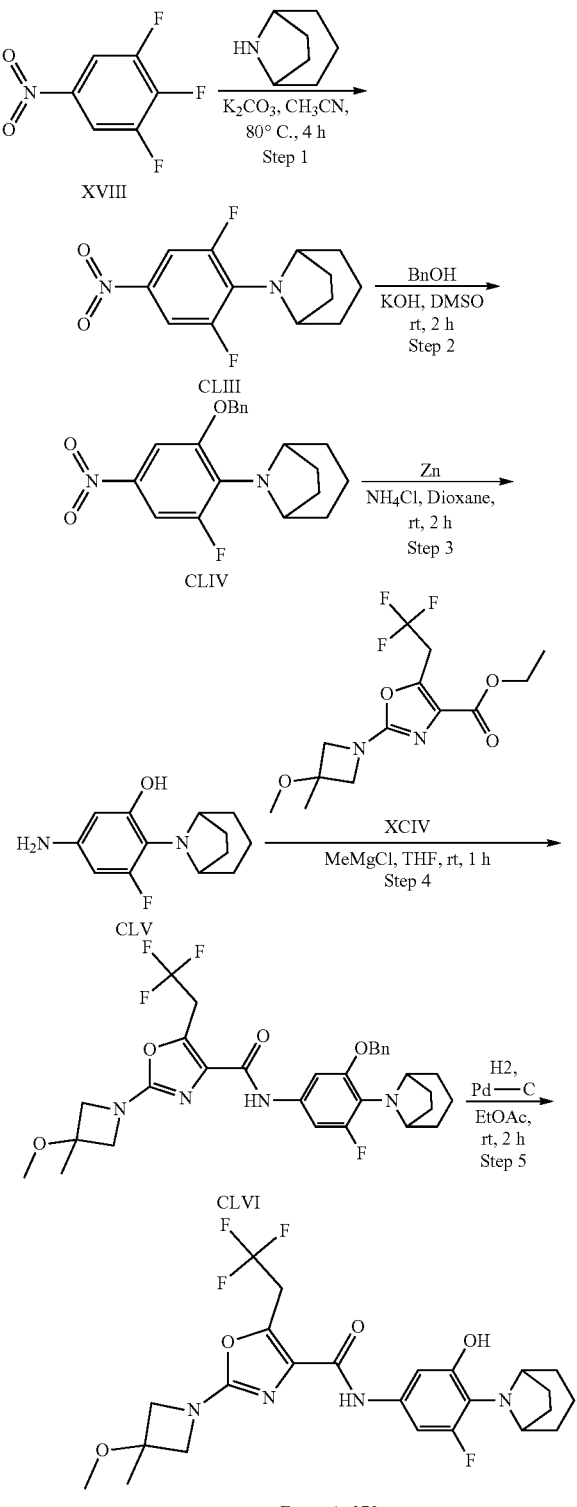

Example 272

Step 1: To a stirred solution of 8-azabicyclo[3.2.1] octane (350 mg, 3.1 mmol) and K₂CO₃ (1.17 g, 8.47 mmol) in CH₃CN (12 mL) was added 1,2,3-trifluoro-5-nitrobenzene, XVIII (500 mg, 2.82 mmol) and then it was allowed to stir for 4 h at 80° C. After completion [Monitored by TLC], reaction mixture was concentrated under reduced pressure. The resultant crude was purified through flash column chromatography using 5% EtOAc in hexane as an eluent to afford 8-(2,6-difluoro-4-nitrophenyl)-8-azabicyclo[3.2.1] octane, CLIII (700 mg, 92%) as yellow solid.

Step 2: To a stirred solution of benzyl alcohol (322 mg, 2.98 mmol), KOH dust (455 mg, 8.13 mmol) in DMSO (5 mL) was added 8-(2,6-difluoro-4-nitrophenyl)-8-azabicyclo [3.2.1]octane, CLIII (480 mg, 2.71 mmol) and stirred for 2 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using 5% EtOAc in hexane as an eluent to afford 8-(2-(benzyloxy)-6-fluoro-4-nitrophenyl)-8-azabicyclo [3.2.1]octane, CLIV (590 mg, 61%) as yellow solid.

Step 3: To a stirred solution of 8-(2-(benzyloxy)-6-fluoro-4-nitrophenyl)-8-azabicyclo[3.2.1]octane, CLIV (480 mg, 1.35 mmol) in 1,4 dioxane: water (6 mL, 5:1) was added zinc dust (425 mg, 6.74 mmol) along with ammonium chloride (436 mg, 8.09 mmol) at 0° C. It was then stirred for 2 h at rt. After completion [Monitored by TLC], reaction mixture was filtered through a glass sintered. The filtrate was dried over anhydrous sodium sulfate and concentrated under reduced pressure. The resultant crude was purified by flash column chromatography using 10% EtOAc in hexane to afford 3-(benzyloxy)-4-(8-azabicyclo[3.2.1]octan-8-yl)-5-fluoroaniline, CLV (300 mg, 68%) as off white solid.

Step 4: To a stirred solution of ethyl 2-(3-methoxy-3-methylazetidin-1-yl)-5-(2,2,2-trifluoroethyl)oxazole-4-carboxylate, XCIV (300 mg, 0.93 mmol) and 3-(benzyloxy)-4-(8-azabicyclo[3.2.1]octan-8-yl)-5-fluoroaniline, CLV (300 mg, 0.93 mmol) in dry THF (5 mL) was added MeMgCl (3 M in THF, 0.8 mL, 2.40 mmol) at rt and the resultant reaction mixture was allowed to stir at rt for 1 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography using 10% EtOAc in hexane to afford N-(3-(benzyloxy)-4-(8-azabicyclo[3.2.1] octan-8-yl)-5-fluorophenyl)-2-(3-methoxy-3-methylazetidin-1-yl)-5-(2,2,2-trifluoroethyl)oxazole-4-carboxamide, CLVI (180 mg, 32%) as an off-white solid.

Step 5: To a degassed solution of N-(3-(benzyloxy)-4-(8-azabicyclo[3.2.1]octan-8-yl)-5-fluorophenyl)-2-(3-methoxy-3-methylazetidin-1-yl)-5-(2,2,2-trifluoroethyl) oxazole-4-carboxamide, CLVI (180 mg, 0.30 mmol) in EtOAc Pd—C (10%, 40 mg) was added and the resultant reaction mixture was allowed to stir under hydrogen balloon pressure at rt for 2 h. After completion [Monitored with TLC/LCMS], reaction mixture was filtered and filtrate was concentrated under reduced pressure. The resultant crude was purified by flash column chromatography using 20% EtOAc in hexane to afford N-(4-(8-azabicyclo[3.2.1]octan-8-yl)-3-fluoro-5-hydroxyphenyl)-2-(3-methoxy-3-methylazetidin-1-yl)-5-(2,2,2-trifluoroethyl)oxazole-4-carboxamide, Example 272 (55 mg, 36%).

Examples 273

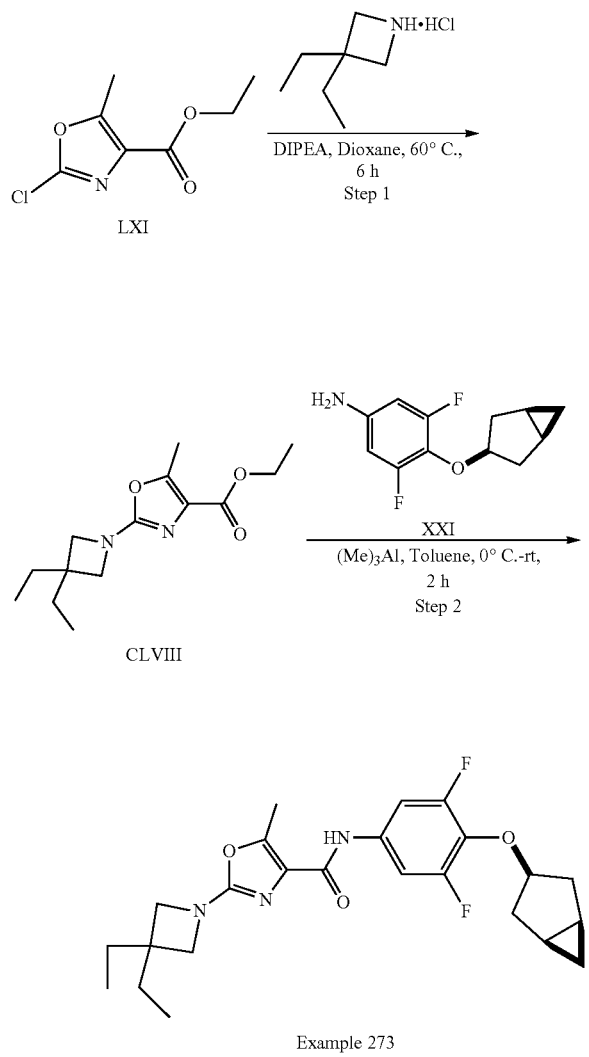

General Procedure for the Synthesis of Examples of General Structure CLX (Examples 274 and 275).

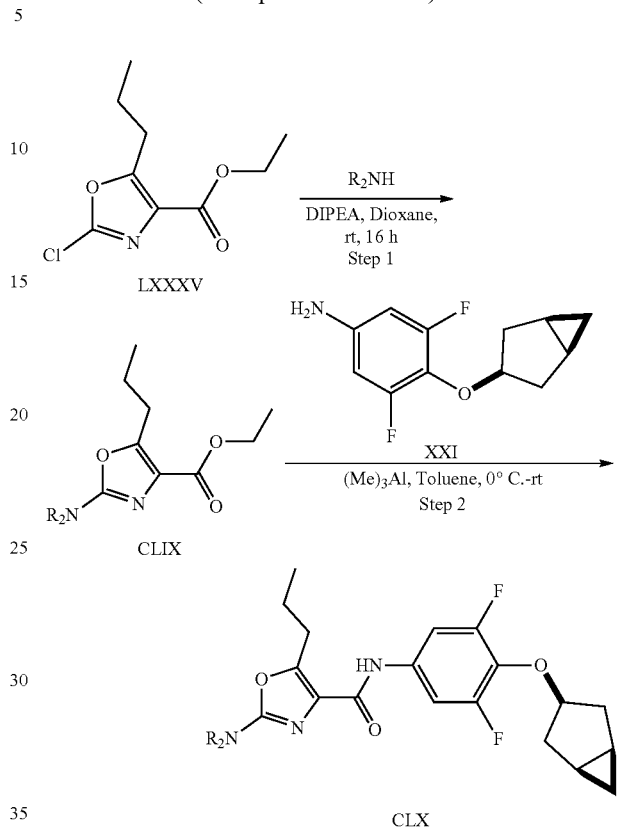

Step 1: To a stirred solution of ethyl 2-chloro-5-(2,2,2-trifluoroethyl)oxazole-4-carboxylate, LXI (300 mg, 1.58 mmol) and DIPEA (1.37 mL, 7.93 mmol) in dioxane (6 mL) was added 3,3-diethylazetidine hydrochloride (286 mg, 1.90 mmol) and the resultant reaction mixture was heated to 60° C. for 6 h and allowed to stir at room temperature for 16 h. After completion [Monitored by TLC], reaction mixture was concentrated under reduced pressure to remove dioxane. Resultant crude was purified through flash column chromatography using 20% EtOAc in hexane to provide CLVIII, (220 mg, 52%) as colorless oil.

Step 2: To a stirred solution of CLVIII (70 mg, 0.63 mmol) in dry toluene (4 mL) was added XXI (53 mg, 0.24 mmol) followed by cooling to 0° C. and dropwise addition of trimethylaluminum (0.5 mL, 2 M in toluene) and the resultant reaction mixture was stirred at 0° C. to rt for 2 h. After completion [Monitored with TLC], the reaction mixture was quenched with saturated ammonium chloride solution and partitioned with EtOAc. The organic layer was separated, dried over anhydrous sodium sulfate, and concentrated under reduced pressure. The resultant crude product was purified by silica gel column chromatography using 20% EtOAc in hexane to afford Example 273 (15 mg, 13%).

Step 1: To a stirred solution of LXXXV (1.0 eq.) and DIPEA (5 eq.) in dioxane (3 mL/mmol LXXXV) was added R₂NH (1.2 eq.) and the resultant reaction mixture was allowed to stir at room temperature for 16 h. After completion [Monitored by TLC], reaction mixture was concentrated under reduced pressure to remove dioxane. Resultant crude was purified through flash column chromatography to provide CLIX.

Step 2: To a stirred solution of CLIX (1.0 eq) and amine XXI (0.8 eq) in dry toluene (30 mL/g CLIX), trimethylaluminum (2 M in toluene, 4.0 eq) dropwise at 0° C., and the resultant reaction mixture was allowed to stir at rt. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography to afford products of general structure CLX.

All amines used as starting materials were purchased from commercial suppliers.

Example 274

The above referenced compound was synthesized utilizing the procedures outlined in the scheme above using pyrrolidine as amine in step 1 to afford N-(4-(cis-bicyclo[3.1.0]hexan-3-yloxy)-3,5-difluorophenyl)-5-propyl-2-(pyrrolidin-1-yl)oxazole-4-carboxamide (60 mg, 35%).

Example 275

The above referenced compound was synthesized utilizing the procedures outlined in the scheme above using octahydrocyclopenta[b]pyrrole as amine in step 1 to afford N-(4-(cis-bicyclo[3.1.0]hexan-3-yloxy)-3,5-difluorophenyl)-2-(hexahydrocyclopenta[b]pyrrol-1(2H)-yl)-5-propyloxazole-4-carboxamide (40 mg, 25%).

Preparation of Intermediate ethyl 2-chloro-5-(2-fluoroethyl)oxazole-4-carboxylate (CLXVII)

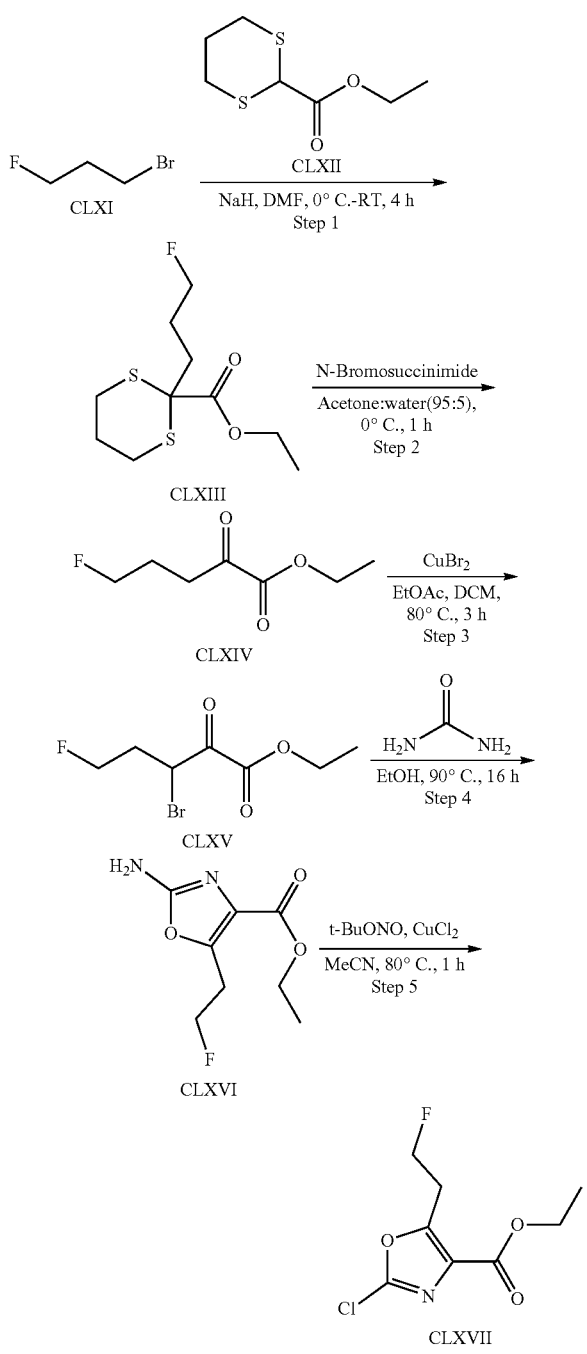

Step 1: To a solution of CLXI (20 g, 143.88 mmol) and CLXII (18.23 g, 94.96 mmol) in DMF (150 mL) was added NaH (5.7 g) at 0° C. and then it was allowed to warm up to room temperature gradually for a duration about 4 h. After completion of reaction [Monitored by TLC (KMnO4 stain)], cold water (1 L) was added, and extracted with ethyl acetate (2×500 mL). Combined organic layer was washed with brine solution, dried over anhydrous $Na_2SO_4$ and concentrated to vacuo to obtain the crude, which was purified on silica gel flash chromatography (2% EtOAc in hexane) to afford ethyl 2-(3-fluoropropyl)-1,3-dithiane-2-carboxylate, CLXIII (20 g, 83%) as colorless liquid.

Step 2: Solution of CLXIII (20 g, 79.36 mmol) in acetone 400 mL (5 mL/mmol) was added dropwise over 5 minutes to a stirred suspension of N-bromosuccinimide (98.88 g, 555.55 mmol) in acetone/water 1.6 L (95/5, v/v, 3 mL/mmol) at 0° C. The reaction mixture was stirred at the same temperature for 1 hour, while the progress of the reaction was monitored by thin layer chromatography, and then aqueous sodium sulphite was added. the mixture was stirred until the colour faded from the organic layer. Diluted with a mixture of methylene chloride/hexane (1/1, v/v, 1 L) and was washed with aq 5% NaHCO3 solution (500 mL×2), water (500 mL×2), phases were separated and dried over magnesium sulfate. The solvent was removed under reduced pressure to obtain the crude, which was purified on silica gel flash chromatography (10% EtOAc in hexane) to afford ethyl 5-fluoro-2-oxopentanoate, CLXIV (9 g, 70%) as colorless liquid.

Step 3: To the solution of ethyl 5-fluoro-2-oxopentanoate, CLXIV (11 g, 67.90 mmol) in ethyl acetate (330 mL) and DCM (220 mL) was added $CuBr_2$ (37.85 g, 169.75 mmol) and the resultant reaction mixture was allowed to stir at 80° C. for 3 h. After completion [Monitored by TLC (KMnO4 stain)], the reaction mixture was filtered through celite and filtrate part was concentrated to afford the crude. Purification of the residue was carried out by silica gel column chromatography (5% EtOAc in hexane) to obtain desired product ethyl 3-bromo-5-fluoro-2-oxopentanoate, CLXV (12 g, 73%) as a as colorless liquid.

Step 4: To the stirred solution ethyl 3-bromo-5-fluoro-2-oxopentanoate, CLXV (12 g, 49.79 mmol) in ethanol (240 mL) was added urea (8.96 g 149.37 mmol) at room temperature and then it was heated to 90° C. for 16 h. After completion [Monitored by TLC, LC-MS], reaction mixture was concentrated to remove ethanol. The crude reaction mixture was then treated with saturated aqueous solution of $NaHCO_3$ (200 mL) and extracted with DCM (2×400 mL). Organic layer was washed with water (2×200 mL) and was dried over anhydrous $Na_2SO_4$ and concentrated under reduced pressure. Crude residue thus obtained was triturated with 50% diethyl ether/pentane, resultant precipitate was filtered through sintered glass funnel and dried under vacuum to afford ethyl 2-amino-5-(2-fluoroethyl)oxazole-4-carboxylate, CLXVI (7 g, 69.5%) as off-white solid.

Step 5: The suspension of $CuCl_2$ (4.73 g, 35.34 mmol) and tert-Butyl nitrite (6.72 mL, 56.13 mmol) in 200 mL of acetonitrile was stirred at 70° C. for 15 min. Then suspension of ethyl 2-chloro-5-(2-fluoroethyl)oxazole-4-carboxylate, CLXVI (7 g, 34.65 mmol) in acetonitrile (80 mL) was then added to the hot reaction mixture dropwise and the reaction mixture was allowed to stir at 80° C. for 1 h. After completion of [Monitored by TLC], reaction mixture was concentrated to remove acetonitrile and water (100 mL) and then EtOAc (100 mL) was added and the mixture was filtered through celite bed. Then the filtrate was diluted with ethyl acetate (500 mL) and water (400 mL), organic layer was separated, dried over anhydrous sodium sulfate, and concentrated under reduced pressure. The crude was purified by silica gel column chromatography (10% EtOAc in hexane) to afford ethyl 2-chloro-5-(2-fluoroethyl)oxazole-4-carboxylate, CLXVII (5 g, 65%).

General Procedure for the Synthesis of Examples of General Structure CLXIX (Examples 276-288).

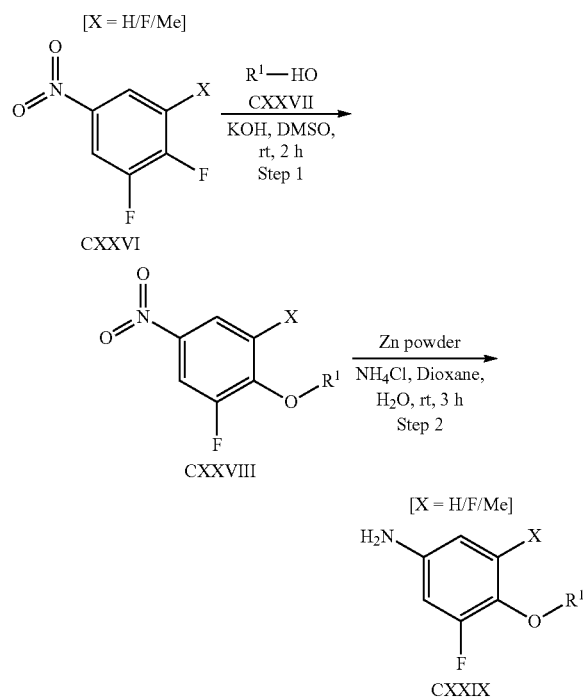

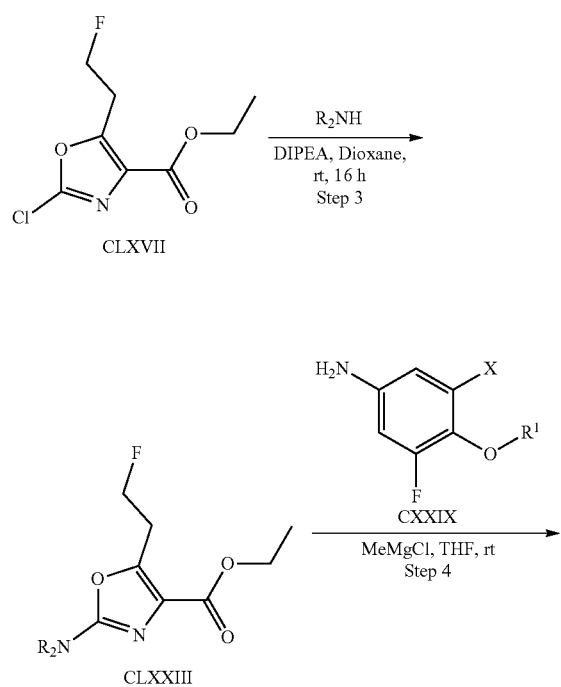

Step 1. To a stirred solution of CXXVI (1.0 eq) and CXXVII (1.2 eq) in DMSO (3 mL/mmol), was added KOH (3.0 eq). The reaction was stirred for 2 h at rt. After completion [Monitored by TLC], the resultant reaction mixture was partitioned between EtOAc and water. Organic layer was dried over anhydrous sodium sulfate and concentrated under reduced pressure. The crude was purified through flash column chromatography using EtOAc in hexane as an eluent to afford products of general structure CXXVIII.

Step 2: To a stirred solution of CXXVIII (1 eq.) in (20 mL/g) of 1,4 dioxane:water (5:1) was added zinc dust (7 eq.) along with ammonium chloride (7 eq.) at 0° C. It was then stirred for 3 h at rt. After completion [Monitored by TLC], reaction mixture was filtered through a glass sintered. The filtrate was dried over anhydrous sodium sulfate and concentrated under reduced pressure. The resultant crude was purified by flash column chromatography using 10% EtOAc in hexane to afford products of general structure CXXIX.

Step 3: To a stirred solution of CLXVII (1.0 eq.) and DIPEA (3.0 equiv) in dioxane (3 mL/mmol) was added $R_2NH$ (1.1 eq.) and resultant reaction mixture was allowed to stir at room temperature for 16 h. After completion [Monitored by TLC], reaction mixture was concentrated under reduced pressure to remove dioxane. Resultant crude was purified through combiflash column chromatography to afford products of general structure CLXVIII.

Step 4: To a stirred solution of CLXVIII (1.0 eq.) and CXXIX (1.0 eq.) in dry THF (30 mL/g), was added MeMgCl (3 M in THF, 2.4 eq) dropwise and was stirred for 1 h at rt. The reaction was monitored by TLC. After completion reaction mixture was quenched with 1 N HCl and extracted with EtOAc and washed with water. Organic layer was separated, dried over anhydrous sodium sulfate, and concentrated under reduced pressure. Resultant crude was purified by combiflash column chromatography to afford products of general structure CLXIX.

All the alcohols and amines used as starting materials were purchased from commercial suppliers.

Example 276

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3,5-difluorophenyl)-5-(2-fluoroethyl)-2-(3-methoxy-3-methylazetidin-1-yl)oxazole-4-carboxamide (90 mg, 55.36%).

Example 277

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and 3-ethyl-3-methoxyazetidine as the amine in step 3, to provide N-(4-(bicyclo[3.1.1]heptan-3-yloxy)-3-fluoro-5-methylphenyl)-2-(3-ethyl-3-methoxyazetidin-1-yl)-5-(2-fluoroethyl)oxazole-4-carboxamide (35 mg, 24%).

Example 278

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and pyrrolidine as the amine in step 3, to provide N-(4-(bicyclo[3.1.1]heptan-3-yloxy)-3-fluoro-5-methylphenyl)-5-(2-fluoroethyl)-2-(pyrrolidin-1-yl)oxazole-4-carboxamide (30 mg, 27%).

Example 279

The above referenced compound was synthesized utilizing the procedures outlined in the scheme above wherein compound CXXVI was 3,4,5-trifluoronitrobenzene, using bicyclo[3.1.1]heptan-3-ol as the alcohol in step 1 and pyrrolidine as the amine in step 3, to provide N-(4-(bicyclo[3.1.1]heptan-3-yloxy)-3,5-difluorophenyl)-5-(2-fluoroethyl)-2-(pyrrolidin-1-yl)oxazole-4-carboxamide (30 mg, 26.73%).

Example 280

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3-methoxy-3-methylazetidine hydrochloride as the amine in step 3, to provide N-(4-(cis-bicyclo[3.1.0]hexan-3-yloxy)-3-fluoro-5-methylphenyl)-5-(2-fluoroethyl)-2-(3-methoxy-3-methylazetidin-1-yl)oxazole-4-carboxamide (58 mg, 30.86%).

Example 281

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and 3-methoxy-3-methylazetidine hydrochloride as the amine in step 3, to provide N-(4-(bicyclo[3.1.1]heptan-3-yloxy)-3-fluoro-5-methylphenyl)-5-(2-fluoroethyl)-2-(3-methoxy-3-methylazetidin-1-yl)oxazole-4-carboxamide (15 mg, 10.59%).

Example 282

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and 3,3-diethylazetidine hydrochloride as the amine in step 3, to provide N-(4-(bicyclo[3.1.1]heptan-3-yloxy)-3-fluoro-5-methylphenyl)-2-(3,3-diethylazetidin-1-yl)-5-(2-fluoroethyl)oxazole-4-carboxamide (20 mg, 20.37%).

Example 283

The above referenced compound was synthesized utilizing the procedures outlined in the scheme above wherein compound CXXVI was 1,2-difluoro-4-nitrobenzene, using bicyclo[3.1.1]heptan-3-ol as the alcohol in step 1 and 3,3-diethylazetidine hydrochloride as the amine in step 3, to provide N-(4-(bicyclo[3.1.1]heptan-3-yloxy)-3-fluorophenyl)-2-(3,3-diethylazetidin-1-yl)-5-(2-fluoroethyl)oxazole-4-carboxamide (70 mg, 55.14%).

Example 284

The above referenced compound was synthesized utilizing the procedures outlined in the scheme above wherein compound CXXVI was 3,4,5-trifluoronitrobenzene, using bicyclo[3.1.1]heptan-3-ol as the alcohol in step 1 and 5-azaspiro[2.4]heptane as the amine in step 3, to provide N-(4-(bicyclo[3.1.1]heptan-3-yloxy)-3,5-difluorophenyl)-5-(2-fluoroethyl)-2-(5-azaspiro[2.4]heptan-5-yl)oxazole-4-carboxamide (40 mg, 29.68%).

Example 285

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3-fluoro-5-methylphenyl)-2-(3,3-diethylazetidin-1-yl)-5-(2-fluoroethyl)oxazole-4-carboxamide (33 mg, 19.27%).

Example 286

The above referenced compound was synthesized utilizing the procedures outlined in the scheme above wherein compound CXXVI was 3,4,5-trifluoronitrobenzene, using bicyclo[3.1.1]heptan-3-ol as the alcohol in step 1 and 3,3-diethylazetidine hydrochloride as the amine in step 3, to provide N-(4-(bicyclo[3.1.1]heptan-3-yloxy)-3,5-difluorophenyl)-2-(3,3-diethylazetidin-1-yl)-5-(2-fluoroethyl)oxazole-4-carboxamide (50 mg, 37.94%).

Example 287

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 3,3-diethylazetidine hydrochloride as the amine in step 3, to provide N-(4-(cis-bicyclo[3.1.0]hexan-3-yloxy)-3,5-difluorophenyl)-2-(3,3-diethylazetidin-1-yl)-5-(2-fluoroethyl)oxazole-4-carboxamide (100 mg, 56.81%).

Example 288

The above referenced compound was synthesized utilizing the procedures outlined in the scheme above wherein compound CXXVI was 3,4,5-trifluoronitrobenzene, using cis-bicyclo[3.1.0]hexan-3-ol as the alcohol in step 1 and 5-azaspiro[2.4]heptane as the amine in step 3, to provide N-(4-(cis-bicyclo[3.1.0]hexan-3-yloxy)-3,5-difluorophenyl)-5-(2-fluoroethyl)-2-(5-azaspiro[2.4]heptan-5-yl)oxazole-4-carboxamide (40 mg, 24.47%).

General Procedure for the Synthesis of Examples of General Structure CLXIX (Examples 289-292).

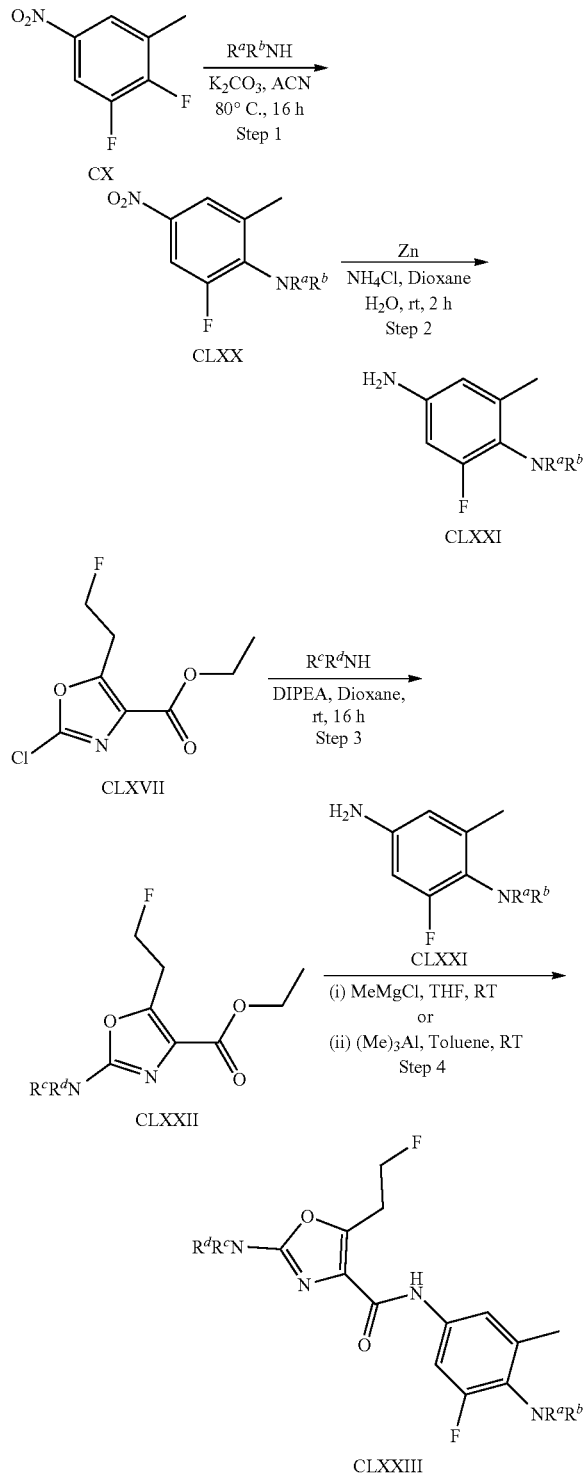

Step 1: To a stirred solution of compound CX (1.0 eq) and potassium carbonate (2.0 eq) in acetonitrile (3 mL/mmol) was added amine $R^aR^bNH$ (1.1 eq). The reaction mass was heated at 80° C. for 16 h. After completion [Monitored by TLC or LC-MS], reaction mixture was concentrated to remove volatiles. The crude reaction mixture was then diluted with EtOAc and washed with brine. The organic layer was separated, dried over anhydrous sodium sulfate, and concentrated under reduced pressure. The crude material was purified through flash column chromatography using EtOAc/hexane as eluent to afford the intermediate compound CLXX.

Step 2: To a stirred solution of compound CLXX in 1,4 dioxane:water (5:1) was added zinc dust (7.0 eq) followed by with ammonium chloride (7.0 eq) at 0° C. It was then stirred for 2 h at rt. After completion [Monitored by TLC], the reaction mixture was filtered through a sintered glass. The filtrate was dried over anhydrous $Na_2SO_4$, concentrated under reduced pressure and purified through flash column chromatography using EtOAc-hexane as eluent to afford intermediate compound CLXXI.

Step 3: To a stirred solution of compound CLXVII (1.0 eq.) in dioxane (3 mL/g) was added amine $R^cR^dNH$ (1.1 eq.) and DIPEA (3.0 equiv), the resultant reaction mixture was allowed to stir at room temperature for 16 h. After completion [Monitored by TLC], reaction mixture was concentrated under reduced pressure to remove dioxane. Resultant crude was purified through flash column chromatography using EtOAc-Hexane as eluent to provide CLXXII.

Step 4, Condition (i): To a stirred solution of CLXXII (1.0 eq.) and ester CLXXI (1.0 eq.) in dry THF (30 mL/g), was added MeMgCl (3 M in THF, 2.4 eq) dropwise and was stirred for 1 h at RT. The reaction was monitored by TLC. After completion reaction mixture was quenched with 1 N HCl and extracted with EtOAc and washed with water. Organic layer was separated, dried over anhydrous sodium sulfate, and concentrated under reduced pressure. Resultant crude was purified by combiflash column chromatography to afford products of general structure CLXXIII. Example 292 was synthesized following condition (ii): To a stirred solution of CLXXII (1.0 eq) in dry toluene (30 mL/g), CLXXI (1.0 eq) was added followed by dropwise addition of trimethylaluminum (2 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. The resulting crude product was purified by flash column chromatography to afford products of general structure CLXXIII.

All amines used as starting materials for Step 1 were purchased from chemical providers.

Example 289

The above referenced compound was synthesized utilizing the procedures outlined in the scheme above using 8-azabicyclo[3.2.1]octane as the amine in step 1 and 3,3-diethylazetidine hydrochloride as the amine in step 3, to provide N-(4-(8-azabicyclo[3.2.1]octan-8-yl)-3-fluoro-5-methylphenyl)-2-(3,3-diethylazetidin-1-yl)-5-(2-fluoroethyl)oxazole-4-carboxamide (21 mg, 20%).

Example 290

The above referenced compound was synthesized utilizing the procedures outlined in the scheme above using 8-azabicyclo[3.2.1]octane as the amine in step 1 and 3-methoxy-3-methylazetidine hydrochloride as the amine in step 3, to provide N-(4-(bicyclo[3.1.1]heptan-3-yloxy)-3- fluoro-5-methylphenyl)-5-(2-fluoroethyl)-2-(3-methoxy-3-methylazetidin-1-yl)oxazole-4-carboxamide (19 mg, 25.42%).

Example 291

The above referenced compound was synthesized utilizing the procedures outlined in the scheme above using 8-azabicyclo[3.2.1]octane as the amine in step 1 and 3-ethyl-3-methoxyazetidine as the amine in step 3, to provide N-(4-(8-azabicyclo[3.2.1]octan-8-yl)-3-fluoro-5-methylphenyl)-2-(3-ethyl-3-methoxyazetidin-1-yl)-5-(2-fluoroethyl)oxazole-4-carboxamide (15 mg, 8.38%).

Example 292

The above referenced compound was synthesized utilizing the procedures outlined in the scheme above using bicyclo[3.1.1]heptan-3-amine as the amine in step 1 and step 1 was performed at 120° C. for 48 h, utilizing 3,3-diethylazetidine hydrochloride as the amine in step 3, to provide N-(4-(bicyclo[3.1.1]heptan-3-ylamino)-3-fluoro-5-methylphenyl)-2-(3,3-diethylazetidin-1-yl)-5-(2-fluoroethyl)oxazole-4-carboxamide (30 mg, 36%).

General Procedure for the Synthesis of Examples of General Structure CLXXVII (Examples 293-296).

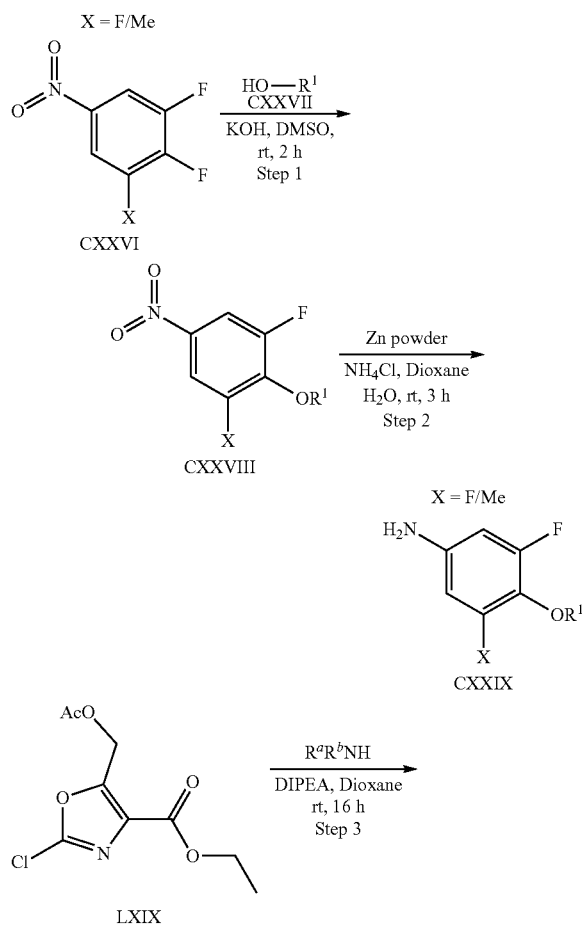

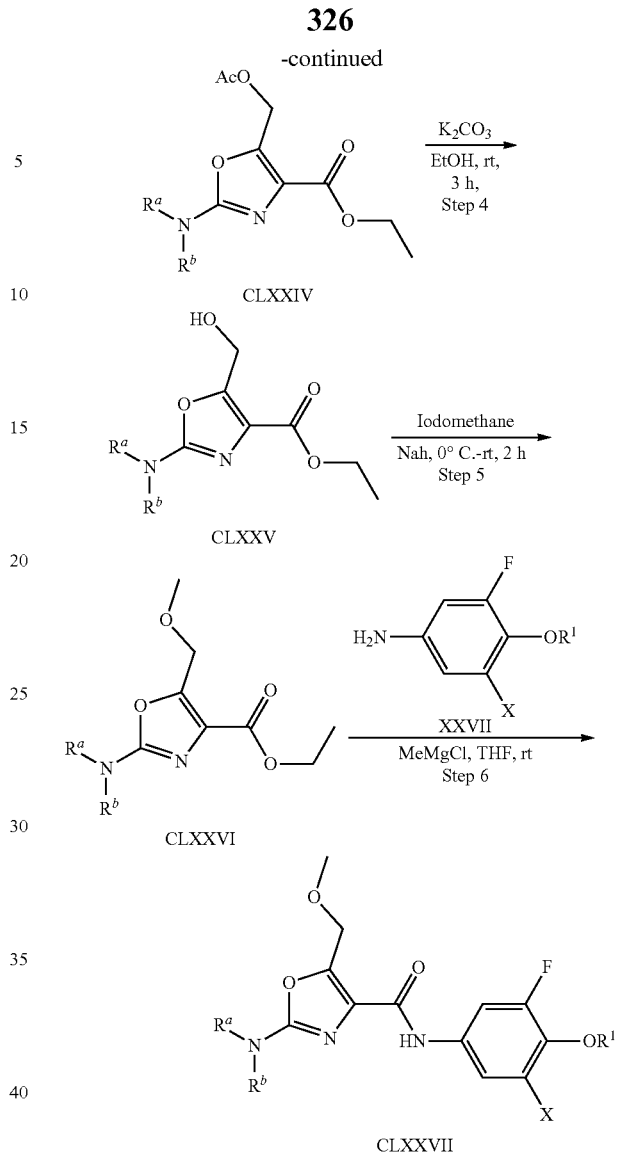

All amines and alcohols used as starting materials were purchased from commercial suppliers.

Step 1. To a stirred solution of CXXVI (1.0 eq) and CXXVII (1.2 eq) in DMSO (3 mL/mmol), was added KOH (3.0 eq). The reaction was stirred for 2 h at rt. After completion [Monitored by TLC], the resultant reaction mixture was partitioned between EtOAc and water. Organic layer was dried over anhydrous sodium sulfate and concentrated under reduced pressure. The crude was purified through flash column chromatography using EtOAc in hexane as an eluent to afford products of general structure CXXVIII.

Step 2: To a stirred solution of CXXVIII (1 eq) in (20 mL/g CXXVIII) 1,4 dioxane: water (5:1) was added zinc dust (7 eq.) along with ammonium chloride (7 eq.) at 0° C. It was then stirred for 3 h at rt. After completion [Monitored by TLC], reaction mixture was filtered through a glass sintered. The filtrate was dried over anhydrous sodium sulfate and concentrated under reduced pressure. The resultant crude was purified by flash column chromatography using EtOAc in hexane to afford products of general structure CXXIX.

Step 3: To the suspension of ethyl 5-(acetoxymethyl)-2-chlorooxazole-4-carboxylate, LXIX (1.0 eq) and DIPEA (5.0 eq) in dioxane (15 mL/g) was added $R^aR^bNH$ (1.2 eq) the resulting mixture was stirred at rt for 16 h. After completion of reaction [Monitored by TLC], the reaction mixture was filtered and the filtrate was concentrated and purified through silica gel column chromatography using EtOAc in hexane as an eluent to afford products of general structure CLXXIV.

Step 4: To a suspension of CLXXIV in EtOH (15 mL) was added $K_2CO_3$ (2.0 eq) and then it was stirred at for 3 h at rt. After completion of the reaction [Monitored by TLC], the reaction mixture was filtered, and the filtrate was concentrated and purified through silica gel column chromatography using EtOAc in Hexane as an eluent to afford products of general structure CLXXV.

Step 5: To a stirred solution of CLXXV (1.0 eq) in DMF (5 mL/mmol) was added NaH (2.0 eq) was added portion wise under ice cool condition. After 15 minutes $CH_3I$ (3.0 eq) was added to it and the reaction mixture was stirred for 2 h at room temperature. After completion [Monitored with TLC], the reaction mixture was quenched with saturated ammonium chloride solution and partitioned with EtOAc. Organic layer was separated, dried over anhydrous sodium sulfate, and concentrated under reduced pressure to get the crude product. The resultant crude material was purified by silica gel flash column chromatography using EtOAc-Hexane as eluting solvent to afford products of general structure CLXXVI.

Step 6: To a stirred solution of CLXXVI (1.0 eq) in dry THF (30 mL/g), XXVII (0.8 eq) was added, followed by dropwise addition of MeMgCl (3 M in THF, 2.5 eq) at rt and the resultant reaction mixture was allowed to stir for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography to afford example with the general formula CLXXVII. For Example 296 following condition was applied: To a stirred solution of CLXXVI (1.0 eq) in dry toluene (30 mL/g), 4-(cis-bicyclo[3.1.0]hexan-3-yloxy)-3,5-difluoroaniline XXVII (0.8 eq) was added, followed by dropwise addition of trimethylaluminum (2 M in toluene, 4.0 eq) at 0° C. and the resultant reaction mixture was allowed to stir at rt for 2 h. After completion [Monitored with TLC/LCMS], reaction mixture was quenched with saturated ammonium chloride solution and partitioned with EtOAc. Organic layer was separated, dried over anhydrous sodium sulfate, and concentrated under reduced pressure. The resultant crude was purified by flash column chromatography to afford example with the general formula CLXXVII.

Example 293

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3,3-diethylazetidine as the amine in step 3 affording N-(4-(cis-bicyclo[3.1.0]hexan-3-yloxy)-3-fluoro-5-methylphenyl)-2-(3,3-diethylazetidin-1-yl)-5-(methoxymethyl)oxazole-4-carboxamide (25 mg, 19%).

Example 294

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3-methoxy-3-methylazetidine as the amine in step 3 affording N-(4-(cis-bicyclo[3.1.0]hexan-3-yloxy)-3-fluoro-5-methylphenyl)-2-(3-methoxy-3-methylazetidin-1-yl)-5-(methoxymethyl)oxazole-4-carboxamide (40 mg, 27%).

Example 295

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3,3-diethylazetidine as the amine in step 3 affording N-(4-(cis-bicyclo[3.1.0]hexan-3-yloxy)-3,5-difluorophenyl)-2-(3,3-diethylazetidin-1-yl)-5-(methoxymethyl)oxazole-4-carboxamide (25 mg, 17%).

Example 296

The above referenced compound was synthesized utilizing the procedures outlined in the scheme above wherein compound CXXVI was 1,2-difluoro-3-methyl-5-nitrobenzene, using bicyclo[3.1.1]heptan-3-ol as the alcohol in step 1 and (3-methylazetidin-3-yl)methanol as the amine in step 3 affording N-(4-(bicyclo[3.1.1]heptan-3-yloxy)-3-fluoro-5-methylphenyl)-2-(3-(hydroxymethyl)-3-methylazetidin-1-yl)-5-(methoxymethyl)oxazole-4-carboxamide (50 mg, 35%).

General Procedure for the Synthesis of Examples of General Structure CLXXXI (Examples 297-308).

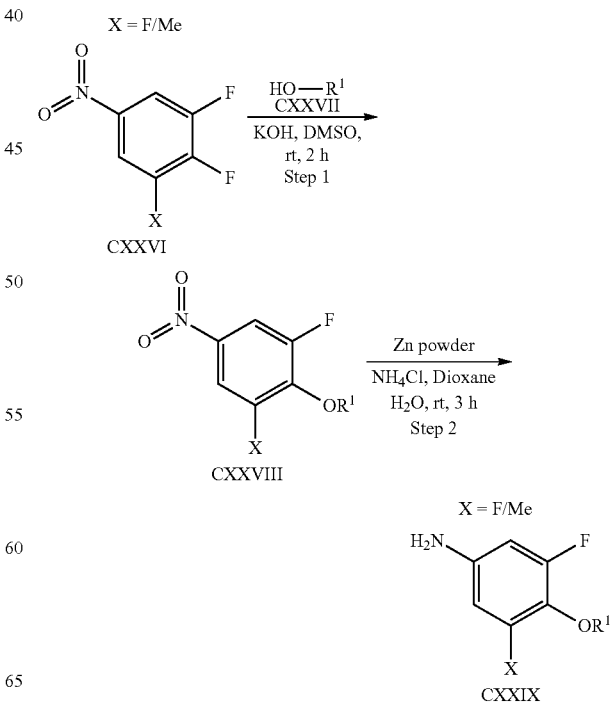

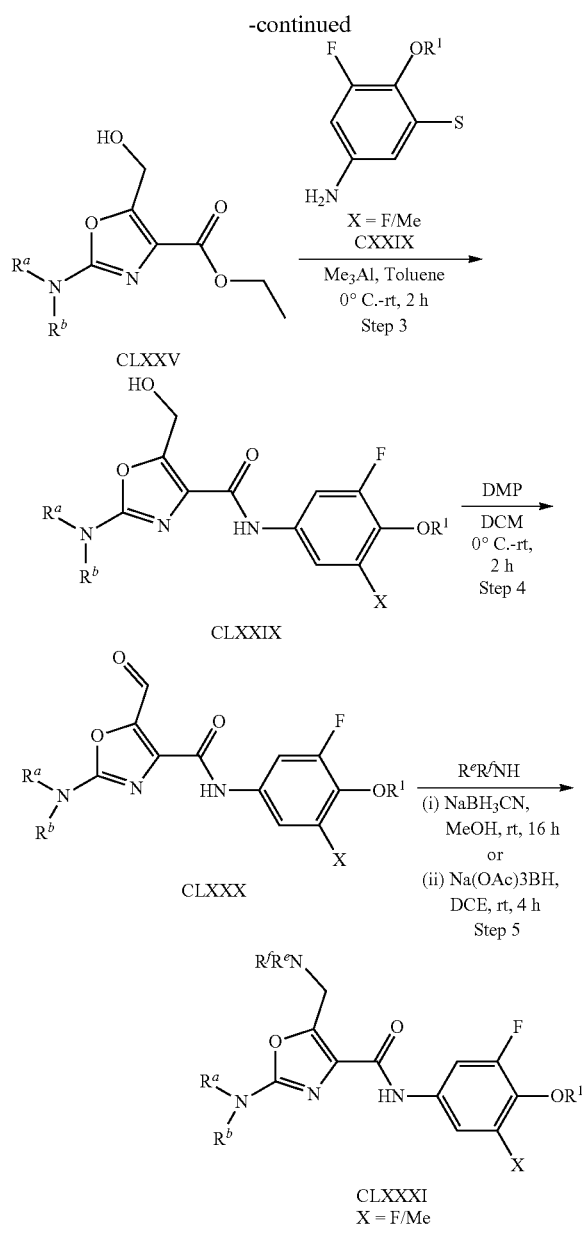

CLXXXI
X = F/Me

Step 1: To a stirred solution of alcohol CXXVII (1.1 eq) KOH dust (3.0 eq) in DMSO (10 mL/g) was added CXXVI (1.0 eq), and stirred for 2 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using EtOAc in hexane as an eluent to afford products of general structure CXXVIII.

Step 2: To a stirred solution of CXXVIII (1.0 eq) in 1,4 dioxane: water (10 mL/g, 5:1) was added zinc dust (7.0 eq) along with ammonium chloride (7.0 eq) at 0° C. It was then stirred for 3 h at rt. After completion [Monitored by TLC], reaction mixture was filtered through a glass sintered. The filtrate was dried over anhydrous sodium sulfate and concentrated under reduced pressure. The resultant crude was purified by flash column chromatography using 10% EtOAc in hexane to afford products of general structure CXXIX.

Step 3: To a stirred solution of CLXXV (1.0 eq) in dry toluene (30 mL/g), CXXIX (0.8 eq) was added followed by dropwise addition of trimethyl aluminum (2 M in toluene, 4.0 eq) at 0° C. and the resultant reaction mixture was allowed to stir at rt for 2 h. After completion [Monitored with TLC/LCMS], the reaction mixture was quenched with saturated ammonium chloride solution and partitioned with EtOAc. Organic layer was separated, dried over anhydrous sodium sulfate, and concentrated under reduced pressure. The resulting crude product was purified by flash column chromatography to afford products of general structure CLXXIX.

Step 4: To a stirred solution of CLXXIX (1.0 eq) in DCM (20 mL/g) was added DMP (2.0 eq) at 0° C. It was then warm up to rt and stirred for 2 h at rt. After completion [Monitored by TLC], reaction mixture was quenched with the solution of mixture of $Na_2S_2O_3$ and $NaHCO_3$ two times. The resultant crude was purified by flash column chromatography using EtOAc in hexane to afford products of general structure CLXXX.

Step 5: To a stirred solution of CLXXX (1 eq.), $R^cR^dNH$ (3.0 eq.) and catalytic amount of AcOH in MeOH (3 mL/mmol CLXXX) was stirred for 2 h at rt. Then $NaBH_3CN$ was added to the above reaction mass under ice cold condition and allowed to stir for 16 h at rt. After completion [Monitored with TLC], the reaction mixture was quenched with saturated solution of sodium bicarbonate and diluted with DCM. Organic layer was separated, dried over anhydrous sodium sulfate, and concentrated under reduced pressure to get the crude product. The resultant crude material was purified by silica gel flash column chromatography using EtOAc-Hexane as eluting solvent to afford examples with the general formula CLXXXI. Example 297 was synthesized following condition (ii) as follows: To a stirred solution of CLXXX (1 eq.), $R^cR^dNH$ (3.0 eq.) and catalytic amount of AcOH in DCE (3 mL/mmol CLXXX) was stirred for 2 h at rt. Then $Na(OAC)_3BH$ (2 eq.) was added to the above reaction mass under ice cold condition and allowed to stir for 2 h at rt. After completion [Monitored with TLC], the reaction mixture was quenched with saturated solution of sodium bicarbonate and diluted with DCM. Organic layer was separated, dried over anhydrous sodium sulfate, and concentrated under reduced pressure to get the crude product. The resultant crude material was purified by silica gel flash column chromatography using EtOAc-Hexane as eluting solvent to afford examples with the general formula CLXXXI.

All alcohols and amines used as starting materials were purchased from chemical providers.

Example 297

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3,3-diethylazetidine hydrochloride as amine in step 3 and azetidine as the amine in step 5, to provide 5-(azetidin-1-ylmethyl)-N-(4-(cis-bicyclo[3.1.0]hexan-3-yloxy)-3-fluoro-5-methylphenyl)-2-(3,3-diethylazetidin-1-yl)oxazole-4-carboxamide (22 mg, 17%).

Example 298

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and 3,3-diethylazetidine hydrochloride as amine in step 3 and pyrrolidine as the amine in step 5, to provide N-(4-(cis-bicyclo[3.1.0]hexan-3-yloxy)-3-fluoro-5-methylphenyl)-2-(3,3-diethylazetidin-1-yl)-5-(pyrrolidin-1-ylmethyl)oxazole-4-carboxamide (40 mg, 21%).

Example 299

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3,3-diethylazetidine hydrochloride as amine in step 3 and pyrrolidine as the amine in step 5, to provide N-(4-(cis-bicyclo[3.1.0]hexan-3-yloxy)-3,5-difluorophenyl)-2-(3,3-diethylazetidin-1-yl)-5-(pyrrolidin-1-ylmethyl)oxazole-4-carboxamide (15 mg, 13%).

Example 300

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3,3-diethylazetidine hydrochloride as amine in step 3 and azetidine as the amine in step 5, to provide 5-(azetidin-1-ylmethyl)-N-(4-(cis-bicyclo[3.1.0]hexan-3-yloxy)-3,5-difluorophenyl)-2-(3,3-diethylazetidin-1-yl)oxazole-4-carboxamide (10 mg, 18%).

Example 301

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3,3-diethylazetidine hydrochloride as amine in step 3 and dimethyl amine as the amine in step 5, to provide N-(4-(cis-bicyclo[3.1.0]hexan-3-yloxy)-3,5-difluorophenyl)-2-(3,3-diethylazetidin-1-yl)-5-((dimethylamino)methyl)oxazole-4-carboxamide (16 mg, 17%).

Example 302

The above referenced compound was synthesized utilizing the procedures outlined in the scheme above wherein compound CXXVI was 1,2,3-trifluoro-5-nitrobenzene, using bicyclo[3.1.1]heptan-3-ol as the alcohol in step 1 and 3-ethyl-3-methoxyazetidine as amine in step 3 and N-ethylmethylamine as the amine in step 5, to provide N-(4-(bicyclo[3.1.1]heptan-3-yloxy)-3,5-difluorophenyl)-5-((ethyl(methyl)amino)methyl)-2-(3-ethyl-3-methoxyazetidin-1-yl)oxazole-4-carboxamide (20 mg, 30.%).

Example 303

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3-ethyl-3-methoxyazetidine as amine in step 3 and dimethyl amine as the amine in step 5, to provide N-(4-(cis-bicyclo[3.1.0]hexan-3-yloxy)-3,5-difluorophenyl)-5-((dimethylamino)methyl)-2-(3-ethyl-3-methoxyazetidin-1-yl)oxazole-4-carboxamide (20 mg, 31%).

Example 304

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and 3-ethyl-3-methoxyazetidine as amine in step 3 and N-ethylmethylamine as the amine in step 5, to provide N-(4-(cis-bicyclo[3.1.0]hexan-3-yloxy)-3,5-difluorophenyl)-5-((ethyl(methyl)amino)methyl)-2-(3-ethyl-3-methoxyazetidin-1-yl)oxazole-4-carboxamide (30 mg, 18%).

Example 305

The above referenced compound was synthesized utilizing the procedures outlined in the scheme above wherein compound CXXVI was 1,2-difluoro-3-methyl-5-nitrobenzene, using cis-bicyclo[3.1.0]hexan-3-ol as the alcohol in step 1 and pyrrolidine as amine in step 3 and azetidine as the amine in step 5, to provide 5-(azetidin-1-ylmethyl)-N-(4-(cis-bicyclo[3.1.0]hexan-3-yloxy)-3-fluoro-5-methylphenyl)-2-(pyrrolidin-1-yl)oxazole-4-carboxamide (30 mg, 62%).

Example 306

The above referenced compound was synthesized utilizing the procedures outlined in the scheme above wherein compound CXXVI was 1,2,3-trifluoro-5-nitrobenzene, using cis-bicyclo[3.1.0]hexan-3-ol as the alcohol in step 1 and pyrrolidine as amine in step 3 and azetidine as the amine in step 5, to provide 5-(azetidin-1-ylmethyl)-N-(4-(cis-bicyclo[3.1.0]hexan-3-yloxy)-3,5-difluorophenyl)-2-(pyrrolidin-1-yl)oxazole-4-carboxamide (15 mg, 14%).

Example 307

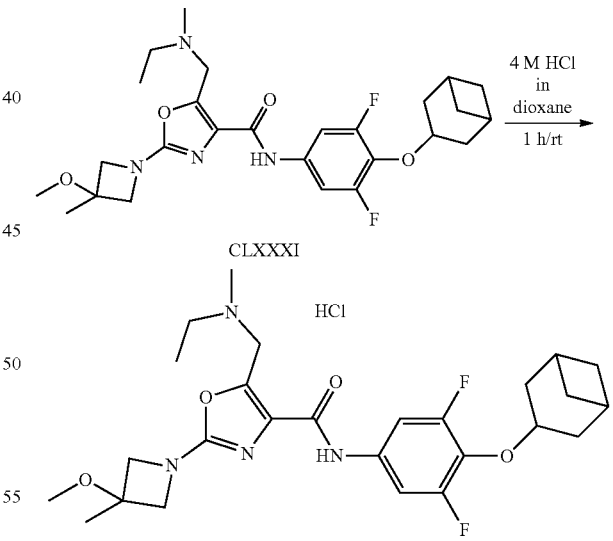

Example 307

Compound CLXXXI was synthesized utilizing the procedures outlined in the scheme above wherein compound CXXVI was 1,2,3-trifluoro-5-nitrobenzene, using bicyclo[3.1.1]heptan-3-ol as the alcohol in step 1 and 3-methoxy-3-methylazetidine hydrochloride as amine in step 3 and N-ethylmethylamine as the amine in step 5, to provide CLXXXI, N-(4-(bicyclo[3.1.1]heptan-3-yloxy)-3,5-difluorophenyl)-5-((ethyl(methyl)amino)methyl)-2-(3-methoxy- 3-methylazetidin-1-yl)oxazole-4-carboxamide as an off-white solid (38 mg, 34.73%). Compound CLXXXI was then treated with 4 M HCl in dioxane solution (2 mL) for 1 h at rt. Then the reaction mixture was evaporated and the crude was triturated with diethyl ether and dried to afford N-(4-(bicyclo[3.1.1]heptan-3-yloxy)-3,5-difluorophenyl)-5-((ethyl(methyl)amino)methyl)-2-(3-methoxy-3-methylazetidin-1-yl)oxazole-4-carboxamide hydrochloride, Example 307 (22 mg, 53.98%).

Example 308

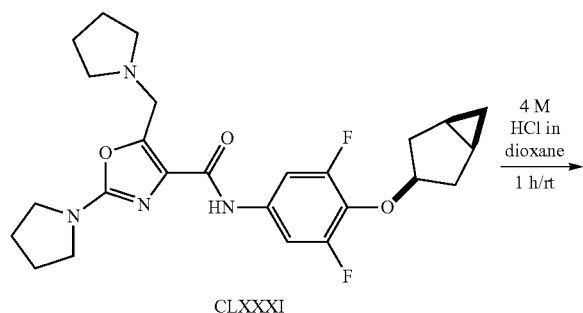

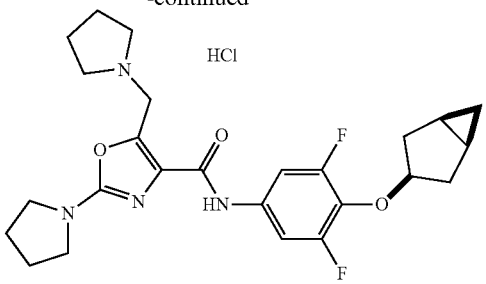

Example 308

Compound CLXXXI was synthesized utilizing the procedures outlined in the scheme above wherein compound CXXVI was 1,2,3-trifluoro-5-nitrobenzene, using bicyclo[3.1.0]hexan-3-ol as the alcohol in step 1 and pyrrolidine as amine in step 3 and pyrrolidine as the amine in step 5, to provide, N-(4-(cis-bicyclo[3.1.0]hexan-3-yloxy)-3,5-difluorophenyl)-2-(pyrrolidin-1-yl)-5-(pyrrolidin-1-ylmethyl)oxazole-4-carboxamide, CLXXXI (35 mg, 61%) as an off-white solid. Compound CLXXXI was then treated with 4 M HCl in dioxane solution (2 mL) for 1 h at rt. Then the reaction mixture was evaporated and the crude was triturated with diethyl ether and dried to afford N-(4-(cis-bicyclo[3.1.0]hexan-3-yloxy)-3,5-difluorophenyl)-2-(pyrrolidin-1-yl)-5-(pyrrolidin-1-ylmethyl)oxazole-4-carboxamide hydrochloride, Example 308 (35 mg, 93%).

Example 309

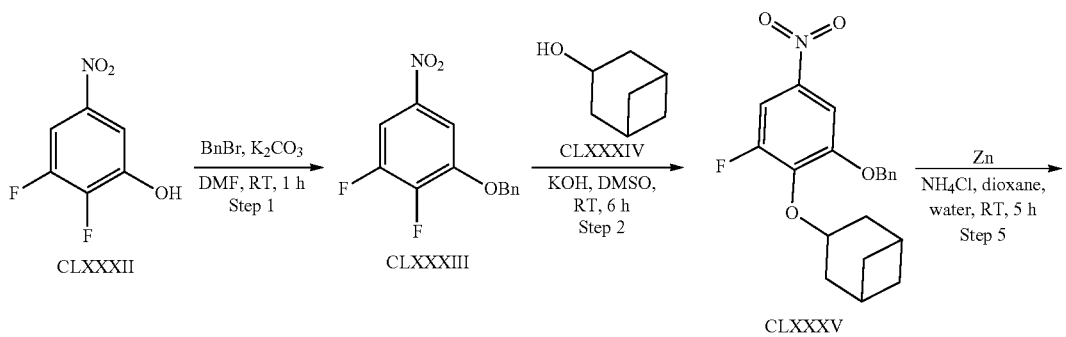

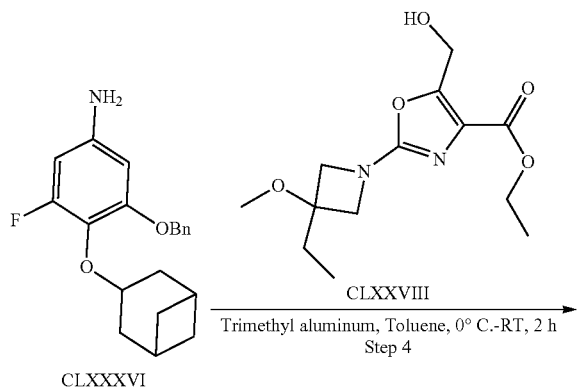

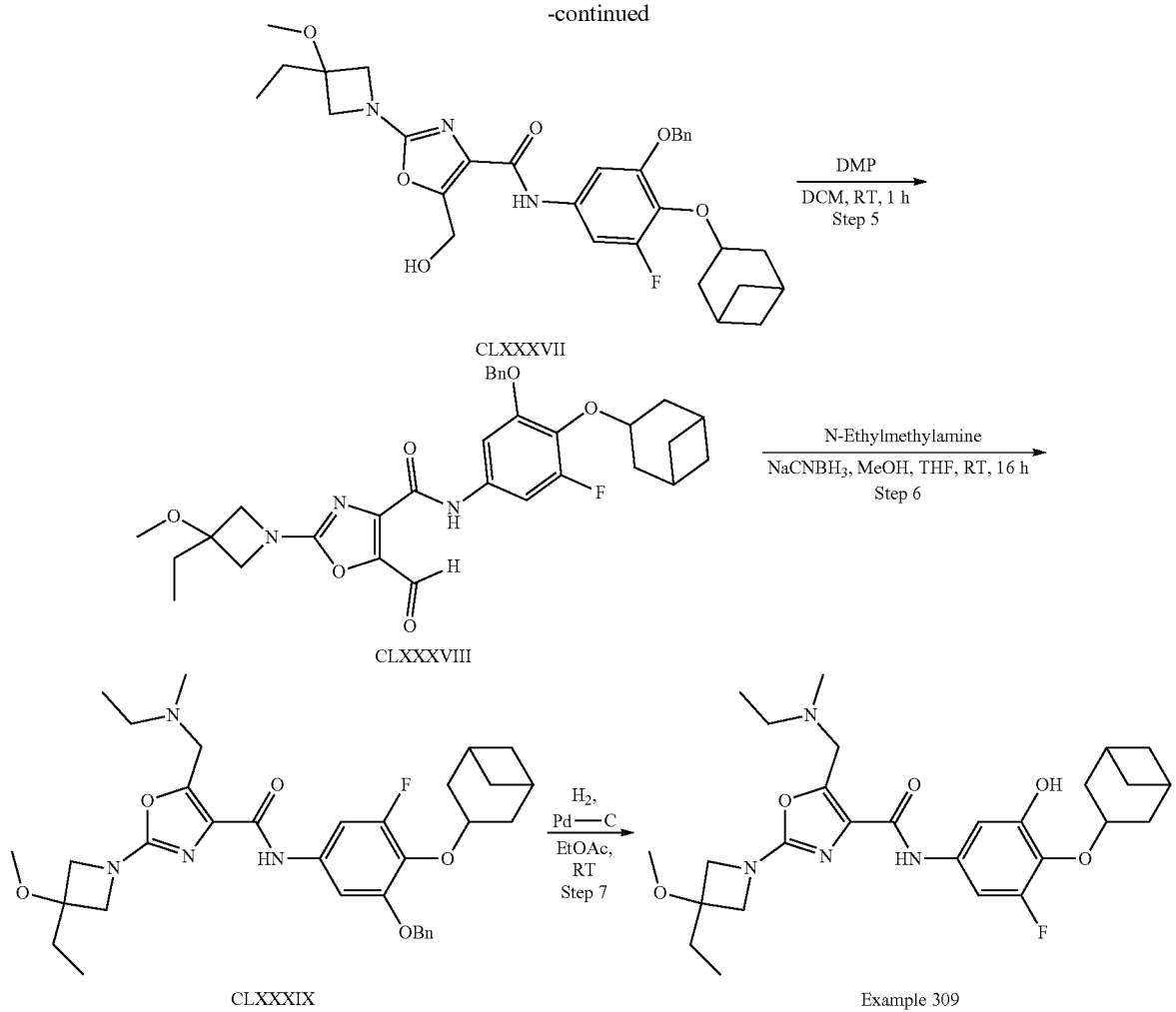

Step 1: To a stirred solution of CLXXXII (400 mg, 2.28 mmol) and K2CO₃ (948 mg, 6.86 mmol) in DMF was added benzyl bromide (781 mg, 4.57 mmol) was added slowly. The resulting reaction mixture was allowed to stir for 1 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using 0-5% EtOAc in hexane as an eluent to afford CLXXXIII (460 mg, 75.91%) as off white solid.

Step 2: To a stirred solution of alcohol CLXXXIV (233 mg, 2.083 mmol) and CLXXXIII (460 mg, 1.735 mmol) in DMSO (5 mL) was added KOH (291 mg, 5.206 mmol) and resulting reaction mixture was allowed to stir for 6 h at rt. After completion [Monitored by TLC], reaction mixture was partitioned between EtOAc and water. The organic layer was separated, dried over anhydrous sodium sulfate, and concentrated under reduced pressure. The resultant crude was purified through flash column chromatography using 0-5% EtOAc in hexane as an eluent to afford CLXXXV (470 mg, 75.78%) as off white solid.

Step 3: To a stirred solution of CLXXXV (470 mg, 1.315 mmol) in 1,4-dioxane (5 mL), Zn dust (598 mg, 9.208 mmol) was added. After 5 minutes of stirring, aqueous solution of NH₄Cl (568 mg, 10.523 mmol) was added and resulting reaction mass was stirred for 5 h at rt. After completion of reaction (monitored by TLC), the reaction mass was filtered and the filtrate was evaporated under reduced pressure to get the crude. The crude compound was purified by column chromatography using 10-15% EtOAc in hexane as an eluent to afford CLXXXVI (350 mg, 81.27%) as brown liquid.

Step 4: To a stirred solution of CLXXVIII (300 mg, 1.056 mmol) in toluene (14 mL) was added CLXXXVI (345 mg, 1.056 mmol). Then trimethyl aluminum solution (2 M in toluene) (2.2 mL, 4.223 mmol) was added to the above reaction mixture under ice cold condition. It was stirred at 0° C.-rt for 2 h. After completion of reaction [monitored by TLC], the reaction mixture was quenched with saturated aqueous ammonium chloride solution (30 mL) and extracted with ethyl acetate. The organic layer was dried over anhydrous sodium sulfate and concentrated under reduced pressure to get the crude. The crude compound was purified by column chromatography using 20-25% EtOAc in hexane as an eluent to afford CLXXXVII (250 mg, 41.86%) as yellow sticky liquid.

Step 5: The CLXXXVII (250 mg, 0.442 mmol) was stirred and dissolved in DCM (8 mL) and then the reaction mixture was cooled to 0° C. followed by slow addition of dess-martin periodinane (225.107 mg, 0.531 mmol) and left for stirring for 1 h under r.t. After completion of reaction (monitored by TLC) the reaction mixture was quenched using saturated aq solution of sodium thiosulfate and sodium bicarbonate, diluted with DCM, and washed with water. The organic layer was collected, dried using sodium sulfate and evaporated under reduced pressure to afford the crude. The crude compound was purified by column chromatography using 25-30% EtOAc in hexane as an eluent to afford CLXXXVIII (100 mg, 40%) as pale yellow solid.

Step 6: To a stirred solution of CLXXXVIII (100 mg, 0.178 mmol) in methanol (5 mL) and THF (0.4 mL), N-ethylmethylamine (21 mg, 0.355 mmol) was added along with addition of 0.1 mL acetic acid. After 4 h, NaBH$_3$CN (22 mg, 0.355 mmol) was added under ice-cold condition. The resulting reaction mixture was then allowed to stir for 16 h at r.t. After completion of reaction [monitored by TLC], the reaction mixture was quenched with saturated aqueous NaHCO$_3$ solution (20 mL), extracted with ethyl acetate (20 mL), and washed with water. The organic layer was dried over anhydrous sodium sulfate and concentrated under reduced pressure to get the crude. The crude compound was purified by column chromatography using 70-80% EtOAc in hexane as an eluent to afford CLXXXIX (45 mg, 50%) as yellow gummy.

Step 7: To a stirred solution of CLXXXIX (45 mg, 0.074 mmol) in EtOAc (4 mL), was added 10% Pd/C (20 mg) and stirred under hydrogen atmosphere for 2 h. After completion of reaction (monitored by TLC), the reaction mixture was filtered through celite, concentrated under reduced pressure to get the crude. The crude compound was purified by column chromatography using 1-5% MeOH in DCM as an eluent to afford Example 309 (10 mg, 26%).

Preparation of Examples with the General Formula CXCIV (Examples 310-315):

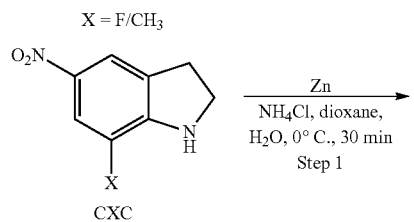

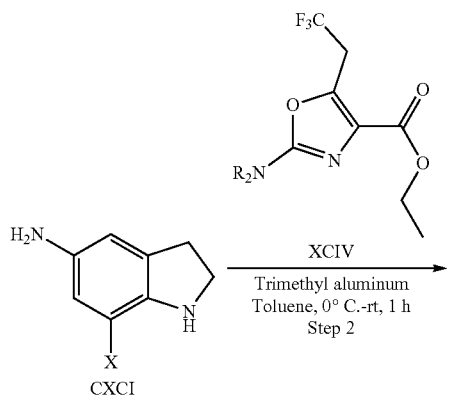

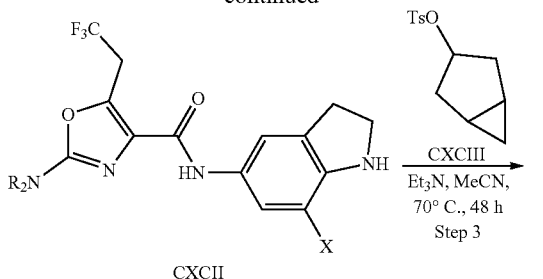

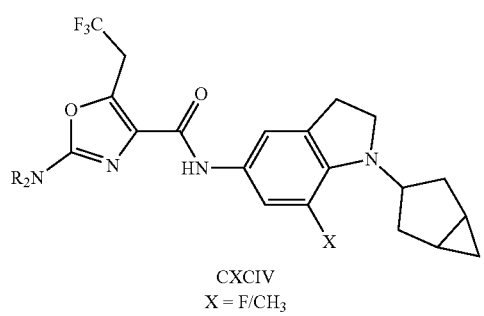

Step 1: To a stirred solution of nitro compound CXC (1.0 eq.) in dioxane (20 mL/g), Zn dust (8.0 eq.) was added, then NH$_4$Cl (8.0 eq.) dissolved in H$_2$O (4 mL/g) was added at 0° C. and and the resultant reaction mixture was allowed to stir at 0° C. for 30 min. After completion of reaction [Monitored by TLC], diluted with EtOAc and was stirred for 10 min, the reaction mixture was filtered through celite to remove the Zn residues and solvent was evaporated. The residue was dissolved in EtOAc was washed with H$_2$O, brine, and dried over Na$_2$SO$_4$, the organic phase was evaporated to obtain the crude product. Resultant crude was purified through flash column chromatography to afford products of general structure CXCI.

Step 2: To a stirred solution of CXCI (1.0 eq) and XCIV (1.0 eq) in dry toluene (30 mL/g CXCI), trimethylaluminum (1 M in toluene, 4.0 eq) dropwise at 0° C., and the resultant reaction mixture was allowed to stir at rt for 1 h. After completion [Monitored with TLC], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography to afford products of general structure CXCII.

Step 3: To a suspension of CXCII (1.0 eq) and tosyl compound CXCIII (2.0 eq) in acetonitrile (20 mL/g CXCII) in a screw cap vial, triethylamine (5.0 eq) was added into the reaction mixture and was stirred at 70° C. for 48 h. Reaction was monitored by TLC. Then, reaction was concentrated in vacuo to obtain the crude. Purification of the residue was carried out by silica gel column chromatography to afford products of general structure CXCIV.

Preparation of bicyclo[3.1.0]hexan-3-yl 4-methylbenzenesulfonate

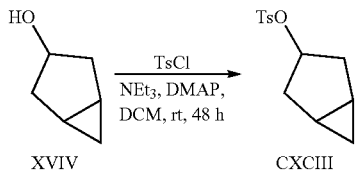

Synthesis of bicyclo[3.1.0]hexan-3-yl 4-methylbenzenesulfonate CXCIII: To a stirred solution of bicyclo[3.1.0]hexan-3-ol (1.0 g, 10.19 mmol) in DCM (40 mL) at 0° C. under $N_2$ and NEt3 (6.0 mL, 43.81 mmol) was added. Then, into the solution tosyl chloride (3.88 g, 20.38 mmol) was added, followed by addition of DMAP (0.5 g, 4.07 mmol) at 0° C. The reaction mixture was stirred for 48 h at RT. After completion [Monitored by TLC, Phosphomolybdic Acid (PMA) Stain], reaction mixture was diluted with DCM (200 mL) and water (100 mL) and organic layer was separated, dried over anhydrous sodium sulfate, and concentrated under reduced pressure. The crude material was purified by flash column chromatography using 10% EtOAc-hexane as an eluent to afford bicyclo[3.1.0]hexan-3-yl 4-methylbenzenesulfonate, CXCIII (1.1 g, 43%).

Example 310

The above referenced compound was synthesized utilizing the procedures outlined in the scheme above wherein compound CXC was 7-methyl-5-nitroindoline in step 1 and XCIV was ethyl 2-(3,3-diethylazetidin-1-yl)-5-(2,2,2-trifluoroethyl)oxazole-4-carboxylate in step 2, to provide N-(1-(bicyclo[3.1.0]hexan-3-yl)-7-methylindolin-5-yl)-2-(3,3-diethylazetidin-1-yl)-5-(2,2,2-trifluoroethyl)oxazole-4-carboxamide (35 mg, 20%).

Example 311

The above referenced compound was synthesized utilizing the procedures outlined in the scheme above wherein compound CXC was 7-fluoro-5-nitroindoline in step 1 and XCIV was ethyl 2-(3,3-diethylazetidin-1-yl)-5-(2,2,2-trifluoroethyl)oxazole-4-carboxylate in step 2, to provide N-(1-(bicyclo[3.1.0]hexan-3-yl)-7-fluoroindolin-5-yl)-2-(3,3-diethylazetidin-1-yl)-5-(2,2,2-trifluoroethyl)oxazole-4-carboxamide (25 mg, 21%).

Example 312

The above referenced compound was synthesized utilizing the procedures outlined in the scheme above wherein compound CXC was 7-fluoro-5-nitroindoline in step 1 and XCIV was ethyl 2-(3-methoxy-3-methylazetidin-1-yl)-5-(2,2,2-trifluoroethyl)oxazole-4-carboxylate in step 2, to provide N-(1-(bicyclo[3.1.0]hexan-3-yl)-7-fluoroindolin-5-yl)-2-(3-methoxy-3-methylazetidin-1-yl)-5-(2,2,2-trifluoroethyl)oxazole-4-carboxamide (25 mg, 14.5%).

Example 313

The above referenced compound was synthesized utilizing the procedures outlined in the scheme above wherein compound CXC was 7-fluoro-5-nitroindoline in step 1 and XCIV was ethyl 2-(3-ethyl-3-methoxyazetidin-1-yl)-5-(2,2,2-trifluoroethyl)oxazole-4-carboxylate in step 2, to provide N-(1-(bicyclo[3.1.0]hexan-3-yl)-7-fluoroindolin-5-yl)-2-(3-ethyl-3-methoxyazetidin-1-yl)-5-(2,2,2-trifluoroethyl)oxazole-4-carboxamide (60 mg, 42%).

Example 314

The above referenced compound was synthesized utilizing the procedures outlined in the scheme above wherein compound CXC was 7-fluoro-5-nitroindoline in step 1 and XCIV was ethyl 2-(2-oxa-6-azaspiro[3.4]octan-6-yl)-5-(2,2,2-trifluoroethyl)oxazole-4-carboxylate in step 2, to provide N-(1-(bicyclo[3.1.0]hexan-3-yl)-7-fluoroindolin-5-yl)-2-(2-oxa-6-azaspiro[3.4]octan-6-yl)-5-(2,2,2-trifluoroethyl)oxazole-4-carboxamide (20 mg, 17%).

Example 315

The above referenced compound was synthesized utilizing the procedures outlined in the scheme above wherein compound CXC was 7-fluoro-5-nitroindoline in step 1 and XCIV was ethyl 2-(pyrrolidin-1-yl)-5-(2,2,2-trifluoroethyl)oxazole-4-carboxylate in step 2, to provide N-(1-(bicyclo[3.1.0]hexan-3-yl)-7-fluoroindolin-5-yl)-2-(pyrrolidin-1-yl)-5-(2,2,2-trifluoroethyl)oxazole-4-carboxamide (20 mg, 17%).

Example 316

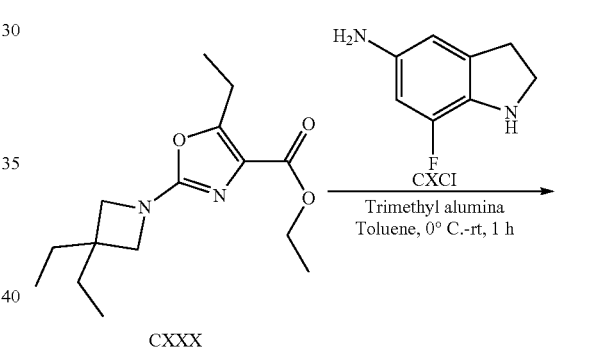

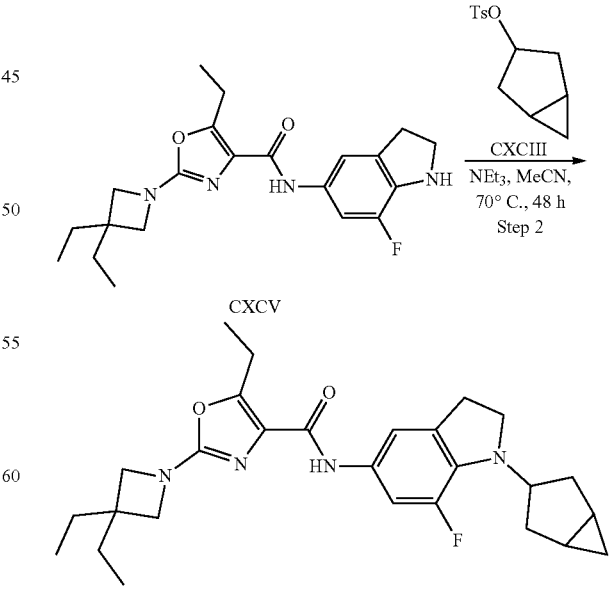

Example 316

Step 1: To a stirred solution of ethyl 2-(3,3-diethylazetidin-1-yl)-5-ethyloxazole-4-carboxylate, CXXX (230 mg, 0.82 mmol) and 7-fluoroindolin-5-amine CXCI (124.76 mg, 0.82 mmol) in dry toluene (5 mL), 2 M trimethylaluminum in toluene (1.5 mL) dropwise at 0° C., and the resultant reaction mixture was allowed to stir at rt for 1 h. After completion [Monitored with TLC], the reaction mixture was quenched with saturated ammonium chloride solution and partitioned with EtOAc. Organic layer was separated, dried over anhydrous sodium sulfate, and concentrated under reduced pressure. Resultant crude was purified by flash column chromatography using 20% EtOAc in hexane as an eluent to afford 2-(3,3-diethylazetidin-1-yl)-5-ethyl-N-(7-fluoroindolin-5-yl)oxazole-4-carboxamide, CXCV (200 mg, 63%) as off white solid.

Step 2: To a suspension of CXCV (95 mg, 0.25 mmol) and tosyl compound CXCIII (155.03 mg, 0.61 mmol) in acetonitrile (3 mL) in a screw cap vial, triethylamine (0.25 mL) was added into the reaction mixture and was stirred at 70° C. for 48 h. Reaction was monitored by TLC. Then, reaction was concentrated in vacuo to obtain the crude. Purification of the residue was carried out by silica gel column chromatography using 1000 EtOAc in hexane as an eluent to obtain N-(1-(bicyclo[3.1.0]hexan-3-yl)-7-fluoroindolin-5-yl)-2-(3,3-diethylazetidin-1-yl)-5-ethyloxazole-4-carboxamide, Example 316 (35 mg, 300%).

The analytical data for examples 1-123 is found in the table below:

| Ex. | NMR Data | [M + H] | Rt (min) | LCMS Method |
|---|---|---|---|---|
| 1 | $^1$H NMR (DMSO-$d_6$) δ ppm 9.92 (s, 1H), 7.80 (dd, 1H, J = 13.6, 2.3 Hz), 7.56 (d, 1H, J = 9 Hz), 7.44-7.42 (m, 2H), 7.35-7.33 (m, 2H), 7.2 (t, 1H, J = 9.28 Hz), 4.88 (s, 4H), 4.82-4.81 (m, 1H), 4.19-4.14 (m, 2H), 2.23-2.14 (m, 3 H), 1.85-1.83 (m, 3H). | 526.23 | 3.47 | B |
| 2 | $^1$H NMR (DMSO-$d_6$) δ ppm 10.08 (s, 1H), 7.79 (dd, 1H, J = 13.6, 2.44 Hz), 7.57-7.54 (m, 1H), 7.19 (t, 1H, J = 9.28 Hz), 4.90-4.70 (m, 1H), 4.42 (t, 2H, J = 8.68 Hz), 4.34-4.30 (m, 2H), 4.20-4.10 (m, 2H), 4.00-3.90 (m, 1H), 2.21-2.14 (m, 3H), 1.9-1.83 (m, 2H). | 489.24 | 3.22 | B |
| 3 | $^1$H NMR (DMSO-$d_6$) δ ppm 9.80 (s, 1H), 7.80 (dd, 1H, J = 13.64 Hz, 2.36 Hz), 7.55 (d, 1H, J = 8.88 Hz), 7.20 (t, 1H, J = 9.3 Hz), 4.80-4.73 (m, 2H), 4.13-4.08 (m, 2H), 3.62-3.27 (m, 3H), 2.33-2.21 (m, 1H), 2.22-2.21 (m, 3H), 2.02-2.00 (m, 1H), 1.85-1.72 (m, 4H) | 508.35 | 3.13 | B |
| 4 | $^1$H NMR (DMSO-$d_6$) δ ppm 9.83 (s, 1H), 7.77 (dd, 1H, J = 13.6, 2.4 Hz), 7.48 (d, 1H, J = 8.8 Hz), 7.18 (t, 1H, J = 9.2 Hz), 4.75-4.71 (m, 1H), 4.13-4.05 (m, 2H), 3.78-3.76 (m, 2H), 3.50-3.48 (m, 2H), 3.35 (s, 1H), 2.97-2.95 (m, 3H), 2.33-2.13 (m, 2H), 1.92-1.80 (m, 1H), 1.28-1.18 (m, 6H) | 522.45 | 5.66 | K |
| 5 | $^1$H NMR (DMSO-$d_6$) δ ppm 9.98 (s, 1H), 8.02 (d, 1H, J = 8.0 Hz), 7.80 (d, 1H, J = 13.4 Hz), 7.58 (d, 1H, J = 8.9 Hz), 7.30-7.22 (m, 3H), 7.00 (t, 1H, J = 7.4 Hz), 4.85-4.81 (m, 1H), 4.30-4.18 (m, 4H), 3.26 (t, 2H, J = 8.6 Hz), 2.33-2.15 (m, 3H), 1.86-1.83 (m, 2H), 1.76-1.73 (m, 1H). | 526.23 | 3.51 | B |
| 6 | $^1$H NMR (DMSO-$d_6$) δ ppm 9.83 (s, 1H), 7.77 (dd, 1H, J = 13.5, 1.9 Hz), 7.53 (d, 1H, J = 9.2 Hz), 7.21 (t, 1H, J = 9.3 Hz), 4.81-4.80 (brm, 1H), 4.12 (q, 2H, J = 10.6 Hz), 3.72-3.70 (m, 4H), 3.50-3.49 (m, 4H), 2.22-2.13 (m, 3H), 1.84-1.83 (m, 2H), 1.91-1.85 (m, 1H). | 494.31 | 3.25 | B |
| 7 | $^1$H NMR (DMSO-$d_6$) δ ppm 9.81 (s, 1H), 7.8 (dd, 1H, J = 13.5 Hz, 1.96 Hz), 7.20 (t, 1H, J = 9.3 Hz), 4.81-4.80 (m, 1H), 4.15-4.08 (m, 2H), 3.64-3.54 (m, 2H), 3.48-3.40 (m, 2H), 3.38-3.3 (m, 2H), 3.26 (s, 3H), 3.25-3.23 (m, 1H), 2.59-2.49 (m, 1H), 2.21-2.13 (m, 3H), 2.05-2.03(m, 1H), 1.84-1.70 (m, 4H). | 522.3 | 7 | K |
| 8 | $^1$H NMR (DMSO-$d_6$) δ ppm 10.01 (s, 1H), 7.78 (d, 1H, J = 13.6 Hz), 7.56 (d, 1H, J = 8.8 Hz), 7.19 (t, 1H, J = 9.2 Hz), 4.82-4.78 (m, 1H), 4.34-4.33 (m, 3H), 4.17-4.09 (m, 2H), 3.97-3.96 (m, 2H), 3.24 (s, 3H), 3.26 (s, 3H), 2.21-2.11 (m, 3H), 1.89-1.78 (m, 3H). | 494.2 | 3.27 | B |
| 9 | $^1$H NMR (CDCl$_3$) δ ppm 8.62 (s, 1H), 7.75 (dd, 1H, J = 13.6 Hz, 2.4 Hz), 7.20 (d, 1H, J = 8.9 Hz), 7.01 (t, 1H, J = 8.9 Hz), 4.51-4.48 (m, 1H), 4.37 (s, 2H), 3.96-3.89 (m, 2H), 2.23-2.12 (m, 3H), 2.02-1.95 (m, 2H), 1.85-1.72 (m, 5H), 1.55-1.46 (m, 4H). | 504.23 | 3.5 | B |
| 10 | $^1$H NMR (DMSO-$d_6$) δ ppm 9.85 (s, 1H), 7.78 (dd, 1H, J = 13.6 Hz, 2 Hz), 7.54 (d, 1H, J = 8.7 Hz), 7.2 (t, 1H, J = 9.2 Hz), 4.82-4.78 (m, 1H), 4.16-4.08 (m, 2H), 3.86-3.83 (m, 4H), 2.72-2.65 (m, 2H), 2.49-2.46 (m, 1H), 2.21-2.11 (m, 2H), 1.86-1.69 (m, 3H) | 526.23 | 3.38 | B |
| 11 | $^1$H NMR (DMSO-$d_6$) δ ppm 9.62 (s, 1H), 7.75 (d, 1H, J = 13.6 Hz), 7.5 (d, 1H, J = 8.8 Hz), 7.2 (t, 1H, J = 9.2 Hz), 4.8 (bs, 1H), 4.16-4.05 (m, 2H), 3.67 (s, 2H), 2.32-2.18 (m, 3H), 1.98 (s, 4H), 1.84-1.72 (m, 3H), 1.66 (s, 2H), 0.68 (s, 2H). | 504.26 | 3.53 | B |
| 12 | $^1$H NMR (DMSO-$d_6$) δ ppm 9.83 (s, 1H), 7.79 (d, 1H, J = 13.6 Hz), 7.55 (d, 1H, J = 7.6 Hz), 7.2 (t, 1H, J = 9.2 Hz), 4.82-4.78 (m, 1H), 4.53 (t, 1H, J = 5.1 Hz), 4.13-4.08 (m, 2H), 3.37-3.34 (m, 2H), 3.03 (m, 2H), 2.21-2.06 (m, 3H), 1.84-1.71 (m, 3H). | 520.2 | 3.25 | B |
| 13 | $^1$H NMR (DMSO-$d_6$) δ ppm 9.82 (s, 1H), 7.8 (dd, 1H, J = 13.6 Hz, 2.4 Hz), 7.55 (d, 1H, J = 9.2 Hz), 7.2 (t, 1H, J = 9.6 Hz), 4.82-4.78 (m, 1H), 4.16-4.08 (m, 2H), 3.82-3.77 (m, 2H), 3.62-3.54 (m, 4H), 3.5-3.44 (m, 2H), 2.53 (bs 1H), 2.21-2.11 (m, 3H), 2.00-1.7 (m, 6H). | 534.36 | 3.34 | B |

-continued

| Ex. | NMR Data | [M + H] | Rt (min) | LCMS Method |
|---|---|---|---|---|
| 14 | $^1$H NMR (DMSO-d$_6$) δ ppm 9.98 (s, 1H), 7.79 (dd, 1H, J = 14 Hz 2.4 Hz), 7.56 (d, 1H, J = 10.2 Hz), 7.19 (t, 1H, J = 9.6 Hz), 4.72-4.71 (m, 1H), 4.12 (q, 2H, J = 10.5 Hz), 3.92 (s, 4H), 3.56 (t, 4H, J = 9.2), 2.22-2.14 (m, 3H), 1.89 (bs, 2H), 1.81-1.74 (m, 5H). | 534.33 | 2.25 | Y |
| 15 | $^1$H NMR (DMSO-d$_6$) δ ppm 9.8 (s, 1H), 7.8 (dd, 1H, J = 16 Hz, 2.3 Hz), 7.55 (d, 1H, J = 9 Hz), 7.2 (t, 1H, J = 9.3 Hz), 4.82-4.78 (m, 1H), 4.15 (q, 2H, J = 10.6 Hz), 3.51-3.46 (m, 4H), 2.23-2.11 (m, 3H), 2.04-1.8 (m, 10H), 1.71 (m, 1H). | 518.35 | 3.6 | B |
| 16 | $^1$H NMR (DMSO-d$_6$) δ ppm 10.13 (s, 1H), 7.79 (dd, 1H, J = 13.7 Hz, 2 Hz), 7.57 (d, 1H, J = 9 Hz), 7.19 (t, 1H, J = 9.3 Hz), 4.82-4.78 (m, 1H), 4.63 (t, 4H, J = 12.3 Hz), 4.2 (q, 2H, J = 10.5 Hz), 2.21-2.11 (m, 3H), 1.89-1.7 (m, 3H). | 500.3 | 2.33 | Y |
| 17 | $^1$H NMR (DMSO-d$_6$) δ ppm 10.04 (s, 1H), 7.79 (d, 1H, J = 13.2 Hz), 7.56 (d, 1H, J = 8.4 Hz), 7.19 (t, 1H, J = 9.2 Hz), 4.79 (bs, 1H), 4.25 (s, 4H), 4.17 (q, 2H, J = 10.4 Hz), 2.89 (t, 4H, J = 12.3 Hz), 2.21-2.18 (m, 3H), 1.84-1.69 (m, 3H). | 540.36 | 3.29 | B |
| 18 | $^1$H NMR (DMSO-d$_6$) δ ppm 10.07 (s, 1H), 7.79 (dd, 1H, J = 13.6 Hz, 2.4 Hz), 7.56 (d, 1H, J = 8.9 Hz), 7.19 (t, 1H, J = 9.2 Hz), 4.82-4.78 (m, 1H), 4.42 (t, 2H, J = 8.8 Hz), 4.19-4.11 (m, 4H), 3.8-3.78 (m, 1H), 2.23-2.11 (m, 3H), 1.86-1.69 (m, 3H). | 532.25 | 3.38 | B |
| 19 | $^1$H NMR (DMSO-d$_6$) δ ppm 9.84 (s, 1H), 7.8 (d, 1H, J = 13.5 Hz), 7.55 (d, 1H, J = 9 Hz), 7.2 (t, 1H, J = 9.2 Hz), 4.82-4.71 (m, 1H), 4.61 (d, 2H, J = 6.1 Hz), 4.51 (d, 2H, J = 6.1 Hz), 4.16 (q, 2H, J = 10.6 Hz), 3.73 (s, 2H), 3.51 (t, 2H, J = 6.8 Hz), 2.32-2.11 (m, 5H), 1.86-1.74 (m, 3H). | 520.32 | 3.27 | B |
| 20 | $^1$H NMR (DMSO-d$_6$) δ ppm 9.98 (s, 1H), 7.79 (dd, 1H, J = 13.6 Hz, 2.4 Hz), 7.56 (d, 1H, J = 9.5 Hz), 7.19 (t, 1H, J = 9.3 Hz), 4.81-4.78 (m, 1H), 4.16 (q, 2H, J = 10.6 Hz), 3.77 (s, 4H), 2.33-2.11 (m, 3H), 1.88-1.69 (m, 3H), 1.29 (s, 6H). | 492.27 | 3.43 | B |
| 21 | $^1$H NMR (DMSO-d$_6$) δ ppm 9.79 (s, 1H), 7.79 (dd, 1H, J = 13.6 Hz, 2.3 Hz), 7.54 (d, 1H, J = 9 Hz), 7.19 (t, 1H, J = 9.2 Hz), 4.81-4.77 (m, 1H), 4.15 (q, 2H, J = 10.6 Hz), 3.65 (t, 2H, J = 6.8 Hz), 3.4 (s, 2H), 2.21-2.11 (m, 3H), 1.9 (t, 2H, J = 6.8 Hz), 1.84-1.7 (m, 3H), 0.68-0.66 (m, 2H), 0.63-0.6 (m, 2H). | 504.45 | 2.17 | B |
| 22 | $^1$H NMR (DMSO-d$_6$) δ ppm 9.82 (s, 1H), 7.8 (dd, 2H, J = 13.7 Hz, 2.3 Hz), 7.55 (d, 1H, J = 9 Hz), 7.2 (t, 1H, J = 9.3 Hz) 4.88-4.78 (m, 1H), 3.49-3.32 (m, 4H), 2.21-1.98 (m, 3H), 1.98-1.92 (m, 4H), 1.89-1.69 (m, 3H), 1.87-1.71 (m, 3H). | 478.33 | 7.06 | K |
| 23 | $^1$H NMR (DMSO-d$_6$) δ ppm 9.8 (s, 1H), 7.79 (dd, 1H, J = 13.6 Hz, 2.1 Hz), 7.55 (d, 1H, J = 9 Hz), 7.2 (t, 1H, J = 9.2 Hz) 4.83-4.8 (m, 1H), 4.13-4.1 (m, 2H), 3.69-3.65 (m, 2H), 3.31-3.23 (m, 2H), 2.76 (bs, 2H), 2.21-2.16 (m, 3H), 1.84-1.68 (m, 6H), 1.56-1.44 (m, 3H). | 518.3 | 3.61 | B |
| 24 | $^1$H NMR (DMSO-d$_6$) δ ppm 10.0 (s, 1H), 7.79(dd, 1H, J = 13.7, 2.1 Hz), 7.56 (d, 1H, J = 8.8 Hz), 7.95 (t, 1H, J = 9.2 Hz), 4.79 (brm, 1H), 4.53-4.51 (m, 1H), 4.39-4.35 (m, 2H), 4.14-4.09 (m, 2H) 3.95-3.92 (m, 2H), 3.65-3.62 (m, 1H), 2.32-2.11 (m, 3H), 1.84-1.71 (m, 3H), 1.11 (d, 6H, J = 6.2 Hz). | 522.22 | 3.41 | B |
| 25 | $^1$H NMR (DMSO-d$_6$) δ ppm 9.72 (s, 1H), 7.66 (dd, 1H, J = 2.16, 14.88 Hz), 7.49 (d, 1H, J = 8.80 Hz), 6.98 (t, 1H, J = 9.44 Hz), 4.15-4.05 (m, 6H), 3.51-3.49 (m, 4H), 2.93-2.90 (m, 4H), 1.90-1.88 (m, 4H), 1.63-1.60 (m, 4H), 1.52-1.51 (m, 2H). | 545.42 | 3.08 | B |
| 26 | $^1$H NMR (DMSO-d$_6$) δ ppm 9.72 (s, 1H), 7.68 (dd, 1H, J = 15.0, 2.24 Hz), 7.49 (d, 1H, J = 8.8 Hz), 6.98 (t, 1H, J = 9.4 Hz), 4.53 (t, 1H, J = 5.1 Hz), 4.16-4.08 (m, 2H), 3.88-3.83 (m, 1H), 3.75-3.57 (m, 4H), 3.37-3.34 (m, 2H), 3.02 (brm, 1H), 2.93-2.90 (m, 3H), 2.12-2.05 (m, 1H), 1.83-1.81 (m, 1H), 1.64-1.61 (m, 4H), 1.52-1.51 (m, 2H). | 483.37 | 2.11 | A |
| 27 | $^1$H NMR (DMSO-d$_6$) δ ppm 9.67 (s, 1H), 7.65 (d, 1H, J = 14.8 Hz), 7.46 (d, 1H, J = 8.4 Hz), 6.95 (t, 1H, J = 9.2 Hz), 4.09 (q, 2H, J = 10.6 Hz), 6.63 (t, 2H, J = 6.8 Hz), 3.38 (s, 2H), 2.89 (t, 4H, J = 4.9 Hz), 1.88 (t, 2H, J = 6.8 Hz), 1.62-1.60 (m, 4H), 1.50-1.49 (m, 2H), 0.66-0.58 (m, 4H). | 467.35 | 2.39 | A |
| 28 | $^1$H NMR (DMSO-d$_6$) δ ppm 9.73 (s, 1H), 7.68(dd, 1H, J = 15.0, 2.32 Hz), 7.50-7.48 (m, 1H), 6.98 (t, 1H, J = 9.5 Hz), 4.13-4.08 (m, 2H), 3.58-3.53 (m, 4H), 2.93-2.90 (m, 4H), 2.73-2.61 (m, 4H), 2.12-1.88 (m, 3H), 2.09 (t, 2H, J-6.7 Hz), 1.62 (brm, 4H), 1.52 (brm, 2H). | 517.42 | 3.42 | B |
| 29 | $^1$H NMR (DMSO-d$_6$) δ ppm 9.67 (s, 1H), 7.68(dd, 1H, J = 15.0, 2.32 Hz), 7.49 (d, 1H, J = 8.7 Hz), 6.84 (t, 1H, J = 9.4 Hz), 4.14-4.09 (m, 2H), 4.01-3.98 (m, 1H), 3.56-3.47 (m, 2H), 2.92 (t, 4H, J = 4.9 Hz), 2.12-1.88 (m, 3H), 1.64 (brm, 5H), 1.54-1.51 (m, 2H), 1.26 (d, 3H, J = 6.2 Hz). | 455.38 | 2.35 | A |

-continued

| Ex. | NMR Data | [M + H] | Rt (min) | LCMS Method |
|---|---|---|---|---|
| 30 | $^1$H NMR (DMSO) δ ppm 9.91 (s, 1H), 7.67 (d, 1H, J = 15 Hz), 7.51 (d, 1H, J = 8.6 Hz), 6.96 (t, 1H), 4.24 (s, 4H), 4.14-4.11 (m, 2H), 2.92-2.86 (m, 8H), 1.63-1.62 (m, 4H), 1.52-1.5 (m, 2H). | 503.33 | 2.33 | A |
| 31 | $^1$H NMR (DMSO-$d_6$) δ ppm 9.70 (s, 1H), 7.69 (dd, 1H, J = 15 Hz 2.2 Hz), 7.5 (d, 1H, J = 9 Hz), 6.97 (t, 1H, J = 9.3 Hz), 4.15-4.07 (m, 2H, J = 7.1 Hz), 3.82-3.78 (m, 2H), 3.62-3.54 (m, 4H), 3.5-3.44 (m, 2H), 2.91 (t, 4H, J = 5 Hz), 2.0-1.87 (m, 4H), 1.64-1.62(m, 4H), 1.52-1.51 (m, 2H). | 497.46 | 3.12 | B |
| 32 | $^1$H NMR (DMSO-$d_6$) δ ppm 9.71 (s, 1H), 7.7 (d, 1H, J = 14.6 Hz), 7.5 (d, 1H, J = 8.3 Hz), 6.97 (t, 1H), 4.13-4.1 (m, 2H), 3.47 (bs, 4H), 2.91 (bs, 4H), 1.94 (bs, 4H), 1.64 (bs, 4H), 1.51 (bs, 2H). | 441.29 | 2.29 | A |
| 33 | $^1$H NMR (DMSO-$d_6$) δ ppm 9.73 (s, 1H), 7.69 (d, 1H, J = 14.8 Hz), 7.5 (d, 1H, J = 9.1 Hz), 6.98 (t, 1H, J = 9.2 Hz), 4.61 (d, 2H, J = 6 Hz), 4.51 (d, 2H, J = 6 Hz), 4.15 (q, 2H, J = 10.6 Hz), 3.73 (s, 2H), 3.5 (t, 2H, J = 6.7 Hz), 2.91-2.90 (m, 4H), 2.26 (t, J = 6.8 Hz), 1.63 (bs, 4H), 1.52 (bs, 2H). | 483.27 | 3.05 | B |
| 34 | $^1$H NMR (DMSO-$d_6$) δ ppm 10.2 (s, 1H), 7.67 (d, 2H, J = 10.7 Hz), 4.72 (t, 1H, J = 12 Hz), 4.25 (s, 4H), 4.16 (q, 2H, J = 10.5 Hz), 2.89 (t, 4H, J = 12.4 Hz), 2.08-2.06 (m, 2H), 1.93-1.89 (m, 2H), 1.33-1.32 (m, 2H), 0.69-0.68 (m, 1H), 0.48 (m, 1H). | 534.24 | 3.9 | B |
| 35 | $^1$H NMR (DMSO-$d_6$) δ ppm 10.03 (s, 1H), 7.68 (d, 2H, J = 10.7 Hz), 4.72 (t, 1H, J = 12.5 Hz), 4.61 (d, 2H, J = 6.1 Hz), 4.51 (d, 2H, J = 6.1 Hz), 4.15 (q, 2H, J = 10.6 Hz), 3.73 (s, 2H), 3.51 (t, 2H, J = 6.9 Hz), 2.26 (t, 2H, J = 6.9 Hz), 2.08-2.06 (m, 2H), 1.93-1.89 (m, 2H), 1.33-1.31 (m, 1H), 0.7-0.67 (m, 1H), 0.5-0.48 (m, 1H) | 514.22 | 3.43 | B |
| 36 | $^1$H NMR (DMSO-$d_6$) δ ppm 10.02 (s, 1H), 7.67 (d, 2H, J = 10.6 Hz), 4.72 (m, 1H), 4.53 (bs, 1H), 4.15 (q, 2H, J = 10.5 Hz), 3.86 (m, 1H), 3.75-3.61 (m, 4H), 3.36-3.35 (m, 1H), 3.02 (bs, 1H), 2.01-2.06 (m, 3H), 1.93-1.89 (m, 2H), 1.83 (bs, 1H), 1.33-1.32 (bs, 2H), 0.68-0.69 (m, 1H), 0.48 (bs, 1H). | 514.25 | 3.5 | B |
| 37 | $^1$H NMR (DMSO-$d_6$) δ ppm 10.18 (s, 1H), 7.67 (d, 2H, J = 11 Hz), 4.71 (t, 1H, J = 8.3 Hz), 4.15 (q, 2H, J = 10.6 Hz), 3.83 (s, 4H), 2.09-2.06 (m, 2H), 1.92-1.89 (m, 2H), 1.33-1.28 (m, 8H), 0.7-0.67 (m, 2H), 0.5-0.47 (m, 1H). | 486.29 | 2.91 | B |
| 38 | $^1$H NMR (DMSO-$d_6$) δ ppm 10.01 (s, 1H), 7.67 (d, 1H, J = 11 Hz), 4.72 (t, 1H, J = 6.2 Hz), 4.15 (q, 2H, J = 10.6 Hz), 3.65 (t, 2H, J = 6.8 Hz), 3.4 (s, 2H), 2.15-2. 13 (m, 2H), 1.93-1.88 (m, 4H), 1.34-1.32 (m, 2H), 0.69-0.62 (m, 5H), 0.51-0.49 (bs, 1H). | 498.27 | 3.72 | B |
| 39 | $^1$H NMR (CDCl$_3$) δ ppm 8.72 (bs, 1H), 7.31 (m, 2H), 4.76 (s, 1H), 3.95 (q, 2H, J = 10 Hz), 3.51 (t, 4H, J = 6.5 Hz), 2.05-1.99 (m, 8H), 1.32-1.3 (m, 2H), 0.82(q, 1H, J = 4.1 Hz), 0.53-0.47 (m, 1H). | 472.23 | 3.57 | B |
| 40 | $^1$H NMR (DMSO-$d_6$) δ ppm 9.96 (s, 1H), 7.64 (d, 2H, J = 10.8 Hz), 4.7 (t, 1H, J = 6 Hz), 4.12 (q, 2H, J = 10.6 Hz), 3.65 (t, 2H, J = 8.72), 3.28-3.23 (m, 2H), 2.74 (bs, 2H), 2.07-2.04 (m, 2H), 1.91-1.87 (m, 2H), 1.78-1.74 (m, 2H), 1.7-1.64 (m, 1H), 1.57-1.5 (m, 1H), 1.5-1.43 (m, 2H), 1.31-1.29 (m, 2H), 0.67-0.66 (m, 1H), 0.46-0.45 (m, 1H). | 512.2 | 4.19 | I |
| 41 | $^1$H NMR (DMSO-$d_6$) δ ppm 10.18 (s, 1H), 7.67 (d, 2H, J = 10.8 Hz), 4.7 (t, 1H, J = 6.2 Hz), 4.15 (q, 2H, J = 10.6 Hz), 3.98 (s, 4H), 2.09-2.07 (m, 2H), 1.93-1.89 (m, 2H), 1.83-1.79 (m, 4H), 1.59-1.54 (m, 4H), 1.33-1.3 (m, 2H), 0.69-0.66 (m, 1H), 0.53-0.48 (m, 1H). | 512.3 | 3.88 | B |
| 42 | $^1$H NMR (DMSO-$d_6$) δ ppm 9.85 (s, 1 H), 7.83-7.80 (m, 1H), 7.59 (d, 1 H, J = 9.2 Hz), 7.26 (t, 1 H, J = 9.6 Hz), 4.80 (q, 2 H, J = 8.9 Hz), 4.13-410 (m, 2 H), 3.48 (s, 4 H), 1.94 (s, 4 H). | 456.15 | 3.46 | B |
| 43 | $^1$H NMR (DMSO-$d_6$) δ ppm 9.76 (s, 1 H), 7.73 (dd, 1 H, J = 13.72, 2.32 Hz), 7.52 (d, 1 H, J = 8.96 Hz), 7.07 (t, 1 H, J = 9.28 Hz), 4.75-4.73 (m, 1 H), 4.12 (q, 2 H J = 10.68 Hz), 3.79 (t, 1 H, J = 6 Hz), 3.47 (t, 4 H, J = 6.36 Hz), 3.18 (s, 3 H), 2.36-2.29 (m, 1 H), 1.95-1.90 (m, 5 H), 1.81-1.73 (m, 4 H), 1.68-1.64 (m, 1 H). | 472.36 | 3.26 | B |
| 44 | $^1$H NMR (DMSO-$d_6$) δ ppm 9.81 (s, 1 H), 7.80 (dd, 1 H, J = 13.7, 2.44 Hz), 7.55 (d, 1 H, J = 8.92 Hz), 7.04 (t, 1 H, J = 9.28 Hz), 4.78-4.77 (m, 1 H), 4.16-4.08 (m, 2 H), 3.49-3.46 (m, 4 H), 3.29-3.14 (m, 2 H), 2.79-2.66 (m, 2 H), 1.95-1.92 (m, 4 H). | 464.22 | 2.64 | B |
| 45 | $^1$H NMR (DMSO-$d_6$) δ ppm 9.79 (s, 1H), 7.77 (d, 1H, J = 13.4 Hz), 7.54 (d, 1H, J = 7.8 Hz), 7.08 (t, 1H, J = 8.8 Hz), 5.05 (s, 1H), 4.14-4.04 (m, 3H), 3.85 (d, 1H, J = 10.2 Hz), 3.48 (bs, 4H), 2.14-2.09 (m, 1H), 1.94-1.88 (M, 5H), 1.29-1.15 (m, 6H) | 472.4 | 3.25 | B |
| 46 | $^1$H NMR (DMSO-$d_6$) δ ppm 9.79 (s, 1H), 7.73 (d, 1H, J = 13.7 Hz), 7.53 (d, 1H, J = 8.9 Hz), 7.10 (t, 1H, J = 9.2 Hz), 4.72 (brs, 1H), 4.16-4.07 (m, 2H), 4.49-4.46 (m, 4H), 2.36-2.28 (m, 4H), 2.15-2.11 (m, 2H), 1.95-1.92 (m, 4H). | 490.23 | 3.44 | B |

-continued

| Ex. | NMR Data | [M + H] | Rt (min) | LCMS Method |
|---|---|---|---|---|
| 47 | $^1$H NMR (DMSO-d$_6$) δ ppm 9.80 (s, 1H), 7.78 (dd, 1H, J = 13.7, 2.1 Hz), 7.54 (d, 1H, J = 8.9 Hz), 7.12 (t, 1H, J = 9.3 Hz), 5.04 (bm, 1H), 4.15 (q, 2H, J = 10.6 Hz), 3.89-3.82 (m, 3H), 3.79-3.73 (m, 1H), 3.48 (t, 4H, J = 12.6 Hz), 2.24-2.15 (m, 1H), 2.01-1.93 (m, 5H). | 444.22 | 2.11 | A |
| 48 | $^1$H NMR (DMSO-d$_6$) δ ppm 9.93 (s, 1H), 7.71 (d, 1H, J = 10.4 Hz), 7.52 (d, 1H, J = 8.2 Hz), 7.09 (t, 1H, J = 11.6 Hz), 4.82 (brs, 1H,), 4.24 (s, 4H), 4.12 (q, 2H, J = 12.8 Hz), 2.89 (t, 2H, J = 12.2 Hz), 1.62-1.60 (m, 2H), 1.71 (brm, 4H), 1.58 (brm, 2H). | 504.38 | 2.43 | A |
| 49 | $^1$H NMR (DMSO-d$_6$) δ ppm 9.85 (s, 1H), 7.81 (dd, 1H, J = 13.6, 2.3 Hz), 7.57 (d, 1H, J = 8.9 Hz), 7.20 (t, 1H, J = 9.3 Hz), 5.13-5.10 (brm, 1H), 4.37-4.33 (m, 1H), 4.16-3.92 (m, 6H), 3.49 (t, 4H, J = 6.4 Hz), 1.96-1.93 (m, 4H). | 480.23 | 3.24 | B |
| 50 | $^1$H NMR (DMSO-d$_6$) δ ppm 9.75 (s, 1H), 7.74(dd, 1H, J = 15.0, 2.32 Hz), 7.52 (dd, 1H, J = 8.8, 1.36 Hz), 7.09 (dd, 1H, J = 11.8, 6.72 Hz), 4.82-4.80 (m, 1H), 4.16-4.08 (m, 2H), 3.49-3.46 (m, 4H), , 1.38-2.12 (m, 2H), 1.92 (brm, 6H), 1.78-1.76 (m, 2H), 1.29-1.23 (m, 2H), 1.04 (d, 3H, J = 6.7 Hz). | 456.43 | 3.59 | B |
| 51 | $^1$H NMR (DMSO-d$_6$) δ ppm 9.74 (s, 1H), 7.73 (dd, 1H, J = 13.6 Hz, 2.08 Hz), 7.53 (d, 1H, J = 9 Hz), 7.21 (t, 1H, J = 9.3 Hz), 5.07-5.01 (m, 1H), 4.15-4.08 (m, 2H), 3.49-3.48 (m, 4H), 2.05-1.94 (m, 5H), 1.81-1.74 (m, 2H), 1.65-1.6 (m, 1H), 1.39-1.38 (m, 1H), 0.55-0.51 (m, 1H), 0.44-0.4 (m, 1H). | 454.3 | 2.7 | B |
| 52 | $^1$H NMR (DMSO-d$_6$) δ ppm 9.77 (s, 1H), 7.75 (dd, 1H, J = 13.6 Hz, 2.4 Hz), 7.48 (d, 1H, J = 8.3 Hz), 6.89 (t, 1H, J = 9.3 Hz), 4.15-4.08 (m, 2H), 3.48-3.44 (m, 4H), 2.85-2.68 (m, 1H), 2.49-2.16 (m, 3H), 2.08-1.94 (m, 5H), 1.95-1.89 (m, 1H), 1.78-1.72 (m, 1H), 1.65-1.6 (m, 1H), 1.5-1.49 (m, 1H), 1.2-1.1(m, 1H). | 468.21 | 3.57 | B |
| 53 | $^1$H NMR (DMSO-d$_6$) δ ppm 9.76 (s, 1H), 7.76 (d, 1H, J = 13.5 Hz), 7.55 (d, 1H, J = 8 Hz), 7.13 (t, 1H, J = 9.1 Hz), 4.13-4.10 (m, 2H), 3.99 (d, 2H, J = 6 Hz), 3.48 (s, 4H), 2.66-2.63 (m, 1H), 2.32-2.07 (m, 3H), 1.94 (s, 6H), 1.64-1.62 (m, 1H). | 492.28 | 3.5 | B |
| 54 | $^1$H NMR (DMSO-d$_6$) δ ppm 9.67 (s, 1H), 7.73 (dd, 1H, J = 16 Hz, 2.4 Hz), 7.51 (d, 1H, J = 8.8 Hz), 7.1 (t, 1H, J = 9.6 Hz), 4.84-4.81 (m, 1H), 4.14-3.99 (m, 3H), 3.55-3.47 (m, 2H), 2.12-1.86 (m, 5H), 1.73-1.69 (m, 4H), 1.68-1.58 (m, 3H), 1.26-1.22 (m, 3H). | 456.36 | 2.49 | A |
| 55 | $^1$H NMR (DMSO-d$_6$) δ ppm 9.74 (s, 1H), 7.75 (d, 1H, J = 13.6 Hz), 7.52 (d, 1H, J = 8.8 Hz), 7.09 (t, 1H, J = 9.6 Hz), 4.22-4.21 (m, 1H), 4.15-4.08 (m, 2H), 3.48 (bs, 4H), 2.12 (bs, 1H), 1.95 (bs, 4H), 1.71-1.59 (m, 4H), 1.47-1.43(m, 1H), 1.05 (s, 3H), 0.98 (s, 3H). | 470.42 | 3.7 | B |
| 56 | $^1$H NMR (DMSO-d$_6$) δ ppm 9.78 (s, 1H), 7.78 (d, 1H, J = 13.6 Hz), 7.54 (d, 1H, J = 8.9 Hz), 7.2 (t, 1H, J = 8.9 Hz), 4.5 (bs, 1H), 4.15-4.08 (m, 2H), 3.86-3.83 (bs, 2H), 3.48 (bs, 6H), 1.94 (bs, 6H), 1.6 (bs, 2H). | 458.3 | 3.18 | B |
| 57 | $^1$H NMR (DMSO-d$_6$) δ ppm 9.72 (s, 1H), 7.74 (dd, 1H, J = 13.8 Hz, 2.4 Hz), 7.51 (d, 1H, J = 8.9 Hz), 7.09 (t, 1H, J = 9.3 Hz), 4.82 (t, 1H, 5.7 Hz), 3.65 (t, 2H, J = 6.8 Hz), 3.4 (s, 2H), 1.91-1.87 (m, 4H), 1.73-1.71 (m, 4H), 1.62-1.58 (m, 2H), 0.68-0.62 (m, 4H). | 468.35 | 2.49 | A |
| 58 | $^1$H NMR (DMSO-d$_6$) δ ppm 9.78 (s, 1H), 7.78 (d, 1H, J = 13.6 Hz), 7.57 (d, 1H, J = 9.08 Hz), 7.18 (t, 1H, J = 9.28 Hz), 4.82 (t, 1H, 6 Hz), 4.13-4.1 (m, 2H), 3.5 (bs, 4H), 2.82-2.77 (m, 2H), 1.95 (bs, 4H). | 470.2 | 3.49 | B |
| 59 | $^1$H NMR (DMSO-d$_6$) δ ppm 9.74 (s, 1H), 7.75 (d, 1H, J = 13.6 Hz), 7.52 (d, 1H, J = 8.4 Hz), 7.11 (t, 1H, J = 9.2 Hz), 4.35-4.31 (m, 1H), 4.15-4.08 (m, 2H), 3.48 (bs, 4H), 1.94 (bs, 4H), 1.67-1.54 (m, 2H), 1.22 (d, 3H, J = 6 Hz), 0.92 (t, 3H, J = 7.4 Hz). | 430.21 | 3.58 | B |
| 60 | $^1$H NMR (DMSO-d$_6$) δ ppm 9.8 (s, 1H), 7.78 (dd, 1H, J = 13.6 Hz, 2.3 Hz), 7.55 (d, 1H, J = 9 Hz), 7.17 (t, 1H, J = 9.1 Hz), 4.71-4.69 (m, 1H), 4.13-4.08 (m, 2H), 3.48 (t, 4H, J = 6.5 Hz), 2.74-2.7 (m, 4H), 1.94 (t, 4, J = 6.5 Hz), 1.95-1.88 (m, 4H), 1.78-1.69 (m, 3H), 1. 1(d, 6H, J = 6 Hz). | 484.21 | 3.43 | B |
| 61 | $^1$H NMR (DMSO-d$_6$) δ ppm 9.75 (s, 1H), 7.73 (d, 1H, J = 12 Hz), 7.52 (d, 1H, J = 9.2 Hz), 7.1 (t, 1H, J = 9.2 Hz), 4.82 (bs, 1H), 3.86-3.83 (m, 1H), 3.75-3.59 (m, 4H), 3.37-3.34 (m, 1H), 3.03 (bs, 1H), 2.11-2.06 (m, 1H), 1.88-1.85 (m, 3H), 1.71 (bs, 4H), 1.58 (bs, 2H). | 484.36 | 2.3 | A |
| 62 | $^1$H NMR (DMSO-d$_6$) δ ppm 9.75 (s, 1H), 7.74 (d, 1H, J = 13.9 Hz), 7.52 (d, 1H, J = 7.4 Hz), 7.1 (t, 1H, J = 9.4 Hz), 4.82 (bs, 1H), 4.15 (q, 1H, J = 10.5 Hz), 3.48 (m, 4H), 1.94-1.87 (m, 5H), 1.71 (m, 4H), 1.58 (m, 2H). | 442.33 | 2.37 | A |

| Ex. | NMR Data | [M + H] | Rt (min) | LCMS Method |
|---|---|---|---|---|
| 63 | $^1$H NMR (DMSO-d$_6$) δ ppm 8.73 (s, 1H), 7.8 (dd, 1H, J = 12.9 Hz, 2.5 Hz), 7.23 (d, 1H, J = 12.1 Hz), 7.03 (t, 1H, J = 9 Hz), 4.70-4.66 (m, 1H), 4.35-4.3 (m, 1H), 4.09-4.08 (m, 3H), 3.99-3.82 (m, 2H), 3.7-3.67 (m, 2H), 3.41 (s, 2H), 1.91 (t, 2H, J = 6.8 Hz), 0.67 (d, 4H, J = 3.7 Hz). | 506.21 | 3.39 | B |
| 64 | $^1$H NMR (DMSO-d$_6$) δ ppm 9.75 (s, 1H), 7.74 (dd, 1H, J = 13.7 Hz, 2.2 Hz), 7.52 (d, 1H, J = 9 Hz), 7.10 (t, 1H, J = 9.3 Hz), 4.82 (bs, 1H), 4.61 (d, 2H, J = 6 Hz), 4.51 (d, 2H, J = 6 Hz), 4.15 (q, 2H, J = 10.6), 3.73 (s, 2H), 3.51 (t, 2H, J = 8.7 Hz), 2.26 (t, 2H, J = 8.8 Hz), 1.88-1.87 (m, 2H), 1.73-1.71 (m, 4H), 1.58 (m, 2H). | 484.4 | 3.26 | B |
| 65 | $^1$H NMR (DMSO-d$_6$) δ ppm 9.75 (s, 1H), 7.74 (dd, 1H, J = 13.7 Hz, 2.3 Hz), 7.51 (d, 1H, J = 8.9 Hz), 7.13 (t, 1H, J = 9.3 Hz), 4.28-4.25 (m, 1H), 4.15 (d, 2H, J = 8.2 Hz), 3.49-3.46 (m, 4H), 1.96-1.88 (m, 5H), 1.7 (bs, 2H), 1.57-1.27 (m, 6H). | 456.24 | 3.5 | B |
| 66 | $^1$H NMR (DMSO-d$_6$) δ ppm 9.79 (s, 1H), 7.77 (dd, 1H, J = 13.6 Hz, 2.4 Hz), 7.54 (d, 1H, J = 9.3 Hz), 7.17 (t, 1H, J = 9.3 Hz), 4.31-4.30 (m, 1H), 4.16-4.08 (q, 2H, J = 10.6 Hz), 3.80-3.77 (m, 1H), 3.61-3.58 (m, 1H), 3.53-3.33 (m, 6H), 1.99-1.92 (m, 5H), 1.79-1.77 (m, 1H), 1.76-1.71 (m, 1H), 1.56-1.49 (m, 1H). | 458.27 | 3.22 | B |
| 67 | $^1$H NMR (DMSO-d$_6$) δ ppm 8.65 (s, 1H), 7.57 (dd, 1H, J = 12.7 Hz, 2.3 Hz), 7.22 (d, 1H, J = 9.3 Hz), 6.92 (t, 1H, J = 8.9 Hz), 4.36-4.35 (bs, 1H), 3.97 (q, 2H, J = 10 Hz), 3.51 (t, 4H, J = 6.5 Hz), 2.37-2.36 (m, 1H), 2.03-1.99 (m, 4H), 1.86-1.81 (m, 6H), 1.77-1.75 (m, 4H), 1.68 (m, 1H), 0.81 (bs, 1H). | 482.4 | 3.88 | B |
| 68 | $^1$H NMR (DMSO-d$_6$) δ ppm 9.82 (s, 1H), 7.79 (d, 1H, J = 13.5 Hz), 7.55 (d, 1H, J = 9.1 Hz), 7.25 (t, 1H, J = 9.1 Hz), 4.61-4.60 (d, 2H, J = 6 Hz), 4.60-4.61 (bs, 1H), 4.51 (d, 2H, J = 6 Hz), 4.16 (q, 2H, J = 10.6 Hz), 3.73 (s, 2H), 3.51 (t, 2H, J = 6.8 Hz), 2.26 (t, 2H, J = 9 Hz), 2.1-2.07 (bs, 1H), 1.89 (bs, 2H), 1.76-1.74 (bs, 1H), 1.6-1.59 (bs, 3H), 1.46 (bs, 1H). | 534.27 | 2.59 | B |
| 69 | $^1$H NMR (DMSO-d$_6$) δ ppm 9.85 (s, 1H), 7.83 (dd, 1H, J = 13.6 Hz, 2.3 Hz), 7.58 (d, 1H, J = 8.9 Hz), 7.19 (t, 1H, J = 9.3 Hz), 5.13-5.1 (m, 1H), 4.37-4.33 (m, 1H), 4.16-3.92 (m, 5H), 3.5-3.46 (m, 4H), 1.96-1.92 (m, 4H). | 480.23 | 3.24 | B |
| 70 | $^1$H NMR (DMSO-d$_6$) δ ppm 10.25 (s, 1H), 7.73 (d, 2H, J = 11 Hz), 4.89-4.86 (m, 1H), 4.26-4.24 (m, 1H), 4.16-3.97 (m, 5H), 3.83 (s, 4H), 1.29 (s, 6H). | 512.23 | 2.68 | B |
| 71 | $^1$H NMR (DMSO-d$_6$) δ ppm 9.84 (s, 1H), 7.83 (dd, 1H, J = 13.6 Hz, 2 Hz), 7.58 (d, 1H, J = 8.8 Hz), 7.19 (t, 1H, J = 9.2 Hz) 5.13-5.1 (m, 1H), 4.37-4.33 (m, 1H), 4.16-3.93 (m, 5H), 3.5-3.47 (m, 4H), 1.96-1.94 (m, 4H). | 480.24 | 6.88 | K |
| 72 | $^1$H NMR (DMSO-d$_6$) δ ppm 10.2 (s, 1H), 7.69 (d, 1H, J = 10.7 Hz), 4.16 (q, 2H, J = 10.7 Hz), 4.03 (bs, 1H), 3.83-3.75 (m, 5H), 3.53-3.51 (m, 3H), 1.94 (bs, 1H), 1.81 (bs, 1H), 1.71 (bs, 1H), 1.44 (bs, 1H), 1.29 (s, 6H). | 490.4 | 3.81 | B |
| 73 | $^1$H NMR (DMSO-d$_6$) δ ppm 9.76 (s, 1H), 7.74 (dd, 1H, J = 13.6 Hz, 2.2 Hz), 7.51 (d, 1H, J = 9 Hz), 7.02 (t, 1H, J = 9.2 Hz), 4.89 (t, 1H, J = 8.4 Hz), 4.61 (d, 2H, J = 6.1 Hz), 4.51 (d, 2H, J = 6.1 Hz), 4.16 (q, 2H, J = 10.6 Hz), 3.73 (s, 2H), 3.51 (t, 2H, J = 6.9 Hz), 2.32-2.11 (m, 5H), 1.86-1.74 (m, 3H). | 496.27 | 3.29 | B |
| 74 | $^1$H NMR (DMSO-d$_6$) δ ppm 9.74 (s, 1H), 7.74 (dd, 2H, J = 13.7 Hz, 2.5 Hz), 7.51 (d, 1H, J = 9 Hz), 7.02 (t, 1H, J = 9.2 Hz), 4.89 (t, 1H, J = 6.4 Hz), 4.15 (q, 2H, J = 10.6 Hz), 3.49-3.46 (m, 4H), 2.19-2.15 (m, 2H), 1.95-1.85 (m, 6H), 1.34-1.32 (m, 2H), 0.55-0.52 (m, 1H), 0.45-0.43 (m, 1H). | 454.23 | 3.53 | B |
| 75 | $^1$H NMR (DMSO-d$_6$) δ ppm 8.62 (s, 1H), 7.53 (dd, 1H, J = 12.6 Hz, 1.9 Hz), 7.22 (d, 1H, J = 8.7 Hz), 6.81 (t, 1H, J = 8.8 Hz), 4.78 (t, 1H, J = 6.2 Hz), 3.96 (q, 2H, J = 10 Hz), 3.68 (t, 2H, J = 6.8 Hz), 3.4 (s, 2H), 2.15-2.13 (m, 2H), 2.06-2.02 (m, 2H), 1.91 (t, 2H, J = 6.8 Hz), 1.33-1.31 (m, 2H), 0.69-0.66 (m, 5 H), 0.51-0.49 (bs, 1H). | 480.27 | 3.58 | B |
| 76 | $^1$H NMR (DMSO-d$_6$) δ ppm 9.81 (s, 1H), 7.8 (dd, 1H, J = 13.6 Hz, 2.5 Hz), 7.55 (d, 1H, J = 8.9 Hz), 7.24 (t, J = 9.1 Hz), 4.6-4.5 (m, 1H), 4.13 (q, 2H), 3.48 (t, 4H, J = 6.5 Hz), 2.1 (bs, 1H), 1.96-1.91 (m, 5H), 1.7-1.6 (m, 1H, 1.6-1.57 (m, 3H),, 1.4-1.3 (m, 1H). | 492.25 | 3.41 | B |
| 77 | $^1$H NMR (DMSO-d$_6$) δ ppm 9.96 (s, 1 H), 7.72 (dd, 1 H, J = 14.8, 2.10 Hz), 7.53 (d, 1 H, J = 8.80 Hz), 7.06 (t, 1 H, J = 9.60 Hz), 4.24 (s, 4 H), 4.17-4.09 (m, 4 H, J = 5.48 Hz), 2.89 (t, 4 H, J = 12.52 Hz), 2.15-2.05 (m, 4 H). | 539.2 | 2.3 | A |
| 78 | $^1$H NMR (DMSO-d$_6$) δ ppm 10.15 (s, 1 H), 8.19 (d, 1 H, J = 2.16 Hz), 8.00 (d, 1 H, J = 8.64 Hz), 7.47 (t, 1 H, J = 8.80 Hz), 4.25 (s, 4 H), 4.13 (q, 2 H, J = 10.60 Hz), 2.89 (t, 4 H, J = 12.48 Hz), 2.77 (t, 4 H J = 4.96 Hz), 1.52-1.70 (m, 4 H), 1.52-1.50 (m, 2 H). | 553.28 | 2.58 | A |

-continued

| Ex. | NMR Data | [M + H] | Rt (min) | LCMS Method |
|---|---|---|---|---|
| 79 | $^1$H NMR (DMSO-d$_6$) δ ppm 9.90 (s, 1H), 7.64 (dd, 1H, J = 14.7, 2.4 Hz), 7.49 (d, 1H, J = 8.8 Hz), 7.04 (t, 1H, J = 8.9 Hz), 4.25 (s, 4H), 4.20-4.09 (m, 2H), 3.67-3.61 (m, 1H), 2.89 (t, 4H, J = 12.5 Hz), 2.61 (s, 3H), 1.73-1.70 (m, 2H), 1.69-1.60 (m, 2H), 1.54-1.45 (m, 4H) | 517.32 | 2.18 | A |
| 80 | $^1$H NMR (DMSO-d$_6$) δ ppm 9.73 (s, 1H), 7.67 (d, 1H, J = 14.3 Hz), 7.49 (d, 1H, J = 8.8 Hz), 7.03 (t, 1H, J = 9.2 Hz), 4.16-4.08 (m, 2H), 3.89-3.86 (m, 1H), 3.49 (bs, 4H), 2.52-2.50 (m, 3H), 2.01-1.95 (m, 6H), 1.48 (dd, 2H, J = 13.4, 5.8 Hz), 1.20 (bs, 2H), 0.61-0.59 (m, 1H), 0.39 (d, 1H, J = 4 Hz) | 467.37 | 3.33 | B |
| 81 | $^1$H NMR (DMSO-d$_6$ at 100° C.) δ ppm 9.67 (s, 1H), 7.55 (d, 2H, J = 11.2 Hz), 4.12-3.97 (m, 2H), 3.60-3.51 (m, 5H), 2.79 (s, 3H), 2.12-1.82 (m, 7H), 1.68-1.64 (m, 3H). | 509.3 | 3.5 | B |
| 82 | $^1$H NMR (DMSO-d$_6$) δ ppm 9.74 (s, 1H), 7.7 (d, 1H, J = 13.6 Hz), 7.5 (d, 1H, J = 8.4 Hz), 7.11 (t, 1H, J = 9.2 Hz), 4.16-4.08 (m, 2H), 3.87-3.82 (m, 2H), 3.48 (bs, 4H), 2.8 (s, 3H), 2.13-2.03 (m, 2H), 1.96-1.94 (m, 4H), 1.88-1.83(m, 1H), 1.72-1.65 (m, 2H), 1.63-1.61 (m, 1H). | 491.29 | 3.46 | B |
| 83 | $^1$H NMR (DMSO-d$_6$) δ ppm 9.58 (s, 1H), 7.62 (d, 1H, J = 15 Hz), 7.41 (d, 1H, J = 8.3 Hz), 6.57 (t, 1H, J = 8.4 Hz), 4.2 (s, 2H), 4.12-4.1 (m, 2H), 3.47 (bs, 4H), 2.54-2.56 (m, 2H), 2.09-2.06 (m, 2H), 1.94 (bs, 3H), 1.86-1.8 (m, 1H), 1.66-1.62 (m, 3H), 1.4-1.38 (m, 1H). | 453.3 | 3.34 | B |
| 84 | $^1$H NMR (DMSO-d$_6$) δ ppm 9.35 (s, 1H), 8.89(brm, 1H), 7.38 (s, 1H), 7.04 (t, 1H, J = 8.4 Hz), 6.84 (t, 1H, J = 8.5 Hz), 4.15-4.07 (m, 2H), 3.47 (brm, 4H), 2.82 (brm, 4H), 1.94 (brm, 4H), 1.64 (brm, 4H), 1.49 (brm, 2H). | 439.4 | 2.54 | B |
| 85 | $^1$H NMR (DMSO-d$_6$) δ ppm 9.36 (s, 1H), 8.81 (s, 1H), 7.35 (d, 1H, J = 2.4 Hz), 7.04 (dd, 1H, J = 8.7, 2.2 Hz), 6.81 (d, 1H, J = 8.7 Hz), 4.73 (brm, 1H), 4.13-4.07 (m, 2H), 3.49-3.45 (m, 4H) 1.95-1.82 (m, 4H), 1.82-1.73 (m, 6H), 1.56-1.54 (m, 2H). | 440.27 | 3.24 | B |
| 86 | $^1$H NMR (DMSO-d$_6$) δ ppm 9.46 (s, 1H), 9.22 (s, 1H), 7.45 (s, 1H), 7.04 (dd, 1H, J = 8.8, 1.9 Hz), 6.91 (d, 1H, J = 8.7 Hz), 4.65 (brm, 1H), 4.13-4.07 (m, 2H), 3.49-3.46 (m, 4H) 2.11-2.06 (m, 3H), 1.94 (brm, 4H), 1.83-1.58 (m, 3H). | 476.17 | 3.17 | B |
| 87 | $^1$H NMR (CDCl$_3$) δ ppm 8.73 (s, 1H), 7.61-7.57 (m, 1H), 7.19-7.12 (m, 2H), 3.96-3.84 (m, 2H), 3.73-3.66 (m, 1H), 3.51 (t, 4H, J = 6.48 Hz), 3.27-3.17 (m, 2H), 2.15-1.99 (m, 6H), 1.90 (d, 1 H, J = 6.56 Hz), 1.66-1.60 (m, 3 H), 0.93 (t, 3H, J = 7.04 Hz). | 505.32 | 3.49 | B |
| 88 | $^1$H NMR (DMSO-d$_6$) δ ppm 9.96 (s, 1H), 7.79-7.75 (m, 1H), 7.55 (d, 1H, J = 7.16 Hz), 7.19 (t, 1H, J = 9.32 Hz), 4.81-4.77 (m, 1H), 4.15-4.08 (m, 4H), 3.87-3.84 (m, 2H), 2.77-2.74 (m, 3H), 2.27-2.11 (m, 3H), 1.89-1.74 (m, 3H). | 493.28 | 2.63 | B |
| 89 | $^1$H NMR (CDCl$_3$) δ ppm 8.51 (s, 1H), 7.53 (d, 1H, J = 13.3 Hz), 7.21 (d, 1H, J = 7 Hz), 6.89 (t, 1H, J = 8.8 Hz), 4.17 (s, 4H), 2.97 (s, 4H), 2.81 (t, 4H, J = 11.8 Hz), 2.54 (s, 3H), 1.72 (s, 4H). | 435.45 | 2.05 | A |
| 90 | $^1$H NMR (DMSO-d$_6$) δ ppm 9.45 (s, 1H), 7.69 (d, 1H, J = 13.2 Hz), 7.47 (d, 1H, J = 8.1 Hz), 6.96 (t, 1H, J = 9.3 Hz), 4.59 (d, 2H, 5.9 Hz), 4.51 (d, 2H, J = 5.9 Hz), 3.7 (s, 2H), 3.47 (t, 2H, J = 7 Hz), 2.91 (s, 4H), 2.23 (t, 2H, J = 6.8 Hz), 1.63 (bs, 4H), 1.5 (bs, 2H). | 415.33 | 1.82 | A |
| 91 | $^1$H NMR (DMSO-d$_6$) δ ppm 9.42 (s, 1H), 7.69 (d, 1H, J = 13 Hz), 7.45 (d, 1H, J = 7 Hz), 6.96 (t, 1H, J = 9.1 Hz), 3.61 (t, 2H, J = 7.1 Hz), 3.37 (s, 2H), 2.9 (bs, 4H), 2.48 (s, 3H), 1.87 (t, 2H, J = 6.8 Hz), 1.63 (bs, 4H), 1.51(bs, 2H), 0.64 (d, 4H, J = 12 hz). | 399.32 | 2.13 | A |
| 92 | $^1$H NMR (DMSO-d$_6$) δ ppm 9.4 (s, 1H), 7.69 (dd, 1H, J = 15 Hz, 2.3 Hz), 7.46 (dd, 1H, J = 8.5 Hz, 1.8 Hz), 6.96 (t, 1H, J = 9.3 Hz) 3.47-3.43 (m, 4H), 2.91 (t, 4H, J = 5.1 Hz), 2.49 (s, 3H), 2.02-1.88 (m, 8H), 1.66-1.61 (m, 4H), 1.53-1.51 (m, 2H). | 413.31 | 2.27 | A |
| 93 | $^1$H NMR (DMSO-d$_6$) δ ppm 9.38 (s, 1H), 7.68 (dd, 1H, J = 15 Hz, 2.3 Hz), 7.46 (dd, 1H, J = 8.5 Hz, 1.87 Hz), 6.97 (t, 1H, J = 9.3 Hz), 4.77 (t, 1H, J = 5.6 Hz), 3.89-3.88 (m, 1H), 3.54-3.43 (m, 3H), 2.91 (t, 4H, J = 5.1 Hz), 2.45 (s, 3H), 1.98-1.92 (m, 4H), 1.66-1.61 (m, 4H), 1.53-1.51 (m, 2H). | 403.32 | 1.78 | A |
| 94 | $^1$H NMR (DMSO-d$_6$) δ ppm 9.47 (s, 1H), 7.69 (d, 1H, J = 15 Hz), 7.47 (d, 1H, J = 8.8 Hz), 6.96 (t, 1H, J = 9.4 Hz), 3.41 (s, 4H), 2.9 (s, 4H), 2.62 (s, 4H), 1.63-1.5 (m, 7H), 0.45-0.34 (m, 4H). | 428.32 | 1.54 | A |
| 95 | $^1$H NMR (DMSO-d$_6$) δ ppm 9.34 (s, 1H), 7.68 (dd, 1H, J = 15 Hz 2.3 Hz), 7.46 (dd, 1H, J = 10.5 Hz), 6.98-6.89 (m, 2H), 3.92 (q, 1H), 3.76-3.70 (m, 2H), 2.91 (t, 4H, J = 5.1 Hz), 2.45 (s, 3H), 1.98-1.92 (m, 3H), 1.82-1.73 (m, 4H), 1.63-1.58 (m, 7H), 1.56-1.5 (m, 3H). | 443.34 | 2.15 | A |

| Ex. | NMR Data | [M + H] | Rt (min) | LCMS Method |
|---|---|---|---|---|
| 96 | $^1$H NMR (DMSO-d$_6$) δ ppm 9.41 (s, 1H), 7.69-7.65 (m, 1H), 7.47-7.44 (m, 1H), 6.96 (t, 1H, J = 9.44 Hz), 4.72 (t, 1H, J = 5.20 Hz), 3.57-3.51 (m, 2H), 3.46-3.36 (m, 3H), 3.26-3.23 (m, 1H), 2.92-2.88 (m, 4H), 2.5 (s, 3H), 2.42-2.40 (m, 1H), 2.05-1.95 (m, 1 H), 1.8-1.7 (m, 1 H), 1.63-1.61 (m, 4H), 1.52-1.50 (m, 2H). | 403.27 | 1.73 | B |
| 97 | $^1$H NMR (DMSO-d$_6$) δ ppm 9.43 (s, 1H), 7.69 (dd, 1H, J = 15 Hz 2.3 Hz), 7.47 (dd, 1H, J = 8.5 Hz, 1.9 Hz), 6.96 (t, 1H, J = 9.3 Hz) 5.02 (d, 1H, 3.6 Hz), 4.36 (bs, 1H), 3.55-3.38 (m, 3H), 3.3-3.27 (m, 1H), 2.91(t, 4H, J = 5.2 Hz), 1.99-1.95 (m, 1H), 1.88-1.86 (m, 1H), 1.66-1.61 (m, 4H), 1.53-1.51 (m, 2H). | 389.31 | 1.67 | A |
| 98 | $^1$H NMR (DMSO-d$_6$) δ ppm 9.52 (s, 1H), 7.68 (dd, 1H, J = 15 Hz, 2.3 Hz), 7.47 (d, 1H, J = 8.6 Hz), 6.97 (t, 1H, J = 9.3 Hz), 4.21 (s, 2H), 3.7 (d, 2H, J = 11 Hz), 3.58 (d, 2H, J = 11 Hz), 2.91 (t, 4H, J = 5.1 Hz), 1.96-1.9 (m, 4H), 1.66-1.61 (m, 4H), 1.53-1.5 (m, 2H). | 415.28 | 1.95 | A |
| 99 | $^1$H NMR (DMSO-d$_6$) δ ppm 9.66 (s, 1H), 7.7 (dd, 1H, J = 15 Hz, 2.08 Hz), 7.5 (d, 1H, J = 8.6 Hz), 6.97 (t, 1H, J = 9.6 Hz), 3.25 (s, 2H), 2.92-2.9 (m, 4H), 1.95-1.92 (m, 4H), 1.63 (bs, 4H), 1.52 (bs, 2H). | 403.32 | 1.99 | A |
| 100 | $^1$H NMR (DMSO-d$_6$) δ ppm 9.62 (s, 1H), 7.69 (dd, 1H, J = 14.9, 2.2 Hz), 7.49 (d, 1H, J = 8.7 Hz), 6.97 (t, 1H, J = 9.4 Hz), 4.69 (s, 2H), 3.50-3.45 (m, 6H), 2.93-2.90 (m, 4H), 1.95-1.92 (m, 4H), 1.66-1.61 (m, 4H), 1.54-1.10 (m, 2H), 1.11 (t, 1H, J = 6.9 Hz). | 417.35 | 2.14 | A |
| 101 | $^1$H NMR (DMSO-d$_6$) δ ppm 9.68 (s, 1H), 7.75-7.71 (dd, 1H, J = 2.40 Hz), 7.51 (d, 1H, J = 8.96 Hz), 7.11 (t, 1H, J = 9.28 Hz), 4.83-4.81 (m, 1H), 4.65 (s, 2H), 3.50-3.46 (m, 4H), 3.25 (s, 3H), 1.98-1.85 (bs, 6H), 1.73 (bs, 4H), 1.60 (bs, 2H). | 404.32 | 2.2 | A |
| 102 | $^1$H NMR (DMSO-d$_6$) δ ppm 9.87 (s, 1H), 7.58 (d, 2H, J = 11.84 Hz), 4.64 (s, 2H), 3.50 (t, 4H, J = 6.6 Hz), 3.25 (s, 3H), 3.01 (bs, 4H), 1.95-1.92 (m, 4H), 1.58 (bs, 4H), 1.52 (bs, 2H). | 421.21 | 2.33 | A |
| 103 | $^1$H NMR (DMSO-d$_6$) δ ppm 9.57 (s, 1H), 7.69 (d, 1H, J = 14.96 Hz), 7.48 (d, 1H, J = 8.68 Hz), 7.00 (t, 1H, J = 9.34 Hz), 4.68 (s, 2H), 4.03 (bs, 1H), 3.58-3.48 (m, 2H), 3.25 (s, 3H), 2.93-2.90 (m, 4H), 2.14-1.86 (m, 3H), 1.64 (bs, 5H), 1.52 (bs, 2H), 1.26 (d, 3H, J = 6.2 Hz). | 417.36 | 2.1 | A |
| 104 | $^1$H NMR (DMSO-d$_6$) δ ppm 9.85 (s, 1H), 7.67 (d, 1H, J = 15.0 Hz), 7.49 (d, 1H, J = 8.6 Hz), 6.97 (t, 1H, J = 9.2 Hz), 4.65 (s, 2H), 4.24 (s, 4H), 3.25 (s, 3H), 2.92-4.86 (m, 7H), 1.64 (brm, 4H), 1.52-1.51 (m, 2H). | 465.33 | 2.09 | A |
| 105 | $^1$H NMR (DMSO-d$_6$) δ ppm 9.74 (s, 1H), 7.75 (d, 1H, J = 13.6 Hz), 7.47 (d, 1H, J = 8.8 Hz), 7.17 (t, 1H, J = 9.2 Hz), 4.74-4.70 (m, 1H), 4.67 (s, 2H), 3.50-3.47 (s, 4H), 3.25 (s, 3H), 2.21-2.11 (m, 3H), 1.98-1.92 (m, 4H), 1.88-1.71 (m, 3H). | 440.2 | 3.18 | B |
| 106 | $^1$H NMR (DMSO-d$_6$) δ ppm 9.41 (s, 1H), 7.67 (dd, 1H, J = 2.2, 15 Hz), 7.47-7.45 (m, 1H), 6.98 (t, J = 9.5 Hz, 1H), 3.60-3.55 (m, 1H), 3.52-3.50 (m, 1H), 3.41-3.39 (m, 1H), 3.30-3.32 (m, 6H), 3.16-3.12 (m, 1H), 2.92-2.89 (m, 4H), 2.48-2.42 (m, 3H), 2.21-2.3 (m, 1H), 2.04-2.00 (m, 3H), 1.66-1.62 (m, 5H), 1.52-1.50 (m, 2H). | 442.44 | 2.17 | B |
| 107 | $^1$H NMR (DMSO-d$_6$) δ ppm 7.64 (d, 1H, J = 15 Hz), 7.41 (d, 1H, J = 8.2 Hz), 6.96 (t, 1H, J = 9.3 Hz), 3.61-.360 (m, 6H), 3.42-3.39 (m, 1H), 3.17-3.15 (m, 1H), 2.91 (t, 4H, J = 5.08 Hz), 2.53-2.46 (m, 6H), 2.38-2.32 (m, 2H), 1.96-1.86 (m, 4H), 1.65-1.62 (m, 4H), 1.5-1.49 (m, 2H). | 506.42 | 2.28 | B |
| 108 | $^1$H NMR (CDCl$_3$) δ ppm 9.61 (s, 1H), 7.75 (dd, 1H, J = 15 Hz, 2.4 Hz), 6.97 (d, 1H, J = 9.3 Hz), 7.01 (t, 1H, J = 8.9 Hz), 4.7 (s, 2H), 3.66-3.63 (m, 1H), 3.48 (t, 4H, J=), 2.91 (t, 4H, J = 4.8 Hz), 1.93 (t, 4H, J = 6.4 Hz), 1.64 (d, 4H, J = 4.8 Hz), 1.52 (d, 2H, J = 4.6 Hz), 1.1 (d, 6H, J = 6 Hz). | 431.31 | 2.16 | A |
| 109 | $^1$H NMR (DMSO-d$_6$) δ ppm 9.72 (s, 1H), 7.8 (dd, 1H, J = 13.6 Hz, 2.12 Hz), 7.54 (d, 1H, J = 9.1 Hz), 7.19 (t, 1H, J = 9.3 Hz), 4.82-4.78 (m, 2H), 4.7 (s, 2H), 3.66-3.63 (m, 1H), 3.49-3.47 (m, 4H), 2.21-2.11 (m, 3H), 1.95-1.88 (m, 4H), 1.78-1.69 (m, 3H), 1.1(d, 6H, J = 6 Hz). | 468.31 | 7.05 | K |
| 110 | $^1$H NMR (DMSO-d$_6$) δ ppm 9.52 (s, 1H), 7.8 (dd, 1H, J = 13.7 Hz, 2.1 Hz), 7.52 (d, 1H, J = 8.7 Hz), 7.17 (t, 1H, J = 9.2 Hz), 4.79-4.78 (m, 1H), 3.47-3.31 (m, 4H), 2.9 (t, 2H, J = 7.3 Hz), 2.21-2.13 (m, 3H), 1.94-1.92 (m, 4H), 1.84-1.57 (m, 5H), 0.91 (t, 3H, J = 7.3 Hz). | 438.29 | 3.46 | B |
| 111 | $^1$H NMR (DMSO-d$_6$) δ ppm 8.69 (s, 1H), 7.68 (dd, 1H, J = 12.8 Hz, 2 Hz), 7.22 (d, 1H, J = 8 Hz), 6.99 (t, 1H, J = 8.9 Hz), 4.5-4.47 (bs, 1H), 3.48 (bs, 4H), 2.88 (d, 2H, J = 7.1 Hz), 2.28-2.16 (m, 3H), 1.97-1.93 (m, 7H), 1.78-1.72 (m, 1H), 0.97 (d, 6H, 8.7 Hz). | 452.28 | 3.53 | B |

-continued

| Ex. | NMR Data | [M + H] | Rt (min) | LCMS Method |
|---|---|---|---|---|
| 112 | $^1$H NMR (CD$_3$OD δ ppm 1.61-1.76 (m, 2 H) 1.79-1.98 (m, 4 H) 2.00-2.10 (m, 4 H) 2.58 (s, 3 H) 2.99-3.07 (m, 4 H) 3.49-3.60 (m, 4 H) 7.00- 7.13 (m, 1 H) 7.33 (ddd, J = 8.80, 2.45, 1.11 Hz, 1 H) 7.58 (dd, J = 14.52, 2.47 Hz, 1 H) | 373.2 | 2.3 | X |
| 113 | $^1$H NMR ((CD$_3$OD) δ ppm 1.60 (q, J-5.75 Hz, 2 H) 1.75 (dt, J = 10.98, 5.71 Hz, 4 H) 2.69 (s, 3 H) 2.88-3.07 (m, 4 H) 6.17-6.54 (m, 2 H) 7.04 (t, J = 9.13 Hz, 1 H) 7.36 (ddd, J-8.72, 2.41, 1.13 Hz, 1 H) 7.43-7.47 (m, 2 H) 7.59 (dd, J = 14.38, 2.38 Hz, 1 H) | 369.3 | 2 | X |
| 114 | $^1$H NMR (CD$_3$OD) δ ppm 1.57-1.64 (m, 2 H) 1.68 (br s, 6 H) 1.76 (quin, J-5.63 Hz, 4 H) 2.54 (s, 3 H) 2.98-3.05 (m, 4 H) 3.46-3.57 (m, 4 H) 6.99-7.11 (m, 1 H) 7.30 (ddd, J = 8.72, 2.41, 1.13 Hz, 1 H) 7.58 (dd, J = 14.45, 2.44 Hz, 1 H) | 387.2 | 2.5 | X |
| 115 | $^1$H NMR (CD$_3$OD) δ ppm 1.23 (d, J-6.75 Hz, 6 H) 1.55-1.66 (m, 2 H) 1.74 (quin, J = 5.60 Hz, 2 H) 2.52 (s, 3 H) 2.93 (s, 3 H) 2.96-3.03 (m, 4 H) 4.36 (spt, J-6.73 Hz, 1 H) 7.03 (t, J = 9.13 Hz, 1 H) 7.28 (ddd, J-8.76, 2.38, 1.13 Hz, 1 H) 7.52-7.64 (m, 1 H) | 375.2 | 2.5 | X |
| 116 | $^1$H NMR (CD$_3$OD) δ ppm 1.53-1.66 (m, 2 H) 1.74 (dt, J = 10.98, 5.71 Hz, 4 H) 2.54 (s, 3 H) 2.94-3.05 (m, 4 H) 3.43-3.54 (m, 4 H) 3.74-3.81 (m, 4 H) 7.03 (t, J-9.13 Hz, 1 H) 7.28 (ddd, J = 8.66, 2.41, 1.06 Hz, 1 H) 7.56 (dd, J = 14.38, 2.38 Hz, 1 H) | 389.2 | 2.1 | X |
| 117 | $^1$H NMR (CD$_3$OD) δ ppm 1.51-1.65 (m, 2 H) 1.74 (quin, J = 5.60 Hz, 4 H) 2.52 (s, 3 H) 2.94-3.03 (m, 4 H) 3.07 (s, 6 H) 6.97-7.07 (m, 1 H) 7.24-7.34 (m, 1 H) 7.57 (dd, J = 14.45, 2.44 Hz, 1 H) | 347.2 | 2.1 | X |
| 118 | $^1$H NMR (DMSO-d$_6$) δ ppm 10.03 (s, 1 H), 8.46 (d, 1 H, J = 2.6 Hz), 7.95 (d, 1 H, J = 1.08 Hz), 7.71 (dd, 1 H, J = 15 Hz, 2.3 Hz), 7.53 (d, 1 H, J = 8.7 Hz), 6.99 (t, 1 H, J = 9.3 Hz), 6.69 (t, 1 H, J = 2 Hz), 2.92 (t, 4 H J = 5.1 Hz), 2.68 (s, 3 H), 1.67-1.61 (m, 4 H), 1.23 (m, 2H). | 370.3 | 1.84 | A |
| 119 | Not Determined | 387.2 | 2.5 | X |
| 120 | $^1$H NMR (CD$_3$OD) δ ppm 1.57-1.74 (m, 4 H) 1.77-1.96 (m, 4 H) 1.99-2.08 (m, 4 H) 2.53 (s, 3 H) 3.49-3.56 (m, 4 H) 4.79-4.85 (m, 1 H) 7.03 (t, J-9.07 Hz, 1 H) 7.23-7.31 (m, 1 H) 7.60 (dd, J = 13.26, 2.50 Hz, 1 H) | 374.2 | 2.6 | X |
| 121 | Not Determined | 409.3 | 2.7 | X |
| 122 | $^1$H NMR (CD$_3$OD) δ ppm 1.46 (d, J-6.63 Hz, 3 H) 1.86-1.95 (m, 2 H) 1.96-2.01 (m, 1 H) 2.04-2.13 (m, 4 H) 2.43-2.51 (m, 2 H) 2.69-2.77 (m, 1 H) 2.85 (s, 3 H) 3.30 (br d, J = 5.50 Hz, 3 H) 3.36 (dd, J = 9.57, 7.94 Hz, 1 H) 3.71-3.87 (m, 1 H) 3.91-4.05 (m, 2 H) 7.35 (t, J = 9.13 Hz, 1 H) 7.60 (ddd, J-8.69, 2.38, 1.06 Hz, 1 H) 7.90 (dd, J = 14.45, 2.44 Hz, 1 H) | 387.3 | 2.4 | X |
| 123 | $^1$H NMR (CD$_3$OD) δ ppm 1.54-1.65 (m, 2 H) 1.68-1.80 (m, 4 H) 1.84-1.93 (m, 1 H) 2.17-2.25 (m, 1 H) 2.53 (s, 3 H) 2.94-3.03 (m, 4 H) 3.05-3.12 (m, 1 H) 3.37-3.44 (m, 1 H) 3.53-3.60 (m, 1 H) 3.64-3.74 (m, 2 H) 3.83 (td, J = 8.13, 5.38 Hz, 1 H) 3.93-4.02 (m, 1 H) 4.57-4.65 (m, 1 H) 6.96-7.08 (m, 1 H) 7.25-7.33 (m, 1 H) 7.57 (dd, J = 14.51, 2.38 Hz, 1 H) | 415.2 | 2.3 | X |

The analytical data for examples 124-316 is found in the table below:

| Ex. | NMR Data | [M + H] | Rt (min) | LCMS Method |
|---|---|---|---|---|
| 124 | $^1$H NMR (400 MHz, DMSO-d$_6$) δ 9.86 (s, 1H), 7.59-7.55 (m, 1H), 7.46 (s, 1H), 4.60-4.58 (m, 1H), 4.15-4.08 (m, 2H), 3.97 (d, 2H, J = 7.5 Hz), 3.76 (d, 2H, J = 7.5 Hz), 3.36-3.31 (m, 5H), 2.19 (s, 3H), 2.10-2.06 (m, 2H), 1.94-1.93 (m, 2H), 1.32-1.28 (m, 6H), 0.69-0.51 (m, 2H). | 512.3 | 2.66 | B |
| 125 | $^1$H NMR (400 MHz, DMSO-d$_6$) δ 9.83 (s, 1H), 7.58-7.54 (m, 1H), 7.45 (s, 1H), 4.58 (t, 1H, J = 6.4 Hz), 4.15-4.07 (m, 2H), 3.91 (d, 2H, J = 7.8 Hz), 3.78 (d, 2H, J = 7.88 Hz), 3.40 (s, 3H), 3.31 (s, 2H), 2.19 (s, 3H), 2.10-1.92 (m, 4H), 1.69-1.63 (m, 2H), 1.33-1.31 (m, 2H), 0.88-0.83 (m, 3H), 0.71-0.68 (m, 1H), 0.52-0.50 (m, 1H). | 526.3 | 3.57 | B |
| 126 | $^1$H NMR (DMSO-d$_6$) δ ppm 10.1 (s, 1H), 7.85 (s, 1H), 7.78 (d, 1H, J = 12.6 Hz), 4.95-4.93 (m, 1H), 4.73 (t, 1H, J = 5.96 Hz), 4.15-4.08 (m, 2H), 3.93 (d, 2H, J = 7.6 Hz), 3.75 (d, 2H, J = 7.7 Hz), 3.45 (d, 2H, J = 4.6 Hz), 2.11-2.08 (m, 2H), 1.91.96 (m, 2H), 1.64-1.60 (m, 2H), 1.40-1.32 (m, 2H), 0.86 (t, 3H, J = 7.2 Hz), 0.79-0.78 (m, 1H), 0.50-0.49 (m, 1H). | 532.3 | 3.4 | B |

| Ex. | NMR Data | [M + H] | Rt (min) | LCMS Method |
|---|---|---|---|---|
| 127 | ¹H NMR (DMSO-d₆) δ ppm 10.1 (s, 1H), 7.85 (s, 1H), 7.78 (d, 1H, J = 13.4 Hz), 4.73 (t, 1H, J = 6.2 Hz), 4.20-4.07 (m, 2H), 3.78 (s, 4H), 2.20-2.08 (m, 2H), 1.98-1.96 (m, 2H), 1.64-1.59 (m, 4H), 1.40-1.30 (m, 2H), 0.84-0.78 (m, 7H), 0.60-0.40 (m, 2H). | 530.3 | 3.84 | B |
| 128 | ¹H NMR (DMSO-d₆) δ ppm 9.85 (s, 1H), 7.58 (dd, 1H, J = 2.08 Hz, 13.7 Hz), 7.46 (s, 1H), 5.01 (t, 1H, J = 5.3 Hz), 4.58 (t, 1H, J = 6.4 Hz), 4.15-4.07 (m, 2H), 3.99 (d, 2H, J = 7.6 Hz), 3.71 (d, 2H, J = 7.6 Hz), 3.39 (d, 2H, J = 5.5 Hz), 2.19 (s, 3H), 2.10-2.06 (m, 2H), 1.96-1.94 (m, 2H), 1.33-1.31 (m, 2H), 1.24 (s, 3H), 0.71-0.69 (m, 1H), 0.52-0.51 (m, 1H). | 498.3 | 3.34 | B |
| 129 | ¹H NMR (DMSO-d₆) δ ppm 9.85 (s, 1H), 7.58 (dd, 1H, J = 2.3 Hz, 13.6 Hz), 7.48 (s, 1H), 5.01 (t, 1H, J = 5.36 Hz), 4.59-4.56 (m, 1H), 4.16-4.08 (m, 2H), 3.99 (d, 2H, J = 7.6 Hz), 3.71 (d, 2H, J = 7.6 Hz), 3.40-3.31 (m, 2H), 2.49-2.27 (m, 4H), 2.21 (s, 3H), 2.08-1.87 (m, 3H), 1.52-1.31 (m, 2H), 1.24 (s, 3H). | 512.4 | 3.39 | B |
| 130 | ¹H NMR (DMSO-d₆) δ ppm 10.21 (s, 1H), 7.85 (s, 1H), 7.78 (d, 1H, J = 13.56 Hz), 4.73 (t, 1H, J = 6.12 Hz), 4.16-4.07 (m, 4H), 3.96 (d, 2H, J = 8.48 Hz), 3.20 (s, 3H), 2.12-2.07 (m, 2H), 1.98-1.96 (m, 2H), 1.46 (s, 3H), 1.40-1.30 (m, 2H), 0.80-0.70 (m, 1H), 0.60-0.40 (m, 1H). | 518.3 | 3.49 | B |
| 131 | ¹H NMR (DMSO-d₆) δ ppm 9.84 (s, 1H), 7.57 (d, 1H, J = 13.5 Hz), 7.45 (s, 1H), 4.60-4.50 (m, 1H), 4.15-4.07 (m, 2H), 3.77 (s, 4H), 2.18 (s, 3H), 2.10-2.0 (m, 2H), 1.94-1.91 (m, 2H), 1.62-1.61 (m, 4H), 1.40-1.30 (m, 2H), 0.94-0.51 (m, 8H). | 510.1 | 4.36 | K |
| 132 | ¹H NMR (DMSO-d₆) δ ppm 10.19 (s, 1H), 7.66-7.64 (m, 2H), 4.15-4.0 (m, 3H), 3.78 (s, 4H), 2.0-1.90 (m, 1H), 1.77-1.23 (m, 11H), 0.84-0.80 (m, 6H), 0.30-0.10 (m, 4H). | 542.41 | 3.76 | B |
| 133 | ¹H NMR (DMSO-d₆) δ ppm 9.97 (s, 1H), 7.74 (d, 1H, J = 12.3 Hz), 7.52 (d, 1H, J = 8.8 Hz), 7.22 (t, 1H, J = 9.2 Hz), 4.63-4.58 (m, 1H), 4.38 (s, 2H), 4.17-4.06 (m, 4H), 3.96 (d, 2H, J = 8.5 Hz), 3.20 (s, 3H), 2.02-1.97 (m, 2H), 1.90-1.70 (m, 4H), 1.58 (t, 2H, J = 10.1 Hz), 1.46 (s, 3H). | 514.39 | 3.01 | B |
| 134 | ¹H NMR (DMSO-d₆) δ ppm 10.1 (s, 1H), 7.66 (d, 2H, J = 10.0 Hz), 4.15-3.90 (m, 3H), 3.78 (s, 4H), 2.07-1.20 (m, 18H), 0.83 (t, 6H, J = 7.3 Hz). | 555.41 | 3.95 | B |
| 135 | ¹H NMR (DMSO-d₆) δ ppm 9.90 (s, 1H), 7.73 (d, 1H, J = 13.7 Hz), 7.53 (d, 1H, J = 8.7 Hz), 7.13 (t, 1H, J = 9.24 Hz), 5.02-4.87 (m, 2H), 4.16-4.08 (m, 2H), 3.99 (d, 2H, J = 7.6 Hz), 3.71 (d, 2H, J = 7.56 Hz), 3.40-3.38 (m, 2H), 2.41-2.35 (m, 4H), 2.05-1.83 (m, 4H), 1.50 (t, 1H, J = 8.32 Hz), 1.38 (t, 1H, J = 8.5 Hz), 1.24 (s, 3H). | 498.34 | 3.25 | B |
| 136 | ¹H NMR (DMSO-d₆) δ ppm 10.01 (s, 1H), 7.67 (d, 2H, J = 10.7 Hz), 4.20-4.10 (m, 2H), 4.0 (s, 2H), 3.50-3.40 (m, 4H), 2.0-1.90 (m, 4H), 1.75-1.73 (m, 7H). | 472.39 | 3.56 | B |
| 137 | ¹H NMR (DMSO-d₆) δ ppm 10.19 (s, 1H), 7.69-7.66 (m, 2H), 4.15-4.02 (m, 3H), 3.78-3.74 (m, 5H), 3.59-3.49 (m, 3H), 1.94-1.43 (m, 8H), 0.83 (t, 6H, J = 7.3 Hz). | 518.35 | 3.49 | B |
| 138 | ¹H NMR (DMSO-d₆) δ ppm 10.02 (s, 1H), 7.68 (d, 2H, J = 10.6 Hz), 4.78 (s, 1H), 4.15-4.07 (m, 2H), 3.50-3.40 (m, 4H), 2.10-1.72 (m, 8H), 1.60-1.40 (m, 1H), 1.30-1.20 (m, 1H), 0.55-0.39 (m, 4H). | 486.32 | 3.68 | B |
| 139 | ¹H NMR (DMSO-d₆) δ ppm 10.02 (s, 1H), 7.67 (d, 2H, J = 10.5 Hz), 4.90-4.80 (m, 1H), 4.13-4.10 (m, 2H), 3.50-3.40 (m, 4H), 1.67-2.30 (m, 4H), 2.10-1.70 (m, 10H). | 486.29 | 3.76 | B |
| 140 | ¹H NMR (DMSO-d₆) δ ppm 9.90 (s, 1H), 7.71 (d, 1H, J = 11.8 Hz), 7.53 (d, 1H, J = 8.44 Hz), 7.22-7.20 (m, 1H), 5.04-5.03 (m, 1H), 4.16-4.10 (m, 2H), 3.90-3.80 (m, 4H), 2.0-1.29 (m, 12H), 0.70-0.67 (m, 1H), 0.50-0.47 (m, 1H). | 468.3 | 3.61 | B |
| 141 | ¹H NMR (DMSO-d₆) δ ppm 10.01 (s, 1H), 7.64 (d, 2H, J = 10.96 Hz), 4.70-4.50 (m, 1H), 4.14-4.06 (m, 2H), 3.50-3.40 (m, 4H), 2.38-1.80 (m, 8H), 1.60-1.0 (m, 6H). | 486.29 | 3.69 | B |
| 142 | ¹H NMR (DMSO-d₆) δ ppm 10.36 (s, 1H), 8.10 (d, 1H, J = 14.3 Hz), 8.03 (s, 1H), 4.95 (t, 1H, J = 6.3 Hz), 4.17-4.07 (m, 4H), 3.97 (d, 2H, J = 8.48 Hz), 3.21 (s, 3H), 2.18-2.15 (m, 2H), 1.98-1.97 (m, 2H), 1.46 (s, 3H), 1.36-1.34 (m, 2H), 0.73-0.70 (m, 1H), 0.54-0.50 (m, 1H). | 509.36 | 3.44 | B |
| 143 | ¹H NMR (DMSO-d₆) δ ppm 9.74 (s, 1H), 7.74 (dd, 1H, J = 2.1 Hz, 13.6 Hz), 7.52 (d, 1H, J = 8.2 Hz), 7.14 (t, 1H, J = 9.24 Hz), 4.90-4.87 (m, 1H), 4.16-4.08 (m, 2H), 3.49-3.46 (m, 4H), 2.42-2.36 (m, 4H), 2.07-2.05 (m, 2H), 2.02-1.94 (m, 4H), 1.96-1.88 (m, 2H), 1.52 (t, 1H, J = 8.3 Hz), 1.41 (t, 1H, J = 8.6 Hz). | 468.36 | 3.37 | B |

| Ex. | NMR Data | [M + H] | Rt (min) | LCMS Method |
|---|---|---|---|---|
| 144 | $^1$H NMR (DMSO-d$_6$) δ ppm 9.96 (s, 1H), 7.65 (d, 2H, J = 11.0 Hz), 4.80-4.70 (m, 1H), 4.40-4.30 (m, 1H), 4.13-4.10 (m, 2H), 3.91 (d, 1H, J = 9.76 Hz), 3.70-3.54 (m, 5H), 3.10-3.0 (m, 1H), 2.20-1.70 (m, 6H), 1.34-1.32 (m, 2H), 0.69-0.67 (m, 1H), 0.40-0.39 (m, 1H). | 514.39 | 3.34 | B |
| 145 | $^1$H NMR (400 MHz, DMSO-d$_6$) δ ppm 10.19 (s, 1H), 7.67 (d, 2H, J = 10.9 Hz), 4.64-4.61 (m, 1H), 4.15-4.07 (m, 2H), 3.78 (s, 4H), 2.33-2.25 (m, 4H), 2.05-1.93 (m, 4H), 1.64-1.54 (m, 5H), 1.30-1.22 (m, 1H) 0.82 (t, 6H, J = 7.4 Hz). | 528.42 | 3.75 | B |
| 146 | $^1$H NMR (DMSO-d$_6$) δ ppm 10.08 (s, 1H), 8.10 (d, 1H, J = 2.4 Hz), 8.03 (s, 1H), 7.98 (d, 1H, J = 9.28 Hz), 7.15 (d, 1H, J = 9.24 Hz), 5.06 (t, 1H, J = 6.44 Hz), 4.17-4.07 (m, 4H), 3.97 (d, 2H, J = 8.52 Hz), 3.21 (s, 3H), 2.25-2.23 (m, 2H), 1.89-1.86 (m, 2H), 1.46 (s, 3H), 1.36-1.34 (m, 2H), 0.58-0.57 (m, 1H), 0.49-0.48 (m, 1H). | 491.36 | 3.26 | B |
| 147 | $^1$H NMR (400 MHz, DMSO-d$_6$) δ 9.87 (s, 1H), 7.65-7.62 (m, 2H), 4.72 (t, 1H, J = 6.28 Hz), 4.13-4.05 (m, 2H), 3.63-3.53 (m, 4H), 3.30-3.25 (m, 4H), 2.09-2.0 (m, 4H), 1.92-1.9 (m, 2H), 1.34-1.32 (m, 2H), 0.86 (d, 6H, J = 6.6 Hz), 0.70-0.67 (m, 1H), 0.48-0.47 (m, 1H). | 532.46 | 3.66 | B |
| 148 | $^1$H NMR (400 MHz, DMSO-d$_6$) δ 10.23 (s, 1H), 7.67 (d, 2H, J = 10.7 Hz), 4.67-4.62 (m, 1H), 4.16-4.09 (m, 2H), 4.04 (d, 2H, J = 8.68 Hz), 3.96 (d, 2H, J = 8.68 Hz), 3.18 (s, 3H), 2.33-2.25 (m, 4H), 2.07-1.80 (m, 6H), 1.56 (t, 1H, J = 7.6 Hz), 1.29 (t, 1H, J = 8.7 Hz), 0.82 (t, 3H, J = 7.2 Hz). | 530.4 | 3.54 | B |
| 149 | $^1$H NMR (400 MHz, DMSO-d$_6$) δ 9.91 (s, 1H), 7.73 (d, 1H, J = 13.5 Hz), 7.52 (d, 1H, J = 8.0 Hz), 7.13 (t, 1H, J = 8.68 Hz), 4.90-4.80 (m, 1H), 4.14-3.94 (m, 6H), 3.18 (s, 3H), 2.50-2.36 (m, 4H), 2.03-1.84 (m, 6H), 1.52-1.36 (m, 2H), 0.90-0.80 (m, 3H). | 512.4 | 3.46 | B |
| 150 | $^1$H NMR (DMSO-d$_6$) δ ppm 10.2 (s, 1H), 7.66 (d, 2H, J = 10.3 Hz), 4.16-4.11 (m, 3H), 4.04 (d, 2H, J = 8.6 Hz), 3.96 (d, 2H, J = 8.68 Hz), 3.18 (s, 3H), 2.32-2.26 (m, 2H), 1.84-1.38 (m, 7H), 1.16-0.96 (m, 3H), 0.83 (t, 3H, J = 7.08 Hz). | 530.4 | 4.05 | B |
| 151 | $^1$H NMR (DMSO-d$_6$) δ ppm 10.19 (s, 1H), 7.65 (d, 2H, J = 10.5 Hz), 4.60-4.57 (m, 1H), 4.16-4.08 (m, 2H), 4.04 (d, 2H, J = 8.6 Hz), 3.96 (d, 2H, J = 8.68 Hz), 3.18 (s, 3H), 2.39-1.80 (m, 6H), 1.57-1.09 (m, 6H), 0.83 (t, 3H, J = 7.3 Hz). | 530.4 | 4.07 | B |
| 152 | $^1$H NMR (400 MHz, DMSO-d$_6$) δ 9.87 (s, 1H), 7.65-7.63 (m, 2H), 4.72 (t, 1H, J = 6.16 Hz), 4.13-4.06 (m, 2H), 3.62-3.52 (m, 4H), 3.40 (t, 2H, J = 7.08 Hz), 3.26 (s, 3H), 2.09-2.07 (m, 2H), 1.94-1.9 (m, 2H), 1.63-1.57 (m, 2H), 1.34-1.32 (m, 2H), 0.86 (t, 3H, J = 7.3 Hz), 0.70-0.67 (m, 1H) 0.50-0.45 (m, 1H). | 518.39 | 3.98 | B |
| 153 | $^1$H NMR (DMSO-d$_6$) δ ppm 9.79 (s, 1H), 7.74-7.69 (m, 2H), 7.51 (d, 1H, J = 8.4 Hz), 7.02 (t, 1H, J = 8.4 Hz), 5.01 (s, 1H), 4.89 (t, 1H, J = 6.32 Hz , 6.52 Hz), 4.80-4.78 (m, 3H), 4.16-4.08 (m, 2H), 3.75 (d, 2H, J = 12.1 Hz), 3.57-3.53 (m, 2H), 2.17-2.15 (m, 2H), 1.9-1.88 (d, 2H), 1.34-1.32 (m, 2H), 0.55-0.45 (m, 2H). | 498.1 | 3.37 | G |
| 154 | $^1$H NMR (DMSO-d$_6$) δ ppm 9.81 (s, 1H), 7.74-7.69 (m, 1H), 7.52-7.49 (m, 1H), 7.02 (t, 1H, J = 9.2 Hz), 4.89 (t, 1H, J = 6.4 Hz), 4.18-4.10 (m, 2H), 3.76-3.50 (m, 2H), 3.18-3.11 (m, 1H), 2.20-1.40 (m, 7H), 1.34-1.31 (m, 2H) 0.74-0.44 (m, 4H). | 466.3 | 3.59 | B |
| 155 | $^1$H NMR (DMSO-d$_6$) δ ppm 10.16 (s, 1H), 7.68-7.64 (m, 2H), 5.0-4.93 (m, 1H), 4.15-4.10 (m, 2H), 3.78 (s, 4H), 1.90-1.31 (m, 10H), 0.84-0.65 (m, 7H), 0.46-0.41 (m, 1H). | 514.3 | 2.69 | E |
| 156 | $^1$H NMR (DMSO-d$_6$) δ ppm 9.74 (s, 1H), 7.73-7.69 (m, 1H), 7.50 (d, 1H, J = 8.96 Hz), 7.04-6.99 (m, 1H), 4.89 (t, 1H, J = 6.36 Hz), 4.14-4.06 (m, 2H), 3.65 (d, 2H, J = 10.0 Hz), 3.55 (d, 2H, J = 9.68 Hz), 2.20-2.18 (m, 2H), 1.9-1.88 (m, 2H), 1.70-1.60 (m, 2H), 1.40-1.30 (m, 2H), 0.85-0.18 (m, 4H). | 466.28 | 3.54 | B |
| 157 | $^1$H NMR (DMSO-d$_6$) δ ppm 9.99 (s, 1H), 7.66 (d, 2H, J = 10.96 Hz), 4.72 (t, 1H, J = 6.32 Hz), 4.58-4.47 (m, 2H), 4.16-4.08 (m, 2H), 3.78-3.72 (m, 3H), 3.50-3.40 (m, 1H), 2.17-2.02 (m, 6H), 1.92-1.9 (m, 2H), 1.34-1.32 (m, 2H), 0.70-0.67 (m, 1H), 0.48-0.47 (m, 1H). | 514.32 | 3.49 | B |
| 158 | $^1$H NMR (DMSO-d$_6$) δ ppm 9.93 (s, 1H), 7.76-7.72 (m, 1H), 7.53 (d, 1H, J = 8.9 Hz), 7.17 (t, 1H, J = 9.2 Hz), 4.40-4.29 (m, 1H), 4.15-4.07 (m, 2H), 3.80-3.78 (m, 5H), 3.62-3.47 (m, 3H), 2.0-1.40 (m, 8H), 0.83 (d, 6H, J = 7.24 Hz). | 500.36 | 3.47 | B |
| 159 | $^1$H NMR (DMSO-d$_6$) δ ppm 9.92 (s, 1H), 7.72 (d, 1H, J = 13.6 Hz), 7.52-7.49 (m, 1H), 7.04-6.99 (m, 1H), 4.90-4.87 (m, 1H), 4.16-4.08 (m, 2H), 4.04 (d, 2H, J = 8.8 Hz), 3.95 (d, 2H, J = 8.8 Hz), 3.18 (s, 3H), 2.17-2.15 (m, 2H), 1.89-1.80 (m, 4H), 1.34-1.32 (m, 2H), 0.83 (t, 3H, J = 7.2 Hz), 0.54-0.47 (m, 2H). | 498.37 | 3.46 | B |

| Ex. | NMR Data | [M + H] | Rt (min) | LCMS Method |
|---|---|---|---|---|
| 160 | $^1$H NMR (DMSO-d$_6$) δ ppm 10.21 (s, 1H), 7.68 (d, 2H, J = 10.6 Hz), 4.16-4.03 (m, 5H), 3.96 (d, 2H, J = 8.68 Hz), 3.77 (d, 1H, J = 11.2 Hz), 3.57-3.50 (m, 3H), 3.18 (s, 3H), 2.0-1.43 (m, 6H), 0.83 (t, 3H, J = 7.12 Hz). | 520.39 | 3.32 | B |
| 161 | $^1$H NMR (DMSO-d$_6$) δ ppm 9.77 (s, 1H), 7.73 (d, 1H, J = 13.6 Hz), 7.51 (d, 1H, J = 9.2 Hz), 7.02 (t, 1H, J = 9.2 Hz), 4.89 (t, 1H, J = 6.4 Hz), 4.18-4.10 (m, 2H), 3.63 (d, 2H, J = 10.8 Hz), 3.41-3.37 (m, 2H), 3.10-2.90 (m, 2H), 2.21-2.16 (m, 4H), 1.9-1.88 (m, 2H), 1.70-1.60 (m, 2H), 1.40-1.30 (m, 2H), 0.54-0.46 (m, 2H). | 480.4 | 3.57 | B |
| 162 | $^1$H NMR (DMSO-d$_6$) δ ppm 9.70 (s, 1H), 7.72 (d, 1H, J = 13.5 Hz), 7.50-7.48 (m, 1H), 7.02 (t, 1H, J = 9.1 Hz), 4.91-4.88 (m, 1H), 4.20-4.05 (m, 3H), 3.57-3.48 (m, 2H), 2.90-2.78 (m, 1H), 2.17-1.32 (m, 14H), 0.54-0.46 (m, 2H). | 494.34 | 3.62 | B |
| 163 | $^1$H NMR (DMSO-d$_6$) δ ppm 7.45 (s, 1H), 5.94 (d, 2H, J = 7.24 Hz), 3.99-3.97 (m, 1H), 3.61-3.53 (m, 2H), 3.40-3.13 (m, 3H), 2.41-2.07 (m, 7H), 1.93-1.65 (m, 6H), 1.34-1.15 (m, 4H). | 526.33 | 3.77 | B |
| 164 | $^1$H NMR (DMSO-d$_6$) δ ppm 9.89 (s, 1H), 7.57 (d, 1H, J = 13.7 Hz), 7.46 (s, 1H), 4.58 (t, 1H, J = 6.08 Hz), 4.16-4.06 (m, 4H), 3.95 (d, 2H, J = 8.5 Hz), 3.20 (s, 3H), 2.19 (s, 3H), 2.08-2.06 (m, 2H), 1.94-1.91 (m, 2H), 1.46 (s, 3H), 1.33-1.31 (m, 2H), 0.70-0.69 (m, 1H), 0.51-0.51 (m, 1H). | 498.3 | 3.53 | B |
| 165 | $^1$H NMR (DMSO-d$_6$) δ ppm 10.1 (s, 1H), 7.67-7.64 (m, 2H), 4.71 (t, 1H, J = 6.3 Hz), 4.15-4.08 (m, 2H), 3.91 (d, 2H, J = 7.88 Hz), 3.79 (d, 2H, J = 7.88 Hz), 3.40 (s, 2H), 3.32-3.29 (m, 3H), 2.10-2.06 (m, 2H), 1.92-1.9 (m, 2H), 1.69-1.63 (m, 2H), 1.33-1.30 (m, 2H), 0.86 (t, 3H, J = 7.4 Hz), 0.70-0.67 (m, 1H), 0.50-0.47 (m, 1H). | 530.33 | 3.73 | B |
| 166 | $^1$H NMR (DMSO-d$_6$) δ ppm 10.16(s, 1H), 8.76 (s, 1H), 7.68 (d, 2H, J = 10.6 Hz), 4.79 (s, 2H), 4.74-4.71 (m, 1H), 4.65 (s, 2H), 4.21-4.13 (m, 2H), 2.09-2.07 (m, 2H), 1.92-1.9 (m, 2H), 1.34-1.32 (m, 2H), 0.70-0.69 (m, 1H), 0.48-0.47 (m, 1H). | 511.36 | 3.49 | B |
| 167 | $^1$H NMR (DMSO-d$_6$) δ ppm 10.19 (s, 1H), 7.66 (d, 2H, J = 10.4 Hz), 4.73-4.70 (m, 1H), 4.16-4.08 (m, 2H), 4.04 (d, 2H, J = 8.8 Hz), 3.96 (d, 2H, J = 8.4 Hz), 3.18 (s, 3H), 2.09-2.06 (m, 2H), 1.92-1.9 (m, 2H), 1.85-1.80 (m, 2H), 1.33-1.32 (m, 2H), 0.83 (t, 3H, J = 6.8 Hz), 0.70-0.67 (m, 1H), 0.50-0.47 (m, 1H). | 516.31 | 3.52 | B |
| 168 | $^1$H NMR (DMSO-d$_6$) δ ppm 10.18 (s, 1H), 7.66 (d, 2H, J = 11.0 Hz), 4.72 (t, 1H, J = 11.0 Hz), 4.16-4.08 (m, 2H), 3.90 (s, 4H), 3.48 (s, 4H), 3.32-3.30 (m, 6H), 2.10-2.06 (m, 2H), 1.92-1.9 (m, 2H), 1.34-1.30 (m, 2H), 0.70-0.67 (m, 1H), 0.50-0.47 (m, 1H). | 546.35 | 3.5 | B |
| 169 | $^1$H NMR (DMSO-d$_6$) δ ppm 10.03 (s, 1H), 7.69 (d, 2H, J = 10.4 Hz), 4.65-4.64 (m, 1H), 4.15-4.08 (m, 2H), 3.60-3.40 (m, 4H), 2.33-2.25 (m, 4H), 2.08-1.94 (m, 8H), 1.57 (t, 1H, J = 8.44 Hz), 1.31-1.23 (m, 1H). | 486.29 | 3.59 | B |
| 170 | $^1$H NMR (DMSO-d$_6$) δ ppm 10.07 (s, 1H), 7.67-7.62 (m, 2H), 4.72 (t, 1H, J = 6.24 Hz), 4.20-4.12 (m, 2H), 3.95 (t, 2H, J = 7.24 Hz), 2.67-2.49 (m, 4H), 2.13-2.07 (m, 4H), 1.92-1.9 (m, 2H), 1.76-1.63 (m, 2H), 1.34-1.23 (m, 2H), 0.70-0.67 (m, 1H), 0.50-0.47 (m, 1H). | 498.31 | 3.78 | B |
| 171 | $^1$H NMR (DMSO-d$_6$) δ ppm 9.89 (s, 1H), 7.71 (d, 1H, J = 13.6 Hz), 7.51 (d, 1H, J = 8.76 Hz), 7.01 (t, 1H, J = 8.76 Hz), 4.90-4.87 (m, 1H), 4.16-4.02 (m, 2H), 3.90 (s, 3H), 3.60-3.50 (m, 5H), 2.17-2.15 (m, 2H), 1.9-1.88 (m, 2H), 1.80-1.70 (m, 4H), 1.33-1.15 (m, 2H), 0.54-0.46 (m, 2H). | 510.32 | 3.43 | B |
| 172 | $^1$H NMR (DMSO-d$_6$) δ ppm 9.82 (s, 1H), 7.66-7.63 (m, 2H), 4.80-4.70 (m, 1H), 4.16-4.08 (m, 2H), 3.60-3.50 (m, 2H), 2.10-1.90 (m, 8H), 1.43 (s, 6H), 1.34-1.33 (m, 2H), 0.70-0.68 (m, 1H), 0.50-0.40 (m, 1H). | 500.32 | 3.86 | B |
| 173 | $^1$H NMR (DMSO-d$_6$) δ ppm 10.21 (s, 1H), 7.67-7.64 (m, 2H), 4.73-4.70 (m, 1H), 4.19-4.09 (m, 5H), 3.77 (t, 2H, J = 6.52 Hz), 2.13-1.84 (m, 8H), 1.33-1.23 (m, 3H), 0.70-0.67 (m, 1H), 0.50-0.47 (m, 1H). | 514.29 | 3.61 | B |
| 174 | $^1$H NMR (DMSO-d$_6$) δ ppm 9.90 (s, 1H), 7.67-7.64 (m, 2H), 4.74-4.72 (m, 1H), 4.14-4.06 (m, 2H), 3.59-3.52 (m, 3H), 2.09-2.07 (m, 2H), 1.92-1.9 (m, 2H), 1.73-1.23 (m, 10H), 0.85-0.47 (m, 3H). | 500.29 | 3.89 | B |
| 175 | $^1$H NMR (DMSO-d$_6$) δ ppm 10.1 (s, 1H), 7.66 (d, 2H, J = 11.0 Hz), 4.72 (s, 1H), 4.47 (t, 1H, J = 6.68 Hz), 4.14-4.09 (m, 2H), 3.49 (s, 2H), 2.95-2.93 (m, 1H), 2.09-1.89 (m, 6H), 1.39-1.32 (m, 4H), 0.69-0.47 (m, 2H). | 484.3 | 3.55 | B |

| Ex. | NMR Data | [M + H] | Rt (min) | LCMS Method |
|---|---|---|---|---|
| 176 | ¹H NMR (DMSO-d₆) δ ppm 10.0 (s, 1H), 7.68-7.63 (m, 2H), 4.72 (t, 1H, J = 6.32 Hz), 4.16-4.08 (m, 2H), 3.85-3.82 (m, 2H), 3.69-3.64 (m, 2H), 2.76-2.66 (m, 2H), 2.09-2.06 (m, 2H), 1.92-1.9 (m, 2H), 1.34-1.31 (m, 2H), 1.17-1.13 (m, 6H), 0.70-0.67 (m, 1H), 0.50-0.46 (m, 1H). | 516.3 | 3.61 | B |
| 177 | ¹H NMR (DMSO-d₆) δ ppm 10.05 (s, 1H), 7.67 (d, 2H, J = 11.0 Hz), 4.72 (t, 1H, J = 6.2 Hz), 4.18-4.10 (m, 2H), 3.63 (d, 2H, J = 10.76 Hz), 3.42-3.38 (m, 2H), 3.10-3.0 (m, 2H), 2.23-2.07 (m, 4H), 1.92-1.9 (m, 2H), 1.70-1.69 (m, 2H), 1.35-1.31 (m, 2H), 0.70-0.47 (m, 2H). | 498.31 | 2.36 | B |
| 178 | ¹H NMR (DMSO-d₆) δ ppm 10.21 (s, 1H), 7.66 (d, 2H, J = 10.8 Hz), 4.73 (t, 1H, J = 6.2 Hz), 4.16-4.07 (m, 4H), 3.96-3.94 (m, 2H), 3.21 (s, 3H), 2.09-2.06 (m, 2H), 1.93-1.89 (m, 2H), 1.46 (s, 3H), 1.33-1.23 (m, 2H), 0.70-0.67 (m, 1H), 0.50-0.44 (m, 1H) | 502.3 | 3.44 | B |
| 179 | ¹H NMR (DMSO-d₆) δ ppm 10.02 (s, 1H), 7.66 (d, 2H, J = 10.8 Hz), 4.72-4.7 (m, 1H), 4.54-4.52 (m, 1H), 4.15-4.08 (m, 2H), 3.86-3.75 (m, 1H), 3.75-3.61 (m, 5H), 3.10-3.0 (m, 1H), 2.09-1.83 (m, 6H), 1.34-1.33 (m, 2H), 0.69-0.67 (m, 1H), 0.48-0.47 (m, 1H). | 514.32 | 3.53 | B |
| 180 | ¹H NMR (DMSO-d₆) δ ppm 10.02 (s, 1H), 7.66 (d, 2H, J = 10.6 Hz), 4.72-4.53 (m, 2H), 4.15-4.02 (m, 2H), 3.86-3.84 (m, 1H), 3.73-3.62 (m, 5H), 3.10-3.0 (m, 1H), 2.06-1.82 (m, 6H), 1.40-1.30 (m, 2H), 0.69-0.67 (m, 1H), 0.48-0.47 (m, 1H). | 514.32 | 3.53 | B |
| 181 | ¹H NMR (DMSO-d₆) δ ppm 10.02 (s, 1H), 7.65 (d, 2H, J = 10.76 Hz), 4.80-4.70 (m, 1H), 4.14-4.11 (m, 2H), 3.70-3.49 (m, 8H), 2.09-2.06 (m, 2H), 1.92-1.9 (m, 2H), 1.40-1.30 (m, 2H), 1.0-0.47 (m, 2H). | 488.28 | 3.52 | B |
| 182 | ¹H NMR (400 MHz, DMSO-d₆) δ 10.07 (s, 1H), 7.65 (d, 2H, J = 10.9 Hz), 4.73-4.68 (m, 2H), 4.62 (s, 1H), 4.16-4.08 (m, 2H), 3.79-3.74 (m, 2H), 3.55 (d, 1H, J = 9.8 Hz), 3.42 (d, 1H, J = 9.9 Hz), 2.09-1.89 (m, 6H), 1.33-1.31 (m, 2H), 0.70-0.67 (m, 1H), 0.50-0.47 (m, 1H). | 500.26 | 3.45 | B |
| 183 | ¹H NMR (CDCl₃) δ ppm 8.67 (s, 1H), 7.27-7.23 (m, 2H), 4.76 (s, 1H), 3.93-3.78 (m, 6H), 2.10-2.0 (m, 4H), 1.70-1.64 (m, 4H), 1.30-1.26 (m, 2H), 0.89-0.80 (m, 7H), 0.50-0.49 (m, 1H). | 514.09 | 7.05 | D |
| 184 | ¹H NMR (DMSO-d₆) δ ppm 10.0 (s, 1H), 7.69 (d, 2H, J = 10.88 Hz), 4.72-4.70 (m, 1H), 4.13-4.08 (m, 2H), 3.75-3.72 (m, 2H), 3.47-3.45 (m, 2H), 3.32 (s, 2H), 2.09-2.06 (m, 2H), 1.70-1.68 (m, 2H), 1.34-1.32 (m, 2H), 1.20 (s, 6H), 0.70-0.67 (m, 1H), 0.50-0.47 (m, 1H). [Presence of two protons at ~3.32 PPM was confirmed by CDCl₃ NMR] | 516.3 | 3.65 | B |
| 185 | ¹H NMR (DMSO-d₆) δ ppm 10.01 (s, 1H), 7.66 (d, 2H, J = 10.8 Hz), 4.72 (t, 1H, J = 6.35 Hz), 4.15-4.07 (m, 2H), 3.69-3.65 (m, 2H), 3.27-3.23 (m, 1H), 2.80-2.70 (m, 2H), 2.40-2.30 (m, 1H), 2.09-2.07 (m, 2H), 1.93-1.32 (m, 10H), 0.69-0.68 (m, 1H), 0.48-0.47 (m, 1H). | 512.3 | 3.8 | B |
| 186 | ¹H NMR (DMSO-d₆) δ ppm 10.02 (s, 1H), 7.65 (d, 2H, J = 10.8 Hz), 4.80-4.70 (m, 1H), 4.15-4.07 (m, 2H), 3.79-3.39 (m, 8H), 3.10-3.0 (m, 2H), 2.10-1.89 (m, 4H), 1.40-1.30 (m, 2H), 0.69-0.48 (m, 2H). | 514.29 | 3.47 | B |
| 187 | ¹H NMR (DMSO-d₆) δ ppm 9.74 (s, 1H), 7.74 (dd, 1H, J = 2.2 Hz), 7.50 (d, 1H, J = 8.88 Hz), 7.02 (t, 1H, J = 9.2 Hz), 4.89 (t, 1H, J = 6.36 Hz), 4.54-4.52 (m, 1H), 4.15-4.07 (m, 2H), 3.86-3.59 (m, 4H), 3.36-3.30 (m, 1H), 3.04-3.01 (m, 1H), 2.17-2.06 (m, 3H), 1.89-1.81 (m, 4H), 1.34-1.32 (m, 2H), 0.54-0.46 (m, 2H). | 496.27 | 3.44 | B |
| 188 | ¹H NMR (DMSO-d₆) δ ppm 10.17 (s, 1H), 7.66 (d, 2H, J = 10.92 Hz), 4.72 (t, 1H, J = 6.3 Hz), 4.16-4.08 (m, 2H), 3.90-3.80 (m, 4H), 3.53-3.51 (m, 4H), 2.09-1.75 (m, 8H), 1.33-1.31 (m, 2H), 0.70-0.67 (m, 1H), 0.50-0.45 (m, 1H). | 528.1 | 3.52 | B |
| 189 | ¹H NMR (DMSO-d₆) δ ppm 10.2 (s, 1H), 7.66 (d, 2H, J = 10.88 Hz), 4.72 (t, 1H, J = 6.3 Hz), 4.16-4.08 (m, 6H), 3.82 (s, 2H), 3.71 (t, 2H, J = 6.88 Hz), 2.17 (t, 2H, J = 6.88 Hz), 2.09-2.06 (m, 2H), 1.93-1.89 (m, 2H), 1.33-1.31 (m, 2H), 0.70-0.67 (m, 1H), 0.48-0.47 (m, 1H). | 514.29 | 3.45 | B |
| 190 | ¹H NMR (DMSO-d₆) δ ppm 9.73 (s, 1H), 7.73 (d, 1H, J = 13.6 Hz), 7.52-7.50 (m, 1H), 7.10-7.06 (m, 1H), 4.15-4.07 (m, 2H), 3.76 (d, 2H, J = 7.32 Hz), 3.50-3.40 (m, 4H), 2.80-2.60 (m, 1H), 2.16-1.94 (m, 6H), 1.51-1.29 (m, 4H), 0.58-0.57 (m, 1H), 0.09-0.08 (m, 1H). | 468.31 | 7.75 | K |
| 191 | ¹H NMR (DMSO-d₆) δ ppm 10.1 (s, 1H), 8.35 (s, 1H), 8.08 (d, 1H, J = 12.3 Hz), 5.52-5.49 (m, 1H), 4.15-4.08 (m, 2H), 3.78 (s, 4H), 2.25-2.22 (m, 2H), 1.85-1.83 (m, 2H), 1.65-1.33 (m, 6H), 0.85-0.49 (m, 8H). | 497.35 | 3.78 | B |

-continued

| Ex. | NMR Data | [M + H] | Rt (min) | LCMS Method |
|---|---|---|---|---|
| 192 | $^1$H NMR (400 MHz, DMSO-d$_6$) δ 9.64 (s, 1H), 7.47-7.43 (m, 1H), 7.33 (s, 1H), 4.12-4.07 (m, 2H), 3.90-3.77 (m, 5H), 2.32-2.08 (m, 8H), 1.76-1.52 (m, 8H), 1.22-1.18 (m, 1H), 0.83 (t, 6H, J = 7.3 Hz). | 523.5 | 4.02 | -B |
| 193 | $^1$H NMR (DMSO-d$_6$) δ ppm 9.52 (s, 1H), 7.48 (d, 1H, J = 13.5 Hz), 7.32 (s, 1H), 4.12-4.10 (m, 2H), 3.86-3.80 (m, 2H), 3.50-3.40 (m, 4H), 2.32-1.54 (m, 14H), 1.22-1.18 (m, 2H). | 481.4 | 3.42 | B |
| 194 | $^1$H NMR (DMSO-d$_6$) δ ppm 9.52 (s, 1H), 7.49 (d, 1H, J = 14.5 Hz), 7.33 (s, 1H), 4.15-4.07 (m, 2H), 4.0 (d, 1H, J = 7.96 Hz), 3.50-3.40 (m, 5H), 2.24 (s, 3H), 2.0-1.39 (m, 13H), 1.21-1.18 (m, 2H). | 495.4 | 3.6 | B |
| 195 | $^1$H NMR (DMSO-d$_6$) δ ppm 9.74 (s, 1H), 7.43-7.41 (m, 2H), 4.16-4.06 (m, 4H), 3.95 (d, 2H, J = 8.5 Hz), 3.61 (s, 2H), 3.20 (s, 3H), 2.30 (s, 3H), 1.94-1.68 (m, 7H), 1.55-1.46 (m, 6H). | 511.45 | 405 | B |
| 196 | $^1$H NMR (DMSO-d$_6$ at 100° C.) δ ppm 9.76 (s, 1H), 7.87-7.82 (m, 2H), 4.22 (s, 2H), 4.11-3.95 (m, 6H), 3.24 (s, 2H), 2.04-1.27 (m, 14H). | 522.4 | 3.4 | B |
| 197 | $^1$H NMR (DMSO-d$_6$) δ ppm 9.98 (s, 1H), 8.04 (d, 1H, J = 2.4 Hz), 7.82 (d, 1H, J = 9.2 Hz), 7.04 (d, 1H, J = 9.24 Hz), 4.32 (s, 2H), 4.14-4.06 (m, 4H), 3.96 (d, 2H, J = 8.52 Hz), 3.21 (s, 3H), 1.92-1.46 (m, 13H). | 504.4 | 3.32 | B |
| 198 | $^1$H NMR (DMSO-d$_6$) δ ppm 9.93 (s, 1H), 7.58 (d, 2H, J = 12.2 Hz), 4.52-4.44 (m, 2H), 4.15-4.07 (m, 2H), 3.70-3.46 (m, 7H), 3.29-3.22 (m, 1H), 1.95-1.82 (m, 8H). | 487.36 | 3.2 | B |
| 199 | $^1$H NMR (400 MHz, DMSO-d$_6$) δ 9.77 (s, 1H), 7.53 (d, 2H, J = 12.56 Hz), 4.12-4.09 (m, 2H), 4.00 (bs, 2H), 3.77-3.71 (m, 8H), 1.90 (bs, 2H), 1.73-1.71 (m, 4H), 1.44 (bs, 4H). | 515.41 | 3.43 | B |
| 200 | $^1$H NMR (400 MHz, DMSO-d$_6$) δ 10.02 (s, 1H), 7.54 (d, 2H, J = 12.44 Hz), 4.15-4.07 (m, 2H), 3.99 (bs, 2H), 3.82 (s, 4H), 1.91-1.89 (m, 2H), 1.76-1.67 (m, 5H), 1.50-1.41 (m, 3H), 1.28 (s, 6H). | 499.42 | 3.59 | B |
| 201 | $^1$H NMR (400 MHz, DMSO-d$_6$) δ 9.85 (s, 1H), 7.53 (d, 2H, J = 11.76 Hz), 4.15-4.07 (m, 2H), 3.99 (bs, 2H), 3.82-3.78 (m, 2H), 3.70-3.66 (m, 2H), 3.59-3.37 (m, 2H), 3.41-3.39 (m, 2H), 3.02 (bs, 2H), 1.90 (bs, 2H), 1.77-1.68 (m, 5H), 1.50-1.41 (m, 3H). | 527.43 | 3.39 | B |
| 202 | $^1$H NMR (DMSO-d$_6$) δ ppm 9.61 (s, 1H), 7.64 (d, 1H, J = 17.6 Hz), 7.45 (d, 1H, J = 8.8 Hz), 6.83 (t, 1H, J = 9.6 Hz), 4.61 (d, 2H, J = 6.0 Hz), 4.51 (d, 2H, J = 6.0 Hz), 4.16-4.08 (m, 2H), 3.73 (s, 2H), 3.60-3.59 (m, 4H), 3.51 (t, 2H, J = 6.8 Hz), 2.26 (t, 2H, J = 6.8 Hz), 2.10-2.09 (m, 2H), 1.46-1.44 (m, 2H). Note: Some aliphatic protons missing, merged with DMSO/ H2O peak.<br>$^1$H NMR (MeOD) δ ppm 7.50 (dd, 1H, J = 2.32, 16.68), 7.25 (d, 1H, J = 8.7 Hz), 6.89 (t, 1H, J = 9.2 Hz), 6.83 (t, 1H, J = 9.6 Hz), 4.72 (d, 2H, J = 6.2 Hz), 4.65 (d, 2H, J = 6.2 Hz), 4.01-3.9 (m, 2H), 3.79 (s, 2H), 3.64 (s, 4H), 3.59 (t, 2H, J = 6.9 Hz), 2.51 (bs, 2H), 2.36 (t, 2H, J = 6.9 Hz), 2.16-2.18 (m, 2H), 1.53-1.52 (m, 2H). | 495.4 | 3.3 | B |
| 203 | $^1$H NMR (DMSO-d$_6$) δ ppm 10.14 (s, 1H), 7.61-7.58 (m, 2H), 4.16-4.09 (m, 2H), 4.05 (d, 2H, J = 8.8 Hz), 3.96 (d, 2H, J = 8.8 Hz), 3.50-3.40 (m, 4H), 3.18 (s, 3H), 2.50-2.40 (m, 2H), 2.13-2.09 (m, 2H), 1.86-1.80 (m, 2H), 1.59-1.56 (m, 2H), 0.83 (t, 3H, J = 7.2 Hz). | 515.41 | 3.57 | B |
| 204 | $^1$H NMR (DMSO-d$_6$) δ ppm 10.1 (s, 1H), 7.56-7.52 (m, 2H), 4.16-4.08 (m, 2H), 4.04 (d, 2H, J = 8.72 Hz), 3.95 (d, 2H, J = 8.72 Hz), 3.38-3.33 (m, 1H), 3.17-3.13 (m, 4H), 2.85-2.78 (m, 2H), 1.97-1.71 (m, 4H), 1.08-0.96 (m, 2H), 0.82 (t, 3H, J = 7.2 Hz), 0.63-0.42 (m, 2H). | 515.41 | 3.56 | B |
| 205 | $^1$H NMR (DMSO-d$_6$) δ ppm 10.09 (s, 1H), 7.55-7.52 (m, 2H), 4.16-4.08 (m, 3H), 4.04 (d, 2H, J = 8.72 Hz), 3.95 (d, 2H, J = 8.68 Hz), 3.50-3.40 (m, 1H), 3.18 (s, 3H), 3.15-3.12 (m, 1H), 2.70-2.66 (m, 1H), 2.0-1.30 (m, 10H), 0.90-0.83 (m, 3H). | 529.44 | 3.64 | B |
| 206 | $^1$H NMR (400 MHz, DMSO-d$_6$) δ 10.03 (s, 1H), 7.56-7.48 (m, 2H), 4.16-3.93 (m, 6H), 3.18 (s, 3H), 1.91-1.41 (m, 12H), 0.82 (t, 3H, J = 7.2 Hz). | 529.3 | 4.28 | B |
| 207 | $^1$H NMR (400 MHz, DMSO-d$_6$) δ 10.04 (s, 1H), 7.54-7.50 (m, 2H), 4.13-3.94 (m, 8H), 3.20 (s, 3H), 1.91-1.69 (m, 6H), 1.50-1.41 (m, 6H), 1.25-1.23 (m, 1H). | 515.38 | 4.01 | B |
| 208 | $^1$H NMR (400 MHz, DMSO-d$_6$) δ 9.98 (s, 1H), 7.62-7.59 (m, 2H), 4.61 (d, 2H, J = 5.9 Hz), 4.51 (d, 2H, J = 5.96 Hz), 4.16-4.08 (m, 2H), 3.74 (s, 2H), 3.51 (t, 2H, J = 6.8 Hz), 3.42 (s, 4H), 2.41-2.40 (m, 2H), 2.26 (t, 2H, J = 6.8 Hz), 2.12-2.11 (m, 2H), 1.58 (d, 2H, J = 6.5 Hz). | 513.39 | 3.7 | B |

| Ex. | NMR Data | [M + H] | Rt (min) | LCMS Method |
|---|---|---|---|---|
| 209 | $^1$H NMR (DMSO-d$_6$) δ ppm 9.98 (s, 1H), 7.62 (d, 2H, J = 10.9 Hz), 4.16-4.08 (m, 2H), 3.50-3.42 (m, 8H), 2.50-2.40 (m, 2H), 2.12-2.10 (m, 2H), 2.0-1.90 (m, 4H), 1.59-1.57 (m, 2H). | 471.27 | 3.71 | B |
| 210 | $^1$H NMR (DMSO-d$_6$) δ ppm 9.83 (s, 1H), 7.53 (d, 2H, J = 12.6 Hz), 4.15-3.99 (m, 4H), 3.50-3.40 (m, 4H), 1.98-1.17 (m, 17H). | 485.32 | 3.69 | B |
| 211 | $^1$H NMR (DMSO-d$_6$) δ ppm 10.09 (s, 1H), 7.56-7.53 (m, 2H), 4.14-4.07 (m, 2H), 3.80-3.70 (m, 4H), 3.39-3.35 (m, 1H), 3.15 (d, 1H, J = 11.3 Hz), 2.84-2.80 (m, 2H), 2.0-1.59 (m, 6H), 1.07-0.96 (m, 2H), 0.82 (t, 6H, J = 7.28 Hz), 0.70-0.67 (m, 1H), 0.48-0.47 (m, 1H). | 513.35 | 8.37 | K |
| 212 | $^1$H NMR (DMSO-d$_6$) δ ppm 9.84 (s, 1H), 7.65 (d, 1H, J = 14.8 Hz), 7.48 (d, 1H, J = 8.64 Hz), 6.96-6.92 (m, 1H), 4.15-4.07 (m, 2H), 3.80-3.70 (m, 4H), 3.25-3.16 (m, 2H), 2.83-2.66 (m, 2H), 2.0-1.59 (m, 6H), 1.13-0.60 (m, 9H), 0.40-0.30 (m, 1H). | 495.32 | 3.67 | B |
| 213 | $^1$H NMR (DMSO-d$_6$) δ ppm 9.95 (s, 1H), 7.58-7.55 (m, 2H), 4.15-4.07 (m, 2H), 3.49-3.46 (m, 4H), 2.99-2.97 (m, 2H), 2.68 (s, 2H), 1.95-1.92 (m, 4H), 1.62-1.59 (m, 2H), 1.32-1.29 (m, 2H), 0.96 (s, 6H). | 487.36 | 3.8 | B |
| 214 | $^1$H NMR (DMSO-d$_6$) δ ppm 9.90 (s, 1H), 7.55 (d, 2H, J = 11.96 Hz), 4.15-4.07 (m, 2H), 3.50-3.36 (m, 6H), 2.98 (d, 2H, J = 8.92 Hz), 2.70-2.50 (m, 2H) 2.0-1.90 (m, 4H), 1.77-1.39 (m, 6H). | 485.34 | 3.62 | B |
| 215 | $^1$H NMR (DMSO-d$_6$) δ ppm 10.1 (s, 1H), 7.57-7.53 (m, 2H), 4.15-4.07 (m, 2H), 3.78-3.72 (m, 4H), 3.0-2.90 (m, 4H), 1.64-1.40 (m, 9H), 0.87-0.81 (m, 6H). | 501.38 | 3.76 | B |
| 216 | $^1$H NMR (DMSO-d$_6$) δ ppm 9.85 (s, 1H), 7.66 (d, 1H, J = 14.96 Hz), 7.50 (d, 1H, J = 8.72 Hz), 6.97 (t, 1H, J = 9.3 Hz), 4.15-4.07 (m, 2H), 3.77 (s, 4H), 2.92-2.90 (m, 4H), 1.64-1.50 (m, 10H), 0.83 (t, 6H, J = 7.3 Hz). | 483.39 | 3.58 | B |
| 217 | $^1$H NMR (DMSO-d$_6$ at 100° C.) δ ppm 9.32 (s, 1H), 7.47 (d, 1H, J = 14.4 Hz), 7.36 (s, 1H), 4.11-4.03 (m, 2H), 3.73-3.48 (m, 5H), 2.67 (s, 3H), 2.34-1.61 (m, 16H), 1.10-1.0 (m, 1H). | 495.4 | 3.75 | B |
| 218 | $^1$H NMR (DMSO-d$_6$) δ ppm 10.1 (s, 1H), 7.63 (d, 2H, J = 9.76 Hz), 4.16-4.08 (m, 2H), 3.63 (s, 2H), 3.50-3.47 (m, 4H), 2.79 (d, 2H, J = 8.48 Hz), 2.34-2.32 (m, 2H), 1.96-1.92 (m, 4H), 1.31-1.29 (m, 2H), 0.56-0.53 (m, 1H), 0.28-0.25 (m, 1H). | 471.31 | 2.59 | B |
| 219 | $^1$H NMR (400 MHz, DMSO-d$_6$) δ 9.92 (s, 1H), 7.84 (s, 1H), 7.78 (d, 1H, J = 12.7 Hz), 4.72 (t, 1H, J = 6.2 Hz), 4.0 (d, 2H, J = 8.5 Hz), 3.91 (d, 2H, J = 8.5 Hz), 3.17 (s, 3H), 2.95-2.90 (m, 2H), 2.10-2.07 (m, 2H), 1.98-1.96 (m, 2H, J), 1.82-1.80 (m, 2H), 1.33-1.23 (m, 3H), 1.14 (t, 3H, J = 7.4 Hz), 0.84-0.49 (m, 4H). | 478.3 | 3.47 | B |
| 220 | $^1$H NMR (400 MHz, DMSO-d$_6$) δ 9.89 (s, 1H), 7.85 (d, 1H, J = 1.88 Hz), 7.78 (d, 1H, J = 13.5 Hz), 4.92 (t, 1H, J = 5.3 Hz), 4.72 (t, 1H, J = 6.4 Hz), 3.88 (d, 2H, J = 7.68 Hz), 3.71 (d, 2H, J = 7.76 Hz), 3.45-3.43 (m, 2H), 2.95-2.89 (m, 2H), 2.12-2.08 (m, 2H), 1.98-1.96 (m, 2H), 1.65-1.32 (m, 4H), 1.14 (t, 3H, J = 7.5 Hz), 0.86 (t, 3H, J = 7.4 Hz), 0.80-0.77 (m, 1H), 0.52-0.47 (m, 1H). | 478.3 | 3.3 | B |
| 221 | $^1$H NMR (400 MHz, DMSO-d$_6$) δ 9.88 (s, 1H), 7.85-7.75 (m, 2H), 4.71 (t, 1H, J = 6.1 Hz), 3.74 (s, 4H), 2.94-2.89 (m, 2H), 2.10-2.08 (m, 2H), 1.98-1.96 (m, 2H), 1.63-1.58 (m, 4H), 1.33-1.31 (m, 2H), 1.13 (t, 3H, J = 7.4 Hz), 0.84-0.78 (m, 7H), 0.50-0.49 (m, 1H). | 476.3 | 3.69 | B |
| 222 | $^1$H NMR (400 MHz, DMSO-d$_6$) δ 9.74 (s, 1H), 7.85 (s, 1H), 7.81-7.80 (m, 1H), 4.72 (t, 1H, J = 13.96 Hz), 3.47-3.44 (m, 4H), 2.95-2.90 (m, 2H), 2.12-1.90 (m, 8H), 1.34-1.32 (m, 2H), 1.15 (t, 3H, J = 7.5 Hz), 0.80-0.78 (m, 1H), 0.52-0.47 (m, 1H). | 434.3 | 3.51 | B |
| 223 | $^1$H NMR (400 MHz, DMSO-d$_6$) δ 9.94 (s, 1H), 7.85 (s, 1H), 7.80-7.76 (m, 1H), 4.80-4.70 (m, 1H), 4.05 (d, 2H, J = 8.2 Hz), 3.91 (d, 2H, J = 7.9 Hz), 3.20 (s, 3H), 2.94-2.92 (m, 2H), 2.10-2.08 (m, 2H), 1.98-1.96 (m, 2H), 1.45 (s, 3H), 1.40-1.30 (m, 2H), 1.14 (t, 3H, J = 6.56 Hz), 0.85-0.79 (m, 1H), 0.50-0.40 (m, 1H). | 464.3 | 3.45 | B |
| 224 | $^1$H NMR (DMSO-d$_6$) δ ppm 9.56 (s, 1H), 7.60 (dd, 1H, J = 2.1 Hz 13.7 Hz), 7.44 (s, 1H), 5.0-4.90 (m, 1H), 4.58-4.54 (m, 1H), 3.94 (d, 2H, J = 7.56 Hz), 3.67 (d, 2H, J = 7.5 Hz), 3.38-3.38 (m, 2H), 2.95-2.89 (m, 2H), 2.34-2.27 (m, 4H), 2.22 (s, 3H), 2.08-1.88 (m, 4H), 1.50 (t, 1H, J = 8.44 Hz), 1.34 (t, 1H, J = 8.7 Hz), 1.23 (s, 3H), 1.14 (t, 3H, J = 7.44 Hz). | 458.4 | 3.29 | B |
| 225 | $^1$H NMR (DMSO-d$_6$) δ ppm 9.43 (s, 1H), 7.62 (d, 1H, J = 13.5 Hz), 7.42 (s, 1H), 4.58-4.55 (m, 1H), 3.50-3.40 (m, 4H), 2.96-2.90 (m, 2H), 2.33-1.90 (m, 15H), 1.52-1.32 (m, 2H), 1.15 (t, 3H, J = 7.48 Hz). | 428.3 | 3.57 | B |

| Ex. | NMR Data | [M + H] | Rt (min) | LCMS Method |
|---|---|---|---|---|
| 226 | ¹H NMR (DMSO-d₆) δ ppm 9.60 (s, 1H), 7.58 (d, 1H, J = 13.7 Hz), 7.42 (s, 1H), 4.57 (t, 1H, J = 6.44 Hz), 4.04 (d, 2H, J = 8.4 Hz), 3.90 (d, 2H, J = 8.3 Hz), 3.19 (s, 3H), 2.95-2.89 (m, 2H), 2.18 (s, 3H), 2.10-2.06 (m, 2H), 1.94-1.91 (m, 2H), 1.45 (s, 3H), 1.33-1.31 (m, 2H), 1.14 (t, 3H, J = 7.4 Hz & 7.56 Hz), 0.70-0.50 (m, 2H). | 444.42 | 7.13 | K |
| 227 | ¹H NMR (DMSO-d₆) δ ppm 9.58 (s, 1H), 7.60-7.56 (m, 1H), 7.42 (s, 1H), 4.60-4.50 (m, 1H), 4.0 (d, 2H, J = 8.6 Hz), 3.90 (d, 2H, J = 8.6 Hz), 3.17 (s, 3H), 2.95-2.89 (m, 2H), 2.18 (s, 3H), 2.08-2.06 (m, 2H), 1.94-1.91 (m, 2H), 1.82-1.79 (m, 2H), 1.33-1.31 (m, 2H), 1.14 (t, 3H, J = 14.4 Hz), 0.82 (t, 3H, J = 14.4 Hz), 0.70-0.69 (m, 1H), 0.50-0.49 (m, 1H). | 458.45 | 7.87 | K |
| 228 | ¹H NMR (DMSO-d₆) δ ppm 9.64 (s, 1H), 7.74 (d, 1H, J = 13.7 Hz), 7.50 (d, 1H, J = 8.6 Hz), 7.12 (d, 1H, J = 9.2 Hz), 4.87-4.86 (m, 1H), 4.0 (d, 2H, J = 8.64 Hz), 3.91 (d, 2H, J = 8.6 Hz), 3.17 (s, 3H), 2.96-2.90 (m, 2H), 2.41-2.35 (m, 4H), 2.05-1.79 (m, 6H), 1.52-1.36 (m, 2H), 1.14 (t, 3H, J = 7.4 Hz), 0.83 (t, 3H, J = 7.1 Hz). | 458.41 | 3.38 | B |
| 229 | ¹H NMR (DMSO-d₆) δ ppm 9.75 (s, 1H), 7.68 (d, 2H, J = 10.8 Hz), 4.65-4.59 (m, 1H), 3.47 (m, 4H), 2.96-2.90 (m, 2H), 2.33-1.90 (m, 12H), 1.56 (t, 1H, J = 8.4 Hz), 1.31-1.26 (m, 1H), 1.15 (t, 3H, J = 7.5 Hz). | 432.37 | 3.59 | B |
| 230 | ¹H NMR (DMSO-d₆) δ ppm 9.94 (s, 1H), 7.68 (m, 2H), 4.64-4.62 (m, 1H), 4.01 (d, 2H, J = 8.68 Hz), 3.91 (d, 2H, J = 8.68 Hz), 3.17 (s, 3H), 2.96-2.90 (m, 2H), 2.33-1.79 (m, 10H), 1.56 (t, 1H, J = 8.6 Hz), 1.29 (t, 1H, J = 8.68 Hz), 1.15 (t, 3H, J = 7.5 Hz), 0.83 (t, 3H, J = 7.2 Hz). | 476.37 | 3.48 | B |
| 231 | ¹H NMR (400 MHz, DMSO-d₆) δ 9.69 (s, 1H), 7.66-7.63 (m, 2H), 4.71 (t, 1H, J = 6.2 Hz), 3.77-3.66 (m, 8H), 2.95-2.90 (m, 2H), 2.09-2.06 (m, 2H), 1.93-1.86 (m, 4H), 1.34-1.32 (m, 2H), 1.15 (t, 3H, J = 7.44 Hz), 0.70-0.67 (m, 1H) 0.50-0.45 (m, 1H). | 448.38 | 3.82 | B |
| 232 | ¹H NMR (400 MHz, DMSO-d₆) δ 10.33 (s, 1H), 8.46 (d, 1H, J = 2.1 Hz), 7.95 (s, 1H), 7.68 (d, 2H, J = 10.8 Hz), 6.69 (s, 1H), 4.72 (t, 1H, J = 6.1 Hz), 3.14-3.08 (m, 2H), 2.09-2.07 (m, 2H), 1.94-1.9 (m, 2H), 1.34-1.25 (m, 5H), 0.70-0.47 (m, 2H). | 415.33 | 3.57 | B |
| 233 | ¹H NMR (400 MHz, DMSO-d₆) δ 9.76 (s, 1H), 7.66 (d, 2H, J = 11.08 Hz), 4.70 (t, 1H, J = 5.8 Hz), 4.52 (t, 1H, J = 5.0 Hz), 3.87-3.34 (m, 6H), 3.0-2.90 (m, 3H), 2.10-2.06 (m, 3H), 1.92 (m, 2H), 1.80-1.70 (m, 1H), 1.40-1.30 (m, 2H), 1.15 (t, 3H, J = 7.5 Hz), 0.70-0.67 (m, 1H), 0.48-0.47 (m, 1H). | 460.39 | 3.61 | B |
| 234 | ¹H NMR (400 MHz, DMSO-d₆) δ 9.94 (s, 1H), 7.70-7.67 (m, 2H), 4.87 (s, 1H), 4.01 (d, 2H, J = 8.6 Hz), 3.92-3.74 (m, 6H), 3.17 (s, 3H), 2.96-2.90 (m, 2H), 2.06-1.79 (m, 4H), 1.15 (t, 3H, J = 7.4 Hz), 0.83 (t, 3H, J = 7.2 Hz). | 452.4 | 3.38 | B |
| 235 | ¹H NMR (400 MHz, DMSO-d₆) δ 9.73 (s, 1H), 7.66 (d, 2H, J = 10.6 Hz), 4.70 (t, 1H, J = 6.2 Hz), 3.63 (t, 2H, J = 6.76 Hz), 3.38 (s, 2H), 2.96-2.90 (m, 2H), 2.08-1.86 (m, 6H), 1.33-1.31 (m, 2H), 1.15 (t, 3H, J = 7.4 Hz), 0.70-0.67 (m, 1H), 0.48-0.47 (m, 1H). | 444.31 | 3.71 | -B |
| 236 | ¹H NMR (DMSO-d₆) δ ppm 9.91 (s, 1H), 7.68-7.64 (m, 2H), 4.03-4.01 (m, 1H), 3.78-3.74 (m, 5H), 3.58-3.49 (m, 3H), 2.95-2.89 (m, 2H), 1.96-1.43 (m, 8H), 1.14 (t, 3H, J = 7.48 Hz), 0.83 (t, 6H, J = 7.28 Hz). | 464.36 | 3.49 | B |
| 237 | ¹H NMR (DMSO-d₆) δ ppm 9.75 (s, 1H), 7.65 (d, 2H, J = 10.68 Hz), 4.70 (t, 1H, J = 6.24 Hz), 3.82-3.36 (m, 8H), 3.0-2.90 (m, 4H), 2.10-2.06 (m, 2H), 1.92-1.9 (m, 2H), 1.33-1.27 (m, 2H), 1.15 (t, 3H, J = 7.5 Hz), 0.70-0.67 (m, 1H), 0.48-0.47 (m, 1H). | 460.2 | 3.58 | B |
| 238 | ¹H NMR (DMSO-d₆) δ ppm 9.91 (s, 1H), 7.67-7.64 (m, 2H), 4.80-4.70 (m, 1H), 4.01 (d, 2H, J = 8.6 Hz), 3.91 (d, 2H, J = 8.6 Hz), 3.17 (s, 3H), 3.0-2.90 (m, 2H), 2.10-2.0 (m, 2H), 1.92-1.9 (m, 2H), 1.82-1.80 (m, 2H), 1.40-1.30 (m, 2H), 1.14 (t, 3H, J = 7.52 Hz), 0.83 (t, 3H, J = 7.24 Hz), 0.70-0.67 (m, 1H), 0.48-0.47 (m, 1H). | 462.34 | 3.66 | B |
| 239 | ¹H NMR (DMSO-d₆) δ ppm 9.94 (s, 1H), 7.66 (d, 2H, J = 10.9 Hz), 4.72-4.69 (m, 1H), 4.05 (d, 2H, J = 8.44 Hz), 3.91 (d, 2H, J = 8.44 Hz), 3.20 (s, 3H), 2.95-2.90 (m, 2H), 2.10-2.05 (m, 2H), 1.92-1.9 (m, 2H), 1.45 (s, 3H), 1.33-1.31 (m, 2H), 1.14 (t, 3H, J = 7.45 Hz), 0.69-0.68 (m, 1H), 0.49-0.46 (m, 1H). | 448.38 | 3.46 | B |
| 240 | ¹H NMR (DMSO-d₆) δ ppm 9.72 (s, 1H), 7.66 (d, 2H, J = 10.6 Hz), 4.71 (t, 1H, J = 6.2 Hz), 3.65-3.61 (m, 2H), 3.30-3.21 (m, 2H), 2.95-2.73 (m, 4H), 2.10-1.32 (m, 12H), 1.15 (t, 3H, J = 7.44 Hz), 0.70-0.67 (m, 1H), 0.48-0.47 (m, 1H). | 458.44 | 3.73 | B |

-continued

| Ex. | NMR Data | [M + H] | Rt (min) | LCMS Method |
|---|---|---|---|---|
| 241 | $^1$H NMR (DMSO-d$_6$) δ ppm 9.78 (s, 1H), 7.68-7.64 (m, 2H), 4.71 (t, 1H, J = 6.3 Hz), 3.61 (d, 2H, J = 10.68 Hz), 3.35-3.15 (m, 2H), 3.01-2.92 (m, 4H), 2.24-2.06 (m, 2.06 (m, 4H), 1.92-1.9 (m, 2H), 1.72-1.66 (m, 2H), 1.34-1.31 (m, 2H), 1.17 (d, 3H, J = 7.5 Hz), 0.70-0.67 (m, 1H), 0.50-0.47 (m, 1H). | 444.41 | 3.62 | B |
| 242 | $^1$H NMR (DMSO-d$_6$) δ ppm 8.66 (s, 1H), 7.40-7.26 (m, 2H), 4.80-4.70 (m, 1H), 3.55-3.52 (m, 4H), 3.02-2.96 (m, 2H), 2.10-2.0 (m, 4H), 1.80-1.59 (m, 8H), 1.31-1.20 (m, 5H), 0.87-0.47 (m, 2H). | 446.43 | 3.71 | B |
| 243 | $^1$H NMR (DMSO-d$_6$) δ ppm 9.87 (s, 1H), 7.65 (d, 2H, J = 11.1 Hz), 4.72-4.62 (m, 1H), 3.74 (s, 4H), 2.95-2.89 (m, 2H), 2.10-2.07 (m, 2H), 1.92-1.9 (m, 2H), 1.63-1.58 (m, 4H), 1.33-1.31 (m, 2H), 1.14 (t, 3H, J = 7.44 Hz), 0.83 (t, 6H, J = 7.3 Hz), 0.70-0.67 (m, 1H), 0.50-0.47 (m, 1H). | 460.36 | 3.74 | B |
| 244 | $^1$H NMR (DMSO-d$_6$) δ ppm 9.74 (s, 1H), 7.66 (d, 2H, J = 11.16 Hz), 4.70 (t, 1H, J = 6.22 Hz), 3.47-3.44 (m, 4H), 2.96-2.90 (m, 2H), 2.09-2.06 (m, 2H), 1.93-1.89 (m, 6H), 1.33-1.31 (m, 2H), 1.15 (t, 3H, J = 7.5 Hz), 0.70-0.67 (m, 1H), 0.50-0.45 (m, 1H). | 418.31 | 3.65 | B |
| 245 | $^1$H NMR (DMSO-d$_6$) δ ppm 9.59 (s, 1H), 7.72 (d, 1H, J = 13.5 Hz), 7.48-7.46 (m, 1H), 7.01-6.97 (m, 1H), 5.0-4.80 (m, 1H), 3.80-3.60 (m, 4H), 3.0-2.80 (m, 2H), 2.17-2.14 (m, 2H), 1.9-1.88 (m, 2H), 1.70-1.50 (m, 4H), 1.40-1.12 (m, 5H), 0.90-0.80 (m, 6H), 0.54-0.46 (m, 2H). | 442.49 | 3.66 | B |
| 246 | $^1$H NMR (DMSO-d$_6$) δ ppm 9.62 (s, 1H), 7.72 (d, 1H, J = 13.4 Hz), 7.48 (d, 1H, J = 9.4 Hz), 7.0 (t, 1H, J = 9.2 Hz), 4.89-4.86 (m, 1H), 4.0 (d, 2H, J = 8.6 Hz), 3.91 (d, 2H, J = 8.6 Hz), 3.17 (s, 3H), 2.96-2.90 (m, 2H), 2.18-2.15 (m, 2H), 1.89-1.79 (m, 4H), 1.35-1.31 (m, 2H), 1.14 (t, 3H, J = 7.48 Hz), 0.83 (t, 3H, J = 7.16 Hz), 0.54-0.45 (m, 2H). | 444.44 | 3.44 | B |
| 247 | $^1$H NMR (DMSO-d$_6$) δ ppm 9.50 (s, 1H), 7.74 (d, 1H, J = 13.64 Hz), 7.48 (d, 1H, J = 8.88 Hz), 7.0 (t, 1H, J = 9.32 Hz , 9.04 Hz), 4.89-4.86 (m, 1H), 3.61 (d, 2H, J = 10.5 Hz), 3.31-3.35 (m, 2H), 3.01 (m, 4H), 2.19-2.15 (m, 4H), 1.91-1.88 (m, 2H), 1.70-1.60 (m, 2H), 1.33-1.15 (m, 5H), 0.55-0.45 (m, 2H). [Presence of two protons at 3.35-3.31 ppm was confirmed by CDCl$_3$ NMR] | 426.45 | 3.57 | B |
| 248 | $^1$H NMR (400 MHz, DMSO-d$_6$) δ 9.26 (s, 1H), 7.50 (s, 1H), 7.46-7.44 (m, 1H), 6.73 (d, 1H, J = 8.8 Hz), 4.83 (t, 1H, J = 6.5 Hz), 4.04 (d, 2H, J = 8.4 Hz), 3.90 (d, 2H, J = 8.5 Hz), 3.20 (s, 3H), 2.95-2.90 (m, 2H), 2.20-2.18 (m, 2H), 2.07 (s, 3H), 1.86-1.84 (m, 2H), 1.45 (s, 3H), 1.34-1.32 (m, 2H), 1.14 (t, 3H, J = 7.5 Hz), 0.54-0.48 (m, 2H). | 426.4 | 7.51 | -K |
| 249 | $^1$H NMR (400 MHz, DMSO-d$_6$) δ 9.64 (s, 1H), 7.94 (d, 1H, J = 2.36 Hz), 7.63-7.60 (m, 1H), 6.99 (d, 1H, J = 9.08 Hz), 4.93 (t, 1H, J = 6.4 Hz), 4.04 (d, 2H, J = 8.4 Hz), 3.91 (d, 2H, J = 8.48 Hz), 3.20 (s, 3H), 2.95-2.90 (m, 2H), 2.19-2.17 (m, 2H), 1.86-1.84 (m, 2H), 1.45 (s, 3H), 1.34-1.23 (m, 2H), 1.14 (t, 3H, J = 7.5 Hz), 0.67-0.64 (m, 1H), 0.48-0.43 (m, 1H). | 446.3 | 3.49 | -B |
| 250 | $^1$H NMR (DMSO-d$_6$) δ ppm 9.31 (s, 1H), 7.41-7.37 (m, 1H), 6.89 (t, 1H, J = 10.3 Hz), 4.95 (t, 1H, J = 6.8 Hz), 4.0 (d, 2H, J = 8.8 Hz), 3.90 (d, 2H, J = 8.4 Hz), 3.17 (s, 3H), 2.94-2.89 (m, 2H), 2.22-2.20 (m, 2H), 1.91-1.79 (m, 4H), 1.40-1.30 (m, 2H), 1.14 (t, 3H, J = 7.6 Hz), 0.83 (t, 3H, J = 7.2 Hz), 0.50-0.40 (m, 2H). | 462.51 | 3.48 | B |
| 251 | $^1$H NMR (400 MHz, DMSO-d$_6$) δ 9.12 (s, 1H), 7.60-7.58 (m, 2H), 3.83-3.79 (m, 2H), 3.66-3.55 (m, 4H), 3.41-3.37 (m, 6H), 3.0-2.91 (m, 4H), 2.41-2.40 (m, 2H), 2.20-2.10 (m, 2H), 1.59-1.57 (m, 2H), 1.16 (t, 3H, J = 7.4 Hz). | 462.52 | 2.72 | A |
| 252 | $^1$H NMR (400 MHz, DMSO-d$_6$) δ 9.24 (s, 1H), 7.51-7.47 (m, 1H), 7.27 (s, 1H), 3.86-3.75 (m, 1H), 3.50-3.40 (m, 4H), 2.95-2.90 (m, 2H), 2.31-1.52 (m, 16H), 1.22-1.13 (m, 4H). | 427.4 | 3.56 | B |
| 253 | $^1$H NMR (400 MHz, DMSO-d$_6$) δ 9.34 (s, 1H), 7.48-7.44 (m, 1H), 7.29 (s, 1H), 3.86-3.69 (m, 5H), 2.94-2.89 (m, 2H) 2.29-1.11 (m, 21H), 0.82 (t, 6H, J = 6.96 Hz). | 469.4 | 3.58 | B |
| 254 | $^1$H NMR (DMSO-d$_6$) δ ppm 9.85 (s, 1H), 7.59 (d, 2H, J = 11.6 Hz), 4.01 (d, 2H, J = 8.64 Hz), 3.92 (d, 2H, J = 8.68 Hz), 3.41 (s, 4H), 3.18 (s, 3H), 2.96-2.91 (m, 2H), 2.50-2.41 (m, 2H), 2.11-2.07 (m, 2H), 1.85-1.79 (m, 4H), 1.59-1.57 (m, 2H), 1.15 (t, 3H, J = 7.44 Hz), 0.83 (t, 3H, J = 7.12 Hz). | 461.52 | 3.64 | B |
| 255 | $^1$H NMR (DMSO-d$_6$) δ ppm 9.70 (s, 1H), 7.61 (d, 2H, J = 11.3 Hz), 3.46-3.41 (m, 8H), 2.96-2.91 (m, 2H), 2.49-2.41 (m, 2H), 2.20-1.90 (m, 6H), 1.58-1.57 (m, 2H), 1.16 (t, 3H, J = 7.36 Hz). | 417.38 | 3.9 | B |

| Ex. | NMR Data | [M + H] | Rt (min) | LCMS Method |
|---|---|---|---|---|
| 256 | $^1$H NMR (400 MHz, DMSO-$d_6$) δ 9.87 (s, 1H), 7.61-7.58 (m, 2H), 3.79 (s, 4H), 3.40 (s, 4H), 2.95-2.90 (m, 2H), 2.41-2.39 (m, 2H), 2.11-2.09 (m, 2H), 1.58-1.56 (m, 2H), 1.28 (s, 6H), 1.14 (t, 3H, J = 7.5 Hz). | 431.38 | 3.97 | B |
| 257 | $^1$H NMR (400 MHz, DMSO-$d_6$) δ 9.70 (s, 1H), 7.76-7.69 (m, 1H), 7.17 (t, 1H, J = 7.72 Hz), 4.95 (t, 1H, J = 6.32), 4.0 (d, 2H, J = 8.6 Hz), 3.91 (d, 2H, J = 8.6 Hz), 3.17 (s, 3H), 2.95-2.89 (m, 2H), 2.20-2.18 (m, 2H), 1.89-1.79 (m, 4H), 1.35-1.33 (m, 2H), 1.17 (t, 3H, J = 7.44 Hz), 0.84 (t, 3H, J = 7.16 Hz), 0.50-0.49 (m, 2H). | 459.38 | 3.84 | B |
| 258 | $^1$H NMR (400 MHz, DMSO-$d_6$) δ 9.87 (s, 1H), 7.60 (d, 2H, J = 10.5 Hz), 4.05 (d, 2H, J = 8.4 Hz), 3.92 (d, 2H, J = 8.4 Hz), 3.41 (s, 3H), 3.20 (s, 3H), 2.96-2.91 (m, 2H), 2.50-2.40 (m, 2H), 2.12-2.10 (m, 2H), 1.59-1.57 (m, 2H), 1.46 (s, 3H), 1.15 (t, 3H, J = 7.4 Hz). | 447.39 | 3.92 | B |
| 259 | $^1$H NMR (400 MHz, DMSO-$d_6$) δ 9.90 (s, 1H), 7.61-7.58 (m, 2H), 4.20 (s, 4H), 3.40 (s, 4H), 2.96-2.85 (m, 6H), 2.42-2.39 (m, 2H), 2.11-2.09 (m, 2H), 1.58-1.56 (m, 2H), 1.14 (t, 3H, J = 7.5 Hz). | 479.38 | 3.99 | B |
| 260 | $^1$H NMR (400 MHz, DMSO-$d_6$) δ 9.40 (s, 1H), 9.19 (s, 1H), 7.29-7.27 (m, 1H), 6.92 (d, 1H, J = 2.16 Hz), 4.74-4.67 (m, 1H), 4.14-4.06 (m, 2H), 3.77 (s, 4H), 2.32-2.21 (m, 4H), 2.15 (s, 3H), 2.08-1.84 (m, 4H), 1.65-1.59 (m, 4H), 1.50 (t, 1H, J = 8.4 Hz), 1.32 (t, 1H, J = 8.6 Hz), 0.83 (t, 6H, J = 7.28 Hz). | 522.4 | 3.68 | -B |
| 261 | $^1$H NMR (400 MHz, DMSO-$d_6$) δ 9.81 (d, 2H, J = 6.44 Hz), 7.45 (s, 1H), 7.32 (s, 1H), 4.77 (t, 1H, J = 6.5 Hz), 4.14-4.06 (m, 2H), 3.78 (s, 4H), 2.32-1.87 (m, 8H), 1.65-1.59 (m, 5H), 1.31-1.23 (m, 1H), 0.83 (t, 6H, J = 7.3 Hz). | 542.3 | 3.84 | B |
| 262 | $^1$H NMR (400 MHz, DMSO-$d_6$) δ 9.41 (s, 1H), 9.25 (s, 1H), 7.30 (d, 1H, J = 2.4 Hz), 6.89 (s, 1H), 4.80-4.60 (m, 1H), 4.11-4.09 (m, 2H), 3.77 (s, 4H), 2.11 (s, 3H), 2.0-1.91 (m, 4H), 1.64-1.59 (m, 4H), 1.29-1.27 (m, 2H), 0.84-0.79 (m, 7H), 0.50-0.50 (m, 1H). | 508.3 | 3.5 | B |
| 263 | $^1$H NMR (DMSO-$d_6$) δ ppm 9.47 (s, 1H), 9.25 (s, 1H), 7.30 (d, 1H, J = 2.2 Hz), 6.90 (d, 1H, J = 1.7 Hz), 4.70 (t, 1H, J = 6.12 Hz), 4.15-4.01 (m, 4H), 3.95 (d, 2H, J = 8.5 Hz), 3.20 (s, 3H), 2.11 (s, 3H), 2.01-1.91 (m, 4H), 1.46 (s, 3H), 1.29-1.27 (m, 2H), 0.81-0.78 (m, 1H), 0.50-0.45 (m, 1H). | 496.2 | 1.96 | D |
| 264 | $^1$H NMR (DMSO-$d_6$) δ ppm 9.79 (s, 1H), 9.73 (s, 1H), 7.32 (s, 1H), 7.12 (d, 1H, J = 13.0 Hz), 4.70-4.60 (m, 1H), 4.14-4.07 (m, 2H), 3.77 (s, 4H), 2.31-1.92 (m, 8H), 1.64-1.57 (m, 4H), 1.29-1.23 (m, 2H), 0.83 (t, 6H, J = 7.2 Hz). | 526.4 | 3.66 | B |
| 265 | $^1$H NMR (DMSO-$d_6$) δ ppm 9.84 (s, 1H), 9.74 (s, 1H), 7.33 (s, 1H), 7.14-7.10 (m, 1H), 4.66-4.63 (m, 1H), 4.16-4.06 (m, 4H), 3.96 (d, 2H, J = 8.56 Hz), 3.20 (m, 3H), 2.31-1.88 (m, 8H), 1.59 (t, 1H, J = 8.4 Hz), 1.46 (s, 3H), 1.29-1.25 (m, 1H). | 514.35 | 3.44 | B |
| 266 | $^1$H NMR (DMSO-$d_6$) δ ppm 9.82 (s, 1H), 9.74 (s, 1H), 7.32 (s, 1H), 7.12 (d, 1H, J = 12.8 Hz), 4.66-4.64 (m, 1H), 4.15-4.08 (m, 2H), 4.04 (d, 2H, J = 8.72 Hz), 3.95 (d, 2H, J = 8.68 Hz), 3.18 (s, 3H), 2.31-1.80 (m, 10H), 1.59 (t, 1H, J = 8.4 Hz), 1.29-1.25 (m, 1H), 0.83 (t, 3H, J = 7.1 Hz). | 528.38 | 3.36 | B |
| 267 | $^1$H NMR (DMSO-$d_6$) δ ppm 9.82 (s, 1H), 9.79 (s, 1H), 7.33 (s, 1H), 7.11 (d, 1H, J = 12.8 Hz), 4.74 (t, 1H, J = 6.2 Hz), 4.15-4.06 (m, 4H), 3.95 (d, 2H, J = 8.5 Hz), 3.20 (s, 3H), 2.0-1.96 (m, 2H), 1.92-1.9 (m, 2H), 1.46 (s, 3H), 1.28-1.26 (m, 2H), 0.85-0.82 (m, 1H), 0.45-0.40 (m, 1H). | 500.36 | 3.23 | -B |
| 268 | $^1$H NMR (DMSO-$d_6$) δ ppm 9.79 (s, 2H) 7.32 (s, 1H), 7.10 (d, 1H, J = 12.9 Hz), 4.74 (t, 1H, J = 6.04 Hz), 4.15-4.02 (m, 4H), 3.95 (d, 2H, J = 8.64 Hz), 3.18 (s, 3H), 1.98-1.80 (m, 6H), 1.28-1.19 (m, 2H), 0.85-0.81 (m, 4H), 0.50-0.40 (m, 1H). | 514.55 | 3.31 | B |
| 269 | $^1$H NMR (DMSO-$d_6$) δ ppm 9.79-9.77 (m, 2H), 7.31 (s, 1H), 7.11 (d, 1H, J = 12.76 Hz), 4.75 (t, 1H, J = 5.36 Hz), 4.14-4.04 (m, 2H), 3.77 (s, 4H), 1.97-1.88 (m, 4H), 1.64-1.59 (m, 4H), 1.27-1.26 (m, 2H), 0.84-0.81 (m, 7H), 0.43-0.42 (m, 1H). | 512.4 | 3.56 | B |
| 270 | $^1$H NMR (DMSO-$d_6$) δ ppm 9.50 (s, 1H), 8.88 (s, 1H), 7.36 (s, 1H), 7.01 (d, 1H, J = 7.88 Hz), 6.70 (d, 1H, J = 8.68 Hz), 4.79-4.76 (m, 1H), 4.12-4.07 (m, 2H), 3.77 (s, 4H), 2.11-2.09 (m, 2H), 1.92-1.9 (m, 2H), 1.64-1.59 (m, 4H), 1.29-1.20 (m, 2H), 0.84-0.42 (m, 8H). | 494.34 | 3.49 | B |
| 271 | $^1$H NMR (400 MHz, DMSO-$d_6$) δ 9.84 (s, 1H), 9.55 (s, 1H), 7.45-7.43 (m, 1H), 7.29 (d, 1H, J = 2.28 Hz), 4.80-4.70 (m, 1H), 4.04 (d, 2H, J = 8.44 Hz), 3.90 (d, 2H, J = 8.48 Hz), 3.20 (s, 3H), 2.95-2.89 (m, 2H), 2.0-1.90 (m, 4H), 1.45 (s, 3H), 1.29-1.27 (m, 2H), 1.14 (t, 3H, J = 7.5 Hz), 0.94-0.93 (m, 1H), 0.50-0.40 (m, 1H). | 462.3 | 3.33 | B |

| Ex. | NMR Data | [M + H] | Rt (min) | LCMS Method |
|---|---|---|---|---|
| 272 | $^1$H NMR (DMSO-d$_6$) δ ppm 9.69 (s, 1H), 9.25 (s, 1H), 7.23 (s, 1H), 7.0 (dd, 1H, J = 2.3 Hz, 15.2 Hz), 4.15-4.06 (m, 4H), 3.95 (d, 2H, J = 8.5 Hz), 3.87 (s, 2H), 3.20 (s, 3H), 1.91-1.49 (m, 8H), 1.46 (s, 3H), 1.41-1.35 (m, 2H). | 513.46 | 6.97 | C |
| 273 | $^1$H NMR (DMSO-d$_6$) δ ppm 9.87 (s, 1H), 7.65 (d, 2H, J = 11.08 Hz), 4.72-4.70 (m, 1H), 3.74 (s, 4H), 2.5 (s, 3H), 2.10-2.07 (m, 2H), 1.93-1.89 (m, 2H), 1.61-1.58 (m, 4H), 1.32 (bs, 2H), 0.81 (t, 6H, J = 7.2 Hz), 0.68 (bs, 1H), 0.48 (bs, 1H). | 446.33 | 3.63 | B |
| 274 | $^1$H NMR (DMSO-d$_6$) δ ppm 9.73 (s, 1H), 7.68-7.63 (m, 2H), 4.70 (t, 1H, J = 6.2 Hz), 3.47-3.43 (m, 4H), 2.89 (t, 2H, J = 7.32 Hz), 2.08-2.05 (m, 2H), 1.93-1.89 (m, 6H), 1.62-1.57 (m, 2H), 1.33-1.31 (m, 2H), 0.90 (t, 3H, J = 7.3 Hz), 0.70-0.67 (m, 1H), 0.50-0.47 (m, 1H). | 432.3 | 2.18 | B |
| 275 | $^1$H NMR (DMSO-d$_6$) δ ppm 9.67 (s, 1H), 7.65 (d, 2H, J = 10.6 Hz), 4.80-4.70 (m, 1H), 4.20-4.10 (m, 1H), 3.52-3.48 (m, 2H), 2.92-2.77 (m, 3H), 2.08-1.33 (m, 16H), 0.90 (t, 3H, J = 7.2 Hz), 0.70-0.67 (m, 1H), 0.50-0.47 (m, 1H). | 472.37 | 3.82 | B |
| 276 | $^1$H NMR (400 MHz, DMSO-d$_6$) δ 10.0 (s, 1H), 7.67-7.64 (m, 2H), 4.70 (t, 2H, J = 5.8 Hz), 4.59 (t, 1H, J = 5.9 Hz), 4.06 (d, 2H, J = 8.4 Hz), 3.93 (d, 2H, J = 8.4 Hz), 3.38-3.35 (m, 2H), 3.20 (s, 3H), 2.08-2.05 (m, 2H), 1.92-1.9 (m, 2H), 1.45 (s, 3H), 1.33-1.31 (m, 2H), 0.70-0.68 (m, 1H), 0.50-0.40 (m, 1H). | 466.3 | 3.22 | B |
| 277 | $^1$H NMR (DMSO-d$_6$) δ ppm 9.69 (s, 1H), 7.61-7.57 (m, 1H), 7.45 (s, 1H), 4.70 (t, 1H, J = 6.0 Hz), 4.60-4.55 (m, 2H), 4.01 (d, 2H, J = 8.6 Hz), 3.92 (d, 2H, J = 8.6 Hz), 3.38-3.29 (m, 2H), 3.17 (s, 3H), 2.33-2.27 (m, 4H), 2.23 (s, 3H), 2.10-1.79 (m, 6H), 1.50 (t, 1H, J = 8.4 Hz), 1.33 (t, 1H, J = 8.9 Hz), 0.83 (t, 3H, J = 7.2 Hz). | 490.31 | 3.85 | B |
| 278 | $^1$H NMR (DMSO-d$_6$) δ ppm 9.53 (s, 1H), 7.62 (d, 1H, J = 13.7 Hz), 7.44 (s, 1H), 4.71 (t, 1H, J = 5.88 Hz), 4.60-4.55 (m, 2H), 3.47-3.29 (m, 7H), 2.33-2.27 (m, 3H), 2.23 (s, 3H), 2.10-1.87 (m, 8H), 1.50 (t, 1H, J = 8.32 Hz), 1.34 (t, 1H, J = 8.6 Hz). | 446.4 | 3.48 | B |
| 279 | $^1$H NMR (DMSO-d$_6$) δ ppm 9.87 (s, 1H), 7.71-7.65 (m, 2H), 4.71 (t, 1H, J = 5.9 Hz), 4.64-4.58 (m, 2H), 3.48-3.45 (m, 4H), 3.37 (t, 1H, J = 5.96 Hz), 3.31-3.29 (m, 1H), 2.33-2.25 (m, 3H), 2.06-1.91 (m, 9H), 1.56 (t, 1H, J = 8.6 Hz), 1.29 (t, 1H, J = 8.68 Hz). | 450.3 | 3.48 | B |
| 280 | $^1$H NMR (DMSO-d$_6$) δ ppm 9.71 (s, 1H), 7.58 (dd, 1H, J = 2.3, 13.7 Hz), 7.44 (s, 1H), 4.70 (t, 1H, J = 6.0 Hz), 4.60-4.56 (m, 2H), 4.05 (d, 2H, J = 8.5 Hz), 3.92 (d, 2H, J = 8.5 Hz), 3.38-3.28 (m, 2H), 3.20 (s, 3H), 2.18 (s, 3H), 2.09-2.05 (m, 2H), 1.95-1.92 (m, 2H), 1.45 (s, 3H), 1.35-1.30 (m, 2H), 0.71-0.68 (m, 1H), 0.53-0.48 (m, 1H). | 462.3 | 3.34 | B |
| 281 | $^1$H NMR (DMSO-d$_6$) δ ppm 9.71 (s, 1H), 7.61-7.57 (m, 1H), 7.46 (s, 1H), 4.70 (t, 1H, J = 5.9 Hz), 4.60-4.55 (m, 2H), 4.06 (d, 2H, J = 8.4 Hz), 3.92 (d, 2H, J = 8.5 Hz), 3.20 (s, 3H), 2.33-1.90 (m, 9H), 1.52-1.46 (m, 3H), 1.34 (t, 1H, J = 8.7 Hz).<br>Note: Some aliphatic protons missing-merged with DMSO H$_2$O peak.<br>$^1$H NMR (MeOD) δ ppm 7.49-7.45 (dd, 1H, J = 2.48, 17.32), 7.17 (bs, 1H), 4.70 (t, 2H, J = 6.16 Hz), 4.58 (t, 1H, J = 6.2 Hz), 4.11 (d, 2H, J = 8.44 Hz), 3.94 (d, 2H, J = 8.48 Hz), 3.39 (t, 1H, J = 6.16 Hz), 3.33 (t, 1H, J = 6.44 Hz), 3.28 (s, 3H), 2.37-2.33 (m, 4H), 2.28 (s, 1H), 2.16-2.14 (m, 1H), 2.03-1.97(m, 1H), 1.58-1.54 (m, 1H), 1.53 (s, 3H), 1.41-1.36 (m, 1H). | 476.4 | 3.38 | B |
| 282 | $^1$H NMR (DMSO-d$_6$) δ ppm 9.64 (s, 1H), 7.59 (dd, 1H, J = 2.2 Hz 13.6 Hz), 7.44 (s, 1H), 4.70 (t, 1H, J = 6.0 Hz), 4.59-4.55 (m, 2H), 3.75 (s, 4H), 3.38-3.28 (m, 2H), 2.34-2.27 (m, 4H), 2.23 (s, 3H), 2.10-1.87 (m, 4H), 1.64-1.58 (m, 4H), 1.52 (t, 1H, J = 8.36 Hz), 1.34 (t, 1H, J = 8.8 Hz), 0.85-0.83 (m, 6H). | 488.38 | 3.67 | B |
| 283 | $^1$H NMR (DMSO-d$_6$) δ ppm 9.71 (s, 1H), 7.74 (d, 1H, J = 13.6 Hz), 7.51 (d, 1H, J = 8.7 Hz), 7.14-7.10 (m, 1H), 4.88-4.57 (m, 3H), 3.75 (s, 4H), 3.36-3.30 (m, 2H), 2.41-1.36 (m, 14H), 0.84-0.81 (m, 6H). | 474.4 | 9.61 | K |
| 284 | $^1$H NMR (DMSO-d$_6$) δ ppm 9.84 (s, 1H), 7.68 (d, 2H, J = 10.9 Hz), 4.71 (t, 1H, J = 6.0 Hz), 4.64-4.58 (m, 2H), 3.64 (t, 2H, J = 6.8 Hz), 3.39-3.30 (m, 4H), 2.33-2.25 (m, 5H), 2.07-1.87 (m, 6H), 1.56 (t, 1H, J = 8.5 Hz), 1.29 (t, 1H, J = 8.6 Hz), 0.67-0.60 (m, 4H). | 476.3 | 9.46 | K |
| 285 | $^1$H NMR (DMSO-d$_6$) δ ppm 9.64 (s, 1H), 7.59 (dd, 1H, J = 2.0 Hz, 13.7 Hz), 7.43 (s, 1H), 4.69 (t, 1H, J = 6.0 Hz), 4.58 (t, 2H, J = 6.1 Hz), 3.75 (s, 3H), 3.37-3.34 (m, 1H), 2.18 (s, 3H), 2.10-2.07 (m, 2H), 1.94-1.91 (m, 2H), 1.64-1.58 (m, 4H), 1.33-1.23 (m, 4H), 0.83 (t, 6H, J = 7.3 Hz), 0.70-0.69 (m, 2H), 0.50-0.48 (m, 2H). | 474.4 | 3.57 | B |

-continued

| Ex. | NMR Data | [M + H] | Rt (min) | LCMS Method |
|---|---|---|---|---|
| 286 | ¹H NMR (DMSO-d₆) δ ppm 10.01 (s, 1H), 7.68-7.65 (m, 2H), 4.70-4.57 (m, 3H), 3.75 (s, 4H), 3.37-3.28 (m, 2H), 2.33-1.93 (m, 8H), 1.64-1.54 (m, 5H), 1.28 (t, 1H, J = 8.5 Hz), 0.87-0.81 (m, 6H). | 492.4 | 3.59 | B |
| 287 | ¹H NMR (DMSO-d₆) δ ppm 9.99 (s, 1H), 7.66 (d, 2H, J = 11.2 Hz), 4.72-4.68 (m, 2H), 4.58 (t, 1H, J = 6.0 Hz), 3.75 (s, 4H), 3.36 (t, 1H, J = 6.0 Hz), 2.08-2.05 (m, 2H), 1.94-1.91 (m, 2H), 1.64-1.58 (m, 4H), 1.33-1.31 (m, 2H), 0.87-0.79 (m, 7H), 0.70-0.67 (m, 1H), 0.50-0.47 (m, 1H) | 478.41 | 3.57 | B |
| 288 | ¹H NMR (DMSO-d₆) δ ppm 9.85 (s, 1H), 7.66 (d, 2H, J = 10.8 Hz), 4.71 (t, 2H, J = 6.04 Hz), 4.59 (t, 1H, J = 6.0 Hz), 3.63 (t, 2H, J = 6.8 Hz), 3.38-3.35 (m, 3H), 3.29-3.31 (m, 1H), 2.09-1.86 (m, 6H), 1.40-1.30 (m, 2H), 0.70-0.48 (m, 6H). | 462.36 | 3.38 | B |
| 289 | ¹H NMR (DMSO-d₆) δ ppm 9.53 (s, 1H), 7.45-7.40 (m, 2H), 4.69 (t, 1H, J = 5.9 Hz), 4.57 (t, 1H, J = 5.9 Hz), 3.74 (s, 4H), 3.60 (s, 2H), 3.40-3.30 (m, 2H), 2.29 (s, 3H), 1.93-1.45 (m, 14H), 0.82 (t, 6H, J = 7.2 Hz). | 487.5 | 8.33 | K |
| 290 | ¹H NMR (DMSO-d₆) δ ppm 9.58 (s, 1H), 7.46-7.41 (m, 2H), 4.70 (t, 1H, J = 6.0 Hz), 4.58 (t, 1H, J = 6.0 Hz), 4.05 (d, 2H, J = 8.5 Hz), 3.92 (d, 2H, J = 8.5 Hz), 3.61 (s, 2H), 3.37-3.34 (m, 2H), 3.20 (s, 3H) 2.29 (s, 3H), 1.94-1.45 (m, 13H). | 475.2 | 2.26 | B |
| 291 | ¹H NMR (DMSO-d₆) δ ppm 9.55 (s, 1H), 7.45-7.41 (m, 2H), 4.70 (t, 1H, J = 5.16 Hz), 4.58 (t, 1H, J = 5.72 Hz), 4.01 (d, 2H, J = 8.08 Hz), 3.92 (d, 2H, J = 8.64 Hz), 3.61 (s, 2H), 3.17 (s, 2H), 2.32-2.20 (m, 3H), 1.98-1.15 (m, 12H), 0.84-0.81 (m, 3H).<br>Note: Some aliphatic protons missing; merged with DMSO H₂O peak.<br>¹H NMR (CDCl₃) δ ppm 8.50 (bs, 1H), 7.31(s, 1H), 7.11 (s, 1H), 4.72 (t, 1H, J = 5.84 Hz), 4.61 (t, 1H, J = 5.64 Hz), 4.06 (d, 2H, J = 8.32 Hz), 3.89 (d, 2H, J = 8.36 Hz), 3.65 (bs, 2H), 3.43 (t, 1H, J = 5.92 Hz), 3.37 (t, 1H, J = 5.96 Hz), 3.24 (s, 3H), 2.36 (s, 3H), 2.03 (bs, 2H), 1.09-1.86 (m, 4H), 1.71 (bs, 3H, J-7.24), 0.86 (bs, 2H). | 489.4 | 3.51 | B |
| 292 | ¹H NMR (400 MHz, DMSO-d₆) δ 9.45 (s, 1H), 7.48-7.44 (m, 1H), 7.31 (s, 1H), 4.69 (t, 1H, J = 6.0 Hz), 4.58 (t, 1H, J = 6.1 Hz), 3.87-3.75 (m, 6H), 3.37-3.33 (m, 1H), 2.32-2.08 (m, 8H), 1.76-1.52 (m, 8H), 1.23-1.18 (m, 1H), 0.83 (t, 6H, J = 7.28 Hz & 7.48 Hz). | 487.4 | 3.78 | B |
| 293 | ¹H NMR (DMSO-d₆) δ ppm 9.76 (s, 1H), 7.58 (d, 1H, J = 13.7 Hz), 7.43 (s, 1H), 4.63 (s, 2H), 4.59-4.56 (m, 1H), 3.77 (s, 4H), 3.24 (s, 3H), 2.18 (s, 3H), 2.13-2.06 (m, 2H), 1.96-1.94 (m, 2H), 1.64-1.59 (m, 4H), 1.33-1.31 (m, 2H), 0.83 (t, 6H, J = 7.2 Hz), 0.71-0.69 (m, 1H), 0.52-0.51 (m, 1H). | 472.5 | 7.93 | K |
| 294 | ¹H NMR (DMSO-d₆) δ ppm 9.80 (s, 1H), 7.60-7.56 (m, 1H), 7.44 (s, 1H), 4.64 (s, 2H), 4.58 (t, 1H, J = 6.4 Hz), 4.08 (d, 2H, J = 8.5 Hz), 3.95 (d, 2H, J = 8.5 Hz), 3.24 (s, 3H), 3.20 (s, 3H), 2.18 (s, 3H), 2.10-2.06 (m, 2H), 1.94-1.91 (m, 2H), 1.46 (s, 3H), 1.33-1.31 (m, 2H), 0.70-0.69 (m, 1H), 0.50-0.48 (m, 1H). | 460.39 | 3.27 | B |
| 295 | ¹H NMR (DMSO-d₆) δ ppm 10.1 (s, 1H), 7.66 (d, 2H, J = 10.7 Hz), 4.72-4.69 (m, 1H), 4.63 (s, 2H), 3.78 (s, 4H), 3.24 (s, 3H), 2.10-2.06 (m, 2H), 1.92-1.9 (m, 2H), 1.64-1.59 (m, 4H), 1.40-1.20 (m, 2H), 0.85-0.47 (m, 8H). | 474.25 | 3.65 | B |
| 296 | ¹H NMR (400 MHz, DMSO-d₆) δ 9.78 (s, 1H), 7.60-7.57 (m, 1H), 7.46 (s, 1H), 5.10-5.0 (m, 1H), 4.64 (s, 2H), 4.60-4.50 (m, 1H), 3.98 (d, 2H, J = 7.64 Hz), 3.71 (d, 2H, J = 7.64 Hz), 3.40 (d, 2H, J = 5.1 Hz), 3.24 (s, 3H), 2.34-2.27 (m, 4H), 2.23 (s, 3H), 2.20-1.90 (m, 4H), 1.50-1.34 (m, 2H), 1.24 (s, 3H). | 474.3 | 3.09 | B |
| 297 | ¹H NMR (400 MHz, DMSO-d₆) δ 9.84 (s, 1H), 7.59-7.55 (m, 1H), 7.39 (s, 1H), 4.57 (t, 1H, J = 6.4 Hz), 3.77-3.74 (m, 6H), 3.17 (t, 4H, J = 7.0 Hz), 2.19 (s, 3H), 2.08-1.90 (m, 6H), 1.63-1.58 (m, 4H), 1.40-1.31 (m, 2H), 0.82 (t, 6H, J = 7.3 Hz), 0.70-0.50 (m, 2H). | 497.4 | 2.22 | B |
| 298 | ¹H NMR (400 MHz, DMSO-d₆) δ 9.85 (s, 1H), 7.58-7.55 (m, 1H), 7.37 (s, 1H), 4.59-4.56 (m, 1H), 4.0-3.80 (m, 2H), 3.74 (s, 4H), 2.18 (s, 3H), 2.10-2.06 (m, 2H), 1.94 (d, 2H, J = 14.4 Hz), 1.67-1.58 (m, 8H), 1.33-1.31 (m, 2H), 0.83 (t, 6H, J = 7.3 Hz), 0.70-0.50 (m, 2H).<br>Note: Some aliphatic protons missing, merged with DMSO/ H₂O peak.<br>¹H NMR (400 MHz, MeOD) δ 7.47 (d, 1H, J = 13.8 Hz), 7.12 (s, 1H), 4.66 (s, 1H), 4.04 (s, 2H), 3.81 (bs, 4H), 2.71 (bs, 4H), 2.24 (s, 3H), 2.10-2.02 (m, 4H), 1.84 (bs, 4H), 1.71-1.69 (bs, 4H), 1.33-1.28 (bs, 2H), 0.91-0.88 (bs, 6H), 0.76(bs, 1H), 0.51 (bs, 2H). | 511.4 | 2.85 | B |

| Ex. | NMR Data | [M + H] | Rt (min) | LCMS Method |
|---|---|---|---|---|
| 299 | $^1$H NMR (DMSO-$d_6$) δ ppm 10.13 (s, 1H), 7.62 (d, 2H, J = 11.0 Hz), 4.70 (t, 1H, J = 6.28 Hz), 3.89 (s, 2H), 3.75 (s, 4H), 2.50-2.40 (m, 4H), 2.09-2.05 (m, 2H), 1.93-1.91 (m, 2H), 1.66-1.58 (m, 8H), 1.33-1.31 (m, 2H), 0.82 (t, 6H, J = 7.24 Hz), 0.70-0.67 (m, 1H), 0.50-0.46 (m, 1H). | 515.5 | 2.81 | B |
| 300 | $^1$H NMR (DMSO-$d_6$) δ ppm 10.1 (s, 1H), 7.64 (d, 2H, J = 11.2 Hz), 4.80-4.70 (m, 1H), 3.77-3.75 (m, 6H), 3.20-3.10 (m, 4H), 2.10-1.89 (m, 6H), 1.62-1.32 (m, 6H), 0.84-0.47 (m, 8H). | 501.5 | 2.83 | B |
| 301 | $^1$H NMR (400 MHz, DMSO-$d_6$) δ 10.18 (s, 1H), 7.62 (d, 2H, J = 11.0 Hz), 4.80-4.60 (m, 1H), 3.75-3.74 (m, 6H), 2.17 (s, 6H), 2.10-2.0 (m, 2H), 1.91-1.9 (m, 2H), 1.64-1.58 (m, 4H), 1.33-1.31 (m, 2H), 0.83 (t, 6H, J = 7.4 Hz), 0.70-0.67 (m, 1H), 0.48-0.47 (m, 1H). | 489.44 | 3.01 | B |
| 302 | $^1$H NMR (DMSO-$d_6$) δ ppm 10.21 (s, 1H), 7.63 (d, 2H, J = 10.7 Hz), 4.70-4.60 (m, 1H), 4.02 (d, 2H, J = 8.7 Hz), 3.93 (d, 2H, J = 8.7 Hz), 3.84 (s, 2H), 3.17 (s, 3H), 2.41-1.81 (m, 15H), 1.56-1.26 (m, 2H), 0.99 (t, 3H, J = 7.0 Hz), 0.83 (t, 3H, J = 7.3 Hz). | 519.49 | 2.79 | B |
| 303 | $^1$H NMR (DMSO-$d_6$) δ ppm 10.23 (s, 1H), 7.64-7.60 (m, 2H), 4.70 (t, 1H, J = 6.36 Hz), 4.02 (d, 2H, J = 8.68 Hz), 3.93 (d, 2H, J = 8.64 Hz), 3.75 (s, 2H), 3.17 (s, 3H), 2.18 (s, 6H), 2.08-2.05 (m, 2H), 1.92-1.79 (m, 4H), 1.33-1.31 (m, 2H), 0.82 (t, 3H, J = 7.2 Hz, 7.32 Hz), 0.70-0.69 (m, 1H), 0.47-0.46 (m, 1H). | 491.43 | 2.58 | B |
| 304 | $^1$H NMR (400 MHz, DMSO-$d_6$) δ 10.21 (s, 1H), 7.63 (d, 2H, J = 10.92 Hz), 4.72 (t, 1H, J = 6.24 Hz), 4.02 (d, 2H, J = 8.68 Hz), 3.91 (d, 2H, J = 8.67 Hz), 3.83 (s, 2H), 3.17 (s, 3H), 2.43-2.37 (m, 2H), 2.17 (s, 3H), 2.09-2.05 (m, 2H), 1.93-1.89 (m, 2H), 1.84-1.79 (m, 2H), 1.33-1.31 (m, 2H), 1.01 (t, 3H, J = 7.08 Hz), 0.84 (t, 3H, J = 7.08 Hz), 0.70-0.67 (m, 1H), 0.48-0.47 (m, 1H). | 505.48 | 2.64 | B |
| 305 | $^1$H NMR (DMSO-$d_6$) δ ppm 9.73 (s, 1H), 7.60 (dd, 1H, J = 2.3 Hz, 13.8 Hz), 7.38 (s, 1H), 4.58 (t, 1H, J = 6.4 Hz), 3.78 (s, 2H), 3.45 (t, 4H, J = 13.8 Hz), 3.18 (t, 4H, J = 6.96 Hz), 2.19 (s, 3H), 2.10-2.06 (m, 2H), 1.97-1.91 (m, 8H), 1.33-1.30 (m, 2H), 0.71-0.69 (m, 1H), 0.52-0.51 (m, 1H). | 455.4 | 2.67 | B |
| 306 | $^1$H NMR (DMSO-$d_6$) δ ppm 10.07 (s, 1H), 7.66-7.64 (m, 2H), 4.71 (t, 1H, J = 6.2 Hz), 3.93 (s, 2H), 3.48-3.33 (m, 8H), 2.09-1.89 (m, 10H), 1.34-1.32 (m, 2H), 0.70-0.69 (m, 1H), 0.50-0.48 (m, 1H). | 459.4 | 2.64 | B |
| 307 | $^1$H NMR (400 MHz, DMSO-$d_6$) δ 10.43 (s, 1H), 9.86 (s, 1H), 7.71-7.68 (m, 2H), 4.69-4.56 (m, 3H), 4.13 (d, 2H, J = 8.56 Hz), 3.99 (d, 2H, J = 8.44 Hz), 3.22 (s, 3H), 3.15-3.10 (m, 2H), 2.78 (s, 3H), 2.32-1.93 (m, 8H), 1.56 (t, 1H, J = 8.36 Hz), 1.48 (s, 3H), 1.30-1.27 (m, 4H). | 505.3 | 2.68 | B |
| 308 | $^1$H NMR (400 MHz, DMSO-$d_6$) δ 10.78 (s, 1H), 10.2 (s, 1H), 7.71-7.68 (m, 2H), 4.81-4.65 (m, 3H), 3.56-3.52 (m, 6H), 3.20-3.10 (m, 2H), 2.09-1.89 (m, 12H), 1.40-1.30 (m, 2H), 0.70-0.60 (m, 1H), 0.50-0.40 (m, 1H). | 473.4 | 2.66 | B |
| 309 | $^1$H NMR (DMSO-$d_6$) δ ppm 9.94 (s, 1H), 9.74 (s, 1H), 7.27 (s, 1H), 7.10-7.0 (m, 1H), 4.70-4.60 (m, 1H), 4.01 (d, 2H, J = 8.6 Hz), 3.92 (d, 2H, J = 8.7 Hz), 3.82 (s, 2H), 3.17 (s, 3H), 2.42-1.81 (m, 14H), 1.60-1.50 (m, 1H), 1.30-1.20 (m, 2H), 1.0 (t, 3H, J = 7.0 Hz), 0.85-0.83 (m, 3H). | 517.5 | 2.26 | B |
| 310 | $^1$H NMR (400 MHz, DMSO-$d_6$) δ 9.32 (s, 1H), 7.29 (s, 1H), 7.13 (s, 1H), 4.62-4.58 (m, 1H), 4.14-4.06 (m, 2H), 3.76 (s, 4H), 3.22 (t, 2H, J = 8.6 Hz), 2.82-2.77 (m, 2H), 2.54 (s, 3H), 2.01-1.98 (m, 2H), 1.64-1.59 (m, 4H), 1.34-1.19 (m, 5H), 0.84-0.81 (m, 7H). | 517.4 | 2.97 | B |
| 311 | $^1$H NMR (DMSO-$d_6$) δ ppm 9.68 (s, 1H), 7.37-7.31 (m, 2H), 4.64-4.55 (m, 1H), 4.14-4.06 (m, 2H), 3.78-3.76 (m, 4H), 3.24 (t, 2H, J = 8.5 Hz), 2.89-2.83 (m, 2H), 2.10-2.03 (m, 2H), 1.64-1.23 (m, 8H), 0.86-0.77 (m, 7H), 0.18-0.15 (m, 1H). | 521.47 | 9.56 | C |
| 312 | $^1$H NMR (DMSO-$d_6$) δ ppm 9.72 (s, 1H), 7.37-7.31 (m, 2H), 4.59 (t, 1H, J = 8.64 Hz), 4.15-4.05 (m, 4H), 3.94 (d, 2H, J = 8.4 Hz), 3.26-3.20 (m, 5H), 2.88-2.84 (m, 2H), 2.10-2.0 (m, 2H), 1.46-1.39 (m, 5H), 1.30-1.20 (m, 2H), 0.80-0.70 (m, 1H), 0.20-0.10 (m, 1H). | 509.3 | 4.09 | E |
| 313 | $^1$H NMR (DMSO-$d_6$) δ ppm 9.70 (s, 1H), 7.37-7.31 (m, 2H), 4.62-4.57 (m, 1H), 4.15-4.07 (m, 2H), 4.03 (d, 2H, J = 8.6 Hz), 3.94 (d, 2H, J = 8.7 Hz), 3.24 (t, 2H, J = 8.4 Hz), 3.17 (s, 3H), 2.86 (t, 2H, J = 8.28 Hz), 2.10-2.0 (m, 2H), 1.85-1.79 (m, 2H), 1.45-1.40 (m, 2H), 1.30-1.20 (m, 2H), 0.84-0.79 (m, 4H), 0.20-0.10 (m, 1H). | 523.42 | 3.47 | B |

| Ex. | NMR Data | [M + H] | Rt (min) | LCMS Method |
|---|---|---|---|---|
| 314 | $^1$H NMR (DMSO-$d_6$) δ ppm 9.53 (s, 1H), 7.40-7.30 (m, 2H), 4.60-4.59 (m, 3H), 4.50 (d, 2H, J = 6.1 Hz), 4.12-4.09 (m, 2H), 3.72 (s, 2H), 3.49 (t, 2H, J = 6.9 Hz), 3.29-3.23 (m, 2H), 2.87 (t, 2H, J = 8.3 Hz), 2.25 (t, 2H, J = 6.9 Hz), 2.10-2.0 (m, 2H), 1.45-1.40 (m, 2H), 0.85-0.79 (m, 3H) 0.17-0.16 (m, 1H). | 521.4 | 3.18 | B |
| 315 | $^1$H NMR (DMSO-$d_6$) δ ppm 9.52 (s, 1H), 7.39-7.30 (m, 2H), 4.62-4.57 (m, 1H), 4.14-4.06 (m, 2H), 3.48-3.23 (m, 6H), 2.86 (t, 2H, J = 8.36 Hz), 2.07-1.92 (m, 6H), 1.45-1.23 (m, 4H), 0.80-0.79 (m, 1H), 0.17-0.15 (m, 1H). | 479.42 | 3.45 | B |
| 316 | $^1$H NMR (400 MHz, DMSO-$d_6$) δ 9.35 (s, 1H), 7.37-7.33 (m, 1H), 7.27 (s, 1H), 4.59 (t, 1H, J = 8.4 Hz), 3.72 (s, 4H), 3.26-3.21 (m, 2H), 2.93-2.83 (m, 4H), 2.10-2.0 (m, 2H), 1.61-1.23 (m, 8H), 1.13 (t, 3H, J = 7.4 Hz), 0.84-0.80 (m, 7H), 0.17-0.16 (m, 1H). | 467.4 | 3.58 | B |

LCMS Methods

Method A

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C8 column (1.7 μm, 50×2.1 mm) with a flow rate of 0.800 mL/min. Two mobile phases were used, mobile phase A: 0.05% HCOOH in water; mobile phase B: 0.0500 HCOOH in ACN: Water (90:10)], and they were employed to run a gradient conditions from 10% B for 0.75 minutes, from 10% to 50% in 0.25 minutes, and from 50% to 98% in 1.00 minutes, 98% B for 0.25 minutes and then 10% B in 0.35 minutes and hold these conditions for 0.40 minutes in order to re-equilibrate the column (Total Run Time 3.00 minutes). An injection volume of 0.5 μl was used.

Method B

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C8 column (1.7 μm, 50×2.1 mm) with a flow rate of 0.800 mL/min. Two mobile phases were used, mobile phase A: 0.05% HCOOH in water; mobile phase B: 0.05% HCOOH in ACN: Water (90:10)], and they were employed to run a gradient conditions from 5% B for 0.75 minutes, from 5% to 25% in 0.75 minutes, and from 25% to 95% in 1.50 minutes, 95% B for 1.00 minutes and 5% B in 0.50 minutes and hold these conditions for 0.60 minutes in order to re-equilibrate the column (Total Run Time 5.10 minutes). An injection volume of 0.5 μl was used.

Method C

The HPLC measurement was performed using Waters Acquity H Class UPLC comprising a quaternary pump with degasser, a sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Luna Omega Polar C18 column (3 μm, 100×4.6 mm) with a flow rate of 1.00 mL/min. Two mobile phases were used, mobile phase A: 0.05% TFA in water; mobile phase B: ACN, and they were employed to run a gradient condition from 2% B for 1.00 minutes, from 2% to 50% in 4.00 minutes, and from 50% to 95% in 4.00 minutes, 95% B for 3.00 minutes and then 5% B in 0.50 minutes. (Total Run Time 12.50 minutes). An injection volume of 0.5 μl was used.

Method D

The HPLC measurement was performed using Waters Acquity UPLC comprising a binary pump with degasser, a sample manager, a column oven (set at 50° C.), a diode-array detector DAD and a column as specified in the respective methods below. Flow from the column was split to a MS spectrometer. The MS detector (Waters ZQ SQD) was configured with an electrospray ionization source. Mass spectra were acquired by scanning from 100 to 1000 in 0.40 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.1 Software. Reversed phase HPLC was carried out on a YMC Triart C18 column (3 μm, 33×2.1 mm) with a flow rate of 1.00 mL/min. Two mobile phases were used, mobile phase A: 0.05% HCOOH in water; mobile phase B: 0.05% HCOOH in ACN: Water (90:10)], and they were employed to run a gradient conditions from 2% B for 0.75 minutes, from 2% to 10% in 0.25 minutes, and from 10% to 98% in 1.00 minutes, 98% B for 0.50 minutes and then 2% B in 0.40 minutes and hold these conditions for 0.10 minutes in order to re-equilibrate the column (Total Run Time 3.00 minutes). An injection volume of 0.5 to 3 µl was used (Depending on the sample concentration).

Method E

The HPLC measurement was performed using Shimadzu HPLC comprising a binary pump with degasser, a sample manager a dual channel UV detector and a column as specified in the respective methods below. Flow from the column was split to a MS spectrometer. The MS detector (Applied Biosystems API2000/2000 Trap) was configured with an electrospray ionization source. Mass spectra were acquired by scanning from 100 to 800 in 0.40 second. The ion spray voltage 5500 V in positive and 4500 V in negative ionization mode and the source temperature was maintained at 300° C. and Deculturing Potential 8-50 V depending on compound. Data acquisition was performed with Analyst 1.6.3 Software. Reversed phase HPLC was carried out on a Waters Xbridge C18/Agilent Zorbax C18 column (5 µm, 50×4.6 mm) with a flow rate of 1.20 mL/min. Two mobile phases were used, mobile phase A: 10 mm Ammonium Acetate in water; mobile phase B: ACN, and they were employed to run a gradient conditions from 10% B to 30% B in 1.50 minutes, and from 30% to 90% in 1.50 minutes, 90% B for 1.00 minutes and 10% B in 1.00 minutes and hold these conditions for 0.10 minutes. Pre run Equilibration Time 0.50 min (Total Run Time 5.10 minutes). An injection volume of 1 µl to 3 µl was used (Depending on the sample concentration).

Method G

The HPLC measurement was performed using Waters Acquity H Class UPLC comprising a quaternary pump with degasser, sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Xbridge C18 column (3.5 µm, 50×3 mm) with a flow rate of 1.20 mL/min. Two mobile phases were used, mobile phase A: 5 Mm $NH_4oAc$ in water; mobile phase B: 5 Mm $NH_4oAc$ in ACN: Water (90:10)], and they were employed to run a gradient conditions from 5% B for 0.75 minutes, from 5% to 15% in 0.50 minutes, from 15% to 70% in 1.25 minutes and from 70% to 98% in 1.25 minutes, 98% B for 0.50 minutes and 5% B in 0.25 minutes and hold these conditions for 0.60 minutes in order to re-equilibrate the column (Total Run Time 5.10 minutes). An injection volume of 0.5 µl was used.

Method I

The HPLC measurement was performed using Waters Acquity H Class UPLC comprising a quaternary pump with degasser, an sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Xbridge C18 column (3.5 µm, 50×3 mm) with a flow rate of 1.20 mL/min. Two mobile phases were used, mobile phase A: 5 Mm $NH_4oAc$ in water; mobile phase B: 5 Mm $NH_4oAc$ in ACN: Water (90:10)], and they were employed to run a gradient conditions from 5% B for 0.75 minutes, from 5% to 15% in 0.50 minutes, from 15% to 70% in 1.25 minutes and from 70% to 98% in 1.25 minutes, 98% B for 0.50 minutes and 5% B in 0.25 minutes and hold these conditions for 0.60 minutes in order to re-equilibrate the column (Total Run Time 5.10 minutes). An injection volume of 0.5 µl was used.

Method K

The HPLC measurement was performed using Waters Acquity H Class UPLC comprising a quaternary pump with degasser, an sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C8 column (1.7 µm, 50×2.1 mm) with a flow rate of 0.800 mL/min. Two mobile phases were used, mobile phase A: 0.05% HCOOH in water; mobile phase B: 0.05% HCOOH in ACN: Water (90:10)], and they were employed to run a gradient conditions from 5% B for 1.00 minutes, from 5% to 50% in 4.00 minutes, and from 50% to 90% in 3.00 minutes, 90% B for 2.00 minutes and then 5% B in 1.50 minutes and hold these conditions for 0.50 minutes in order to re-equilibrate the column (Total Run Time 12.00 minutes). An injection volume of 0.5 µl was used.

Method X

HPLC measurement was performed using a VANQUISH FLEX module comprising a quaternary pump with degasser, an autosampler, a column oven (set at 40° C.), a diode-array detector DAD and a column as specified in the respective methods below. The MS detector (ISQ Thermo Scientific) was configured with an electrospray ionization source. Mass spectra were acquired by scanning from 100 to 700 in 0.2 second. The capillary needle voltage was 3 kV in positive and 2 kV in negative ionization mode and the source temperature was maintained at 250° C. Nitrogen was used as the nebulizer gas.

Reversed phase HPLC was carried out on a Luna Omega-C18 column Phenomenex (1.6 µm, 50×2.1 mm) with a flow rate of 0.600 mL/min. Two mobile phases were used, mobile phase A: water (LC-MS grade) 0.1% FA; mobile phase B: acetonitrile (LiChrosolv for LC-MS Merck), and they were employed to run a gradient conditions from 15% B for 0.2 minutes, from 15% to 95% in 1.6 minutes, 95% B for 0.60 minutes and 15% B in 0.10 minutes and hold these conditions for 1.05 minutes in order to re-equilibrate the column (Total Run Time 3.55 minutes). An injection volume of 0.8 µl was used.

Method Y

The HPLC measurement was performed using Waters Acquity H Class UPLC comprising a quaternary pump with degasser, an sample manager, a column oven (set at 50° C.), a diode-array detector DAD and a column as specified in the respective methods below. Flow from the column was split to a MS spectrometer. The MS detector (Waters SQ Detector 2) was configured with an electrospray ionization source. Mass spectra were acquired by scanning from 160 to 1200 in 0.20 second. The capillary needle voltage was 3.50 kV in positive and negative ionization mode and the source temperature was maintained at 150° C. Nitrogen was used as the desolvation gas, the flow was 750 L/Hour. Data acquisition was performed with Mass Lynx 4.2 Software. Reversed phase HPLC was carried out on a Waters Acquity BEH C18 column (1.7 µm, 50×2.1 mm) with a flow rate of 0.800 mL/min. Two mobile phases were used, mobile phase A: 0.05% HCOOH in water; mobile phase B: 0.05% HCOOH in ACN: Water (90:10)], and they were employed to run a gradient conditions from 10% B for 0.75 minutes, from 10% to 50% in 0.25 minutes, and from 50% to 98% in 1.00 minutes, 98% B for 0.25 minutes and then 10% B in 0.35 minutes and hold these conditions for 0.40 minutes in order to re-equilibrate the column (Total Run Time 3.00 minutes). An injection volume of 0.5 µl was used.

Example A: Cellular TRPML1 Assay

Cell Line

The final clone for the TRPML1 assay is HEKT-REx/GCaMP6f/TRPML1. GCaMP6f is a genetically encoded calcium indicator that is stably expressed in this cell line and used as a fluorescent read-out.

Assay Protocol

Experiments were performed in 384 MTP format. Cells are seeded at 15000 cells/well in 20 µl/well of Optimem+0.5% FBS without selection antibiotics. Twenty-four hours later, cells are assayed for the response to various compounds using the $Ca^{2+}$ sensitive GCaMP6f protein stably expressed in the cells as readout.

The experiment was performed in a 384-well format according to the following procedures:
  24 h after seeding, the cells were pre-incubated at room temperature for about 10 min.
  Started the experiment at the FLIPR$^{TETRA}$ by injecting 10 µL/w of 3× concentrated test compounds and controls in $Ca^{2+}$ free Tyrode's buffer. Monitored the kinetic response over a period of 300 seconds.
  Final DMSO concentration: 0.5%

Data from FLIPR$^{TETRA}$ measurements were analyzed with the Genedata Screener© software.

Data Analysis

| Compound % Activity | Calculate the Kinetic Response Value (KRV) as: $(MAX_{CA}$ − Baseline)/Baseline = [(max(sec5 ... 290) − mean (sec 1 ... sec2))/mean (sec 1 ... sec2)] Normalize the KRV to the median (<>) of Neutral and Stimulator control wells: Activity[%]_Ago = $$100 * \left( \frac{x - <NeutralControls>}{<StimulatorControls> - <NeutralControls>} \right)$$ |

Example B: TFEB Translocation Assay

Reporter and Cell line

Reporter TFEB: the reporter is fused to a sequence of monomeric red fluorescent protein.

The reporter TFEB have been stably expressed in U2OS cell line and used as read-out.

Assay Protocol

Experiments were performed in 384 MTP well format. Cells were seeded in 384-w at a density of 4000 cells/well in 20 µl/well complete growth medium without antibiotics. Twenty-four hours later, cells were treated with compounds and incubated for further 2 hours. Then the cells were imaged and assayed for the response to various compounds using the reporter for TFEB expressed in the cells as readout.

The experiments were performed in a 384-well format according to the following procedure:
  24 h after seeding, cell culture medium was carefully removed and replaced with 20 µl of Opti-MEM (30' incubation at 37° C. before compound addition)
  Then, cells were incubated with compounds diluted in Opti-MEM+0.015% Tween 80 at the desired concentration, with the reference molecule (agonist) Torin-1 at a top concentration of 1 µM (max signal), and with the other reference molecule (agonist) MLSA-5 at top concentration of 20 µM for 2 hours at 37° C. and 5% CO2. The final percentage of DMSO was 0.5% in all the conditions.
  Staining of the nuclei was obtained by incubating the cells with 24 µM/well of Hoechst 3342 in standard Tyrode's buffer for 15 min at RT
  Then the cells were fixed with PFA 4% for 30 min at RT
  After three washes with standard Tyrode's buffer, samples were acquired by recording two fluorescence emission channels (DS-red and blue) at 20× magnification and with at least 3 fields of view per well in an Operetta CLS microscope (PerkinElmer).
  Image analysis was performed by using Harmony software (PerkinElmer). The image analysis involved the following steps: flat-field illumination correction, nuclei segmentation, cytoplasm segmentation and calculation of intensity fluorescence in the cytosol and nuclei compartments. Measurements of signal intensity ratio (nucleus to cytoplasm) was used to obtain information on the effects of compounds on the TFEB translocation.
  Data from image analysis measurements were finally loaded and analyzed for normalization and fitting procedures in Genedata Screener© software.

Data Analysis

Feature: Mean translocation ratio (mean/well)

Data normalization: Stimulator—Neutral control

Normalization results are expressed as "activity %", meaning that our values are placed on an equivalent scale in order to make them comparable across plates. The GeneData Screener method we have used, normalizes the median of the Stimulator control wells (Torin-1) to 100% and the median of the Neutral control wells (DMSO) to 0%

$$Activity[\%]=100*(x-<Min>)/(<"Max">-<Min>)$$

The data from example A and example B is found in Table 3.

TABLE 3

Activity of TRPML1 agonists

| Ex. | TRPML1 FLIPR pEC$_{50}$ | TFEB Translocation pEC$_{50}$ |
|---|---|---|
| 1 | C | NT |
| 2 | B | NT |
| 3 | B | B |
| 4 | B | A |
| 5 | B | NT |
| 6 | B | A |
| 7 | B | NT |
| 8 | B | NT |
| 9 | B | NT |
| 10 | B | NT |
| 11 | B | NT |

TABLE 3-continued

Activity of TRPML1 agonists

| Ex. | TRPML1 FLIPR pEC$_{50}$ | TFEB Translocation pEC$_{50}$ |
| --- | --- | --- |
| 12 | B | NT |
| 13 | B | B |
| 14 | B | NT |
| 15 | A | A |
| 16 | A | NT |
| 17 | A | A |
| 18 | A | NT |
| 19 | A | A |
| 20 | A | A |
| 21 | A | A |
| 22 | A | A |
| 23 | A | NT |
| 24 | B | NT |
| 25 | C | NT |
| 26 | B | NT |
| 27 | B | NT |
| 28 | B | B |
| 29 | B | NT |
| 30 | B | B |
| 31 | B | B |
| 32 | B | B |
| 33 | A | B |
| 34 | A | NT |
| 35 | A | NT |
| 36 | A | A |
| 37 | A | NT |
| 38 | A | A |
| 39 | A | A |
| 40 | A | NT |
| 41 | A | NT |
| 42 | B | NT |
| 43 | B | NT |
| 44 | B | NT |
| 45 | B | NT |
| 46 | B | NT |
| 47 | B | B |
| 48 | B | A |
| 49 | B | NT |
| 50 | B | B |
| 51 | B | NT |
| 52 | B | NT |
| 53 | B | NT |
| 54 | B | C |
| 55 | B | B |
| 56 | B | NT |
| 57 | B | NT |
| 58 | B | NT |
| 59 | B | NT |
| 60 | B | NT |
| 61 | B | NT |
| 62 | B | NT |
| 63 | B | NT |
| 64 | B | B |
| 65 | B | NT |
| 66 | B | NT |
| 67 | B | NT |
| 68 | A | A |
| 69 | A | NT |
| 70 | A | NT |
| 71 | A | A |
| 72 | A | NT |
| 73 | A | A |
| 74 | A | A |
| 75 | A | A |
| 76 | A | A |
| 77 | B | B |
| 78 | B | B |
| 79 | B | NT |
| 80 | B | NT |
| 81 | B | NT |
| 82 | B | A |
| 83 | A | A |
| 84 | B | C |
| 85 | B | NT |
| 86 | B | NT |
| 87 | C | NT |
| 88 | C | NT |
| 89 | B | NT |
| 90 | B | B |
| 91 | B | B |
| 92 | C | NT |
| 93 | C | NT |
| 94 | C | NT |
| 95 | C | NT |
| 96 | C | C |
| 97 | C | NT |
| 98 | C | NT |
| 99 | B | B |
| 100 | B | B |
| 101 | C | NT |
| 102 | B | NT |
| 103 | C | NT |
| 104 | B | NT |
| 105 | B | NT |
| 106 | C | NT |
| 107 | C | NT |
| 108 | B | A |
| 109 | B | NT |
| 110 | B | NT |
| 111 | B | A |
| 112 | B | B |
| 113 | B | NT |
| 114 | C | NT |
| 115 | C | NT |
| 116 | C | C |
| 117 | C | NT |
| 118 | C | B |
| 119 | B | NT |
| 120 | B | B |
| 121 | C | NT |
| 122 | C | NT |
| 123 | B | NT |
| 124 | A | A |
| 125 | A | A |
| 126 | A | A |
| 127 | A | A |
| 128 | A | A |
| 129 | A | A |
| 130 | A | A |
| 131 | A | A |
| 132 | B | NT |
| 133 | B | NT |
| 134 | B | NT |
| 135 | A | A |
| 136 | A | NT |
| 137 | A | NT |
| 138 | A | NT |
| 139 | C | NT |
| 140 | B | A |
| 141 | A | NT |
| 142 | A | A |
| 143 | A | A |
| 144 | A | A |
| 145 | A | A |
| 146 | B | NT |
| 147 | B | NT |
| 148 | A | A |
| 149 | A | A |
| 150 | A | A |
| 151 | A | NT |
| 152 | C | NT |
| 153 | A | NT |
| 154 | A | A |
| 155 | A | A |
| 156 | A | A |
| 157 | A | A |
| 158 | A | NT |
| 159 | A | A |
| 160 | A | NT |
| 161 | A | A |
| 162 | A | A |
| 163 | A | A |

TABLE 3-continued

Activity of TRPML1 agonists

| Ex. | TRPML1 FLIPR pEC$_{50}$ | TFEB Translocation pEC$_{50}$ |
|---|---|---|
| 164 | A | A |
| 165 | A | A |
| 166 | A | NT |
| 167 | A | NT |
| 168 | A | NT |
| 169 | A | NT |
| 170 | A | A |
| 171 | A | A |
| 172 | A | A |
| 173 | A | A |
| 174 | A | A |
| 175 | A | NT |
| 176 | C | NT |
| 177 | A | A |
| 178 | A | A |
| 179 | A | A |
| 180 | A | A |
| 181 | B | NT |
| 182 | B | NT |
| 183 | A | A |
| 184 | B | NT |
| 185 | A | A |
| 186 | A | A |
| 187 | A | NT |
| 188 | A | A |
| 189 | A | A |
| 190 | B | NT |
| 191 | B | NT |
| 192 | B | NT |
| 193 | A | A |
| 194 | C | NT |
| 195 | A | A |
| 196 | A | A |
| 197 | A | A |
| 198 | B | NT |
| 199 | B | NT |
| 200 | A | A |
| 201 | A | A |
| 202 | A | A |
| 203 | A | A |
| 204 | A | NT |
| 205 | B | NT |
| 206 | A | A |
| 207 | A | A |
| 208 | A | NT |
| 209 | A | NT |
| 210 | A | NT |
| 211 | A | NT |
| 212 | A | NT |
| 213 | A | NT |
| 214 | A | NT |
| 215 | A | NT |
| 216 | A | NT |
| 217 | C | NT |
| 218 | C | NT |
| 219 | A | A |
| 220 | A | A |
| 221 | A | A |
| 222 | A | A |
| 223 | A | A |
| 224 | A | A |
| 225 | A | A |
| 226 | A | A |
| 227 | A | A |
| 228 | A | A |
| 229 | A | A |
| 230 | A | A |
| 231 | B | NT |
| 232 | B | NT |
| 233 | B | NT |
| 234 | B | NT |
| 235 | A | A |
| 236 | A | NT |
| 237 | A | NT |
| 238 | A | A |
| 239 | A | A |
| 240 | A | A |
| 241 | A | A |
| 242 | A | NT |
| 243 | A | NT |
| 244 | A | A |
| 245 | A | A |
| 246 | A | NT |
| 247 | A | A |
| 248 | B | NT |
| 249 | A | A |
| 250 | C | NT |
| 251 | B | NT |
| 252 | B | NT |
| 253 | B | NT |
| 254 | A | A |
| 255 | A | A |
| 256 | A | A |
| 257 | B | NT |
| 258 | B | NT |
| 259 | B | A |
| 260 | A | A |
| 261 | A | A |
| 262 | A | A |
| 263 | A | NT |
| 264 | A | A |
| 265 | B | NT |
| 266 | B | NT |
| 267 | B | NT |
| 268 | B | NT |
| 269 | A | A |
| 270 | B | NT |
| 271 | B | NT |
| 272 | A | A |
| 273 | A | NT |
| 274 | A | A |
| 275 | A | A |
| 276 | A | A |
| 277 | A | A |
| 278 | A | A |
| 279 | A | A |
| 280 | A | A |
| 281 | A | A |
| 282 | A | A |
| 283 | A | A |
| 284 | A | A |
| 285 | A | A |
| 286 | A | A |
| 287 | A | A |
| 288 | A | A |
| 289 | A | A |
| 290 | A | A |
| 291 | A | NT |
| 292 | B | NT |
| 293 | A | A |
| 294 | A | A |
| 295 | A | A |
| 296 | A | A |
| 297 | B | NT |
| 298 | B | NT |
| 299 | A | A |
| 300 | B | NT |
| 301 | B | NT |
| 302 | A | A |
| 303 | A | A |
| 304 | A | A |
| 305 | B | NT |
| 306 | B | NT |
| 307 | A | A |
| 308 | A | A |
| 309 | B | B |
| 310 | B | NT |
| 311 | B | NT |

TABLE 3-continued

Activity of TRPML1 agonists

| Ex. | TRPML1 FLIPR pEC$_{50}$ | TFEB Translocation pEC$_{50}$ |
|---|---|---|
| 312 | B | NT |
| 313 | B | NT |
| 314 | B | NT |
| 315 | B | A |
| 316 | A | A |

A = 8.0-6.0
B = 6.0-5.0
C = 5.0-4.0
NT = not tested

What is claimed is:

1. A compound of Formula (Ia), or a pharmaceutically acceptable salt or stereoisomer thereof:

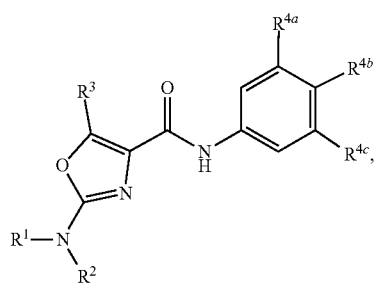

Formula (Ia)

wherein:

$R^1$ and $R^2$ are taken together to form a heterocycloalkyl optionally substituted with one or more $R^{1a}$;

each $R^{1a}$ is independently deuterium, halogen, —CN, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R; or two $R^{1a}$ on the same atom are taken together to form an oxo;

$R^3$ is C$_1$-C$_6$alkyl, C$_1$-C$_6$haloalkyl, or C$_1$-C$_6$heteroalkyl, wherein each alkyl is independently and optionally substituted with one or more R;

$R^{4a}$ is hydrogen, deuterium, halogen, —CN, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$heteroalkyl, or cycloalkyl;

$R^{4b}$ is deuterium, halogen, —CN, —OH, —OR$^a$, —O-cycloalkyl, —O-heterocycloalkyl, —NR$^c$R$^d$, —NR$^b$—cycloalkyl, —NRb-heterocycloalkyl, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R; and $R^{4c}$ is deuterium, halogen, —CN, —OH, —OR$^a$, C$_1$-C$_6$alkyl, C$_1$-C$_6$haloalkyl, C$_1$-C$_6$deuteroalkyl, C$_1$-C$_6$hydroxyalkyl, C$_1$-C$_6$heteroalkyl, or cycloalkyl;

each R$^a$ is independently C$_1$-C$_6$alkyl, C$_1$-C$_6$haloalkyl, C$_1$-C$_6$deuteroalkyl, cycloalkyl, heterocycloalkyl, C$_1$-C$_6$alkylene(cycloalkyl), or C$_1$-C$_6$alkylene(heterocycloalkyl); wherein each alkyl, alkylene, cycloalkyl, and heterocycloalkyl is independently and optionally substituted with one or more R;

each R$^b$ is independently hydrogen, C$_1$-C$_6$alkyl, or C$_1$-C$_6$haloalkyl;

each R$^c$ and R$^d$ are independently hydrogen, C$_1$-C$_6$alkyl, C$_1$-C$_6$haloalkyl, C$_1$-C$_6$deuteroalkyl, cycloalkyl, or heterocycloalkyl; wherein each alkyl, cycloalkyl, and heterocycloalkyl is independently and optionally substituted with one or more R;

or R$^c$ and R$^d$ are taken together with the atom to which they are attached to form a heterocycloalkyl optionally substituted with one or more R; and each R is independently deuterium, halogen, —CN, —OH, —NH$_2$, —NHC$_1$-C$_3$ alkyl, —N(C$_1$-C$_3$ alkyl)$_2$, C$_1$-C$_3$ alkyl, C$_1$-C$_3$ alkoxy, C$_1$-C$_3$ haloalkyl, C$_1$-C$_3$ deuteroalkyl, C$_1$-C$_3$ haloalkoxy, C$_1$-C$_3$ hydroxyalkyl, C$_1$-C$_3$ aminoalkyl, C$_1$-C$_3$ heteroalkyl, C$_3$-C$_6$ cycloalkyl, or 3- to 6-membered heterocycloalkyl; wherein each cycloalkyl and heterocycloalkyl is independently optionally substituted with one or more halogen; or two R on the same atom form an oxo.

2. The compound of claim 1, or a pharmaceutically acceptable salt or stereoisomer thereof, wherein $R^{4a}$ is hydrogen, halogen, C$_1$-C$_6$alkyl, or C$_1$-C$_6$haloalkyl.

3. The compound of claim 1, or a pharmaceutically acceptable salt or stereoisomer thereof, wherein $R^{4a}$ is hydrogen or halogen.

4. The compound of claim 1, or a pharmaceutically acceptable salt or stereoisomer thereof, wherein $R^{4a}$ is halogen.

5. The compound of claim 1, or a pharmaceutically acceptable salt or stereoisomer thereof, wherein $R^{4b}$ is —OR$^a$, —O-cycloalkyl, —O-heterocycloalkyl, —NR$^c$R$^d$, —NR$^b$—cycloalkyl, or heterocycloalkyl.

6. The compound of claim 1, or a pharmaceutically acceptable salt or stereoisomer thereof, wherein $R^{4b}$ is

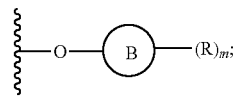

wherein Ring B is bicyclic cycloalkyl and m is 0-4.

7. The compound of claim 1, or a pharmaceutically acceptable salt or stereoisomer thereof, wherein $R^{4b}$ is

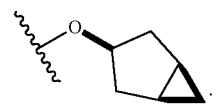

8. The compound of claim 1, or a pharmaceutically acceptable salt or stereoisomer thereof, wherein $R^{4b}$ is heterocycloalkyl.

9. The compound of claim 1, or a pharmaceutically acceptable salt or stereoisomer thereof, wherein $R^{4c}$ is halogen, —CN, —OH, C$_1$-C$_6$alkyl, or C$_1$-C$_6$haloalkyl.

10. The compound of claim 1, or a pharmaceutically acceptable salt or stereoisomer thereof, wherein $R^{4c}$ is halogen or C$_1$-C$_6$alkyl.

11. The compound of claim 1, or a pharmaceutically acceptable salt or stereoisomer thereof, wherein $R^{4c}$ is halogen.

12. The compound of claim 1, or a pharmaceutically acceptable salt or stereoisomer thereof, wherein $R^1$ and $R^2$ are taken together to form an azetidinyl, pyrrolidinyl, piperidinyl, morpholinyl, or piperazinyl; each optionally substituted with one or more $R^{1a}$.

13. The compound of claim 1, or a pharmaceutically acceptable salt or stereoisomer thereof, wherein $R^1$ and $R^2$ are taken together to form a bicyclic heterocycloalkyl optionally substituted with one or more $R^{1a}$.

14. The compound of claim 1, or a pharmaceutically acceptable salt or stereoisomer thereof, wherein each $R^{1a}$ is independently —$OR^a$, $C_1$-$C_6$alkyl, $C_1$-$C_6$hydroxyalkyl, or $C_1$-$C_6$heteroalkyl.

15. The compound of claim 1, or a pharmaceutically acceptable salt or stereoisomer thereof, wherein each $R^{1a}$ is independently —$OR^a$ or $C_1$-$C_6$alkyl.

16. The compound of claim 1, or a pharmaceutically acceptable salt or stereoisomer thereof, wherein $R^3$ is $C_1$-$C_6$alkyl, $C_1$-$C_6$haloalkyl, or $C_1$-$C_6$heteroalkyl.

17. The compound of claim 1 selected from the group consisting of

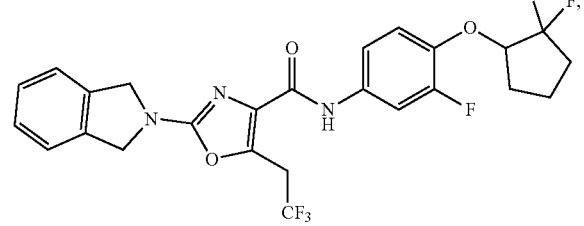

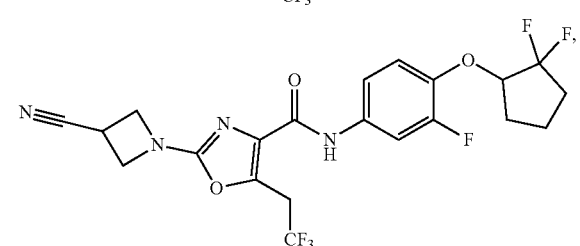

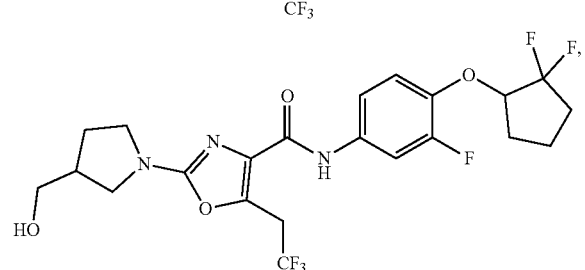

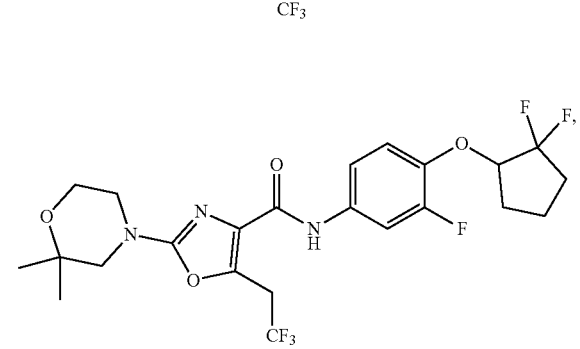

-continued

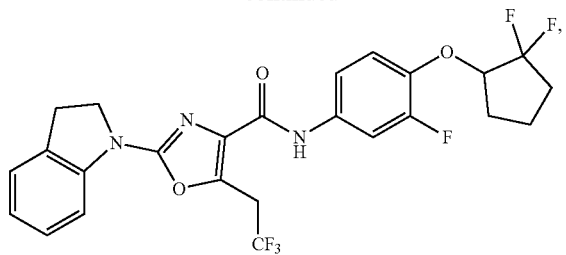

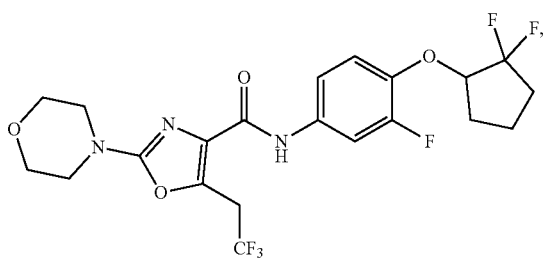

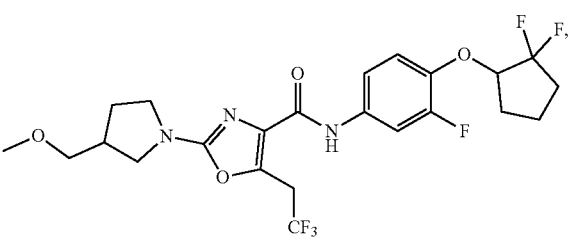

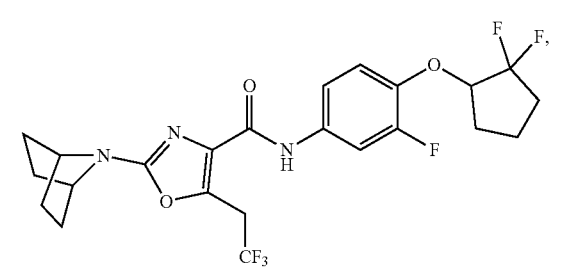

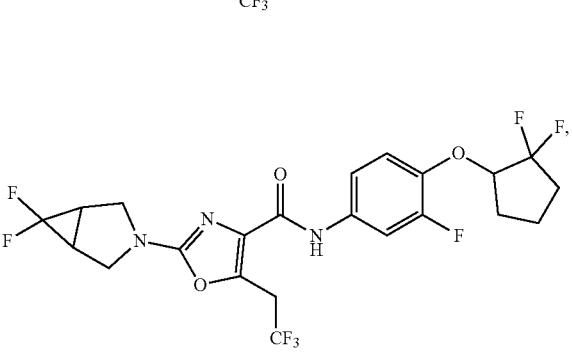

-continued
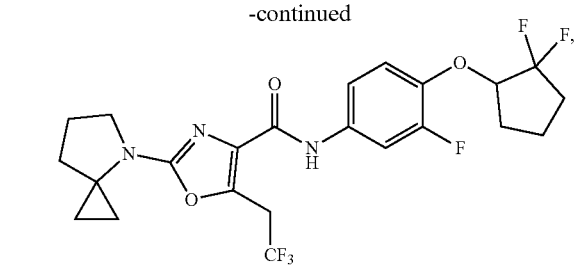
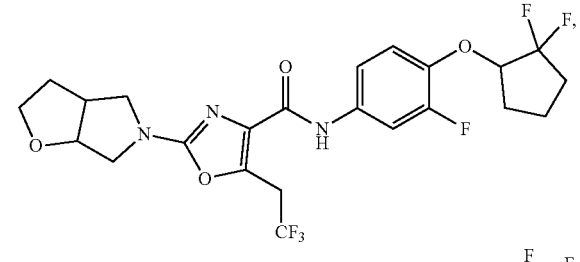
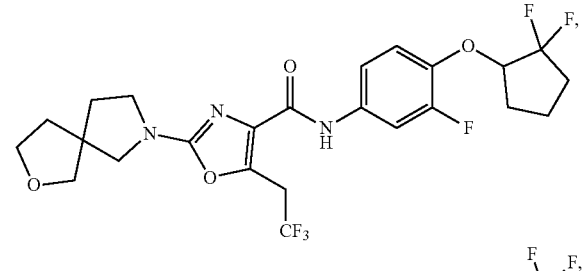
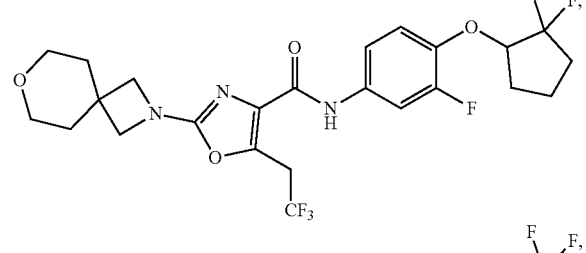
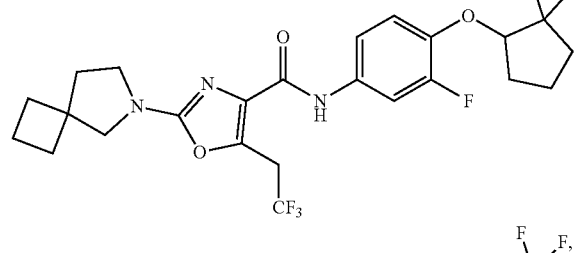
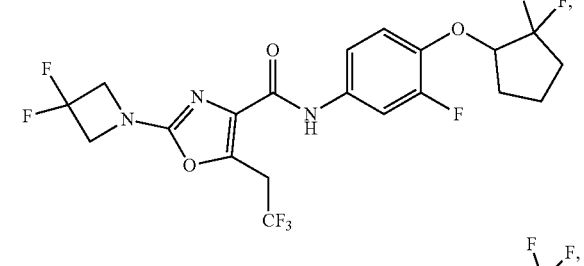
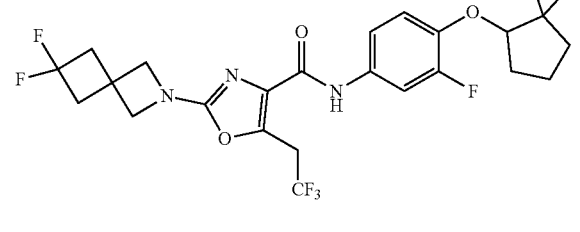
-continued
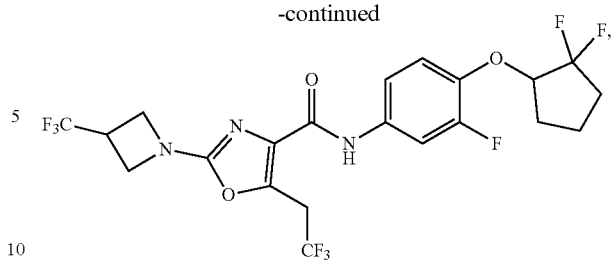
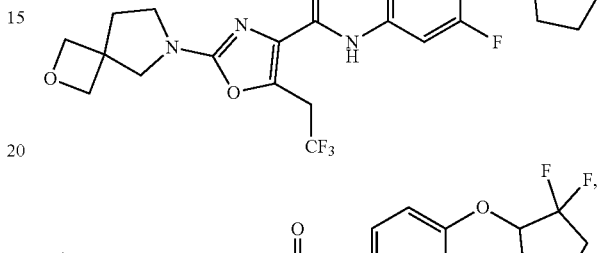
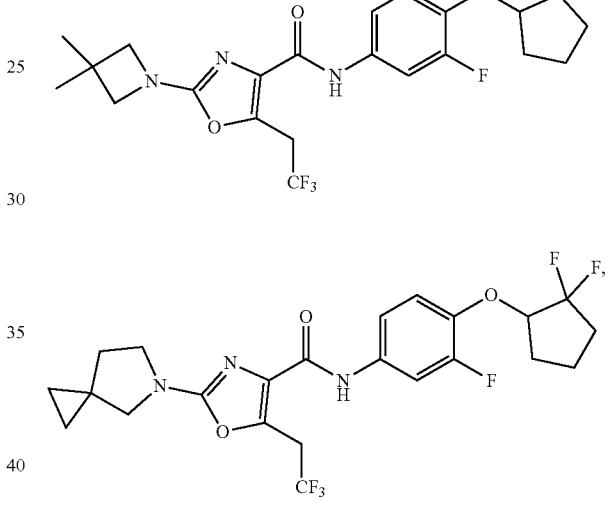
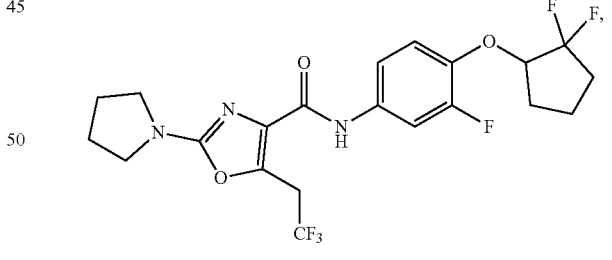
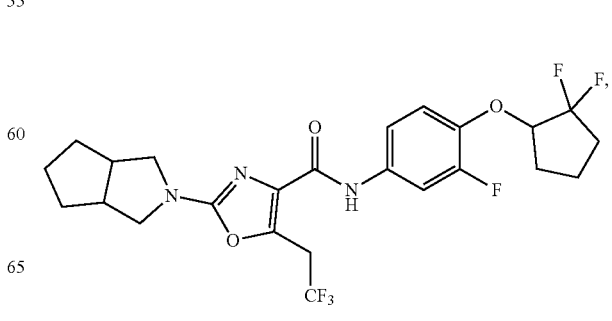

397
-continued
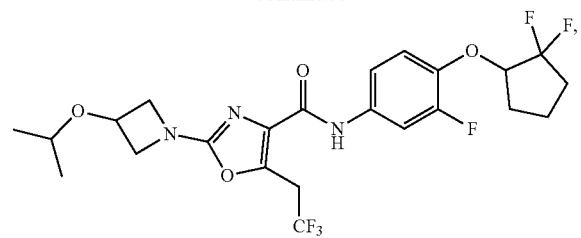
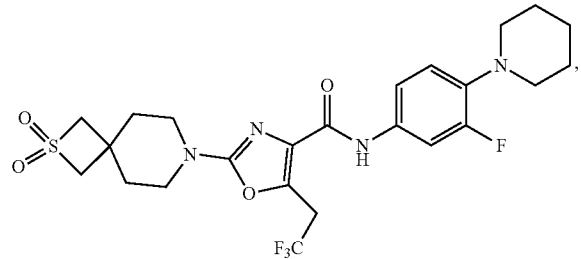
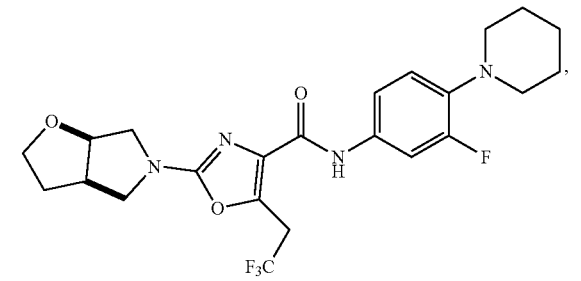
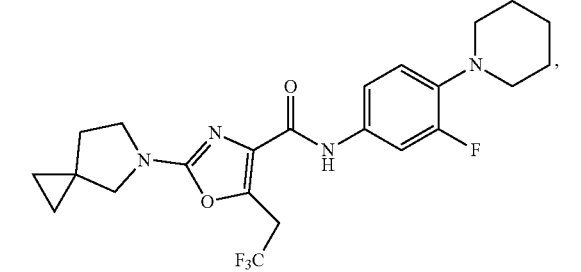
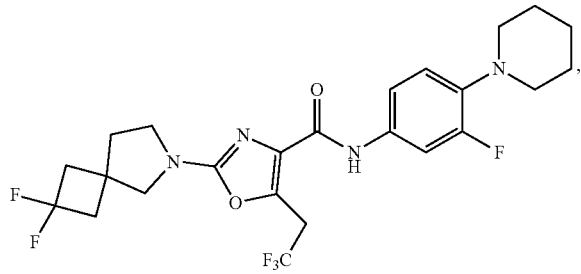
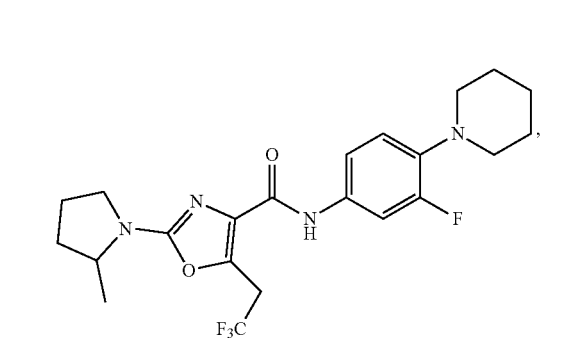
398
-continued
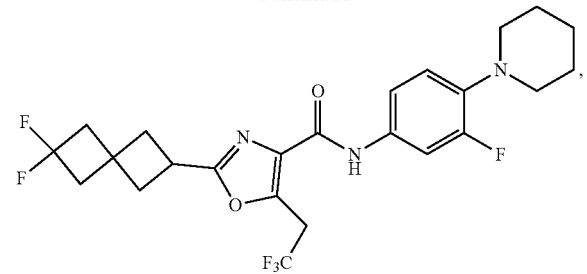
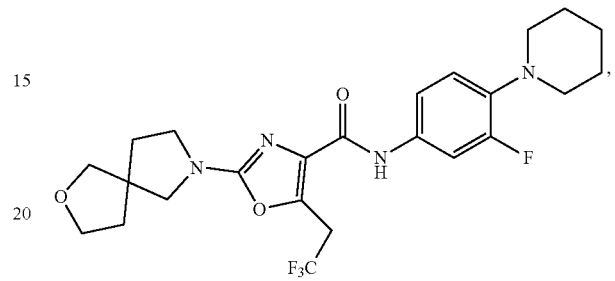
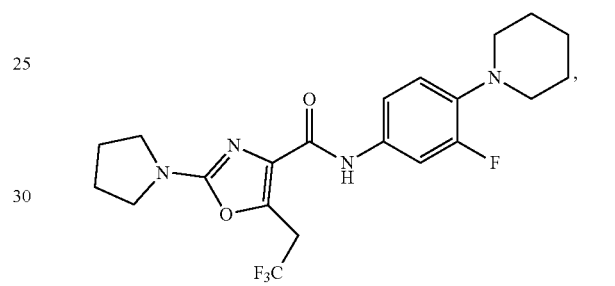
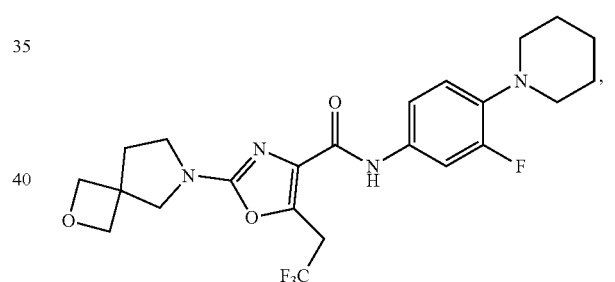
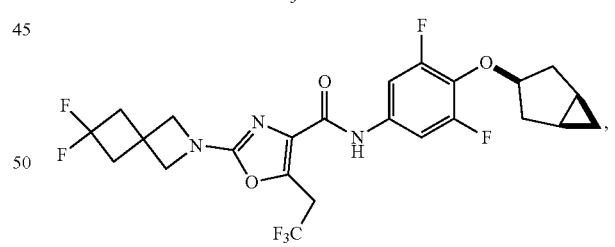
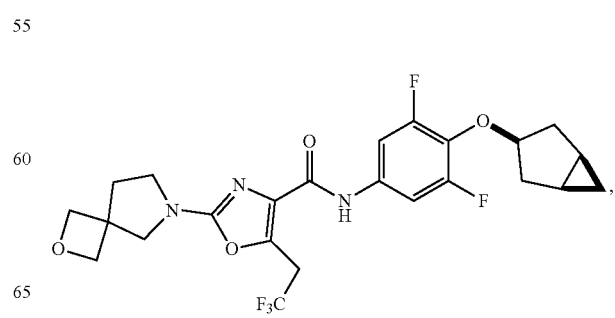

399
-continued
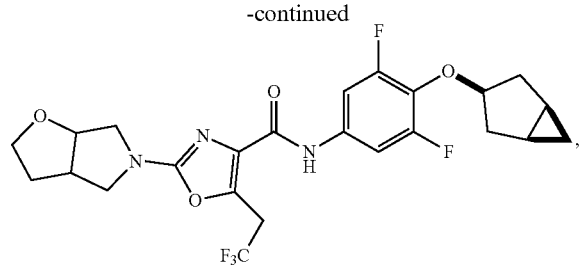
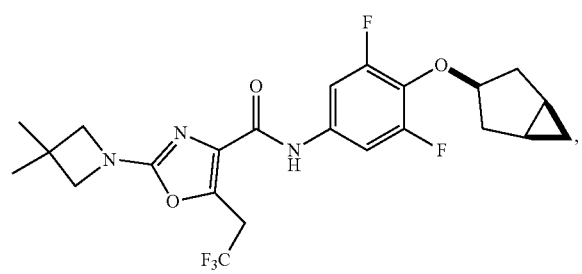
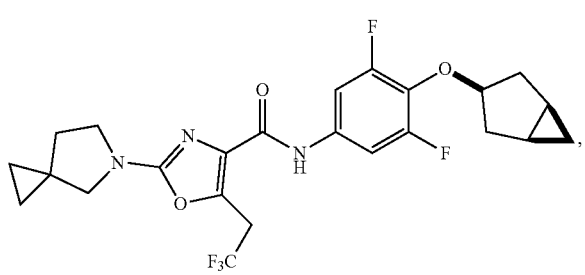
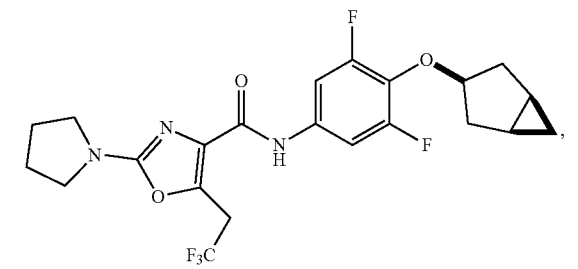
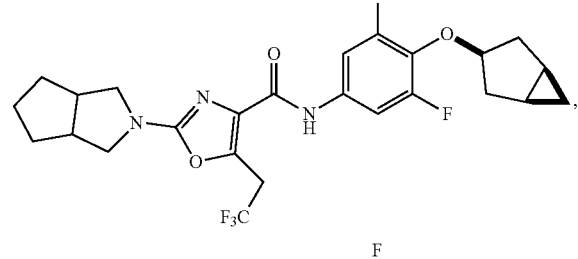
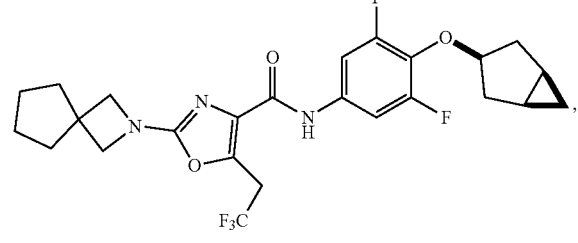
400
-continued
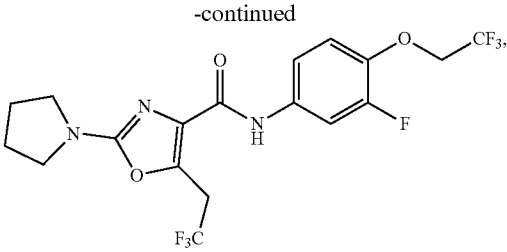
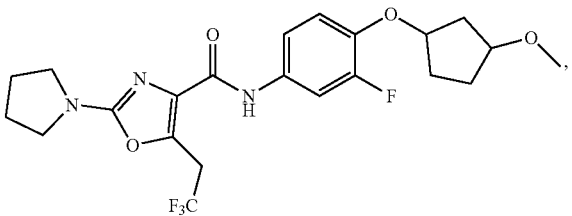
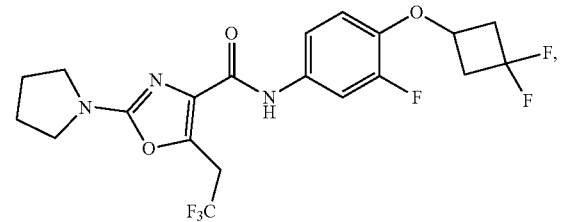
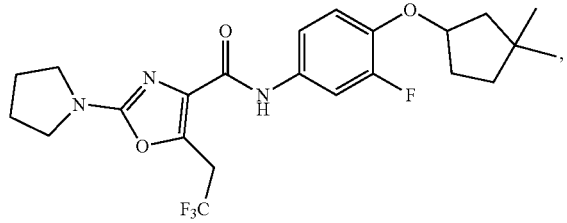
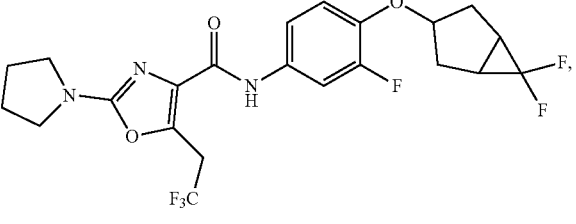
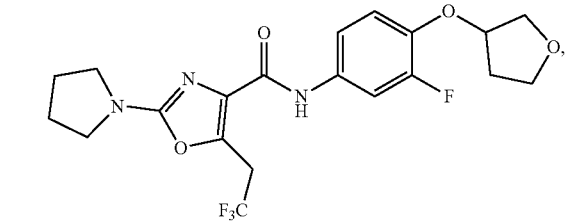
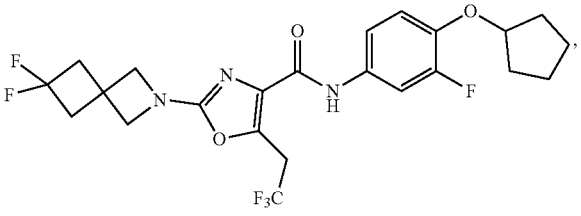

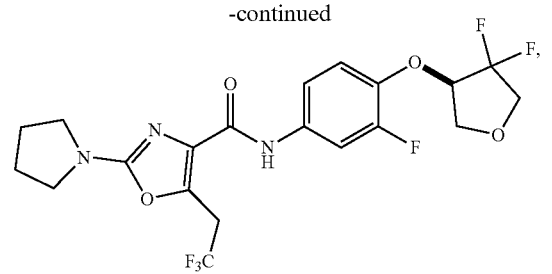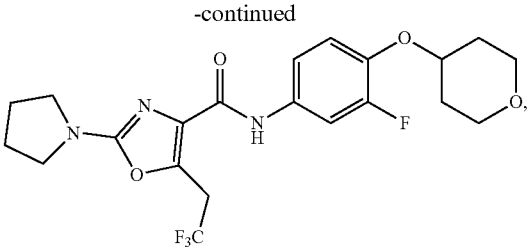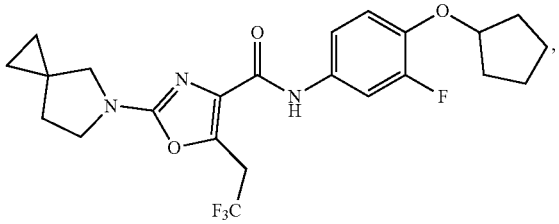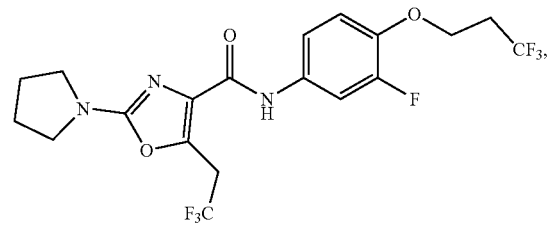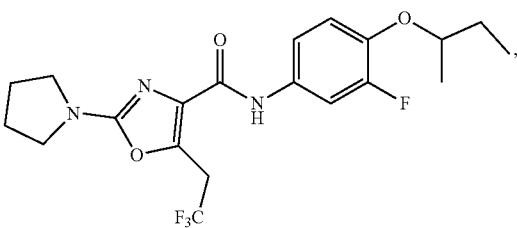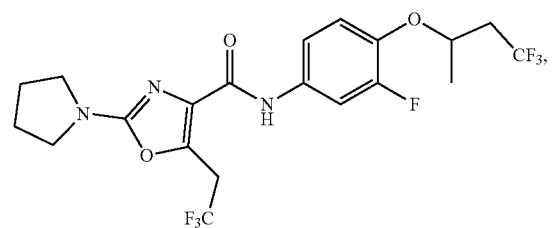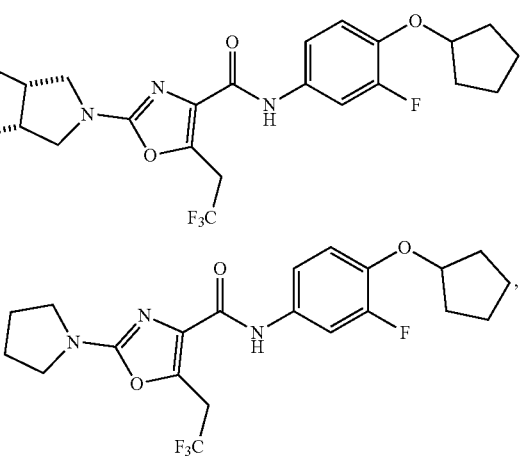

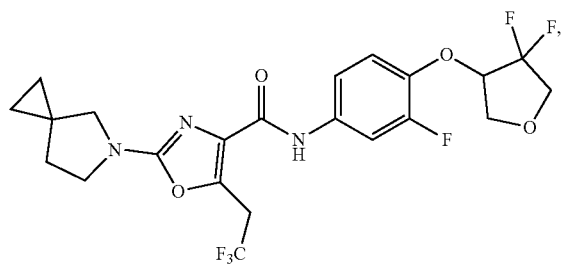
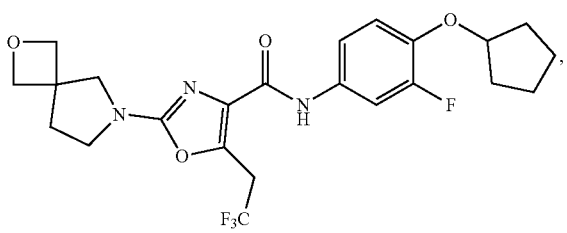
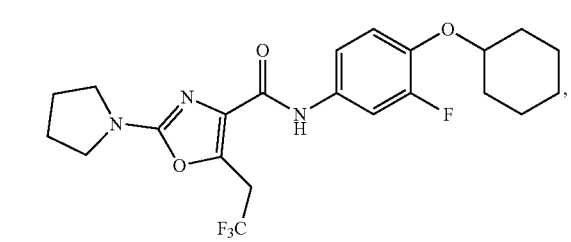
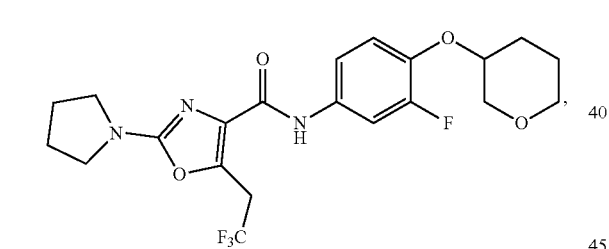
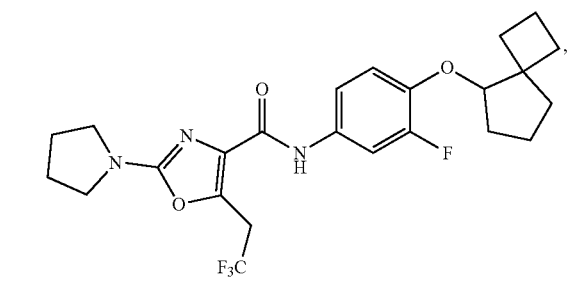
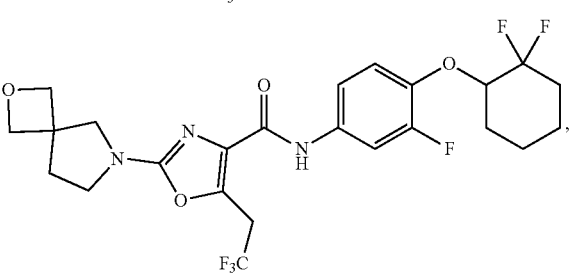
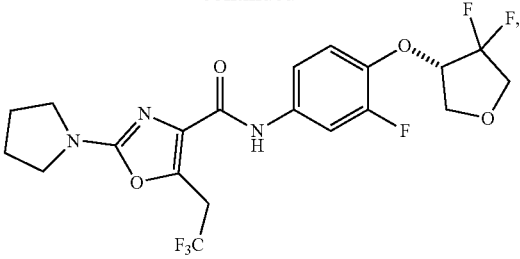
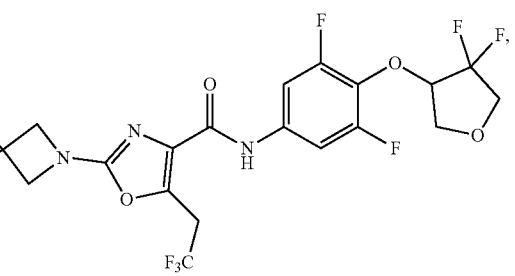
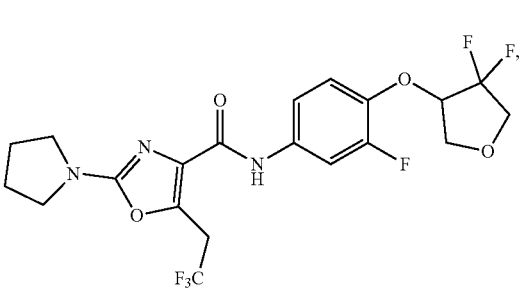
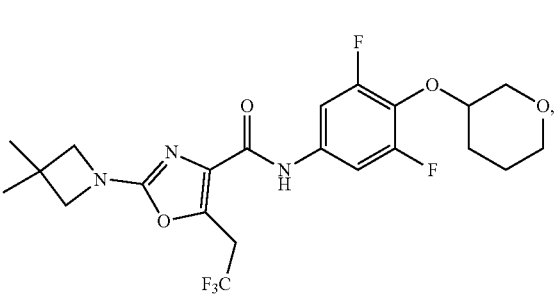
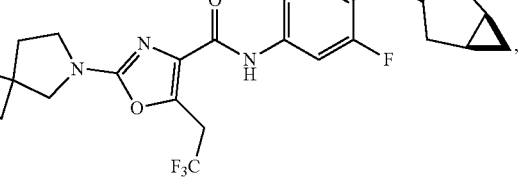
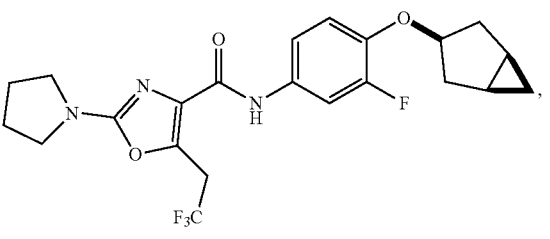

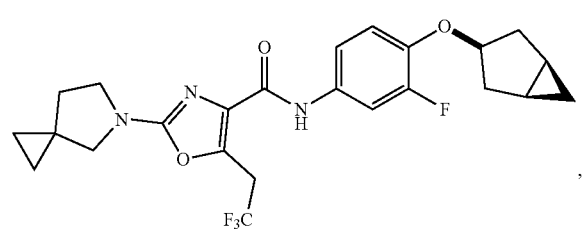
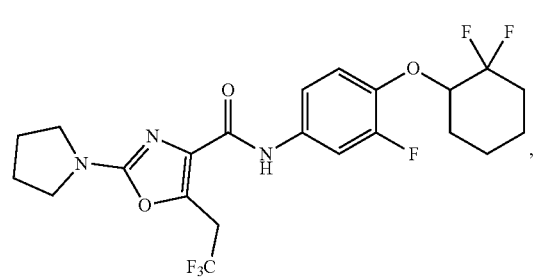
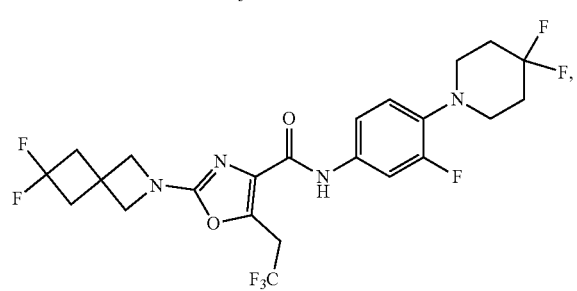
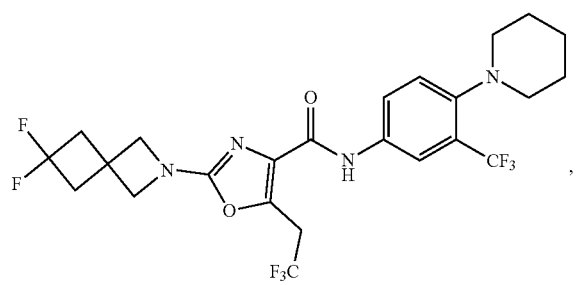
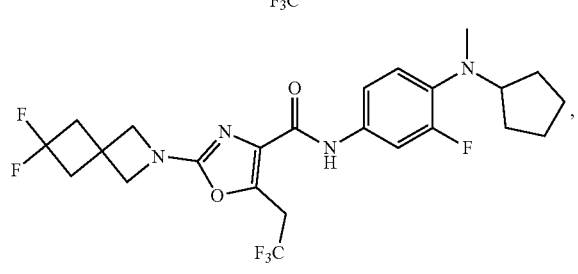
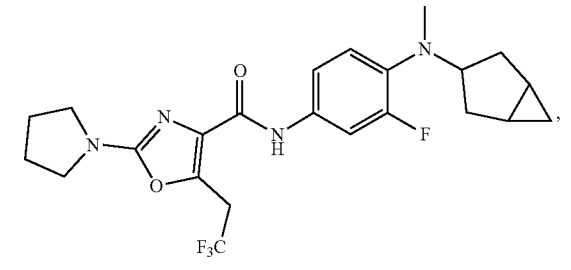
-continued
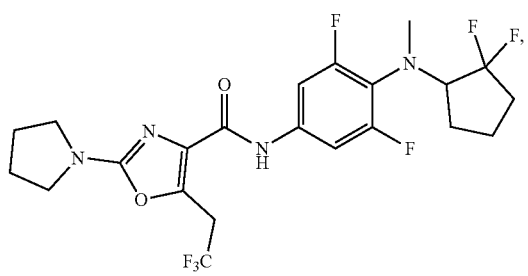
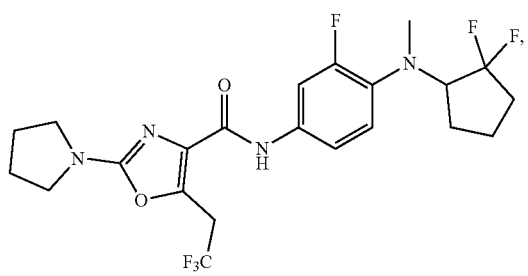
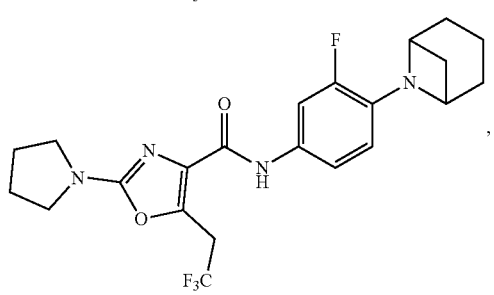
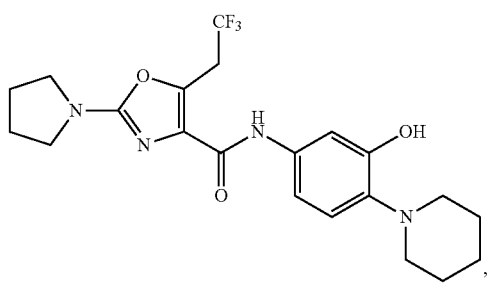
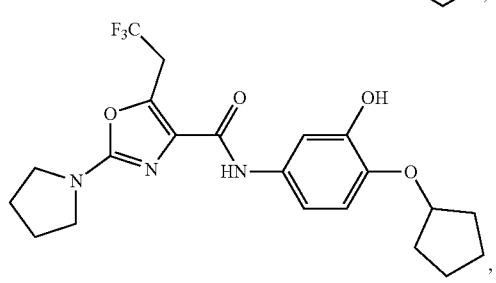
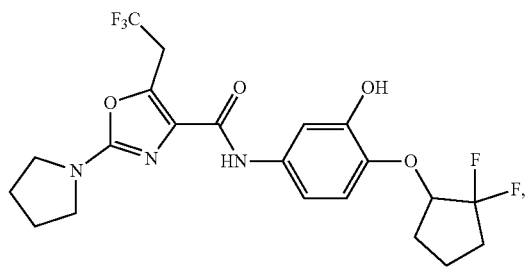

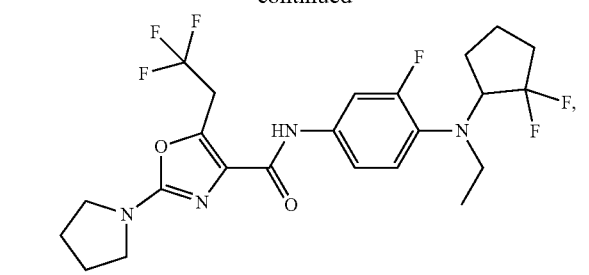
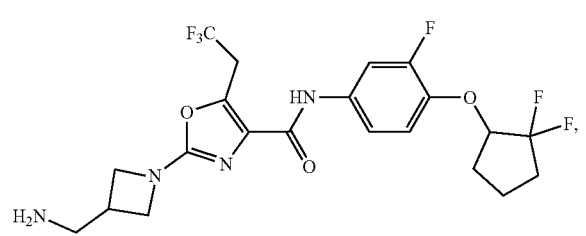
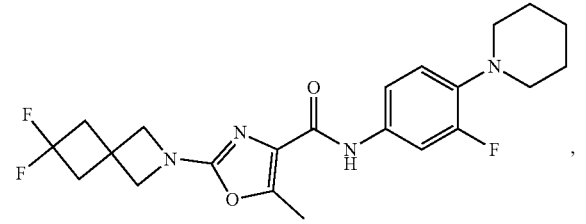
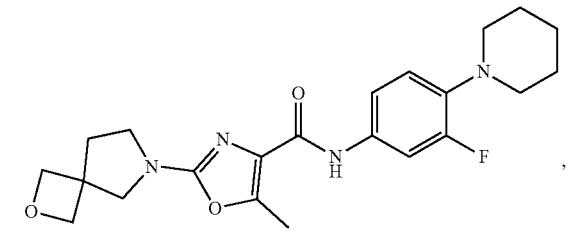
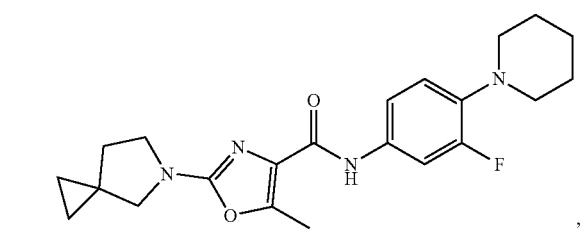
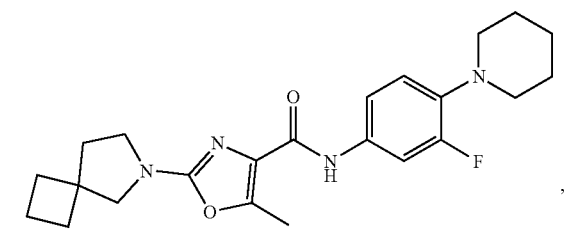
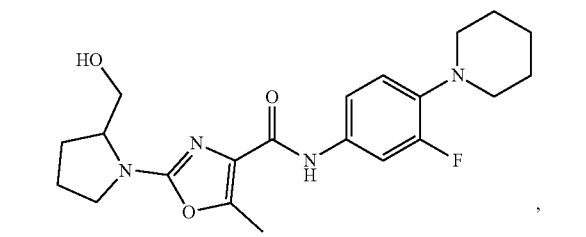
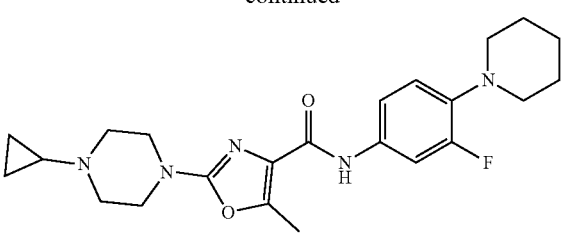
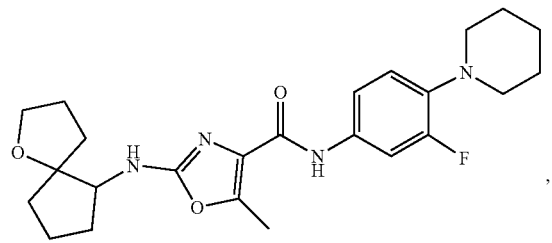
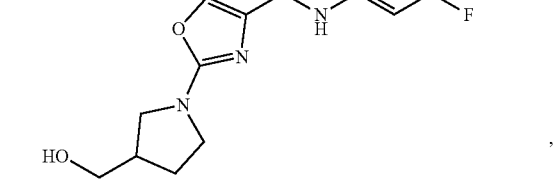
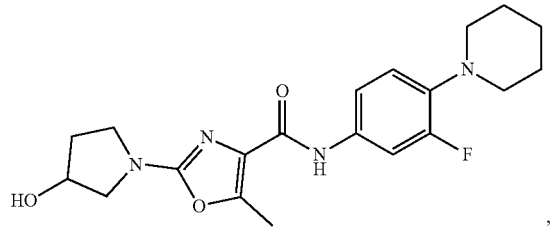
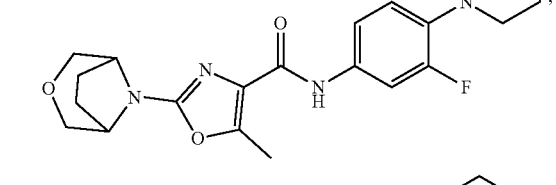
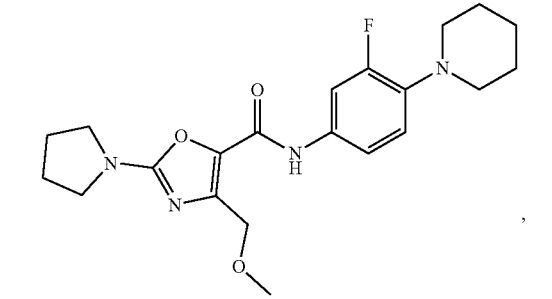

-continued

411
-continued
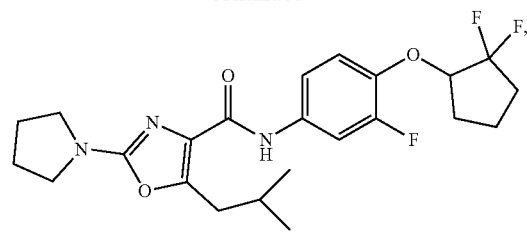
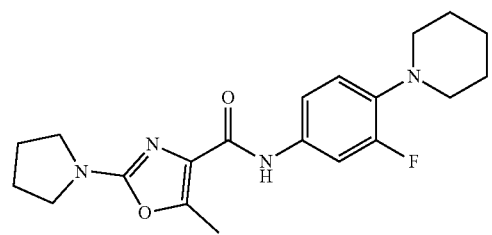
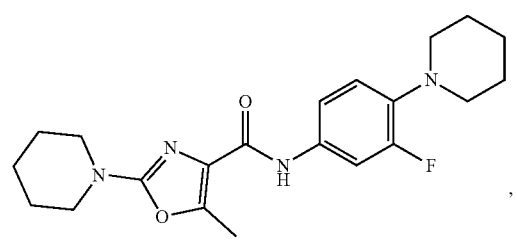
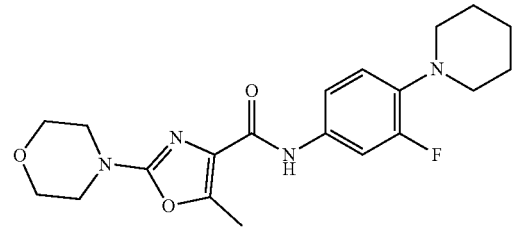
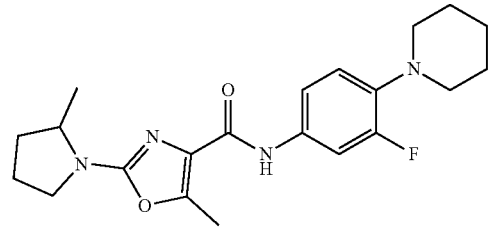
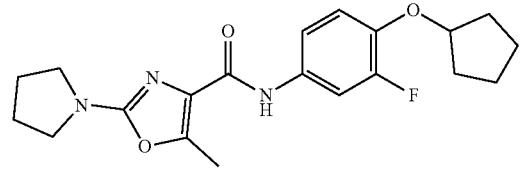
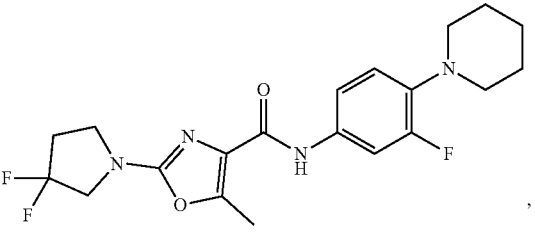
412
-continued
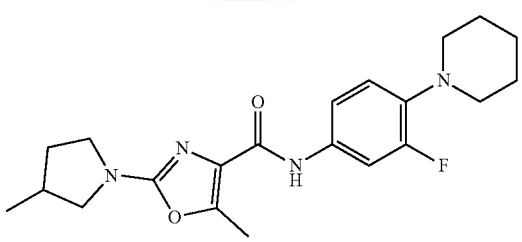
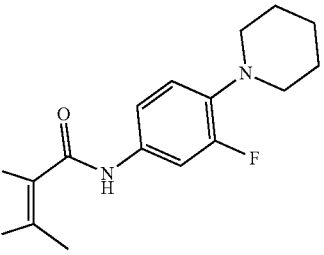
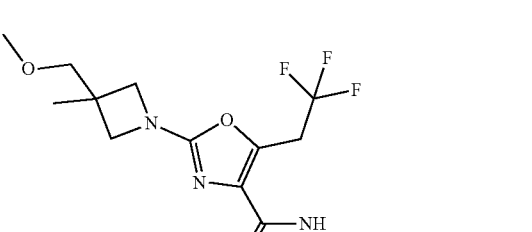
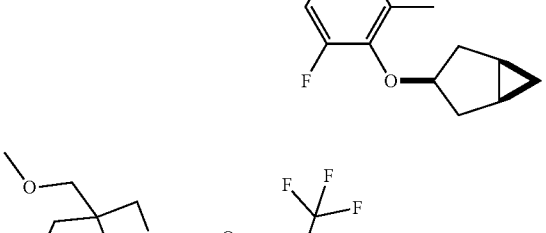
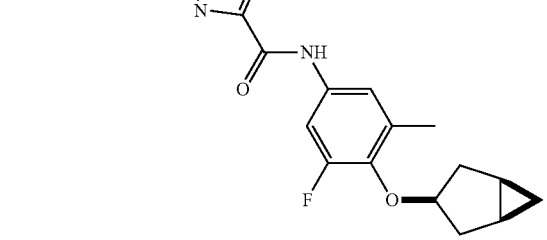
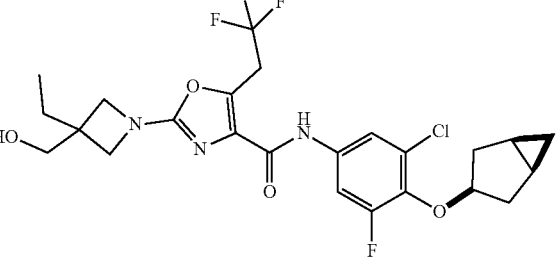

413
-continued
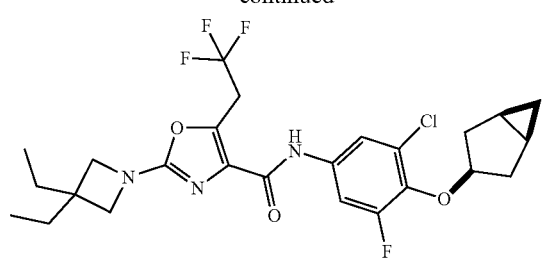
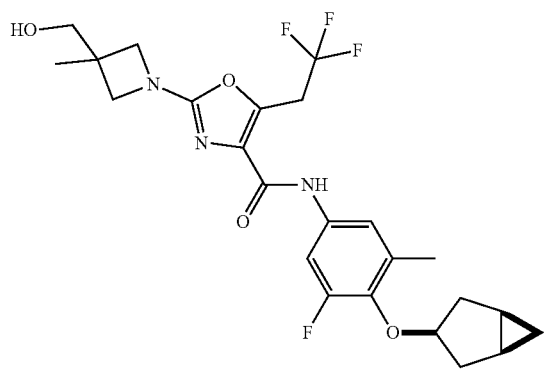
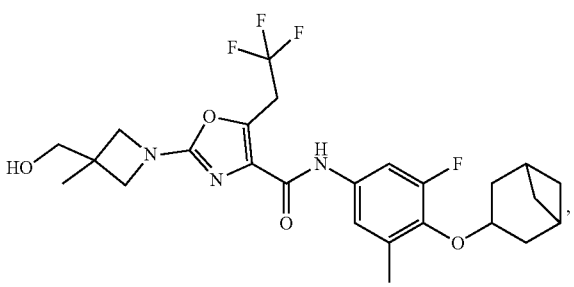
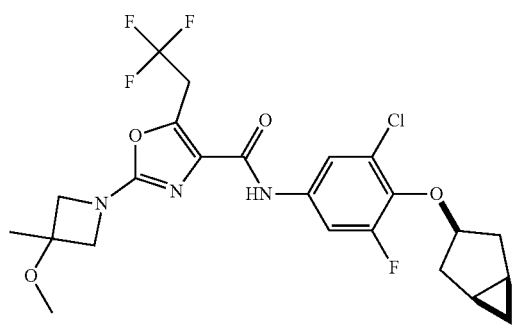
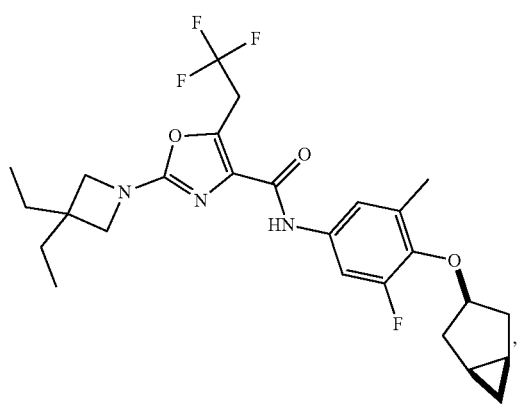
414
-continued
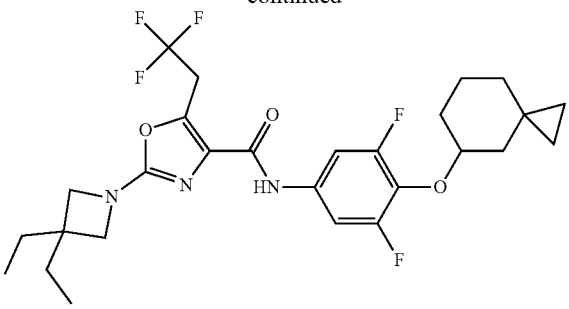
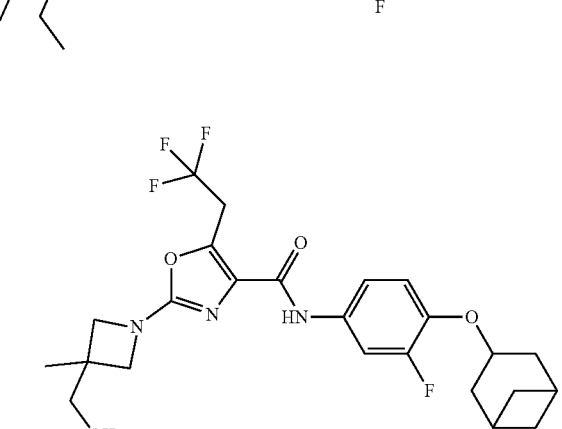
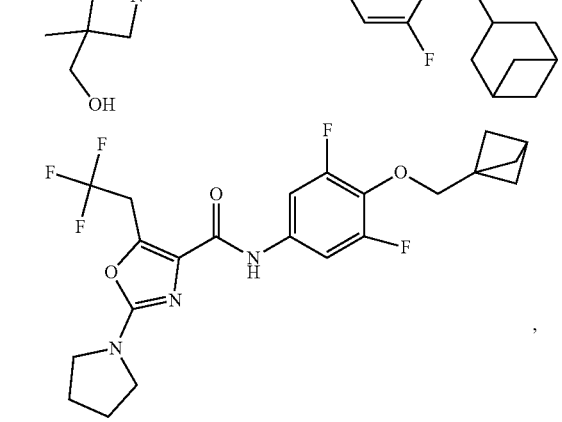

415
-continued
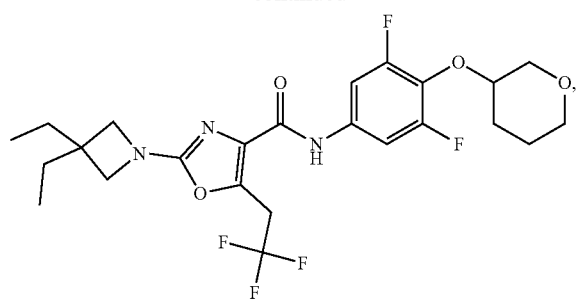
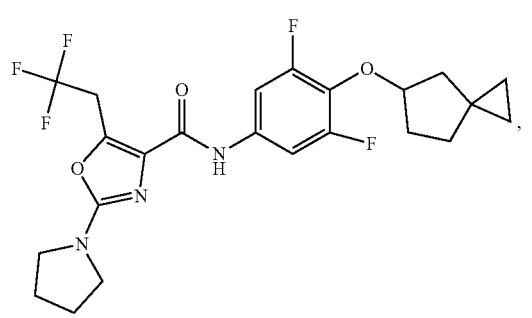
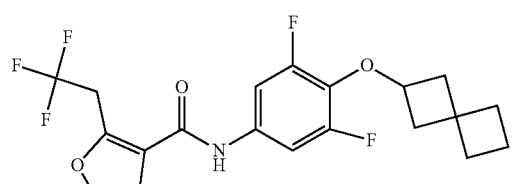
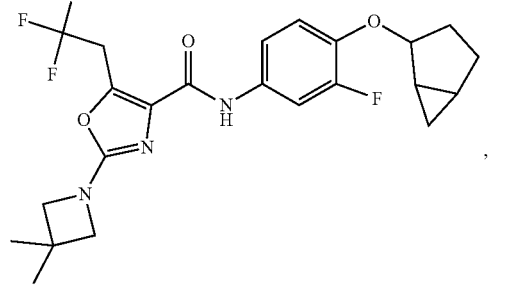
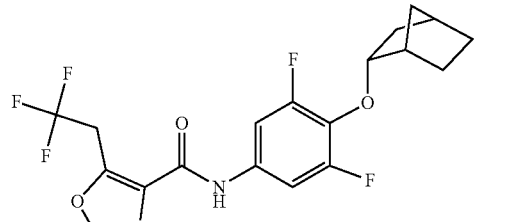
416
-continued
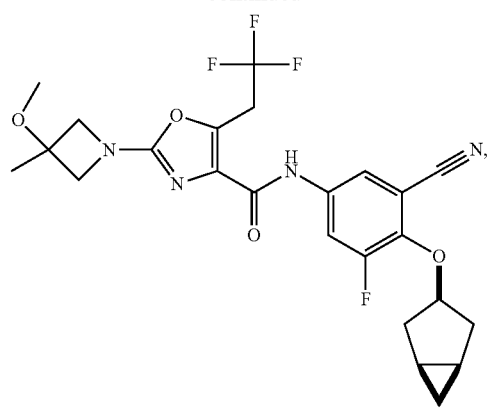
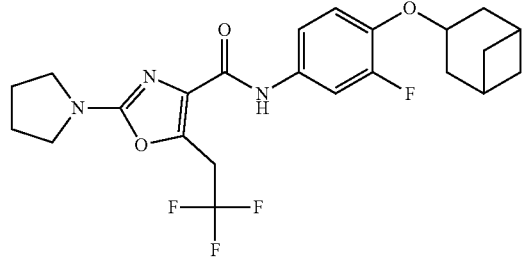
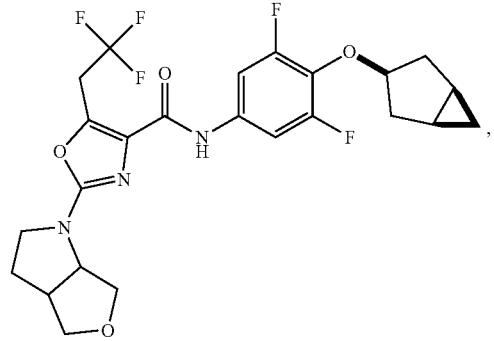
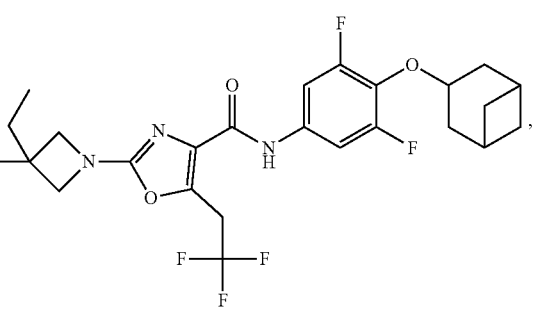

417
-continued
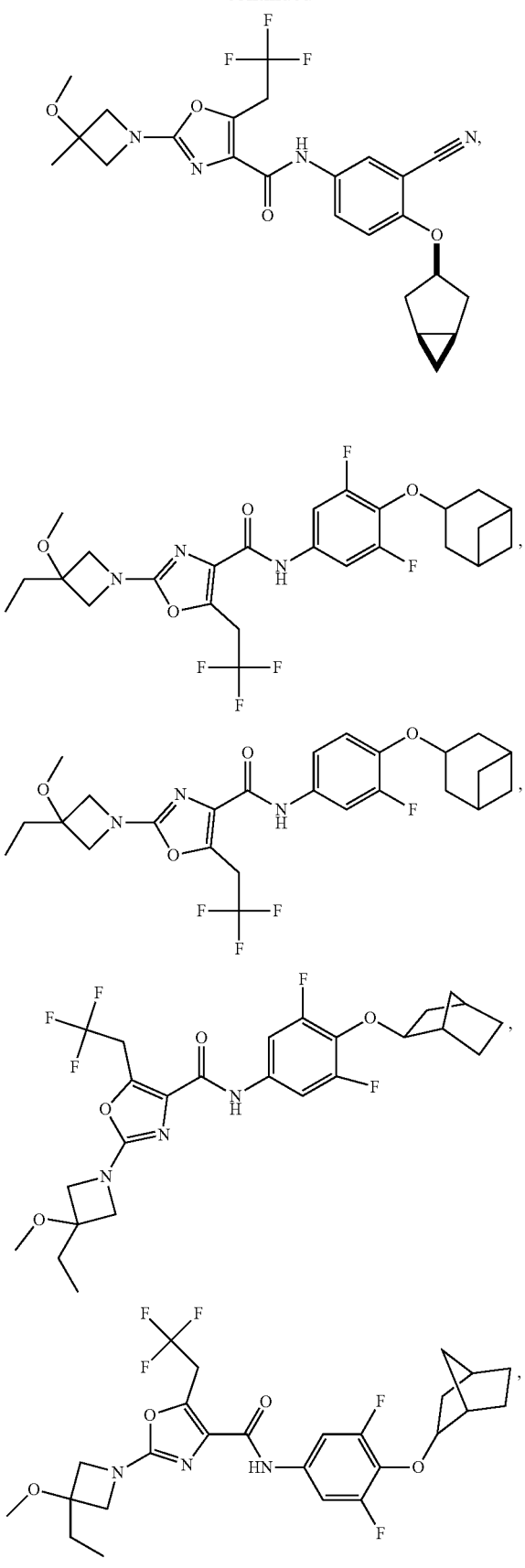
418
-continued
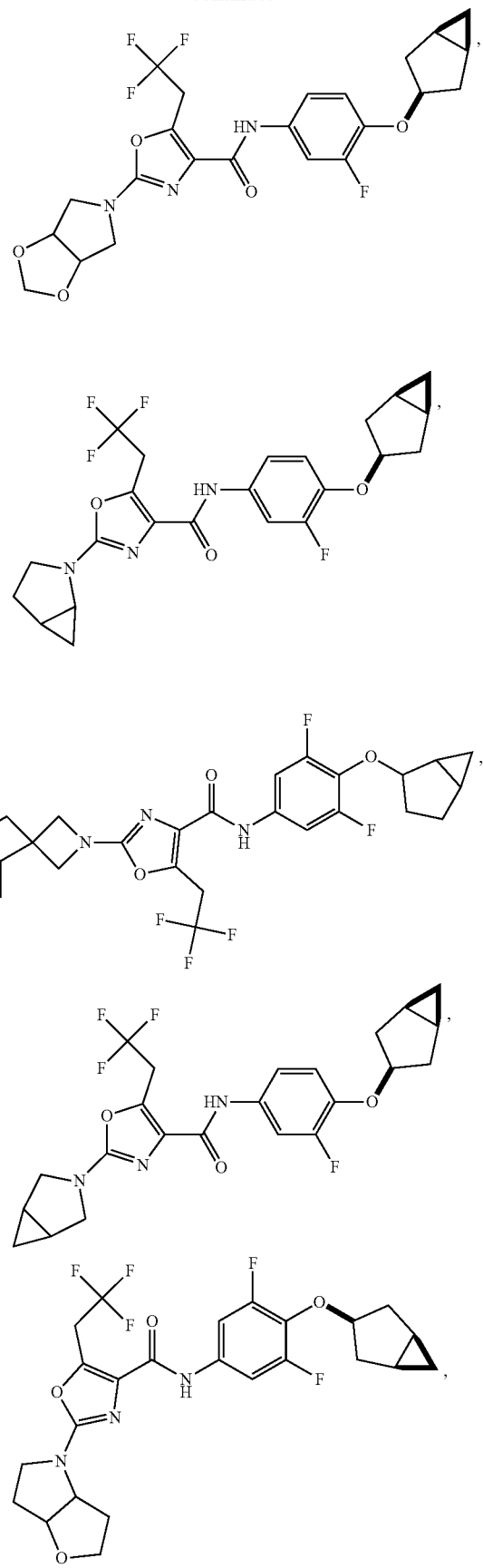

419
-continued
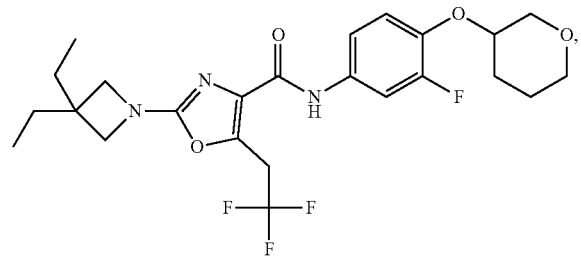
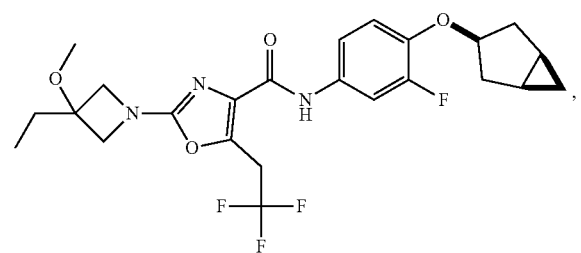
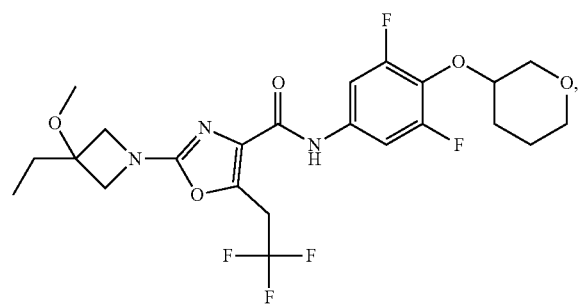
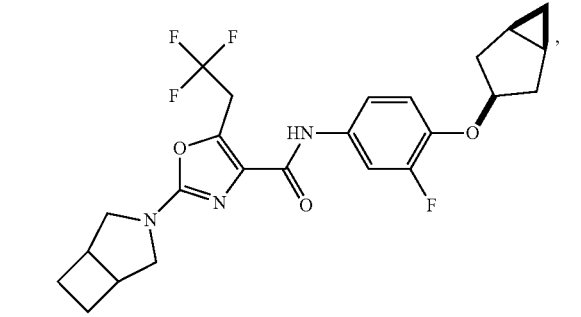
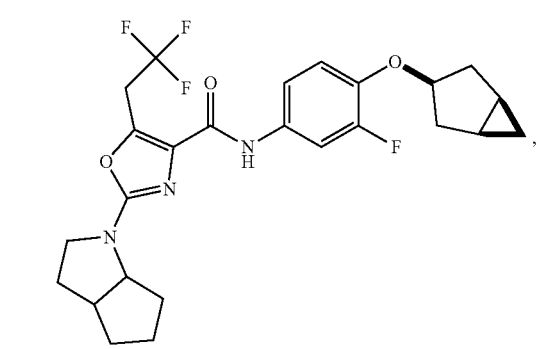
420
-continued
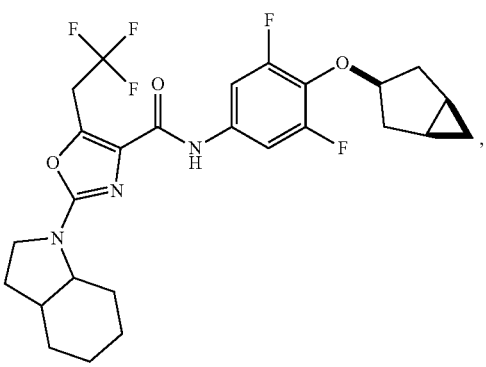
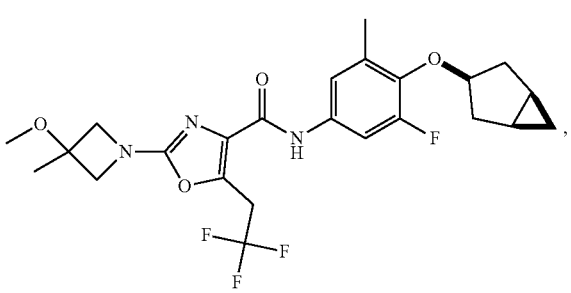
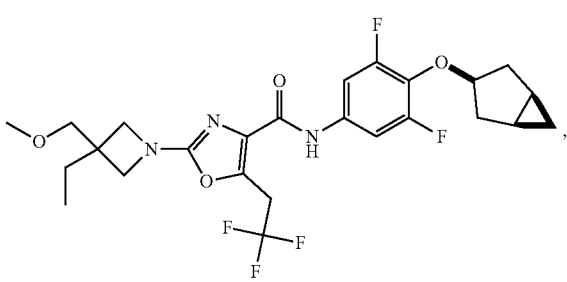
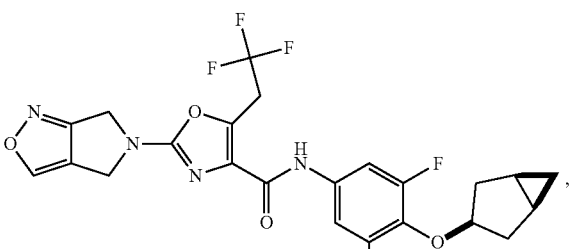
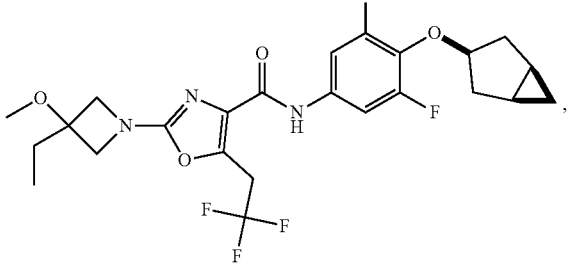

421
-continued
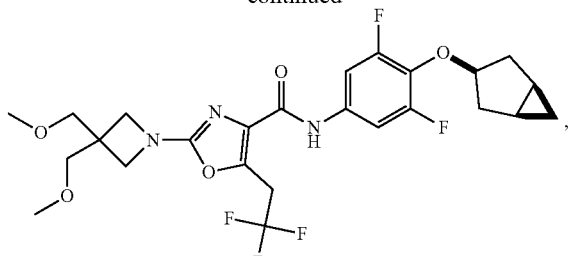,
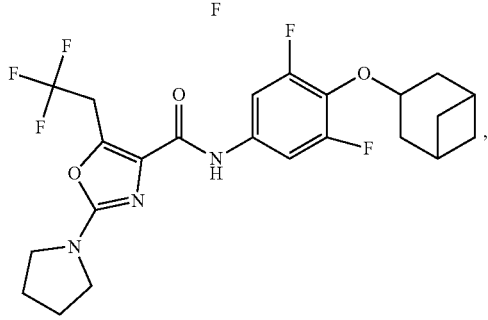,
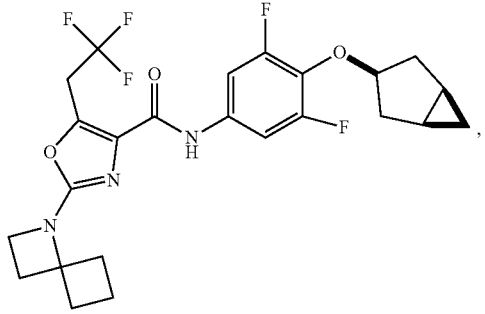,
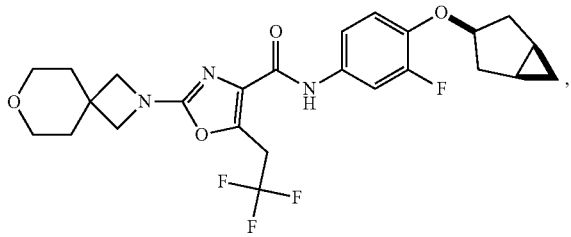,
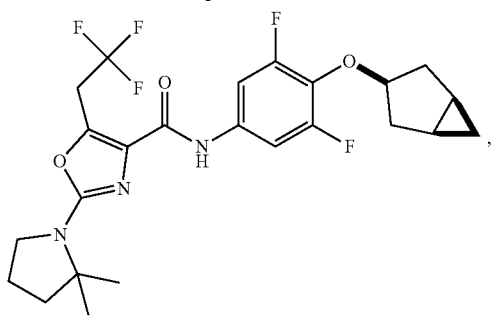,
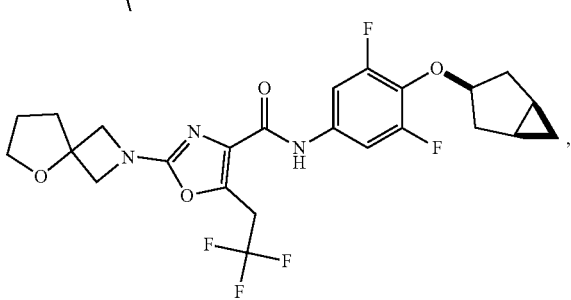,
422
-continued
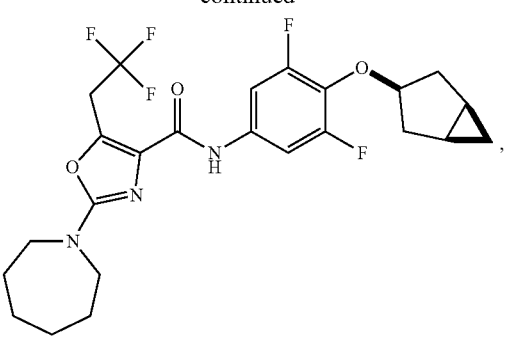,
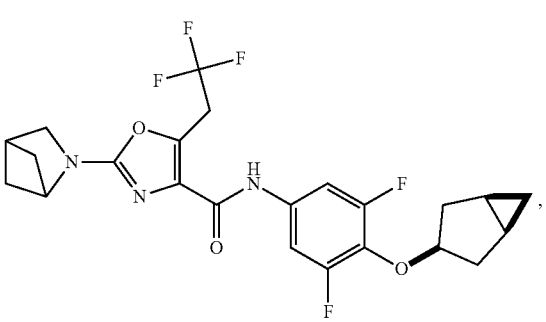,
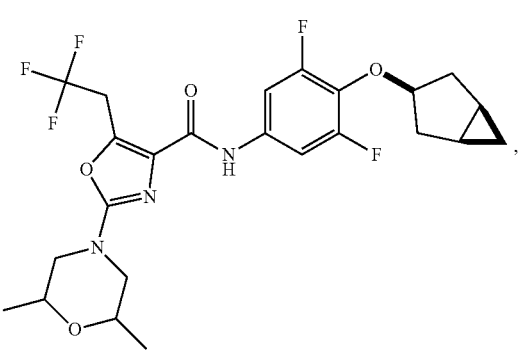,
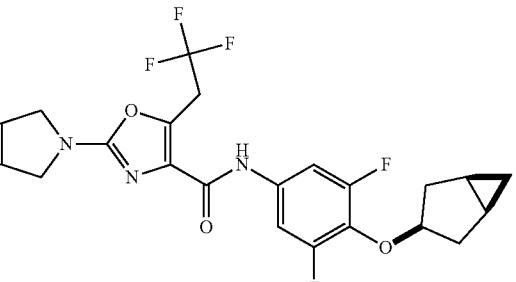,
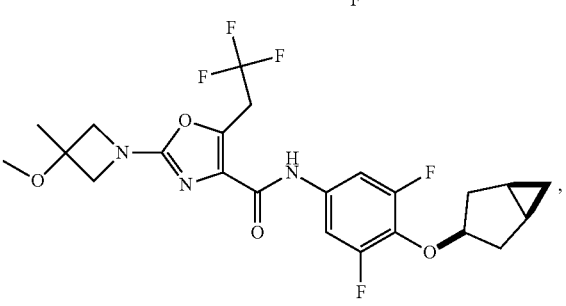, 423
-continued
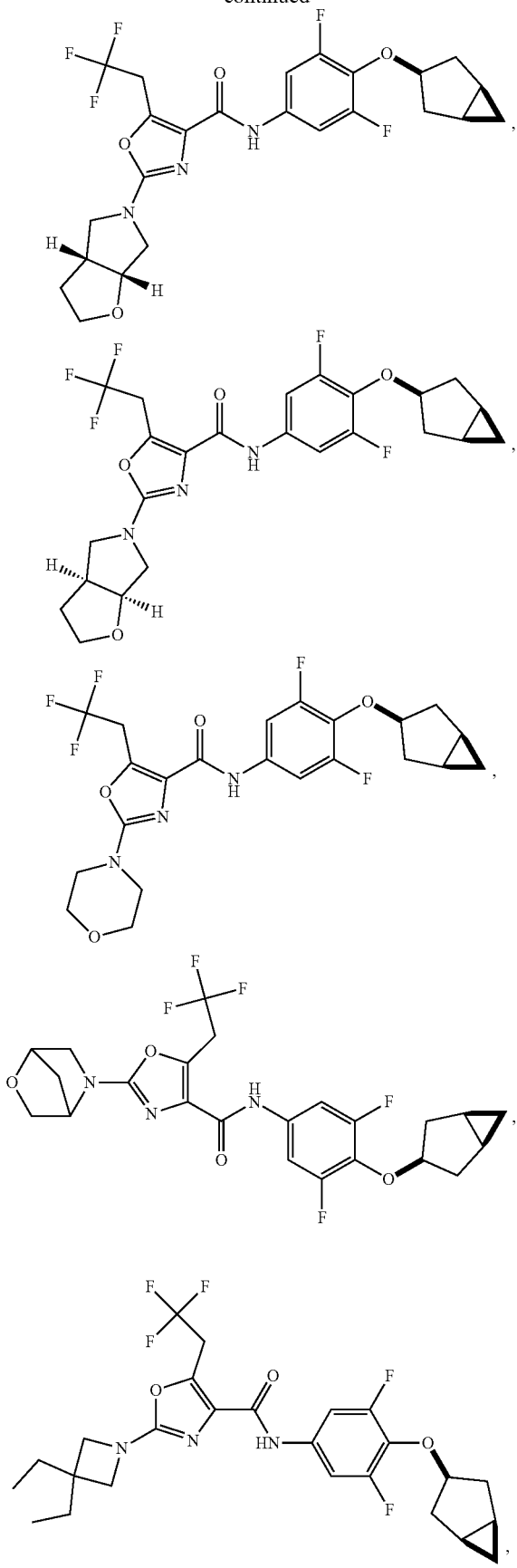
424
-continued
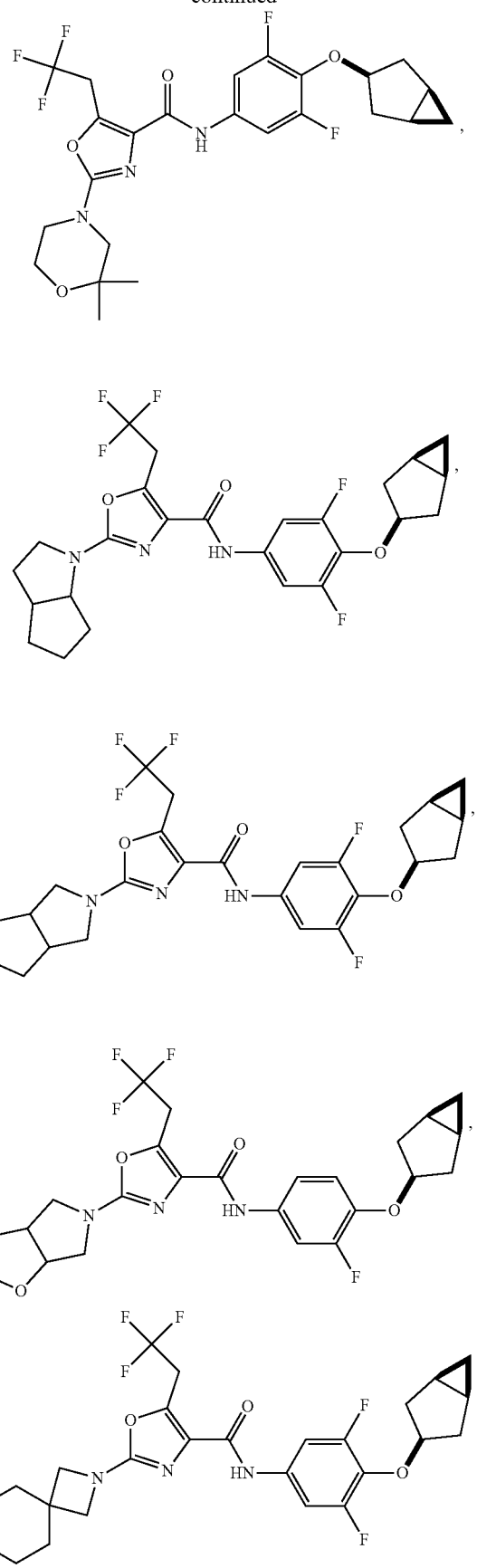

425
-continued
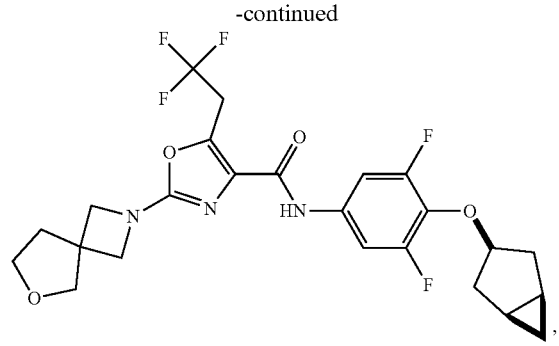
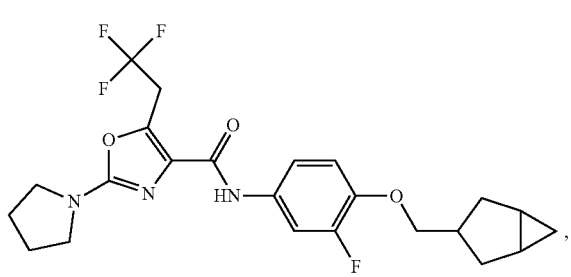
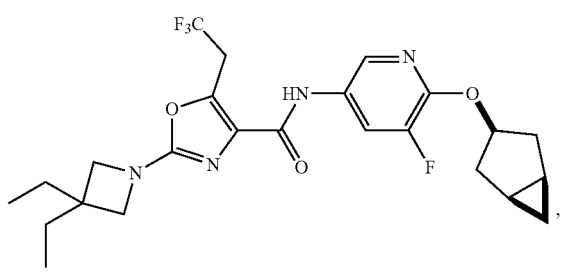
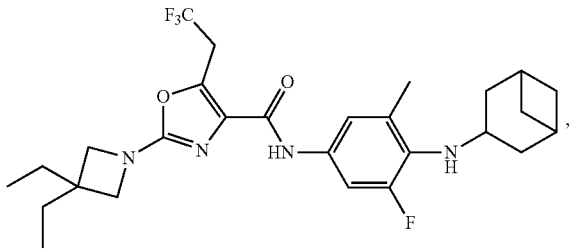
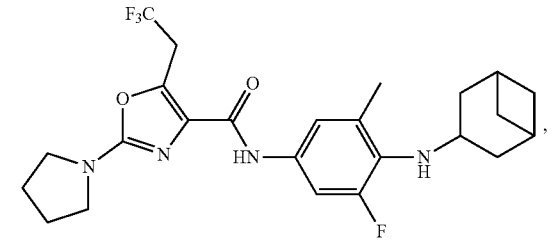
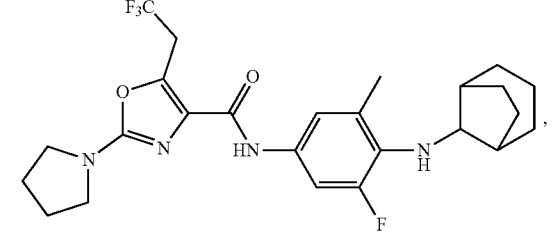
426
-continued
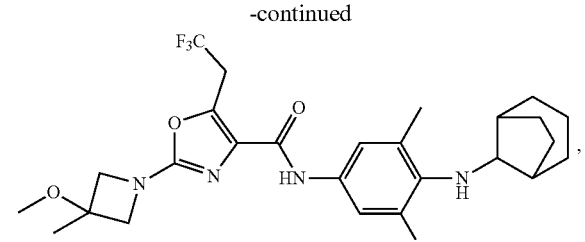
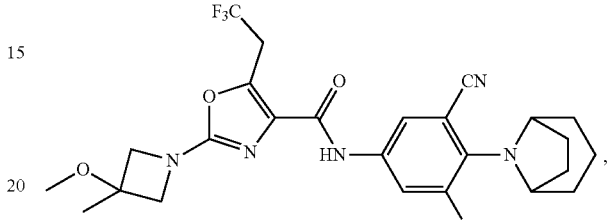
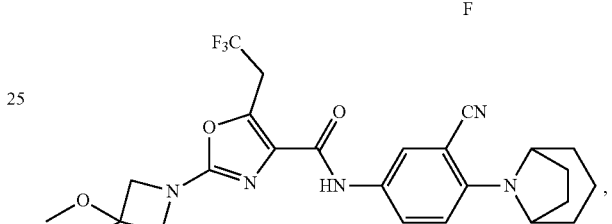
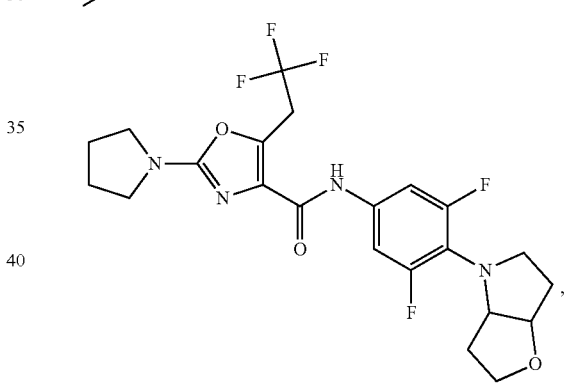
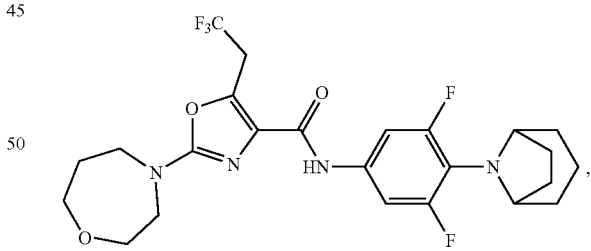
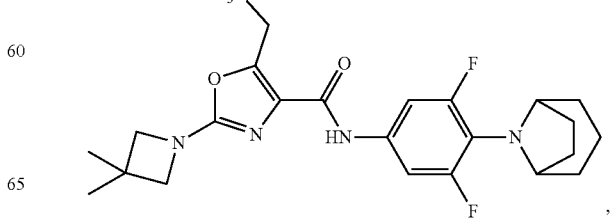

427
-continued
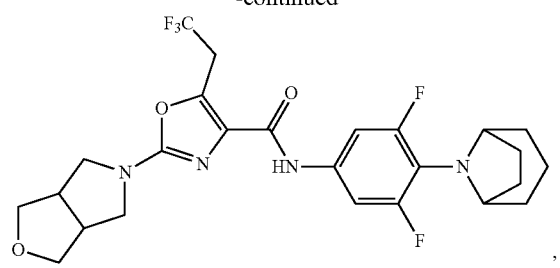
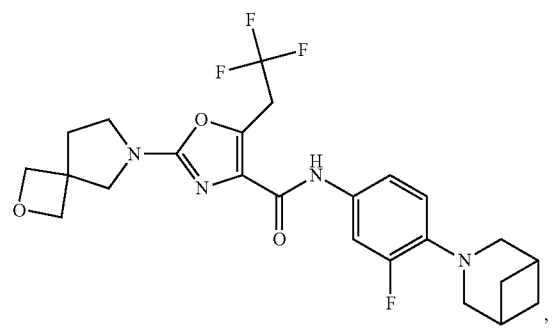
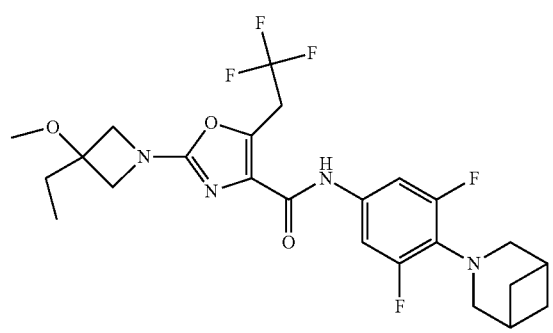
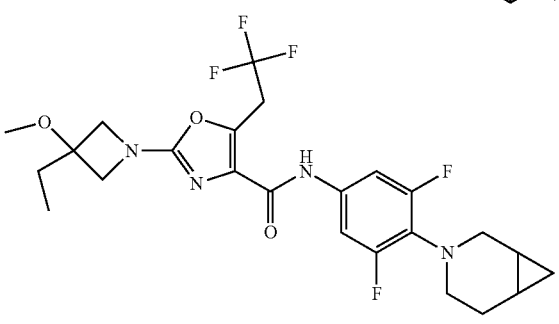
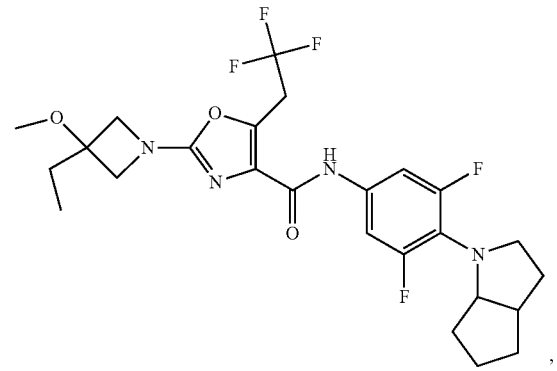
428
-continued
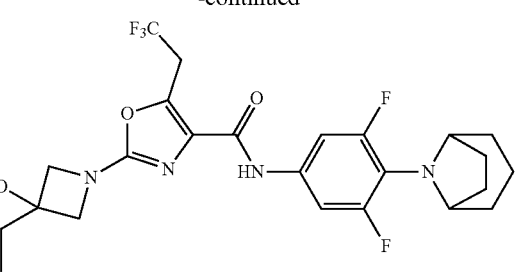
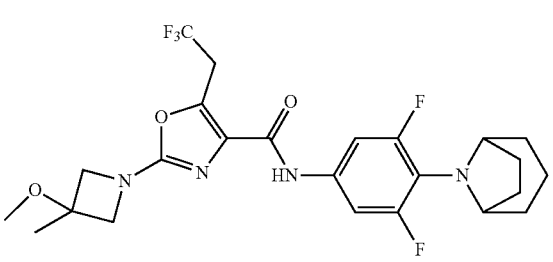
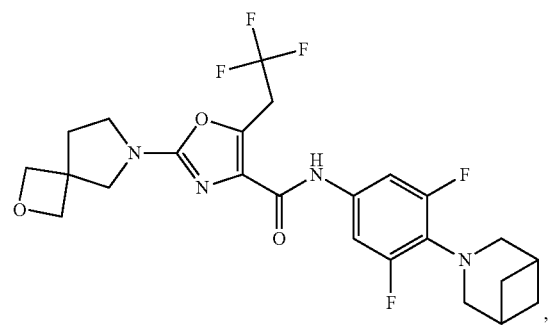
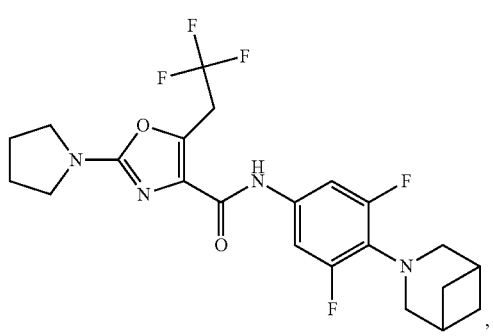
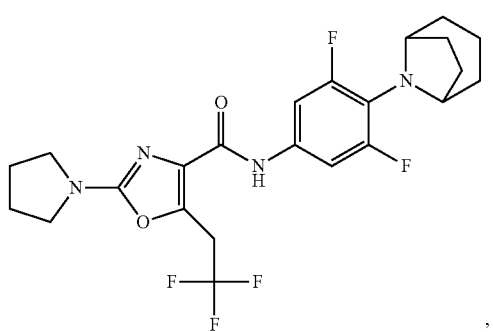

429
-continued
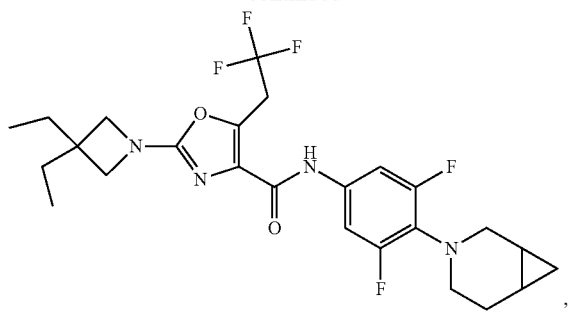
,
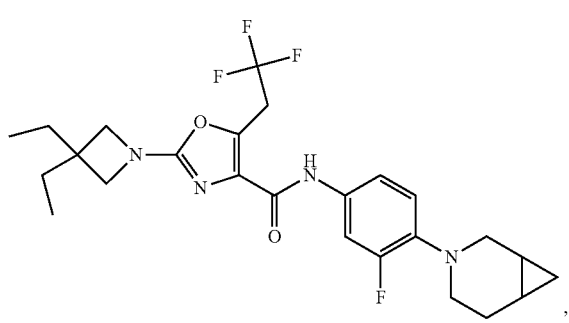
,
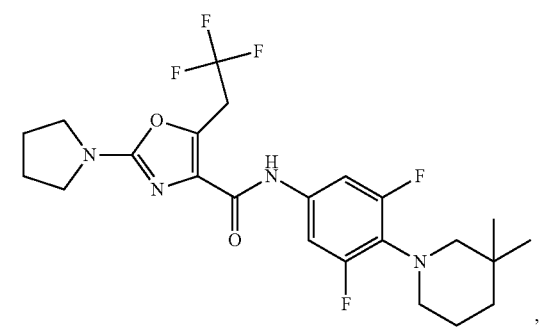
,
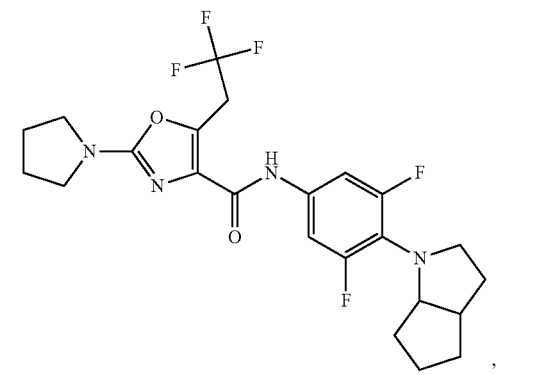
,
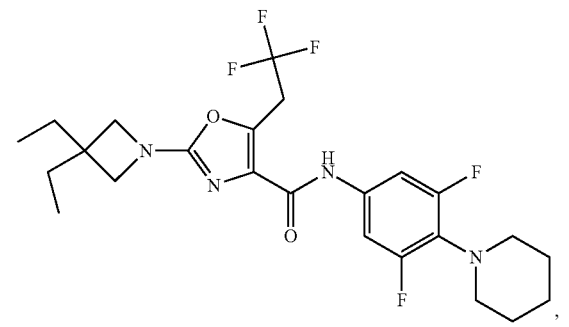
,
430
-continued
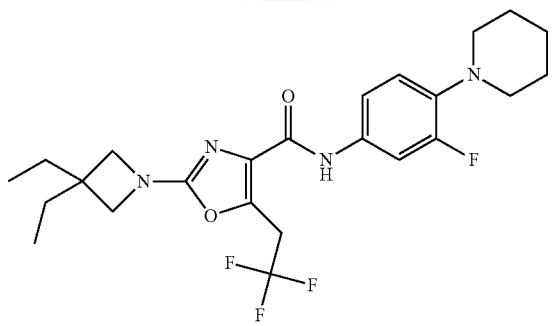
,
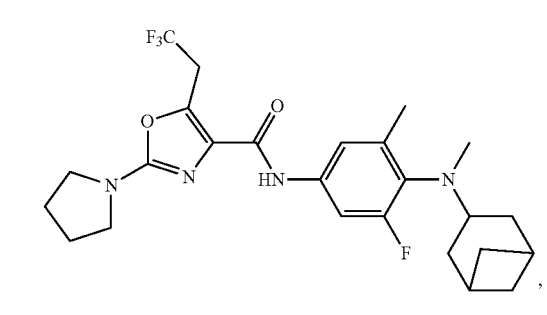
,
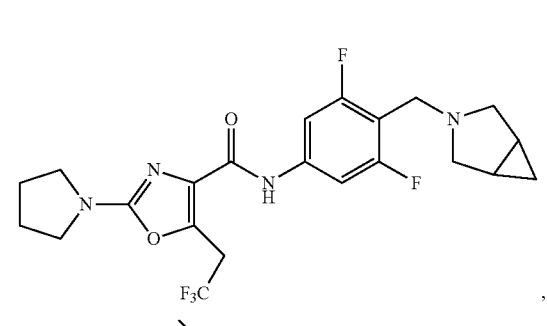
,
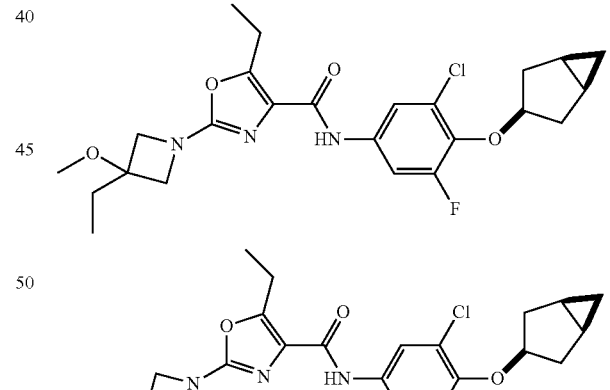
,
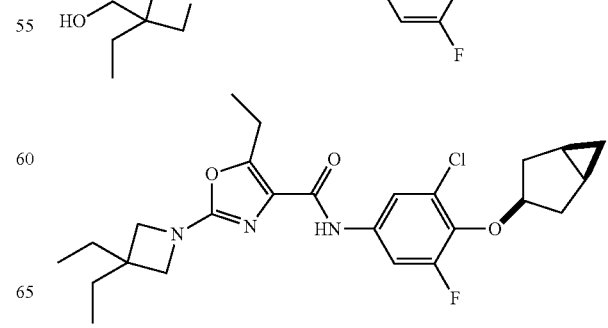
, 431
-continued
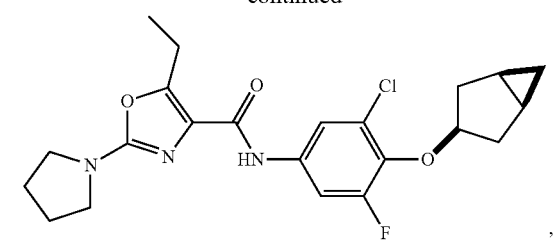
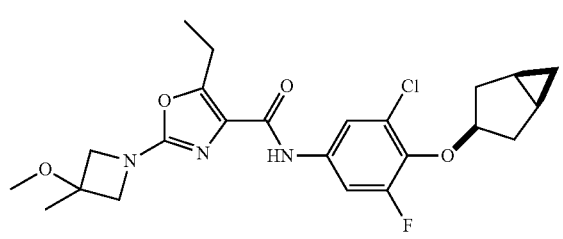
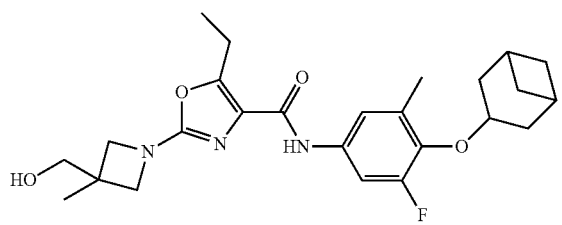
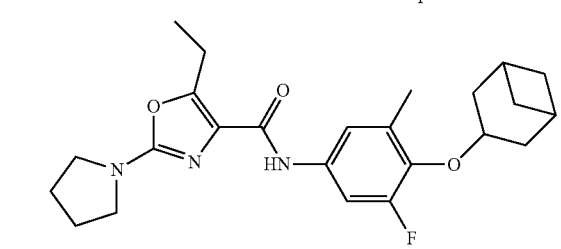
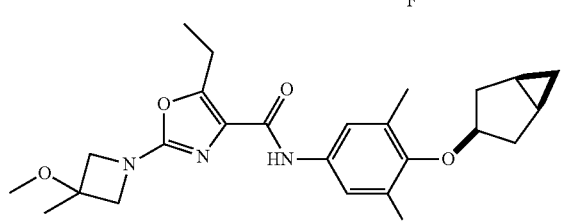
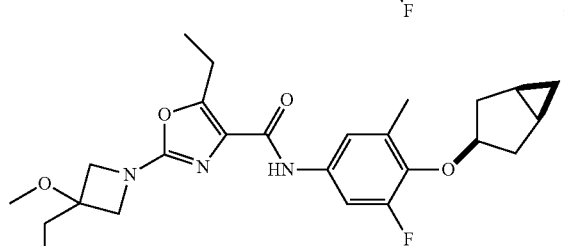
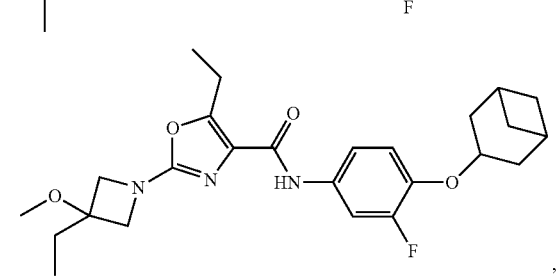
432
-continued
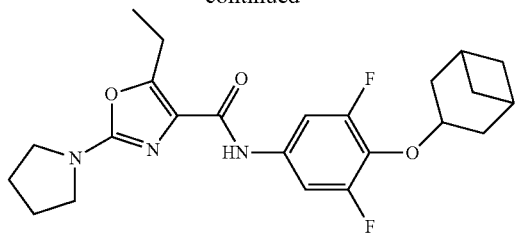
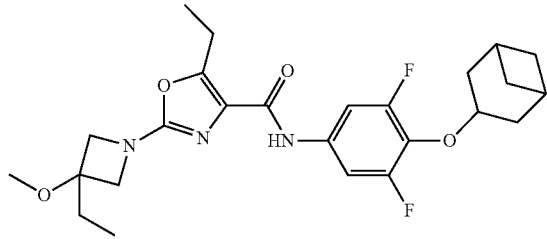
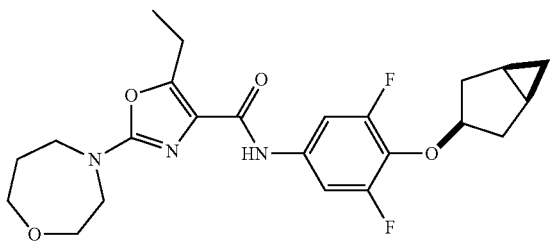
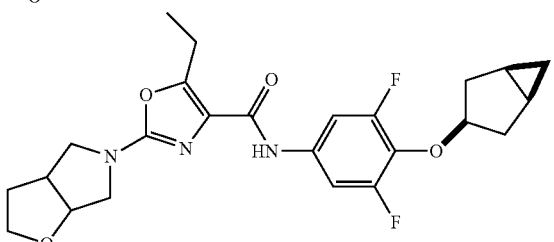
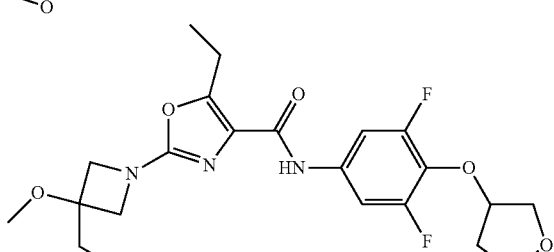
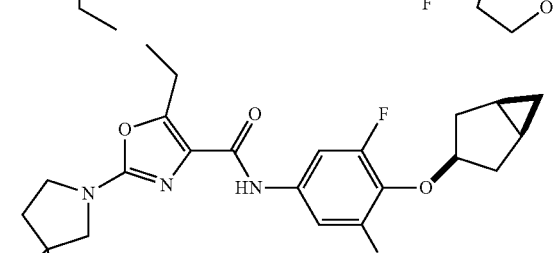
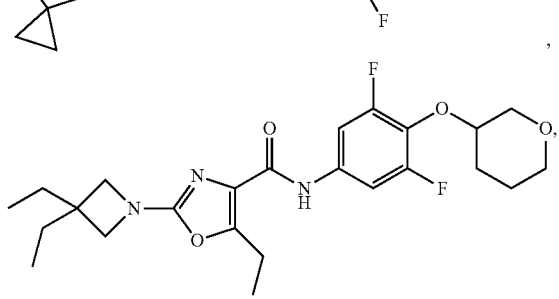

433
-continued
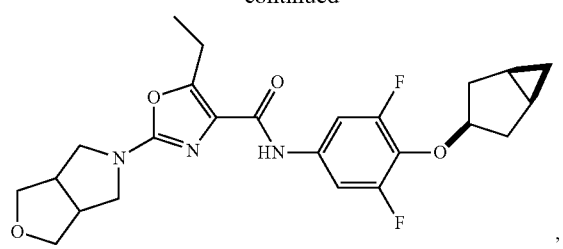
,
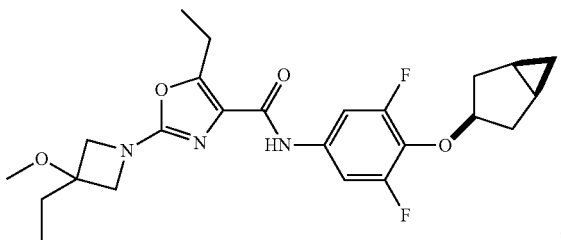
,
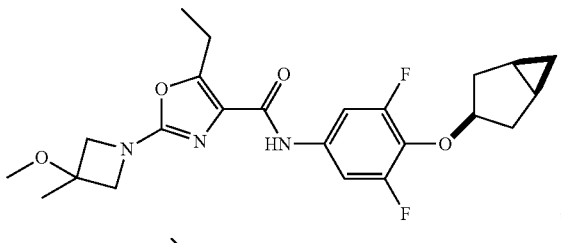
,
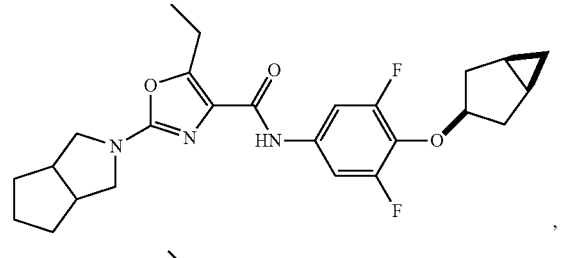
,
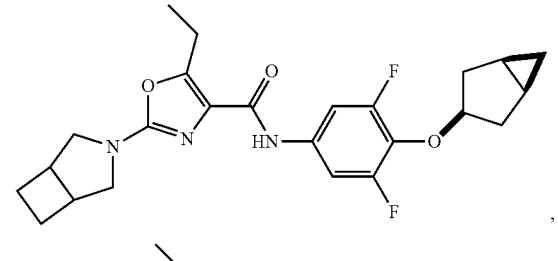
,
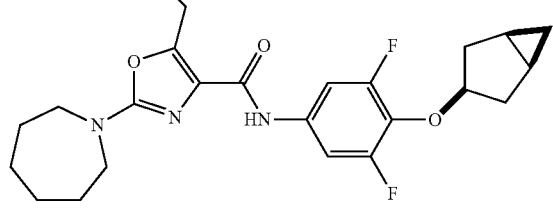
,
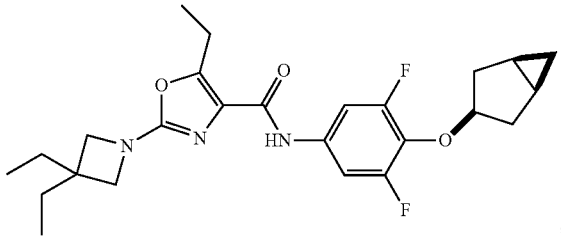
,
434
-continued
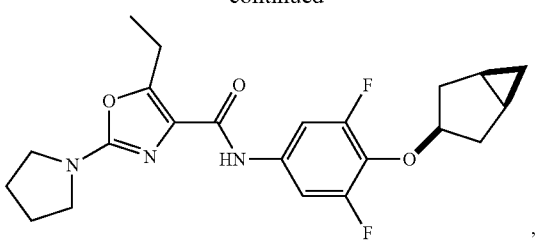
,
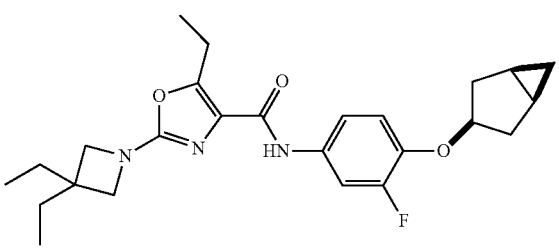
,
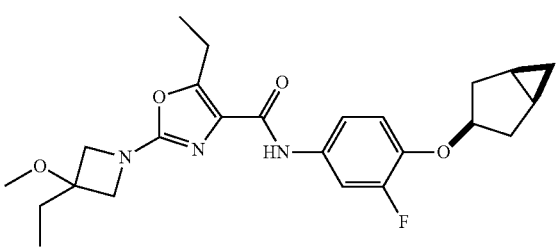
,
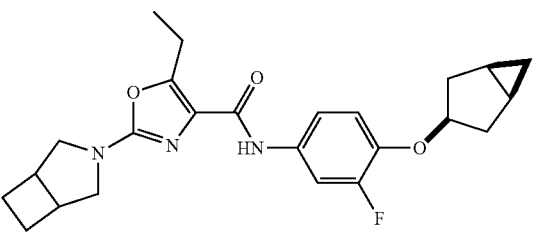
,
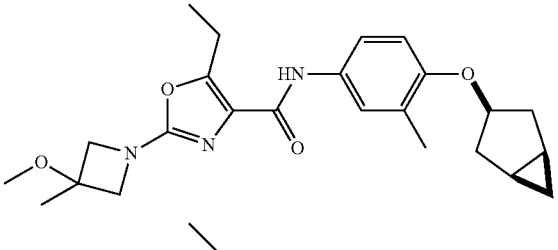
,
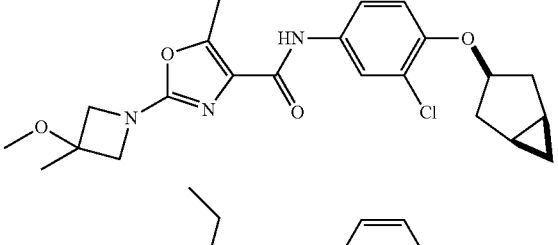
,
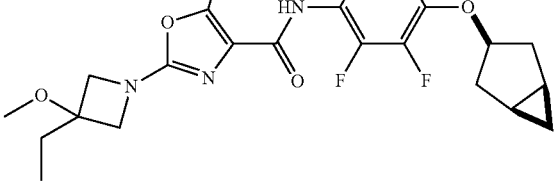
, 435
-continued
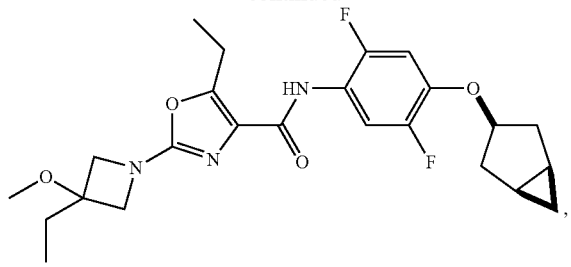
436
-continued
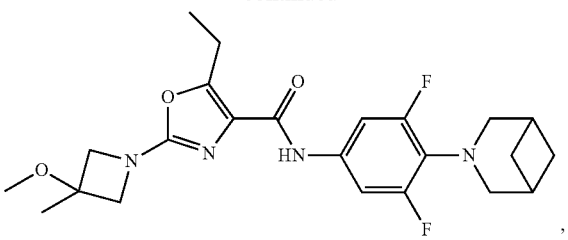
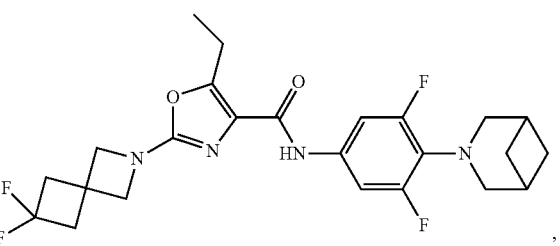
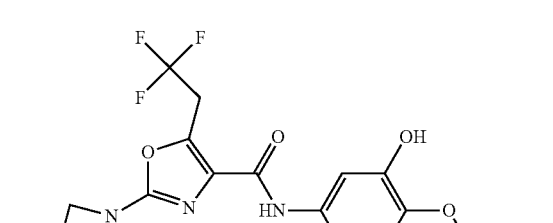
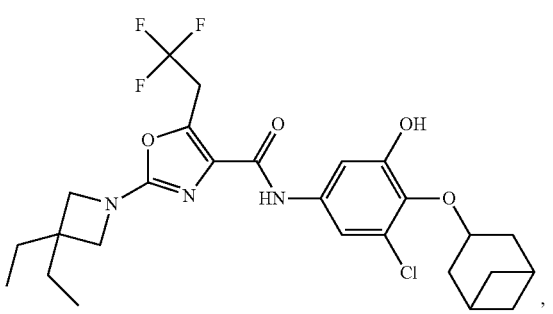
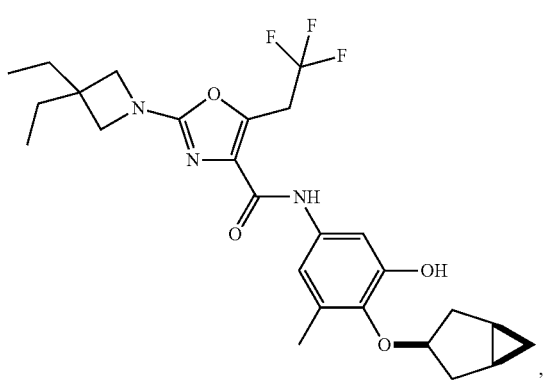

437
-continued

438
-continued

439
-continued
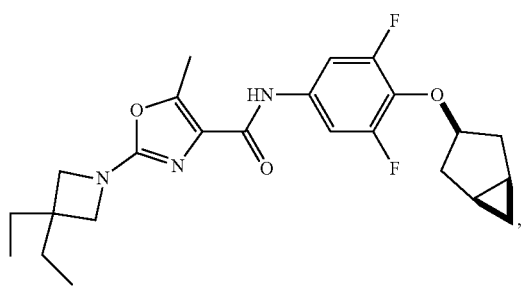
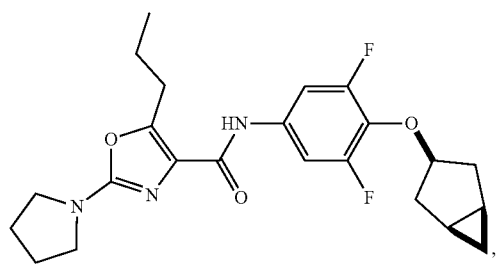
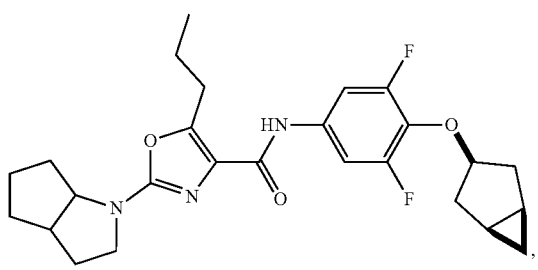
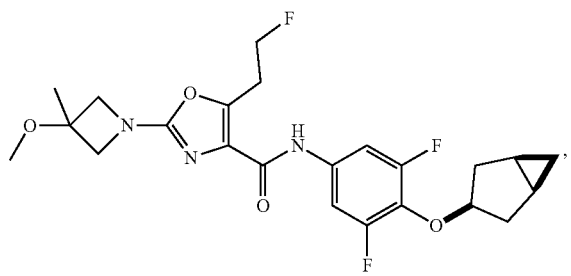
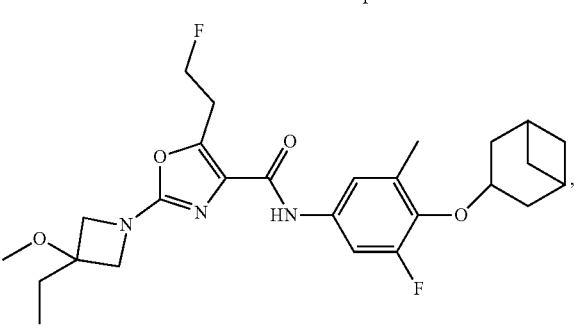
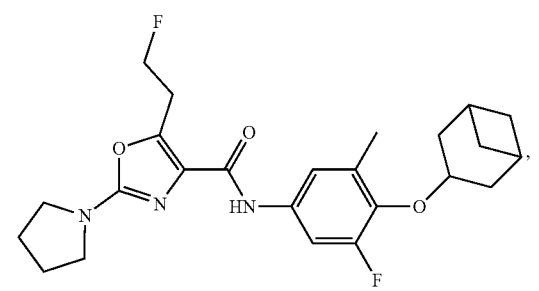
440
-continued
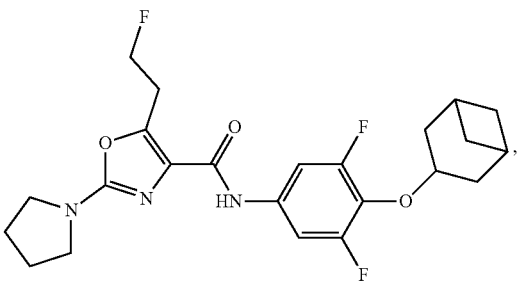
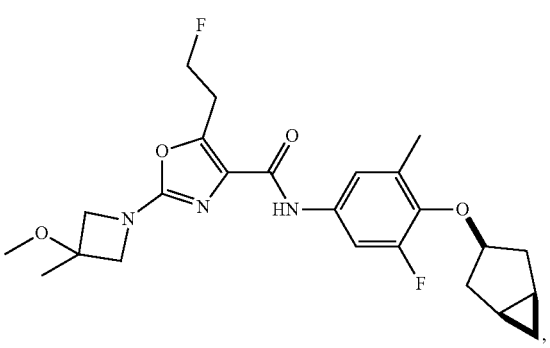
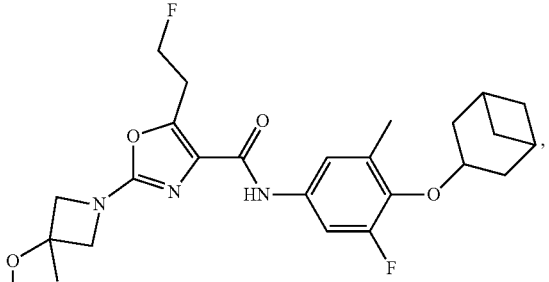
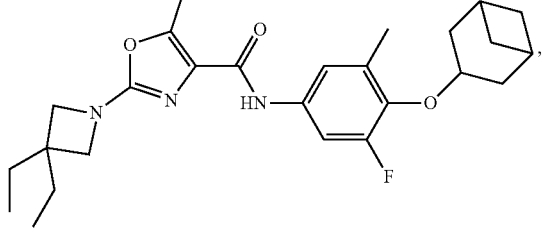
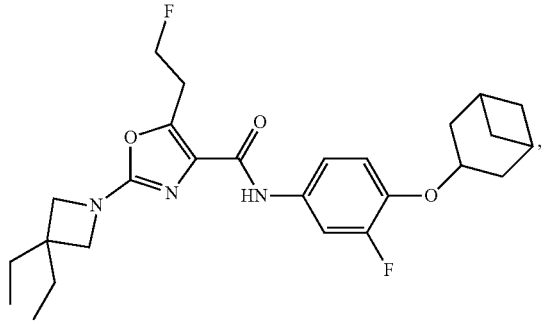

441
-continued
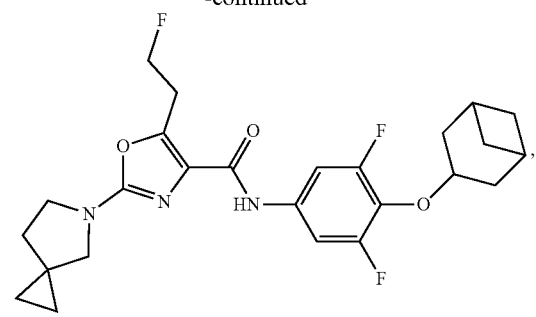
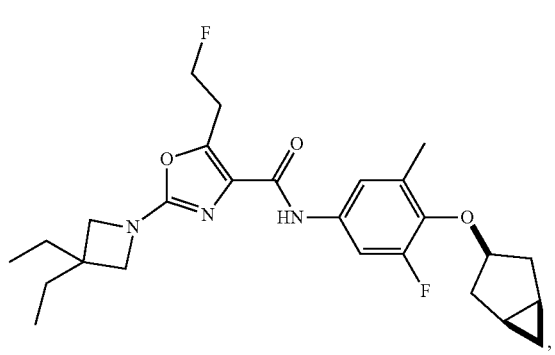
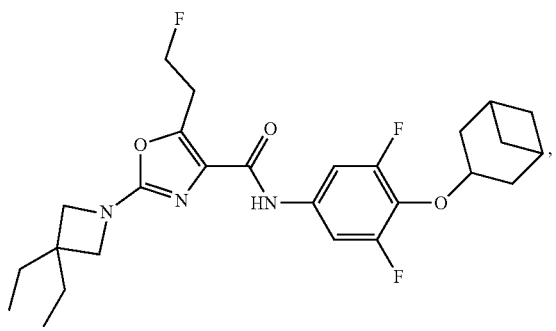
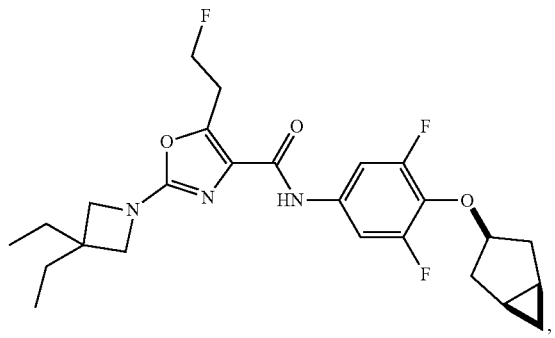
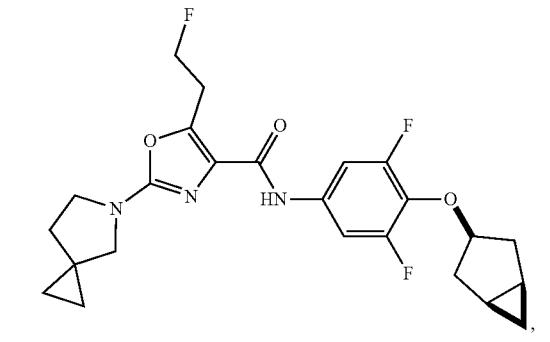
442
-continued
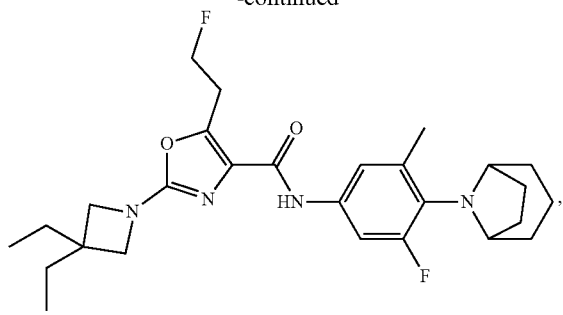
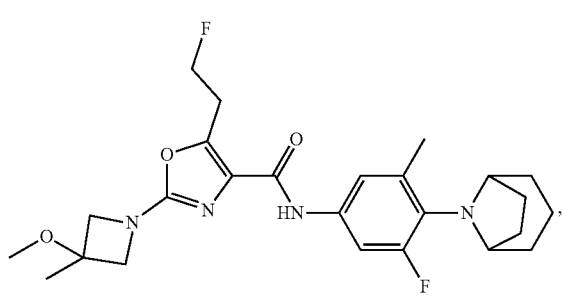
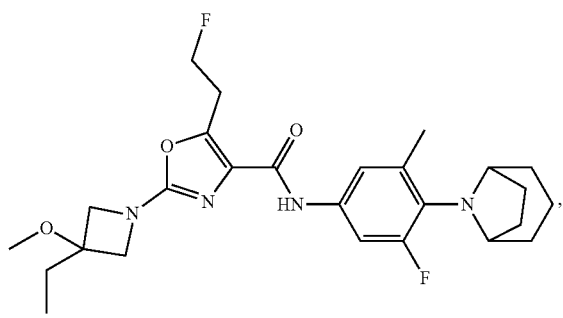
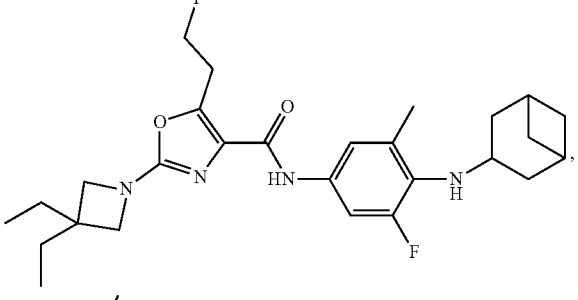
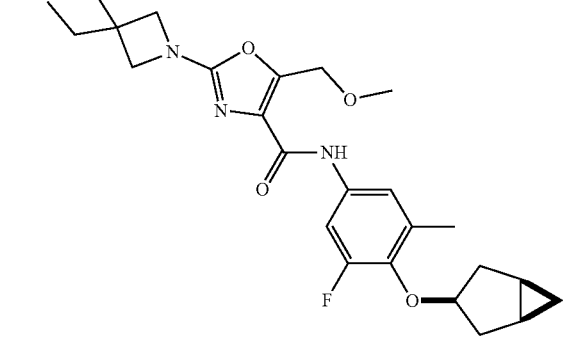

443
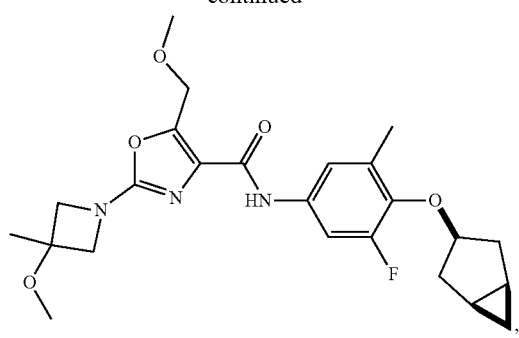
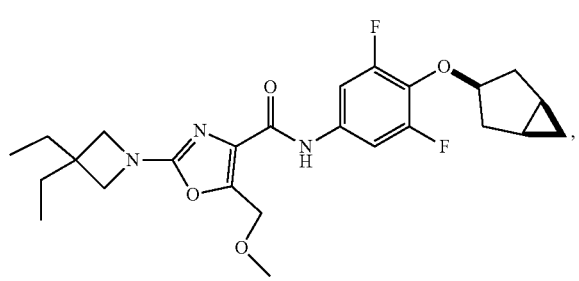
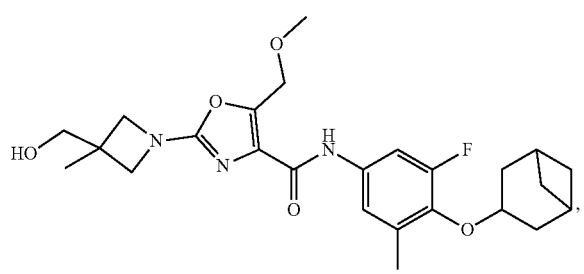
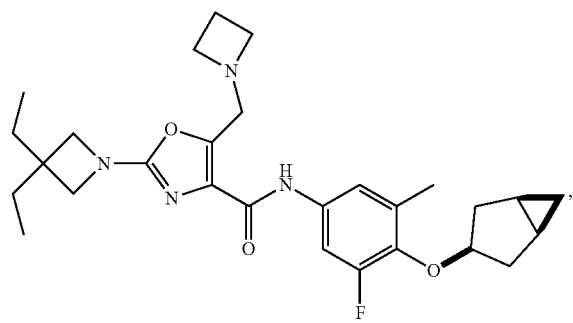
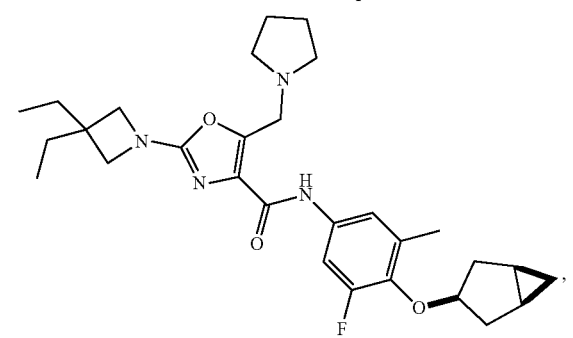
444
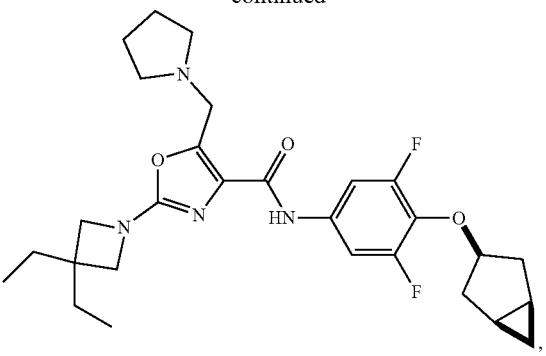
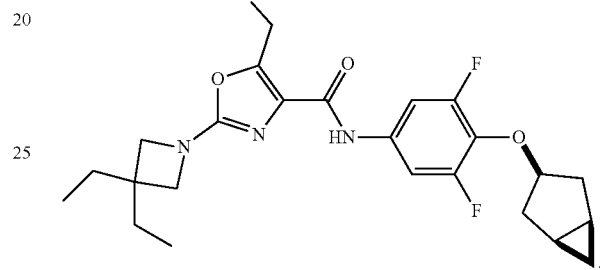
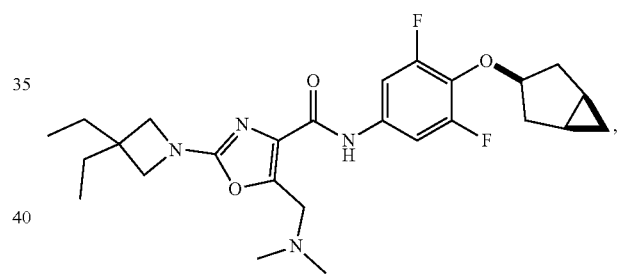
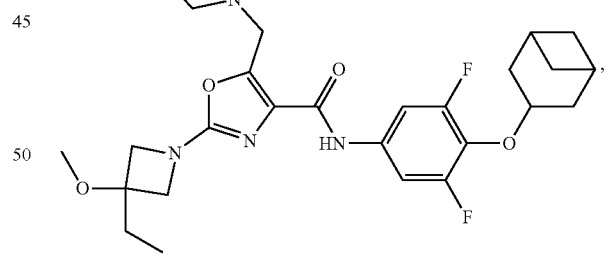
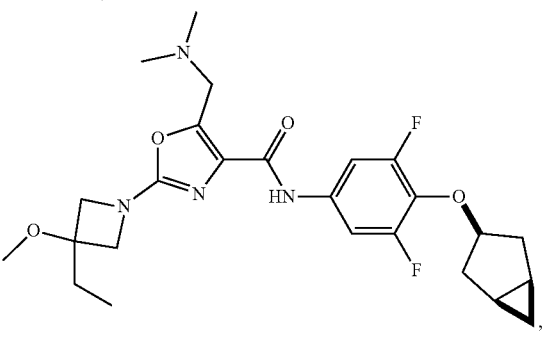

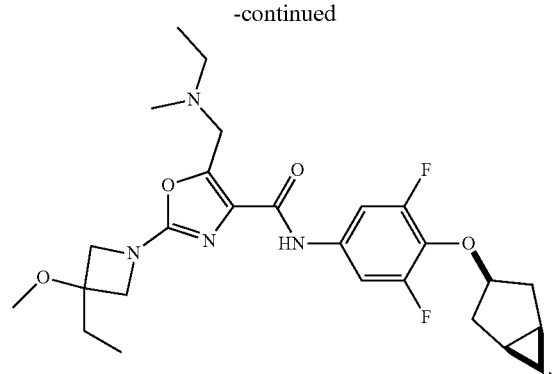
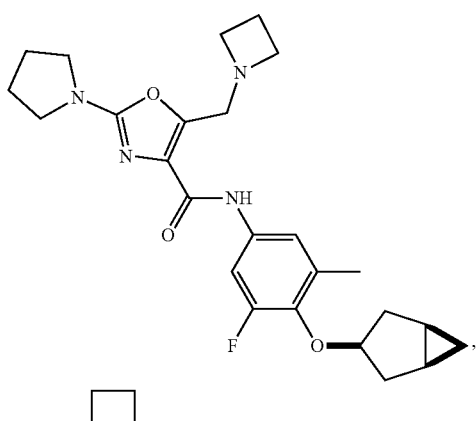
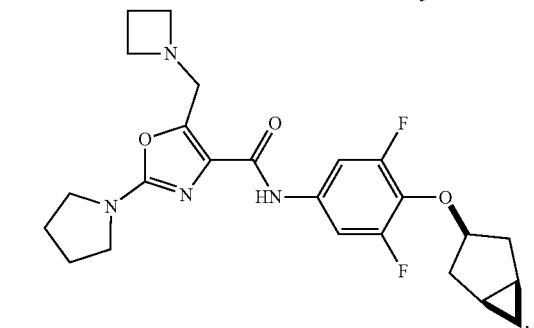
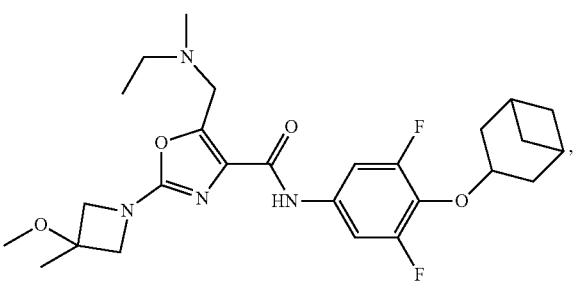
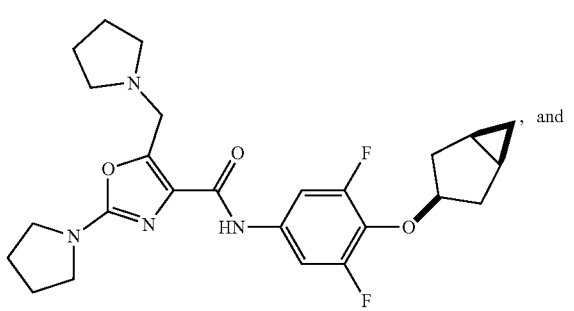
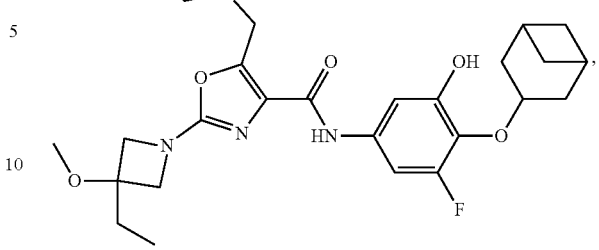
or a pharmaceutically acceptable salt or stereoisomer thereof.
18. The compound of claim 17 that is
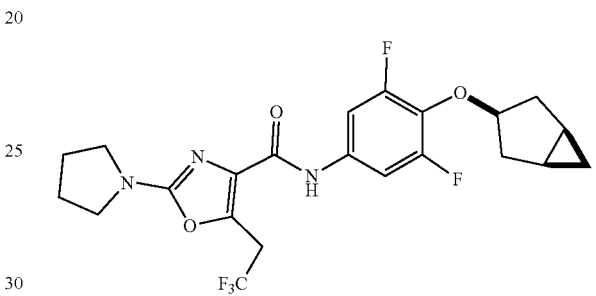
or a pharmaceutically acceptable salt thereof.
19. The compound of claim 17 that is
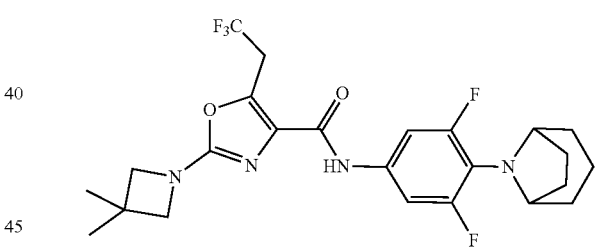
or a pharmaceutically acceptable salt thereof.
20. The compound of claim 17 that is
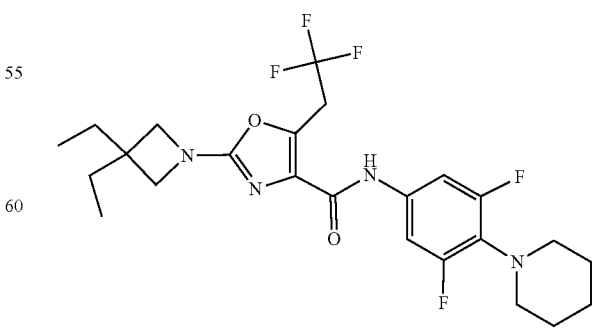
or a pharmaceutically acceptable salt thereof.

21. The compound of claim 17 that is

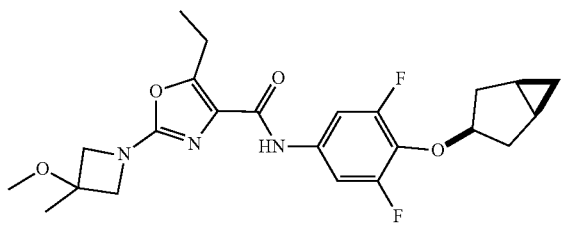

or a pharmaceutically acceptable salt thereof.

22. The compound of claim 17 that is

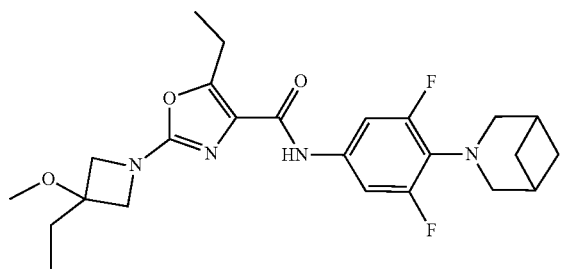 [SMILES: CCc1oc(N2CC(CC)(OC)C2)nc1C(=O)Nc1cc(F)c(N2CC3CC(C3)C2)c(F)c1]

or a pharmaceutically acceptable salt thereof.

23. The compound of claim 17 that is

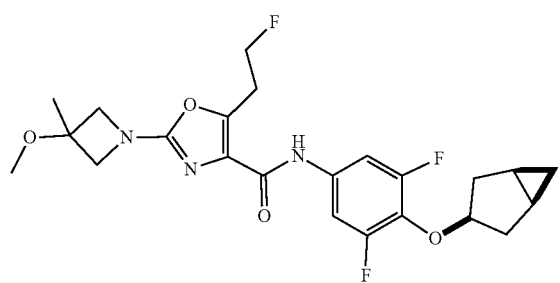

or a pharmaceutically acceptable salt thereof.

24. The compound of claim 17 that is

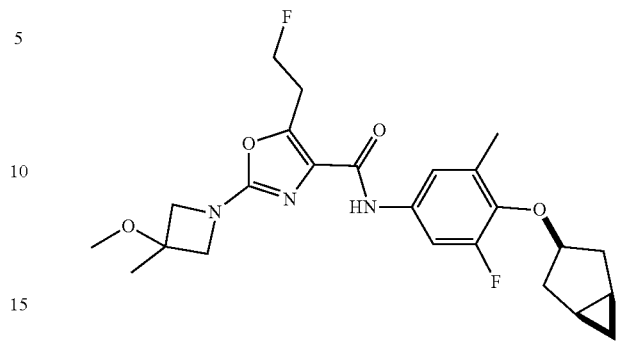

or a pharmaceutically acceptable salt thereof.

25. The compound of claim 17 that is

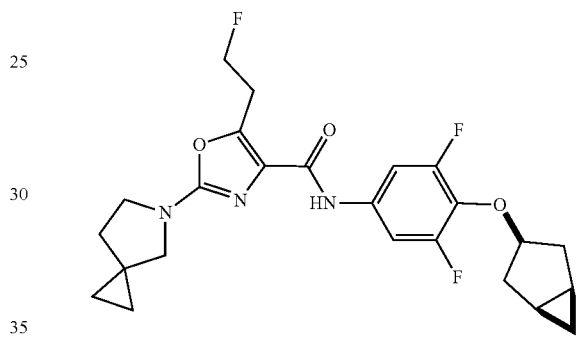

or a pharmaceutically acceptable salt thereof.

26. A pharmaceutical composition comprising a compound of claim 1, or a pharmaceutically acceptable salt or stereoisomer thereof, and a pharmaceutically acceptable excipient.

* * * * *

UNITED STATES PATENT AND TRADEMARK OFFICE
CERTIFICATE OF CORRECTION

PATENT NO. : 12,098,145 B2
APPLICATION NO. : 18/543599
DATED : September 24, 2024
INVENTOR(S) : James Guy Breitenbucher et al.

Page 1 of 1

It is certified that error appears in the above-identified patent and that said Letters Patent is hereby corrected as shown below:

In the Claims

Claim 17, Column 400, Lines 33-41:

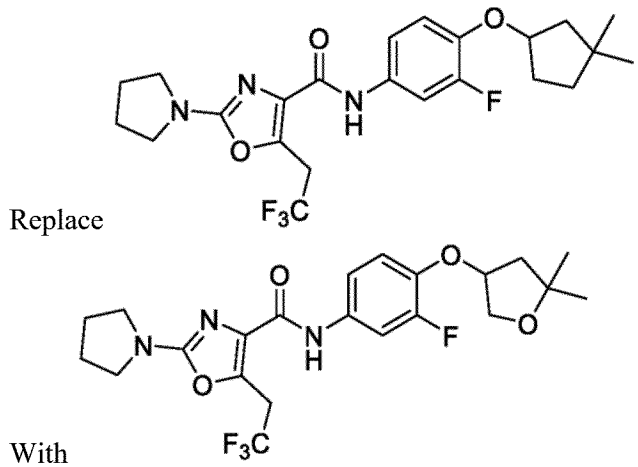

Replace

With

Signed and Sealed this
Third Day of December, 2024

Katherine Kelly Vidal
*Director of the United States Patent and Trademark Office*